United States Patent
Fretz et al.

(10) Patent No.: US 9,920,010 B2
(45) Date of Patent: Mar. 20, 2018

(54) CXCR7 RECEPTOR MODULATORS

(71) Applicant: IDORSIA PHARMACEUTICALS LTD, Allschwil (CH)

(72) Inventors: Heinz Fretz, Allschwil (CH); Philippe Guerry, Allschwil (CH); Thierry Kimmerlin, Allschwil (CH); Francois Lehembre, Allschwil (CH); Julien Pothier, Allschwil (CH); Hervé Siendt, Allschwil (CH); Anja Valdenaire, Basel (CH)

(73) Assignee: IDORSIA PHARMACEUTICALS LTD, Allschwil (CH)

( * ) Notice: Subject to any disclaimer, the term of this patent is extended or adjusted under 35 U.S.C. 154(b) by 0 days.

(21) Appl. No.: 14/892,959

(22) PCT Filed: May 28, 2014

(86) PCT No.: PCT/IB2014/061774
§ 371 (c)(1),
(2) Date: Nov. 20, 2015

(87) PCT Pub. No.: WO2014/191929
PCT Pub. Date: Dec. 4, 2014

(65) Prior Publication Data
US 2016/0107997 A1 Apr. 21, 2016

(30) Foreign Application Priority Data
May 30, 2013 (WO) .................. PCT/IB2013/054478

(51) Int. Cl.
| | | |
|---|---|---|
| C07D 217/04 | (2006.01) | |
| C07D 217/06 | (2006.01) | |
| C07D 211/56 | (2006.01) | |
| C07D 401/12 | (2006.01) | |
| C07D 403/12 | (2006.01) | |
| C07D 405/12 | (2006.01) | |

(52) U.S. Cl.
CPC .......... *C07D 217/04* (2013.01); *C07D 211/56* (2013.01); *C07D 217/06* (2013.01); *C07D 401/12* (2013.01); *C07D 403/12* (2013.01); *C07D 405/12* (2013.01)

(58) Field of Classification Search
CPC .. C07D 217/04; C07D 217/06; C07D 211/56; C07D 401/12; C07D 403/12; C07D 405/12
See application file for complete search history.

(56) References Cited

FOREIGN PATENT DOCUMENTS

| WO | WO 1999/42456 A2 | 8/1999 |
| WO | WO 2002/46164 A1 | 6/2002 |
| WO | WO 2004/058705 A2 | 7/2004 |
| WO | WO 2007/059108 A2 | 5/2007 |
| WO | WO 2009/076404 A1 | 6/2009 |
| WO | WO 2013/190508 A2 | 12/2013 |
| WO | WO 2016/087370 A1 | 6/2016 |

OTHER PUBLICATIONS

Voskoglou-Nomikos et al., Clinical Cancer Research, vol. 9, 4227-4239.*
ptcl.chem.ox.ac.uk/MSDS structure activity relationship; Jaworska, 1-8, 2004.*
Cancer and Metastasis Reviews (1998), 17(1), 91-106.*
Science (1999), vol. 286, 531-537.*
International Search Report of PCT/IB2014/061774 dated Sep. 1, 2014.
Brown, "Inhibiting Vasculogenesis After Radiation: A New Paradigm to Improve Local Control by Radiotherapy", Seminars Radiation Oncology, 23(4); 281-7, 2013.
Burns et al.; "A Novel Chemokine Receptor for SDF-1 and I-TAC Involved in Cell Survival, Cell Adhesion, and Tumor Development", Journal of Experimental Medicine, 203(9), 2201-2213, 2006.
Calatozzolo et al, "Expression of the New CXCL 12 Receptor, CXCR7, in Gliomas", Cancer Biology and Therapy, 11:2, 1-12, 2011.
Clark et al, "Affinity of 2-(Tetrahydroisoquinolin-1-ylmethyl)- and 2-(Isoindolin-2-ylmethyl)imidazolines for a-Adrenoceptors. Differential Affinity of Imidazolines for the [3H]Idazoxan-Labeled a2-Adrenoceptor vs the [3H]Yohimbine-Labeled Site", J. Med. Chem., 33(2), 596-600, 1990.
Cruz-Orengo et al, "CXCR7 Influences Leukocyte Entry Into the CNS Parenchyma by Controlling Abluminal CXCL12 Abundance During Autoimmunity", Journal of Experimental Medicine, 208(2), 327-339, 2011.
Ding et al, "Divergent Angiocrine Signals from Vascular Niche Balance Liver Regeneration and Fibrosis", Nature, 505(7481):97-102, 2014.

(Continued)

*Primary Examiner* — Rebecca L Anderson
(74) *Attorney, Agent, or Firm* — Arent Fox LLP

(57) ABSTRACT

The present invention relates to derivatives of formula (I)

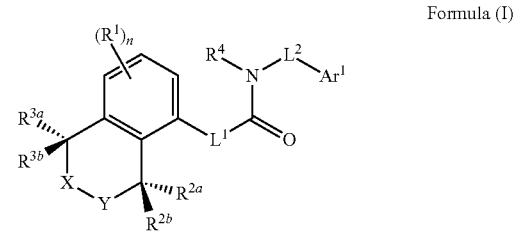

Formula (I)

wherein $(R^1)_n$, $R^{2a}$, $R^{2b}$, $R^{3a}$, $R^{3b}$, $R^4$, $L^1$, $L^2$, X, Y and $Ar^1$ are as described in the description, to their preparation, to pharmaceutically acceptable salts thereof, and to their use as pharmaceuticals, to pharmaceutical compositions containing one or more compounds of formula (I), and especially to their use as CXCR7 receptor modulators.

36 Claims, No Drawings

(56) References Cited

OTHER PUBLICATIONS

Duda et al, "CXCL12 (SDF1a)-CXCR4/CXCR7 Pathway Inhibition: An Emerging Sensitizer for Anti-Cancer Therapies?", Clinical Cancer Research, 17(8), 2074-80, 2011.
Ebsworth et al, "The CXCR7 Inhibitor CCX650 Significantly Prolongs Survival in the C6 Rat Model of Glioblastomas", Neuro Oncology, 15, Suppl 3:iii37-iii61, ET-023, 2013.
Ebsworth et al, "The Effect of the CXCR7 Inhibitor CCX662 on Survival in the ENU Rat Model of Gliobastoma", J Clinical Oncology, 30, Suppl, Abstr e13580, 2012.
Glossop et al, "A Microwave-Assisted Alternative Synthesis of 8-Amino-2-Methyl1-3,4-Dihydroisoquinolin-1-One", Synthesis, 7, 981-983, 2007.
Hatterman et al, "CXCL12 Mediates Apoptosis Resistance in Rat C6 Glioma Cells", Oncology Reports, 27: 1348-1352, 2012.
Hatterman et al, "The Chemokine Receptor CXCR7 is Highly Expressed in Human Glioma Cells and Mediates Antiapoptotic Effects", Cancer Research, 70 8:3299-3308, 2010.
Ikeda et al, Modulation of Circadian Glucocorticoid Oscillation via Adrenal Opioid-CXCR7 Signaling Alters Emotional Behavior, Cell, 155, 1323-1336, 2013.
Kioi et al, "Inhibition of Vasculogenesis, but not Angiogenesis, Prevents the Recurrence of Glioblastoma After Irradiation in Mice", The Journal of Clinical Investigation, 120(3), 694-705, 2010.
Liu et al, "Blockade of SDF-1 After Irradiation Inhibits Tumor Recurrences of Autochthonous Brain Tumors in Rats", Neuro-Oncology, 16(1), 21-28, 2014.
Liu et al, "Inhibition of Recurrences of Experimental Brain Tumors and Brain Metastases After Irradiation by Blocking the Activity of SDF-1 Using the Spiegelmer NOX-A12", Neuro-Oncology, 15 Suppl 3, iii189-iii190, RB-002. doi: 10.1093/neuonc/not188, 2013.
Miao et al, "CXCR7 (RDC1) Promotes Breast and Lung Tumor Growth in Vivo and is Expressed on Tumor Associated Vasculature", PNAS, 104(40), 15735-15740, 2007.
Naumann et al, CXCR7 Functions as a Scavenger for CXCL12 and CXCL11, Plos One, 5(2), e9175, 2010.
Neumeyer, "Facile Synthesis of Isoindoline and Substituted Isoindolines", Journal of Pharmaceutical Sciences, 53, 981, 1964.
Salmaggi et al, "CXCL12, CXCR4 and CXCR7 Expression in Brain Metastases", Cancer Biology and Therapy, 8:17, 1-7, 2009.
Sartina et al, "Antagonism of CXCR7 Attenuates Chronic Hypoxia-Induced Pulmonary Hypertension", Pediatric Research, 71(6), 682-688, 2012.
Stahl et al, Handbook of Phramaceutical Salts Properties, Selection and Use, 2008.
Sun et al, "CXCL12/CXCR4/CXCR7 Chemokine Axis and Cancer Progression", Cancer Metastasis Rev. Author Manuscript, 29(4), 709-722, 2010.
Vassylyev et al, "Catalytic Properties of Several Supported Pd(II) Complexes for Suzuki Coupling Reactions", Tetrahedron, 62(29), 6869-6875, 2006.
Walters et al, "Inhibition of CXCR7 Extends Survival Following Irradiation of Brain Tumours in Mice and Rats", British Journal of Cancer, 1-10 | doi: 10.1038/bjc.2013.830, 2014.
Wang et al, "The Role of CXCR7/RDC1 as a Chemokine Receptor for CXCL12/Sdf-1 in Prostate Cancer", Journal of Biochemical Chemistry, 293(7), 4283-4294, 2008.
Watanabe et al, "Pathogenic Role of CXCR7 in Rheumatoid Arthritis", Arthritis and Rheumatism, 62(11), 3211-3220, 2010.
Williams et al, "Pharmaceutical Manufacturing", Remington,The Science and Practice of Pharmacy, 21st Edition, Part 5, 2005.
Wouters et al, "Pharnaceutical Salts and Co-Crystals", RSC Publishing, 2012.
Zheng et al, "Chemokine Receptor CXCR7 Regulates the Invasion, Angiogenesis and Tumor Growth of Human Hepatocellular Carcinoma Cells", Journal of Experimental and Clinical Cancer Research, 29, 31, 2010.

* cited by examiner

CXCR7 RECEPTOR MODULATORS

CROSS-REFERENCE TO RELATED APPLICATIONS

This application is a National Stage entry of International Application No. PCT/IB2014/061774, filed May 28, 2014, which claims priority to International Application No. PCT/IB2013/054478, filed May 30, 2013.

The present invention relates to novel CXCR7 receptor modulators of formula (I) and their use as pharmaceuticals. The invention also concerns related aspects including processes for the preparation of the compounds, pharmaceutical compositions containing one or more compounds of formula (I), and their use as CXCR7 receptor modulators. The invention further relates to the compounds of formula (I) and their use as pharmaceuticals in combination with one or more therapeutic agents and/or radiotherapy in the treatment of cancers, especially in the treatment of malignant glioma, in particular glioblastoma multiforme.

Chemokine receptors are a group of G-protein coupled receptors (GPCRs) that bind peptidic chemokine ligands with high affinity. The predominant function of chemokine receptors is to guide leukocyte trafficking to lymphoid organs and tissues under resting conditions as well as during inflammation, but a role for certain chemokine receptors on non-hematopoietic cells and their progenitors has also been recognized.

Signaling networks and metabolic profiles of cancer cells differ in a microenvironment dependent manner. This is a major reason for lack of therapeutic response of tumors at certain organ sites and of tumor metastases in comparison to primary tumors. CXCL12 (alias stromal cell-derived factor 1, SDF-1; alias Pre-B cell growth stimulating factor, PBSF), a stroma-derived chemo-attractant, exerts anti-apoptotic effects, displays pro-angiogenic properties and plays a key role in seeding circulating tumor cells to metastatic sites. CXCL12 binds and activates two receptors, CXCR7 (alias ACKR3, alias RDC1, alias CMKOR1, alias GPR159) and CXCR4 (alias Fusin, alias Leukocyte-derived seven-trans-membrane-domain receptor; LESTR, alias D2S201E, alias seven-transmembrane-segment receptor, alias HM89, alias lipopolysaccharide-associated protein 3; lap3, alias LPS-associated protein 3).

The expression of the CXCL12 receptor CXCR7 correlates with diseases progression in cancer (among others in hormone refractory prostate cancer, in renal cell carcinoma, cervical cancer, papillary thyroid carcinoma, bladder cancer, Ewing's sarcoma, colorectal cancers, lung cancer, meningiomas, MALT lymphoma and in tumors in the brain). CXCR7 is also expressed in hepatocellular carcinoma, breast cancer, osteosarcoma, leukemia, gallbladder cancer, alveolar rhabdomyosarcoma, myeloma, non-small cell lung cancer, oral cancers and pancreas cancer (for review see Sun et al.; CXCL12/CXCR4/CXCR7 Chemokine Axis and Cancer Progression; Cancer Metastasis Rev. 2010, 29(4), 709-722).

CXCR7 silencing and targeting have been shown to reduce tumor growth in experimental disease models as single agents, or in combination with cytotoxic therapies [Wang et al.; The role of CXCR7/RDC1 as a chemokine Receptor for CXCL12/SDF-1 in prostate cancer; Journal of Biochemical Chemistry 2008, 293(7), 4283-4294; Ebsworth et al.; The effect of the CXCR7 inhibitor CCX662 on survival in the ENU rat model of gliobastoma; J Clin Oncol 2012, 30, (suppl; abstr e13580); Zheng et al.; Chemokine receptor CXCR7 regulates the invasion, angiogenesis and tumor growth of human hepatocellular carcinoma cells; Journal of Experimental and Clinical Cancer Research. 2010, 29: 31; Miao et al.; CXCR7 (RDC1) promotes breast and lung tumor growth in vivo and is expressed on tumor associated vasculature; PNAS 2007, 104(40), 15735-15740; Burns et al.; A novel chemokine receptor for SDF-1 and I-TAC involved in cell survival, cell adhesion, and tumor development; Journal of Experimental Medicine 2006, 203 (9), 2201-2213; Walters et al.; "Inhibition of CXCR7 extends survival following irradiation of brain tumours in mice and rats", British Journal of Cancer (2014), 1-10|doi: 10.1038/bjc.2013.830], including among others hepatocellular carcinoma, Kaposi's sarcoma, T cell leukemia, lymphoma, lung carcinomas, breast cancer, rhabdomyosarcoma, prostate cancer, pancreatic cancer and glioblastoma; to alter tumor-associated blood vessels; to reduce tumor cell seeding; to reduce rheumatoid arthritis clinical scores; to decrease the clinical severity of experimental autoimmune encephalomyelitis; to attenuate chronic hypoxia induced pulmonary hypertension, to induce anxiolytic-like behaviour, to trigger an angiocrine response to initiate liver regeneration and resolve fibrosis, and to improve beneficial effects of mesenchymal stem cells based therapies for renal ischemia/reperfusion injury [Cruz-Orengo et al.; CXCR7 influences leukocyte entry into the CNS parenchyma by controlling abluminal CXCL12 abundance during autoimmunity; Journal of Experimental Medicine 2011, 208(2), 327-339; Sartina et al.; Antagonism of CXCR7 attenuates chronic hypoxia-induced pulmonary hypertension; Pediatric Research 2012, 71(6), 682-688; Watanabe et al.; Pathogenic role of CXCR7 in rheumatoid arthritis; Arthritis and Rheumatism 2010, 62(11), 3211-3220; Ding et al, Divergent angiocrine signals from vascular niche balance liver regeneration and fibrosis; Nature 2014; 505(7481):97-102; Ikeda et al, Modulation of Circadian Glucocorticoid Oscillation via Adrenal Opioid-CXCR7 Signaling Alters Emotional Behavior; Cell 2013, 155(6):1323-36].

Recent studies have provided increasing evidence that activation of the CXCL12 pathway is a potential mechanism of tumor resistance to both conventional therapies and biological agents via multiple complementary actions: (i) by directly promoting cancer cell survival, invasion, and the cancer stem and/or tumor-initiating cell phenotype; (ii) by recruiting "distal stroma" (i.e., myeloid bone marrow-derived cells) to indirectly facilitate tumor recurrence and metastasis; and (iii) by promoting angiogenesis directly or in a paracrine manner. Duda D G et al (*Clin Cancer Res;* 2011, 17(8); 2074-80) recently discussed preclinical and clinical data that support the potential use of anti-CXCL12 agents including CXCR7 modulators as sensitizers to currently available therapies in cancer treatments. Modulators of the CXCL12 pathway were described to lead to changes of tumor properties, by alterating the recruitment of immune and inflammatory infiltrating cells and by inhibiting vasculogenesis (Brown B J, *Semin Radiat Oncol;* 2013, 23(4); 281-7). Kioi et al (*J clin invest;* 2010, 120(3); 694-705) showed that pharmacologic inhibition of the CXCL12 pathway prevented the influx in tumors of some monocytes and the postirradiation development of functional tumor vasculature resulting in abrogation of tumor regrowth.

Specifically, the potential role of CXCR7 in brain tumors, malignant glioma and in glioblastoma multiforme is known from the literature. Modulators of the CXCL12 pathway including CXCR7 modulators have been mentioned as potential therapeutic agents for treating brain cancer in combination with chemotherapeutic agents or radiotherapy. For example, Hattermann et al (Cancer research, 2010, 70

(8):3299-3308) teach that CXCL12 "stimulation prevented camptothecin- and temozolomide-induced apoptosis and that a CXCR7 antagonist reduced the antiapoptotic effect of CXCL12". The authors concluded that "CXCR7 is a functional receptor for CXCL12 in astrocytomas/glioblastomas and mediates resistance to drug-induced apoptosis". Furthermore, Hattermann et al (Oncology reports, 27: 1348-1352, 2012) teach that "CXCL12 abrogates the antiproliferative effect of temozolomide". The authors also teach that this effect could be almost completely abolished by a CXCR7 specific antagonist, "indicating that the anti-apoptotic effect of CXCL12 is mainly mediated via CXCR7". Ebsworth et al (Neuro Oncol (2013) 15 (suppl 3):iii37-iii61. ET-023) teach that a CXCR7 antagonist significantly prolongs survival when administered in combination with radiotherapy in a rat model of glioblastoma. This finding is supported by another study by Ebsworth et al (J Clin Oncol 30, 2012 (suppl; abstr e13580) disclosing that in vivo inhibition of CXCR7 in concert with radiotherapy results in a significant extension of survival time in another rat model of glioblastoma. In addition, Liu S C et al (Neuro-Oncology 2014; 16(1):21-28) teach that inhibition of CXCL12 after irradiation inhibits tumor recurrence in autochronous brain tumors in rats. Liu S C et al (Neuro Oncol (2013) 15 (suppl 3):iii189-iii190. RB-002. doi: 10.1093/neuonc/not188) also teach that inhibition of CXCL12 in a brain metastasis model after irradiation produced a marked inhibition of tumor growth and prolongation of lifespan compared to irradiation alone. Calatozzolo C et al (Cancer Biology and Therapy 2011, 11:2, 1-12) teach in in vitro experiments that CXCR7 antagonists showed complete inhibition of glioma proliferation.

CXCR7 is also reported to be expressed in brain metastases (Salmaggi et al, Cancer Biology and therapy 2009, 8:17, 1-7). The authors concluded that the CXCL12/CXCR4/CXCR7 pathway could be an interesting target for further researches investigating the role of these molecules in invasion and proliferation of metastatic cells.

Furthermore, CXCL12 depletion sensitizes cancer cells to chemotherapy in vivo and CXCL12 treatment blocks colonic carcinoma metastasis. CXCR7 is also a receptor for CXCL11 (alias small inducible cytokine subfamily b, member 11; scyb11, alias interferon-gamma-inducible protein 9; ip9, alias small inducible cytokine subfamily b, member 9b; scyb9b) and therefore modulators of CXCR7 activity can also be used in indications with CXCL11-associated pathology. CXCR7 functions also as a receptor for the opioid peptide BAM22 and its related peptides (peptide E, peptides BAM12, BAM14, BAM18) and therefore modulators of CXCR7 activity possibly may also be used in indications with opioid peptides associated pathologies (Ikeda et al Cell 155, 1323-1336, Dec. 5, 2013). CXCR7 has also been shown to function as a scavenger receptor for CXCL12. Thus, CXCR7 targeting has been shown to alter CXCL12 local concentration leading to a deregulation of the CXCL12 concentration gradient. The biological properties of CXCR7 modulators thus include, but are not limited to, any physiological function and/or cellular function linked and/or controlled by CXCL12 (Duda et al.; CXCL12 (SDF1alpha)-CXCR4/CXCR7 pathway inhibition: an emerging sensitizer for anticancer therapies?; Clin. Cancer Res. 2011 17(8) 2074-2080; Naumann et al.; CXCR7 function as a scavenger for CXCL12 and CXCL11; Plos One 2010, 5(2)e9175).

CXCR7 modulation (using small molecules antagonizing CXCL12 binding on CXCR7, or anti-CXCR7 antibodies, or RNA interference techniques to silence CXCR7 expression), CXCL12 modulation of activity/expression, or CXCR7 expression may, thus, be associated with diseases and disorders including cancer, notably carcinomas, leukemias, adenocarcinomas, malignant gliomas, glioblastoma multiforme, brain metastases, multiple myelomas, renal clear cell carcinoma, prostate cancer, pancreatic adenocarcinoma, melanoma, metastatic melanoma, rhabdomyosarcoma, hepatocellular carcinoma, colon tumors, breast cancer, non-small cell lung cancer, oral tumors, adult T-cell leukemia, gallbladder cancer, brain tumors, esophageal cancer, Ewing's sarcoma, bladder cancer, meningiomas, lymphoma, viral-induced tumors, Burkitt's lymphoma, Hodgkin's lymphoma, MALT lymphoma, papillary thyroid carcinoma, cervical cancer, osteosarcoma, lymphoproliferative disease, Kaposi's sarcoma, and choriocarcinoma; primary intra-ocular B-cell lymphoma; inflammation; multiple sclerosis; renal allograft rejection; rheumatoid arthritis; auto-immune encephalomyelitis; demyelinating diseases; systemic lupus erythematosus; osteoarthritis; pulmonary vascular diseases; acute renal failure; ischemia; inflammatory bowel disease; injured central nervous system; HSCs transplantation; cerebral ischemia; pulmonary hypertension; Shiga-toxin-associated heomolytic uremic syndrome; preeclampsia; chronic rhinosinusitis; HIV/AIDS; atherosclerosis; acute lung injury; asthma; diseases involving CXCR7 and/or CXCL12 and/or CXCL11 mediated metastasis, chemotaxis, cell adhesion, trans-endothelial migration, cell proliferation and/or survival. Further disorders associated with CXCR7 modulation may include proliferative diabetic retinopathy, West Nile virus encephalitis, vascular injury and pulmonary fibrosis. Even further disorders associated with CXCR7 modulation may include hypertension; liver fibrosis; cirrhosis; acute coronary syndrome; stress-related disorders; and diseases involving opioid peptides.

WO2009/076404 discloses certain carboxamide compounds comprising a bicyclic ring, which are antagonists of the chemokine CCR2 receptor. WO1999/042456 and WO2002/046164 disclose certain tetrahydroisoquinoline compounds which are active as positive AMPA receptor modulators, respectively, as estrogen receptor-β ligands.

The present invention provides novel modulators of the CXCR7 receptor which act as CXCR7 receptor agonists and/or as functional antagonists, and may be useful for the prevention or treatment of diseases which respond to the activation of the CXCL12 receptors and/or CXCL11 receptors; including autoimmune disorders (e.g. rheumatoid arthritis, multiple sclerosis, inflammatory bowel disease, systemic lupus erythematosus, lupus nephritis, interstitial cystitis, celiac disease), inflammatory diseases (e.g. asthma, chronic obstructive pulmonary disorder, atherosclerosis, myocarditis, sarcoidosis), transplant rejection, hematopoietic stem cell transplantation, fibrosis (e.g. liver cirrhosis), and especially cancer.

1) A first aspect of the invention relates to compounds of the formula (I)

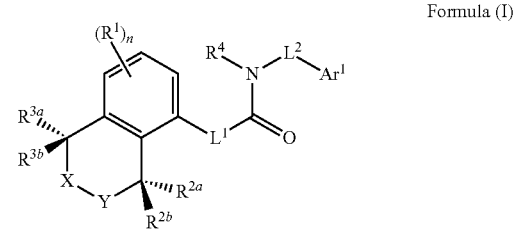

Formula (I)

wherein

X represents NR$^5$, and Y represents CHR$^Y$ wherein R$^Y$ represents hydrogen, or (C$_{1-3}$)alkyl (especially methyl); and R$^{3a}$ and R$^{3b}$ together with the carbon atom to which they are attached to form a carbonyl group, or two of R$^{2a}$, R$^{2b}$, R$^{3a}$ and R$^{3b}$ independently represent hydrogen, or (C$_{1-3}$)alkyl (especially methyl);

and the remaining of R$^{2a}$, R$^{2b}$, R$^{3a}$ and R$^{3b}$ represent hydrogen; or X represents CHR$^X$ wherein R$^X$ represents hydrogen, or (C$_{1-3}$)alkyl (especially methyl), and Y represents NR$^5$; and R$^{2a}$ and R$^{2b}$ together with the carbon atom to which they are attached to form a carbonyl group, or two of R$^{2a}$, R$^{2b}$, R$^{3a}$ and R$^{3b}$ independently represent hydrogen, or (C$_{1-3}$)alkyl (especially methyl);

and the remaining of R$^{2a}$, R$^{2b}$, R$^{3a}$ and R$^{3b}$ represent hydrogen; or X represents NR$^5$ and Y represents a direct bond; R$^{2a}$ and R$^{2b}$ both represent hydrogen; and R$^{3a}$ and R$^{3b}$ both represent hydrogen; or X represents NR$^5$, Y represents —C(O)—; and R$^{2a}$, R$^{2b}$ R$^{3a}$ and R$^{3b}$ all represent hydrogen; or X represents —C(O)—, Y represents NR$^5$; and R$^{2a}$, R$^{2b}$ R$^{3a}$ and R$^{3b}$ all represent hydrogen;

R$^5$ represents (C$_{1-6}$)alkyl;

(C$_{1-4}$)alkyl mono-substituted with (C$_{1-3}$)alkoxy, cyano, vinyl; ethynyl, or (C$_{1-3}$)alkoxy-carbonyl;

—CO—R$^{10}$ wherein R$^{10}$ represents (C$_{1-5}$)alkyl; (C$_{1-5}$)alkoxy; phenyl; phenyl-oxy-; phenyl-(C$_{1-3}$)alkyl-; phenyl-(C$_{1-3}$)alkyl-oxy-; (C$_{3-6}$)cycloalkyl-(C$_{1-3}$)alkyl; (C$_{3-4}$)alkenoxy; (C$_{3-4}$)alkynoxy; (C$_{1-3}$)fluoroalkyl; (C$_{1-3}$)fluoroalkoxy; (C$_{1-3}$)alkoxy-(C$_{2-3}$)alkoxy; (C$_{1-3}$)alkoxy-(C$_{1-3}$)alkyl; (C$_{3-5}$)cycloalkyl optionally containing one ring oxygen atom, wherein said cycloalkyl is optionally mono- or di-substituted wherein the substituents independently are fluoro or (C$_1$)fluoroalkyl; unsubstituted 5-membered heteroaryl (especially furanyl); or —NR$^{10a}$R$^{10b}$ wherein R$^{10a}$ and R$^{10b}$ independently represent hydrogen, (C$_{1-4}$)alkyl or (C$_{3-6}$)cycloalkyl, or R$^{10a}$ and R$^{10b}$ together with the nitrogen to which they are attached to form a 5- to 7-membered saturated ring;

—SO$_2$—R$^{11}$ wherein R$^{11}$ represents (C$_{1-5}$)alkyl or phenyl;

(C$_{2-4}$)fluroalkyl;

(C$_{3-6}$)cycloalkyl optionally containing one ring oxygen atom;

(C$_{3-6}$)cycloalkyl-(C$_{1-3}$)alkyl, wherein the (C$_{3-6}$)cycloalkyl group optionally contains one ring oxygen atom; wherein said cycloalkyl is optionally substituted with one or two methyl substituents;

phenyl-(C$_{0-3}$)alkyl-, or 5- or 6-membered heteroaryl-(C$_{0-3}$)alkyl-, wherein the phenyl or 5- or 6-membered heteroaryl independently is especially unsubstituted, or mono-, or di-substituted, wherein the substituents are independently selected from (C$_{1-4}$)alkyl (especially methyl), (C$_{1-4}$)alkoxy (especially methoxy), halogen, (C$_{1-3}$)fluoroalkyl (especially trifluoromethyl), (C$_{1-3}$)fluoroalkoxy (especially trifluoromethoxy), and cyano;

(R$^1$)$_n$ represents one or two optional substituents (i.e. n represents the integer 0, 1, or 2) independently selected from (C$_{1-4}$)alkyl (especially methyl), (C$_{1-4}$)alkoxy (especially methoxy), halogen, (C$_{1-3}$)fluoroalkyl (especially trifluoromethyl), (C$_{1-3}$)fluoroalkoxy (especially trifluoromethoxy), and cyano;

L$^1$ represents a one- or two-membered linker group selected from —NH—CH$_2$—*; —NR$^{16a}$—CH$_2$—* wherein R$^{16a}$ represents (C$_{1-3}$)alkyl (especially methyl or ethyl); —NH—CHR$^{16b}$—* wherein R$^{16b}$ represents (C$_{1-3}$)alkyl (especially methyl); —NH—CR$^{16c}$R$^{16d}$—* wherein R$^{16c}$ and R$^{16d}$ together with the carbon to which they are attached to form a (C$_{3-6}$)cycloalkyl (especially a cyclopropyl) ring; —CH$_2$—NH—*; —O—CH$_2$—*; —O—CHR$^{17a}$—* wherein R$^{17a}$ represents (C$_{1-3}$)alkyl (especially methyl); —O—CR$^{17b}$R$^{17c}$—* wherein R$^{17b}$ and R$^{17c}$ together with the carbon to which they are attached to form a (C$_{3-6}$)cycloalkyl (especially a cyclobutyl) ring; —CH$_2$—; —CH$_2$CH$_2$—; —CH=CH—; and —CH=C(CH$_3$)—*; wherein the asterisks indicate the bond with which the group L$^1$ is attached to the carbonyl group;

L$^2$ represents —(C$_{1-4}$)alkylene- or —(C$_{3-4}$)alkenylene- (especially a linker group selected from —CH$_2$—, —CH(CH$_3$)—, —CH$_2$—CH$_2$—, —CH$_2$—CH$_2$—CH$_2$—, *—CH$_2$—CH=CH—, and *—CH$_2$—C(CH$_3$)=CH—, wherein the asterisks indicate the bond with which the group L$^2$ is attached to the amide nitrogen atom);

Ar$^1$ represents phenyl, or 5- or 6-membered heteroaryl (especially pyridinyl); wherein said phenyl or 5- or 6-membered heteroaryl independently is unsubstituted, mono-, di- or tri-substituted, wherein the substituents are independently selected from (C$_{1-4}$)alkyl (especially methyl); (C$_{1-4}$)alkoxy (especially methoxy); (C$_{1-3}$)fluoroalkyl (especially trifluoromethyl); (C$_{1-3}$)fluoroalkoxy (especially trifluoromethoxy); halogen; cyano; or NR$^{18a}$R$^{18b}$ wherein R$^{18a}$ and R$^{18b}$ independently represent hydrogen or (C$_{1-3}$)alkyl (especially NR$^{18a}$R$^{18b}$ represents dimethylamino); and R$^4$ represents (C$_{2-6}$)alkyl;

(C$_{2-5}$)alkyl which is mono-substituted with (C$_{1-4}$)alkoxy, benzyloxy, cyano, or hydroxy; or disubstituted wherein the substituents are independently selected from (C$_{1-3}$)alkoxy, or hydroxy (C$_{2-3}$)fluoroalkyl which is optionally further substituted with one hydroxy;

—(C$_{2-4}$)alkylene-NR$^6$R$^7$, wherein R$^6$ and R$^7$ independently represent hydrogen; (C$_{1-4}$)alkyl; —CO—(C$_{1-4}$)alkoxy; (C$_{3-5}$)alkenyl; (C$_{3-4}$)alkynyl; benzyl; —SO$_2$—(C$_{1-3}$)alkyl; (C$_{2-3}$)fluoroalkyl; or (C$_{3-6}$)cycloalkyl or (C$_{3-6}$)cycloalkyl-(C$_{1-3}$)alkyl, wherein in the above groups the (C$_{3-6}$)cycloalkyl group optionally contains one ring oxygen atom, and wherein said (C$_{3-6}$)cycloalkyl group is optionally substituted with methyl;

—(C$_{1-3}$)alkylene-CO—R$^8$, wherein R$^8$ represents (C$_{1-4}$)alkoxy (especially ethoxy); or R$^8$ represents NR$^{81}$R$^{82}$ wherein R$^{81}$ and R$^{82}$ independently represent hydrogen or (C$_{1-4}$)alkyl, or R$^{81}$ and R$^{82}$ together with the nitrogen to which they are attached to form a 4- to 6-membered saturated ring optionally substituted with two fluoro substituents (especially such NR$^{81}$R$^{82}$ represents amino, 3,3-difluoroazetidinyl);

—(C$_{1-3}$)alkylene-SO$_2$—R$^9$ wherein R$^9$ represents (C$_{1-3}$)alkyl (especially methyl), or amino;

(C$_{3-6}$)cycloalkyl or (C$_{3-6}$)cycloalkyl-(C$_{1-3}$)alkyl, wherein the cycloalkyl group is optionally mono-substituted with —CO—(C$_{1-4}$)alkoxy or hydroxy;

(C$_{4-7}$)heterocyclyl or (C$_{4-7}$)heterocyclyl-(C$_{1-3}$)alkyl, wherein in the above groups the (C$_{4-7}$)heterocyclyl independently contains one or two ring heteroatoms independently selected from nitrogen, sulfur and oxygen; wherein in the above groups said (C$_{4-7}$)heterocyclyl independently is unsubstituted, or mono-, di-, or tri-substituted wherein the substituents are independently selected from:
one oxo substituent attached to a ring carbon atom in alpha position to a ring nitrogen (thus forming together with the nitrogen an amide group, or, in case a ring oxygen is additionally adjacent, a carbamate group, or, in case second ring nitrogen is additionally adjacent, a urea group); and/or
two methyl substituents attached to a ring carbon atom in alpha position to a ring nitrogen atom (thus forming together with the nitrogen a —C(CH$_3$)$_2$—N— group); and/or
two oxo substituents at a ring sulfur ring atom (thus forming a —SO$_2$— group); and/or
(C$_{1-4}$)alkyl (especially methyl) or —CO—(C$_{1-4}$)alkoxy attached to a ring nitrogen atom having a free valency; and/or
two fluoro substituents attached to a ring carbon atom; and/or
in case of a (C$_{4-7}$)heterocyclyl-(C$_{1-3}$)alkyl group, methyl attached to a ring carbon atom which is attached to the linking (C$_{1-3}$)alkyl group;
2-oxo-2,3-dihydropyridin-4-yl-(C$_{1-2}$)alkyl;
phenyl-(C$_{1-3}$)alkyl-, or 5- or 6-membered heteroaryl-(C$_{1-3}$)alkyl-, wherein the phenyl or 5- or 6-membered heteroaryl independently is unsubstituted, mono-, or di-substituted, wherein the substituents are independently selected from (C$_{1-4}$)alkyl (especially methyl, ethyl), (C$_{1-4}$)alkoxy (especially methoxy), halogen, (C$_{1-3}$)fluoroalkyl (especially trifluoromethyl), (C$_{1-3}$) fluoroalkoxy (especially trifluoromethoxy), and cyano.

The compounds of formula (I) may contain one or more stereogenic or asymmetric centers, such as one or more asymmetric carbon atoms. The compounds of formula (I) may thus be present as mixtures of stereoisomers or preferably as pure stereoisomers. Mixtures of stereoisomers may be separated in a manner known to a person skilled in the art.

The present invention also includes isotopically labelled, especially $^2$H (deuterium) labelled compounds of formula (I) according to embodiments 1) to 33), which compounds are identical to the compounds of formula (I) except that one or more atoms have each been replaced by an atom having the same atomic number but an atomic mass different from the atomic mass usually found in nature. Isotopically labelled, especially $^2$H (deuterium) labelled compounds of formula (I) and salts thereof are within the scope of the present invention. Substitution of hydrogen with the heavier isotope $^2$H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of formula (I) are not isotopically labelled, or they are labelled only with one or more deuterium atoms. In a sub-embodiment, the compounds of formula (I) are not isotopically labelled at all. Isotopically labelled compounds of formula (I) may be prepared in analogy to the methods described hereinafter, but using the appropriate isotopic variation of suitable reagents or starting materials.

In this patent application, a bond drawn as a dotted line shows the point of attachment of the radical drawn. For example, the radical drawn below

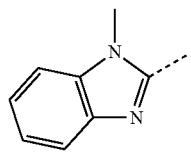

is the 1-methyl-1H-benzoimidazol-2-yl group.

Where the plural form is used for compounds, salts, pharmaceutical compositions, diseases and the like, this is intended to mean also a single compound, salt, or the like.

Any reference to compounds of formula (I) according to embodiments 1) to 33) is to be understood as referring also to the salts (and especially the pharmaceutically acceptable salts) of such compounds, as appropriate and expedient.

The term "pharmaceutically acceptable salts" refers to salts that retain the desired biological activity of the subject compound and exhibit minimal undesired toxicological effects. Such salts include inorganic or organic acid and/or base addition salts depending on the presence of basic and/or acidic groups in the subject compound. For reference see for example "Handbook of Pharmaceutical Salts. Properties, Selection and Use.", P. Heinrich Stahl, Camille G. Wermuth (Eds.), Wiley-VCH, 2008; and "Pharmaceutical Salts and Co-crystals", Johan Wouters and Luc Quere (Eds.), RSC Publishing, 2012.

Definitions provided herein are intended to apply uniformly to the compounds of formula (I), as defined in any one of embodiments 1) to 31), and, mutatis mutandis, throughout the description and the claims unless an otherwise expressly set out definition provides a broader or narrower definition. It is well understood that a definition or preferred definition of a term defines and may replace the respective term independently of (and in combination with) any definition or preferred definition of any or all other terms as defined herein.

The term "halogen" means fluorine, chlorine, or bromine, preferably fluorine or chlorine.

The term "alkyl", used alone or in combination, refers to a saturated straight or branched chain hydrocarbon group containing one to six carbon atoms. The term "(C$_{x-y}$)alkyl" (x and y each being an integer), refers to an alkyl group as defined before, containing x to y carbon atoms. For example a (C$_{1-6}$)alkyl group contains from one to six carbon atoms. Examples of alkyl groups are methyl, ethyl, propyl, isopropyl, butyl, isobutyl, tert.-butyl, 3-methyl-butyl, 2,2-dimethyl-propyl and 3,3-dimethyl-butyl. For avoidance of any doubt, in case a group is referred to as e.g. propyl or butyl, it is meant to be n-propyl, respectively n-butyl. Preferred are methyl and ethyl. Most preferred is methyl. Examples of (C$_{2-6}$)alkyl groups as used for R$^4$ are ethyl, 3-methyl-butyl and, in addition, 3,3-dimethyl-butyl. Examples of (C$_{1-6}$) alkyl groups as used for R$^5$ are methyl, ethyl, isopropyl, isobutyl, 2,2-dimethyl-propyl, 3,3-dimethyl-butyl, and, in addition, propyl, 1-methyl-propyl, and 1,2-dimethyl-propyl; preferred R$^5$ alkyl groups are ethyl, isobutyl and, in addition, propyl. Examples of (C$_{1-5}$)alkyl groups as used for R$^{10}$ are methyl, ethyl, isopropyl, isobutyl, and, in addition, propyl, tert.-butyl, and 2,2-dimethyl-propyl, preferred are methyl and ethyl.

Examples of substituted (C$_{2-5}$)alkyl groups as used for R$^4$ are 2-methoxy-ethyl, 2-hydroxy-ethyl, 2-cyano-ethyl, 2-benzyloxy-ethyl, 2-hydroxy-propyl, 2-hydroxy-2-methyl-propyl, 3-hydroxy-3-methyl-butyl, 2-methoxy-ethyl, and 2-hydroxy-3-methoxy-propyl; especially 2-hydroxy-3- methoxy-propyl and 2-hydroxy-2-methyl-propyl. Preferred are $(C_{2-4})$alkyl groups mono-substituted with hydroxy, such as especially 2-hydroxy-2-methyl-propyl.

The term "—$(C_{x-y})$alkylene-", used alone or in combination, refers to bivalently bound alkyl group as defined before containing x to y carbon atoms. Preferably, the points of attachment of a —$(C_{1-y})$alkylene group are in 1,1-diyl, in 1,2-diyl, or in 1,3-diyl arrangement. Preferably, the points of attachment of a —$(C_{2-y})$alkylene group are in 1,2-diyl or in 1,3-diyl arrangement. For the linker $L^2$, examples of —$(C_{1-4})$alkylene- groups are methylene, ethylene, ethane-1,1-diyl, and propylene. For the substituent —$(C_{2-4})$alkylene-$NR^6R^7$ as used for $R^4$ examples of —$(C_{2-4})$alkylene-groups are notably ethylene and propylene, preferred is ethylene.

Examples of —$(C_{1-3})$alkylene-CO—$R^8$ groups as used for $R^4$ are ethoxycarbonyl-methyl, 3-amino-3-oxopropyl, and, in addition, (3,3-difluoroazetidinyl)-3-oxo-propyl.

Examples of —$(C_{1-3})$alkylene-$SO_2$—$R^9$ groups as used for $R^4$ are 2-(methane-sulfonyl)-ethyl and 2-(sulfamoyl)-ethyl.

Examples of —$(C_{2-4})$alkylene-$NR^6R^7$ groups as used for $R^4$ are 2-amino-ethyl, 2-methylamino-ethyl, 2-dimethylamino-ethyl, 2-diethylamino-ethyl, 2-(butylmethylamino)-ethyl, 3-dimethylamino-propyl, and 2-[(tert.-butoxycarbonyl)-amino]-ethyl. In addition, further examples are 2-[(tert.-butoxycarbonyl)-methylamino]-ethyl, 2-[(tert.-butoxycarbonyl)-ethylamino]-ethyl, 2-ethylamino-ethyl, 2-(ethyl-methylamino)-ethyl, 2-(isopropyl-methylamino)-ethyl, 2-(diisopropylamino)-ethyl, 2-(allyl-methylamino)-ethyl, 2-(methyl-prop-2-ynyl-amino)-ethyl, 2-[(2-fluoro-ethyl)-methylamino]-ethyl, 2-[(2,2,2-trifluoroethyl)-amino]-ethyl, 2-[methyl-(2,2,2-trifluoroethyl)-amino]-ethyl, 2-[(2-fluoro-1-methylethyl)-methylamino]-ethyl, 2-methanesulfonylamino-ethyl, 2-[(cyclopropyl)-methylamino]-ethyl, 2-[(cyclopropylmethyl)-methylamino]-ethyl, 2-[(cyclobutyl)-methylamino]-ethyl, 2-[(cyclopentyl)-methylamino]-ethyl, 2-[methyl-(tetrahydrofuran-3-yl)-amino]-ethyl, 2-[ethyl-(3-methyl-oxetan-3-yl-methyl)-amino]-ethyl. Preferred are 2-methylamino-ethyl, 2-dimethylamino-ethyl, and 2-ethylamino-ethyl; especially 2-dimethylamino-ethyl.

The term "alkoxy", used alone or in combination, refers to an alkyl-O— group wherein the alkyl group is as defined before. The term "$(C_{x-y})$alkoxy" (x and y each being an integer) refers to an alkoxy group as defined before containing x to y carbon atoms. For example a $(C_{1-4})$alkoxy group means a group of the formula $(C_{1-4})$alkyl-O— in which the term "$(C_{1-4})$alkyl" has the previously given significance. Examples of alkoxy groups are methoxy, ethoxy, n-propoxy, isopropoxy, n-butoxy, isobutoxy, sec.-butoxy and tert.-butoxy. Preferred are ethoxy and especially methoxy. Examples of $(C_{1-5})$alkoxy groups as used for $R^{10}$ are methoxy, ethoxy, isopropoxy, isobutoxy, tert.-butoxy, 2,2-dimethyl-propoxy, and, in addition, propoxy.

The term "alkenyl", used alone or in combination, refers to a straight or branched hydrocarbon chain containing two to five carbon atoms and one carbon-carbon double bond. The term "$(C_{x-y})$alkenyl" (x and y each being an integer), refers to an alkenyl group as defined before containing x to y carbon atoms. For example a $(C_2-C_5)$alkenyl group contains from two to five carbon atoms. Examples of alkenyl groups are vinyl, prop-1-en-1-yl, 2-methylprop-1-en-1-yl, but-2-en-2-yl, buta-1,3-dien-1-yl, and especially allyl.

The term "alkynyl", used alone or in combination, refers to a straight or branched hydrocarbon chain containing two to five carbon atoms and one carbon-carbon triple bond. The term "$(C_{x-y})$alkynyl" (x and y each being an integer), refers to an alkynyl group as defined before containing x to y carbon atoms. For example a $(C_2-C_5)$alkynyl group contains from two to five carbon atoms. An example of an alkynyl group is prop-2-yn-1-yl.

The term "—$(C_{3-4})$alkenylene-", used alone or in combination, refers to bivalently bound alkenyl group as defined before containing three or four carbon atoms. Preferably, the points of attachment of any bivalently bound alkenyl group are in 1,3-diyl arrangement. For the linker $L^2$, examples of —$(C_{1-4})$alkenylene- groups are *—$CH_2$—CH=CH—, and *—$CH_2$—C($CH_3$)=CH—, wherein the asterisks indicate the bond with which the group $L^2$ is attached to the amide nitrogen atom.

The term "fluoroalkyl" refers to an alkyl group as defined before containing one to three carbon atoms in which one or more (and possibly all) hydrogen atoms have been replaced with fluorine. The term "$(C_{x-y})$fluoroalkyl" (x and y each being an integer) refers to a fluoroalkyl group as defined before containing x to y carbon atoms. For example a $(C_{1-3})$fluoroalkyl group contains from one to three carbon atoms in which one to seven hydrogen atoms have been replaced with fluorine. Representative examples of fluoroalkyl groups include trifluoromethyl, 2-fluoroethyl, 2,2-difluoroethyl and 2,2,2-trifluoroethyl. Preferred are $(C_1)$ fluoroalkyl groups such as trifluoromethyl. Examples of $(C_{2-4})$fluoroalkyl groups as used for $R^5$ are 2,2,2-trifluoroethyl, and, in addition, 2-fluoroethyl and especially 3-fluoropropyl. An example of $(C_{1-3})$fluoroalkyl as used for the substituent $R^{10}$ is 1,1-difluoroethyl. Examples of optionally substituted $(C_{2-3})$fluoroalkyl groups as used for $R^4$ are 3,3,3-trifluoro-propyl and 2-hydroxy-3,3,3-trifluoro-propyl.

The term "fluoroalkoxy" refers to an alkoxy group as defined before containing one to three carbon atoms in which one or more (and possibly all) hydrogen atoms have been replaced with fluorine. The term "$(C_{x-y})$fluoroalkoxy" (x and y each being an integer) refers to a fluoroalkoxy group as defined before containing x to y carbon atoms. For example a $(C_{1-3})$fluoroalkoxy group contains from one to three carbon atoms in which one to seven hydrogen atoms have been replaced with fluorine. Representative examples of fluoroalkoxy groups include trifluoromethoxy, difluoromethoxy, 2-fluoroethoxy, 2,2-difluoroethoxy and 2,2,2-trifluoroethoxy. Preferred are $(C_1)$fluoroalkoxy groups such as trifluoromethoxy and difluoromethoxy.

The term "cyano" refers to a group —CN.

The term "cycloalkyl", used alone or in combination, refers to a saturated monocyclic hydrocarbon ring containing three to six carbon atoms. The term "$(C_{x-y})$cycloalkyl" (x and y each being an integer), refers to a cycloalkyl group as defined before containing x to y carbon atoms. For example a $(C_{3-6})$cycloalkyl group contains from three to six carbon atoms. Examples of cycloalkyl groups are cyclopropyl, cyclobutyl, cyclopentyl, cyclohexyl, and cycloheptyl. Preferred are cyclopropyl, cyclopentyl and cyclohexyl; especially cyclopropyl. Examples of $(C_{3-6})$cycloalkyl groups as used for the group $R^5$ are cyclobutyl and cyclopentyl; especially cyclobutyl. In case the $(C_{3-6})$cycloalkyl group as used for the group $R^4$ is optionally mono-substituted with —CO—$(C_{1-4})$alkoxy or hydroxy, an example is 4-hydroxy-cyclohexyl.

The term "$(C_{x-y})$cycloalkyl-$(C_{x-y})$alkyl" refers to a $(C_{x-y})$ cycloalkyl group as defined before, which is linked through a $(C_{x-y})$alkylene group as defined before to the rest of the molecule. A particular example of such groups is cyclopropyl-methyl. Examples of $(C_{3-6})$cycloalkyl-$(C_{1-3})$alkyl groups as used for the group $R^5$ are cyclopropyl-methyl and cyclohexyl-methyl; preferred is cyclopropyl-methyl. An example of $(C_{3-6})$cycloalkyl-$(C_{1-3})$alkyl groups as used for the group $R^{10}$ is cyclohexyl-methyl. An example of $(C_{3-6})$cycloalkyl-$(C_{1-3})$alkyl groups as used for the group $R^4$ is cyclopropyl-methyl. In case the cycloalkyl of a $(C_{3-6})$cycloalkyl-$(C_{1-3})$alkyl group as used for the group $R^4$ is optionally mono-substituted with —CO—$(C_{1-4})$alkoxy or hydroxy, examples are (2-(ethoxycarbonyl)cyclopropyl) methyl and, especially (1-hydroxy-cyclopentyl)-methyl.

The term "cycloalkyl optionally containing one ring oxygen atom", used alone or in combination, refers to a cycloalkyl group as defined before. In addition, one ring carbon atom of said cycloalkyl may be replaced by an oxygen atom. Examples of such groups are especially cycloalkyl groups such as cyclopropyl, cyclobutyl, cyclopentyl, cyclohexyl, and cycloheptyl; as well as oxygen containing groups such as oxetanyl, tetrahydrofuranyl, and tetrahydro-2H-pyranyl. As used for the substituent $R^5$ (i.e. said cycloalkyl optionally containing one ring oxygen atom is attached to a nitrogen atom) a ring oxygen atom, if present, is preferably separated from said nitrogen atom by at least two ring carbon atoms. Examples of such groups as used for the substituent $R^5$ are especially cycloalkyl groups such as cyclobutyl and cyclopentyl; as well as oxetan-3-yl, and tetrahydrofuran-3-yl. Preferred is cyclobutyl. Examples of optionally substituted cycloalkyl optionally containing one ring oxygen atom as used for the group $R^{10}$ are cyclopropyl, cyclobutyl, 2-fluorocyclopropyl, 2,2-difluorocyclopropyl, 1-trifluoromethyl-cyclopropyl, and tetrahydrofuran-3-yl. Preferred are 2-fluorocyclopropyl, and 2,2-difluorocyclopropyl.

Examples of optionally substituted $(C_{3-6})$cycloalkyl-$(C_{1-3})$alkyl groups optionally containing one ring oxygen atom as used for the substituent $R^5$ are cyclopropyl-methyl, cyclobutylmethyl, cyclohexyl-methyl, 1-cyclopropyl-ethyl, and (3-methyl-oxetan-3-yl)-methyl; notably unsubstituted $(C_{3-6})$cycloalkyl-$(C_{1-3})$alkyl groups as defined herein above, such as especially cyclopropyl-methyl, and cyclobutylmethyl.

The term "heterocyclyl", used alone or in combination and if not explicitly defined in a more narrow way, refers to a saturated monocyclic hydrocarbon ring containing one or two (especially one) ring heteroatoms independently selected from nitrogen, oxygen and sulfur (especially one or two nitrogen atoms, or one nitrogen atom and one oxygen atom, or one sulfur atom). The term "$(C_{x-y})$heterocyclyl" refers to such a heterocyclyl group containing x to y ring atoms. Heterocyclyl groups are unsubstituted or substituted as explicitly defined. Examples of heterocyclyl groups as used for the group $R^4$ are pyrrolidin-3-yl, 1-methyl-pyrrolidin-3-yl, 1-(tert.-butoxycarbonyl)-pyrrolidin-3-yl, piperidin-3-yl, 1-methyl-piperidin-3-yl, piperidin-4-yl, 1-methyl-piperidin-4-yl, tetrahydro-pyran-4-yl, and 1,1-dioxo-tetrahydrothiophen-3-yl, and, in addition, 1-(tert.-butoxycarbonyl)-piperidin-4-yl. Preferred are 1-methyl-pyrrolidin-3-yl, 1-methyl-piperidin-3-yl, 1-methyl-piperidin-4-yl, and especially pyrrolidin-3-yl.

The term "$(C_{x-y})$ heterocyclyl-$(C_{x-y})$alkyl" refers to a $(C_{x-y})$heterocyclyl group as defined before, which is linked through a $(C_{x-y})$alkylene group as defined before to the rest of the molecule. For the $(C_{4-6})$heterocyclyl-$(C_{1-3})$alkyl groups as used for $R^4$ examples of —$(C_{1-3})$alkylene- groups are especially methylene, and ethylene. Examples of heterocyclyl groups part of such $(C_{4-6})$heterocyclyl-$(C_{1-3})$alkyl groups as used for the group $R^4$ are pyrrolidin-1-yl, 1-methyl-pyrrolidin-2-yl, 1-methyl-pyrrolidin-3-yl, 2-oxo-pyrrolidin-1-yl, 1-(tert.-butoxycarbonyl)-pyrrolidin-3-yl, 3-(tert.-butoxycarbonyl)-2,2-dimethyl-oxazolidin-4-yl, 2-oxo-imidazolidin-1-yl, piperidin-1-yl, 1-methyl-piperidin-2-yl, 1-methyl-piperidin-3-yl, 1-methyl-piperidin-4-yl, morpholin-4-yl, and, in addition 3-methyl-oxetan-3-yl, pyrrolidin-3-yl, [1,4]dioxan-2-yl, piperazin-1-yl, azepan-1-yl, 3,3-difluoroazetidin-1-yl, 3,3-difluoropyrrolidin-1-yl, 3,3-difluoropiperdin-1-yl, 4,4-difluoropiperdin-1-yl, and 1-(tert.-butoxycarbonyl)-piperazin-4-yl. Particular examples of $(C_{4-6})$heterocyclyl-$(C_{1-3})$alkyl groups as used for $R^4$ are 2-(pyrrolidin-1-yl)-ethyl, 2-(2-oxo-imidazolidin-1-yl)-ethyl, 2-(1-methyl-pyrrolidin-2-yl)-ethyl, 2-(2-oxo-pyrrolidin-1-yl)-ethyl, 2-(morpholin-4-yl)-ethyl, and (3-(tert.-butoxycarbonyl)-2,2-dimethyl-oxazolidin-4-yl)-methyl, and, in addition, 3-methyl-oxetan-3-yl-methyl, pyrrolidin-3-yl-methyl, 3-(pyrrolidin-1-yl)-propyl, [1,4]dioxan-2-yl-methyl, 2-(piperazin-1-yl)-ethyl, 2-(piperidin-1-yl)-ethyl, 2-(azepan-1-yl)-ethyl, 2-(3,3-difluoroazetidin-1-yl)-ethyl, 2-(3,3-difluoropyrrolidin-1-yl)-ethyl, 2-(3,3-difluoropiperdin-1-yl)-ethyl, 2-(4,4-difluoropiperdin-1-yl)-ethyl, (1-(tert.-butoxycarbonyl)-pyrrolidin-3-yl)-methyl, 2-(1-(tert.-butoxycarbonyl)-piperazin-4-yl)-ethyl. Preferred are 2-(pyrrolidin-1-yl)-ethyl, 2-(morpholin-4-yl)-ethyl, [1,4]dioxan-2-yl-methyl, 2-(piperazin-1-yl)-ethyl, and 2-(4,4-difluoropiperdin-1-yl)-ethyl; especially 2-(pyrrolidin-1-yl)-ethyl.

The term "aryl", used alone or in combination, means phenyl or naphthyl, especially phenyl. The above-mentioned aryl groups are unsubstituted or substituted as explicitly defined.

Examples of the substituent $Ar^1$ representing phenyl are especially those which are unsubstituted or mono-, or di-substituted wherein the substituents are independently selected from $(C_{1-4})$alkyl; $(C_{1-4})$alkoxy; $(C_{1-3})$fluoroalkyl; $(C_{1-3})$fluoroalkoxy; halogen; and cyano. In a sub-embodiment, the substituents are independently selected from $(C_{1-4})$alkyl; $(C_{1-4})$alkoxy; $(C_{1-3})$fluoroalkyl; and halogen. Particular examples are phenyl, 2-fluoro-phenyl, 3-fluoro-phenyl, 4-fluoro-phenyl, 2,4-difluoro-phenyl, 2-chloro-phenyl, 3-chloro-phenyl, 4-chloro-phenyl, 2-chloro-4-fluoro-phenyl, 2-methyl-phenyl, 3-methyl-phenyl, 4-methyl-phenyl, 2,3-dimethyl-phenyl, 2-methoxy-phenyl, 3-methoxy-phenyl, 4-methoxy-phenyl, 3,4-dimethoxy-phenyl, 2-trifluoromethyl-phenyl, 3-trifluoromethyl-phenyl, 4-trifluoromethyl-phenyl, 4-fluoro-2-trifluoromethyl-phenyl, and, in addition, 2-bromo-phenyl, 3-bromo-phenyl, 4-bromo-phenyl, 2,6-difluoro-phenyl, 2-trifluoromethoxy-phenyl, 3-trifluoromethoxy-phenyl, and 4-trifluoromethoxy-phenyl. Preferred are 2-chloro-phenyl, 2-trifluoromethyl-phenyl, and 2-bromo-phenyl.

The term "aryl-$(C_{x-y})$alkyl-" refers to an aryl group as defined before; in the particular case of a "phenyl-$(C_{x-y})$alkyl-" group it refers to a phenyl group, which is linked to the rest of the molecule through a $(C_{x-y})$alkylene group as defined before (especially through a methylene or ethylene group). The aryl/phenyl group part of aryl/phenyl-$(C_{x-y})$alkyl- is unsubstituted or substituted as explicitly defined. Examples of phenyl-$(C_{0-3})$alkyl- groups as used for the substituent $R^5$ are benzyl, and phenyl-ethyl. Examples of phenyl-$(C_{1-3})$alkyl- groups as used for the substituent $R^4$ are benzyl, 2-trifluoromethyl-benzyl, and 2-(4-fluoro-phenyl)-ethyl.

The term "heteroaryl", used alone or in combination, means a 5- to 10-membered monocyclic or bicyclic aromatic ring containing one to a maximum of four heteroatoms, each independently selected from oxygen, nitrogen and sulfur. Examples of such heteroaryl groups are furanyl, oxazolyl, isoxazolyl, oxadiazolyl, thiophenyl, thiazolyl, isothiazolyl, thiadiazolyl, pyrrolyl, imidazolyl, pyrazolyl, triazolyl, pyridinyl, pyrimidinyl, pyridazinyl, pyrazinyl, indolyl, isoindolyl, benzofuranyl, isobenzofuranyl, benzothiophenyl, indazolyl, benzimidazolyl, benzoxazolyl, benzisoxazolyl, benzothiazolyl, benzoisothiazolyl, benzotriazolyl, benzoxadiazolyl, benzothiadiazolyl, quinolinyl, isoquinolinyl, naphthyridinyl, cinnolinyl, quinazolinyl, quinoxalinyl, phthalazinyl, pyrrolopyridinyl, pyrazolopyridinyl, pyrazolopyrimidinyl, pyrrolopyrazinyl, imidazopyridinyl, imidazopyridazinyl, and imidazothiazolyl. The above-mentioned heteroaryl groups are unsubstituted or substituted as explicitly defined. In case $Ar^1$ represents "5- or 6-membered heteroaryl", the term means the above-mentioned 5- or 6-membered groups. Notably, the term refers to 5-membered heteroaryl containing at least one nitrogen atom and optionally one further heteroatom selected from nitrogen, oxygen or sulfur; such as especially pyrazolyl, imidazolyl, or thiazolyl; or to 6-membered heteroaryl containing one or two nitrogen atoms; such as pyrimidinyl, pyrazinyl, or pyridinyl; especially pyridinyl. For the substituent $Ar^1$, such 5- or 6-membered heteroaryl group is unsubstituted or mono-, or di-substituted wherein the substituents are independently selected from $(C_{1-4})$alkyl; $(C_{1-4})$alkoxy; $(C_{1-3})$fluoroalkyl; $(C_{1-3})$fluoroalkoxy; halogen; and cyano. In a sub-embodiment, the substituents are independently selected from $(C_{1-4})$alkyl; $(C_{1-4})$alkoxy; $(C_{1-3})$fluoroalkyl; and halogen; especially $(C_{1-4})$alkyl; $(C_{1-3})$fluoroalkyl; and halogen. Examples are 1-methyl-imidazol-2-yl, 1-ethyl-1H-pyrazol-3-yl, 4-methyl-thiazol-2-yl, pyridin-2-yl, 3-chloro-pyridin-2-yl, 3-trifluoromethyl-pyridin-2-yl, 6-trifluoromethyl-pyridin-2-yl, and, in addition, thiazol-2-yl, isoxazol-5-yl, 5-methyl-isoxazol-3-yl, 1-methyl-1H-pyrazol-5-yl, pyrimidin-2-yl, pyrimidin-4-yl, pyridin-3-yl, pyridin-4-yl, 3-fluoro-pyridin-2-yl, 5-fluoro-pyridin-2-yl, 3-chloro-pyridin-5-yl, 5-chloro-pyridin-2-yl, 3-bromo-pyridin-2-yl, 3-bromo-pyridin-4-yl, 3-methyl-pyridin-2-yl, 5-methyl-pyridin-2-yl, 6-methyl-pyridin-2-yl, 2-dimethylamino-pyrimidin-5-yl, 5-(4-fluorophenyl-amino)-pyridin-2-yl; preferred are 3-chloro-pyridin-2-yl, 3-trifluoromethyl-pyridin-2-yl, 6-trifluoromethyl-pyridin-2-yl, 3-bromo-pyridin-2-yl, 3-methyl-pyridin-2-yl, 6-methyl-pyridin-2-yl.

The term "heteroaryl-$(C_{x-y})$alkyl-" refers to a heteroaryl group as defined before which is linked to the rest of the molecule through a $(C_{x-y})$alkylene group as defined before (especially through a methylene or ethylene group). The heteroaryl group part of heteroaryl-$(C_{x-y})$alkyl- is unsubstituted or substituted as explicitly defined. Especially it is unsubstituted or mono-substituted with $(C_{1-4})$alkyl. Examples of heteroaryl-$(C_{1-3})$alkyl- groups as used for the substituent $R^4$ are (1-methyl-imidazol-2-yl)-methyl, 1-(1-ethyl-1H-pyrazol-3-yl)-ethan-1-yl, (4-methyl-thiazol-2-yl)-methyl, (pyridin-2-yl)-methyl and, in addition, isoxazol-5-ylmethyl. Examples of heteroaryl-$(C_{0-3})$alkyl- groups as used for the substituent $R^5$ are furan-2-yl-methyl and especially the heteroaryl-$(C_0)$alkyl- groups thiazolyl, pyridinyl, pyrimidinyl; in particular 5-trifluoromethyl-thiazol-2-yl, pyridin-2-yl, and pyrimidin-2-yl.

Further embodiments of the invention are presented hereinafter:

2) A second embodiment relates to compounds according to embodiment 1), wherein

X represents $NR^5$, and Y represents $CHR^Y$ wherein $R^Y$ represents hydrogen, or $(C_{1-3})$alkyl (especially methyl); and $R^{3a}$ and $R^{3b}$ together with the carbon atom to which they are attached to form a carbonyl group, or two of $R^{2a}$, $R^{2b}$, $R^{3a}$ and $R^{3b}$ independently represent hydrogen, or $(C_{1-3})$alkyl (especially methyl);

and the remaining of $R^{2a}$, $R^{2b}$, $R^{3a}$ and $R^{3b}$ represent hydrogen; or X represents $CHR^X$ wherein $R^X$ represents hydrogen, or $(C_{1-3})$alkyl (especially methyl), and Y represents $NR^5$; and $R^{2a}$ and $R^{2b}$ together with the carbon atom to which they are attached to form a carbonyl group, or two of $R^{2a}$, $R^{2b}$, $R^{3a}$ and $R^{3b}$ independently represent hydrogen, or $(C_{1-3})$alkyl (especially methyl);

and the remaining of $R^{2a}$, $R^{2b}$, $R^{3a}$ and $R^{3b}$ represent hydrogen; or X represents $NR^5$, Y represents —C(O)—; and $R^{2a}$, $R^{2b}$ $R^{3a}$ and $R^{3b}$ all represent hydrogen; or X represents -C(O)—, Y represents $NR^5$; and $R^{2a}$, $R^{2b}$ $R^{3a}$ and $R^{3b}$ all represent hydrogen;

wherein in first sub-embodiment X represents $NR^5$, and in a second sub-embodiment Y represents $NR^5$, wherein $R^X$, $R^Y$, $R^{2a}$, $R^{2b}$ $R^{3a}$ and $R^{3b}$ are as defined above.

3) Another embodiment relates to compounds according to embodiment 1), wherein

X represents $NR^5$ and:

Y represents $CH_2$; and $R^{2a}$, $R^{2b}$ $R^{3a}$ and $R^{3b}$ represent hydrogen; or Y represents $CHR^Y$ wherein $R^Y$ represents $(C_{1-3})$alkyl (especially methyl); and $R^{2a}$, $R^{2b}$ $R^{3a}$ and $R^{3b}$ represent hydrogen; or Y represents $CH_2$; $R^{2a}$ and $R^{2b}$ both represent $(C_{1-3})$alkyl (especially methyl); and $R^{3a}$ and $R^{3b}$ both represent hydrogen; or Y represents $CH_2$; $R^{2a}$ and $R^{2b}$ both represent hydrogen; one of $R^{3a}$ and $R^{3b}$ represents $(C_{1-3})$alkyl (especially methyl), and the remaining of $R^{3a}$ and $R^{3b}$ represents hydrogen;

or Y represents $NR^5$ and:

X represents $CH_2$; and $R^{2a}$, $R^{2b}$ $R^{3a}$ and $R^{3b}$ represent hydrogen; or X represents $CHR^X$ wherein $R^X$ represents $(C_{1-3})$alkyl (especially methyl); and $R^{2a}$, $R^{2b}$ $R^{3a}$ and $R^{3b}$ represent hydrogen; or X represents $CH_2$; $R^{3a}$ and $R^{3b}$ both represent $(C_{1-3})$alkyl (especially methyl); and $R^{2a}$ and $R^{2b}$ both represent hydrogen; or X represents $CH_2$; $R^{3a}$ and $R^{3b}$ both represent hydrogen; one of $R^{2a}$ and $R^{2b}$ represents $(C_{1-3})$alkyl (especially methyl), and the remaining of $R^{2a}$ and $R^{2b}$ represents hydrogen;

wherein in first sub-embodiment X represents $NR^5$, and in a second sub-embodiment Y represents $NR^5$, wherein $R^X$, $R^Y$, $R^{2a}$, $R^{2b}$ $R^{3a}$ and $R^{3b}$ are as defined above.

4) Another embodiment relates to compounds according to embodiment 1), wherein

X represents $NR^5$ and

Y represents $CH_2$; and $R^{2a}$, $R^{2b}$ $R^{3a}$ and $R^{3b}$ represent hydrogen; or Y represents $CH_2$; $R^{2a}$ and $R^{2b}$ both represent $(C_{1-3})$ alkyl (especially methyl); and $R^{3a}$ and $R^{3b}$ both represent hydrogen; or Y represents $CH_2$; $R^{2a}$ and $R^{2b}$ both represent hydrogen; one of $R^{3a}$ and $R^{3b}$ represents $(C_{1-3})$alkyl (especially methyl), and the remaining of $R^{3a}$ and $R^{3b}$ represents hydrogen;

or Y represents $NR^5$ and:

X represents $CH_2$; and $R^{2a}$, $R^{2b}$ $R^{3a}$ and $R^{3b}$ represent hydrogen; or wherein in first sub-embodiment X represents $NR^5$, and in a second sub-embodiment Y represents $NR^5$, wherein $R^{2a}$, $R^{2b}$ $R^{3a}$ and $R^{3b}$ are as defined above.

5) Another embodiment relates to compounds according to any one of embodiments 1) to 4), wherein $R^5$ represents

- $(C_{1-6})$alkyl; [in particular methyl, ethyl, propyl, isopropyl, isobutyl, 1-methyl-propyl, 1,2-dimethyl-propyl, 2,2-dimethyl-propyl, 3,3-dimethyl-butyl];
- $(C_{1-4})$alkyl mono-substituted with $(C_{1-3})$alkoxy, cyano, vinyl; ethynyl; or $(C_{1-3})$alkoxy-carbonyl; [in particular allyl, prop-2-ynyl, cyanomethyl, 2-methoxy-ethyl, 2-methoxy-1-methyl-ethyl, methoxycarbonyl-methyl, ethoxycarbonyl-methyl];
- —CO—$R^{10}$ wherein $R^{10}$ represents $(C_{1-5})$alkyl; $(C_{1-5})$alkoxy; phenyl; phenyl-oxy-; phenyl-$(C_{1-3})$alkyl-; phenyl-$(C_{1-3})$alkyl-oxy-; $(C_{3-6})$cycloalkyl-$(C_{1-3})$alkyl; $(C_{3-4})$alkenoxy; $(C_{3-4})$alkynoxy; $(C_{1-3})$fluoroalkyl; $(C_{1-3})$fluoroalkoxy; $(C_{1-3})$alkoxy-$(C_{2-3})$alkoxy; $(C_{1-3})$alkoxy-$(C_{1-3})$alkyl; $(C_{3-6})$cycloalkyl optionally containing one ring oxygen atom, wherein said cycloalkyl is optionally mono- or di-substituted wherein the substituents independently are fluoro or $(C_1)$fluoroalkyl; unsubstituted 5-membered heteroaryl (especially furanyl); or —$NR^{10a}R^{10b}$ wherein $R^{10a}$ and $R^{10b}$ independently represent hydrogen, $(C_{1-4})$alkyl or $(C_{3-6})$cycloalkyl, or $R^{10a}$ and $R^{10b}$ together with the nitrogen to which they are attached to form a 5- to 7-membered saturated ring; [in particular such —CO—$R^{10}$ is methyl-carbonyl, ethyl-carbonyl, propyl-carbonyl, isopropyl-carbonyl, isobutyl-carbonyl, tert.-butyl-carbonyl, (2,2-dimethyl-propyl)-carbonyl, methoxymethyl-carbonyl, cyclopropyl-carbonyl, cyclobutyl-carbonyl, (2-fluorocyclopropyl)-carbonyl, (cyclohexyl-methyl)-carbonyl, (2,2-difluorocyclopropyl)-carbonyl, (1-trifluoromethyl-cyclopropyl)-carbonyl, (tetrahydrofuran-3-yl)-carbonyl, (1,1-difluoroethyl)-carbonyl, carbamoyl, methylcarbamoyl, ethylcarbamoyl, isopropylcarbamoyl, butyl-carbamoyl, tert.-butyl-carbamoyl, cyclohexyl-carbamoyl, dimethylcarbamoyl, (pyrrolidin-1-yl)-carbonyl, methoxycarbonyl, ethoxycarbonyl, propoxycarbonyl, isopropoxycarbonyl, isobutoxycarbonyl, tert.-butoxycarbonyl, (2,2-dimethyl-propoxy)-carbonyl, allyloxy-carbonyl, prop-2-ynyloxycarbonyl, (2-fluoro-ethoxy)-carbonyl, (2-methoxy-ethoxy)-carbonyl, furan-2-yl-carbonyl, benzoyl, phenoxy-carbonyl, benzyl-carbonyl, benzyloxy-carbonyl];
- —$SO_2$—$R^{11}$ wherein $R^{11}$ represents $(C_{1-5})$alkyl or phenyl; [in particular such —$SO_2$—$R^{11}$ is methylsulfonyl, ethylsulfonyl, phenylsulfonyl];
- $(C_{2-4})$fluroroalkyl; [in particular 2-fluoroethyl, 2,2,2-trifluoroethyl, 3-fluoropropyl];
- $(C_{3-6})$cycloalkyl optionally containing one ring oxygen atom; [in particular cyclobutyl, oxetan-3-yl, cyclopentyl, tetrahydrofuran-3-yl];
- $(C_{3-6})$cycloalkyl-$(C_{1-3})$alkyl, wherein the $(C_{3-6})$cycloalkyl group optionally contains one ring oxygen atom; wherein said cycloalkyl is optionally substituted with one methyl substituent; [in particular such $(C_{3-6})$cycloalkyl-$(C_{1-3})$alkyl is cyclopropyl-methyl, cyclobutylmethyl, cyclohexyl-methyl, 1-cyclopropyl-ethyl, (3-methyl-oxetan-3-yl)-methyl];
- phenyl-$(C_{0-3})$alkyl-, or 5- or 6-membered heteroaryl-$(C_{0-3})$alkyl-, wherein the phenyl or 5- or 6-membered heteroaryl independently is unsubstituted, or mono-, or di-substituted, wherein the substituents are independently selected from $(C_{1-4})$alkyl (especially methyl), $(C_{1-4})$alkoxy (especially methoxy), halogen, $(C_{1-3})$fluoroalkyl (especially trifluoromethyl), $(C_{1-3})$fluoroalkoxy (especially trifluoromethoxy), and cyano [in particular unsubstituted phenyl-$(C_{1-2})$alkyl-; or thiazolyl, pyridinyl, or pyrimidinyl which are independently unsubstituted or mono-substituted with trifluoromethyl; especially benzyl or phenethyl; or 5-trifluoromethyl-thiazol-2-yl, pyridin-2-yl, or pyrimidin-2-yl];

6) Another embodiment relates to compounds according to any one of embodiments 1) to 4), wherein $R^5$ represents

- $(C_{1-6})$alkyl; [in particular methyl, ethyl, propyl, isopropyl, isobutyl, 1-methyl-propyl, 1,2-dimethyl-propyl, 2,2-dimethyl-propyl, 3,3-dimethyl-butyl; especially ethyl, propyl, or isobutyl];
- $(C_{1-4})$alkyl mono-substituted with $(C_{1-3})$alkoxy; [in particular 2-methoxy-ethyl];
- —CO—$R^{10}$ wherein $R^{10}$ represents $(C_{1-5})$alkyl; $(C_{1-5})$alkoxy; phenyl; phenyl-oxy-; phenyl-$(C_{1-3})$alkyl-; phenyl-$(C_{1-3})$alkyl-oxy-; $(C_{3-6})$cycloalkyl-$(C_{1-3})$alkyl; $(C_{3-4})$alkenoxy; $(C_{3-4})$alkynoxy; $(C_{1-3})$fluoroalkyl; $(C_{1-3})$fluoroalkoxy; $(C_{1-3})$alkoxy-$(C_{2-3})$alkoxy; $(C_{1-3})$alkoxy-$(C_{1-3})$alkyl; $(C_{3-6})$cycloalkyl optionally containing one ring oxygen atom, wherein said cycloalkyl is optionally mono- or di-substituted wherein the substituents independently are fluoro or $(C_1)$fluoroalkyl; or —$NR^{10a}R^{10b}$ wherein $R^{10a}$ and $R^{10b}$ independently represent hydrogen, $(C_{1-4})$alkyl or $(C_{3-6})$cycloalkyl, or $R^{10a}$ and $R^{10b}$ together with the nitrogen to which they are attached to form a 5- to 7-membered saturated ring; [in particular such —CO—$R^{10}$ is methyl-carbonyl, ethyl-carbonyl, propyl-carbonyl, isopropyl-carbonyl, isobutyl-carbonyl, tert.-butyl-carbonyl, (2,2-dimethyl-propyl)-carbonyl, methoxymethyl-carbonyl, cyclopropyl-carbonyl, cyclobutyl-carbonyl, (2-fluorocyclopropyl)-carbonyl, (cyclohexyl-methyl)-carbonyl, (2,2-difluorocyclopropyl)-carbonyl, (1-trifluoromethyl-cyclopropyl)-carbonyl, (tetrahydrofuran-3-yl)-carbonyl (1,1-difluoroethyl)-carbonyl, carbamoyl, methylcarbamoyl, ethylcarbamoyl, isopropylcarbamoyl, butyl-carbamoyl, tert.-butyl-carbamoyl, cyclohexyl-carbamoyl, dimethylcarbamoyl, (pyrrolidin-1-yl)-carbonyl, methoxycarbonyl, ethoxycarbonyl, propoxycarbonyl, isopropoxycarbonyl, isobutoxycarbonyl, tert.-butoxycarbonyl, (2,2-dimethyl-propoxy)-carbonyl, allyloxy-carbonyl, prop-2-ynyloxycarbonyl, (2-fluoro-ethoxy)-carbonyl, (2-methoxy-ethoxy)-carbonyl, furan-2-yl-carbonyl, benzoyl, phenoxy-carbonyl, benzyl-carbonyl, benzyloxy-carbonyl];
- —$SO_2$—$R^{11}$ wherein $R^{11}$ represents $(C_{1-5})$alkyl or phenyl; [in particular such —$SO_2$—$R^{11}$ is methylsulfonyl, ethylsulfonyl, phenylsulfonyl];
- $(C_{2-4})$fluroroalkyl; [in particular 2-fluoroethyl, 2,2,2-trifluoroethyl, 3-fluoropropyl];
- $(C_{3-6})$cycloalkyl optionally containing one ring oxygen atom; [in particular cyclobutyl, oxetan-3-yl, cyclopentyl, tetrahydrofuran-3-yl];
- $(C_{3-6})$cycloalkyl-$(C_{1-3})$alkyl, wherein the $(C_{3-6})$cycloalkyl group optionally contains one ring oxygen atom; wherein said cycloalkyl is optionally substituted with one methyl substituent; [in particular such $(C_{3-6})$cycloalkyl-$(C_{1-3})$alkyl is cyclopropyl-methyl, cyclobutylmethyl, cyclohexyl-methyl, 1-cyclopropyl-ethyl, (3-methyl-oxetan-3-yl)-methyl];
- phenyl-$(C_{1-3})$alkyl-, wherein the phenyl is unsubstituted [in particular benzyl or phenethyl]; or
- 5- or 6-membered heteroaryl (especially thiazolyl, pyridinyl, pyrimidinyl) wherein the 5- or 6-membered heteroaryl is unsubstituted, or mono-, or di-substituted, wherein the substituents are independently selected from ($C_{1-4}$)alkyl (especially methyl), ($C_{1-4}$)alkoxy (especially methoxy), halogen, ($C_{1-3}$)fluoroalkyl (especially trifluoromethyl), ($C_{1-3}$)fluoroalkoxy (especially trifluoromethoxy), and cyano [in particular thiazolyl, pyridinyl, or pyrimidinyl which are independently unsubstituted or mono-substituted with trifluoromethyl; especially 5-trifluoromethyl-thiazol-2-yl, pyridin-2-yl, or pyrimidin-2-yl].

7) Another embodiment relates to compounds according to any one of embodiments 1) to 4), wherein $R^5$ represents
- ($C_{1-6}$)alkyl; [in particular methyl, ethyl, propyl, isopropyl, isobutyl, 1-methyl-propyl, 1,2-dimethyl-propyl, 2,2-dimethyl-propyl, 3,3-dimethyl-butyl; especially ethyl, propyl, or isobutyl];
- ($C_{1-4}$)alkyl mono-substituted with ($C_{1-3}$)alkoxy [in particular 2-methoxy-ethyl];
- —CO—$R^{10}$ wherein $R^{10}$ represents ($C_{1-5}$)alkyl; ($C_{1-3}$)alkoxy-($C_{1-3}$)alkyl; or ($C_{3-6}$)cycloalkyl optionally containing one ring oxygen atom, wherein said cycloalkyl is unsubstituted, or mono- or di-substituted with fluoro; [in particular such —CO—$R^{10}$ is methyl-carbonyl, ethyl-carbonyl, propyl-carbonyl, isopropyl-carbonyl, isobutyl-carbonyl, tert.-butyl-carbonyl, (2,2-dimethyl-propyl)-carbonyl, methoxymethyl-carbonyl, cyclopropyl-carbonyl, cyclobutyl-carbonyl, (2-fluorocyclopropyl)-carbonyl, (2,2-difluorocyclopropyl)-carbonyl, (tetrahydrofuran-3-yl)-carbonyl, (1,1-difluoroethyl)-carbonyl; especially methyl-carbonyl, ethyl-carbonyl, methoxymethyl-carbonyl, (2-fluorocyclopropyl)-carbonyl, or (2,2-difluorocyclopropyl)-carbonyl];
- ($C_{2-4}$)fluroalkyl; [in particular 2-fluoroethyl, 2,2,2-trifluoroethyl, 3-fluoropropyl; especially 3-fluoropropyl];
- ($C_{3-6}$)cycloalkyl optionally containing one ring oxygen atom; [in particular cyclobutyl, oxetan-3-yl, cyclopentyl, tetrahydrofuran-3-yl; especially cyclobutyl]; or
- ($C_{3-6}$)cycloalkyl-($C_{1-3}$)alkyl [in particular cyclopropylmethyl, cyclobutylmethyl, cyclohexyl-methyl, 1-cyclopropyl-ethyl; especially cyclopropyl-methyl, or cyclobutylmethyl].

8) Another embodiment relates to compounds according to any one of embodiments 1) to 7), wherein $(R^1)_n$ represents one optional substituent (i.e. n represents the integer 0, or 1) independently selected from ($C_{1-4}$)alkyl (especially methyl), ($C_{1-4}$)alkoxy (especially methoxy), halogen, ($C_{1-3}$)fluoroalkyl (especially trifluoromethyl), ($C_{1-3}$)fluoroalkoxy (especially trifluoromethoxy), and cyano; (especially $(R^1)_n$ is absent, or it represents one methyl, methoxy halogen, or trifluoromethyl substituent; preferably $(R^1)_n$ is absent).

9) Another embodiment relates to compounds according to any one of embodiments 1) to 8), wherein $L^1$ represents a two-membered linker group selected from —NH—CH$_2$—*, —NR$^{16a}$—CH$_2$—* wherein $R^{16a}$ represents ($C_{1-3}$)alkyl (especially methyl), —O—CH$_2$—*, —CH$_2$CH$_2$—, —CH=CH—, and —CH=C(CH$_3$)—*; wherein the asterisks indicate the bond with which the group $L^1$ is attached to the carbonyl group.

10) Another embodiment relates to compounds according to any one of embodiments 1) to 8), wherein $L^1$ represents a two-membered linker group selected from —NH—CH$_2$—*, —O—CH$_2$—*, —CH$_2$CH$_2$—, and —CH=CH— (notably $L^1$ represents —NH—CH$_2$—* or —CH$_2$CH$_2$—); wherein the asterisks indicate the bond with which the group $L^1$ is attached to the carbonyl group.

11) Another embodiment relates to compounds according to any one of embodiments 1) to 8), wherein $L^1$ represents —NH—CH$_2$—* or —CH$_2$CH$_2$—; wherein the asterisk indicates the bond with which the group $L^1$ is attached to the carbonyl group.

12) Another embodiment relates to compounds according to any one of embodiments 1) to 11), wherein $L^2$ represents a linker group selected from —CH$_2$—, —CH(CH$_3$)—, —CH$_2$—CH$_2$—, —CH$_2$—CH$_2$—CH$_2$—, *—CH$_2$—CH=CH—, and *—CH$_2$—C(CH$_3$)=CH—, wherein the asterisks indicate the bond with which the group $L^2$ is attached to the amide nitrogen atom.

13) Another embodiment relates to compounds according to any one of embodiments 1) to 11), wherein $L^2$ represents —($C_{1-3}$)alkylene- (notably a linker group selected from —CH$_2$—, —CH(CH$_3$)—, —CH$_2$-2CH—; especially —CH$_2$—).

14) Another embodiment relates to compounds according to any one of embodiments 1) to 11), wherein $L^2$ represents —CH$_2$—.

15) Another embodiment relates to compounds according to any one of embodiments 1) to 14), wherein $Ar^1$ represents phenyl, or 5- or 6-membered heteroaryl (especially pyridinyl); wherein said phenyl or 5- or 6-membered heteroaryl independently is unsubstituted, mono-, or di-substituted, wherein the substituents are independently selected from ($C_{1-4}$)alkyl (especially methyl); ($C_{1-4}$)alkoxy (especially methoxy); ($C_{1-3}$)fluoroalkyl (especially trifluoromethyl); ($C_{1-3}$)fluoroalkoxy (especially trifluoromethoxy); halogen; cyano; or NR$^{18a}$R$^{18b}$ wherein $R^{18a}$ and $R^{18b}$ independently represent ($C_{1-3}$)alkyl (especially NR$^{18a}$R$^{18b}$ represents dimethylamino); [in particular $Ar^1$ represents phenyl, 2-fluoro-phenyl, 3-fluoro-phenyl, 4-fluoro-phenyl, 2,4-difluoro-phenyl, 2-chloro-phenyl, 3-chloro-phenyl, 4-chloro-phenyl, 2-chloro-4-fluoro-phenyl, 2-methyl-phenyl, 3-methyl-phenyl, 4-methyl-phenyl, 2,3-dimethyl-phenyl, 2-methoxy-phenyl, 3-methoxy-phenyl, 4-methoxy-phenyl, 3,4-dimethoxy-phenyl, 2-trifluoromethyl-phenyl, 3-trifluoromethyl-phenyl, 4-trifluoromethyl-phenyl, 4-fluoro-2-trifluoromethyl-phenyl, 2-bromo-phenyl, 3-bromo-phenyl, 4-bromo-phenyl, 2,6-difluoro-phenyl, 2-trifluoromethoxy-phenyl, 3-trifluoromethoxy-phenyl, 4-trifluoromethoxy-phenyl; or $Ar^1$ represents 1-methyl-imidazol-2-yl, 1-ethyl-1H-pyrazol-3-yl, 4-methyl-thiazol-2-yl, pyridin-2-yl, 3-chloro-pyridin-2-yl, 3-trifluoromethyl-pyridin-2-yl, 6-trifluoromethyl-pyridin-2-yl, thiazol-2-yl, isoxazol-5-yl, 5-methyl-isoxazol-3-yl, 1-methyl-1H-pyrazol-5-yl, pyrimidin-2-yl, pyrimidin-4-yl, pyridin-3-yl, pyridin-4-yl, 3-fluoro-pyridin-2-yl, 5-fluoro-pyridin-2-yl, 3-chloro-pyridin-5-yl, 5-chloro-pyridin-2-yl, 3-bromo-pyridin-2-yl, 3-bromo-pyridin-4-yl, 3-methyl-pyridin-2-yl, 5-methyl-pyridin-2-yl, 6-methyl-pyridin-2-yl, 2-dimethylamino-pyrimidin-5-yl, 5-(4-fluorophenyl-amino)-pyridin-2-yl].

16) Another embodiment relates to compounds according to any one of embodiments 1) to 14), wherein $Ar^1$ represents
- phenyl which is unsubstituted, mono-, or di-substituted, wherein the substituents are independently selected from ($C_{1-4}$)alkyl; ($C_{1-4}$)alkoxy; ($C_{1-3}$)fluoroalkyl; ($C_{1-3}$)fluoroalkoxy; halogen; and cyano (especially mono-substituted with methyl; methoxy; trifluoromethyl, trifluoromethoxy; or halogen); [in particular such $Ar^1$ represents phenyl, 2-fluoro-phenyl, 3-fluoro-phenyl, 4-fluoro-phenyl, 2,4-difluoro-phenyl, 2-chloro-phenyl, 3-chloro-phenyl, 4-chloro-phenyl, 2-chloro-4-fluoro-phenyl, 2-methyl-phenyl, 3-methyl-phenyl, 4-methyl-phenyl, 2,3-dimethyl-phenyl, 2-methoxy-phenyl, 3-methoxy-phenyl, 4-methoxy-phenyl, 3,4-dimethoxy-phenyl, 2-trifluoromethyl-phenyl, 3-trifluoromethyl-phenyl, 4-trifluoromethyl-phenyl, 4-fluoro-2-trifluoromethyl-phenyl, 2-bromo-phenyl, 3-bromo-phenyl, 4-bromo-phenyl, 2,6-difluoro-phenyl, 2-trifluoromethoxy-phenyl, 3-trifluoromethoxy-phenyl, 4-trifluoromethoxy-phenyl; especially 2-chloro-phenyl, 2-bromo-phenyl, 2-trifluoromethyl-phenyl]; or 6-membered heteroaryl (in particular pyridinyl); which is unsubstituted, mono-, or di-substituted, wherein the substituents are independently selected from $(C_{1-4})$alkyl; $(C_{1-4})$alkoxy; $(C_{1-3})$fluoroalkyl; $(C_{1-3})$fluoroalkoxy; halogen; and cyano (especially mono-substituted with methyl, trifluoromethyl or halogen); [in particular such $Ar^1$ represents pyridin-2-yl, 3-chloro-pyridin-2-yl, 3-trifluoromethyl-pyridin-2-yl, 6-trifluoromethyl-pyridin-2-yl, pyrimidin-2-yl, pyrimidin-4-yl, pyridin-3-yl, pyridin-4-yl, 3-fluoro-pyridin-2-yl, 5-fluoro-pyridin-2-yl, 3-chloro-pyridin-5-yl, 5-chloro-pyridin-2-yl, 3-bromo-pyridin-2-yl, 3-bromo-pyridin-4-yl, 3-methyl-pyridin-2-yl, 5-methyl-pyridin-2-yl, 6-methyl-pyridin-2-yl, 2-dimethylamino-pyrimidin-5-yl, 5-(4-fluorophenyl-amino)-pyridin-2-yl; especially 3-chloro-pyridin-2-yl, 3-trifluoromethyl-pyridin-2-yl, 6-trifluoromethyl-pyridin-2-yl, 3-bromo-pyridin-2-yl, 6-methyl-pyridin-2-yl]; or 5-membered heteroaryl (in particular imidazolyl, pyrazolyl, thiazolyl or isoxazolyl); which is unsubstituted, mono-, or di-substituted, wherein the substituents are independently selected from $(C_{1-4})$alkyl; $(C_{1-4})$alkoxy; $(C_{1-3})$fluoroalkyl; $(C_{1-3})$fluoroalkoxy; halogen; and cyano (especially mono-substituted with $(C_{1-2})$alkyl); [in particular such $Ar^1$ represents 1-methyl-imidazol-2-yl, 1-ethyl-1H-pyrazol-3-yl, 4-methyl-thiazol-2-yl, thiazol-2-yl, isoxazol-5-yl, 5-methyl-isoxazol-3-yl, 1-methyl-1H-pyrazol-5-yl].

17) Another embodiment relates to compounds according to any one of embodiments 1) to 15), wherein $Ar^1$ represents phenyl which is unsubstituted, mono-, or di-substituted, wherein the substituents are independently selected from $(C_{1-4})$alkyl; $(C_{1-4})$alkoxy; $(C_{1-3})$fluoroalkyl; $(C_{1-3})$fluoroalkoxy; halogen; and cyano (especially mono-substituted with methyl; methoxy; trifluoromethyl, trifluoromethoxy; or halogen); [in particular such $Ar^1$ represents phenyl, 2-fluoro-phenyl, 3-fluoro-phenyl, 4-fluoro-phenyl, 2,4-difluoro-phenyl, 2-chloro-phenyl, 3-chloro-phenyl, 4-chloro-phenyl, 2-chloro-4-fluoro-phenyl, 2-methyl-phenyl, 3-methyl-phenyl, 4-methyl-phenyl, 2,3-dimethyl-phenyl, 2-methoxy-phenyl, 3-methoxy-phenyl, 4-methoxy-phenyl, 3,4-dimethoxy-phenyl, 2-trifluoromethyl-phenyl, 3-trifluoromethyl-phenyl, 4-trifluoromethyl-phenyl, 4-fluoro-2-trifluoromethyl-phenyl, 2-bromo-phenyl, 3-bromo-phenyl, 4-bromo-phenyl, 2,6-difluoro-phenyl, 2-trifluoromethoxy-phenyl, 3-trifluoromethoxy-phenyl, 4-trifluoromethoxy-phenyl; especially 2-chloro-phenyl, 2-bromo-phenyl, 2-trifluoromethyl-phenyl]; or 6-membered heteroaryl (in particular pyridinyl); which is unsubstituted, mono-, or di-substituted, wherein the substituents are independently selected from $(C_{1-4})$alkyl; $(C_{1-4})$alkoxy; $(C_{1-3})$fluoroalkyl; $(C_{1-3})$fluoroalkoxy; halogen; and cyano (especially mono-substituted with methyl, trifluoromethyl or halogen); [in particular such $Ar^1$ represents pyridin-2-yl, 3-chloro-pyridin-2-yl, 3-trifluoromethyl-pyridin-2-yl, 6-trifluoromethyl-pyridin-2-yl, pyrimidin-2-yl, pyrimidin-4-yl, pyridin-3-yl, pyridin-4-yl, 3-fluoro-pyridin-2-yl, 5-fluoro-pyridin-2-yl, 3-chloro-pyridin-5-yl, 5-chloro-pyridin-2-yl, 3-bromo-pyridin-2-yl, 3-bromo-pyridin-4-yl, 3-methyl-pyridin-2-yl, 5-methyl-pyridin-2-yl, 6-methyl-pyridin-2-yl, 2-dimethylamino-pyrimidin-5-yl, 5-(4-fluorophenyl-amino)-pyridin-2-yl; especially 3-chloro-pyridin-2-yl, 3-trifluoromethyl-pyridin-2-yl, 6-trifluoromethyl-pyridin-2-yl, 3-bromo-pyridin-2-yl, 3-methyl-pyridin-2-yl, 6-methyl-pyridin-2-yl].

18) Another embodiment relates to compounds according to any one of embodiments 1) to 17), wherein $R^4$ represents
- $(C_{2-5})$alkyl which is mono-substituted with $(C_{1-4})$alkoxy, benzyloxy, cyano, or hydroxy; or disubstituted wherein the substituents are independently selected from $(C_{1-3})$ alkoxy or hydroxy (especially mono-substituted with hydroxy; or disubstituted wherein the substituents are independently methoxy or hydroxy); [in particular such substituted $(C_{2-5})$alkyl is 2-methoxy-ethyl, 2-hydroxy-ethyl, 2-hydroxy-propyl, 2-hydroxy-2-methyl-propyl, 3-hydroxy-3-methyl-butyl, 2-methoxy-ethyl, 2-hydroxy-3-methoxy-propyl];
- —$(C_{2-4})$alkylene-$NR^6R^7$, wherein $R^6$ and $R^7$ independently represent hydrogen; $(C_{1-4})$alkyl; $(C_{2-3})$fluoroalkyl; $(C_{3-6})$cycloalkyl; or $(C_{3-6})$cycloalkyl-$(C_{1-3})$alkyl; [in particular such —$(C_{2-4})$alkylene-$NR^6R^7$ is 2-amino-ethyl, 2-methylamino-ethyl, 2-dimethylamino-ethyl, 2-diethylamino-ethyl, 3-(dimethylamino)-propyl, 2-(butyl-methylamino)-ethyl, 2-ethylamino-ethyl, 2-(ethyl-methylamino)-ethyl, 2-(isopropyl-methylamino)-ethyl, 2-(diisopropylamino)-ethyl, 2-[(2-fluoroethyl)-methylamino]-ethyl, 2-[(2,2,2-trifluoroethyl)-amino]-ethyl, 2-[methyl-(2,2,2-trifluoroethyl)-amino]-ethyl, 2-[(2-fluoro-1-methyl-ethyl)-methylamino]-ethyl, 2-[(cyclopropyl)-methylamino]-ethyl, 2-[(cyclopropylmethyl)-methylamino]-ethyl, 2-[(cyclobutyl)-methylamino]-ethyl, 2-[(cyclopentyl)-methylamino]-ethyl];
- $(C_{3-6})$cycloalkyl optionally mono-substituted with hydroxy; [in particular cyclopropyl, or 4-hydroxy-cyclohexyl];
- $(C_{3-6})$cycloalkyl-$(C_{1-3})$alkyl, wherein the cycloalkyl group is optionally mono-substituted with —CO—$(C_{1-4})$alkoxy or hydroxy; [in particular cyclopropylmethyl, (1-hydroxy-cyclopentyl)-methyl, (2-(ethoxycarbonyl)-cyclopropyl)-methyl]; or
- $(C_{4-7})$heterocyclyl or $(C_{4-7})$heterocyclyl-$(C_{1-3})$alkyl, wherein in the above groups the $(C_{4-7})$heterocyclyl independently contains one or two ring heteroatoms independently selected from nitrogen and oxygen; wherein in the above groups said $(C_{4-7})$heterocyclyl independently is unsubstituted, or mono-, di-, or tri-substituted wherein the substituents are independently selected from:
  - one oxo substituent attached to a ring carbon atom in alpha position to a ring nitrogen (thus forming together with the nitrogen an amide group, or, in case a ring oxygen is additionally adjacent, a carbamate group, or, in case second ring nitrogen is additionally adjacent, a urea group); and/or
  - two methyl substituents attached to a ring carbon atom in alpha position to a ring nitrogen atom (thus forming together with the nitrogen a —$C(CH_3)_2$—N— group); and/or
  - $(C_{1-4})$alkyl (especially methyl) attached to a ring nitrogen atom having a free valency; and/or
  - two fluoro substituents attached to a ring carbon atom; and/or
  - in case of a $(C_{4-7})$heterocyclyl-$(C_{1-3})$alkyl group, methyl attached to a ring carbon atom which is attached to the linking $(C_{1-3})$alkyl group;

[in particular such $(C_{4-7})$heterocyclyl is pyrrolidin-3-yl, 1-methyl-pyrrolidin-3-yl, piperidin-3-yl, 1-methyl-piperidin-3-yl, piperidin-4-yl, 1-methyl-piperidin-4-yl, tetrahydro-pyran-4-yl; and such $(C_{4-7})$heterocyclyl-$(C_{1-3})$alkyl is 2-(pyrrolidin-1-yl)-ethyl, 2-(2-oxo-imidazolidin-1-yl)-ethyl, 2-(1-methyl-pyrrolidin-2-yl)-ethyl, 2-(2-oxo-pyrrolidin-1-yl)-ethyl, 2-(morpholin-4-yl)-ethyl, 3-methyl-oxetan-3-yl-methyl, pyrrolidin-3-yl-methyl, 3-(pyrrolidin-1-yl)-propyl, [1,4]dioxan-2-yl-methyl, 2-(piperazin-1-yl)-ethyl, 2-(piperidin-1-yl)-ethyl, 2-(azepan-1-yl)-ethyl, 2-(3,3-difluoroazetidin-1-yl)-ethyl, 2-(3,3-difluoropyrrolidin-1-yl)-ethyl, 2-(3,3-difluoropiperdin-1-yl)-ethyl, 2-(4,4-difluoropiperdin-1-yl)-ethyl].

19) Another embodiment relates to compounds according to any one of embodiments 1) to 17), wherein $R^4$ represents
- $(C_{2-5})$alkyl which is mono-substituted with hydroxy; or disubstituted wherein the substituents are independently methoxy or hydroxy; [in particular such substituted $(C_{2-5})$alkyl is 2-methoxy-ethyl, 2-hydroxy-ethyl, 2-hydroxy-propyl, 2-hydroxy-2-methyl-propyl, 3-hydroxy-3-methyl-butyl, 2-methoxy-ethyl, 2-hydroxy-3-methoxy-propyl];
- —$(C_{2-4})$alkylene-$NR^6R^7$, wherein $R^6$ represents hydrogen or $(C_{1-4})$alkyl (especially methyl); and $R^7$ represents $(C_{1-4})$alkyl; $(C_{2-3})$fluoroalkyl; $(C_{3-6})$cycloalkyl; or $(C_{3-6})$cycloalkyl-$(C_{1-3})$alkyl; [in particular such —$(C_{2-4})$alkylene-$NR^6R^7$ is 2-amino-ethyl, 2-methylamino-ethyl, 2-dimethylamino-ethyl, 2-diethylamino-ethyl, 3-(dimethylamino)-propyl, 2-(butyl-methyl-amino)-ethyl, 2-ethylamino-ethyl, 2-(ethyl-methylamino)-ethyl, 2-(isopropyl-methylamino)-ethyl, 2-(diisopropylamino)-ethyl, 2-[(2-fluoroethyl)-methylamino]-ethyl, 2-[(2,2,2-trifluoroethyl)-amino]-ethyl, 2-[methyl-(2,2,2-trifluoroethyl)-amino]-ethyl, 2-[(2-fluoro-1-methylethyl)-methylamino]-ethyl, 2-[(cyclopropyl)-methylamino]-ethyl, 2-[(cyclopropylmethyl)-methylamino]-ethyl, 2-[(cyclobutyl)-methylamino]-ethyl, 2-[(cyclopentyl)-methylamino]-ethyl];
- $(C_{3-6})$cycloalkyl-$(C_{1-3})$alkyl, wherein the cycloalkyl group is optionally mono-substituted with hydroxy; [in particular cyclopropyl-methyl, or (1-hydroxy-cyclopentyl)-methyl];
- $(C_{4-7})$heterocyclyl or $(C_{4-7})$heterocyclyl-$(C_{1-3})$alkyl, wherein in the above groups the $(C_{4-7})$heterocyclyl independently contains one or two ring heteroatoms independently selected from nitrogen and oxygen; wherein in the above groups said $(C_{4-7})$heterocyclyl independently is unsubstituted, or mono-, or di-substituted wherein the substituents are independently selected from:
  - one oxo substituent attached to a ring carbon atom in alpha position to a ring nitrogen (thus forming together with the nitrogen an amide group, or, in case a ring oxygen is additionally adjacent, a carbamate group, or, in case second ring nitrogen is additionally adjacent, a urea group); and/or
  - $(C_{1-4})$alkyl (especially methyl) attached to a ring nitrogen atom having a free valency; or
  - two fluoro substituents attached to a ring carbon atom;
  [in particular such $(C_{4-7})$heterocyclyl is pyrrolidin-3-yl, 1-methyl-pyrrolidin-3-yl, piperidin-3-yl, 1-methyl-piperidin-3-yl, piperidin-4-yl, 1-methyl-piperidin-4-yl, tetrahydro-pyran-4-yl; and such $(C_{4-7})$heterocyclyl-$(C_{1-3})$alkyl is 2-(pyrrolidin-1-yl)-ethyl, 2-(2-oxo-imidazolidin-1-yl)-ethyl, 2-(1-methyl-pyrrolidin-2-yl)-ethyl, 2-(2-oxo-pyrrolidin-1-yl)-ethyl, 2-(morpholin-4-yl)-ethyl, pyrrolidin-3-yl-methyl, 3-(pyrrolidin-1-yl)-propyl, [1,4]dioxan-2-yl-methyl, 2-(piperazin-1-yl)-ethyl, 2-(piperidin-1-yl)-ethyl, 2-(azepan-1-yl)-ethyl, 2-(3,3-difluoroazetidin-1-yl)-ethyl, 2-(3,3-difluoropyrrolidin-1-yl)-ethyl, 2-(3,3-difluoropiperdin-1-yl)-ethyl, 2-(4,4-difluoropiperdin-1-yl)-ethyl].

20) Another embodiment relates to compounds according to any one of embodiments 1) to 17), wherein $R^4$ represents
- $(C_{2-5})$alkyl which is mono-substituted with hydroxy (in particular 2-methoxy-ethyl, 2-hydroxy-ethyl, 2-hydroxy-propyl, 2-hydroxy-2-methyl-propyl, 3-hydroxy-3-methyl-butyl, 2-methoxy-ethyl, especially 2-hydroxy-2-methyl-propyl];
- $(C_{2-5})$alkyl which is disubstituted wherein the substituents are independently methoxy or hydroxy; [in particular 2-hydroxy-3-methoxy-propyl];
- —$(C_{2-4})$alkylene-$NR^6R^7$, wherein $R^6$ represents hydrogen or $(C_{1-4})$alkyl (especially methyl); and $R^7$ represents $(C_{1-4})$alkyl; $(C_{2-3})$fluoroalkyl; $(C_{3-6})$cycloalkyl; or $(C_{3-6})$cycloalkyl-$(C_{1-3})$alkyl; [in particular such —$(C_{2-4})$alkylene-$NR^6R^7$ is 2-amino-ethyl, 2-methylamino-ethyl, 2-dimethylamino-ethyl, 2-diethylamino-ethyl, 3-(dimethylamino)-propyl, 2-(butyl-methyl-amino)-ethyl, 2-ethylamino-ethyl, 2-(ethyl-methylamino)-ethyl, 2-(isopropyl-methylamino)-ethyl, 2-(diisopropylamino)-ethyl, 2-[(2-fluoroethyl)-methylamino]-ethyl, 2-[(2,2,2-trifluoroethyl)-amino]-ethyl, 2-[methyl-(2,2,2-trifluoroethyl)-amino]-ethyl, 2-[(2-fluoro-1-methylethyl)-methylamino]-ethyl, 2-[(cyclopropyl)-methylamino]-ethyl, 2-[(cyclopropylmethyl)-methylamino]-ethyl, 2-[(cyclobutyl)-methylamino]-ethyl, 2-[(cyclopentyl)-methylamino]-ethyl; especially 2-methylamino-ethyl, 2-dimethylamino-ethyl, or 2-ethylamino-ethyl];
- $(C_{3-6})$cycloalkyl-$(C_{1-3})$alkyl, wherein the cycloalkyl group is mono-substituted with hydroxy; [in particular (1-hydroxy-cyclopentyl)-methyl];
- $(C_{4-7})$heterocyclyl wherein the $(C_{4-7})$heterocyclyl contains one ring heteroatom selected from nitrogen or oxygen; wherein in the above groups said $(C_{4-7})$heterocyclyl independently is unsubstituted, or mono-substituted with $(C_{1-4})$alkyl (especially methyl) attached to a ring nitrogen atom having a free valency; [in particular pyrrolidin-3-yl, 1-methyl-pyrrolidin-3-yl, piperidin-3-yl, 1-methyl-piperidin-3-yl, piperidin-4-yl, 1-methyl-piperidin-4-yl, or tetrahydro-pyran-4-yl; especially pyrrolidin-3-yl];
- $(C_{4-7})$heterocyclyl-$(C_{1-3})$alkyl, wherein the $(C_{4-7})$heterocyclyl contains one or two ring heteroatoms independently selected from nitrogen and oxygen; wherein in the above groups said $(C_{4-7})$heterocyclyl independently is unsubstituted, or mono-, or di-substituted wherein the substituents are selected from:
  - $(C_{1-4})$alkyl (especially methyl) attached to a ring nitrogen atom having a free valency; or
  - two fluoro substituents attached to a ring carbon atom;
  [in particular 2-(pyrrolidin-1-yl)-ethyl, 2-(1-methyl-pyrrolidin-2-yl)-ethyl, 2-(morpholin-4-yl)-ethyl, pyrrolidin-3-yl-methyl, 3-(pyrrolidin-1-yl)-propyl, [1,4]dioxan-2-yl-methyl, 2-(piperazin-1-yl)-ethyl, 2-(piperidin-1-yl)-ethyl, 2-(azepan-1-yl)-ethyl, 2-(3,3-difluoroazetidin-1-yl)-ethyl, 2-(3,3-difluoropyrrolidin-1-yl)-ethyl, 2-(3,3-difluoropiperdin-1-yl)-ethyl, or 2-(4,4-difluoropiperdin-1-yl)-ethyl; especially 2-(pyrrolidin-1-yl)-ethyl, 2-(morpholin-4-yl)-ethyl, pyrrolidin-3-yl-methyl, [1,4]dioxan-2-yl-methyl, 2-(piperazin-1-yl)-ethyl, 2-(4,4-difluoropiperdin-1-yl)-ethyl].

21) Another embodiment relates to compounds according to any one of embodiments 1) to 17), wherein $R^4$ represents 2-methoxy-ethyl, 2-hydroxy-ethyl, 2-hydroxy-propyl, 2-hydroxy-2-methyl-propyl, 3-hydroxy-3-methyl-butyl, or 2-methoxy-ethyl (especially 2-hydroxy-2-methyl-propyl);

2-hydroxy-3-methoxy-propyl;

—$(C_{2-4})$alkylene-$NR^6R^7$ selected from 2-amino-ethyl, 2-methylamino-ethyl, 2-dimethylamino-ethyl, 2-diethylamino-ethyl, 3-(dimethylamino)-propyl, 2-(butylmethylamino)-ethyl, 2-ethylamino-ethyl, 2-(ethylmethylamino)-ethyl, 2-(isopropyl-methylamino)-ethyl, 2-(diisopropylamino)-ethyl, 2-[(2-fluoroethyl)-methylamino]-ethyl, 2-[(2,2,2-trifluoroethyl)-amino]-ethyl, 2-[methyl-(2,2,2-trifluoroethyl)-amino]-ethyl, 2-[(2-fluoro-1-methylethyl)-methylamino]-ethyl, 2-[(cyclopropyl)-methylamino]-ethyl, 2-[(cyclopropylmethyl)-methylamino]-ethyl, 2-[(cyclobutyl)-methylamino]-ethyl, and 2-[(cyclopentyl)-methylamino]-ethyl; especially 2-methylamino-ethyl, 2-dimethylamino-ethyl, or 2-ethylamino-ethyl;

(1-hydroxy-cyclopentyl)-methyl;

$(C_{4-7})$heterocyclyl selected from pyrrolidin-3-yl, 1-methyl-pyrrolidin-3-yl, piperidin-3-yl, 1-methyl-piperidin-3-yl, piperidin-4-yl, 1-methyl-piperidin-4-yl, and tetrahydro-pyran-4-yl; especially pyrrolidin-3-yl;

$(C_{4-7})$heterocyclyl-$(C_{1-3})$alkyl selected from 2-(pyrrolidin-1-yl)-ethyl, 2-(1-methyl-pyrrolidin-2-yl)-ethyl, 2-(morpholin-4-yl)-ethyl, pyrrolidin-3-yl-methyl, 3-(pyrrolidin-1-yl)-propyl, [1,4]dioxan-2-yl-methyl, 2-(piperazin-1-yl)-ethyl, 2-(piperidin-1-yl)-ethyl, 2-(azepan-1-yl)-ethyl, 2-(3,3-difluoroazetidin-1-yl)-ethyl, 2-(3,3-difluoropyrrolidin-1-yl)-ethyl, 2-(3,3-difluoropiperdin-1-yl)-ethyl, and 2-(4,4-difluoropiperdin-1-yl)-ethyl; especially 2-(pyrrolidin-1-yl)-ethyl, 2-(morpholin-4-yl)-ethyl, pyrrolidin-3-yl-methyl, [1,4]dioxan-2-yl-methyl, 2-(piperazin-1-yl)-ethyl, or 2-(4,4-difluoropiperdin-1-yl)-ethyl.

22) The invention, thus, relates to compounds of the formula (I) as defined in embodiment 1), or to such compounds further limited by the characteristics of any one of embodiments 2) to 21), under consideration of their respective dependencies; to pharmaceutically acceptable salts thereof; and to the use of such compounds as medicaments especially in the treatment of disorders relating to a dysfunction of the CXCR7 receptor or its ligands as described herein below. For avoidance of any doubt, especially the following embodiments relating to the compounds of formula (I) are thus possible and intended and herewith specifically disclosed in individualized form:

1, 3+1, 4+1, 5+1, 5+3+1, 5+4+1, 6+1, 6+3+1, 6+4+1, 7+1, 7+3+1, 7+4+1, 8+1, 8+3+1, 8+4+1, 8+5+1, 8+5+3+1, 8+5+4+1, 8+6+1, 8+6+3+1, 8+6+4+1, 8+7+1, 8+7+3+1, 8+7+4+1, 10+1, 10+3+1, 10+4+1, 10+5+1, 10+5+3+1, 10+5+4+1, 10+6+1, 10+6+3+1, 10+6+4+1, 10+7+1, 10+7+3+1, 10+7+4+1, 10+8+1, 10+8+3+1, 10+8+4+1, 10+8+5+1, 10+8+5+3+1, 10+8+5+4+1, 10+8+6+1, 10+8+6+3+1, 10+8+6+4+1, 10+8+7+1, 10+8+7+3+1, 10+8+7+4+1, 13+1, 13+3+1, 13+4+1, 13+5+1, 13+5+3+1, 13+5+4+1, 13+6+1, 13+6+3+1, 13+6+4+1, 13+7+1, 13+7+3+1, 13+7+4+1, 13+8+1, 13+8+3+1, 13+8+4+1, 13+8+5+1, 13+8+5+3+1, 13+8+5+4+1, 13+8+6+1, 13+8+6+3+1, 13+8+6+4+1, 13+8+7+1, 13+8+7+3+1, 13+8+7+4+1, 13+10+1, 13+10+3+1, 13+10+4+1, 13+10+5+1, 13+10+5+3+1, 13+10+5+4+1, 13+10+6+1, 13+10+6+3+1, 13+10+6+4+1, 13+10+7+1, 13+10+7+3+1, 13+10+7+4+1, 13+10+8+1, 13+10+8+3+1, 13+10+8+4+1, 13+10+8+5+1, 13+10+8+5+3+1, 13+10+8+5+4+1, 13+10+8+6+1, 13+10+8+6+3+1, 13+10+8+6+4+1, 13+10+8+7+1, 13+10+8+7+3+1, 13+10+8+7+4+1, 17+1, 17+3+1, 17+4+1, 17+5+1, 17+5+3+1, 17+5+4+1, 17+6+1, 17+6+3+1, 17+6+4+1, 17+7+1, 17+7+3+1, 17+7+4+1, 17+8+1, 17+8+3+1, 17+8+4+1, 17+8+5+1, 17+8+5+3+1, 17+8+5+4+1, 17+8+6+1, 17+8+6+3+1, 17+8+6+4+1, 17+8+7+1, 17+8+7+3+1, 17+8+7+4+1, 17+10+1, 17+10+3+1, 17+10+4+1, 17+10+5+1, 17+10+5+3+1, 17+10+5+4+1, 17+10+6+1, 17+10+6+3+1, 17+10+6+4+1, 17+10+7+1, 17+10+7+3+1, 17+10+7+4+1, 17+10+8+1, 17+10+8+3+1, 17+10+8+4+1, 17+10+8+5+1, 17+10+8+5+3+1, 17+10+8+5+4+1, 17+10+8+6+1, 17+10+8+6+3+1, 17+10+8+6+4+1, 17+10+8+7+1, 17+10+8+7+3+1, 17+10+8+7+4+1, 17+13+1, 17+13+3+1, 17+13+4+1, 17+13+5+1, 17+13+5+3+1, 17+13+5+4+1, 17+13+6+1, 17+13+6+3+1, 17+13+6+4+1, 17+13+7+1, 17+13+7+3+1, 17+13+7+4+1, 17+13+8+1, 17+13+8+3+1, 17+13+8+4+1, 17+13+8+5+1, 17+13+8+5+3+1, 17+13+8+5+4+1, 17+13+8+6+1, 17+13+8+6+3+1, 17+13+8+6+4+1, 17+13+8+7+1, 17+13+8+7+3+1, 17+13+8+7+4+1, 17+13+10+1, 17+13+10+3+1, 17+13+10+4+1, 17+13+10+5+1, 17+13+10+5+3+1, 17+13+10+5+4+1, 17+13+10+6+1, 17+13+10+6+3+1, 17+13+10+6+4+1, 17+13+10+7+1, 17+13+10+7+3+1, 17+13+10+7+4+1, 17+13+10+8+1, 17+13+10+8+3+1, 17+13+10+8+4+1, 17+13+10+8+5+1, 17+13+10+8+5+3+1, 17+13+10+8+5+4+1, 17+13+10+8+6+1, 17+13+10+8+6+3+1, 17+13+10+8+6+4+1, 17+13+10+8+7+1, 17+13+10+8+7+3+1, 17+13+10+8+7+4+1, 19+1, 19+3+1, 19+4+1, 19+5+1, 19+5+3+1, 19+5+4+1, 19+6+1, 19+6+3+1, 19+6+4+1, 19+7+1, 19+7+3+1, 19+7+4+1, 19+8+1, 19+8+3+1, 19+8+4+1, 19+8+5+1, 19+8+5+3+1, 19+8+5+4+1, 19+8+6+1, 19+8+6+3+1, 19+8+6+4+1, 19+8+7+1, 19+8+7+3+1, 19+8+7+4+1, 19+10+1, 19+10+3+1, 19+10+4+1, 19+10+5+1, 19+10+5+3+1, 19+10+5+4+1, 19+10+6+1, 19+10+6+3+1, 19+10+6+4+1, 19+10+7+1, 19+10+7+3+1, 19+10+7+4+1, 19+10+8+1, 19+10+8+3+1, 19+10+8+4+1, 19+10+8+5+1, 19+10+8+5+3+1, 19+10+8+5+4+1, 19+10+8+6+1, 19+10+8+6+3+1, 19+10+8+6+4+1, 19+10+8+7+1, 19+10+8+7+3+1, 19+10+8+7+4+1, 19+13+1, 19+13+3+1, 19+13+4+1, 19+13+5+1, 19+13+5+3+1, 19+13+5+4+1, 19+13+6+1, 19+13+6+3+1, 19+13+6+4+1, 19+13+7+1, 19+13+7+3+1, 19+13+7+4+1, 19+13+8+1, 19+13+8+3+1, 19+13+8+4+1, 19+13+8+5+1, 19+13+8+5+3+1, 19+13+8+5+4+1, 19+13+8+6+1, 19+13+8+6+3+1, 19+13+8+6+4+1, 19+13+8+7+1, 19+13+8+7+3+1, 19+13+8+7+4+1, 19+13+10+1, 19+13+10+3+1, 19+13+10+4+1, 19+13+10+5+1, 19+13+10+5+3+1, 19+13+10+5+4+1, 19+13+10+6+1, 19+13+10+6+3+1, 19+13+10+6+4+1, 19+13+10+7+1, 19+13+10+7+3+1, 19+13+10+7+4+1, 19+13+10+8+1, 19+13+10+8+3+1, 19+13+10+8+4+1, 19+13+10+8+5+1, 19+13+10+8+5+3+1, 19+13+10+8+5+4+1, 19+13+10+8+6+1, 19+13+10+8+6+3+1, 19+13+10+8+6+4+1, 19+13+10+8+7+1, 19+13+10+8+7+3+1, 19+13+10+8+7+4+1, 19+17+1, 19+17+3+1, 19+17+4+1, 19+17+5+1, 19+17+5+3+1, 19+17+5+4+1, 19+17+6+1, 19+17+6+3+1, 19+17+6+4+1, 19+17+7+1, 19+17+7+3+1, 19+17+7+4+1, 19+17+8+1, 19+17+8+3+1, 19+17+8+4+1, 19+17+8+5+1, 19+17+8+5+3+1, 19+17+8+5+4+1, 19+17+8+6+1, 19+17+8+6+3+1, 19+17+8+6+4+1, 19+17+8+7+1, 19+17+8+7+3+1, 19+17+8+7+4+1, 19+17+10+1, 19+17+10+3+1, 19+17+10+4+1, 19+17+10+5+1, 19+17+10+5+3+1, 19+17+10+5+4+1, 19+17+10+6+1, 19+17+10+6+3+1, 19+17+10+6+4+1, 19+17+10+7+1, 19+17+10+7+3+1, 19+17+10+7+4+1, 19+17+10+8+1, 19+17+10+8+3+1, 19+17+10+8+4+1, 19+17+10+8+5+1, 19+17+10+8+5+3+1, 19+17+10+8+5+4+1, 19+17+10+8+6+1, 19+17+10+8+6+3+1, 19+17+10+8+6+4+1, 19+17+10+8+7+1, 19+17+10+8+7+3+1, 19+17+10+8+7+4+1, 19+17+13+1, 19+17+13+

3+1, 19+17+13+4+1, 19+17+13+5+1, 19+17+13+5+3+1, 19+17+13+5+4+1, 19+17+13+6+1, 19+17+13+6+3+1, 19+17+13+6+4+1, 19+17+13+7+1, 19+17+13+7+3+1, 19+17+13+7+4+1, 19+17+13+8+1, 19+17+13+8+3+1, 19+17+13+8+4+1, 19+17+13+8+5+1, 19+17+13+8+5+3+1, 19+17+13+8+5+4+1, 19+17+13+8+6+1, 19+17+13+8+6+3+1, 19+17+13+8+6+4+1, 19+17+13+8+7+1, 19+17+13+8+7+3+1, 19+17+13+8+7+4+1, 19+17+13+10+1, 19+17+13+10+3+1, 19+17+13+10+4+1, 19+17+13+10+5+1, 19+17+13+10+5+3+1, 19+17+13+10+5+4+1, 19+17+13+10+6+1, 19+17+13+10+6+3+1, 19+17+13+10+6+4+1, 19+17+13+10+7+1, 19+17+13+10+7+3+1, 19+17+13+10+7+4+1, 19+17+13+10+8+1, 19+17+13+10+8+3+1, 19+17+13+10+8+4+1, 19+17+13+10+8+5+1, 19+17+13+10+8+5+3+1, 19+17+13+10+8+5+4+1, 19+17+13+10+8+6+1, 19+17+13+10+8+6+3+1, 19+17+13+10+8+6+4+1, 19+17+13+10+8+7+1, 19+17+13+10+8+7+3+1, 19+17+13+10+8+7+4+1, 21+1, 21+3+1, 21+4+1, 21+5+1, 21+5+3+1, 21+5+4+1, 21+6+1, 21+6+3+1, 21+6+4+1, 21+7+1, 21+7+3+1, 21+7+4+1, 21+8+1, 21+8+3+1, 21+8+4+1, 21+8+5+1, 21+8+5+3+1, 21+8+5+4+1, 21+8+6+1, 21+8+6+3+1, 21+8+6+4+1, 21+8+7+1, 21+8+7+3+1, 21+8+7+4+1, 21+10+1, 21+10+3+1, 21+10+4+1, 21+10+5+1, 21+10+5+3+1, 21+10+5+4+1, 21+10+6+1, 21+10+6+3+1, 21+10+6+4+1, 21+10+7+1, 21+10+7+3+1, 21+10+7+4+1, 21+10+8+1, 21+10+8+3+1, 21+10+8+4+1, 21+10+8+5+1, 21+10+8+5+3+1, 21+10+8+5+4+1, 21+10+8+6+1, 21+10+8+6+3+1, 21+10+8+6+4+1, 21+10+8+7+1, 21+10+8+7+3+1, 21+10+8+7+4+1, 21+13+1, 21+13+3+1, 21+13+4+1, 21+13+5+1, 21+13+5+3+1, 21+13+5+4+1, 21+13+6+1, 21+13+6+3+1, 21+13+6+4+1, 21+13+7+1, 21+13+7+3+1, 21+13+7+4+1, 21+13+8+1, 21+13+8+3+1, 21+13+8+4+1, 21+13+8+5+1, 21+13+8+5+3+1, 21+13+8+5+4+1, 21+13+8+6+1, 21+13+8+6+3+1, 21+13+8+6+4+1, 21+13+8+7+1, 21+13+8+7+3+1, 21+13+8+7+4+1, 21+13+10+1, 21+13+10+3+1, 21+13+10+4+1, 21+13+10+5+1, 21+13+10+5+3+1, 21+13+10+5+4+1, 21+13+10+6+1, 21+13+10+6+3+1, 21+13+10+6+4+1, 21+13+10+7+1, 21+13+10+7+3+1, 21+13+10+7+4+1, 21+13+10+8+1, 21+13+10+8+3+1, 21+13+10+8+4+1, 21+13+10+8+5+1, 21+13+10+8+5+3+1, 21+13+10+8+5+4+1, 21+13+10+8+6+1, 21+13+10+8+6+3+1, 21+13+10+8+6+4+1, 21+13+10+8+7+1, 21+13+10+8+7+3+1, 21+13+10+8+7+4+1, 21+17+1, 21+17+3+1, 21+17+4+1, 21+17+5+1, 21+17+5+3+1, 21+17+5+4+1, 21+17+6+1, 21+17+6+3+1, 21+17+6+4+1, 21+17+7+1, 21+17+7+3+1, 21+17+7+4+1, 21+17+8+1, 21+17+8+3+1, 21+17+8+4+1, 21+17+8+5+1, 21+17+8+5+3+1, 21+17+8+5+4+1, 21+17+8+6+1, 21+17+8+6+3+1, 21+17+8+6+4+1, 21+17+8+7+1, 21+17+8+7+3+1, 21+17+8+7+4+1, 21+17+10+1, 21+17+10+3+1, 21+17+10+4+1, 21+17+10+5+1, 21+17+10+5+3+1, 21+17+10+5+4+1, 21+17+10+6+1, 21+17+10+6+3+1, 21+17+10+6+4+1, 21+17+10+7+1, 21+17+10+7+3+1, 21+17+10+7+4+1, 21+17+10+8+1, 21+17+10+8+3+1, 21+17+10+8+4+1, 21+17+10+8+5+1, 21+17+10+8+5+3+1, 21+17+10+8+5+4+1, 21+17+10+8+6+1, 21+17+10+8+6+3+1, 21+17+10+8+6+4+1, 21+17+10+8+7+1, 21+17+10+8+7+3+1, 21+17+10+8+7+4+1, 21+17+13+1, 21+17+13+3+1, 21+17+13+4+1, 21+17+13+5+1, 21+17+13+5+3+1, 21+17+13+5+4+1, 21+17+13+6+1, 21+17+13+6+3+1, 21+17+13+6+4+1, 21+17+13+7+1, 21+17+13+7+3+1, 21+17+13+7+4+1, 21+17+13+8+1, 21+17+13+8+3+1, 21+17+13+8+4+1, 21+17+13+8+5+1, 21+17+13+8+5+3+1, 21+17+13+8+5+4+1, 21+17+13+8+6+1, 21+17+13+8+6+3+1, 21+17+13+8+6+4+1, 21+17+13+8+7+1, 21+17+13+8+7+3+1, 21+17+13+8+7+4+1, 21+17+13+10+1, 21+17+13+10+3+1, 21+17+13+10+4+1, 21+17+13+10+5+1, 21+17+13+10+5+3+1, 21+17+13+10+5+4+1, 21+17+13+10+6+1, 21+17+13+10+6+3+1, 21+17+13+10+6+4+1, 21+17+13+10+7+1, 21+17+13+10+7+3+1, 21+17+13+10+7+4+1, 21+17+13+10+8+1, 21+17+13+10+8+3+1, 21+17+13+10+8+4+1, 21+17+13+10+8+5+1, 21+17+13+10+8+5+3+1, 21+17+13+10+8+5+4+1, 21+17+13+10+8+6+1, 21+17+13+10+8+6+3+1, 21+17+13+10+8+6+4+1, 21+17+13+10+8+7+1, 21+17+13+10+8+7+3+1, 21+17+13+10+8+7+4+1.

In the list above the numbers refer to the embodiments according to their numbering provided hereinabove whereas "+" indicates the dependency from another embodiment. The different individualized embodiments are separated by commas. In other words, "17+13+4+1" for example refers to embodiment 17) depending on embodiment 13), depending on embodiment 4), depending on embodiment 1), i.e. embodiment "17+13+4+1" corresponds to the compounds of formula (I) according to embodiment 1) further limited by all the features of the embodiments 4), 13), and 17).

23) A second aspect of the invention relates to compounds of the formula (I) according to embodiment 1) which are also compounds of the formula (II)

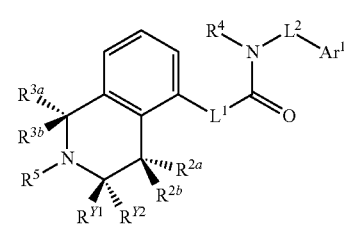

Formula (II)

wherein one of $R^{Y1}$ and $R^{Y2}$ represents hydrogen, or $(C_{1-3})$alkyl (especially methyl); and the other represents hydrogen; and $R^{3a}$ and $R^{3b}$ together with the carbon atom to which they are attached to form a carbonyl group, or two of $R^{2a}$, $R^{2b}$, $R^{3a}$ and $R^{3b}$ independently represent hydrogen, or $(C_{1-3})$alkyl (especially methyl);

and the remaining of $R^{2a}$, $R^{2b}$, $R^{3a}$ and $R^{3b}$ represent hydrogen; or $R^{Y1}$ and $R^{Y2}$ together with the carbon to which they are attached to form a carbonyl group; and $R^{2a}$, $R^{2b}$ $R^{3a}$ and $R^{3b}$ all represent hydrogen;

$R^5$ represents $(C_{1-6})$alkyl; [in particular such $(C_{1-6})$alkyl is methyl, ethyl, propyl, isopropyl, isobutyl, 1-methyl-propyl, 1,2-dimethyl-propyl, 2,2-dimethyl-propyl, 3,3-dimethyl-butyl];

$(C_{1-4})$alkyl mono-substituted with $(C_{1-3})$alkoxy, cyano, vinyl; ethynyl, or $(C_{1-3})$alkoxy-carbonyl; [in particular such mono-substituted $(C_{1-4})$alkyl is allyl, prop-2-ynyl, cyanomethyl, 2-methoxy-ethyl, 2-methoxy-1-methyl-ethyl, methoxycarbonyl-methyl, ethoxycarbonyl-methyl];

—CO—$R^{10}$ wherein $R^{10}$ represents $(C_{1-5})$alkyl; $(C_{1-5})$alkoxy; phenyl; phenyl-oxy-; phenyl-$(C_{1-3})$alkyl-; phenyl-$(C_{1-3})$alkyl-oxy-; $(C_{3-6})$cycloalkyl-$(C_{1-3})$alkyl; $(C_{3-4})$alkenoxy; $(C_{3-4})$alkynoxy; $(C_{1-3})$fluoroalkyl; $(C_{1-3})$fluoroalkoxy; $(C_{1-3})$alkoxy-$(C_{2-3})$alkoxy; $(C_{1-3})$alkoxy-$(C_{1-3})$alkyl; $(C_{3-6})$cycloalkyl optionally containing one ring oxygen atom, wherein said cycloalkyl is optionally mono- or di-substituted wherein the substituents independently are fluoro or $(C_1)$fluoroalkyl;

unsubstituted 5-membered heteroaryl (especially furanyl); or —NR$^{10a}$R$^{10b}$ wherein R$^{10a}$ and R$^{10b}$ independently represent hydrogen, (C$_{1-4}$)alkyl or (C$_{3-6}$)cycloalkyl, or R$^{10a}$ and R$^{10b}$ together with the nitrogen to which they are attached to form a 5- to 7-membered saturated ring; [in particular such —CO—R$^{10}$ is methyl-carbonyl, ethyl-carbonyl, propyl-carbonyl, isopropyl-carbonyl, isobutyl-carbonyl, tert.-butyl-carbonyl, (2,2-dimethyl-propyl)-carbonyl, methoxymethyl-carbonyl, cyclopropyl-carbonyl, cyclobutyl-carbonyl, (2-fluorocyclopropyl)-carbonyl, (cyclohexyl-methyl)-carbonyl, (2,2-difluorocyclopropyl)-carbonyl, (1-trifluoromethyl-cyclopropyl)-carbonyl, (tetrahydrofuran-3-yl)-carbonyl, (1,1-difluoroethyl)-carbonyl, carbamoyl, methylcarbamoyl, ethylcarbamoyl, isopropylcarbamoyl, butyl-carbamoyl, tert.-butyl-carbamoyl, cyclohexyl-carbamoyl, dimethylcarbamoyl, (pyrrolidin-1-yl)-carbonyl, methoxycarbonyl, ethoxycarbonyl, propoxycarbonyl, isopropoxycarbonyl, isobutoxycarbonyl, tert.-butoxycarbonyl, (2,2-dimethyl-propoxy)-carbonyl, allyloxy-carbonyl, prop-2-ynyloxycarbonyl, (2-fluoro-ethoxy)-carbonyl, (2-methoxy-ethoxy)-carbonyl, furan-2-yl-carbonyl, benzoyl, phenoxy-carbonyl, benzyl-carbonyl, benzyloxy-carbonyl];

—SO$_2$—R$^{11}$ wherein R$^{11}$ represents (C$_{1-5}$)alkyl or phenyl; [in particular such —SO$_2$—R$^{11}$ is methylsulfonyl, ethylsulfonyl, phenylsulfonyl];

(C$_{2-4}$)fluroalkyl; [in particular such (C$_{2-4}$)fluroalkyl is 2-fluoroethyl, 2,2,2-trifluoroethyl, 3-fluoropropyl];

(C$_{3-6}$)cycloalkyl optionally containing one ring oxygen atom; [in particular such (C$_{3-6}$)cycloalkyl is cyclobutyl, oxetan-3-yl, cyclopentyl, tetrahydrofuran-3-yl];

(C$_{3-6}$)cycloalkyl-(C$_{1-3}$)alkyl, wherein the (C$_{3-6}$)cycloalkyl group optionally contains one ring oxygen atom; wherein said cycloalkyl is optionally substituted with one or two methyl substituents; [in particular such (C$_{3-6}$)cycloalkyl-(C$_{1-3}$)alkyl is cyclopropyl-methyl, cyclobutylmethyl, cyclohexyl-methyl, 1-cyclopropyl-ethyl, (3-methyl-oxetan-3-yl)-methyl];

phenyl-(C$_{0-3}$)alkyl-, or 5- or 6-membered heteroaryl-(C$_{0-3}$)alkyl-, wherein the phenyl or 5- or 6-membered heteroaryl independently is especially unsubstituted, or mono-, or di-substituted, wherein the substituents are independently selected from (C$_{1-4}$)alkyl (especially methyl), (C$_{1-4}$)alkoxy (especially methoxy), halogen, (C$_{1-3}$)fluoroalkyl (especially trifluoromethyl), (C$_{1-3}$) fluoroalkoxy (especially trifluoromethoxy), and cyano;

(R$^1$)$_n$ represents one or two optional substituents (i.e. n represents the integer 0, 1, or 2) independently selected from (C$_{1-4}$)alkyl (especially methyl), (C$_{1-4}$)alkoxy (especially methoxy), halogen, (C$_{1-3}$)fluoroalkyl (especially trifluoromethyl), (C$_{1-3}$)fluoroalkoxy (especially trifluoromethoxy), and cyano;

L$^1$ represents a one- or two-membered linker group selected from —NH—CH$_2$—*; —NR$^{16a}$—CH$_2$—* wherein R$^{16a}$ represents (C$_{1-3}$)alkyl (especially methyl or ethyl); —NH—CHR$^{16b}$—* wherein R$^{16b}$ represents (C$_{1-3}$) alkyl (especially methyl); —NH—CR$^{16c}$R$^{16d}$—* wherein R$^{16c}$ and R$^{16d}$ together with the carbon to which they are attached to form a (C$_{3-6}$)cycloalkyl (especially a cyclopropyl) ring; —CH$_2$—NH—**; —O—CH$_2$—*; —O—CHR$^{17a}$—* wherein R$^{17a}$ represents (C$_{1-3}$)alkyl (especially methyl); —O—CR$^{17b}$R$^{17c}$—* wherein R$^{17b}$ and R$^{17c}$ together with the carbon to which they are attached to form a (C$_{3-6}$)cycloalkyl (especially a cyclobutyl) ring; —CH$_2$—; —CH$_2$CH$_2$—; —CH═CH—; and —CH═C (CH$_3$)—*; wherein the asterisks indicate the bond with which the group L$^1$ is attached to the carbonyl group;

L$^2$ represents —(C$_{1-4}$)alkylene- or —(C$_{3-4}$)alkenylene- (especially a linker group selected from —CH$_2$—, —CH (CH$_3$)—, —CH$_2$—CH$_2$—, —CH$_2$—CH$_2$—CH$_2$—, *—CH$_2$—CH═CH—, and *—CH$_2$—C(CH$_3$)═CH—, wherein the asterisks indicate the bond with which the group L$^2$ is attached to the amide nitrogen atom);

Ar$^1$ represents phenyl, or 5- or 6-membered heteroaryl (especially pyridinyl); wherein said phenyl or 5- or 6-membered heteroaryl independently is unsubstituted, mono-, di- or tri-substituted, wherein the substituents are independently selected from (C$_{1-4}$)alkyl (especially methyl); (C$_{1-4}$)alkoxy (especially methoxy); (C$_{1-3}$)fluoroalkyl (especially trifluoromethyl); (C$_{1-3}$)fluoroalkoxy (especially trifluoromethoxy); halogen; cyano; or NR$^{18a}$R$^{18b}$ wherein R$^{18a}$ and R$^{18b}$ independently represent hydrogen or (C$_{1-3}$)alkyl (especially NR$^{18a}$R$^{18b}$ represents dimethylamino); [in particular Ar$^1$ represents phenyl, 2-fluoro-phenyl, 3-fluoro-phenyl, 4-fluoro-phenyl, 2,4-difluoro-phenyl, 2-chloro-phenyl, 3-chloro-phenyl, 4-chloro-phenyl, 2-chloro-4-fluoro-phenyl, 2-methyl-phenyl, 3-methyl-phenyl, 4-methyl-phenyl, 2,3-dimethyl-phenyl, 2-methoxy-phenyl, 3-methoxy-phenyl, 4-methoxy-phenyl, 3,4-dimethoxy-phenyl, 2-trifluoromethyl-phenyl, 3-trifluoromethyl-phenyl, 4-trifluoromethyl-phenyl, 4-fluoro-2-trifluoromethyl-phenyl, 2-bromo-phenyl, 3-bromo-phenyl, 4-bromo-phenyl, 2,6-difluoro-phenyl, 2-trifluoromethoxy-phenyl, 3-trifluoromethoxy-phenyl, 4-trifluoromethoxy-phenyl; or Ar$^1$ represents 1-methyl-imidazol-2-yl, 1-ethyl-1H-pyrazol-3-yl, 4-methyl-thiazol-2-yl, pyridin-2-yl, 3-chloro-pyridin-2-yl, 3-trifluoromethyl-pyridin-2-yl, 6-trifluoromethyl-pyridin-2-yl, thiazol-2-yl, isoxazol-5-yl, 5-methyl-isoxazol-3-yl, 1-methyl-1H-pyrazol-5-yl, pyrimidin-2-yl, pyrimidin-4-yl, pyridin-3-yl, pyridin-4-yl, 3-fluoro-pyridin-2-yl, 5-fluoro-pyridin-2-yl, 3-chloro-pyridin-5-yl, 5-chloro-pyridin-2-yl, 3-bromo-pyridin-2-yl, 3-bromo-pyridin-4-yl, 3-methyl-pyridin-2-yl, 5-methyl-pyridin-2-yl, 6-methyl-pyridin-2-yl, 2-dimethylamino-pyrimidin-5-yl, 5-(4-fluorophenyl-amino)-pyridin-2-yl]; and R$^4$ represents (C$_{2-6}$)alkyl [in particular such (C$_{2-6}$)alkyl is ethyl, 3-methyl-butyl, 3,3-dimethyl-butyl];

(C$_{2-5}$)alkyl which is mono-substituted with (C$_{1-4}$)alkoxy, benzyloxy, cyano, or hydroxy; or disubstituted wherein the substituents are independently selected from (C$_{1-3}$) alkoxy, or hydroxy; [in particular such substituted (C$_{2-5}$)alkyl is 2-methoxy-ethyl, 2-hydroxy-ethyl, 2-cyano-ethyl, 2-benzyloxy-ethyl, 2-hydroxy-propyl, 2-hydroxy-2-methyl-propyl, 3-hydroxy-3-methyl-butyl, 2-methoxy-ethyl, 2-hydroxy-3-methoxy-propyl];

(C$_{2-3}$)fluoroalkyl which is optionally further substituted with one hydroxy; [in particular such (C$_{2-3}$)fluoroalkyl is 3,3,3-trifluoro-propyl, 2-hydroxy-3,3,3-trifluoro-propyl];

—(C$_{2-4}$)alkylene-NR$^6$R$^7$, wherein R$^6$ and R$^7$ independently represent hydrogen; (C$_{1-4}$)alkyl; —CO—(C$_{1-4}$) alkoxy; (C$_{3-5}$)alkenyl; (C$_{3-4}$)alkynyl; benzyl; —SO$_2$— (C$_{1-3}$)alkyl; (C$_{2-3}$)fluoroalkyl; or (C$_{3-6}$)cycloalkyl or (C$_{3-6}$)cycloalkyl-(C$_{1-3}$)alkyl, wherein in the above groups the (C$_{3-6}$)cycloalkyl group optionally contains one ring oxygen atom, and wherein said (C$_{3-6}$)cycloalkyl group is optionally substituted with methyl; [in particular such —(C$_{2-4}$)alkylene-NR$^6$R$^7$ is 2-amino-ethyl, 2-methylamino-ethyl, 2-dimethylamino-ethyl, 2-diethylamino-ethyl, 3-(dimethylamino)-propyl, 2-(butyl-methylamino)-ethyl, 2-[(tert.-butoxycarbonyl)-methylamino]-ethyl, 2-[(tert.-butoxycarbonyl)-amino]-ethyl, 2-[(tert.-butoxycarbonyl)-ethylamino]-ethyl, 2-ethylamino-ethyl, 2-(ethyl-methylamino)-ethyl, 2-(isopropyl-methylamino)-ethyl, 2-(diisopropylamino)-ethyl, 2-(allyl-methylamino)-ethyl, 2-(methyl-prop-2-ynyl-amino)-ethyl, 2-[(2-fluoroethyl)-methylamino]-ethyl, 2-[(2,2,2-trifluoroethyl)-amino]-ethyl, 2-[methyl-(2,2,2-trifluoroethyl)-amino]-ethyl, 2-[(2-fluoro-1-methylethyl)-methylamino]-ethyl, 2-methanesulfonylamino-ethyl, 2-[(cyclopropyl)-methylamino]-ethyl, 2-[(cyclopropylmethyl)-methyl-amino]-ethyl, 2-[(cyclobutyl)-methylamino]-ethyl, 2-[(cyclopentyl)-methylamino]-ethyl, 2-[methyl-(tetrahydrofuran-3-yl)-amino]-ethyl, 2-[ethyl-(3-methyl-oxetan-3-yl-methyl)-amino]-ethyl];

—$(C_{1-3})$alkylene-CO—$R^8$, wherein $R^8$ represents $(C_{1-4})$alkoxy (especially ethoxy); or $R^8$ represents $NR^{81}R^{82}$ wherein $R^{81}$ and $R^{82}$ independently represent hydrogen or $(C_{1-4})$alkyl, or $R^{81}$ and $R^{82}$ together with the nitrogen to which they are attached to form a 4- to 6-membered saturated ring optionally substituted with two fluoro substituents (especially such $NR^{81}R^{82}$ represents amino, 3,3-difluoroazetidinyl);

—$(C_{1-3})$alkylene-$SO_2$—$R^9$ wherein $R^9$ represents $(C_{1-3})$alkyl (especially methyl), or amino;

$(C_{3-6})$cycloalkyl or $(C_{3-6})$cycloalkyl-$(C_{1-3})$alkyl, wherein the cycloalkyl group is optionally mono-substituted with —CO—$(C_{1-4})$alkoxy or hydroxy; [in particular such $(C_{3-6})$cycloalkyl is cyclopropyl, 4-hydroxy-cyclohexyl; and such $(C_{3-6})$cycloalkyl-$(C_{1-3})$alkyl is cyclopropyl-methyl, (1-hydroxy-cyclopentyl)-methyl, (2-(ethoxycarbonyl)-cyclopropyl)-methyl];

$(C_{4-7})$heterocyclyl or $(C_{4-7})$heterocyclyl-$(C_{1-3})$alkyl, wherein in the above groups the $(C_{4-7})$heterocyclyl independently contains one or two ring heteroatoms independently selected from nitrogen, sulfur and oxygen; wherein in the above groups said $(C_{4-7})$heterocyclyl independently is unsubstituted, or mono-, di-, or tri-substituted wherein the substituents are independently selected from:

one oxo substituent attached to a ring carbon atom in alpha position to a ring nitrogen (thus forming together with the nitrogen an amide group, or, in case a ring oxygen is additionally adjacent, a carbamate group, or, in case second ring nitrogen is additionally adjacent, a urea group); and/or two methyl substituents attached to a ring carbon atom in alpha position to a ring nitrogen atom (thus forming together with the nitrogen a —$C(CH_3)_2$—N— group); and/or two oxo substituents at a ring sulfur ring atom (thus forming a —$SO_2$— group); and/or $(C_{1-4})$alkyl (especially methyl) or —CO—$(C_{1-4})$alkoxy attached to a ring nitrogen atom having a free valency; and/or two fluoro substituents attached to a ring carbon atom; and/or in case of a $(C_{4-7})$heterocyclyl-$(C_{1-3})$alkyl group, methyl attached to a ring carbon atom which is attached to the linking $(C_{1-3})$alkyl group;

[in particular such $(C_{4-7})$heterocyclyl is pyrrolidin-3-yl, 1-methyl-pyrrolidin-3-yl, 1-(tert.-butoxycarbonyl)-pyrrolidin-3-yl, piperidin-3-yl, 1-methyl-piperidin-3-yl, piperidin-4-yl, 1-methyl-piperidin-4-yl, tetrahydropyran-4-yl, 1,1-dioxo-tetrahydrothiophen-3-yl, 1-(tert.-butoxycarbonyl)-piperidin-4-yl; and such $(C_{4-7})$ heterocyclyl-$(C_{1-3})$alkyl is 2-(pyrrolidin-1-yl)-ethyl, 2-(2-oxo-imidazolidin-1-yl)-ethyl, 2-(1-methyl-pyrrolidin-2-yl)-ethyl, 2-(2-oxo-pyrrolidin-1-yl)-ethyl, 2-(morpholin-4-yl)-ethyl, (3-(tert.-butoxycarbonyl)-2,2-dimethyl-oxazolidin-4-yl)-methyl, 3-methyl-oxetan-3-yl-methyl, pyrrolidin-3-yl-methyl, 3-(pyrrolidin-1-yl)-propyl, [1,4]dioxan-2-yl-methyl, 2-(piperazin-1-yl)-ethyl, 2-(piperidin-1-yl)-ethyl, 2-(azepan-1-yl)-ethyl, 2-(3,3-difluoroazetidin-1-yl)-ethyl, 2-(3,3-difluoropyrrolidin-1-yl)-ethyl, 2-(3,3-difluoropiperdin-1-yl)-ethyl, 2-(4,4-difluoropiperdin-1-yl)-ethyl, (1-(tert.-butoxycarbonyl)-pyrrolidin-3-yl)-methyl, 2-(1-(tert.-butoxycarbonyl)-piperazin-4-yl)-ethyl];

2-oxo-2,3-dihydropyridin-4-yl-$(C_{1-2})$alkyl;

phenyl-$(C_{1-3})$alkyl-, or 5- or 6-membered heteroaryl-$(C_{1-3})$alkyl-, wherein the phenyl or 5- or 6-membered heteroaryl independently is unsubstituted, mono-, or di-substituted, wherein the substituents are independently selected from $(C_{1-4})$alkyl (especially methyl, ethyl), $(C_{1-4})$alkoxy (especially methoxy), halogen, $(C_{1-3})$fluoroalkyl (especially trifluoromethyl), $(C_{1-3})$fluoroalkoxy (especially trifluoromethoxy), and cyano;

wherein the characteristics disclosed in embodiments 2) to 22) are intended to apply mutatis mutandis also to the compounds formula (II) according to embodiment 23); wherein especially the following embodiments are thus possible and intended and herewith specifically disclosed in individualized form:

23, 23+7, 23+10, 23+10+7, 23+13, 23+13+7, 23+13+10, 23+13+10+7, 23+17, 23+17+7, 23+17, 23+17+13, 23+17+13+7, 23+17+13+10, 23+17+13+10+7, 23+19, 23+19+7, 23+19, 23+19+13, 23+19+13+7, 23+19+13+10, 23+19+13+10+7, 23+19+17, 23+19+17+7, 23+19+17, 23+19+17+13, 23+19+17+13+7, 23+19+17+13+10, 23+19+17+13+10+7, 23+21, 23+21+7, 23+21, 23+21+13, 23+21+13+7, 23+21+13+10, 23+21+13+10+7, 23+21+17, 23+21+17+7, 23+21+17, 23+21+17+13, 23+21+17+13+7, 23+21+17+13+10, 23+21+17+13+10+7.

In the list above the numbers refer to the embodiments according to their numbering provided hereinabove whereas "+" indicates the limitations as outlined above.

24) A third aspect of the invention relates to compounds of the formula (I) according to embodiment 1) which are also compounds of the formula (III)

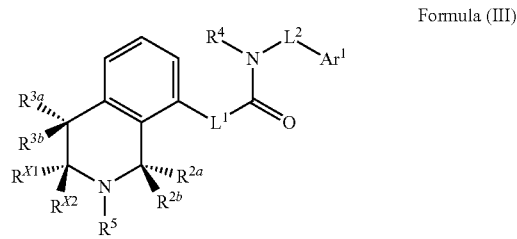

Formula (III)

wherein one of $R^{X1}$ and $R^{X2}$ represents hydrogen, or $(C_{1-3})$alkyl (especially methyl); and the other represents hydrogen; and $R^{3a}$ and $R^{3b}$ together with the carbon atom to which they are attached to form a carbonyl group, or two of $R^{2a}$, $R^{2b}$, $R^{3a}$ and $R^{3b}$ independently represent hydrogen, or $(C_{1-3})$alkyl (especially methyl);

and the remaining of $R^{2a}$, $R^{2b}$, $R^{3a}$ and $R^{3b}$ represent hydrogen; or $R^{X1}$ and $R^{X2}$ together with the carbon to which they are attached to form a carbonyl group; and $R^{2a}$, $R^{2b}$ $R^{3a}$ and $R^{3b}$ all represent hydrogen;

$R^5$ represents $(C_{1-6})$alkyl; [in particular such $(C_{1-6})$alkyl is methyl, ethyl, propyl, isopropyl, isobutyl, 1-methyl-propyl, 1,2-dimethyl-propyl, 2,2-dimethyl-propyl, 3,3-dimethyl-butyl];

$(C_{1-4})$alkyl mono-substituted with $(C_{1-3})$alkoxy, cyano, vinyl; ethynyl; or $(C_{1-3})$alkoxy-carbonyl; [in particular such mono-substituted $(C_{1-4})$alkyl is allyl, prop-2-ynyl, cyanomethyl, 2-methoxy-ethyl, 2-methoxy-1-methyl-ethyl, methoxycarbonyl-methyl, ethoxycarbonyl-methyl];

—CO—$R^{10}$ wherein $R^{10}$ represents $(C_{1-5})$alkyl; $(C_{1-5})$alkoxy; phenyl; phenyl-oxy-; phenyl-$(C_{1-3})$alkyl-; phenyl-$(C_{1-3})$alkyl-oxy-; $(C_{3-6})$cycloalkyl-$(C_{1-3})$alkyl; $(C_{3-4})$alkenoxy; $(C_{3-4})$alkynoxy; $(C_{1-3})$fluoroalkyl; $(C_{1-3})$fluoroalkoxy; $(C_{1-3})$alkoxy-$(C_{2-3})$alkoxy; $(C_{1-3})$alkoxy-$(C_{1-3})$alkyl; $(C_{3-6})$cycloalkyl optionally containing one ring oxygen atom, wherein said cycloalkyl is optionally mono- or di-substituted wherein the substituents independently are fluoro or $(C_1)$fluoroalkyl; unsubstituted 5-membered heteroaryl (especially furanyl); or —$NR^{10a}R^{10b}$ wherein $R^{10a}$ and $R^{10b}$ independently represent hydrogen, $(C_{1-4})$alkyl or $(C_{3-6})$cycloalkyl, or $R^{10a}$ and $R^{10b}$ together with the nitrogen to which they are attached to form a 5- to 7-membered saturated ring; [in particular such —CO—$R^{10}$ is methyl-carbonyl, ethyl-carbonyl, propyl-carbonyl, isopropyl-carbonyl, isobutyl-carbonyl, tert.-butyl-carbonyl, (2,2-dimethyl-propyl)-carbonyl, methoxymethyl-carbonyl, cyclopropyl-carbonyl, cyclobutyl-carbonyl, (2-fluorocyclopropyl)-carbonyl, (cyclohexyl-methyl)-carbonyl, (2,2-difluorocyclopropyl)-carbonyl, (1-trifluoromethyl-cyclopropyl)-carbonyl, (tetrahydrofuran-3-yl)-carbonyl, (1,1-difluoroethyl)-carbonyl, carbamoyl, methylcarbamoyl, ethylcarbamoyl, isopropylcarbamoyl, butyl-carbamoyl, tert.-butyl-carbamoyl, cyclohexyl-carbamoyl, dimethylcarbamoyl, (pyrrolidin-1-yl)-carbonyl, methoxycarbonyl, ethoxycarbonyl, propoxycarbonyl, isopropoxycarbonyl, isobutoxycarbonyl, tert.-butoxycarbonyl, (2,2-dimethyl-propoxy)-carbonyl, allyloxy-carbonyl, prop-2-ynyloxycarbonyl, (2-fluoro-ethoxy)-carbonyl, (2-methoxy-ethoxy)-carbonyl, furan-2-yl-carbonyl, benzoyl, phenoxy-carbonyl, benzyl-carbonyl, benzyloxy-carbonyl];

—$SO_2$—$R^{11}$ wherein $R^{11}$ represents $(C_{1-5})$alkyl or phenyl; [in particular such —$SO_2$—$R^{11}$ is methylsulfonyl, ethylsulfonyl, phenylsulfonyl];

$(C_{2-4})$fluroalkyl; [in particular such $(C_{2-4})$fluroalkyl is 2-fluoroethyl, 2,2,2-trifluoroethyl, 3-fluoropropyl];

$(C_{3-6})$cycloalkyl optionally containing one ring oxygen atom; [in particular such $(C_{3-6})$cycloalkyl is cyclobutyl, oxetan-3-yl, cyclopentyl, tetrahydrofuran-3-yl];

$(C_{3-6})$cycloalkyl-$(C_{1-3})$alkyl, wherein the $(C_{3-6})$cycloalkyl group optionally contains one ring oxygen atom; wherein said cycloalkyl is optionally substituted with one or two methyl substituents; [in particular such $(C_{3-6})$cycloalkyl-$(C_{1-3})$alkyl is cyclopropyl-methyl, cyclobutylmethyl, cyclohexyl-methyl, 1-cyclopropyl-ethyl, (3-methyl-oxetan-3-yl)-methyl];

phenyl-$(C_{0-3})$alkyl-, or 5- or 6-membered heteroaryl-$(C_{0-3})$alkyl-, wherein the phenyl or 5- or 6-membered heteroaryl independently is especially unsubstituted, or mono-, or di-substituted, wherein the substituents are independently selected from $(C_{1-4})$alkyl (especially methyl), $(C_{1-4})$alkoxy (especially methoxy), halogen, $(C_{1-3})$fluoroalkyl (especially trifluoromethyl), $(C_{1-3})$fluoroalkoxy (especially trifluoromethoxy), and cyano;

$(R^1)_n$ represents one or two optional substituents (i.e. n represents the integer 0, 1, or 2) independently selected from $(C_{1-4})$alkyl (especially methyl), $(C_{1-4})$alkoxy (especially methoxy), halogen, $(C_{1-3})$fluoroalkyl (especially trifluoromethyl), $(C_{1-3})$fluoroalkoxy (especially trifluoromethoxy), and cyano;

$L^1$ represents a one- or two-membered linker group selected from —NH—$CH_2$—*; —$NR^{16a}$—$CH_2$—* wherein $R^{16a}$ represents $(C_{1-3})$alkyl (especially methyl or ethyl); —NH—$CHR^{16b}$—* wherein $R^{16b}$ represents $(C_{1-3})$ alkyl (especially methyl); —NH—$CR^{16c}R^{16d}$—* wherein $R^{16c}$ and $R^{16d}$ together with the carbon to which they are attached to form a $(C_{3-6})$cycloalkyl (especially a cyclopropyl) ring; —$CH_2$—NH—**; —O—$CH_2$—*; —O—$CHR^{17a}$—* wherein $R^{17a}$ represents $(C_{1-3})$alkyl (especially methyl); —O—$CR^{17b}R^{17c}$—* wherein $R^{17b}$ and $R^{17c}$ together with the carbon to which they are attached to form a $(C_{3-6})$cycloalkyl (especially a cyclobutyl) ring; —$CH_2$—; —$CH_2CH_2$—; —CH=CH—; and —CH=C($CH_3$)—*; wherein the asterisks indicate the bond with which the group $L^1$ is attached to the carbonyl group;

$L^2$ represents —$(C_{1-4})$alkylene- or —$(C_{3-4})$alkenylene- (especially a linker group selected from —$CH_2$—, —CH($CH_3$)—, —$CH_2$—$CH_2$—, —$CH_2$—$CH_2$—$CH_2$—, *—$CH_2$—CH=CH—, and *—$CH_2$—C($CH_3$)=CH—, wherein the asterisks indicate the bond with which the group $L^2$ is attached to the amide nitrogen atom);

$Ar^1$ represents phenyl, or 5- or 6-membered heteroaryl (especially pyridinyl); wherein said phenyl or 5- or 6-membered heteroaryl independently is unsubstituted, mono-, di- or tri-substituted, wherein the substituents are independently selected from $(C_{1-4})$alkyl (especially methyl); $(C_{1-4})$alkoxy (especially methoxy); $(C_{1-3})$fluoroalkyl (especially trifluoromethyl); $(C_{1-3})$fluoroalkoxy (especially trifluoromethoxy); halogen; cyano; or $NR^{18a}R^{18b}$ wherein $R^{18a}$ and $R^{18b}$ independently represent hydrogen or $(C_{1-3})$alkyl (especially $NR^{18a}R^{18b}$ represents dimethylamino); [in particular $Ar^1$ represents phenyl, 2-fluoro-phenyl, 3-fluoro-phenyl, 4-fluoro-phenyl, 2,4-difluoro-phenyl, 2-chloro-phenyl, 3-chloro-phenyl, 4-chloro-phenyl, 2-chloro-4-fluoro-phenyl, 2-methyl-phenyl, 3-methyl-phenyl, 4-methyl-phenyl, 2,3-dimethyl-phenyl, 2-methoxy-phenyl, 3-methoxy-phenyl, 4-methoxy-phenyl, 3,4-dimethoxy-phenyl, 2-trifluoromethyl-phenyl, 3-trifluoromethyl-phenyl, 4-trifluoromethyl-phenyl, 4-fluoro-2-trifluoromethyl-phenyl, 2-bromo-phenyl, 3-bromo-phenyl, 4-bromo-phenyl, 2,6-difluoro-phenyl, 2-trifluoromethoxy-phenyl, 3-trifluoromethoxy-phenyl, 4-trifluoromethoxy-phenyl; or $Ar^1$ represents 1-methyl-imidazol-2-yl, 1-ethyl-1H-pyrazol-3-yl, 4-methyl-thiazol-2-yl, pyridin-2-yl, 3-chloro-pyridin-2-yl, 3-trifluoromethyl-pyridin-2-yl, 6-trifluoromethyl-pyridin-2-yl, thiazol-2-yl, isoxazol-5-yl, 5-methyl-isoxazol-3-yl, 1-methyl-1H-pyrazol-5-yl, pyrimidin-2-yl, pyrimidin-4-yl, pyridin-3-yl, pyridin-4-yl, 3-fluoro-pyridin-2-yl, 5-fluoro-pyridin-2-yl, 3-chloro-pyridin-5-yl, 5-chloro-pyridin-2-yl, 3-bromo-pyridin-2-yl, 3-bromo-pyridin-4-yl, 3-methyl-pyridin-2-yl, 5-methyl-pyridin-2-yl, 6-methyl-pyridin-2-yl, 2-dimethylamino-pyrimidin-5-yl, 5-(4-fluorophenyl-amino)-pyridin-2-yl]; and $R^4$ represents $(C_{2-6})$alkyl [in particular such $(C_{2-6})$alkyl is ethyl, 3-methyl-butyl, 3,3-dimethyl-butyl];

($C_{2-5}$)alkyl which is mono-substituted with ($C_{1-4}$)alkoxy, benzyloxy, cyano, or hydroxy; or disubstituted wherein the substituents are independently selected from ($C_{1-3}$) alkoxy, or hydroxy; [in particular such substituted ($C_{2-5}$)alkyl is 2-methoxy-ethyl, 2-hydroxy-ethyl, 2-cyano-ethyl, 2-benzyloxy-ethyl, 2-hydroxy-propyl, 2-hydroxy-2-methyl-propyl, 3-hydroxy-3-methyl-butyl, 2-methoxy-ethyl, 2-hydroxy-3-methoxy-propyl];

($C_{2-3}$)fluoroalkyl which is optionally further substituted with one hydroxy; [in particular such ($C_{2-3}$)fluoroalkyl is 3,3,3-trifluoro-propyl, 2-hydroxy-3,3,3-trifluoro-propyl];

—($C_{2-4}$)alkylene-$NR^6R^7$, wherein $R^6$ and $R^7$ independently represent hydrogen; ($C_{1-4}$)alkyl; —CO—($C_{1-4}$) alkoxy; ($C_{3-5}$)alkenyl; ($C_{3-4}$)alkynyl; benzyl; —$SO_2$—($C_{1-3}$)alkyl; ($C_{2-3}$)fluoroalkyl; or ($C_{3-6}$)cycloalkyl or ($C_{3-6}$)cycloalkyl-($C_{1-3}$)alkyl, wherein in the above groups the ($C_{3-6}$)cycloalkyl group optionally contains one ring oxygen atom, and wherein said ($C_{3-6}$)cycloalkyl group is optionally substituted with methyl; [in particular such —($C_{2-4}$)alkylene-$NR^6R^7$ is 2-amino-ethyl, 2-methylamino-ethyl, 2-dimethylamino-ethyl, 2-diethylamino-ethyl, 3-(dimethylamino)-propyl, 2-(butyl-methylamino)-ethyl, 2-[(tert.-butoxycarbonyl)-methylamino]-ethyl, 2-[(tert.-butoxycarbonyl)-amino]-ethyl, 2-[(tert.-butoxycarbonyl)-ethylamino]-ethyl, 2-ethylamino-ethyl, 2-(ethyl-methylamino)-ethyl, 2-(isopropyl-methylamino)-ethyl, 2-(diisopropylamino)-ethyl, 2-(allyl-methylamino)-ethyl, 2-(methyl-prop-2-ynyl-amino)-ethyl, 2-[(2-fluoroethyl)-methylamino]-ethyl, 2-[(2,2,2-trifluoroethyl)-amino]-ethyl, 2-[methyl-(2,2,2-trifluoroethyl)-amino]-ethyl, 2-[(2-fluoro-1-methylethyl)-methylamino]-ethyl, 2-methanesulfonylamino-ethyl, 2-[(cyclopropyl)-methylamino]-ethyl, 2-[(cyclopropylmethyl)-methyl-amino]-ethyl, 2-[(cyclobutyl)-methylamino]-ethyl, 2-[(cyclopentyl)-methylamino]-ethyl, 2-[methyl-(tetrahydrofuran-3-yl)-amino]-ethyl, 2-[ethyl-(3-methyl-oxetan-3-yl-methyl)-amino]-ethyl];

—($C_{1-3}$)alkylene-CO—$R^8$, wherein $R^8$ represents ($C_{1-4}$) alkoxy (especially ethoxy); or $R^8$ represents $NR^{81}R^{82}$ wherein $R^{81}$ and $R^{82}$ independently represent hydrogen or ($C_{1-4}$)alkyl, or $R^{81}$ and $R^{82}$ together with the nitrogen to which they are attached to form a 4- to 6-membered saturated ring optionally substituted with two fluoro substituents (especially such $NR^{81}R^{82}$ represents amino, 3,3-difluoroazetidinyl);

—($C_{1-3}$)alkylene-$SO_2$—$R^9$ wherein $R^9$ represents ($C_{1-3}$) alkyl (especially methyl), or amino;

($C_{3-6}$)cycloalkyl or ($C_{3-6}$)cycloalkyl-($C_{1-3}$)alkyl, wherein the cycloalkyl group is optionally mono-substituted with —CO—($C_{1-4}$)alkoxy or hydroxy; [in particular such ($C_{3-6}$)cycloalkyl is cyclopropyl, 4-hydroxy-cyclohexyl; and such ($C_{3-6}$)cycloalkyl-($C_{1-3}$)alkyl is cyclopropyl-methyl, (1-hydroxy-cyclopentyl)-methyl, (2-(ethoxycarbonyl)-cyclopropyl)-methyl];

($C_{4-7}$)heterocyclyl or ($C_{4-7}$)heterocyclyl-($C_{1-3}$)alkyl, wherein in the above groups the ($C_{4-7}$)heterocyclyl independently contains one or two ring heteroatoms independently selected from nitrogen, sulfur and oxygen; wherein in the above groups said ($C_{4-7}$)heterocyclyl independently is unsubstituted, or mono-, di-, or tri-substituted wherein the substituents are independently selected from:

one oxo substituent attached to a ring carbon atom in alpha position to a ring nitrogen (thus forming together with the nitrogen an amide group, or, in case a ring oxygen is additionally adjacent, a carbamate group, or, in case second ring nitrogen is additionally adjacent, a urea group); and/or two methyl substituents attached to a ring carbon atom in alpha position to a ring nitrogen atom (thus forming together with the nitrogen a —$C(CH_3)_2$—N— group); and/or two oxo substituents at a ring sulfur ring atom (thus forming a —$SO_2$— group); and/or ($C_{1-4}$)alkyl (especially methyl) or —CO—($C_{1-4}$)alkoxy attached to a ring nitrogen atom having a free valency; and/or two fluoro substituents attached to a ring carbon atom; and/or in case of a ($C_{4-7}$)heterocyclyl-($C_{1-3}$)alkyl group, methyl attached to a ring carbon atom which is attached to the linking ($C_{1-3}$)alkyl group;

[in particular such ($C_{4-7}$)heterocyclyl is pyrrolidin-3-yl, 1-methyl-pyrrolidin-3-yl, 1-(tert.-butoxycarbonyl)-pyrrolidin-3-yl, piperidin-3-yl, 1-methyl-piperidin-3-yl, piperidin-4-yl, 1-methyl-piperidin-4-yl, tetrahydropyran-4-yl, 1,1-dioxo-tetrahydrothiophen-3-yl, 1-(tert.-butoxycarbonyl)-piperidin-4-yl; and such ($C_{4-7}$) heterocyclyl-($C_{1-3}$)alkyl is 2-(pyrrolidin-1-yl)-ethyl, 2-(2-oxo-imidazolidin-1-yl)-ethyl, 2-(1-methyl-pyrrolidin-2-yl)-ethyl, 2-(2-oxo-pyrrolidin-1-yl)-ethyl, 2-(morpholin-4-yl)-ethyl, (3-(tert.-butoxycarbonyl)-2,2-dimethyl-oxazolidin-4-yl)-methyl, 3-methyl-oxetan-3-yl-methyl, pyrrolidin-3-yl-methyl, 3-(pyrrolidin-1-yl)-propyl, [1,4]dioxan-2-yl-methyl, 2-(piperazin-1-yl)-ethyl, 2-(piperidin-1-yl)-ethyl, 2-(azepan-1-yl)-ethyl, 2-(3,3-difluoroazetidin-1-yl)-ethyl, 2-(3,3-difluoropyrrolidin-1-yl)-ethyl, 2-(3,3-difluoropiperdin-1-yl)-ethyl, 2-(4,4-difluoropiperdin-1-yl)-ethyl, (1-(tert.-butoxycarbonyl)-pyrrolidin-3-yl)-methyl, 2-(1-(tert.-butoxycarbonyl)-piperazin-4-yl)-ethyl];

2-oxo-2,3-dihydropyridin-4-yl-($C_{1-2}$)alkyl;

phenyl-($C_{1-3}$)alkyl-, or 5- or 6-membered heteroaryl-($C_{1-3}$)alkyl-, wherein the phenyl or 5- or 6-membered heteroaryl independently is unsubstituted, mono-, or di-substituted, wherein the substituents are independently selected from ($C_{1-4}$)alkyl (especially methyl, ethyl), ($C_{1-4}$)alkoxy (especially methoxy), halogen, ($C_{1-3}$)fluoroalkyl (especially trifluoromethyl), ($C_{1-3}$) fluoroalkoxy (especially trifluoromethoxy), and cyano;

wherein the characteristics disclosed in embodiments 2) to 21) are intended to apply mutatis mutandis also to the compounds formula (III) according to embodiment 24); wherein especially the following embodiments are thus possible and intended and herewith specifically disclosed in individualized form:

24, 24+7, 24+10, 24+10+7, 24+13, 24+13+7, 24+13+10, 24+13+10+7, 24+17, 24+17+7, 24+17, 24+17+13, 24+17+13+7, 24+17+13+10, 24+17+13+10+7, 24+19, 24+19+7, 24+19, 24+19+13, 24+19+13+7, 24+19+13+10, 24+19+13+10+7, 24+19+17, 24+19+17+7, 24+19+17, 24+19+17+13, 24+19+17+13+7, 24+19+17+13+10, 24+19+17+13+10+7, 24+21, 24+21+7, 24+21, 24+21+13, 24+21+13+7, 24+21+13+10, 24+21+13+10+7, 24+21+17, 24+21+17+7, 24+21+17, 24+21+17+13, 24+21+17+13+7, 24+21+17+13+10, 24+21+17+13+10+7.

In the list above the numbers refer to the embodiments according to their numbering provided hereinabove whereas "+" indicates the limitations as outlined above.

25) A further aspect of the invention relates to compounds of the formula (I) which are also compounds of the formula ($I_P$),

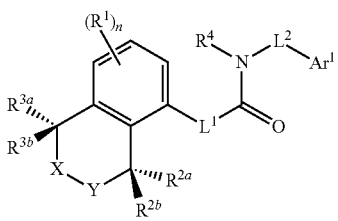

Formula (I$_P$)

wherein
X represents NR$^5$, and Y represents CHR$^Y$ wherein R$^Y$ represents hydrogen, or (C$_{1-3}$)alkyl (especially methyl); and
R$^{3a}$ and R$^{3b}$ together with the carbon atom to which they are attached to form a carbonyl group, or
two of R$^{2a}$, R$^{2b}$ R$^{3a}$ and R$^{3b}$ independently represent hydrogen, or (C$_{1-3}$)alkyl (especially methyl);
and the remaining of R$^{2a}$, R$^{2b}$ R$^{3a}$ and R$^{3b}$ represent hydrogen; or
X represents CHR$^X$ wherein R$^X$ represents hydrogen, or (C$_{1-3}$)alkyl (especially methyl), and Y represents NR$^5$; and
R$^{2a}$ and R$^{2b}$ together with the carbon atom to which they are attached to form a carbonyl group, or
two of R$^{2a}$, R$^{2b}$ R$^{3a}$ and R$^{3b}$ independently represent hydrogen, or (C$_{1-3}$)alkyl (especially methyl);
and the remaining of R$^{2a}$, R$^{2b}$ R$^{3a}$ and R$^{3b}$ represent hydrogen; or
X represents NR$^5$ and Y represents a direct bond; R$^{2a}$ and R$^{2b}$ both represent hydrogen; and R$^{3a}$ and R$^{3b}$ both represent hydrogen;
R$^5$ represents
(C$_{1-6}$)alkyl;
—CO—R$^{10}$ wherein R$^{10}$ represents (C$_{1-5}$)alkyl, (C$_{1-5}$)alkoxy, phenyl, phenyl-oxy-, phenyl-(C$_{1-3}$)alkyl-, phenyl-(C$_{1-3}$)alkyl-oxy-, or (C$_{3-6}$)cycloalkyl-(C$_{1-3}$)alkyl;
—SO$_2$—R$^{11}$ wherein R$^{11}$ represents (C$_{1-5}$)alkyl;
(C$_{2-4}$)fluroroalkyl;
(C$_{3-6}$)cycloalkyl optionally containing one ring oxygen atom;
(C$_{3-6}$)cycloalkyl-(C$_{1-3}$)alkyl, wherein the (C$_{3-6}$)cycloalkyl group optionally contains one ring oxygen atom;
phenyl-(C$_{1-3}$)alkyl-, or 5- or 6-membered heteroaryl-(C$_{1-3}$)alkyl-, wherein the phenyl or 5- or 6-membered heteroaryl independently is especially unsubstituted, or mono-, or di-substituted, wherein the substituents are independently selected from (C$_{1-4}$)alkyl (especially methyl), (C$_{1-4}$)alkoxy (especially methoxy), halogen, (C$_{1-3}$)fluoroalkyl (especially trifluoromethyl), (C$_{1-3}$) fluoroalkoxy (especially trifluoromethoxy), and cyano;
(R$^1$)$_n$ represents one or two optional substituents (i.e. n represents the integer 0, 1, or 2) independently selected from (C$_{1-4}$)alkyl (especially methyl), (C$_{1-4}$)alkoxy (especially methoxy), halogen, (C$_{1-3}$)fluoroalkyl (especially trifluoromethyl), (C$_{1-3}$)fluoroalkoxy (especially trifluoromethoxy), and cyano;
L$^1$ represents a one- or two-membered linker group selected from —NH—CH$_2$—*, —NR$^6$—CH$_2$—* wherein R$^6$ represents (C$_{1-3}$)alkyl, —O—CH$_2$—*, —CH$_2$—, —CH$_2$CH$_2$—, —CH=CH—, and —CH=C(CH$_3$)—*; wherein the asterisks indicate the bond with which the group L$^1$ is attached to the carbonyl group;

L$^2$ represents —(C$_{1-4}$)alkylene- or —(C$_{3-4}$)alkenylene- (especially a linker group selected from —CH$_2$—, —CH(CH$_3$)—, —CH$_2$—CH$_2$—, —CH$_2$—CH$_2$—CH$_2$—, *—CH$_2$—CH=CH—, and *—CH$_2$—C(CH$_3$)=CH—, wherein the asterisks indicate the bond with which the group L$^2$ is attached to the amide nitrogen atom);
Ar$^1$ represents phenyl or 5- or 6-membered heteroaryl; wherein said phenyl or 5- or 6-membered heteroaryl independently is unsubstituted, mono-, di- or tri-substituted, wherein the substituents are independently selected from (C$_{1-4}$)alkyl; (C$_{1-4}$)alkoxy; (C$_{1-3}$)fluoroalkyl; (C$_{1-3}$)fluoroalkoxy; halogen; and cyano; and
R$^4$ represents
(C$_{2-6}$)alkyl;
(C$_{2-4}$)alkyl which is mono-substituted with (C$_{1-4}$)alkoxy, benzyloxy, cyano, or hydroxy;
—(C$_{2-4}$)alkylene-NR$^6$R$^7$, wherein R$^6$ and R$^7$ independently represent hydrogen, (C$_{1-4}$)alkyl, or —CO—(C$_{1-4}$)alkoxy;
—(C$_{1-3}$)alkylene-CO—R$^8$, wherein R$^8$ represents (C$_{1-4}$) alkoxy or amino;
(C$_{3-6}$)cycloalkyl; or (C$_{3-6}$)cycloalkyl-(C$_{1-3}$)alkyl, wherein the cycloalkyl group is optionally mono-substituted with —CO—(C$_{1-4}$)alkoxy;
(C$_{4-6}$)heterocyclyl or (C$_{4-6}$)heterocyclyl-(C$_{1-3}$)alkyl, wherein in the above groups the (C$_{4-6}$)heterocyclyl independently contains one or two ring heteroatoms independently selected from nitrogen, sulfur and oxygen; wherein in the above groups said (C$_{4-6}$)heterocyclyl independently is unsubstituted, or mono-, di-, or tri-substituted wherein the substituents are independently selected from:
one oxo substituent attached to a ring carbon atom in alpha position to a ring nitrogen (thus forming together with the nitrogen an amide group, or, in case a ring oxygen is additionally adjacent, a carbamate group, or, in case second ring nitrogen is additionally adjacent, a urea group); and/or
two methyl substituents attached to a ring carbon atom in alpha position to a ring nitrogen atom (thus forming together with the nitrogen a —C(CH$_3$)$_2$—N— group); and/or
two oxo substituents at a ring sulfur ring atom (thus forming a —SO$_2$— group); and/or
(C$_{1-4}$)alkyl or —CO—(C$_{1-4}$)alkoxy attached to a ring nitrogen atom having a free valency;
2-oxo-2,3-dihydropyridin-4-yl-(C$_{1-2}$)alkyl;
phenyl-(C$_{1-3}$)alkyl-, or 5- or 6-membered heteroaryl-(C$_{1-3}$)alkyl-, wherein the phenyl or 5- or 6-membered heteroaryl independently is unsubstituted, mono-, or di-substituted, wherein the substituents are independently selected from (C$_{1-4}$)alkyl (especially methyl, ethyl), (C$_{1-4}$)alkoxy (especially methoxy), halogen, (C$_{1-3}$)fluoroalkyl (especially trifluoromethyl), (C$_{1-3}$) fluoroalkoxy (especially trifluoromethoxy), and cyano;
wherein the characteristics disclosed in embodiments 2) to 21) are intended to apply mutatis mutandis also to the compounds formula (I$_P$) according to embodiment 25).
Further disclosed are compounds of formula (I$_P$) wherein R$^1$, R$^{2a}$, R$^{2b}$, R$^{3a}$, R$^{3b}$, L$^1$, X, Y and Ar$^1$ as defined in embodiment 25), and wherein R$^4$ and L$^2$, together with the nitrogen to which they are attached to, form a piperazin-1-yl ring which is substituted in position 2 with Ar$^1$, and substituted in position 4 with (C$_{1-4}$)alkyl (especially methyl).
26) Another embodiment relates to compounds according to embodiment 25), and, mutatis mutandis, to any one of embodiments 1) to 4) and 8) to 21), wherein R$^5$ represents (C$_{1-6}$)alkyl (notably methyl, ethyl, isopropyl, isobutyl, 2,2-dimethyl-propyl or 3,3-dimethyl-butyl; especially ethyl or isobutyl);
(C$_{3-6}$)cycloalkyl (especially cyclopentyl); or
(C$_{3-6}$)cycloalkyl-(C$_{1-3}$)alkyl (especially cyclopropyl-methyl).

27) Another embodiment relates to compounds according to embodiments 25) and 26), and, mutatis mutandis, to any one of embodiments 1) to 17), wherein R$^4$ represents
(C$_{2-6}$)alkyl;
(C$_{2-4}$)alkyl which is mono-substituted with (C$_{1-4}$)alkoxy, benzyloxy, cyano, or hydroxy;
—(C$_{2-4}$)alkylene-NR$^6$R$^7$, wherein R$^6$ and R$^7$ independently represent hydrogen, (C$_{1-4}$)alkyl, or —CO—(C$_{1-4}$)alkoxy (notably R$^6$ and R$^7$ independently represent (C$_{1-3}$)alkyl, especially both represent methyl);
—(C$_{1-3}$)alkylene-CO—R$^8$, wherein R$^8$ represents (C$_{1-4}$) alkoxy or amino;
(C$_{3-6}$)cycloalkyl (especially cyclopropyl);
(C$_{3-6}$)cycloalkyl-CH$_2$— (especially cyclopropyl-methyl);
(C$_{4-6}$)heterocyclyl wherein the (C$_{4-6}$)heterocyclyl independently contains one ring heteroatom independently selected from nitrogen, sulfur and oxygen; wherein said (C$_{4-6}$)heterocyclyl is unsubstituted, or mono-, or di-substituted wherein the substituents are independently selected from:
 two oxo substituents at a ring sulfur ring atom (thus forming a —SO$_2$— group); or
 (C$_{1-4}$)alkyl attached to a ring nitrogen atom having a free valency; (especially such (C$_{4-6}$)heterocyclyl is pyrrolidin-3-yl, 1-methyl-pyrrolidin-3-yl, 1-methyl-piperidin-3-yl, 1-methyl-piperidin-4-yl, tetrahydropyran-4-yl, or 1,1-dioxo-tetrahydrothiophen-3-yl)
(C$_{4-6}$)heterocyclyl-(C$_{2-3}$)alkyl, wherein the (C$_{4-6}$)heterocyclyl contains one ring nitrogen atom and optionally one further nitrogen or oxygen atom; wherein said (C$_{4-6}$)heterocyclyl is preferably attached to the C$_{2-3}$) alkyl group at a ring nitrogen atom; wherein said (C$_{4-6}$)heterocyclyl is unsubstituted, or mono-, or di-substituted wherein the substituents are independently selected from:
 one oxo substituent attached to a ring carbon atom in alpha position to a ring nitrogen; and/or
 (C$_{1-4}$)alkyl attached to a ring nitrogen atom having a free valency; (especially the (C$_{4-6}$)heterocyclyl in a (C$_{4-6}$)heterocyclyl-(C$_{2-3}$)alkyl group is pyrrolidin-1-yl, pyrrolidin-2-yl, 1-methyl-pyrrolidin-3-yl, 1-methyl-pyrrolidin-2-yl, 2-oxo-pyrrolidin-1-yl, 2-oxo-imidazolidin-1-yl, piperidin-3-yl, 1-methyl-piperidin-3-yl, piperidin-4-yl, 1-methyl-piperidin-4-yl, or morpholin-4-yl; wherein the (C$_{1-3}$)alkyl group for the above groups is especially ethylene);
phenyl-(C$_{1-3}$)alkyl- wherein the phenyl is unsubstituted, or mono-substituted, wherein the substituents are independently selected from (C$_{1-4}$)alkyl (especially methyl), (C$_{1-4}$)alkoxy (especially methoxy), halogen, (C$_{1-3}$)fluoroalkyl (especially trifluoromethyl), (C$_{1-3}$) fluoroalkoxy (especially trifluoromethoxy), and cyano; or
5- or 6-membered heteroaryl-(C$_{1-3}$)alkyl-, wherein the 5- or 6-membered heteroaryl independently is unsubstituted, or mono-substituted, wherein the substituents are independently selected from (C$_{1-4}$)alkyl (especially methyl, ethyl), (C$_{1-4}$)alkoxy (especially methoxy), halogen, (C$_{1-3}$)fluoroalkyl (especially trifluoromethyl), (C$_{1-3}$)fluoroalkoxy (especially trifluoromethoxy), and cyano.

28) Another embodiment relates to compounds according to embodiments 25) and 26), and, mutatis mutandis, to any one of embodiments 1) to 17), wherein R$^4$ represents
—(C$_{2-4}$)alkylene-NR$^6$R$^7$, wherein R$^6$ and R$^7$ independently represent (C$_{1-3}$)alkyl (especially dimethylamino-ethyl); or
(C$_{4-6}$)heterocyclyl-CH$_2$—CH$_2$—, wherein the (C$_{4-6}$)heterocyclyl is a group selected from pyrrolidin-1-yl, pyrrolidin-2-yl, 1-methyl-pyrrolidin-3-yl, 1-methyl-pyrrolidin-2-yl, 2-oxo-pyrrolidin-1-yl, 2-oxo-imidazolidin-1-yl, and morpholin-4-yl (especially 2-(pyrrolidin-1-yl)-ethyl).

29) The invention, thus, further relates to compounds of the formula (I$_P$) as defined in embodiment 25), or to such compounds further limited by the characteristics of any one of embodiments 26), 27) and/or 28), and/or, mutatis mutandis, limited by the characteristics of any one of embodiments 2) to 21), under consideration of their respective dependencies; to pharmaceutically acceptable salts thereof; and to the use of such compounds as medicaments especially in the treatment of disorders relating to a dysfunction of the CXCR7 receptor or its ligands as described herein below. For avoidance of any doubt, especially the following embodiments relating to the compounds of formula (I$_P$) are thus possible and intended and herewith specifically disclosed in individualized form:
 25+3, 25+4, 25+8+3, 25+8+4, 25+8, 25+8+26+3, 25+8+26+4, 25+8+26, 25+10+3, 25+10+4, 25+10+8+3, 25+10+8+4, 25+10+8, 25+10+8+26+3, 25+10+8+26+4, 25+10+8+26, 25+10, 25+10+26+3, 25+10+26+4, 25+10+26, 25+13+3, 25+13+4, 25+13+8+3, 25+13+8+4, 25+13+8, 25+13+8+26+3, 25+13+8+26+4, 25+13+8+26, 25+13+10+3, 25+13+10+4, 25+13+10+8+3, 25+13+10+8+4, 25+13+10+8, 25+13+10+8+26+3, 25+13+10+8+26+4, 25+13+10+8+26, 25+13+10, 25+13+10+26+3, 25+13+10+26+4, 25+13+10+26, 25+13, 25+13+26+3, 25+13+26+4, 25+13+26, 25+17+3, 25+17+4, 25+17+8+3, 25+17+8+4, 25+17+8, 25+17+8+26+3, 25+17+8+26+4, 25+17+8+26, 25+17+10+3, 25+17+10+4, 25+17+10+8+3, 25+17+10+8+4, 25+17+10+8, 25+17+10+8+26+3, 25+17+10+8+26+4, 25+17+10+8+26, 25+17+10, 25+17+10+26+3, 25+17+10+26+4, 25+17+10+26, 25+17+13+3, 25+17+13+4, 25+17+13+8+3, 25+17+13+8+4, 25+17+13+8, 25+17+13+8+26+3, 25+17+13+8+26+4, 25+17+13+8+26, 25+17+13+10+3, 25+17+13+10+4, 25+17+13+10+8+3, 25+17+13+10+8+4, 25+17+13+10+8, 25+17+13+10+8+26+3, 25+17+13+10+8+26+4, 25+17+13+10+8+26, 25+17+13+10, 25+17+13+10+26+3, 25+17+13+10+26+4, 25+17+13+10+26, 25+17+13, 25+17+13+26+3, 25+17+13+26+4, 25+17+13+26, 25+17, 25+17+26+3, 25+17+26+4, 25+17+26, 1+25, 25+26+3, 25+26+4, 25+26, 25+27+3, 25+27+4, 25+27+8+3, 25+27+8+4, 25+27+8, 25+27+8+26+3, 25+27+8+26+4, 25+27+8+26, 25+27+10+3, 25+27+10+4, 25+27+10+8+3, 25+27+10+8+4, 25+27+10+8, 25+27+10+8+26+3, 25+27+10+8+26+4, 25+27+10+8+26, 25+27+10, 25+27+10+26+3, 25+27+10+26+4, 25+27+10+26, 25+27+13+3, 25+27+13+4, 25+27+13+8+3, 25+27+13+8+4, 25+27+13+8, 25+27+13+8+26+3, 25+27+13+8+26+4, 25+27+13+8+26, 25+27+13+10+3, 25+27+13+10+4, 25+27+13+10+8+3, 25+27+13+10+8+4, 25+27+13+10+8, 25+27+13+10+8+26+3, 25+27+13+10+8+26+4, 25+27+13+10+8+26, 25+27+13+10, 25+27+13+10+26+3, 25+27+13+10+26+4, 25+27+13+10+26, 25+27+13, 25+27+13+26+3, 25+27+13+26+4, 25+27+13+26, 25+27+17+3, 25+27+17+4, 25+27+17+8+3, 25+27+17+8+4, 25+27+17+8, 25+27+17+8+26+3, 25+27+17+8+26+4, 25+27+17+8+26, 25+27+17+10+3, 25+27+17+10+4, 25+27+17+10+8+3, 25+27+17+10+8+4, 25+27+17+10+8, 25+27+17+10+8+

26+3, 25+27+17+10+8+26+4, 25+27+17+10+8+26, 25+27+17+10, 25+27+17+10+26+3, 25+27+17+10+26+4, 25+27+17+10+26, 25+27+17+13+3, 25+27+17+13+4, 25+27+17+13+8+3, 25+27+17+13+8+4, 25+27+17+13+8, 25+27+17+13+8+26+3, 25+27+17+13+8+26+4, 25+27+17+13+8+26, 25+27+17+13+10+3, 25+27+17+13+10+4, 25+27+17+13+10+8+3, 25+27+17+13+10+8+4, 25+27+17+13+10+8, 25+27+17+13+10+8+26+3, 25+27+17+13+10+8+26+4, 25+27+17+13+10+8+26, 25+27+17+13+10, 25+27+17+13+10+26+3, 25+27+17+13+10+26+4, 25+27+17+13+10+26, 25+27+17+13, 25+27+17+13+26+3, 25+27+17+13+26+4, 25+27+17+13+26, 25+27+17, 25+27+17+26+3, 25+27+17+26+4, 25+27+17+26, 25+27, 25+27+26+3, 25+27+26+4, 25+27+26, 25+28+3, 25+28+4, 25+28+8+3, 25+28+8+4, 25+28+8, 25+28+8+26+3, 25+28+8+26+4, 25+28+8+26, 25+28+10+3, 25+28+10+4, 25+28+10+8+3, 25+28+10+8+4, 25+28+10+8, 25+28+10+8+26+3, 25+28+10+8+26+4, 25+28+10+8+26, 25+28+10, 25+28+10+26+3, 25+28+10+26+4, 25+28+10+26, 25+28+13+3, 25+28+13+4, 25+28+13+8+3, 25+28+13+8+4, 25+28+13+8, 25+28+13+8+26+3, 25+28+13+8+26+4, 25+28+13+8+26, 25+28+13+10+3, 25+28+13+10+4, 25+28+13+10+8+3, 25+28+13+10+8+4, 25+28+13+10+8, 25+28+13+10+8+26+3, 25+28+13+10+8+26+4, 25+28+13+10+8+26, 25+28+13+10, 25+28+13+10+26+3, 25+28+13+10+26+4, 25+28+13+10+26, 25+28+13, 25+28+13+26+3, 25+28+13+26+4, 25+28+13+26, 25+28+17+3, 25+28+17+4, 25+28+17+8+3, 25+28+17+8+4, 25+28+17+8, 25+28+17+8+26+3, 25+28+17+8+26+4, 25+28+17+8+26, 25+28+17+10+3, 25+28+17+10+4, 25+28+17+10+8+3, 25+28+17+10+8+4, 25+28+17+10+8, 25+28+17+10+8+26+3, 25+28+17+10+8+26+4, 25+28+17+10+8+26, 25+28+17+10, 25+28+17+10+26+3, 25+28+17+10+26+4, 25+28+17+10+26, 25+28+17+13+3, 25+28+17+13+4, 25+28+17+13+8+3, 25+28+17+13+8+4, 25+28+17+13+8, 25+28+17+13+8+26+3, 25+28+17+13+8+26+4, 25+28+17+13+8+26, 25+28+17+13+10+3, 25+28+17+13+10+4, 25+28+17+13+10+8+3, 25+28+17+13+10+8+4, 25+28+17+13+10+8, 25+28+17+13+10+8+26+3, 25+28+17+13+10+8+26+4, 25+28+17+13+10+8+26, 25+28+17+13+10, 25+28+17+13+10+26+3, 25+28+17+13+10+26+4, 25+28+17+13+10+26, 25+28+17+13, 25+28+17+13+26+3, 25+28+17+13+26+4, 25+28+17+13+26, 25+28+17, 25+28+17+26+3, 25+28+17+26+4, 25+28+17+26, 25+28, 25+28+26+3, 25+28+26+4, 25+28+26.

In the list above the numbers refer to the embodiments according to their numbering provided hereinabove whereas "+" indicates the dependency from another embodiment. The different individualized embodiments are separated by commas. In other words, "25+17" for example refers to embodiment 17) depending on embodiment 25) (wherein it is understood that the compounds of embodiment 25) are also compounds of formula (I) according to embodiment 1)), i.e. embodiment "25+17" corresponds to the compounds of formula (I) according to embodiment 1) further limited by all the features defining the compounds of formula ($I_P$) according to embodiment 25), and further limited by all the features of embodiment 17).

30) A further aspect of the invention relates to compounds of the formula (I) according to embodiment 1) which are also compounds of the formula ($II_P$)

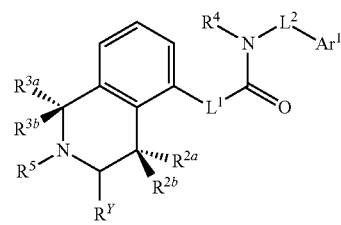

Formula ($II_P$)

wherein
$R^Y$ represents hydrogen, or $(C_{1-3})$alkyl (especially methyl); and
two of $R^{2a}$, $R^{2b}$ $R^{3a}$ and $R^{3b}$ independently represent hydrogen, or $(C_{1-3})$alkyl (especially methyl);
and the remaining of $R^{2a}$, $R^{2b}$ $R^{3a}$ and $R^{3b}$ represent hydrogen;
$R^5$ represents
$(C_{1-6})$alkyl;
—CO—$R^{10}$ wherein $R^{10}$ represents $(C_{1-5})$alkyl, $(C_{1-5})$alkoxy, phenyl, phenyl-oxy-, phenyl-$(C_{1-3})$alkyl-, phenyl-$(C_{1-3})$alkyl-oxy-, or $(C_{3-6})$cycloalkyl-$(C_{1-3})$alkyl,
—SO$_2$—$R^{11}$ wherein $R^{11}$ represents $(C_{1-5})$alkyl;
$(C_{2-4})$fluroalkyl;
$(C_{3-6})$cycloalkyl optionally containing one ring oxygen atom;
$(C_{3-6})$cycloalkyl-$(C_{1-3})$alkyl, wherein the $(C_{3-6})$cycloalkyl group optionally contains one ring oxygen atom;
phenyl-$(C_{1-3})$alkyl-, wherein the phenyl-$(C_{1-3})$alkyl- is unsubstituted;
$L^1$ represents a two-membered linker group selected from —NH—CH$_2$—*, —NR$^6$—CH$_2$—* wherein $R^6$ represents $(C_{1-3})$alkyl, —O—CH$_2$—*, —CH$_2$CH$_2$—, —CH=CH—, and —CH=C(CH$_3$)—*; wherein the asterisks indicate the bond with which the group $L^1$ is attached to the carbonyl group;
$L^2$ represents —$(C_{1-4})$alkylene- or —$(C_{3-4})$alkenylene- (especially a linker group selected from —CH$_2$—, —CH(CH$_3$)—, —CH$_2$—CH$_2$—, —CH$_2$—CH$_2$—CH$_2$—, *—CH$_2$—CH=CH—, and *—CH$_2$—C(CH$_3$)=CH—, wherein the asterisks indicate the bond with which the group $L^2$ is attached to the amide nitrogen atom);
Ar$^1$ represents phenyl or 5- or 6-membered heteroaryl; wherein said phenyl or 5- or 6-membered heteroaryl independently is unsubstituted, mono-, di- or tri-substituted, wherein the substituents are independently selected from $(C_{1-4})$alkyl; $(C_{1-4})$alkoxy; $(C_{1-3})$fluoroalkyl; $(C_{1-3})$fluoroalkoxy; halogen; and cyano; and
$R^4$ represents
$(C_{2-6})$alkyl;
$(C_{2-4})$alkyl which is mono-substituted with $(C_{1-4})$alkoxy, benzyloxy, cyano, or hydroxy;
—$(C_{2-4})$alkylene-NR$^6$R$^7$, wherein $R^6$ and $R^7$ independently represent hydrogen, $(C_{1-4})$alkyl, or —CO—$(C_{1-4})$alkoxy;
—$(C_{1-3})$alkylene-CO—R$^8$, wherein $R^8$ represents $(C_{1-4})$alkoxy or amino;
$(C_{3-6})$cycloalkyl; or $(C_{3-6})$cycloalkyl-$(C_{1-3})$alkyl, wherein the cycloalkyl group is optionally mono-substituted with —CO—$(C_{1-4})$alkoxy;
$(C_{4-6})$heterocyclyl or $(C_{4-6})$heterocyclyl-$(C_{1-3})$alkyl, wherein in the above groups the $(C_{4-6})$heterocyclyl independently contains one or two ring heteroatoms independently selected from nitrogen, sulfur and oxygen; wherein in the above groups said $(C_{4-6})$heterocyclyl independently is unsubstituted, or mono-, di-, or tri-substituted wherein the substituents are independently selected from:
  one oxo substituent attached to a ring carbon atom in alpha position to a ring nitrogen (thus forming together with the nitrogen an amide group, or, in case a ring oxygen is additionally adjacent, a carbamate group, or, in case second ring nitrogen is additionally adjacent, a urea group); and/or
  two methyl substituents attached to a ring carbon atom in alpha position to a ring nitrogen atom (thus forming together with the nitrogen a —C(CH$_3$)$_2$—N— group); and/or
  two oxo substituents at a ring sulfur ring atom (thus forming a —SO$_2$— group); and/or
  $(C_{1-4})$alkyl or —CO—$(C_{1-4})$alkoxy attached to a ring nitrogen atom having a free valency;
  phenyl-$(C_{1-3})$alkyl-, or 5- or 6-membered heteroaryl-$(C_{1-3})$alkyl-, wherein the phenyl or 5- or 6-membered heteroaryl independently is unsubstituted, mono-, or di-substituted, wherein the substituents are independently selected from $(C_{1-4})$alkyl (especially methyl, ethyl), $(C_{1-4})$alkoxy (especially methoxy), halogen, $(C_{1-3})$fluoroalkyl (especially trifluoromethyl), $(C_{1-3})$ fluoroalkoxy (especially trifluoromethoxy), and cyano;

wherein the characteristics disclosed in of any one of embodiments 2) to 29) are intended to apply mutatis mutandis also to the compounds formula (II$_P$) according to embodiment 30); wherein especially the following embodiments are thus possible and intended and herewith specifically disclosed in individualized form:

30+10+26, 30+1+10, 30+13+10+26, 30+13+10, 30+13+26, 30+13, 30+17+10+26, 30+17+10, 30+17+13+10+26, 30+17+13+10, 30+17+13+26, 30+17+13, 30+17+26, 30+17, 30+26, 30+27+10+26, 30+27+10, 30+27+13+10+26, 30+27+13+10, 30+27+13+26, 30+27+13, 30+27+17+10+26, 30+27+17+10, 30+27+17+13+10+26, 30+27+17+13+10, 30+27+17+13+26, 30+27+17+13, 30+27+17+26, 30+27+17, 30+27+26, 30+27, 30+28+10+26, 30+28+10, 30+28+13+10+26, 30+28+13+10, 30+28+13+26, 30+28+13, 30+28+17+10+26, 30+28+17+10, 30+28+17+13+10+26, 30+28+17+13+10, 30+28+17+13+26, 30+28+17+13, 30+28+17+26, 30+28+17, 30+28+26, 30+28, 30.

In the list above the numbers refer to the embodiments according to their numbering provided hereinabove whereas "+" indicates the limitations as outlined above.

31) A further aspect of the invention relates to compounds of the formula (I) according to embodiment 1) which are also compounds of the formula (III$_P$)

Formula (III$_P$)

wherein
R$^X$ represents hydrogen, or $(C_{1-3})$alkyl (especially methyl); and

R$^{2a}$ and R$^{2b}$ together with the carbon atom to which they are attached to form a carbonyl group, or
two of R$^{2a}$, R$^{2b}$ R$^{3a}$ and R$^{3b}$ independently represent hydrogen, or $(C_{1-3})$alkyl (especially methyl);
and the remaining of R$^{2a}$, R$^{2b}$ R$^{3a}$ and R$^{3b}$ represent hydrogen; or
R$^5$ represents
  $(C_{1-6})$alkyl;
  —CO—R$^{10}$ wherein R$^{10}$ represents $(C_{1-5})$alkyl, $(C_{1-5})$ alkoxy, phenyl, phenyl-oxy-, phenyl-$(C_{1-3})$alkyl-, phenyl-$(C_{1-3})$alkyl-oxy-, or $(C_{3-6})$cycloalkyl-$(C_{1-3})$alkyl,
  —SO$_2$—R$^{11}$ wherein R$^{11}$ represents $(C_{1-5})$alkyl;
  $(C_{2-4})$fluoroalkyl;
  $(C_{3-6})$cycloalkyl optionally containing one ring oxygen atom;
  $(C_{3-6})$cycloalkyl-$(C_{1-3})$alkyl, wherein the $(C_{3-6})$cycloalkyl group optionally contains one ring oxygen atom;
  phenyl-$(C_{1-3})$alkyl-, wherein the phenyl-$(C_{1-3})$alkyl- is unsubstituted;
L$^1$ represents a two-membered linker group selected from —NH—CH$_2$—*, —NR$^6$—CH$_2$—* wherein R$^6$ represents $(C_{1-3})$alkyl, —O—CH$_2$—*, —CH$_2$CH$_2$—, —CH=CH—, and —CH=C(CH$_3$)—*; wherein the asterisks indicate the bond with which the group L$^1$ is attached to the carbonyl group;
L$^2$ represents —$(C_{1-4})$alkylene- or —$(C_{3-4})$alkenylene- (especially a linker group selected from —CH$_2$—, —CH (CH$_3$)—, —CH$_2$—CH$_2$—, —CH$_2$—CH$_2$—CH$_2$—, *—CH$_2$—CH=CH—, and *—CH$_2$—C(CH$_3$)=CH—, wherein the asterisks indicate the bond with which the group L$^2$ is attached to the amide nitrogen atom);
Ar$^1$ represents phenyl or 5- or 6-membered heteroaryl; wherein said phenyl or 5- or 6-membered heteroaryl independently is unsubstituted, mono-, di- or tri-substituted, wherein the substituents are independently selected from $(C_{1-4})$alkyl; $(C_{1-4})$alkoxy; $(C_{1-3})$fluoroalkyl; $(C_{1-3})$fluoroalkoxy; halogen; and cyano; and
R$^4$ represents
  $(C_{2-6})$alkyl;
  $(C_{2-4})$alkyl which is mono-substituted with $(C_{1-4})$alkoxy, benzyloxy, cyano, or hydroxy;
  —$(C_{2-4})$alkylene-NR$^6$R$^7$, wherein R$^6$ and R$^7$ independently represent hydrogen, $(C_{1-4})$alkyl, or —CO—$(C_{1-4})$alkoxy;
  —$(C_{1-3})$alkylene-CO—R$^8$, wherein R$^8$ represents $(C_{1-4})$ alkoxy or amino;
  $(C_{3-6})$cycloalkyl; or $(C_{3-6})$cycloalkyl-$(C_{1-3})$alkyl, wherein the cycloalkyl group is optionally mono-substituted with —CO—$(C_{1-4})$alkoxy;
  $(C_{4-6})$heterocyclyl or $(C_{4-6})$heterocyclyl-$(C_{1-3})$alkyl, wherein in the above groups the $(C_{4-6})$heterocyclyl independently contains one or two ring heteroatoms independently selected from nitrogen, sulfur and oxygen; wherein in the above groups said $(C_{4-6})$heterocyclyl independently is unsubstituted, or mono-, di-, or tri-substituted wherein the substituents are independently selected from:
    one oxo substituent attached to a ring carbon atom in alpha position to a ring nitrogen (thus forming together with the nitrogen an amide group, or, in case a ring oxygen is additionally adjacent, a carbamate group, or, in case second ring nitrogen is additionally adjacent, a urea group); and/or two methyl substituents attached to a ring carbon atom in alpha position to a ring nitrogen atom (thus forming together with the nitrogen a —C(CH$_3$)$_2$—N— group); and/or two oxo substituents at a ring sulfur ring atom (thus forming a —SO$_2$— group); and/or (C$_{1-4}$)alkyl or —CO—(C$_{1-4}$)alkoxy attached to a ring nitrogen atom having a free valency;

phenyl-(C$_{1-3}$)alkyl-, or 5- or 6-membered heteroaryl-(C$_{1-3}$)alkyl-, wherein the phenyl or 5- or 6-membered heteroaryl independently is unsubstituted, mono-, or di-substituted, wherein the substituents are independently selected from (C$_{1-4}$)alkyl (especially methyl, ethyl), (C$_{1-4}$)alkoxy (especially methoxy), halogen, (C$_{1-3}$)fluoroalkyl (especially trifluoromethyl), (C$_{1-3}$) fluoroalkoxy (especially trifluoromethoxy), and cyano;

wherein the characteristics disclosed in of any one of embodiments 2) to 29) are intended to apply mutatis mutandis also to the compounds formula (III$_P$) according to embodiment 31); wherein especially the following embodiments are thus possible and intended and herewith specifically disclosed in individualized form:

31+10+26, 31+1+10, 31+13+10+26, 31+13+10, 31+13+26, 31+13, 31+17+10+26, 31+17+10, 31+17+13+10+26, 31+17+13+10, 31+17+13+26, 31+17+13, 31+17+26, 31+17, 31+26, 31+27+10+26, 31+27+10, 31+27+13+10+26, 31+27+13+10, 31+27+13+26, 31+27+13, 31+27+17+10+26, 31+27+17+10, 31+27+17+13+10+26, 31+27+17+13+10, 31+27+17+13+26, 31+27+17+13, 31+27+17+26, 31+27+17, 31+27+26, 31+27, 31+28+10+26, 31+28+10, 31+28+13+10+26, 31+28+13+10, 31+28+13+26, 31+28+13, 31+28+17+10+26, 31+28+17+10, 31+28+17+13+10+26, 31+28+17+13+10, 31+28+17+13+26, 31+28+17+13, 31+28+17+26, 31+28+17, 31+28+26, 31+28, 31.

In the list above the numbers refer to the embodiments according to their numbering provided hereinabove whereas "+" indicates the limitations as outlined above.

32) Another embodiment relates to compounds according to embodiment 1) which are selected from the following compounds:

N-Benzyl-2-(2-cyclopropylmethyl-1,2,3,4-tetrahydro-isoquinolin-5-yl)-N-(2-pyrrolidin-1-yl-ethyl)-acetamide;
N-Benzyl-2-(2-cyclopropylmethyl-1,2,3,4-tetrahydro-isoquinolin-5-yl)-N-[2-(1-methyl-pyrrolidin-2-yl)-ethyl]-acetamide;
2-(2-Cyclopropylmethyl-1,2,3,4-tetrahydro-isoquinolin-5-yl)-N-(2-pyrrolidin-1-yl-ethyl)-N-(2-trifluoromethyl-benzyl)-acetamide;
N-Benzyl-N-(3-dimethylamino-propyl)-2-(2-propionyl-1,2,3,4-tetrahydro-isoquinolin-5-ylamino)-acetamide;
N-(2-Dimethylamino-ethyl)-N-(2-methyl-benzyl)-2-(2-propionyl-1,2,3,4-tetrahydro-isoquinolin-5-ylamino)-acetamide;
N-(2-Chloro-benzyl)-N-(2-dimethylamino-ethyl)-2-(2-propionyl-1,2,3,4-tetrahydro-isoquinolin-5-ylamino)-acetamide;
N-(2-Dimethylamino-ethyl)-N-(3-fluoro-benzyl)-2-(2-propionyl-1,2,3,4-tetrahydro-isoquinolin-5-ylamino)-acetamide;
N-(2-Dimethylamino-ethyl)-N-(2-fluoro-benzyl)-2-(2-propionyl-1,2,3,4-tetrahydro-isoquinolin-5-ylamino)-acetamide;
N-Benzyl-2-(2-propionyl-1,2,3,4-tetrahydro-isoquinolin-5-ylamino)-N-(2-pyrrolidin-1-yl-ethyl)-acetamide;
N-Benzyl-N-(2-diethylamino-ethyl)-2-(2-propionyl-1,2,3,4-tetrahydro-isoquinolin-5-ylamino)-acetamide;
N-Benzyl-N-[2-(butyl-methyl-amino)-ethyl]-2-(2-propionyl-1,2,3,4-tetrahydro-isoquinolin-5-ylamino)-acetamide;
N-Benzyl-N-[2-(1-methyl-pyrrolidin-2-yl)-ethyl]-2-(2-propionyl-1,2,3,4-tetrahydro-isoquinolin-5-ylamino)-acetamide;
N-(2-Dimethylamino-ethyl)-2-(2-propionyl-1,2,3,4-tetrahydro-isoquinolin-5-ylamino)-N-(3-trifluoromethyl-benzyl)-acetamide;
N-(2-Dimethylamino-ethyl)-2-(2-propionyl-1,2,3,4-tetrahydro-isoquinolin-5-ylamino)-N-(2-trifluoromethyl-benzyl)-acetamide;
2-(2-Cyclopropylmethyl-1,2,3,4-tetrahydro-isoquinolin-5-ylamino)-N-(2-dimethylamino-ethyl)-N-phenethyl-acetamide;
N-Benzyl-2-(2-cyclopropylmethyl-1,2,3,4-tetrahydro-isoquinolin-5-ylamino)-N-(3-dimethylamino-propyl)-acetamide;
2-(2-Cyclopropylmethyl-1,2,3,4-tetrahydro-isoquinolin-5-ylamino)-N-(2-dimethylamino-ethyl)-N-(2-fluoro-benzyl)-acetamide;
N-(3-Chloro-pyridin-2-ylmethyl)-2-(2-cyclopropylmethyl-1,2,3,4-tetrahydro-isoquinolin-5-ylamino)-N-(2-dimethylamino-ethyl)-acetamide;
2-(2-Cyclopropylmethyl-1,2,3,4-tetrahydr-isoquinolin-5-ylamino)-N-(2-dimethylamino-ethyl)-N-(2-o-tolyl-ethyl)-acetamide;
N-Benzyl-2-(2-cyclopropylmethyl-1,2,3,4-tetrahydro-isoquinolin-5-ylamino)-N-(2-pyrrolidin-1-yl-ethyl)-acetamide;
N-Benzyl-2-(2-cyclopropylmethyl-1,2,3,4-tetrahydro-isoquinolin-5-ylamino)-N-[2-(1-methyl-pyrrolidin-2-yl)-ethyl]-acetamide;
N-(2-Chloro-benzyl)-2-(2-cyclopropylmethyl-1,2,3,4-tetrahydro-isoquinolin-5-ylamino)-N-(2-pyrrolidin-1-yl-ethyl)-acetamide;
2-(2-Cyclopropylmethyl-1,2,3,4-tetrahydr-isoquinolin-5-ylamino)-N-(2-fluor-benzyl)-N-(2-pyrrolidin-1-yl-ethyl)-acetamide;
2-(2-Cyclopropylmethyl-1,2,3,4-tetrahydro-isoquinolin-5-ylamino)-N-(2-dimethylamino-ethyl)-N-((E)-2-methyl-3-phenyl-allyl)-acetamide;
2-(2-Cyclopropylmethyl-1,2,3,4-tetrahydr-isoquinolin-5-ylamino)-N-(2-dimethylamino-ethyl)-N-(6-trifluromethyl-pyridin-2-ylmethyl)-acetamide;
2-(2-Cyclopropylmethyl-1,2,3,4-tetrahydr-isoquinolin-5-ylamino)-N-(2-dimethylamino-ethyl)-N-(3-trifluromethyl-pyridin-2-ylmethyl)-acetamide;
2-(2-Cyclopropylmethyl-1,2,3,4-tetrahydr-isoquinolin-5-ylamino)-N-[2-(1-methyl-pyrrolidin-2-yl)-ethyl]-N-phenethyl-acetamide;
N-(2-Chloro-4-fluoro-benzyl)-2-(2-cylopropylmethyl-1,2,3,4-tetrahydro-isoquinolin-5-ylamino)-N-(2-pyrrolidin-1-yl-ethyl)-acetamide;
2-(2-Cyclopropylmethyl-1,2,3,4-tetrahydro-isoquinolin-5-ylamino)-N-(2,4-difluoro-benzyl)-N-(2-pyrrolidin-1-yl-ethyl)-acetamide;
2-(2-Cyclopropylmethyl-1,2,3,4-tetrahydro-isoquinolin-5-ylamino)-N-[2-(1-methyl-pyrrolidin-2-yl)-ethyl]-N-(3-phenyl-propyl)-acetamide;
2-(2-Cyclopropylmethyl-1,2,3,4-tetrahydro-isoquinolin-5-ylamino)-N-[2-(1-methyl-pyrrolidin-2-yl)-ethyl]-N-((E)-3-phenyl-allyl)-acetamide;
2-(2-Cyclopropylmethyl-1,2,3,4-tetrahydro-isoquinolin-5-ylamino)-N-(2-dimethylamino-ethyl)-N-(4-fluoro-2-trifluoromethyl-benzyl)-acetamide;

2-(2-Cyclopropylmethyl-1,2,3,4-tetrahydro-isoquinolin-5-ylamino)-N-(2-dimethylamino-ethyl)-N-[2-(3-trifluoromethyl-phenyl)-ethyl]-acetamide;
2-(2-Cyclopropylmethyl-1,2,3,4-tetrahydro-isoquinolin-5-ylamino)-N-(2-dimethylamino-ethyl)-N-[2-(2-trifluoromethyl-phenyl)-ethyl]-acetamide;
2-(2-Cyclopropylmethyl-1,2,3,4-tetrahydro-isoquinolin-5-ylamino)-N-(2-dimethylamino-ethyl)-N-[1-(2-trifluoromethyl-phenyl)-ethyl]-acetamide;
2-(2-Cyclopropylmethyl-1,2,3,4-tetrahydro-isoquinolin-5-ylamino)-N-(2-diethylamino-ethyl)-N-(2-trifluoromethyl-benzyl)-acetamide;
2-(2-Cyclopropylmethyl-1,2,3,4-tetrahydro-isoquinolin-5-ylamino)-N-((E)-2-methyl-3-phenyl-allyl)-N-[2-(1-methyl-pyrrolidin-2-yl)-ethyl]-acetamide;
2-(2-Cyclopropylmethyl-1,2,3,4-tetrahydro-isoquinolin-5-ylamino)-N-(2-pyrrolidin-1-yl-ethyl)-N-(2-trifluoromethyl-benzyl)-acetamide;
2-(2-Cyclopropylmethyl-1,2,3,4-tetrahydro-isoquinolin-5-ylamino)-N-[2-(2-oxo-pyrrolidin-1-yl)-ethyl]-N-(2-trifluoromethyl-benzyl)-acetamide;
2-(2-Cyclopropylmethyl-1,2,3,4-tetrahydro-isoquinolin-5-ylamino)-N-(2-morpholin-4-yl-ethyl)-N-(2-trifluoromethyl-benzyl)-acetamide;
N-(2-Cyano-ethyl)-2-(2-cyclopropylmethyl-1,2,3,4-tetrahydro-isoquinolin-5-ylamino)-N-(2-trifluoromethyl-benzyl)-acetamide;
2-(2-Cyclopropylmethyl-1,2,3,4-tetrahydro-isoquinolin-5-ylamino)-N-(tetrahydro-pyran-4-yl)-N-(2-trifluoromethyl-benzyl)-acetamide;
2-(2-Cyclopropylmethyl-1,2,3,4-tetrahydro-isoquinolin-5-ylamino)-N-(2-dimethylamino-ethyl)-N-(2-trifluoromethyl-benzyl)-acetamide;
2-(2-Cyclopropylmethyl-1,2,3,4-tetrahydro-isoquinolin-5-ylamino)-N-(4-methyl-thiazol-2-ylmethyl)-N-(2-trifluoromethyl-benzyl)-acetamide;
2-(2-Cyclopropylmethyl-1,2,3,4-tetrahydro-isoquinolin-5-ylamino)-N-[1-(1-ethyl-1H-pyrazol-3-yl)-ethyl]-N-(2-trifluoromethyl-benzyl)-acetamide;
N-(2-Dimethylamino-ethyl)-2-[2-(2,2,2-trifluoro-ethyl)-1,2,3,4-tetrahydro-isoquinolin-5-ylamino]-N-(2-trifluoromethyl-benzyl)-acetamide;
2-[(2-Cyclopropylmethyl-1,2,3,4-tetrahydro-isoquinolin-5-yl)-methyl-amino]-N-(2-dimethylamino-ethyl)-N-(2-trifluoromethyl-benzyl)-acetamide;
2-(6-Chloro-2-cyclopropylmethyl-1,2,3,4-tetrahydro-isoquinolin-5-ylamino)-N-(2-dimethylamino-ethyl)-N-(2-trifluoromethyl-benzyl)-acetamide;
2-(2-Cyclopropylmethyl-6-methoxy-1,2,3,4-tetrahydro-isoquinolin-5-ylamino)-N-(2-dimethylamino-ethyl)-N-(2-trifluoromethyl-benzyl)-acetamide;
5-({[(2-Dimethylamino-ethyl)-(2-trifluoromethyl-benzyl)-carbamoyl]-methyl}-amino)-4,4-dimethyl-3,4-dihydro-1H-isoquinoline-2-carboxylic acid tert-butyl ester;
2-(2-Cyclopropylmethyl-4,4-dimethyl-1,2,3,4-tetrahydro-isoquinolin-5-ylamino)-N-(2-dimethylamino-ethyl)-N-(2-trifluoromethyl-benzyl)-acetamide;
2-(2-Cyclopropylmethyl-1,2,3,4-tetrahydro-isoquinolin-5-ylamino)-N-(1-methyl-piperidin-4-yl)-N-(2-trifluoromethyl-benzyl)-acetamide;
N-Benzyl-N-(2-dimethylamino-ethyl)-2-(2-ethyl-1,2,3,4-tetrahydro-isoquinolin-5-ylamino)-acetamide;
N-Benzyl-2-(2-cyclopropylmethyl-1,2,3,4-tetrahydro-isoquinolin-5-ylamino)-N-(2-dimethylamino-ethyl)-acetamide;
N-Benzyl-N-(2-dimethylamino-ethyl)-2-(2-propionyl-1,2,3,4-tetrahydro-isoquinolin-5-ylamino)-acetamide;
N-Benzyl-N-(2-dimethylamino-ethyl)-2-(2-isobutyl-1,2,3,4-tetrahydro-isoquinolin-5-ylamino)-acetamide;
5-({[Benzyl-(2-dimethylamino-ethyl)-carbamoyl]-methyl}-amino)-3,4-dihydro-1H-isoquinoline-2-carboxylic acid methyl ester;
N-Benzyl-2-(2-butyryl-1,2,3,4-tetrahydro-isoquinolin-5-ylamino)-N-(2-dimethylamino-ethyl)-acetamide;
N-(2-Chloro-benzyl)-N-(2-dimethylamino-ethyl)-2-(2-ethyl-1,2,3,4-tetrahydro-isoquinolin-5-ylamino)-acetamide;
N-(2-Chloro-benzyl)-2-(2-cyclopropylmethyl-1,2,3,4-tetrahydro-isoquinolin-5-ylamino)-N-(2-dimethylamino-ethyl)-acetamide;
N-(2-Dimethylamino-ethyl)-2-(2-ethyl-1,2,3,4-tetrahydro-isoquinolin-5-ylamino)-N-(2-trifluoromethyl-benzyl)-acetamide;
2-(2-Cyclopropylmethyl-1,2,3,4-tetrahydro-isoquinolin-5-ylamino)-N-(1-methyl-piperidin-3-yl)-N-(2-trifluoromethyl-benzyl)-acetamide;
2-(2-Ethyl-1,2,3,4-tetrahydro-isoquinolin-5-ylamino)-N-(1-methyl-piperidin-4-yl)-N-(2-trifluoromethyl-benzyl)-acetamide;
(E)-N-Benzyl-N-(2-dimethylamino-ethyl)-3-(2-methyl-1,2,3,4-tetrahydro-isoquinolin-5-yl)-acrylamide;
(E)-N-Benzyl-3-(2-cyclopropylmethyl-1,2,3,4-tetrahydro-isoquinolin-5-yl)-N-(2-dimethylamino-ethyl)-acrylamide;
{Benzyl-[(E)-3-(2-cyclopropylmethyl-1,2,3,4-tetrahydro-isoquinolin-5-yl)-acryloyl]-amino}-acetic acid ethyl ester;
(E)-N-(2-Chloro-benzyl)-N-(2-dimethylamino-ethyl)-3-(2-ethyl-1,2,3,4-tetrahydro-isoquinolin-5-yl)-acrylamide;
(E)-N-(2-Chloro-benzyl)-3-(2-cyclopropylmethyl-1,2,3,4-tetrahydro-isoquinolin-5-yl)-N-(2-dimethylamino-ethyl)-acrylamide;
(E)-N-Benzyl-3-(2-cyclopropylmethyl-1,2,3,4-tetrahydro-isoquinolin-5-yl)-N-(1,1-dioxo-tetrahydro-1|6-thiophen-3-yl)-acrylamide;
(E)-N-(2-Dimethylamino-ethyl)-3-(2-ethyl-1,2,3,4-tetrahydro-isoquinolin-5-yl)-N-(2-trifluoromethyl-benzyl)-acrylamide;
(E)-3-(2-Cyclopropylmethyl-1,2,3,4-tetrahydro-isoquinolin-5-yl)-N-(2-dimethylamino-ethyl)-N-(2-trifluoromethyl-benzyl)-acrylamide;
(E)-3-(2-Ethyl-1,2,3,4-tetrahydro-isoquinolin-5-yl)-N-(1-methyl-piperidin-4-yl)-N-(2-trifluoromethyl-benzyl)-acrylamide;
(E)-3-(2-Cyclopropylmethyl-1,2,3,4-tetra hydro-isoquinolin-5-yl)-N-(1-methyl-piperidin-4-yl)-N-(2-trifluoromethyl-benzyl)-acrylamide;
(E)-3-(2-Cyclopropylmethyl-1,2,3,4-tetra hydro-isoquinolin-5-yl)-N-(2-dimethylamino-ethyl)-2-methyl-N-(2-trifluoromethyl-benzyl)-acryl amide;
N-(2-Chloro-benzyl)-N-(2-dimethylamino-ethyl)-3-(2-ethyl-1,2,3,4-tetrahydro-isoquinolin-5-yl)-propionamide;
N-(2-Chloro-benzyl)-3-(2-cyclopropylmethyl-1,2,3,4-tetrahydro-isoquinolin-5-yl)-N-(2-dimethylamino-ethyl)-propionamide;
N-(2-Dimethylamino-ethyl)-3-(2-ethyl-1,2,3,4-tetra hydro-isoquinolin-5-yl)-N-(2-trifluoromethyl-benzyl)-propionamide;
3-(2-Cyclopropylmethyl-1,2,3,4-tetrahydro-isoquinolin-5-yl)-N-(2-dimethylamino-ethyl)-N-(2-trifluoromethyl-benzyl)-propionamide;
3-(2-Cyclopropylmethyl-1,2,3,4-tetrahydro-isoquinolin-5-yl)-N-(1-methyl-piperidin-4-yl)-N-(2-trifluoromethyl-benzyl)-propionamide;

N-Benzyl-3-(2-cyclopropylmethyl-1,2,3,4-tetrahydro-isoquinolin-5-yl)-N-(2-dimethylamino-ethyl)-propionamide;

N-Benzyl-N-(2-dimethylamino-ethyl)-3-(2-propionyl-1,2,3,4-tetrahydro-isoquinolin-5-yl)-propionamide;

N-Benzyl-2-(2-cyclopropylmethyl-1,2,3,4-tetrahydro-isoquinolin-5-yloxy)-N-(3-methyl-butyl)-acetamide N-Benzyl-2-(2-cyclopropylmethyl-1,2,3,4-tetrahydro-isoquinolin-5-yloxy)-N-(2-dimethylamino-ethyl)-acetamide;

5-{[Benzyl-(2-dimethylamino-ethyl)-carbamoyl]-methoxy}-3,4-dihydro-1H-isoquinoline-2-carboxylic acid methyl ester;

N-Benzyl-N-(2-dimethylamino-ethyl)-2-(2-isobutyl-1,2,3,4-tetrahydro-isoquinolin-5-yloxy)-acetamide;

N-Benzyl-N-(2-dimethylamino-ethyl)-2-(2-propionyl-1,2,3,4-tetrahydro-isoquinolin-5-yloxy)-acetamide;

N-(2-Chloro-benzyl)-N-(2-dimethylamino-ethyl)-2-(2-ethyl-1,2,3,4-tetrahydro-isoquinolin-5-yloxy)-acetamide;

N-(2-Chloro-benzyl)-2-(2-cyclopropylmethyl-1,2,3,4-tetrahydro-isoquinolin-5-yl oxy)-N-(2-dimethylamino-ethyl)-acetamide;

N-(2-Dimethylamino-ethyl)-2-(2-ethyl-1,2,3,4-tetrahydro-isoquinolin-5-yloxy)-N-(2-trifluoromethyl-benzyl)-acetamide;

2-(2-Cyclopropylmethyl-1,2,3,4-tetrahydro-isoquinolin-5-yloxy)-N-(2-dimethylamino-ethyl)-N-(2-trifluoromethyl-benzyl)-acetamide;

N-(2-Dimethylamino-ethyl)-N-(2-fluoro-benzyl)-2-(2-methyl-1,2,3,4-tetrahydro-isoquinolin-5-ylamino)-acetamide;

N-(2-Methylamino-ethyl)-2-(2-propionyl-1,2,3,4-tetrahydro-isoquinolin-5-ylamino)-N-(2-trifluoromethyl-benzyl)-acetamide;

N-Benzyl-2-(2-cyclopropylmethyl-1,2,3,4-tetrahydro-isoquinolin-5-ylamino)-N-pyrrolidin-3-yl-acetamide;

2-(2-Cyclopropylmethyl-1,2,3,4-tetrahydro-isoquinolin-5-ylamino)-N-(2-methylamino-ethyl)-N-(2-trifluoromethyl-benzyl)-acetamide;

N-Benzyl-2-(2-cyclopropylmethyl-1,2,3,4-tetrahydro-isoquinolin-5-ylamino)-N-(1-methyl-pyrrolidin-3-yl)-acetamide;

N-Benzyl-2-(2-cyclopropylmethyl-1,2,3,4-tetrahydro-isoquinolin-8-ylamino)-N-(2-dimethylamino-ethyl)-acetamide;

N-Benzyl-N-(2-dimethylamino-ethyl)-2-(2-isobutyl-1,2,3,4-tetrahydro-isoquinolin-8-ylamino)-acetamide;

8-({[Benzyl-(2-dimethylamino-ethyl)-carbamoyl]-methyl}-amino)-3,4-dihydro-1H-isoquinoline-2-carboxylic acid isopropyl ester;

N-Benzyl-2-(2-benzyl-1,2,3,4-tetrahydro-isoquinolin-8-ylamino)-N-(2-dimethylamino-ethyl)-acetamide;

N-Benzyl-2-(2-cyclohexylmethyl-1,2,3,4-tetrahydro-isoquinolin-8-ylamino)-N-(2-dimethylamino-ethyl)-acetamide;

2-(2-Benzoyl-1,2,3,4-tetrahydro-isoquinolin-8-ylamino)-N-benzyl-N-(2-dimethylamino-ethyl)-acetamide;

N-Benzyl-N-(2-dimethylamino-ethyl)-2-(2-methyl-1,2,3,4-tetrahydro-isoquinolin-8-yloxy)-acetamide;

N-Benzyl-N-(2-dimethylamino-ethyl)-2-(2-ethyl-1,2,3,4-tetrahydro-isoquinolin-8-yloxy)-acetamide;

N-Benzyl-2-(2-cyclopropylmethyl-1,2,3,4-tetrahydro-isoquinolin-8-yloxy)-N-(2-dimethylamino-ethyl)-acetamide;

8-{[Benzyl-(2-dimethylamino-ethyl)-carbamoyl]-methoxy}-3,4-dihydro-1H-isoquinoline-2-carboxylic acid methyl ester;

N-Benzyl-N-(2-dimethylamino-ethyl)-2-(2-isobutyl-1,2,3,4-tetrahydro-isoquinolin-8-yloxy)-acetamide;

N-Benzyl-N-(2-dimethylamino-ethyl)-2-(2-propionyl-1,2,3,4-tetrahydro-isoquinolin-8-yloxy)-acetamide;

2-(2-Benzoyl-1,2,3,4-tetrahydro-isoquinolin-8-yloxy)-N-benzyl-N-(2-dimethylamino-ethyl)-acetamide;

2-((2-Cyclopentyl-1,2,3,4-tetrahydroisoquinolin-5-yl)amino)-N-(2-(dimethylamino)ethyl)-N-(2-(trifluoromethyl)benzyl)acetamide;

2-((2-(Cyclopropylmethyl)-1-methyl-1,2,3,4-tetrahydroisoquinolin-5-yl)amino)-N-(2-(dimethylamino)ethyl)-N-(2-(trifluoromethyl)benzyl)acetamide; and 2-((2-(Cyclopropylmethyl)-3-methyl-1,2,3,4-tetrahydroisoquinolin-5-yl)amino)-N-(2-(dimethylamino)ethyl)-N-(2-(trifluoromethyl)benzyl)acetamide. 33) Another embodiment relates to compounds according to embodiment 1) which are selected from the following compounds:

2-(2-Cyclopropylmethyl-1,2,3,4-tetrahydro-isoquinolin-5-ylamino)-N-[2-(1-methyl-pyrrolidin-2-yl)-ethyl]-N-(2-trifluoromethyl-benzyl)-acetamide;

2-(2-Cyclopropylmethyl-1,2,3,4-tetrahydro-isoquinolin-5-ylamino)-N-(3-pyrrolidin-1-yl-propyl)-N-(2-trifluoromethyl-benzyl)-acetamide;

4-{2-[[2-(2-Cyclopropylmethyl-1,2,3,4-tetrahydro-isoquinolin-5-ylamino)-acetyl]-(2-trifluoromethyl-benzyl)-amino]-ethyl}-piperazine-1-carboxylic acid tert-butyl ester;

2-(2-Cyclopropylmethyl-1,2,3,4-tetrahydro-isoquinolin-5-ylamino)-N-(2-piperidin-1-yl-ethyl)-N-(2-trifluoromethyl-benzyl)-acetamide;

N-(2-Azepan-1-yl-ethyl)-2-(2-cyclopropylmethyl-1,2,3,4-tetrahydro-isoquinolin-5-ylamino)-N-(2-trifluoromethyl-benzyl)-acetamide;

2-(2-Cyclopropylmethyl-1,2,3,4-tetrahydro-isoquinolin-5-ylamino)-N-(2-diisopropylamino-ethyl)-N-(2-trifluoromethyl-benzyl)-acetamide;

N-[2-(Cyclopropyl-methyl-amino)-ethyl]-2-(2-cyclopropylmethyl-1,2,3,4-tetrahydro-isoquinolin-5-ylamino)-N-(2-trifluoromethyl-benzyl)-acetamide;

2-(2-Cyclopropylmethyl-1,2,3,4-tetrahydro-isoquinolin-5-ylamino)-N-(2-dimethylamino-ethyl)-N-(3-trifluoromethoxy-benzyl)-acetamide;

2-(2-Cyclopropylmethyl-1,2,3,4-tetrahydro-isoquinolin-5-ylamino)-N-(4-hydroxy-cyclohexyl)-N-(2-trifluoromethyl-benzyl)-acetamide;

2-(2-Cyclopropylmethyl-1,2,3,4-tetrahydro-isoquinolin-5-ylamino)-N-(2-hydroxy-3-methoxy-propyl)-N-(2-trifluoromethyl-benzyl)-acetamide;

2-(2-Cyclopropylmethyl-1,2,3,4-tetrahydro-isoquinolin-5-ylamino)-N-(2-methoxy-ethyl)-N-(2-trifluoromethyl-benzyl)-acetamide;

2-(2-Cyclopropylmethyl-1,2,3,4-tetrahydro-isoquinolin-5-ylamino)-N-[1,4]dioxan-2-yl methyl-N-(2-trifluoromethyl-benzyl)-acetamide;

2-(2-Cyclopropylmethyl-1,2,3,4-tetrahydro-isoquinolin-5-ylamino)-N-(2-dimethylamino-ethyl)-N-(2-trifluoromethoxy-benzyl)-acetamide;

2-(2-Cyclopropylmethyl-1,2,3,4-tetrahydro-isoquinolin-5-ylamino)-N-(2-methanesulfonyl-ethyl)-N-(2-trifluoromethyl-benzyl)-acetamide;

2-(2-Cyclopropylmethyl-1,2,3,4-tetrahydro-isoquinolin-5-ylamino)-N-[2-(ethyl-methyl-amino)-ethyl]-N-(2-trifluoromethyl-benzyl)-acetamide;

N-(2-Bromo-benzyl)-2-(2-cyclopropylmethyl-1,2,3,4-tetrahydro-isoquinolin-5-ylamino)-N-(2-dimethylamino-ethyl)-acetamide;

N-(3-Bromo-pyridin-2-ylmethyl)-2-(2-cyclopropylmethyl-1,2,3,4-tetrahydro-isoquinolin-5-ylamino)-N-(2-dimethylamino-ethyl)-acetamide;

N-(3-Bromo-benzyl)-2-(2-cyclopropylmethyl-1,2,3,4-tetrahydro-isoquinolin-5-ylamino)-N-(2-dimethylamino-ethyl)-acetamide;

N-(4-Bromo-benzyl)-2-(2-cyclopropylmethyl-1,2,3,4-tetrahydro-isoquinolin-5-ylamino)-N-(2-dimethylamino-ethyl)-acetamide;

N-(3-Bromo-pyridin-4-ylmethyl)-2-(2-cyclopropylmethyl-1,2,3,4-tetrahydro-isoquinolin-5-ylamino)-N-(2-dimethylamino-ethyl)-acetamide;

2-(2-Cyclopropylmethyl-1,2,3,4-tetrahydr-isoquinolin-5-ylamino)-N-(2-hydroxy-propyl)-N-(2-trifluoromethyl-benzyl)-acetamide;

2-(2-Cyclopropylmethyl-1,2,3,4-tetrahydro-isoquinolin-5-ylamino)-N-(2-hydroxy-2-methyl-propyl)-N-(2-trifluoromethyl-benzyl)-acetamide;

2-(2-Cyclopropylmethyl-1,2,3,4-tetrahydro-isoquinolin-5-ylamino)-N-(3,3,3-trifluoro-2-hydroxy-propyl)-N-(2-trifluoromethyl-benzyl)-acetamide;

2-(2-Cyclopropylmethyl-1,2,3,4-tetrahydro-isoquinolin-5-ylamino)-N-(1-hydroxy-cyclopentylmethyl)-N-(2-trifluoromethyl-benzyl)-acetamide;

2-(2-Cyclopropylmethyl-1,2,3,4-tetrahydro-isoquinolin-5-ylamino)-N-{2-[(2-fluoro-ethyl)-methyl-amino]-ethyl}-N-(2-trifluoromethyl-benzyl)-acetamide;

N-[2-(Allyl-methyl-amino)-ethyl]-2-(2-cyclopropylmethyl-1,2,3,4-tetrahydro-isoquinolin-5-ylamino)-N-(2-trifluoromethyl-benzyl)-acetamide;

2-(2-Cyclopropylmethyl-1,2,3,4-tetrahydro-isoquinolin-5-ylamino)-N-[2-(methyl-prop-2-ynyl-amino)-ethyl]-N-(2-trifluoromethyl-benzyl)-acetamide;

2-(2-Cyclopropylmethyl-1,2,3,4-tetrahydr-isoquinolin-5-ylamino)-N-thiazol-5-yl methyl-N-(2-trifluoromethyl-benzyl)-acetamide;

N-(2-Chloro-benzyl)-2-(2-cyclopropylmethyl-1,2,3,4-tetrahydro-isoquinolin-5-ylamino)-N-[2-(4,4-difluoro-piperidin-1-yl)-ethyl]-acetamide;

N-(3-Chloro-pyridin-2-ylmethyl)-2-(2-cyclopropylmethyl-1,2,3,4-tetrahydro-isoquinolin-5-ylamino)-N-[2-(4,4-difluoro-piperidin-1-yl)-ethyl]-acetamide;

2-(2-Cyclopropylmethyl-1,2,3,4-tetrahydro-isoquinolin-5-ylamino)-N-isoxazol-5-yl methyl-N-(2-trifluoromethyl-benzyl)-acetamide;

N-(3-Chloro-pyridin-2-ylmethyl)-2-(2-cyclopropylmethyl-1,2,3,4-tetrahydro-isoquinolin-5-ylamino)-N-(2-hydroxy-2-methyl-propyl)-acetamide;

3-{[[2-(2-Cyclopropylmethyl-1,2,3,4-tetrahydro-isoquinolin-5-ylamino)-acetyl]-(2-trifluoromethyl-benzyl)-amino]-methyl}-pyrrolidine-1-carboxylic acid tert-butyl ester 2-(2-Cyclopropylmethyl-1,2,3,4-tetrahydro-isoquinolin-5-ylamino)-N-(2-dimethylamino-ethyl)-N-(3-methyl-pyridin-2-ylmethyl)-acetamide;

2-(2-Cyclopropylmethyl-1,2,3,4-tetrahydro-isoquinolin-5-ylamino)-N-(2-dimethylamino-ethyl)-N-pyridin-2-yl methyl-acetamide;

2-(2-Cyclopropylmethyl-1,2,3,4-tetrahydro-isoquinolin-5-ylamino)-N-(2-dimethylamino-ethyl)-N-(5-methyl-pyridin-2-ylmethyl)-acetamide;

2-(2-Cyclopropylmethyl-1,2,3,4-tetrahydro-isoquinolin-5-ylamino)-N-(2-dimethylamino-ethyl)-N-(6-methyl-pyridin-2-ylmethyl)-acetamide;

N-(5-Chloro-pyridin-2-ylmethyl)-2-(2-cyclopropylmethyl-1,2,3,4-tetrahydro-isoquinolin-5-ylamino)-N-(2-dimethylamino-ethyl)-acetamide;

2-(2-Cyclopropylmethyl-1,2,3,4-tetrahydro-isoquinolin-5-ylamino)-N-(2-dimethylamino-ethyl)-N-thiazol-2-ylmethyl-acetamide;

2-(2-Cyclopropylmethyl-1,2,3,4-tetrahydro-isoquinolin-5-ylamino)-N-(2-dimethylamino-ethyl)-N-(4-methyl-thiazol-2-yl methyl)-acetamide;

2-(2-Cyclopropylmethyl-1,2,3,4-tetrahydro-isoquinolin-5-ylamino)-N-(2-dimethylamino-ethyl)-N-(5-fluoro-pyridin-2-ylmethyl)-acetamide;

2-(2-Cyclopropylmethyl-1,2,3,4-tetrahydro-isoquinolin-5-ylamino)-N-(2,6-difluoro-benzyl)-N-(2-dimethylamino-ethyl)-acetamide;

2-(2-Cyclopropylmethyl-1,2,3,4-tetrahydro-isoquinolin-5-ylamino)-N-(2-dimethylamino-ethyl)-N-(3-fluoro-pyridin-2-ylmethyl)-acetamide;

2-(2-Cyclopropylmethyl-1,2,3,4-tetrahydr-isoquinolin-5-ylamino)-N-(3,3-dimethyl-butyl)-N-(3-trifluoromethyl-pyridin-2-ylmethyl)-acetamide;

2-(2-Cyclopropylmethyl-1,2,3,4-tetrahydro-isoquinolin-5-ylamino)-N-(3,3-dimethyl-butyl)-N-(3-methyl-pyridin-2-ylmethyl)-acetamide;

2-(2-Cyclopropylmethyl-1,2,3,4-tetrahydro-isoquinolin-5-ylamino)-N-[2-(4,4-difluoro-piperidin-1-yl)-ethyl]-N-(2-trifluoro methyl-benzyl)-acetamide;

2-(2-Cyclopropylmethyl-1,2,3,4-tetrahydro-isoquinolin-5-ylamino)-N-[2-(4,4-difluoro-piperidin-1-yl)-ethyl]-N-(3-trifluoromethyl-pyridin-2-ylmethyl)-acetamide;

2-(2-Cyclopropylmethyl-1,2,3,4-tetrahydro-isoquinolin-5-ylamino)-N-{2-[methyl-(2,2,2-trifluoro-ethyl)-amino]-ethyl}-N-(3-trifluoromethyl-pyridin-2-ylmethyl)-acetamide;

2-(2-Cyclopropylmethyl-1,2,3,4-tetrahydro-isoquinolin-5-ylamino)-N-[2-(3,3-difluoro-piperidin-1-yl)-ethyl]-N-(2-trifluoromethyl-benzyl)-acetamide;

2-(2-Cyclopropylmethyl-1,2,3,4-tetrahydro-isoquinolin-5-ylamino)-N-[2-(3,3-difluoro-pyrrolidin-1-yl)-ethyl]-N-(2-trifluoromethyl-benzyl)-acetamide;

2-(2-Cyclopropylmethyl-1,2,3,4-tetrahydro-isoquinolin-5-ylamino)-N-[2-(3,3-difluoro-piperidin-1-yl)-ethyl]-N-(3-trifluoromethyl-pyridin-2-ylmethyl)-acetamide;

2-(2-Cyclopropylmethyl-1,2,3,4-tetrahydro-isoquinolin-5-ylamino)-N-[2-(3,3-difluoro-pyrrolidin-1-yl)-ethyl]-N-(3-trifluoromethyl-pyridin-2-ylmethyl)-acetamide;

N-(2-Dimethylamino-ethyl)-2-[2-(2-fluoro-ethyl)-1,2,3,4-tetrahydro-isoquinolin-5-ylamino]-N-(2-trifluoromethyl-benzyl)-acetamide;

2-(2-Cyclopropylmethyl-8-fluoro-1,2,3,4-tetrahydro-isoquinolin-5-ylamino)-N-(2-dimethylamino-ethyl)-N-(2-trifluoromethyl-benzyl)-acetamide;

2-(2-Cyclopropylmethyl-8-fluoro-1,2,3,4-tetrahydro-isoquinolin-5-ylamino)-N-(2-dimethylamino-ethyl)-N-(3-trifluoromethyl-pyridin-2-ylmethyl)-acetamide;

2-(2-Cyclopropylmethyl-6-methyl-1,2,3,4-tetrahydro-isoquinolin-5-ylamino)-N-(2-dimethylamino-ethyl)-N-(2-trifluoromethyl-benzyl)-acetamide;

N-(3-Chloro-pyridin-2-ylmethyl)-N-(2-dimethylamino-ethyl)-2-[2-((1 S*,2S*)-2-fluoro-cyclopropanecarbonyl)-1,2,3,4-tetrahydro-isoquinolin-5-ylamino]-acetamide;

N-{2-[(2-Fluoro-ethyl)-methyl-amino]-ethyl}-2-[2-(2-methoxy-ethyl)-1,2,3,4-tetrahydro-isoquinolin-5-ylamino]-N-(2-trifluoromethyl-benzyl)-acetamide;

N-(3-Chloro-pyridin-2-ylmethyl)-N-(2-dimethylamino-ethyl)-2-[2-(2-methoxy-ethyl)-1,2,3,4-tetrahydro-isoquinolin-5-ylamino]-acetamide;

N-(2-Dimethylamino-ethyl)-2-(2-prop-2-ynyl-1,2,3,4-tetrahydro-isoquinolin-5-ylamino)-N-(2-trifluoromethyl-benzyl)-acetamide;

N-(2-Dimethylamino-ethyl)-2-(2-ethyl-3-oxo-1,2,3,4-tetra-hydro-isoquinolin-5-ylamino)-N-(2-trifluoromethyl-benzyl)-acetamide;
2-(2-Ethyl-3-oxo-1,2,3,4-tetrahydro-isoquinolin-5-ylamino)-N-(2-pyrrolidin-1-yl-ethyl)-N-(2-trifluoromethyl-benzyl)-acetamide;
N-(2-Dimethylamino-ethyl)-2-(2-isobutyl-3-oxo-1,2,3,4-tetrahydro-isoquinolin-5-ylamino)-N-(2-trifluoromethyl-benzyl)-acetamide;
N-(2-Dimethylamino-ethyl)-2-(2-isobutyl-3-oxo-1,2,3,4-tetrahydro-isoquinolin-5-ylamino)-N-(3-trifluoromethyl-pyridin-2-ylmethyl)-acetamide;
2-(2-Isobutyl-3-oxo-1,2,3,4-tetrahydro-isoquinolin-5-ylamino)-N-(2-pyrrolidin-1-yl-ethyl)-N-(2-trifluoromethyl-benzyl)-acetamide;
2-(2-Cyclopropylmethyl-1-oxo-1,2,3,4-tetrahydro-isoquinolin-5-ylamino)-N-(2-dimethylamino-ethyl)-N-(2-trifluoromethyl-benzyl)-acetamide;
(E)-N-(2-Dimethylamino-ethyl)-3-[2-(2-methoxy-ethyl)-1,2,3,4-tetrahydro-isoquinolin-5-yl]-N-(2-trifluoromethyl-benzyl)-acrylamide;
(E)-N-(2-Dimethylamino-ethyl)-3-[2-(2-methoxy-ethyl)-1,2,3,4-tetrahydro-isoquinolin-5-yl]-N-(3-trifluoromethyl-pyridin-2-ylmethyl)-acryl amide;
(E)-N-(3-Chloro-pyridin-2-ylmethyl)-N-(2-dimethylamino-ethyl)-3-[2-(2-methoxy-ethyl)-1,2,3,4-tetrahydro-isoquinolin-5-yl]-acrylamide;
(E)-N-(3-Chloro-pyridin-2-ylmethyl)-3-(2-cyclopropylmethyl-1,2,3,4-tetrahydro-isoquinolin-5-yl)-N-(2-hydroxy-2-methyl-propyl)-acrylamide;
(E)-N-(3-Chloro-pyridin-2-ylmethyl)-N-(2-dimethylamino-ethyl)-3-[2-((1R*,2R*)-2-fluoro-cyclopropanecarbonyl)-1,2,3,4-tetrahydro-isoquinolin-5-yl]-acrylamide;
(E)-N-(3-Chloro-pyridin-2-ylmethyl)-3-(2-cyclopropylmethyl-1,2,3,4-tetrahydro-isoquinolin-5-yl)-N-(2-dimethylamino-ethyl)-acrylamide;
(E)-N-(3-Chloro-pyridin-2-ylmethyl)-3-(2-cyclopropylmethyl-1,2,3,4-tetrahydro-isoquinolin-5-yl)-N-[2-(4,4-difluoro-piperidin-1-yl)-ethyl]-acrylamide;
N-(2-Dimethylamino-ethyl)-3-[2-(2-methoxy-ethyl)-1,2,3,4-tetrahydro-isoquinolin-5-yl]-N-(2-trifluoromethyl-benzyl)-propionamide;
N-(2-Dimethylamino-ethyl)-3-[2-(2-methoxy-ethyl)-1,2,3,4-tetrahydro-isoquinolin-5-yl]-N-(3-trifluoromethyl-pyridin-2-ylmethyl)-propionamide;
N-[2-(Allyl-methyl-amino)-ethyl]-3-(2-allyl-1,2,3,4-tetrahydro-isoquinolin-5-yl)-N-(2-trifluoromethyl-benzyl)-propionamide;
3-(2-Allyl-1,2,3,4-tetrahydro-isoquinolin-5-yl)-N-(2-dimethylamino-ethyl)-N-(2-trifluoromethyl-benzyl)-propionamide;
2-(2-Cyclopropylmethyl-1,2,3,4-tetrahydro-isoquinolin-5-yloxy)-N-(2-dimethylamino-ethyl)-N-(2-trifluoromethyl-benzyl)-propionamide;
N-(2-Dimethylamino-ethyl)-2-[2-(tetrahydro-furan-3-yl)-1,2,3,4-tetrahydro-isoquinolin-5-ylamino]-N-(2-trifluoromethyl-benzyl)-acetamide;
2-(2-Cyclobutyl-1,2,3,4-tetrahydro-isoquinolin-5-ylamino)-N-(2-dimethylamino-ethyl)-N-(2-trifluoromethyl-benzyl)-acetamide;
N-(2-Dimethylamino-ethyl)-2-[2-(2-methoxy-1-methyl-ethyl)-1,2,3,4-tetrahydro-isoquinolin-5-ylamino]-N-(2-trifluoromethyl-benzyl)-acetamide;
N-(2-Dimethylamino-ethyl)-2-[2-(1,2-dimethyl-propyl)-1,2,3,4-tetrahydro-isoquinolin-5-ylamino]-N-(2-trifluoromethyl-benzyl)-acetamide;
2-(2-sec-Butyl-1,2,3,4-tetrahydro-isoquinolin-5-ylamino)-N-(2-dimethylamino-ethyl)-N-(2-trifluoromethyl-benzyl)-acetamide;
2-[2-(1-Cyclopropyl-ethyl)-1,2,3,4-tetrahydro-isoquinolin-5-ylamino]-N-(2-dimethylamino-ethyl)-N-(2-trifluoromethyl-benzyl)-acetamide;
N-(2-Dimethylamino-ethyl)-2-[2-(3-methyl-oxetan-3-ylmethyl)-1,2,3,4-tetrahydro-isoquinolin-5-ylamino]-N-(2-trifluoromethyl-benzyl)-acetamide;
N-(2-Dimethylamino-ethyl)-2-[2-(2-methoxy-ethyl)-1,2,3,4-tetrahydro-isoquinolin-5-ylamino]-N-(2-trifluoromethyl-benzyl)-acetamide;
[5-({[(2-Dimethylamino-ethyl)-(2-trifluoromethyl-benzyl)-carbamoyl]-methyl}-amino)-3,4-dihydro-1H-isoquinolin-2-yl]-acetic acid methyl ester;
2-(2-Cyclobutylmethyl-1,2,3,4-tetrahydro-isoquinolin-5-ylamino)-N-(2-dimethylamino-ethyl)-N-(2-trifluoromethyl-benzyl)-acetamide;
2-[2-(2,2-Difluoro-propionyl)-1,2,3,4-tetrahydro-isoquinolin-5-ylamino]-N-(2-dimethylamino-ethyl)-N-(2-trifluoromethyl-benzyl)-acetamide;
N-(2-Dimethylamino-ethyl)-2-[2-((1R*,2R*)-2-fluoro-cyclopropanecarbonyl)-1,2,3,4-tetrahydro-isoquinolin-5-ylamino]-N-(2-trifluoromethyl-benzyl)-acetamide;
2-(2-Cyanomethyl-1,2,3,4-tetrahydro-isoquinolin-5-ylamino)-N-(2-dimethylamino-ethyl)-N-(2-trifluoromethyl-benzyl)-acetamide;
N-(2-Dimethylamino-ethyl)-2-[2-(tetrahydro-furan-3-yl)-1,2,3,4-tetrahydro-isoquinolin-5-ylamino]-N-(3-trifluoromethyl-pyridin-2-ylmethyl)-acetamide;
2-(2-Cyclobutyl-1,2,3,4-tetrahydro-isoquinolin-5-ylamino)-N-(2-dimethylamino-ethyl)-N-(3-trifluoromethyl-pyridin-2-ylmethyl)-acetamide;
2-(2-Cyclobutylmethyl-1,2,3,4-tetrahydro-isoquinolin-5-ylamino)-N-(2-dimethylamino-ethyl)-N-(3-trifluoromethyl-pyridin-2-ylmethyl)-acetamide;
[5-{[(2-Dimethylamino-ethyl)-3-trifluoromethyl-pyridin-2-ylmethyl)carbamoyl]-methyl}-amino)-3,4-dihydro-1H-isoquinolin-2-yl]-acetic acid methyl ester;
N-(2-Dimethylamino-ethyl)-2-[2-(2-methoxy-ethyl)-1,2,3,4-tetrahydro-isoquinolin-5-ylamino]-N-(3-trifluoromethyl-pyridin-2-ylmethyl)-acetamide;
N-(2-Dimethylamino-ethyl)-2-(2-pyridin-2-yl-1,2,3,4-tetrahydro-isoquinolin-5-ylamino)-N-(2-trifluoromethyl-benzyl)-acetamide;
N-(2-Dimethylamino-ethyl)-2-(2-pyrimidin-2-yl-1,2,3,4-tetrahydr-isoquinolin-5-ylamino)-N-(2-trifluoromethyl-benzyl)-acetamide;
N-(2-Dimethylamino-ethyl)-N-(2-trifluoromethyl-benzyl)-2-[2-(4-trifluoromethyl-thiazol-2-yl)-1,2,3,4-tetrahydro-isoquinolin-5-ylamino]-acetamide;
2-(2-Cyclopropylmethyl-1,2,3,4-tetrahydr-isoquinolin-5-ylamino)-N—(R)-1-pyrrolidin-3-ylmethyl-N-(2-trifluoromethyl-benzyl)-acetamide;
2-(2-Cyclopropylmethyl-1,2,3,4-tetrahydro-isoquinolin-5-ylamino)-N—(S)-1-pyrrolidin-3-ylmethyl-N-(2-trifluoromethyl-benzyl)-acetamide;
2-(2-Cyclopropylmethyl-1,2,3,4-tetrahydro-isoquinolin-5-ylamino)-N-pyrrolidin-3-yl-N-(2-trifluoromethyl-benzyl)-acetamide;
2-(2-Cyclopropylmethyl-1-methyl-1,2,3,4-tetrahydro-isoquinolin-5-ylamino)-N-(2-methylamino-ethyl)-N-(2-trifluoromethyl-benzyl)-acetamide;
2-(2-Cyclopropylmethyl-1,2,3,4-tetrahydro-isoquinolin-8-ylamino)-N-(2-methylamino-ethyl)-N-(2-trifluoromethyl-benzyl)-acetamide;

2-(2-Cyclopropanecarbonyl-1,2,3,4-tetrahydro-isoquinolin-5-ylamino)-N-(2-methylamino-ethyl)-N-(2-trifluoromethyl-benzyl)-acetamide;

2-(2-Butyryl-1,2,3,4-tetrahydro-isoquinolin-5-ylamino)-N-(2-methylamino-ethyl)-N-(2-trifluoromethyl-benzyl)-acetamide;

2-(2-Isobutyryl-1,2,3,4-tetrahydro-isoquinolin-5-ylamino)-N-(2-methylamino-ethyl)-N-(2-trifluoromethyl-benzyl)-acetamide;

2-[2-(2-Methoxy-acetyl)-1,2,3,4-tetrahydro-isoquinolin-5-ylamino]-N-(2-methylamino-ethyl)-N-(2-trifluoromethyl-benzyl)-acetamide;

2-(2-Cyclobutanecarbonyl-1,2,3,4-tetrahydro-isoquinolin-5-ylamino)-N-(2-methylamino-ethyl)-N-(2-trifluoromethyl-benzyl)-acetamide;

N-(2-Methylamino-ethyl)-2-[2-(3-methyl-butyryl)-1,2,3,4-tetrahydro-isoquinolin-5-ylamino]-N-(2-trifluoromethyl-benzyl)-acetamide;

N-(2-Methylamino-ethyl)-2-[2-(tetrahydro-furan-3-carbonyl)-1,2,3,4-tetrahydro-isoquinolin-5-ylamino]-N-(2-trifluoromethyl-benzyl)-acetamide;

5-({[(2-Methylamino-ethyl)-(2-trifluoromethyl-benzyl)-carbamoyl]-methyl}-amino)-3,4-dihydro-1H-isoquinoline-2-carboxylic acid methyl ester;

5-({[(2-Methylamino-ethyl)-(2-trifluoromethyl-benzyl)-carbamoyl]-methyl}-amino)-3,4-dihydro-1H-isoquinoline-2-carboxylic acid ethyl ester;

5-({[(2-Methylamino-ethyl)-(2-trifluoromethyl-benzyl)-carbamoyl]-methyl}-amino)-3,4-dihydro-1H-isoquinoline-2-carboxylic acid prop-2-ynyl ester;

5-({[(2-Methylamino-ethyl)-(2-trifluoromethyl-benzyl)-carbamoyl]-methyl}-amino)-3,4-dihydro-1H-isoquinoline-2-carboxylic acid allyl ester;

5-({[(2-Methylamino-ethyl)-(2-trifluoromethyl-benzyl)-carbamoyl]-methyl}-amino)-3,4-dihydro-1H-isoquinoline-2-carboxylic acid 2-fluoro-ethyl ester;

5-({[(2-Methylamino-ethyl)-(2-trifluoromethyl-benzyl)-carbamoyl]-methyl}-amino)-3,4-dihydro-1H-isoquinoline-2-carboxylic acid ethylamide;

2-(2-Acetyl-1,2,3,4-tetrahydro-isoquinolin-5-ylamino)-N-(2-methylamino-ethyl)-N-(3-trifluoromethyl-pyridin-2-ylmethyl)-acetamide;

N-(2-Methylamino-ethyl)-2-(2-propionyl-1,2,3,4-tetrahydro-isoquinolin-5-ylamino)-N-(3-trifluoromethyl-pyridin-2-ylmethyl)-acetamide;

2-(2-Cyclopropanecarbonyl-1,2,3,4-tetrahydro-isoquinolin-5-ylamino)-N-(2-methylamino-ethyl)-N-(3-trifluoromethyl-pyridin-2-ylmethyl)-acetamide;

2-(2-Butyryl-1,2,3,4-tetrahydro-isoquinolin-5-ylamino)-N-(2-methylamino-ethyl)-N-(3-trifluoromethyl-pyridin-2-ylmethyl)-acetamide;

2-(2-Isobutyryl-1,2,3,4-tetrahydro-isoquinolin-5-ylamino)-N-(2-methylamino-ethyl)-N-(3-trifluoromethyl-pyridin-2-ylmethyl)-acetamide;

2-[2-(2-Methoxy-acetyl)-1,2,3,4-tetrahydro-isoquinolin-5-ylamino]-N-(2-methylamino-ethyl)-N-(3-trifluoromethyl-pyridin-2-ylmethyl)-acetamide;

2-(2-Cyclobutanecarbonyl-1,2,3,4-tetrahydro-isoquinolin-5-ylamino)-N-(2-methylamino-ethyl)-N-(3-trifluoromethyl-pyridin-2-ylmethyl)-acetamide;

N-(2-Methylamino-ethyl)-2-[2-(tetrahydro-furan-3-carbonyl)-1,2,3,4-tetrahydro-isoquinolin-5-ylamino]-N-(3-trifluoromethyl-pyridin-2-ylmethyl)-acetamide;

5-({[(2-Methylamino-ethyl)-(3-trifluoromethyl-pyridin-2-ylmethyl)-carbamoyl]-methyl}-amino)-3,4-dihydro-1H-isoquinoline-2-carboxylic acid methyl ester;

5-({[(2-Methylamino-ethyl)-(3-trifluoromethyl-pyridin-2-ylmethyl)-carbamoyl]-methyl}-amino)-3,4-dihydro-1H-isoquinoline-2-carboxylic acid ethyl ester;

5-({[(2-Methylamino-ethyl)-(3-trifluoromethyl-pyridin-2-ylmethyl)-carbamoyl]-methyl}-amino)-3,4-dihydro-1H-isoquinoline-2-carboxylic acid prop-2-ynyl ester;

5-({[2-Methylamino-ethyl)-(3-trifluoromethyl-pyridin-2-ylmethyl)-carbamoyl]-methyl}-amino)-3,4-dihydro-1H-isoquinoline-2-carboxylic acid allyl ester;

5-({[(2-Methylamino-ethyl)-(3-trifluoromethyl-pyridin-2-ylmethyl)-carbamoyl]-methyl}-amino)-3,4-dihydro-1H-isoquinoline-2-carboxylic acid 2-fluoro-ethyl ester;

5-({[(2-Methylamino-ethyl)-(3-trifluoromethyl-pyridin-2-ylmethyl)-carbamoyl]-methyl}-amino)-3,4-dihydro-1H-isoquinoline-2-carboxylic acid ethylamide;

5-({[(2-Methylamino-ethyl)-(3-trifluoromethyl-pyridin-2-ylmethyl)-carbamoyl]-methyl}-amino)-3,4-dihydro-1H-isoquinoline-2-carboxylic acid isopropylamide;

5-({[(2-Methylamino-ethyl)-(3-trifluoromethyl-pyridin-2-ylmethyl)-carbamoyl]-methyl}-amino)-3,4-dihydro-1H-isoquinoline-2-carboxylic acid tert-butylamide;

2-(2-Cyclopropylmethyl-1,2,3,4-tetrahydro-isoquinolin-5-ylamino)-N-[2-(2,2,2-trifluoro-ethylamino)-ethyl]-N-(2-trifluoromethyl-benzyl)-acetamide;

N-(2-Bromo-benzyl)-2-(2-cyclopropylmethyl-1,2,3,4-tetrahydro-isoquinolin-5-ylamino)-N-(2-methylamino-ethyl)-acetamide;

N-(3-Chloro-pyridin-2-ylmethyl)-2-(2-cyclopropylmethyl-1,2,3,4-tetrahydro-isoquinolin-5-ylamino)-N-(2-methylamino-ethyl)-acetamide;

2-(2-Cyclopropylmethyl-1,2,3,4-tetrahydr-isoquinolin-5-ylamino)-N-(2-methylamino-ethyl)-N-(3-trifluoromethyl-pyridin-2-ylmethyl)-acetamide;

2-(2-Cyclopropylmethyl-1,2,3,4-tetrahydro-isoquinolin-5-ylamino)-N-(2-piperazin-1-yl-ethyl)-N-(2-trifluoromethyl-benzyl)-acetamide;

2-(2-Cyclopropylmethyl-1,2,3,4-tetrahydr-isoquinolin-5-ylamino)-N-(2-ethylamino-ethyl)-N-(2-trifluoromethyl-benzyl)-acetamide;

2-(2-Cyclopropylmethyl-1,2,3,4-tetrahydr-isoquinolin-5-ylamino)-N-piperidin-4-yl-N-(2-trifluoromethyl-benzyl)-acetamide;

2-(2-Cyclopropylmethyl-1,2,3,4-tetrahydr-isoquinolin-5-ylamino)-N-pyrrolidin-3-ylmethyl-N-(2-trifluoromethyl-benzyl)-acetamide;

N-(2-Amino-ethyl)-2-(2-cyclopropylmethyl-1,2,3,4-tetrahydro-isoquinolin-5-ylamino)-N-(2-trifluoromethyl-benzyl)-acetamide;

2-(2-Ethyl-1,2,3,4-tetrahydro-isoquinolin-8-ylamino)-N-(2-methylamino-ethyl)-N-(2-trifluoromethyl-benzyl)-acetamide;

2-(2-Acetyl-1,2,3,4-tetrahydro-isoquinolin-5-ylamino)-N-(2-methylamino-ethyl)-N-(2-trifluoromethyl-benzyl)-acetamide;

N-(2-Chloro-benzyl)-2-(2-cyclopropylmethyl-1,2,3,4-tetrahydro-isoquinolin-5-ylamino)-N-(2-methylamino-ethyl)-acetamide;

N-[2-(Cyclobutyl-methyl-amino)-ethyl]-2-(2-cyclopropyl-methyl-1,2,3,4-tetrahydro-isoquinolin-5-ylamino)-N-(2-trifluoromethyl-benzyl)-acetamide;

2-(2-Cyclopropylmethyl-1,2,3,4-tetrahydr-isoquinolin-5-ylamino)-N-{2-[methyl-(tetrahydr-furan-3-yl)-amino]-ethyl}-N-(2-trifluoromethyl-benzyl)-acetamide;

2-(2-Cyclopropylmethyl-1,2,3,4-tetrahydro-isoquinolin-5-ylamino)-N-[2-(isopropyl-methyl-amino)-ethyl]-N-(2-trifluoro methyl-benzyl)-acetamide;

N-[2-(Cyclopropylmethyl-methyl-amino)-ethyl]-2-(2-cyclopropylmethyl-1,2,3,4-tetra hydro-isoquinolin-5-ylamino)-N-(2-trifluoromethyl-benzyl)-acetamide;
N-[2-(Cyclopentyl-methyl-amino)-ethyl]-2-(2-cyclopropylmethyl-1,2,3,4-tetrahydro-isoquinolin-5-ylamino)-N-(2-trifluoro methyl-benzyl)-acetamide;
2-(2-Cyclopropylmethyl-1,2,3,4-tetrahydro-isoquinolin-5-ylamino)-N-{2-[(2-fluoro-1-methyl-ethyl)-methyl-amino]-ethyl}-N-(2-trifluoromethyl-benzyl)-acetamide;
2-(2-Cyclopropylmethyl-1,2,3,4-tetrahydr-isoquinolin-5-ylamino)-N-{2-[ethyl-(3-methyl-oxetan-3-ylmethyl)-amino]-ethyl}-N-(2-trifluoromethyl-benzyl)-acetamide;
3-(2-Cyclopropylmethyl-1,2,3,4-tetrahydro-isoquinolin-8-yl)-N-(2-dimethylamino-ethyl)-N-(2-trifluoromethyl-benzyl)-propionamide;
N-(3-Chloro-pyridin-2-ylmethyl)-2-(2-cyclobutyl-1,2,3,4-tetrahydro-isoquinolin-8-ylamino)-N-(2-dimethylamino-ethyl)-acetamide;
N-(3-Bromo-pyridin-2-ylmethyl)-2-(2-cyclobutyl-1,2,3,4-tetrahydro-isoquinolin-8-ylamino)-N-(2-dimethylamino-ethyl)-acetamide;
N-[2-(Allyl-methyl-amino)-ethyl]-2-(2-allyl-1,2,3,4-tetrahydro-isoquinolin-8-ylamino)-N-(2-trifluoromethyl-benzyl)-acetamide;
2-(2-Allyl-1,2,3,4-tetrahydro-isoquinolin-8-ylamino)-N-(2-dimethylamino-ethyl)-N-(2-trifluoromethoxy-benzyl)-acetamide;
2-(2-Allyl-1,2,3,4-tetrahydro-isoquinolin-8-ylamino)-N-{2-[(2-fluoro-ethyl)-methyl-amino]-ethyl}-N-(2-trifluoromethyl-benzyl)-acetamide;
2-(2-Allyl-1,2,3,4-tetrahydro-isoquinolin-8-ylamino)-N-(2-dimethylamino-ethyl)-N-(2-trifluoromethyl-benzyl)-acetamide;
N-[2-(Allyl-methyl-amino)-ethyl]-3-(2-allyl-1,2,3,4-tetrahydro-isoquinolin-8-yl)-N-(2-trifluoromethyl-benzyl)-propionamide;
3-(2-Allyl-1,2,3,4-tetrahydro-isoquinolin-8-yl)-N-(2-dimethylamino-ethyl)-N-(2-trifluoromethyl-benzyl)-propionamide;
2-(2-Cyclopropylmethyl-1,2,3,4-tetrahydro-isoquinolin-8-ylamino)-N-(2-dimethylamino-ethyl)-N-(2-trifluoromethyl-benzyl)-acetamide;
N-[2-(Cyclopropyl-methyl-amino)-ethyl]-2-(2-cyclopropylmethyl-1,2,3,4-tetrahydro-isoquinolin-8-ylamino)-N-(2-trifluoromethyl-benzyl)-acetamide;
2-(2-Cyclopropylmethyl-1,2,3,4-tetrahydro-isoquinolin-8-ylamino)-N-(2-dimethylamino-ethyl)-N-(3-trifluoro methoxy-benzyl)-acetamide;
2-(2-Cyclopropylmethyl-1,2,3,4-tetrahydro-isoquinolin-8-ylamino)-N-(2-dimethylamino-ethyl)-N-(2-trifluoro methoxy-benzyl)-acetamide;
2-(2-Cyclopropylmethyl-1,2,3,4-tetrahydro-isoquinolin-8-ylamino)-N-[2-(4,4-difluoro-piperidin-1-yl)-ethyl]-N-(2-trifluoro methyl-benzyl)-acetamide;
2-(2-Cyclopropylmethyl-1,2,3,4-tetrahydro-isoquinolin-8-ylamino)-N-[2-(4,4-difluoro-piperidin-1-yl)-ethyl]-N-(3-trifluoromethyl-pyridin-2-ylmethyl)-acetamide;
2-(2-Cyclopropylmethyl-1,2,3,4-tetrahydro-isoquinolin-8-ylamino)-N-[2-(3,3-difluoro-piperidin-1-yl)-ethyl]-N-(3-trifluoromethyl-pyridin-2-ylmethyl)-acetamide;
2-(2-Cyclopropylmethyl-1,2,3,4-tetrahydro-isoquinolin-8-ylamino)-N-[2-(3,3-difluoro-pyrrolidin-1-yl)-ethyl]-N-(3-trifluoromethyl-pyridin-2-ylmethyl)-acetamide;
2-(2-Cyclopropylmethyl-1,2,3,4-tetrahydro-isoquinolin-8-ylamino)-N-[2-(3,3-difluoro-azetidin-1-yl)-2-oxo-ethyl]-N-(2-trifluoromethyl-benzyl)-acetamide;
2-(2-Cyclopropylmethyl-1,2,3,4-tetrahydro-isoquinolin-8-ylamino)-N-[2-(3,3-difluoro-azetidin-1-yl)-2-oxo-ethyl]-N-(3-trifluoromethyl-pyridin-2-ylmethyl)-acetamide;
N-(3-Chloro-pyridin-2-ylmethyl)-2-(2-cyclopropylmethyl-1,2,3,4-tetrahydro-isoquinolin-8-ylamino)-N-(2-dimethylamino-ethyl)-acetamide;
N-(3-Bromo-pyridin-2-ylmethyl)-2-(2-cyclopropylmethyl-1,2,3,4-tetrahydro-isoquinolin-8-ylamino)-N-(2-dimethylamino-ethyl)-acetamide;
2-(2-Ethyl-1,2,3,4-tetrahydro-isoquinolin-8-ylamino)-N-(2-pyrrolidin-1-yl-ethyl)-N-(2-trifluoromethyl-benzyl)-acetamide;
N-Benzyl-N-(2-diethylamino-ethyl)-2-(2-ethyl-1,2,3,4-tetrahydro-isoquinolin-8-ylamino)-acetamide;
N-(2-Dimethylamino-ethyl)-2-(2-ethyl-1,2,3,4-tetrahydro-isoquinolin-8-ylamino)-N-(2-fluoro-benzyl)-acetamide;
2-(2-Ethyl-1,2,3,4-tetrahydro-isoquinolin-8-ylamino)-N-(1-methyl-piperidin-4-yl)-N-(2-trifluoromethyl-benzyl)-acetamide;
N-(2-Dimethylamino-ethyl)-2-(2-ethyl-1,2,3,4-tetrahydro-isoquinolin-8-ylamino)-N-(2-methyl-benzyl)-acetamide;
N-(2-Chloro-benzyl)-N-(2-dimethylamino-ethyl)-2-(2-ethyl-1,2,3,4-tetrahydro-isoquinolin-8-ylamino)-acetamide;
N-(2-Dimethylamino-ethyl)-2-(2-ethyl-1,2,3,4-tetrahydro-isoquinolin-8-ylamino)-N-(3-trifluoromethyl-benzyl)-acetamide;
N-Benzyl-2-(2-ethyl-1,2,3,4-tetrahydro-isoquinolin-8-ylamino)-N-[2-(1-methyl-pyrrolidin-2-yl)-ethyl]-acetamide;
N-Benzyl-2-(2-ethyl-1,2,3,4-tetrahydro-isoquinolin-8-ylamino)-N-(2-pyrrolidin-1-yl-ethyl)-acetamide;
N-(3-Chloro-pyridin-2-ylmethyl)-N-(2-dimethylamino-ethyl)-2-(2-ethyl-1,2,3,4-tetrahydro-isoquinolin-8-ylamino)-acetamide;
N-(2-Diethylamino-ethyl)-2-(2-ethyl-1,2,3,4-tetrahydro-isoquinolin-8-ylamino)-N-(2-trifluoromethyl-benzyl)-acetamide;
2-(2-Ethyl-1,2,3,4-tetrahydro-isoquinolin-8-ylamino)-N-(1-methyl-piperidin-3-yl)-N-(2-trifluoromethyl-benzyl)-acetamide;
N-(2,6-Difluoro-benzyl)-N-(2-dimethylamino-ethyl)-2-(2-ethyl-1,2,3,4-tetrahydro-isoquinolin-8-ylamino)-acetamide;
N-(2-Dimethylamino-ethyl)-2-(2-ethyl-1,2,3,4-tetrahydro-isoquinolin-8-ylamino)-N-(3-methyl-pyridin-2-ylmethyl)-acetamide;
N-(2-Dimethylamino-ethyl)-2-(2-ethyl-1,2,3,4-tetrahydro-isoquinolin-8-ylamino)-N-(6-methyl-pyridin-2-ylmethyl)-acetamide;
N-(2-Dimethylamino-ethyl)-2-(2-ethyl-1,2,3,4-tetrahydro-isoquinolin-8-ylamino)-N-(3-fluor-pyridin-2-ylmethyl)-acetamide;
N-(2-Dimethylamino-ethyl)-2-(2-ethyl-1,2,3,4-tetrahydro-isoquinolin-8-ylamino)-N-(3-trifluoromethyl-pyridin-2-ylmethyl)-acetamide;
N-(2-Dimethylamino-ethyl)-2-(2-ethyl-1,2,3,4-tetrahydro-isoquinolin-8-ylamino)-N-(6-trifluoromethyl-pyridin-2-ylmethyl)-acetamide;
N-(2-Dimethylamino-ethyl)-2-(2-methanesulfonyl-1,2,3,4-tetrahydro-isoquinolin-8-ylamino)-N-(2-trifluoromethyl-benzyl)-acetamide;
8-({[(2-Dimethylamino-ethyl)-(2-trifluoromethyl-benzyl)-carbamoyl]-methyl}-amino)-3,4-dihydro-1H-isoquinoline-2-carboxylic acid dimethylamide;

8-({[(2-Dimethylamino-ethyl)-(2-trifluoromethyl-benzyl)-carbamoyl]-methyl}-amino)-3,4-dihydro-1H-isoquinoline-2-carboxylic acid methylamide;

(E)-N-(2-Dimethylamino-ethyl)-3-(2-ethyl-1,2,3,4-tetrahydro-isoquinolin-8-yl)-N-(2-trifluoromethyl-benzyl)-acrylamide;

N-(2-Dimethylamino-ethyl)-2-[2-(2,2-dimethyl-propionyl)-1,2,3,4-tetrahydro-isoquinolin-8-ylamino]-N-(2-trifluoromethyl-benzyl)-acetamide;

2-(2-Benzoyl-1,2,3,4-tetrahydro-isoquinolin-8-ylamino)-N-(2-dimethylamino-ethyl)-N-(2-trifluoromethyl-benzyl)-acetamide;

8-({[(2-Dimethylamino-ethyl)-(2-trifluoromethyl-benzyl)-carbamoyl]-methyl}-amino)-3,4-dihydro-1H-isoquinoline-2-carboxylic acid isopropyl ester;

2-(2-Cyclohexylmethyl-1,2,3,4-tetrahydro-isoquinolin-8-ylamino)-N-(2-dimethylamino-ethyl)-N-(2-trifluoromethyl-benzyl)-acetamide;

N-(2-Dimethylamino-ethyl)-2-(2-ethyl-1,2,3,4-tetrahydro-isoquinolin-8-ylamino)-N-(2-trifluoromethyl-benzyl)-acetamide;

N-(2-Dimethylamino-ethyl)-2-(2-propyl-1,2,3,4-tetrahydro-isoquinolin-8-ylamino)-N-(2-trifluoromethyl-benzyl)-acetamide;

N-(2-Dimethylamino-ethyl)-2-(2-isobutyl-1,2,3,4-tetrahydro-isoquinolin-8-ylamino)-N-(2-trifluoromethyl-benzyl)-acetamide;

N-(2-Dimethylamino-ethyl)-2-(2-propionyl-1,2,3,4-tetrahydro-isoquinolin-8-ylamino)-N-(2-trifluoromethyl-benzyl)-acetamide;

2-(2-Cyclopropanecarbonyl-1,2,3,4-tetrahydro-isoquinolin-8-ylamino)-N-(2-dimethylamino-ethyl)-N-(2-trifluoromethyl-benzyl)-acetamide;

N-(2-Dimethylamino-ethyl)-2-[2-(pyrrolidine-1-carbonyl)-1,2,3,4-tetrahydro-isoquinolin-8-ylamino]-N-(2-trifluoromethyl-benzyl)-acetamide;

N-(2-Dimethylamino-ethyl)-2-[2-(2,2-dimethyl-propyl)-1,2,3,4-tetrahydro-isoquinolin-8-ylamino]-N-(2-trifluoromethyl-benzyl)-acetamide;

N-(2-Dimethylamino-ethyl)-2-(2-methyl-1,2,3,4-tetrahydro-isoquinolin-8-ylamino)-N-(2-trifluoromethyl-benzyl)-acetamide;

2-(2-Cyclopropylmethyl-1,2,3,4-tetrahydro-isoquinolin-8-ylamino)-N-(2-pyrrolidin-1-yl-ethyl)-N-(2-trifluoromethyl-benzyl)-acetamide;

2-(2-Cyclopropylmethyl-1,2,3,4-tetrahydro-isoquinolin-8-ylamino)-N-(2-dimethylamino-ethyl)-N-(3-trifluoromethyl-pyridin-2-ylmethyl)-acetamide;

N-(2-Dimethylamino-ethyl)-2-(2-ethyl-1,2,3,4-tetrahydro-isoquinolin-8-yloxy)-N-(2-trifluoromethyl-benzyl)-acetamide;

2-((R)-2-Cyclopropylmethyl-1-methyl-1,2,3,4-tetrahydro-isoquinolin-5-ylamino)-N-(2-dimethylamino-ethyl)-N-(2-trifluoromethyl-benzyl)-acetamide;

2-((S)-2-Cyclopropylmethyl-1-methyl-1,2,3,4-tetrahydro-isoquinolin-5-ylamino)-N-(2-dimethylamino-ethyl)-N-(2-trifluoromethyl-benzyl)-acetamide;

N-(2-Dimethylamino-ethyl)-2-[2-((1R,2R)-2-fluoro-cyclopropanecarbonyl)-1,2,3,4-tetrahydro-isoquinolin-5-ylamino]-N-(2-trifluoromethyl-benzyl)-acetamide;

N-(2-Dimethylamino-ethyl)-2-[2-((1S,2S)-2-fluoro-cyclopropanecarbonyl)-1,2,3,4-tetrahydro-isoquinolin-5-ylamino]-N-(2-trifluoromethyl-benzyl)-acetamide;

3-(2-Cyclopropylmethyl-1,2,3,4-tetrahydro-isoquinolin-5-ylmethyl)-1-(2-dimethylamino-ethyl)-1-(2-trifluoromethyl-benzyl)-urea;

2-[2-(2,2-Difluoro-cyclopropanecarbonyl)-1,2,3,4-tetrahydro-isoquinolin-5-ylamino]-N-(2-dimethylamino-ethyl)-N-(2-trifluoromethyl-benzyl)-acetamide;

N-(2-Dimethylamino-ethyl)-2-[2-(furan-2-carbonyl)-1,2,3,4-tetrahydro-isoquinolin-5-ylamino]-N-(2-trifluoromethyl-benzyl)-acetamide;

N-(2-Dimethylamino-ethyl)-2-(2-propyl-1,2,3,4-tetrahydro-isoquinolin-5-ylamino)-N-(2-trifluoromethyl-benzyl)-acetamide.

The compounds of formula (I) according to embodiments 1) to 33) and their pharmaceutically acceptable salts can be used as medicaments, e.g. in the form of pharmaceutical compositions for enteral (such especially oral) or parenteral administration (including topical application or inhalation).

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention or treatment of a disease or disorder mentioned herein comprising administering to a subject a pharmaceutically active amount of a compound of formula (I) according to embodiments 1) to 33).

In a preferred embodiment of the invention, the administered amount is comprised between 1 mg and 1000 mg per day, particularly between 5 mg and 500 mg per day, more particularly between 25 mg and 400 mg per day, especially between 50 mg and 200 mg per day.

Whenever the word "between" is used to describe a numerical range, it is to be understood that the end points of the indicated range are explicitly included in the range. For example: if a temperature range is described to be between 40° C. and 80° C., this means that the end points 40° C. and 80° C. are included in the range; or if a variable is defined as being an integer between 1 and 4, this means that the variable is the integer 1, 2, 3, or 4.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C.

For avoidance of any doubt, if compounds are described as useful for the prevention or treatment of certain diseases, such compounds are likewise suitable for use in the preparation of a medicament for the prevention or treatment of said diseases.

The compounds of formula (I) according to embodiments 1) to 33) are useful for the prevention or treatment of disorders relating to a dysfunction of the CXCR7 receptor or its ligands, i.e. relating to a dysfunction of the CXCR7 receptor, or dysfunction of ligands signalling through CXCR7, or dysfunction of CXCR7 ligands (CXCL12 and CXCL11) signalling through their other receptors (CXCR4 and CXCR3).

Diseases or disorders relating to the CXCR7 receptor or its ligands are especially selected from:

cancers (notably carcinomas, leukemias, adenocarcinomas, malignant glioma, glioblastoma multiforme, brain metastases, multiple myelomas, renal clear cell carcinoma, prostate cancer, pancreatic adenocarcinoma, melanoma, metastatic melanoma, hepatocellular carcinoma, colon tumors, breast cancer, non-small cell lung cancer, colorectal cancer, brain tumors, Ewing's sarcoma, lymphoma, Burkitt's lymphoma, Hodgkin's lymphoma, adult T-cell leukemia, lymphoproliferative disease, and Kaposi's sarcoma; as well as choriocarcinoma; especially malignant glioma, glioblastoma multiforme, brain metastases, pancreatic adenocarcinoma, lymphoma, Burkitt's lymphoma, and Hodgkin's lymphoma);

inflammatory diseases (notably asthma, chronic obstructive pulmonary disorder, atherosclerosis, myocarditis, and sarcoidosis; as well as chronic rhinosinusitis; especially chronic rhinosinusitis, asthma, and atherosclerosis);

autoimmune disorders (notably multiple sclerosis, rheumatoid arthritis, inflammatory bowel disease, systemic lupus erythematosus, lupus nephritis, interstitial cystitis, and celiac disease; as well as auto-immune encephalomyelitis, demyelinating diseases, osteoarthritis, and type I diabetes; especially multiple sclerosis, rheumatoid arthritis, inflammatory bowel disease, and auto-immune encephalomyelitis);

transplant rejection (notably renal allograft rejection, cardiac allograft rejection, and graft-versus-host diseases brought about by hematopoietic stem cell transplantation); and fibrosis (notably liver fibrosis, liver cirrhosis, and idiopathic pulmonary fibrosis; especially liver cirrhosis).

Notably such diseases or disorders relating to the CXCR7 receptor or its ligands are cancers and autoimmune disorders.

In addition, further diseases or disorders relating to the CXCR7 receptor or its ligands are diseases involving CXCR7 and/or CXCL12 and/or CXCL11 mediated metastasis, chemotaxis, cell adhesion, trans-endothelial migration, cell proliferation and/or survival.

In addition, further diseases or disorders relating to the CXCR7 receptor or its ligands are pulmonary vascular diseases; acute renal failure; ischemia including cerebral ischemia; injured central nervous system; HSCs transplantation; pulmonary hypertension; Shiga-toxin-associated heomolytic uremic syndrome; preeclampsia; and HIV/AIDS. Even further diseases and disorder relating to the CXCR7 receptor or its ligands are proliferative diabetic retinopathy; West Nile virus encephalitis; acute coronary syndrome; hypertension; vascular injury; angiogenesis; and brain and neuronal dysfunctions (such as inflammatory components of Alzheimer's disease); stress-related disorders (such as anxiety, depression, and posttraumatic stress disorder); and diseases involving opioid receptors. In a sub-embodiment, such a further particular disease or disorder relating to the CXCR7 receptor or its ligands is especially pulmonary hypertension.

In addition, further particular diseases or disorders relating to a dysfunction of the CXCR7 receptor or its ligands are selected from the group consisting of kidney dysfunction; nasal polyposis; cardiac allograft rejection; cardiac dysfunction; atherosclerosis; asthma; glomerulonephritis; contact dermatitis; inflammatory bowel disease; colitis; psoriasis; and reperfusion injury.

In addition, further particular diseases or disorders relating to a dysfunction of the CXCR7 receptor or its ligands are hematopoietic stem cell mobilizations.

The term "cancer" refers to all sorts of cancers such as carcinomas, leukemias, adenocarcinomas, malignant glioma, glioblastoma multiforme, brain metastases, multiple myelomas, renal clear cell carcinoma, prostate cancer, pancreatic adenocarcinoma, melanoma, metastatic melanoma, rhabdomyosarcoma, hepatocellular carcinoma, colon tumors, breast cancer, non-small cell lung cancer, oral tumors, colorectal cancer, gallbladder cancer, brain tumors, Ewing's sarcoma, bladder cancer, meningioma, lymphoma, viral-induced tumors, Burkitt's lymphoma, Hodgkin's lymphoma, adult T-cell leukemia, lymphoproliferative disease, Kaposi's sarcoma, MALT lymphoma, papillary thyroid carcinoma, cervical cancer, and osteosarcoma; primary intraocular B-cell lymphoma; and diseases involving CXCR7 and/or CXCL12 and/or CXCL11 mediated metastasis. In addition, cancer furthermore comprises mesotheliomas, ovarian cancer, head and neck cancer, small cell lung cancer, esophageal cancer, stomach cancer, hepatobiliary cancer, cancer of the small intestine, rectal cancer, kidney cancer, penile cancer, urethral cancer, testicular cancer, vaginal cancer, uterine cancer, thyroid cancer, parathyroid cancer, adrenal cancer, pancreatic endocrine cancer, carcinoid cancer, bone cancer, skin cancer, retinoblastomas, non-Hodgkin's lymphoma, multicentric Castleman's disease or AIDS-associated cancer, primary effusion lymphoma, and neuroectodermal tumors. The term furthermore comprises choriocarcinoma. Preferably the term refers to carcinomas, leukemias, adenocarcinomas, malignant glioma, glioblastoma multiforme, brain metastases, multiple myelomas, renal clear cell carcinoma, prostate cancer, pancreatic adenocarcinoma, melanoma, metastatic melanoma, hepatocellular carcinoma, colon tumors, breast cancer, non-small cell lung cancer, colorectal cancer, brain tumors, Ewing's sarcoma, lymphoma, Burkitt's lymphoma, Hodgkin's lymphoma, adult T-cell leukemia, lymphoproliferative disease, and Kaposi's sarcoma; especially to malignant glioma, glioblastoma multiforme, brain metastases, pancreatic adenocarcinoma, lymphoma, Burkitt's lymphoma, and Hodgkin's lymphoma.

The term "autoimmune disorders" refers to diseases and disorders comprising rheumatoid arthritis (RA); multiple sclerosis (MS); autoimmune encephalomyelitis; and inflammatory bowel disease (IBD, especially comprising Crohn's disease and ulcerative colitis). In addition, autoimmune diseases further comprise disorders such as systemic lupus erythematosus (SLE); psoriasis; psoriatic arthritis; lupus nephritis; interstitial cystitis; celiac disease; antiphospholipid syndrome; thyroiditis such as Hashimoto's thyroiditis; lymphocytic thyroiditis; myasthenia gravis; type I diabetes; uveitis; episcleritis; scleritis; Kawasaki's disease; uveoretinitis; posterior uveitis; uveitis associated with Behcet's disease; uveomeningitis syndrome; allergic encephalomyelitis; atopic diseases such as rhinitis, conjunctivitis, dermatitis; and post-infectious autoimmune diseases including rheumatic fever and post-infectious glomerulonephritis. The term further comprises auto-immune encephalomyelitis; demyelinating diseases; osteoarthritis. In a sub-embodiment, autoimmune disorders include especially rheumatoid arthritis (RA); multiple sclerosis (MS); and inflammatory bowel disease (comprising Crohn's disease and ulcerative colitis); as well as systemic lupus erythematosus (SLE); lupus nephritis; interstitial cystitis; celiac disease; and type I diabetes; as well as in addition auto-immune encephalomyelitis; demyelinating diseases; and osteoarthritis.

The term "inflammatory diseases" refers to diseases and disorders comprising especially chronic rhinusitis as well as asthma, chronic obstructive pulmonary disorder (COPD), atherosclerosis, myocarditis, dry eye disease, sarcoidosis, and inflammatory myopathies, as well as acute lung injury.

The term "transplant rejection" refers to refers to diseases and disorders comprising rejection of transplanted organs such as kidney, liver, heart, lung, pancreas, cornea, and skin; graft-versus-host diseases brought about by (hematopoietic) stem cell transplantation; chronic allograft rejection and chronic allograft vasculopathy.

Fibrosis may be defined as comprising especially liver cirrhosis, as well as idiopathic pulmonary fibrosis, renal fibrosis, endomyocardial fibrosis, and arthrofibrosis. The term further comprises liver fibrosis.

The compounds of formula (I) as defined in embodiments 1) to 33) are in particular useful as therapeutic agents for the prevention or treatment of a cancer. They can be used as single therapeutic agents or in combination with one or more chemotherapy agents and/or radiotherapy and/or targeted therapy. In a sub-embodiment, when a compound of formula (I) is used for the prevention or treatment of a cancer in combination with one or more chemotherapy agents and/or radiotherapy, such cancer is especially a malignant glioma, in particular a glioblastoma multiforme. Such combined treatment may be effected simultaneously, separately, or over a period of time.

The invention, thus, also relates to pharmaceutical compositions comprising a pharmaceutically acceptable carrier material, and:
  a compound of formula (I) as defined in embodiments 1) to 33);
  and one or more cytotoxic chemotherapy agents.

The invention, thus, further relates to a kit comprising
  a pharmaceutical composition, said composition comprising a pharmaceutically acceptable carrier material, and:
    a compound of formula (I) as defined in embodiments 1) to 33);
  and instructions how to use said pharmaceutical composition for the prevention or the treatment of a cancer (especially of a malignant glioma, in particular of a glioblastoma multiforme), in combination with chemotherapy and/or radiotherapy and/or targeted therapy.

The terms "radiotherapy" or "radiation therapy" or "radiation oncology", refer to the medical use of ionizing radiation in the prevention (adjuvant therapy) and/or treatment of cancer; including external and internal radiotherapy.

The term "targeted therapy" refers to the prevention (adjuvant therapy) and/or treatment of cancer with one or more anti-neoplastic agents such as small molecules or antibodies which attack specific types of cancer cells with less harm to normal cells. Some targeted therapies block the action of certain enzymes, proteins, or other molecules involved in the growth and spread of cancer cells. Other types of targeted therapies help the immune system kill cancer cells (immunotherapies); or deliver toxic substances directly to cancer cells and kill them.

The term "chemotherapy" refers to the treatment of cancer with one or more cytotoxic anti-neoplastic agents ("cytotoxic chemotherapy agents"). Chemotherapy is often used in conjunction with other cancer treatments, such as radiation therapy or surgery. The term especially refers to conventional chemotherapeutic agents which act by killing cells that divide rapidly, one of the main properties of most cancer cells. Chemotherapy may use one drug at a time (single-agent chemotherapy) or several drugs at once (combination chemotherapy or polychemotherapy). Chemotherapy using drugs that convert to cytotoxic activity only upon light exposure is called photochemotherapy or photodynamic therapy.

The term "cytotoxic chemotherapy agent" or "chemotherapy agent" as used herein refers to an active anti-neoplastic agent inducing apoptosis or necrotic cell death. When used in combination with the compounds of formula (I), the term especially refers to conventional cytotoxic chemotherapy agents such as:
a) alkylating agents (for example mechlorethamine, chlorambucil, cyclophosphamide, ifosfamide, streptozocin, carmustine, lomustine, melphalan, busulfan, dacarbazine, temozolomide, thiotepa or altretamine);
b) platinum drugs (for example cisplatin, carboplatin or oxaliplatin);
c) antimetabolite drugs (for example 5-fluorouracil, capecitabine, 6-mercaptopurine, methotrexate, gemcitabine, cytarabine, fludarabine or pemetrexed);
d) anti-tumor antibiotics (for example daunorubicin, doxorubicin, epirubicin, idarubicin, actinomycin-D, bleomycin, mitomycin-C or mitoxantrone);
e) mitotic inhibitors (for example paclitaxel, docetaxel, ixabepilone, vinblastine, vincristine, vinorelbine, vindesine or estramustine); or
f) topoisomerase inhibitors (for example etoposide, teniposide, topotecan, irinotecan, diflomotecan or elomotecan).

When used in combination with the compounds of formula (I), preferred cytotoxic chemotherapy agents are the above-mentioned alkylating agents (notably mechlorethamine, chlorambucil, cyclophosphamide, ifosfamide, streptozocin, carmustine, lomustine, melphalan, busulfan, dacarbazine, 3-methyl-(triazen-1-yl)imidazole-4-carboxamide (MTIC) and prodrugs thereof such as especially temozolomide, thiotepa, altretamine; or pharmaceutically acceptable salts of these compounds; in particular temozolomide); and mitotic inhibitors (notably paclitaxel, docetaxel, ixabepilone, vinblastine, vincristine, vinorelbine, vindesine, estramustine; or pharmaceutically acceptable salts of these compounds; in particular paclitaxel). Most preferred cytotoxic chemotherapy agents to be used in combination with the compounds of formula (I) or (II) are those routinely used in the treatment of glioblastoma multiforme, in particular temozolomide. Equally preferred is radiotherapy.

Chemotherapy may be given with a curative intent or it may aim to prolong life or to palliate symptoms.
a) Combined modality chemotherapy is the use of drugs with other cancer treatments, such as radiation therapy or surgery.
b) Induction chemotherapy is the first line treatment of cancer with a chemotherapeutic drug. This type of chemotherapy is used for curative intent.
c) Consolidation chemotherapy is the given after remission in order to prolong the overall disease free time and improve overall survival. The drug that is administered is the same as the drug that achieved remission.
d) Intensification chemotherapy is identical to consolidation chemotherapy but a different drug than the induction chemotherapy is used.
e) Combination chemotherapy involves treating a patient with a number of different drugs simultaneously. The drugs differ in their mechanism and side effects. The biggest advantage is minimising the chances of resistance developing to any one agent. Also, the drugs can often be used at lower doses, reducing toxicity.

f) Neoadjuvant chemotherapy is given prior to a local treatment such as surgery, and is designed to shrink the primary tumor. It is also given to cancers with a high risk of micrometastatic disease.
g) Adjuvant chemotherapy is given after a local treatment (radiotherapy or surgery). It can be used when there is little evidence of cancer present, but there is risk of recurrence. It is also useful in killing any cancerous cells that have spread to other parts of the body. These micrometastases can be treated with adjuvant chemotherapy and can reduce relapse rates caused by these disseminated cells.
h) Maintenance chemotherapy is a repeated low-dose treatment to prolong remission.
i) Salvage chemotherapy or palliative chemotherapy is given without curative intent, but simply to decrease tumor load and increase life expectancy. For these regimens, a better toxicity profile is generally expected.

When combined with the compounds of formula (I), preventive or curative forms of chemotherapy (or mutatis mutandis: radiotherapy) such as those listed under a), b) c), d), e), and especially g) and/or h) above are preferred.

"Simultaneously" or "simultaneous", when referring to an administration type, means in the present application that the administration type concerned consists in the administration of two or more active ingredients by the same route and at the same time.

"Separately" or "separate", when referring to an administration type, means in the present application that the administration type concerned consists in the administration of two or more active ingredients at approximately the same time by at least two different routes. For example when used in combination with radiotherapy, the present CXCR7 modulators would be used "separately".

By administration "over a period of time" is meant in the present application the administration of two or more active ingredients/or of one or more active ingredients in combination with radiotherapy treatment, at different times. In a sub-embodiment, the term refers to an administration method according to which the entire administration of one of the active ingredients and/or of the radiotherapy treatment, is completed before the administration of the other/the others begins. In this way it is possible to administer one of the active ingredients/to use radiotherapy, for several months before administering the other active ingredient or ingredients. Administration "over a period of time" encompasses situations wherein the active ingredients are not given with the same periodicity (e.g. wherein one active ingredient is given once a day and another is given once a week).

Administration "over a period of time" also encompasses situations wherein the CXCR7 modulators of formula (I) would be used in a treatment that starts after an initial chemotherapeutic or radiotherapeutic treatment (for example an induction chemotherapy), optionally in combination with a further/an ongoing chemotherapeutic or radiotherapeutic treatment (for example in combination with a consolidation chemotherapy, an intensification chemotherapy, an adjuvant chemotherapy, or a maintenance chemotherapy; or radiotherapeutic equivalents thereof); wherein such further/ongoing chemotherapeutic or radiotherapeutic treatment would be simultaneously, separately, or over a period of time in the sense of "not given with the same periodicity".

The compounds of formula (I) as defined in embodiments 1) to 33) are also useful in a method of treating tumors comprising administering an effective amount of the compound of formula (I) wherein said administration leads to a change of tumor properties, and wherein said modification is achieved by modulating the CXCL12 receptor pathway; wherein said treatment may optionally be effected in combination with a conventional chemotherapeutic or radiotherapeutic treatment (in which case the tumor is notably a malignant glioma, in particular a glioblastoma multiforme). Such combined treatment may be effected simultaneously, separately, or over a period of time.

The compounds of formula (I) as defined in embodiments 1) to 33) are also useful in a method of modulating an immune response comprising the administration of an effective amount of the compound of formula (I) wherein said effective amount modulates an inflammatory disease and wherein said response is mediated by the CXCL12 receptor pathway.

Besides, any preferences and (sub-)embodiments indicated for the compounds of formula (I) (whether for the compounds themselves, salts thereof, compositions containing the compounds or salts thereof, or uses of the compounds or salts thereof, etc.) apply mutatis mutandis to compounds of formula (II), (III), ($I_P$), ($II_P$), and ($III_P$).

Preparation of Compounds of Formula (I)

A further aspect of the invention is a process for the preparation of compounds of Formula (I). Compounds according to Formula (I) of the present invention can be prepared from commercially available or well known starting materials according to the methods described in the experimental part, by analogous methods; or according to the general sequence of reactions outlined below, wherein $R^1$, $R^{2a}$, $R^{2b}$, $R^{3a}$, $R^{3b}$, $R^4$, $L^1$, $L^2$, X, Y and $Ar^1$ are as defined for Formula (I). Other abbreviations used herein are explicitly defined, or are as defined in the experimental section. In some instances the generic groups $R^1$, $R^{2a}$, $R^{2b}$, $R^{3a}$, $R^{3b}$, $R^4$, $L^1$, $L^2$, X, Y and $Ar^1$ might be incompatible with the assembly illustrated in the schemes below and so will require the use of protecting groups (PG). The use of protecting groups is well known in the art (see for example "Protective Groups in Organic Synthesis", T.W. Greene, P.G.M. Wuts, Wiley-Interscience, 1999). For the purposes of this discussion, it will be assumed that such protecting groups as necessary are in place. The compounds obtained may also be converted into salts, especially pharmaceutically acceptable salts thereof in a manner known per se.

Amide Coupling as Last Step

Generally examples of Formula (I) are obtained from a carboxylic acid precursor of Structure 1 and an amine of Structure 2 using HATU or another amide coupling reagent in a solvent such as DCM or DMF at room temperature or 0° C. in the presence of a base like TEA or DIPEA.

Structure 1

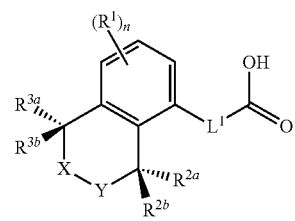

Structure 2

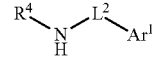

Preparation of Compounds of Structure 1

Compounds of Structure 1 are made by ester cleavage of a compound of Structure 3 in which R represents a tert-Butyl, Ethyl, Methyl group or the like. In a typical reaction a compound of Structure 3 is stirred with a base such as aq. NaOH soln. or aq. LiOH soln. in a solvent such as EtOH, MeOH or THF at room temperature of reflux. In an alternative method, in particular if R is a tert-butyl group a compound of Structure 3 is stirred in DCM at room temperature in the presence of TFA to give a compound of Structure 1.

Structure 3

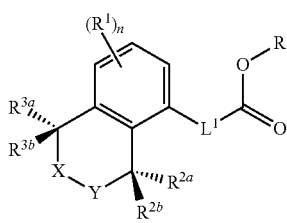

Compounds of Structure 4 which represent a particular case of compounds of Structure 1 can be made by reaction of a compound of Structure 5 with glyoxylic acid monohydrate in presence of NaBH$_3$CN in a solvent such as MeOH or the like.

Structure 4

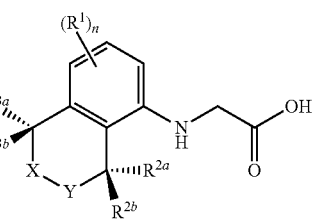

Structure 5

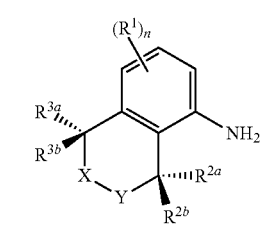

In a particular case wherein $R^{2a}$, $R^{2b}$, $R^{3a}$ and $R^{3b}$ represent H, compounds of Structure 5 can be synthesized from the corresponding 5- or 8-aminoisoquinoline derivatives via a two steps sequence. Thus a 5- or 8-aminoisoquinoline is then reacted with an reagent of type $R^5$LG wherein LG represents a leaving group such as Cl, Br, I, OMs or the like in an alkylation reaction well known by a person skilled in the art. In such a reaction a 5- or 8-aminoisoquinoline is dissolved in a solvent such as MeCN, dioxane, DMF or the like in presence of a reagent of type $R^5$LG and a base such as TEA, DIPEA, K$_2$CO$_3$ or the like at room temperature, or at elevated temperature up to reflux to yield a compound of Structure 6a or a compound of Structure 6b respectively. In the next step a compound of Structure 6a or a compound of Structure 6b is reduced by NaBH$_4$ or Pd/C or the likes in a solvent such as MeOH, EtOH containing or not water and AcOH to yield a compound of Structure 5. In some instances the transformation from a compound of Structure 6a or 6b to a compound of Structure 4 can be made in a one pot-two steps reaction sequence using palladium on charcoal as a catalyst under a pressure of hydrogen gas from 1 to 10 bar.

Structure 6a

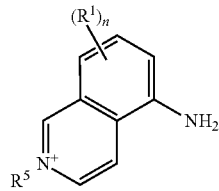

Structure 6b

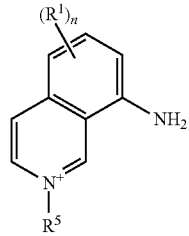

In a particular case compounds of Structure 5 wherein X=NR$^5$ and either one of R$^{3a}$ or R$^{3b}$ but not both represents an alkyl group and respectively wherein Y=NR$^5$ and either one of R$^{2a}$ or R$^{2b}$ but not both represents an alkyl group, a compound of Structure 6a or 6b respectively can be reacted with a Grignard reagent of type R$^{12}$MgCl or R$^{12}$MgBr in a solvent such as ether or THF to give a compound of Structure 7a and 7b respectively. These compounds can then be reduced in a solvent such as MeOH or EtOH with a reducing agent such as NaBH$_4$ at room temperature to give special cases of compounds of Structure 5. In this particular case R$^{12}$ represents one of R$^{3a}$, R$^{3b}$, R$^{2a}$ or R$^{2b}$.

Structure 7a

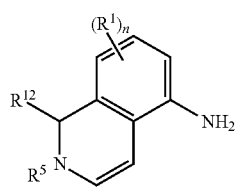

Structure 7b

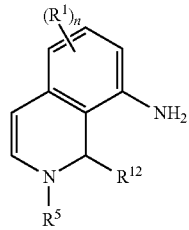

In a particular case a compound of Structure 5 can be made from a compound of Structure 8. In a typical experiment a compound of Structure 8 is reduced with Pd/C in a solvent such as EtOH, THF, EtOAc or the like at RT in presence of H$_2$ or with the help of an H-Cube® hydrogen generator. Alternatively a compound of Structure 5 can be obtained from a compound of Structure 8 by reaction with SnCl$_2$ in a solvent such as DMF or EtOH well known by a person skilled in the art.

Structure 8

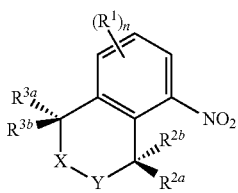

Structure 9

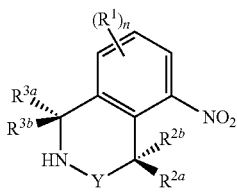

A compound of Structure 8 is commercially available or can be obtained from a compound of Structure 9 by reductive amination using an aldehyde or a ketone of type $R^{13}R^{14}CO$ and a reducing agent such as $NaBH(OAc)_3$, $NaBH_4$ or $NaBH_3CN$ or the like in a solvent such as MeOH, EtOH, DCM, or the like. In this case $R^5$ corresponds to $R^{13}R^{14}CH$. In case X represents NBoc, a compound of Structure 8 can be obtained from a compound of Structure 9 by reaction with Boc anhydride in THF, DCM or water in a presence or absence of a base.

Compounds of Structure 10 which represent a particular case of compounds of Structure 1 can be made by Knoevenagel condensation/decarboxylation sequence of a starting material of Structure 11 with malonic acid in a mixture of pyridine and piperidine used as solvents in a reaction well known by a person skilled in the art. Similarly compounds of Structure 12 which represent a particular case of compounds of Structure 1 can be made by Perkin condensation of a starting material of Structure 11 using propionic anhydride and NaOAc without any solvent at temperature between 150 and 200° C. Compounds of Structure 13 which represent a particular case of compounds of Structure 1 can be made by catalytic hydrogenation of compounds of Structure 10. In a typical experiment well known by a person skilled in the art a compound of Structure 10 is dissolved in MeOH, EtOH or the like in presence or absence of AcOH, then Pd/C is added and the resulting suspension stirred vigorously under an atmosphere of $H_2$.

Structure 10

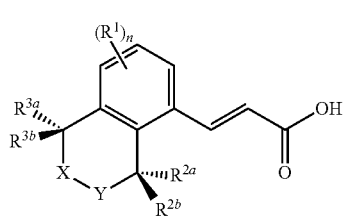

Structure 11

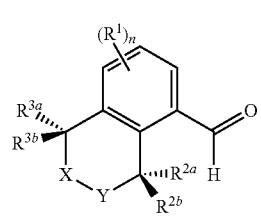

Structure 12

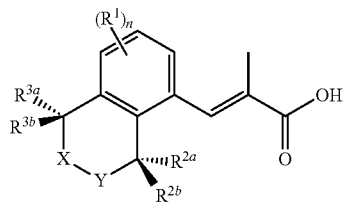

Structure 13

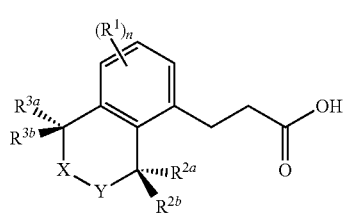

Preparation of Compounds of Structure 3

In case $R^5$ represents a group (PG) such as a Boc or a Cbz group then compounds of Structure 14 which are a particular case of compounds of Structure 3 can be made from compounds of Structure 15 which are a particular case of compounds of Structure 5 and are described in the literature or commercially available. Thus a compound of Structure 15 is reacted with an alkylbromoacetate such as ethylbromoacetate in a solvent such as acetonitrile, in presence of a base such as TEA or DIPEA at room temperature.

Structure 14

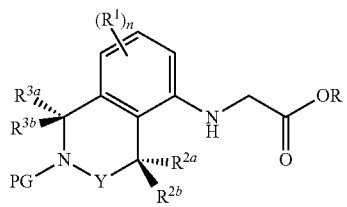

Structure 15

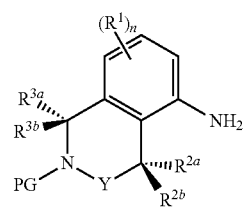

Structure 16

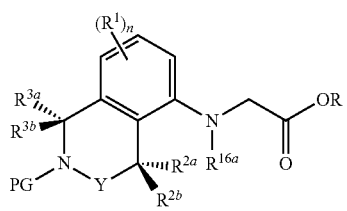

Compound of Structure 14 can be substituted to form the corresponding compound of Structure 16 which are also particular cases of compounds of Structure 3 by reaction with an aldehyde of type $R^{15}CHO$ in a solvent such as DCM in presence of AcOH and a reducing agent such as $NaBH(OAc)_3$. In this case $R^{16a}$ corresponds to the group $R^{15}CH_2$.

In case $R^5$ represents an alkyl, halogenoalkyl, cycloalkyl or cycloalkylalkyl group then a compound of Structure 17 which is a particular case of compounds of Structure 3 can be made in a two-step procedure from a compound of Structure 16. Hence a compound of Structure 16 dissolved in a solvent such as DCM or the like is reacted with TFA or with a solution of HCl in dioxane at room temperature to give a compound of Structure 18 or its corresponding HCl or TFA salt. The compound of structure 18 is then reacted with an reagent of type $R^5LG$ wherein LG represents a leaving group such as Cl, Br, I, OMs, OTf or the like in an alkylation reaction well known by a person skilled in the art. In such a reaction a compound of Structure 18 is dissolved in a solvent such as MeCN, dioxane, DMF or the like in presence of a reagent of type $R^5LG$ and a base such as TEA, DIPEA, $K_2CO_3$ or the like at room temperature, or at elevated temperature up to reflux. A compound of Structure 18 can also be reacted with an aldehyde or a ketone of type $R^{13}R^{14}C=O$ in a solvent such as MeOH, EtOH and a reducing agent such as $NaBH_4$, $NaBH(OAc)_3$, $NaBH_3CN$ or the like at room temperature. In this case a compound of Structure 17 wherein $R^5$ corresponds to $R^{13}R^{14}CH$ is obtained.

Structure 17

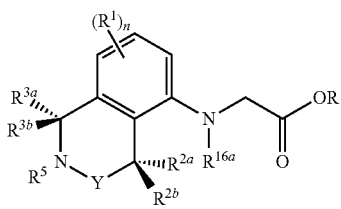

Structure 18

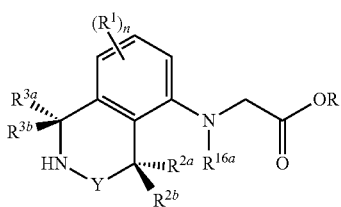

A compound of Structure 19 which is a particular case of compounds of Structure 3 can be made from a compound of Structure 18. In a typical reaction procedure, a compound of Structure 18 is dissolved in a solvent such as DCM, THF or water is reacted with acid chloride or chloroformate $R^{10}COCl$ and a base such as NaOH, $K_2CO_3$, TEA or DIPEA at 0° C. to room temperature, according to a procedure known to a person skilled in the art. Compounds of Structure 17 wherein $R^{16a}$ represents H can also be made from compounds of Structure 20 following a Buchwald-Hartwig type reaction wherein a compound of Structure 20 is reacted with a glycine alkyl ester hydrochloride salt in the presence of a base such as $K_2CO_3$, $Cs_2CO_3$, tBuOK and ligand such as BINAP or the like and a palladium reagent such as $Pd_2(dba)_3$, $Pd(PPh_3)_4$ or the like in a solvent such as toluene, dioxane or DMF at a temperature between 60 and 120° C.

Structure 19

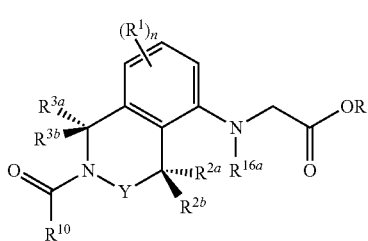

Structure 20

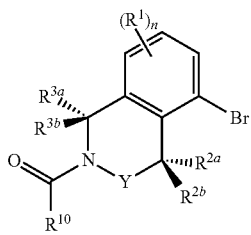

Structure 21

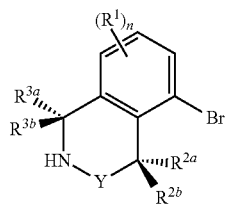

Compounds of Structure 20 can be obtained by reaction of a starting material of Structure 21 dissolved in a solvent such as DCM, THF or water with an acid chloride or chloroformate $R^{10}COCl$ and a base such as NaOH, $K_2CO_3$, TEA or DIPEA at 0° C. to room temperature, according to a procedure known to a person skilled in the art.

Following another procedure, compounds of Structure 22. Which are a particular case of compounds of Structure 3, can be made from compounds of Structure 23a or 23b. In such a procedure a compound of Structure 23a or 23b is allowed to react with a reagent of type $R^5LG$ wherein LG represents a leaving group such as Cl, Br, I, OMs or the like in an alkylation reaction well known by a person skilled in the art. In such a reaction a compound of Structure 23a or 23b is dissolved in a solvent such as MeCN, dioxane, DMF or the like in presence of a reagent of type $R^5LG$ and a base such as TEA, DIPEA, $K_2CO_3$ or the like at room temperature, or at elevated temperature up to reflux to yield a compound of Structure 24a or 24b. Then a compound of Structure 24a or 24b is reduced by $NaBH_4$ in a solvent such as MeOH or EtOH in the presence or the absence of water. Alternatively this last step can be carried out in the presence of $H_2$ with a metal catalyst, especially with Pd/C.

Following yet another procedure, the two steps described for the synthesis of a compound of Structure 22 from a compound of Structure 23a or 23b can be inverted. In a first step a compound of Structure 23a or 23b can be reduced by use of $PtO_2$ in a solvent such as AcOH or EtOH in presence of an acid under catalytic hydrogenation conditions to yield a compound of Structure 25a or 25b respectively. Then a compound of Structure 25a or 25b can be reacted with:

- an aldehyde or a ketone of type $R^{13}R^{14}CO$ and a reducing agent such as $NaBH(OAc)_3$, $NaBH_4$ or $NaBH_3CN$ or the like in a solvent such as MeOH, EtOH, DCM, or the like. In this case $R^5$ corresponds to $R^{13}R^{14}CH$
- a carboxylic acid of type $R^{10}C(O)OH$ in a solvent such as DMF or DCM or a mixture of both with a coupling reagent such as HATU or the like with or without a base such as DIPEA or TEA at a temperature between 0° C. and RT. In this case a compound of Structure 22 wherein $R^5$ corresponds to $R^{10}CO$ is obtained.

Structure 22
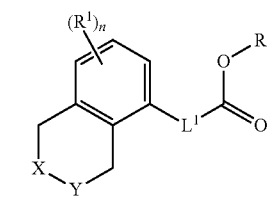

Structure 23a
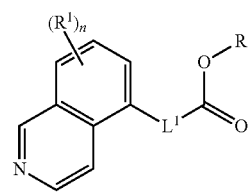

Structure 23b
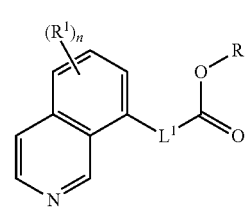

Structure 24a
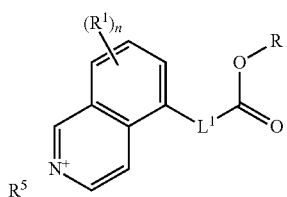

Structure 24b
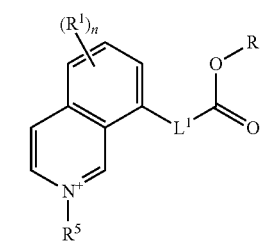

Structure 25a
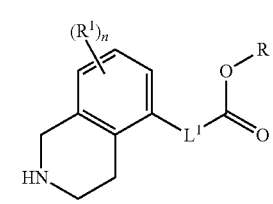

Structure 25b
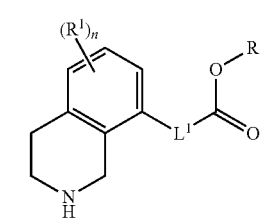

Compounds of Structure 23a or 23b are easily accessible from known procedures or are commercially available. In a particular case wherein $L^1$ represents —NHCH$_2$—, —NHCHR$^{16a}$— or —NHCR$^{16b}$R$^{16c}$—, compounds of Structure 23a or 23b can be obtained by reaction of a compound of Structure 26a or 26b respectively following a Buchwald-Hartwig type reaction wherein a starting material of Structure 27 is reacted with a glycine alkyl ester hydrochloride salt in the presence of a base such as K$_2$CO$_3$, Cs$_2$CO$_3$, tBuOK and ligand such as BINAP or the like and a palladium reagent such as Pd$_2$(dba)$_3$, Pd(PPh$_3$)$_4$ or the like in a solvent such as toluene, dioxane or DMF at a temperature between 60 and 120° C.

Structure 26a
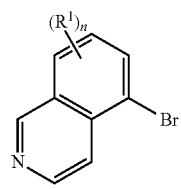

Structure 26b
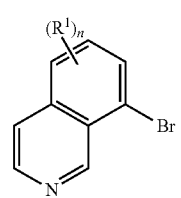

Compounds of Structure 27a and 27b which are a particular case of compounds of Structure 3 can be obtained from commercially available compounds of Structure 28. In a alkylation reaction well known to a person skilled in the art, a starting material of Structure 28 is dissolved in acetone, MeCN, THF or the like and reacted at a temperature between 40 and 80° C. with a reagent of type R$^{17a}$CH(Br)CO$_2$R or R$^{17b}$R$^{17c}$C(Br)CO$_2$R respectively in presence of a base such as TEA, DIPEA, or K$_2$CO$_3$ or the like to yield a compound of Structure 27.

Structure 27a
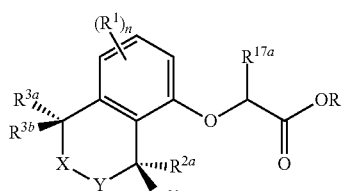

Structure 27b
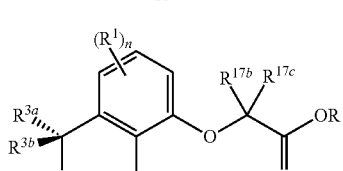

Structure 28
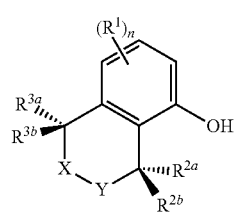

Compounds of Structure 29 which are a particular case of compounds of Structure 22 and as such a particular case of compounds of Structure 3 can be made from compounds of Structure 30. Typically a compound of Structure 30 is dissolved in DCM or THF and reacted with:

- one equivalent of an aldehyde or a ketone of type $R^{13}R^{14}C=O$ in a solvent such as MeOH, EtOH with addition of water and a reducing agent such as $NaBH_4$, $NaBH(OAc)_3$, $NaBH_3CN$ or the like at room temperature with or without addition of a dehydrating agent such as $ZnCl_2$. In this case a compound of Structure 29 wherein $R^5$ corresponds to $R^{13}R^{14}CH$ is obtained.
- an acetyl chloride or a chloroformate of type $R^{10}C(O)Cl$, alternatively an anhydride of type $R^{10}C(O)OC(O)R^{10}$ in a solvent such as DCM or THF or the like with a base such as TEA or DIPEA at a temperature between 0° C. and room temperature. Or alternatively a carboxylic acid of type $R^{10}C(O)OH$ in a solvent such as DMF, DCM or a mixture of both with a coupling reagent such as HATU and the like and a base such as TEA or DIPEA. In this case a compound of Structure 29 wherein $R^5$ corresponds to $R^{10}CO$ is obtained.
- a reagent of type $R^5LG$ wherein LG represents a leaving group such as a Br or Cl atom, a methanesulfonate or a trifluoromethanesulfonate group in a solvent such as DMF, MeCN or THF with a base such as TEA or DIPEA or the like.

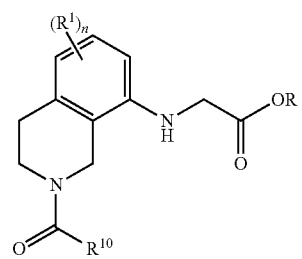

Structure 29

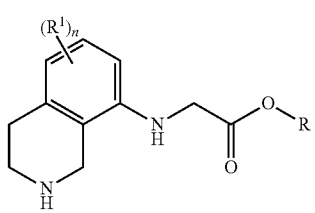

Structure 30

Compounds of Structure 30 can be made from compounds of Structure 31 by a reduction reaction following a method already described for the synthesis of compounds of Structure 25a and 25b from compounds of Structure 23a or 23b respectively. Compounds of Structure 31 are a particular case of compounds of Structure 23a and 23b and are made following the method described for their syntheses. Alternatively compounds of Structure 30 or salts thereof can be made from the corresponding compounds of Structure 32 according to a Boc cleavage reaction wherein a compound of Structure 32 is dissolved in DCM and reacted with TFA or HCl soln. in dioxane. Compounds of Structure 32 are a particular case of compounds of Structure 29.

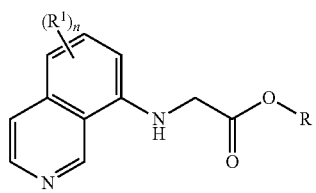

Structure 31

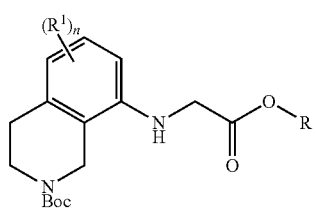

Structure 32

Compounds of Structure 29 can alternatively be made from compounds of Structure 32 over 4 steps. First a compound of Structure 32 is protected on the anilinic N-atom by a TFA amide formation following a reaction wherein a compound of Structure 32 is dissolved in DCM together with a base such as TEA or DIPEA followed by trifluoroacetic anhydride at 0° C. to room temperature to yield a compound of Structure 35. The Boc protecting group of a compound of Structure 35 is then removed in DCM or dioxane or a mixture of both by reaction with TFA or HCl soln. in dioxane to give a compound of Structure 34 or a salt thereof. A compound of Structure 33 is then obtained from a compound of Structure 34 by a reaction analogous to the formation of a compound of Structure 29 from a compound of Structure 30. In the last step, the compound of Structure 33 obtained is reacted in a mixture of MeOH or EtOH and water with a base such as $K_2CO_3$, $Na_2CO_3$ or the like at elevated temperature between 50 and 100° C. to give a compound of Structure 29 following a method of deprotection of trifluoroacetamide well known from a person skilled in the art.

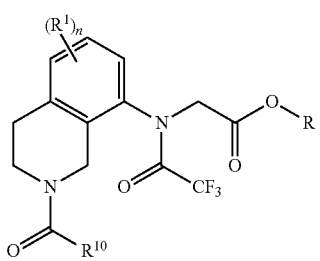

Structure 33

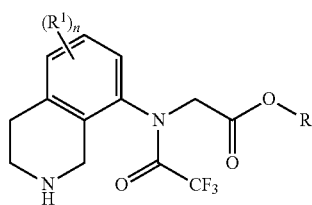

Structure 34

Structure 35

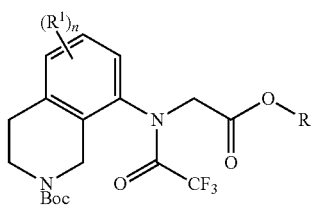

Compounds of Structure 36 which are particular cases of compounds of Structure 3 can be made from compounds of Structure 39 (which are a particular case of compounds of Structure 10) in three steps. Hence a compound of Structure 39 can be esterified to give a compound of Structure 38 by reaction with ethyl iodide in a solvent such as MeCN with a base such as $Cs_2CO_3$ or the like at a temperature above RT for example 55° C. A compound a Structure 37 can be obtained from a compound of Structure 38 by a classical Boc cleavage reaction well known by a person skilled in the art. Finally a compound of Structure 36 is obtained after reaction with:

- a reagent of type $R^5LG$ wherein LG represents a leaving group such as a Br or Cl atom, a methanesulfonate or a trifluoromethanesulfonate group in a solvent such as DMF, MeCN or THF with a base such as TEA or DIPEA or the like.
- one equivalent of an aldehyde or a ketone of type $R^{13}R^{14}C=O$ in a solvent such as MeOH, EtOH with addition of water and a reducing agent such as $NaBH_4$, $NaBH(OAc)_3$, $NaBH_3CN$ or the like at room temperature with or without addition of a dehydrating agent such as $ZnCl_2$. In this case a compound of Structure 36 respectively wherein $R^5$ corresponds to $R^{13}R^{14}CH$ is obtained.
- a carboxylic acid of type $R^{10}C(O)OH$ in a solvent such as DMF, DCM or a mixture of both with a coupling reagent such as HATU and the like and a base such as TEA or DIPEA. In this case a compound of Structure 36 respectively wherein $R^5$ corresponds to $R^{10}CO$ is obtained.

Structure 36

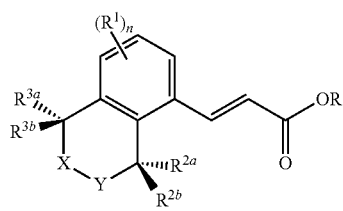

Structure 37

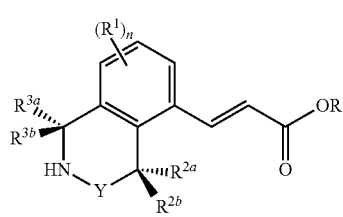

Structure 38

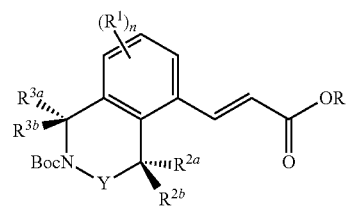

Structure 39

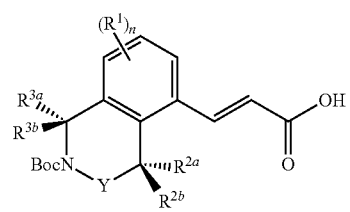

In analogy, compounds of Structure 40 which are particular cases of compounds of Structure 3 can be made from compounds of Structure 38. Hence a compound of Structure 38 can be reduced with palladium on charcoal in a catalytic hydrogenation reaction procedure well known by a person skilled in the art to give a compound of Structure 42. A compound a Structure 41 can be obtained from a compound of Structure 42 by a classical Boc cleavage reaction with TFA or HCl soln. in dioxane in a solvent such as DCM or dioxane. Finally a compound of Structure 40 is obtained after reaction with a reagent of type $R^5LG$ wherein LG represents a leaving group such as a Br or Cl atom, a methanesulfonate or a trifluoromethanesulfonate group in a solvent such as DMF, MeCN or THF with a base such as TEA or DIPEA or the like.

Structure 40

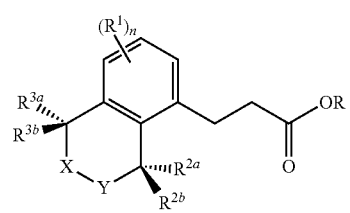

Structure 41

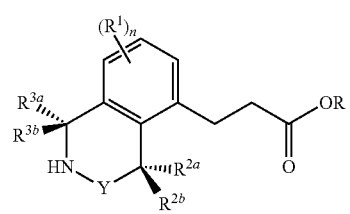

Structure 42

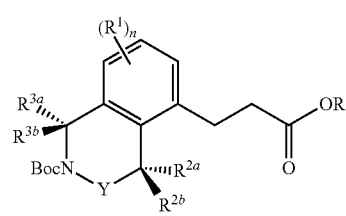

Synthesis of Compounds of Structure 2

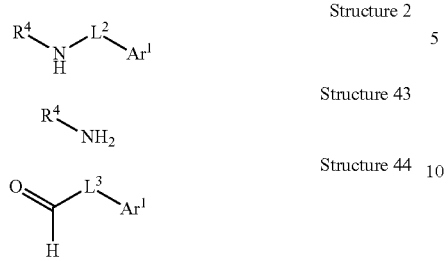

Structure 2

Structure 43

Structure 44

Compounds of Structure 2 are commercially available or are made by condensation of a primary amine of Structure 43 with an aldehyde of Structure 44 in a typical reductive amination reaction with a reducing agent such as NaBH(OAc)$_3$, NaBH$_3$CN or NaBH$_4$ in a solvent such as THF, DCM, MeOH, water or the like at temperatures between 0° C. and reflux, preferentially at room temperature. In this case L$^2$ corresponds to —CH$_2$-L$^3$.

Structure 45

Compounds of Structure 2 can also be obtained by condensation of an amine of Structure 43 and a compound of Structure 45 with LG=halogen like Cl, Br or I in a solvent such as EtOH, MeOH, THF, or dioxane at temperatures between 0° C. and reflux, preferentially at refluxing temperature in the presence of NaI in the case of LG=halogen like Cl or Br.

ture 48 into the amide of Structure 49 involves treatment of the N-protected amine of Structure 48 with the in situ prepared dimethylaluminum amide resulting from the reaction of a trialkyl aluminium compound like trimethyl aluminium with an amine HNR$^6$R$^7$ in a solvent like toluene, DCM or DCE at temperatures between RT and reflux. During this reaction the N-protecting group can be spontaneously cleaved or it as to be removed by treatment with an acid like hydrochloric acid or trifluoroacetic acid in a solvent like MeOH or dioxane. An amine of Structure 50 can be directly used for the preparation of compounds of Structure 1 as it represents a particular case of compounds of Structure 2. Otherwise, reduction of the amide group of a compound of Structure 50 by treatment with a reducing agent like diborane in THF at temperatures between RT and reflux deliver compounds of Structure 51.

Reaction Scheme B

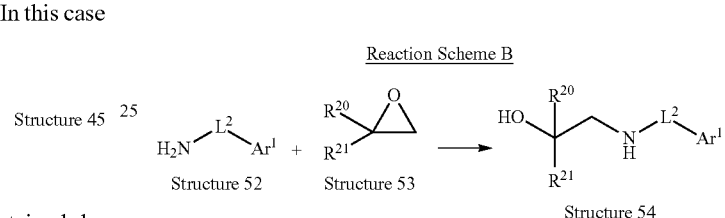

Structure 52    Structure 53    Structure 54

Compounds of Structure 54 which are particular compounds of Structure 2 can also be obtained as illustrated in reaction Scheme B. Thus, by condensation of an amine of Structure 52 and a mono or disubstituted epoxide of Structure 53 in a polar aprotic solvent like MeCN in the presence of calcium trifluoromethanesulfonate at room temperature.

Reaction Scheme A

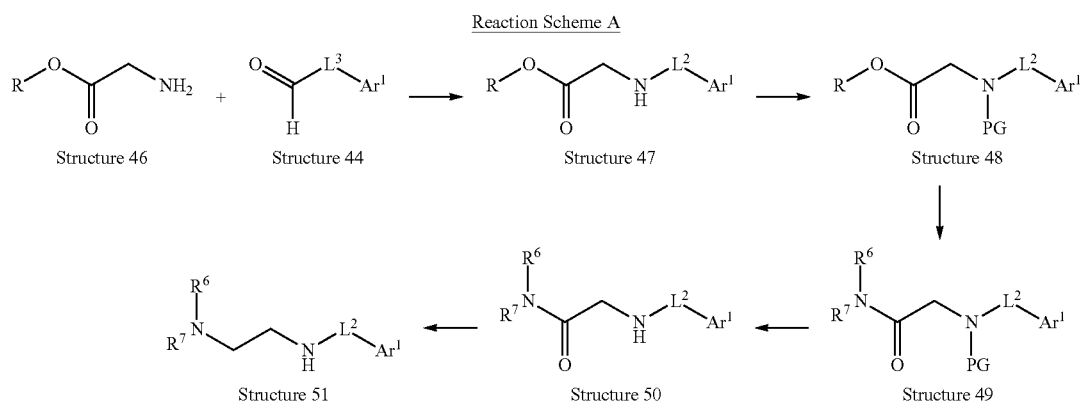

Structure 46    Structure 44    Structure 47    Structure 48

Structure 51    Structure 50    Structure 49

Compounds of Structure 51 which represents a particular case of compounds of Structure 2 may alternatively be prepared as illustrated in reaction Scheme A. An aminoester of Structure 46 is alkylated by treatment with an aldehyde of Structure 44 in a typical reductive amination reaction with a reducing agent such as NaBH(OAc)$_3$, NaBH$_3$CN or NaBH$_4$ in a solvent such as THF, DCM, MeOH, water or the like at temperatures between 0° C. and reflux, preferentially at room temperature. The aminoester of Structure 47 can be protected by treatment with di-tert-butyl dicarbonate in the presence of a base like DIPEA or TEA in a solvent like DCM, AcOEt, dioxane or THF to give the N-protected amine of Structure 48. Transformation of the ester of Struc-

Reaction Scheme C

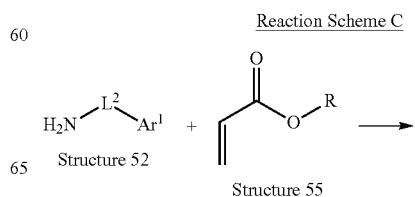

Structure 52    Structure 55

-continued

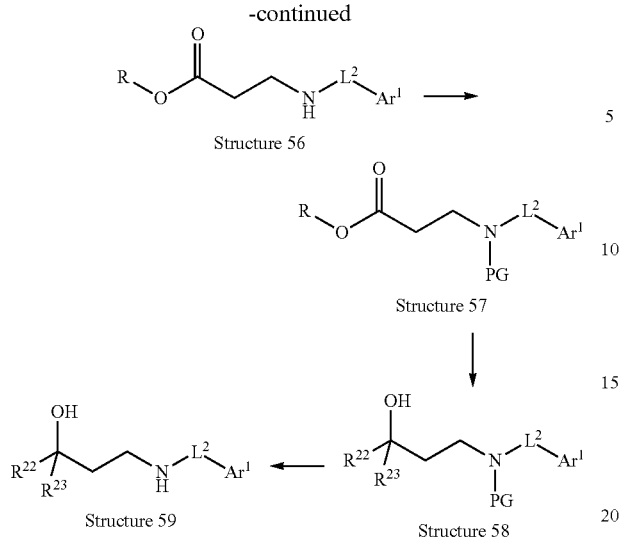

Compounds of Structure 59 which are particular examples of compounds of Structure 2 may alternatively be prepared as illustrated in reaction Scheme C. An amine of Structure 52 is alkylated by treatment with an acryl ester of Structure 55 in a typical Michael addition reaction in a solvent such as MeOH or EtOH or the like at temperatures between 0° C. and reflux, preferentially at room temperature. The aminoester of Structure 56 can be protected by treatment with di-tert-butyl dicarbonate in the presence of a base like DIPEA or TEA in a solvent like DCM, AcOEt, dioxane or THF to give the N-protected amino ester of Structure 57. Transformation of the protected amino ester of Structure 57 into the amino alcohol of Structure 58 involves treatment of the N-protected amine of Structure 57 with an organometallic species like an alkyl magnesium halogenide or alkyl lithium like methyl lithium in a solvent like diethyl ether, THF or dioxane at temperatures between −78° C. and room temperature. The protected amide of Structure 58 is then Boc-deprotected by treatment with an acid, preferentially 4M HCl in dioxane or with TFA in DCM to give the corresponding amine of Structure 59.

Alkylation, acylation, urea formation, carbamoylation (event-TFA amide cleavage) as last step Compounds of Structure 60a or 60b which represent particular cases of compounds of Formula (I) can be obtained directly from compounds of Structure 61a or 61 b respectively.

Thus a compound of Structure 61a or 61b is reacted in the first step with either:
- one equivalent of an aldehyde or a ketone of type $R^{13}R^{14}C=O$ in a solvent such as MeOH, EtOH with addition of water and a reducing agent such as $NaBH_4$, $NaBH(OAc)_3$, $NaBH_3CN$ or the like at room temperature with or without addition of a dehydrating agent such as $ZnCl_2$. In this case a compound of Structure 60a or 60b respectively wherein $R^5$ corresponds to $R^{13}R^{14}CH$ is obtained.
- an acetyl chloride or a chloroformate of type $R^{10}C(O)Cl$ in a solvent such as DCM or THF or the like with a base such as TEA or DIPEA at a temperature between 0° C. and room temperature. Or alternatively a carboxylic acid of type $R^{10}C(O)OH$ in a solvent such as DMF, DCM or a mixture of both with a coupling reagent such as HATU and the like and a base such as TEA or DIPEA. In this case a compound of Structure 60a or 60b respectively wherein $R^5$ corresponds to $R^{10}CO$ is obtained.
- an isocyanate of type $R^{24}NCO$ wherein $R^{24}$ represents an alkyl group such as ethyl, in a solvent such as DCM with a base such as TEA or DIPEA at a temperature between 0° C. and room temperature. In this case a compound of Structure 60a or 60b respectively wherein $R^5$ corresponds to $R^{10}CO$, wherein $R^{10}$ represents $R^{10a}R^{10b}N$ wherein $R^{10a}$ represents $R^{24}$ and $R^{10b}$ represents H is obtained.
- a sulfonyl chloride of type $R^{11}SO_2Cl$ in a solvent such as DCM with a base such as TEA or DIPEA a compound of Structure 60a or 60b respectively is obtained with $R^5$ corresponding to $R^{11}SO_2$.
- a reagent of type $R^5LG$ wherein LG represents a leaving group such as a Br or Cl atom, a methanesulfonate or a trifluoromethanesulfonate group in a solvent such as DMF, MeCN or THF with a base such as TEA or DIPEA or the like.

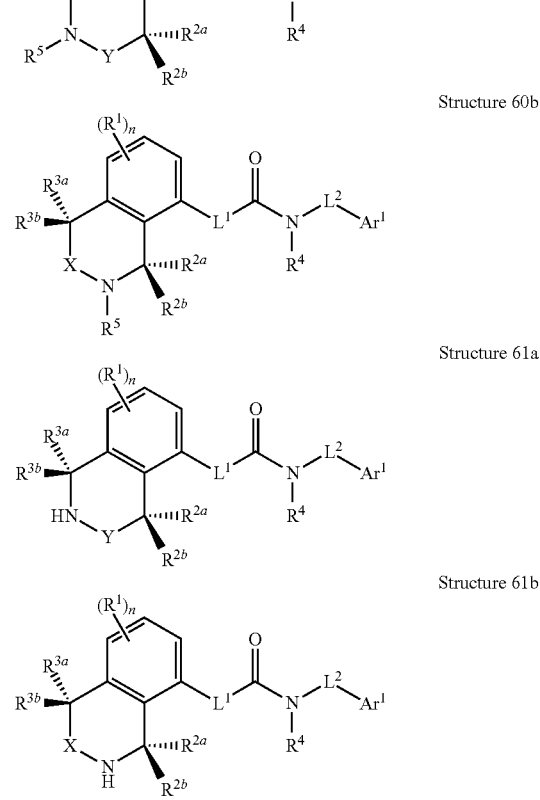

In case $R^{16a}$ is not H, compounds of Structure 62a or 62b which are a particular case of compounds of Formula (I) can be prepared from compounds of Structure 63a and 63b respectively which are particular cases of compounds of Structure 61a and 61b respectively. Following a typical procedure, a compound of Structure 62a or 62b can be obtained by reaction of a compound of Structure 63a or 63b respectively with several equivalents of an aldehyde or a ketone of type $R^{13}R^{14}C=O$ in a solvent such as MeOH, EtOH with addition of water and a reducing agent such as $NaBH_4$, $NaBH(OAc)_3$, $NaBH_3CN$ or the like at room temperature. In this case a compound of Structure 62a or 62b wherein $R^5$ is equal to $R^{16a}$ corresponding to $R^{13}R^{14}CH$ is obtained.

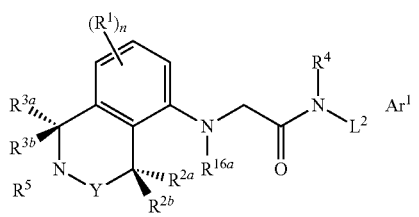

Structure 62a

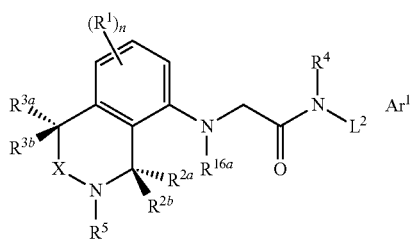

Structure 62b

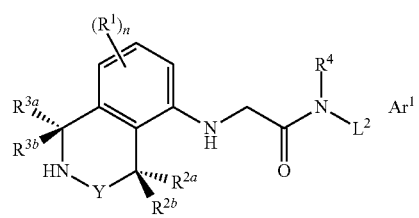

Structure 63a

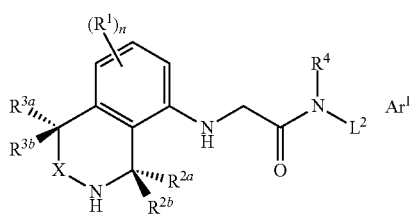

Structure 63b

In case $R^{16a}$ is equal to H, a compound of Structure 62a or 62b can be obtained in a two steps procedure from a compound of Structure 65a or 65b respectively.

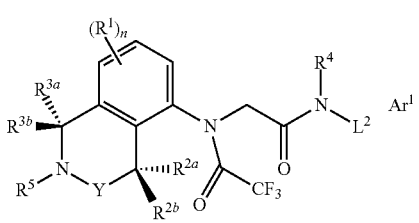

Structure 64a

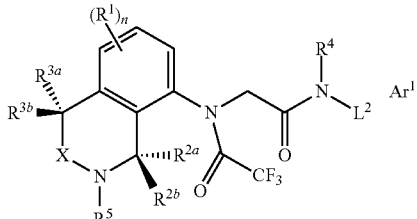

Structure 64b

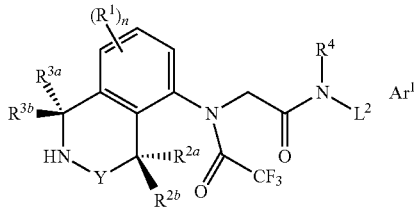

Structure 65a

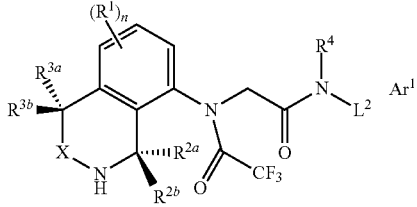

Structure 65b

Thus a compound of Structure 65a or 65b is reacted in the first step with either:

- an aldehyde or a ketone of type $R^{13}R^{14}C=O$ in a solvent such as MeOH, EtOH with addition of water and a reducing agent such as $NaBH_4$, $NaBH(OAc)_3$, $NaBH_3CN$ or the like at room temperature, adding or not $ZnCl_2$ as a dehydrating agent. In this case a compound of Structure 64a or 64b respectively wherein $R^5$ corresponds to $R^{13}R^{14}CH$ is obtained.
- an acetyl chloride or a chloroformate of type $R^{10}C(O)Cl$ in a solvent such as DCM or THF or the like with a base such as TEA or DIPEA at a temperature between 0° C. and room temperature. Or alternatively a carboxylic acid of type $R^{10}C(O)OH$ in a solvent such as DMF, DCM or a mixture of both with a coupling reagent such as HATU and the like and a base such as TEA or DIPEA. In this case a compound of Structure 64a or 64b respectively wherein $R^5$ corresponds to $R^{10}CO$ is obtained
- a sulfonyl chloride of type $R^{11}SO_2Cl$ in a solvent such as DCM with a base such as TEA or DIPEA a compound of Structure 64a or 64b respectively is obtained with $R^5$ corresponding to $R^{11}SO_2$.
- a reagent of type $R^{10a}R^{10b}NC(O)Cl$ in a solvent such as DCM with a base such as TEA or DIPEA or alternatively a reagent of type $R^{17}R^{18}NC(O)O(pNO_2Ph)$ made in situ from the reaction of an amine hydrochloride of type $R^{10a}R^{10b}NH$ HCl and 4-nitrophenylchloroformate in DCM in the presence of a base such as $Na_2CO_3$ or $NaHCO_3$, a compound of Structure 64a or 64b respectively is obtained with $R^5$ corresponding to $R^{10}CO$ wherein $R^{10}$ corresponds to $R^{10a}R^{10b}N$
- a reagent of type $R^5LG$ wherein LG represents a leaving group such as a I, Br or Cl atom, a methanesulfonate or a trifluoromethanesulfonate group and $R^5$ an alkyl residue in a solvent such as DMF, toluene, MeCN or THF with a base such as TEA or DIPEA or the like.

a reagent of type R⁵LG wherein LG represents a leaving group such as a I, Br or Cl atom, a methanesulfonate or a trifluoromethanesulfonate group and R⁵ an aromatic or heteroaromatic residue in a solvent such as toluene, dioxane or DMF, a palladium catalyst such as Pd₂(dba)₃ and a ligand such as DavePhos or the like with a base such as sodium tert-butoxide or the like In the second step, the compound of Structure 64a or 64b obtained from the first step is reacted in a mixture of MeOH or EtOH and water with a base such as K₂CO₃, Na₂CO₃ or the like at elevated temperature between 50 and 100° C. to give a compound of Structure 62a or 62b respectively wherein R¹⁶ᵃ represents H, following a method of deprotection of trifluoroacetamide well known from a person skilled in the art.

Preparation of compounds of Structure 61a and 61b (and compounds of structure 63a and 63b)

Compounds of Structure 61a and 61 b and salts thereof and compounds of Structure 63a and 63b and salt thereof which are particular cases of compounds of Structure 61a and 61b are made from compounds of Structure 66a and 66b respectively wherein PG represents a Boc group or a benzyloxycarbonyl group. In case PG represents a Boc group, in a typical experiment, a compound of Structure 66a or 66b is diluted in a solvent such as DCM and TFA is added. The resulting mixture is allowed to stir at a temperature between 0° C. to 40° C. Alternatively a compound of Structure 66a or 66b is diluted in dioxane, THF or the like and HCl solution in dioxane, THF or ether is added to form a compound of Structure 61a or 61 b respectively. In case PG represents a benzyloxycarbonyl group and L¹ does not represent —C≡C—, a compound of Structure 66a or 66b respectively is dissolved in EtOAc and catalytically reduced by hydrogen in presence of palladium on charcoal to give a compound of Structure 61a or 61 b respectively following a deprotection reaction condition well known by a person skilled in the art.

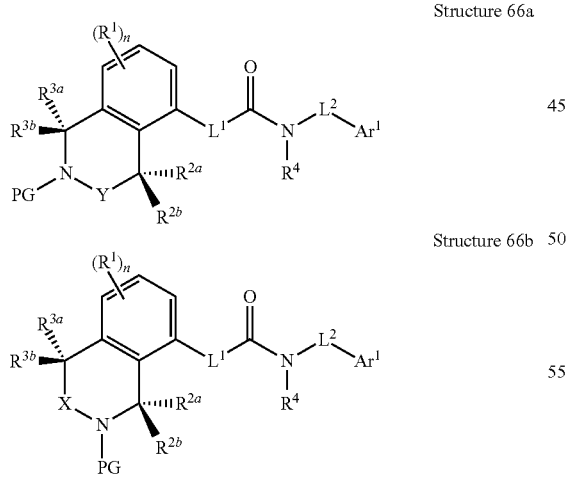

Structure 66a

Structure 66b

Compounds of Structure 66a or 66b can be but are not necessarily special cases of compounds of Formula (I) and can be obtained from compounds of Structure 1 wherein X=NBoc or Y=NBoc respectively or X=NCbz or Y=NCbz respectively following an amide coupling experiment described for the preparation of compounds of Formula (I) from compounds of Structure 1.

Preparation of compounds of Structure 65a and 65b

Compounds of Structure 65a and 65b are made from compounds a Structure 67a and 67b respectively which are a particular case of compounds of Structure 42a and 42b respectively following a typical reaction of Boc deprotection already described for the preparation of compounds of Structure 61a and 61b respectively from compounds of Structure 66a or 66b respectively.

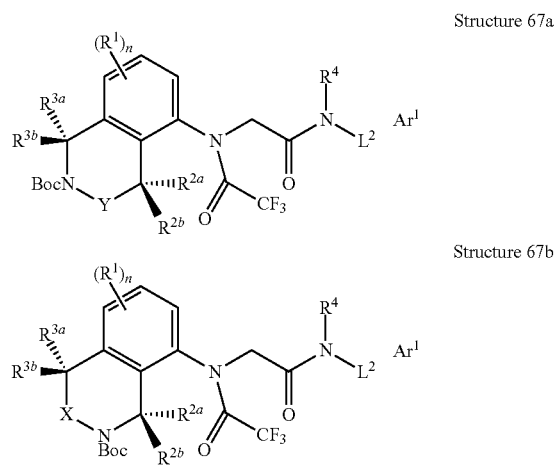

Structure 67a

Structure 67b

Compounds of Structure 67a and 67b can be obtained from compounds of Structure 68a or 68b respectively. In a typical experiment, well known to a person skilled in the art, a compound of Structure 68a or 68b is dissolved in DCM together with a base such as TEA or DIPEA followed by trifluoroacetic anhydride at 0° C. to room temperature. Compounds of Structure 68a or 68b are special cases of compounds of Structure 66a and 66b respectively and as such can be but not necessarily special cases of compounds of Formula (I), and can be obtained from compounds of Structure 1 wherein X=NBoc or Y=NBoc respectively following an amide coupling experiment described for the preparation of compounds of Formula (I) from compounds of Structure 1.

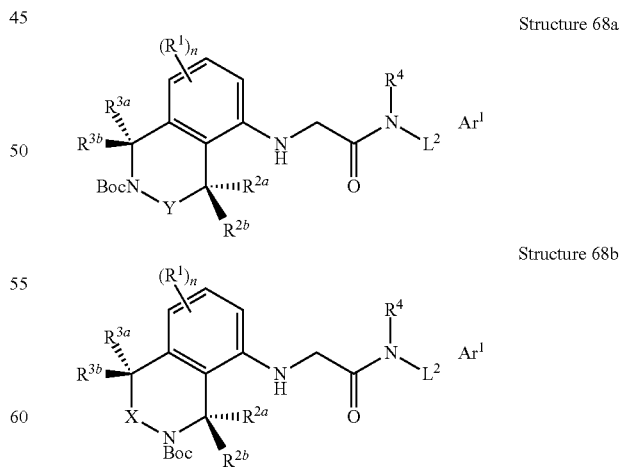

Structure 68a

Structure 68b

Last Two Steps: Quinoline Alkylation Followed by a Reduction

Compounds of Formula (I) can also be obtained from compounds of formula 69a and 69b. In a typical procedure a compound of structure 69a or 69b is stirred in MeOH or EtOH with NaBH₄ at room temperature to give the corresponding compound of Formula (I).

Structure 69a

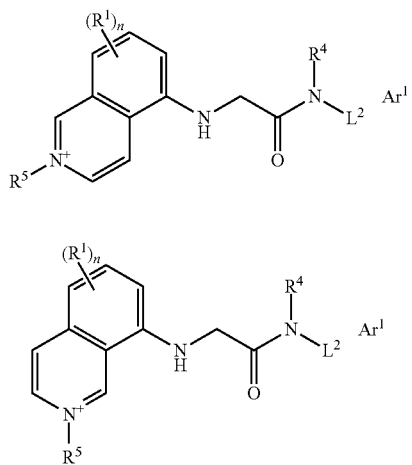

Structure 69b

Compounds of structure 69a and 69b can be made from compounds of Structure 70a and 70b respectively. In such a procedure, compounds of Structure 70a and 70b respectively are reacted with a reagent of type R⁵LG wherein LG represents a leaving group such as Cl, Br, I, OMs in a solvent such as MeCN, dioxane, DMF or the like in presence of a reagent of type R⁵LG and a base such as TEA, DIPEA, K₂CO₃ or the like at room temperature, or at elevated temperature up to reflux.

Structure 70a

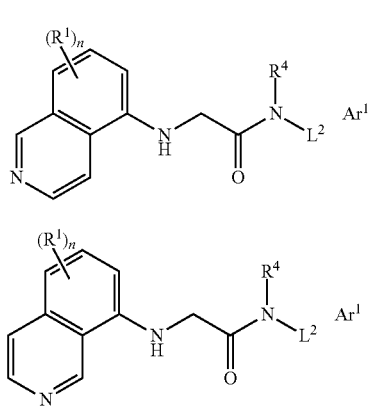

Structure 077b

Compounds of Structure 70a and 70b can be obtained from compounds of Structure 71a and 71b by reaction with an amine of Structure 2 using HATU or another amide coupling reagent in a solvent such as DCM or DMF at room temperature or 0° C. in the presence of a base like TEA or DIPEA.

Structure 71a

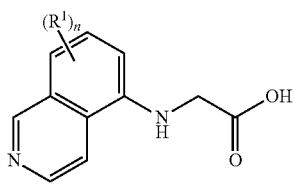

Structure 71b

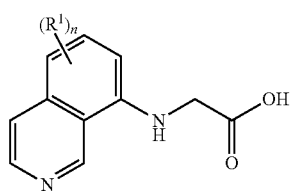

Compounds of Structure 71a and 71b are prepared by reaction of a commercially available 5-amino or 8-aminoisoquinoline respectively with glyoxylic acid hydrate in a solvent such as MeCN or the like with a reducing agent such as NaBH₃CN or the like at room temperature.

Special Cases Modification of Side Chain

In certain particular cases a compound of Structure 72 which is a particular case of compounds of Formula (I) can be obtained from a compound of Structure 73 which can be but is not necessarily a particular case of compound of Formula (I). In a typical experiment a compound of Structure 73 is dissolved in DCM or dioxane and HCl soln. in dioxane or EtOAc or TFA or the like is added at a temperature between 0° C. and room temperature. Compounds of Structure 73 are made according to methods described for the synthesis of compounds of Formula (I). Similarly a compound of Structure 74 wherein W represents N or CH, m is 0 or 1 and p is 1 or 2 can be obtained from a compound of Structure 75 wherein W represents N or CH, m is 0 or 1 and p is 1 or 2 which can be but is not necessarily a particular case of compounds of Formula (I) by the same reaction procedure.

Structure 72

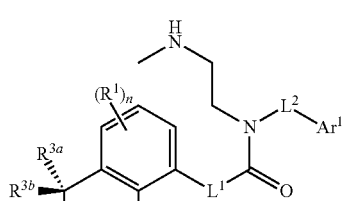

Structure 73

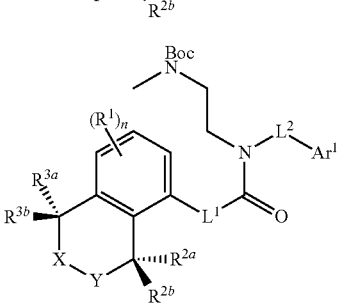

Structure 74

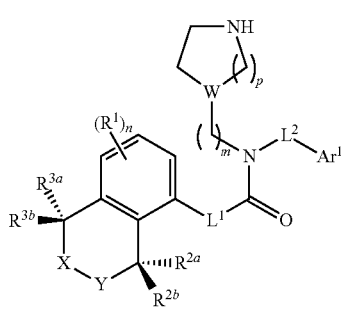

Structure 75

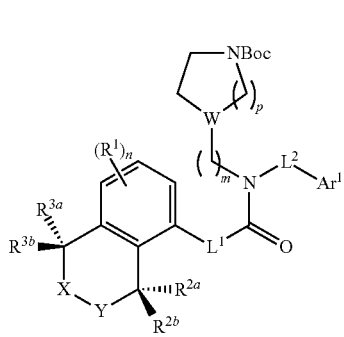

Compounds of Structure 75 can be made according to methods described for the synthesis of compounds of Formula (I). Finally a compound of Structure 76 or a compound of Structure 77 which are particular cases of compounds of Formula (I) can be prepared starting from a compound of Structure 74 or a compound of Structure 72 respectively by a typical reductive-amination reaction procedure wherein a compound of Structure 74 is dissolved in MeOH, EtOH or the like and reacted with formaldehyde (in this case $R^{25}$ represents a methyl group), an aldehyde or a ketone of type $R^{26}R^{27}CO$ (in this case $R^{25}$ represents $R^{26}R^{27}CH$—) and a reducing agent such as $NaBH_4$, $NaBH_3CN$ or $NaBH(OAc)_3$ or the like with or without addition of a acid such as acetic acid and with or without the addition of a dehydrating agent like $ZnCl_2$ or molecular sieve.

Structure 76

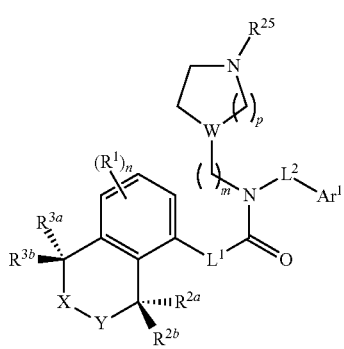

Structure 77

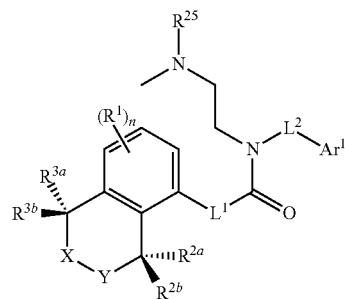

Alternative Preparation of Compounds of Formula (I)

Reaction Scheme D

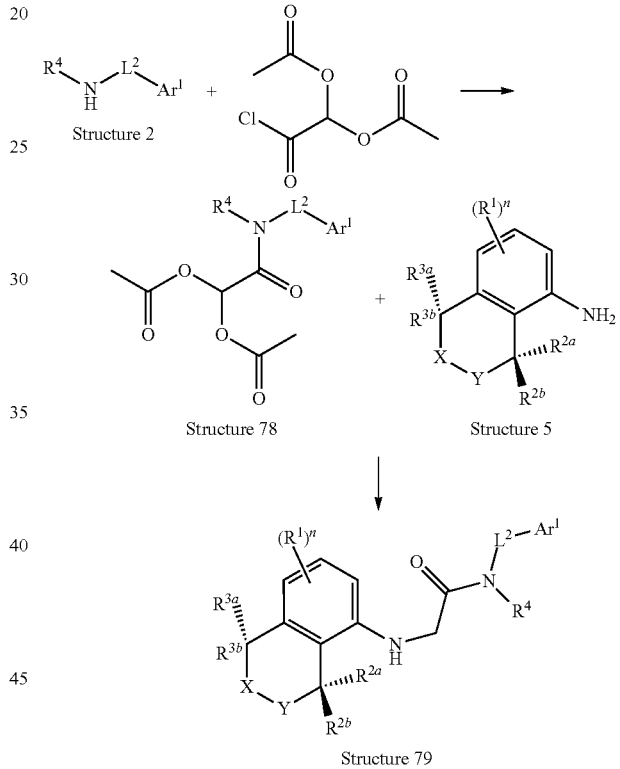

In a particular case wherein $R^{2a}$, $R^{2b}$, $R^{3a}$ and $R^{3b}$ represent H, compounds of Structure 79 which is a particular case of compounds of Formula (I) can be alternatively prepared as illustrated in reaction Scheme D from the corresponding 5- or 8-aminoisoquinoline derivatives via a two step sequence. Thus an amine of Structure 2 is reacted with diacetoxyacetyl chloride (McCaully, R., J. U.S. Pat. No. 3,896,170, 1975) in DCM in the presence of a base like $KHCO_3$, $K_2CO_3$, $NEt_3$ or DIPEA at temperatures between −10° C. and room temperature to give the diacetoxy amide of Structure 78 as a masked glyoxamide derivative. This crude intermediate of Structure 78 is condensed with an aniline of Structure 5 in a solvent like DCM, THF, MeOH or EtOH at temperatures between RT and reflux temperature in the presence of a catalytic amount of an acid like TFA or AcOH to deliver the intermediate imine which is directly treated with a reducing agent such as $NaBH(OAc)_3$, NaBH$_3$CN or NaBH$_4$ at temperatures between 0° C. and reflux, preferentially at room temperature to yield compounds of Structure 70 which are a particular case of compounds of Formula (I).

Special Case with L$_1$C(O)N being a Urea Function

In a particular case compounds of Structure 80 which are particular cases of compounds of Formula (I) are made from compounds of Structure 81a or Structure 81b respectively. In a typical procedure a compound of Structure 81a or 81b respectively is dissolved in DCM or dioxane or a mixture of both and reacted with HCl soln. in dioxane or TFA in a Boc cleavage reaction procedure well known by a person skilled in the art. This affords a compound of Structure 82a or 82b respectively or a salt thereof.

Structure 80

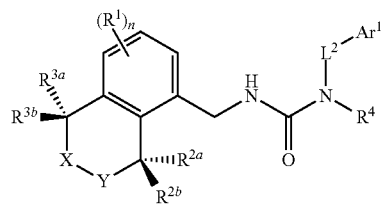

Structure 81a

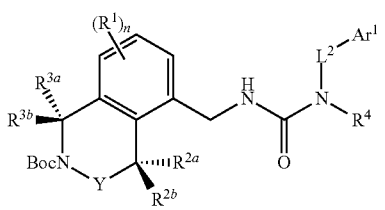

Structure 81b

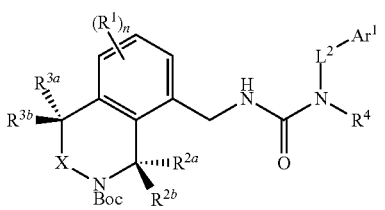

Structure 82a

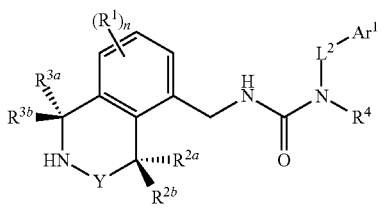

Structure 82b

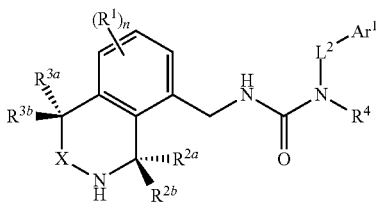

Then a compound of Structure 82a or 82b respectively is reacted with one equivalent of an aldehyde or a ketone of type R$^{13}$R$^{14}$C=O in a solvent such as MeOH, EtOH and a reducing agent such as NaBH$_4$, NaBH(OAc)$_3$, NaBH$_3$CN or the like at room temperature with or without addition of a dehydrating agent such as ZnCl$_2$. In this case a compound of Structure 80 respectively wherein R$^5$ corresponds to R$^{13}$R$^{14}$CH is obtained.

Compounds of Structure 81a or 81b respectively are made by reaction of a compound of Structure 82a or 82b respectively in water in presence of carbonyldiimidazole at 0° C. to room temperature with an amine of Structure 2.

Structure 83a

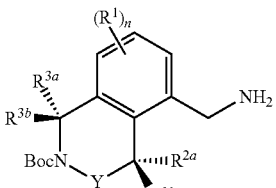

Structure 83b

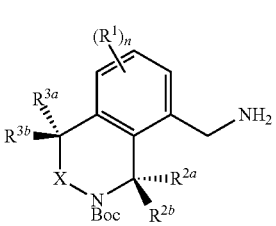

Compounds of Structure 83a and 83b are either commercially available or made according to procedures well known by a person skilled in the art.

Compounds of Structure 80 can also be made directly from compounds of Structure 84 via the method described for the synthesis of compounds of Structure 81a and 81b from compounds of Structure 83a and 83b. Compounds of Structure 84 can be made from compounds of Structure 85 by a reduction with procedure using CoCl$_2$ in the presence of NaBH$_4$ or another reducing agent in a solvent such as methanol at a temperature between RT and reflux.

Structure 84

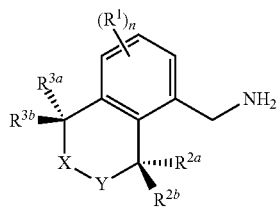

Structure 85

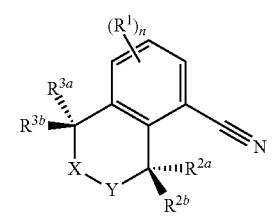

Compounds of Structure 85 can be made from a compound of Structure 86a or 86b which are commercially available or easily accessible via an alkylation method well known from a person skilled in the art.

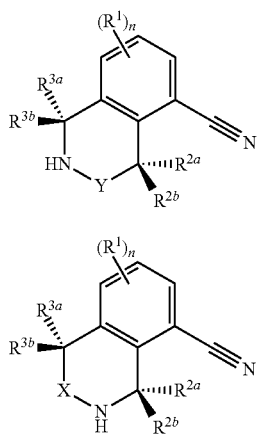

Structure 86a

Structure 86b

EXPERIMENTAL PART

I. Chemistry

All temperatures are stated in ° C. Commercially available starting materials were used as received without further purification. Unless otherwise specified, all reactions were carried out in oven-dried glassware under an atmosphere of nitrogen. All compounds were purified by a method described below: flash column chromatography on silica-gel or preparative HPLC. Compounds described in the invention are characterised by LC-MS data (retention time $t_R$ is given in min; molecular weight obtained from the mass spectrum is given in g/mol) using the conditions listed below. In cases where compounds of the present invention appear as a mixture of conformational isomers, particularly visible in their LC-MS spectra, the retention time of the most abundant conformer is given.

In case a Example compound's or Precursor's name is preceeded with the mention rac- this means this Example compound or Precursor is obtained as a racemic mixture of two enantiomers.

LC-MS Conditions

Method LC-A:

Agilent 1100 series with mass spectrometry detection (MS: Finnigan single quadrupole). Column: Zorbax SB-aq (3.5 m, 4.6×50 mm). Conditions: MeCN [eluent A]; water+0.04% TFA [eluent B]. Gradient: 95% B→5% B over 1.5 min (flow: 4.5 mL/min).

Detection: UV/Vis+MS.

Method LC-B:

Agilent 1100 series with mass spectrometry detection (MS: Finnigan single quadrupole). Column: Waters Atlantis T3 (5 μm, 4.6×30 mm). Conditions: MeCN [eluent A]; water+0.04% TFA [eluent B]. Gradient: 95% B→5% B over 1.5 min (flow: 4.5 mL/min).

Detection: UV/Vis+MS.

Method LC-C:

Waters Acquity Binary, Solvent Manager, MS: Waters SQ Detector, DAD: Acquity UPLC PDA Detector, ELSD: Acquity UPLC ELSD. Column: Acquity UPLC BEH C18 1.7 um 2.1×50 mm from Waters, thermostated in the Acquity UPLC Column Manager at 60° C. Conditions: MeCN+0.045% TFA [eluent A]; water+0.05% TFA [eluent B]. Method: Gradient: 98% B→2% B over 2.0 min. Flow: 1.2 mL/min.

Detection: UV 214 nm and ELSD, and MS, $t_R$ is given in min.

Method LC-F:

Waters Acquity Binary, Solvent Manager, MS: Waters SQ Detector, DAD: Acquity UPLC PDA Detector, ELSD: Acquity UPLC ELSD. Column: Acquity UPLC BEH C18 1.7 um 2.1×50 mm from Waters, thermostated in the Acquity UPLC Column Manager at 60° C. Conditions: MeCN+0.045% formic acid [eluent A]; water+0.05% formic acid [eluent B]. Method: Gradient: 98% B→2% B over 2.0 min. Flow: 1.0 mL/min.

Detection: UV 214 nm and ELSD, and MS, $t_R$ is given in min.

Method LC-F1:

Waters Acquity Binary, Solvent Manager, MS: Waters SQ Detector, DAD: Acquity UPLC PDA Detector, ELSD: Acquity UPLC ELSD. Column: ACQUITY UPLC HSS T3 C18 1.8 um 2.1×50 mm from Waters, thermostated in the Acquity UPLC Column Manager at 60° C. Conditions: MeCN+0.045% formic acid [eluent A]; water+0.05% formic acid [eluent B]. Method: Gradient: 98% B→2% B over 2.0 min. Flow: 1.0 mL/min.

Detection: UV 214 nm and ELSD, and MS, $t_R$ is given in min.

Methods LC-G and LC-H:

Dionex ultimate 3000 system, MS: Thermo MSQ MS, DAD: Dionex 3000 Ultimate, ELSD: PolymerLab ELS 2100, Column: Accucore C18 2.6 μm 2.1×50 mm, thermostated in TCC-3000 column compartment at 40° C. Conditions: MeCN [eluent A]; water+0.05% NH$_4$OH+2% MeCN [eluent B]. Method: Gradient: 95% B→5% B over 1.2 min (LC-G) or 2 min (LC-H). Flow: 1.2 mL/min.

Detection: UV 214 nm and ELSD, and MS, $t_R$ is given in min.

Preparative HPLC with Basic Conditions

Method LC-D:

Column: Waters XBridge (10 μm, 75×30 mm). Conditions: MeCN [eluent A]; water+0.5% NH$_4$OH (25% aq.) [eluent B]; Gradient see Table 1 (flow: 75 mL/min), the starting percentage of Eluent A (x) is determined depending on the polarity of the compound to purify. Detection: UV/Vis+MS

TABLE 1

| t (min) | 0 | 0.01 | 4.0 | 6.0 | 6.2 | 6.6 |
|---|---|---|---|---|---|---|
| Eluent A (%) | x | x | 95 | 95 | x | x |
| Eluent B (%) | 100-x | 100-x | 5 | 5 | 100-x | 100-x |

Preparative HPLC with Acidic Conditions

Method LC-E:

Column: Waters Atlantis T3 (10 μm, 75×30 mm). Conditions: MeCN [eluent A]; water+0.5% formic acid [eluent B]; Gradient see Table 2 (flow: 75 mL/min), the starting percentage of Eluent A (x) is determined depending on the polarity of the compound to purify. Detection: UVNis+MS

TABLE 2

| t (min) | 0 | 0.01 | 4.0 | 6.0 | 6.2 | 6.6 |
|---|---|---|---|---|---|---|
| Eluent A (%) | x | x | 95 | 95 | x | x |
| Eluent B (%) | 100-x | 100-x | 5 | 5 | 100-x | 100-x |

Chiral Preparative and Analytical HPLC Conditions

Method LC-K:

Binary Pump, Dionex HPG-3200SD, Autosampler: Dionex WPS-3000, Column compartment: Dionex TCC-3200, Diode array detector: Dionex DAD-3000, Degaser: Dionex SRD-3400, Column: ChiralPak AD-H 250×4.6 mm ID, 5 μm. Conditions: Isocratic, Eluent (heptane/EtOH/DIPEA 80:20:0.5); flow: 0.8 mL/min. Detection: UV/Vis Method LC-L:

Binary Pump, Dionex HPG-3200SD, Autosampler: Dionex WPS-3000, Column compartment: Dionex TCC-3200, Diode array detector: Dionex DAD-3000, Degaser: Dionex SRD-3400, Column: Column: ChiralPak IA-H 250× 20 mm ID, 5 μm. Conditions: Isocratic, Eluent (EtOH/MeCN/DIPEA 90:10:0.1); flow: 1 mL/min. Detection: UV/Vis Abbreviations (as Used Hereinbefore or Hereinafter)

AcOH acetic acid
aq. aqueous
Ar argon
BINAP racemic 2,2'-bis(diphenylphosphino)-1,1'-binaphthyl
BSA bovine serum albumin
DABCO 1,4-diazabicyclo[2.2.2]octane
DCC N,N'-dicyclohexylcarbodiimide
DCE 1,2-dichloroethane
DCM dichloromethane
deion. deionized
DIPEA diisopropyl-ethylamine, Hünig's base, ethyl-diisopropylamine
dioxane 1,4-dioxane
DMAP 4-dimethylaminopyridine
DMF dimethylformamide
DMSO dimethylsulfoxide
eq. equivalent(s)
Ether diethyl ether
EtOAc ethyl acetate
EtOH ethanol
g gram(s)
h hour(s)
HATU 2-(7-aza-1H-benzotriazole-1-yl)-1,1,3,3-tetramethyluronium hexafluorophosphate
HPLC high performance liquid chromatography
HV high vacuum conditions
LC-MS liquid chromatography-mass spectrometry
MeCN acetonitrile
MeI methyl iodide
MeOH methanol
mg miligram(s)
mL milliliter(s)
mmol millimole(s)
min minute(s)
N normality of a solution
MS mass spectroscopy
$NaBH(OAc)_3$ sodium triacetoxyborohydride
NaOAc sodium acetate
NMR nuclear magnetic resonance spectroscopy
OAc acetate
$Pd_2(dba)_3$ tris(dibenzylideneacetone)dipalladium(0)
prep. preparative
rac racemic
RT room temperature
s second(s)
sat. saturated
soln. solution
T temperature
TBME tert-butyl methyl ether
TEA triethylamine
TFA trifluoroacetic acid
TFAA trifluoroacetic acid anhydride
THF tetrahydrofuran
$t_R$ retention time
X-Phos 2-dicyclohexylphosphino-2',4',6'-triisopropylbiphenyl Example 1

N-Benzyl-2-(2-cyclopropylmethyl-1,2,3,4-tetrahydro-isoquinolin-5-yl)-N-(2-dimethylamino-ethyl)-acetamide To a solution of (2-cyclopropylmethyl-1,2,3,4-tetrahydro-isoquinolin-5-yl)-acetic acid Precursor A1 (44 mg, 0.143 mmol), N-benzyl-N',N'-dimethylethane-1,2-diamine Amine 7 (30.7 mg, 0.172 mmol) and HATU (55 mg, 0.145 mmol) in 1 mL DCM cooled to 0° C. is added DIPEA (22.7 mg, 0.145 mmol). The reaction mixture is allowed to stir at RT for 1 h. Water is added and the resulting organic phase is washed with sat. aq. $NaHCO_3$ soln. and brine then dried over $MgSO_4$, filtered and evaporated under reduced pressure. The crude residue is purified by prep. HPLC (Method D) to yield the title compound as a yellow solid. LC-C: $t_R$=0.55 min; [M+H]$^+$=406.4; $^1$H-NMR (CDCl$_3$), 60:40 mixture of two rotamers, δ: 7.38 (m, 1H), 7.31 (m, 3H), 7.20 (d, J=7.1 Hz, 1H), 7.12 (m, 1H), 7.05 (m, 1H), 6.98 (d, J=7.4 Hz, 1H), 4.69 (s, 0.8H), 4.55 (s, 1.2H), 3.75 (m, 2.8H), 3.63 (s, 1.2H), 3.55 (t, J=6.8 Hz, 1.2H), 3.31 (t, J=7.2 Hz, 0.8H), 2.88 (m, 0.8H), 2.83 (m, 2H), 2.68 (m, 1.2H), 2.53 (t, J=6.9 Hz, 1.2H), 2.44 (m, 2H), 2.37 (t, J=7.3 Hz, 0.8H), 2.27 (m, 3.6H), 2.19 (s, 2.4H), 0.99 (m, 1H), 0.59 (m, 2H), 0.20 (m, 2H)

Examples 2-7 listed in Table 3 are prepared applying the method described for Example 1 using the corresponding Precursor and Amine respectively.

TABLE 3

Examples 2-7

| Example | Compound | $t_R$ [min] (LC-C) | MS Data m/z [M + H]$^+$ |
|---|---|---|---|
| 2 | 2-(2-Cyclopropylmethyl-1,2,3,4-tetrahydro-isoquinolin-5-yl)-N-(2-dimethylamino-ethyl)-N-phenethyl-acetamide | 0.58 | 420.4 |
| 3 | N-Benzyl-2-(2-cyclopropylmethyl-1,2,3,4-tetrahydro-isoquinolin-5-yl)-N-(2-pyrrolidin-1-yl-ethyl)-acetamide | 0.56 | 432.4 |
| 4 | rac-N-Benzyl-2-(2-cyclopropylmethyl-1,2,3,4-tetrahydro-isoquinolin-5-yl)-N-[2-(1-methyl-pyrrolidin-2-yl)-ethyl]-acetamide | 0.58 | 446.4 |

TABLE 3-continued

Examples 2-7

| Example | Compound | $t_R$ [min] (LC-C) | MS Data m/z [M + H]$^+$ |
|---|---|---|---|
| 5 | 2-(2-Cyclopropylmethyl-1,2,3,4-tetrahydro-isoquinolin-5-yl)-N-(2-dimethylamino-ethyl)-N-(3-trifluoromethyl-pyridin-2-ylmethyl)-acetamide | 0.56 | 475.4 |
| 6 | 2-(2-Cyclopropylmethyl-1,2,3,4-tetrahydro-isoquinolin-5-yl)-N-(2-dimethylamino-ethyl)-N-(2-trifluoromethyl-benzyl)-acetamide | 0.63 | 474.4 |
| 7 | 2-(2-Cyclopropylmethyl-1,2,3,4-tetrahydro-isoquinolin-5-yl)-N-(2-pyrrolidin-1-yl-ethyl)-N-(2-trifluoromethyl-benzyl)-acetamide | 0.65 | 500.4 |

Example 8

5-({[Benzyl-(2-dimethylamino-ethyl)-carbamoyl]-methyl}-amino)-3,4-dihydro-1H-isoquinoline-2-carboxylic acid tert-butyl ester To a solution of 5-(carboxymethyl-amino)-3,4-dihydro-1H-isoquinoline-2-carboxylic acid tert-butyl ester Precursor B1 (1.4 g, 4.57 mmol), N-benzyl-N',N'-dimethylethane-1,2-diamine Amine 7 (0.81 g, 4.57 mmol) and HATU (2.09 g, 5.49 mmol) in 15 mL DCM cooled to 0° C. is added DIPEA (1.18 g, 9.14 mmol). The reaction mixture is allowed to stir at RT for 1 h. Water is added and the resulting organic phase is washed with sat. aq. NaHCO$_3$ soln. and brine then dried over MgSO$_4$, filtered and evaporated under reduced pressure. Flash-chromatography on silica-gel (Eluent: EtOAc 100% then EtOAc/MeOH 80:20) yields the title compound as a yellow oil.

LC-B: $t_R$=0.72 min; [M+H]$^+$=467.1

Examples 9-65, 90, 211-251, 295-308 and 315 listed in Table 4 are prepared applying the method described for Example 8 using the corresponding Precursor and Amine respectively.

TABLE 4

Examples 9-65, 90, 211-251, 295-308/315

| Example | Compound | $t_R$ [min] (LC-C) | MS Data m/z [M + H]$^+$ |
|---|---|---|---|
| 9 | 5-({[Benzyl-(3-methyl-butyl)-carbamoyl]-methyl}-amino)-3,4-dihydro-1H-isoquinoline-2-carboxylic acid tert-butyl ester | 1.44 | 466.4 |
| 10 | 5-({[(1-Methyl-piperidin-4-yl)-(2-trifluoromethyl-benzyl)-carbamoyl]-methyl}-amino)-3,4-dihydro-1H-isoquinoline-2-carboxylic acid tert-butyl ester | 1.01 | 561.5 |
| 11 | rac-5-({[(1-Methyl-piperidin-3-yl)-(2-trifluoromethyl-benzyl)-carbamoyl]-methyl}-amino)-3,4-dihydro-1H-isoquinoline-2-carboxylic acid tert-butyl ester | 1.03 | 561.5 |
| 12 | N-Benzyl-N-(3-methyl-butyl)-2-(2-propionyl-1,2,3,4-tetrahydro-isoquinolin-5-ylamino)-acetamide | 1.24 | 422.4 |
| 13 | N-Benzyl-N-(3-dimethylamino-propyl)-2-(2-propionyl-1,2,3,4-tetrahydro-isoquinolin-5-ylamino)-acetamide | 0.74 | 437.4 |
| 14 | N-(2-Dimethylamino-ethyl)-N-(3-methyl-benzyl)-2-(2-propionyl-1,2,3,4-tetrahydro-isoquinolin-5-ylamino)-acetamide | 0.78 | 437.5 |
| 15 | N-(2-Dimethylamino-ethyl)-N-(2-methyl-benzyl)-2-(2-propionyl-1,2,3,4-tetrahydro-isoquinolin-5-ylamino)-acetamide | 0.77 | 437.4 |
| 16 | N-(2-Dimethylamino-ethyl)-N-(4-methyl-benzyl)-2-(2-propionyl-1,2,3,4-tetrahydro-isoquinolin-5-ylamino)-acetamide | 0.78 | 437.4 |
| 17 | N-(2-Dimethylamino-ethyl)-N-phenethyl-2-(2-propionyl-1,2,3,4-tetrahydro-isoquinolin-5-ylamino)-acetamide | 0.76 | 437.4 |
| 18 | N-(3-Chloro-benzyl)-N-(2-dimethylamino-ethyl)-2-(2-propionyl-1,2,3,4-tetrahydro-isoquinolin-5-ylamino)-acetamide | 0.78 | 457.4 |
| 19 | N-(4-Chloro-benzyl)-N-(2-dimethylamino-ethyl)-2-(2-propionyl-1,2,3,4-tetrahydro-isoquinolin-5-ylamino)-acetamide | 0.8 | 457.4 |
| 20 | N-(2-Chloro-benzyl)-N-(2-dimethylamino-ethyl)-2-(2-propionyl-1,2,3,4-tetrahydro-isoquinolin-5-ylamino)-acetamide | 0.77 | 457.4 |
| 21 | N-(2-Dimethylamino-ethyl)-N-(3-fluoro-benzyl)-2-(2-propionyl-1,2,3,4-tetrahydro-isoquinolin-5-ylamino)-acetamide | 0.74 | 441.4 |
| 22 | N-(2-Dimethylamino-ethyl)-N-(4-fluoro-benzyl)-2-(2-propionyl-1,2,3,4-tetrahydro-isoquinolin-5-ylamino)-acetamide | 0.75 | 441.4 |
| 23 | N-(2-Dimethylamino-ethyl)-N-(2-fluoro-benzyl)-2-(2-propionyl-1,2,3,4-tetrahydro-isoquinolin-5-ylamino)-acetamide | 0.73 | 441.4 |
| 24 | N-Benzyl-2-(2-propionyl-1,2,3,4-tetrahydro-isoquinolin-5-ylamino)-N-(2-pyrrolidin-1-yl-ethyl)-acetamide | 0.75 | 449.4 |
| 25 | N-Benzyl-2-(2-propionyl-1,2,3,4-tetrahydro-isoquinolin-5-ylamino)-N-pyridin-2-ylmethyl-acetamide | 0.95 | 443.4 |

TABLE 4-continued

Examples 9-65, 90, 211-251, 295-308/315

| | | | |
|---|---|---|---|
| 26 | N-Benzyl-N-(1-methyl-1H-imidazol-2-ylmethyl)-2-(2-propionyl-1,2,3,4-tetrahydro-isoquinolin-5-ylamino)-acetamide | 0.71 | 446.4 |
| 27 | N-Benzyl-N-(2-diethylamino-ethyl)-2-(2-propionyl-1,2,3,4-tetrahydro-isoquinolin-5-ylamino)-acetamide | 0.76 | 451.4 |
| 28 | N-(2-Dimethylamino-ethyl)-N-(2-methoxy-benzyl)-2-(2-propionyl-1,2,3,4-tetrahydro-isoquinolin-5-ylamino)-acetamide | 0.76 | 453.4 |
| 29 | N-(2-Dimethylamino-ethyl)-N-(3-methoxy-benzyl)-2-(2-propionyl-1,2,3,4-tetrahydro-isoquinolin-5-ylamino)-acetamide | 0.74 | 453.4 |
| 30 | N-(2-Dimethylamino-ethyl)-N-(4-methoxy-benzyl)-2-(2-propionyl-1,2,3,4-tetrahydro-isoquinolin-5-ylamino)-acetamide | 0.73 | 453.4 |
| 31 | N-Benzyl-N-[2-(butyl-methyl-amino)-ethyl]-2-(2-propionyl-1,2,3,4-tetrahydro-isoquinolin-5-ylamino)-acetamide | 0.81 | 465.5 |
| 32 | rac-N-Benzyl-N-[2-(1-methyl-pyrrolidin-2-yl)-ethyl]-2-(2-propionyl-1,2,3,4-tetrahydro-isoquinolin-5-ylamino)-acetamide | 0.76 | 463.4 |
| 33 | N-(2-Dimethylamino-ethyl)-2-(2-propionyl-1,2,3,4-tetrahydro-isoquinolin-5-ylamino)-N-(3-trifluoromethyl-benzyl)-acetamide | 0.82 | 491.4 |
| 34 | N-(2-Dimethylamino-ethyl)-2-(2-propionyl-1,2,3,4-tetrahydro-isoquinolin-5-ylamino)-N-(4-trifluoromethyl-benzyl)-acetamide | 0.83 | 491.4 |
| 35 | N-(2-Dimethylamino-ethyl)-2-(2-propionyl-1,2,3,4-tetrahydro-isoquinolin-5-ylamino)-N-(2-trifluoromethyl-benzyl)-acetamide | 0.81 | 491.4 |
| 36 | 2-(2-Cyclopropylmethyl-1,2,3,4-tetrahydro-isoquinolin-5-ylamino)-N-(2-dimethylamino-ethyl)-N-phenethyl-acetamide | 0.61 | 435.4 |
| 37 | N-Benzyl-2-(2-cyclopropylmethyl-1,2,3,4-tetrahydro-isoquinolin-5-ylamino)-N-(3-dimethylamino-propyl)-acetamide | 0.59 | 435.5 |
| 38 | 2-(2-Cyclopropylmethyl-1,2,3,4-tetrahydro-isoquinolin-5-ylamino)-N-(2-dimethylamino-ethyl)-N-(2-fluoro-benzyl)-acetamide | 0.58 | 439.4 |
| 39 | N-(3-Chloro-pyridin-2-ylmethyl)-2-(2-cyclopropylmethyl-1,2,3,4-tetrahydro-isoquinolin-5-ylamino)-N-(2-dimethylamino-ethyl)-acetamide | 0.54 | 456.4 |
| 40 | 2-(2-Cyclopropylmethyl-1,2,3,4-tetrahydro-isoquinolin-5-ylamino)-N-(2-dimethylamino-ethyl)-N-(2-o-tolyl-ethyl)-acetamide | 0.65 | 449.5 |
| 41 | N-Benzyl-2-(2-cyclopropylmethyl-1,2,3,4-tetrahydro-isoquinolin-5-ylamino)-N-(2-pyrrolidin-1-yl-ethyl)-acetamide | 0.59 | 447.4 |
| 42 | rac-N-Benzyl-2-(2-cyclopropylmethyl-1,2,3,4-tetrahydro-isoquinolin-5-ylamino)-N-[2-(1-methyl-pyrrolidin-2-yl)-ethyl]-acetamide | 0.61 | 461.5 |
| 43 | N-(2-Chloro-benzyl)-2-(2-cyclopropylmethyl-1,2,3,4-tetrahydro-isoquinolin-5-ylamino)-N-(2-pyrrolidin-1-yl-ethyl)-acetamide | 0.63 | 481.4 |
| 44 | 2-(2-Cyclopropylmethyl-1,2,3,4-tetrahydro-isoquinolin-5-ylamino)-N-(2-fluoro-benzyl)-N-(2-pyrrolidin-1-yl-ethyl)-acetamide | 0.6 | 465.4 |
| 45 | 2-(2-Cyclopropylmethyl-1,2,3,4-tetrahydro-isoquinolin-5-ylamino)-N-(2-dimethylamino-ethyl)-N-((E)-2-methyl-3-phenyl-allyl)-acetamide | 0.69 | 461.5 |
| 46 | 2-(2-Cyclopropylmethyl-1,2,3,4-tetrahydro-isoquinolin-5-ylamino)-N-(2-dimethylamino-ethyl)-N-(6-trifluoromethyl-pyridin-2-ylmethyl)-acetamide | 0.61 | 490.4 |
| 47 | 2-(2-Cyclopropylmethyl-1,2,3,4-tetrahydro-isoquinolin-5-ylamino)-N-(2-dimethylamino-ethyl)-N-(3-trifluoromethyl-pyridin-2-ylmethyl)-acetamide | 0.59 | 490.4 |
| 48 | 2-(2-Cyclopropylmethyl-1,2,3,4-tetrahydro-isoquinolin-5-ylamino)-N-(3-methyl-butyl)-N-(2-trifluoromethyl-benzyl)-acetamide | 1.09 | 488.4 |
| 49 | rac-2-(2-Cyclopropylmethyl-1,2,3,4-tetrahydro-isoquinolin-5-ylamino)-N-[2-(1-methyl-pyrrolidin-2-yl)-ethyl]-N-phenethyl-acetamide | 0.65 | 475.5 |
| 50 | N-(2-Chloro-4-fluoro-benzyl)-2-(2-cyclopropylmethyl-1,2,3,4-tetrahydro-isoquinolin-5-ylamino)-N-(2-pyrrolidin-1-yl-ethyl)-acetamide | 0.65 | 499.4 |
| 51 | 2-(2-Cyclopropylmethyl-1,2,3,4-tetrahydro-isoquinolin-5-ylamino)-N-(2,4-difluoro-benzyl)-N-(2-pyrrolidin-1-yl-ethyl)-acetamide | 0.62 | 483.4 |
| 52 | rac-2-(2-Cyclopropylmethyl-1,2,3,4-tetrahydro-isoquinolin-5-ylamino)-N-[2-(1-methyl-pyrrolidin-2-yl)-ethyl]-N-(3-phenyl-propyl)-acetamide | 0.70 | 489.5 |
| 53 | rac-2-(2-Cyclopropylmethyl-1,2,3,4-tetrahydro-isoquinolin-5-ylamino)-N-[2-(1-methyl-pyrrolidin-2-yl)-ethyl]-N-((E)-3-phenyl-allyl)-acetamide | 0.68 | 487.5 |

TABLE 4-continued

Examples 9-65, 90, 211-251, 295-308/315

| | | | |
|---|---|---|---|
| 54 | 2-(2-Cyclopropylmethyl-1,2,3,4-tetrahydro-isoquinolin-5-ylamino)-N-(2-dimethylamino-ethyl)-N-(4-fluoro-2-trifluoromethyl-benzyl)-acetamide | 0.68 | 507.4 |
| 55 | 2-(2-Cyclopropylmethyl-1,2,3,4-tetrahydro-isoquinolin-5-ylamino)-N-(2-dimethylamino-ethyl)-N-[2-(3-trifluoromethyl-phenyl)-ethyl]-acetamide | 0.71 | 503.4 |
| 56 | 2-(2-Cyclopropylmethyl-1,2,3,4-tetrahydro-isoquinolin-5-ylamino)-N-(2-dimethylamino-ethyl)-N-[2-(4-trifluoromethyl-phenyl)-ethyl]-acetamide | 0.71 | 503.4 |
| 57 | 2-(2-Cyclopropylmethyl-1,2,3,4-tetrahydro-isoquinolin-5-ylamino)-N-(2-dimethylamino-ethyl)-N-[2-(2-trifluoromethyl-phenyl)-ethyl]-acetamide | 0.70 | 503.5 |
| 58 | rac-2-(2-Cyclopropylmethyl-1,2,3,4-tetrahydro-isoquinolin-5-ylamino)-N-(2-dimethylamino-ethyl)-N-[1-(2-trifluoromethyl-phenyl)-ethyl]-acetamide | 0.68 | 503.4 |
| 59 | 2-(2-Cyclopropylmethyl-1,2,3,4-tetrahydro-isoquinolin-5-ylamino)-N-[2-(3,4-dimethoxy-phenyl)-ethyl]-N-(2-dimethylamino-ethyl)-acetamide | 0.58 | 495.5 |
| 60 | 2-(2-Cyclopropylmethyl-1,2,3,4-tetrahydro-isoquinolin-5-ylamino)-N-(2-diethylamino-ethyl)-N-(2-trifluoromethyl-benzyl)-acetamide | 0.68 | 517.4 |
| 61 | rac-2-(2-Cyclopropylmethyl-1,2,3,4-tetrahydro-isoquinolin-5-ylamino)-N-((E)-2-methyl-3-phenyl-allyl)-N-[2-(1-methyl-pyrrolidin-2-yl)-ethyl]-acetamide | 0.72 | 501.4 |
| 62 | 2-(2-Cyclopropylmethyl-1,2,3,4-tetrahydro-isoquinolin-5-ylamino)-N-(2-pyrrolidin-1-yl-ethyl)-N-(2-trifluoromethyl-benzyl)-acetamide | 0.67 | 515.4 |
| 63 | 2-(2-Cyclopropylmethyl-1,2,3,4-tetrahydro-isoquinolin-5-ylamino)-N-[2-(2-oxo-pyrrolidin-1-yl)-ethyl]-N-(2-trifluoromethyl-benzyl)-acetamide | 0.82 | 529.4 |
| 64 | 2-(2-Cyclopropylmethyl-1,2,3,4-tetrahydro-isoquinolin-5-ylamino)-N-(2-morpholin-4-yl-ethyl)-N-(2-trifluoromethyl-benzyl)-acetamide | 0.66 | 531.5 |
| 65 | rac-3-{Benzyl-[2-(2-cyclopropylmethyl-1,2,3,4-tetrahydro-isoquinolin-5-ylamino)-acetyl]-amino}-pyrrolidine-1-carboxylic acid tert-butyl ester | 0.96 | 519.5 |
| 90 | 5-({[(2-Dimethylamino-ethyl)-(2-trifluoromethyl-benzyl)-carbamoyl]-methyl}-amino)-4,4-dimethyl-3,4-dihydro-1H-isoquinoline-2-carboxylic acid tert-butyl ester | 1.08 | 563.5 |
| 211 | rac-2-((2-(Cyclopropylmethyl)-1-methyl-1,2,3,4-tetrahydroisoquinolin-5-yl)amino)-N-(2-(dimethylamino)ethyl)-N-(2-(trifluoromethyl)benzyl)acetamide | 0.68 | 503.1 |
| 212 | rac-2-((2-(Cyclopropylmethyl)-3-methyl-1,2,3,4-tetrahydroisoquinolin-5-yl)amino)-N-(2-(dimethylamino)ethyl)-N-(2-(trifluoromethyl)benzyl)acetamide | 0.67 | 503.4 |

| Example No | Example name | $t_R$ [min] (LC-F) unless otherwise indicated | MS Data m/z [M + H]$^+$ |
|---|---|---|---|
| 213 | 2-(2-Cyclopropylmethyl-1,2,3,4-tetrahydro-isoquinolin-5-ylamino)-N-[2-(1-methyl-pyrrolidin-2-yl)-ethyl]-N-(2-trifluoromethyl-benzyl)-acetamide | 0.53 | 529.4 |
| 214 | 2-(2-Cyclopropylmethyl-1,2,3,4-tetrahydro-isoquinolin-5-ylamino)-N-(3-pyrrolidin-1-yl-propyl)-N-(2-trifluoromethyl-benzyl)-acetamide | 0.53 | 529.4 |
| 215 | {2-[[2-(2-Cyclopropylmethyl-1,2,3,4-tetrahydro-isoquinolin-5-ylamino)-acetyl]-(3-trifluoromethyl-pyridin-2-ylmethyl)-amino]-ethyl}-methyl-carbamic acid tert-butyl ester | 0.86 | 576.4 |
| 216 | 4-{2-[[2-(2-Cyclopropylmethyl-1,2,3,4-tetrahydro-isoquinolin-5-ylamino)-acetyl]-(2-trifluoromethyl-benzyl)-amino]-ethyl}-piperazine-1-carboxylic acid tert-butyl ester | 0.69 | 630.4 |
| 217 | 2-(2-Cyclopropylmethyl-1,2,3,4-tetrahydro-isoquinolin-5-ylamino)-N-(2-piperidin-1-yl-ethyl)-N-(2-trifluoromethyl-benzyl)-acetamide | 0.52 | 529.4 |
| 218 | N-(2-Azepan-1-yl-ethyl)-2-(2-cyclopropylmethyl-1,2,3,4-tetrahydro-isoquinolin-5-ylamino)-N-(2-trifluoromethyl-benzyl)-acetamide | 0.54 | 543.4 |
| 219 | 2-(2-Cyclopropylmethyl-1,2,3,4-tetrahydro-isoquinolin-5-ylamino)-N-(2-diisopropylamino-ethyl)-N-(2-trifluoromethyl-benzyl)-acetamide | 0.55 | 545.4 |
| 220 | N-[2-(Cyclopropyl-methyl-amino)-ethyl]-2-(2-cyclopropylmethyl-1,2,3,4-tetrahydro-isoquinolin-5-ylamino)-N-(2-trifluoromethyl-benzyl)-acetamide | 0.54 | 515.4 |

TABLE 4-continued

Examples 9-65, 90, 211-251, 295-308/315

| | | | |
|---|---|---|---|
| 221 | 2-(2-Cyclopropylmethyl-1,2,3,4-tetrahydro-isoquinolin-5-ylamino)-N-(2-dimethylamino-ethyl)-N-(3-trifluoromethoxy-benzyl)-acetamide | 0.53 | 505.3 |
| 222 | 2-(2-Cyclopropylmethyl-1,2,3,4-tetrahydro-isoquinolin-5-ylamino)-N-(4-hydroxy-cyclohexyl)-N-(2-trifluoromethyl-benzyl)-acetamide | 0.75 | 516.4 |
| 223 | 2-(2-Cyclopropylmethyl-1,2,3,4-tetrahydro-isoquinolin-5-ylamino)-N-(2-hydroxy-3-methoxy-propyl)-N-(2-trifluoromethyl-benzyl)-acetamide | 0.74 | 506.3 |
| 224 | 2-(2-Cyclopropylmethyl-1,2,3,4-tetrahydro-isoquinolin-5-ylamino)-N-(2-trifluoromethyl-benzyl)-N-(3,3,3-trifluoro-propyl)-acetamide | 0.89 | 514.3 |
| 225 | 2-(2-Cyclopropylmethyl-1,2,3,4-tetrahydro-isoquinolin-5-ylamino)-N-(2-methoxy-ethyl)-N-(2-trifluoromethyl-benzyl)-acetamide | 0.81 | 476.4 |
| 226 | 2-(2-Cyclopropylmethyl-1,2,3,4-tetrahydro-isoquinolin-5-ylamino)-N-[1,4]dioxan-2-ylmethyl-N-(2-trifluoromethyl-benzyl)-acetamide | 0.79 | 518.3 |
| 227 | 2-(2-Cyclopropylmethyl-1,2,3,4-tetrahydro-isoquinolin-5-ylamino)-N-(2-dimethylamino-ethyl)-N-(2-trifluoromethoxy-benzyl)-acetamide | 0.52 | 505.4 |
| 228 | 2-(2-Cyclopropylmethyl-1,2,3,4-tetrahydro-isoquinolin-5-ylamino)-N-(2-dimethylamino-ethyl)-N-(4-trifluoromethoxy-benzyl)-acetamide | 0.54 | 505.3 |
| 229 | 2-(2-Cyclopropylmethyl-1,2,3,4-tetrahydro-isoquinolin-5-ylamino)-N-(2-methanesulfonyl-ethyl)-N-(2-trifluoromethyl-benzyl)-acetamide | 0.71 | 524.3 |
| 230 | 2-(2-Cyclopropylmethyl-1,2,3,4-tetrahydro-isoquinolin-5-ylamino)-N-(2-methanesulfonylamino-ethyl)-N-(2-trifluoromethyl-benzyl)-acetamide | 0.71 | 539.3 |
| 231 | 2-(2-Cyclopropylmethyl-1,2,3,4-tetrahydro-isoquinolin-5-ylamino)-N-[2-(ethyl-methyl-amino)-ethyl]-N-(2-trifluoromethyl-benzyl)-acetamide | 0.5 | 503.4 |
| 232 | {2-[[2-(2-Cyclopropylmethyl-1,2,3,4-tetrahydro-isoquinolin-5-ylamino)-acetyl]-(2-trifluoromethyl-benzyl)-amino]-ethyl}-ethyl-carbamic acid tert-butyl ester | 0.97 | 589.4 |
| 233 | 2-(2-Cyclopropylmethyl-1,2,3,4-tetrahydro-isoquinolin-5-ylamino)-N-(2-sulfamoyl-ethyl)-N-(2-trifluoromethyl-benzyl)-acetamide | 0.68 | 525.3 |
| 234 | N-(2-Bromo-benzyl)-2-(2-cyclopropylmethyl-1,2,3,4-tetrahydro-isoquinolin-5-ylamino)-N-(2-dimethylamino-ethyl)-acetamide | 0.47 | 499.2 |
| 235 | (2-{(2-Bromo-benzyl)-[2-(2-cyclopropylmethyl-1,2,3,4-tetrahydro-isoquinolin-5-ylamino)-acetyl]-amino}-ethyl)-methyl-carbamic acid tert-butyl ester | 0.91 | 585.3 |
| 236 | N-(3-Bromo-pyridin-2-ylmethyl)-2-(2-cyclopropylmethyl-1,2,3,4-tetrahydro-isoquinolin-5-ylamino)-N-(2-dimethylamino-ethyl)-acetamide | 0.41 | 500.3 |
| 237 | N-(3-Bromo-benzyl)-2-(2-cyclopropylmethyl-1,2,3,4-tetrahydro-isoquinolin-5-ylamino)-N-(2-dimethylamino-ethyl)-acetamide | 0.48 | 499.2 |
| 238 | N-(4-Bromo-benzyl)-2-(2-cyclopropylmethyl-1,2,3,4-tetrahydro-isoquinolin-5-ylamino)-N-(2-dimethylamino-ethyl)-acetamide | 0.49 | 499.3 |
| 239 | N-(3-Bromo-pyridin-4-ylmethyl)-2-(2-cyclopropylmethyl-1,2,3,4-tetrahydro-isoquinolin-5-ylamino)-N-(2-dimethylamino-ethyl)-acetamide | 0.37 | 500.2 |
| 240 | rac-2-(2-Cyclopropylmethyl-1,2,3,4-tetrahydro-isoquinolin-5-ylamino)-N-(2-hydroxy-propyl)-N-(2-trifluoromethyl-benzyl)-acetamide | 0.74 | 476.4 |
| 241 | 2-(2-Cyclopropylmethyl-1,2,3,4-tetrahydro-isoquinolin-5-ylamino)-N-(2-hydroxy-2-methyl-propyl)-N-(2-trifluoromethyl-benzyl)-acetamide | 0.77 | 490.4 |
| 242 | rac-2-(2-Cyclopropylmethyl-1,2,3,4-tetrahydro-isoquinolin-5-ylamino)-N-(3,3,3-trifluoro-2-hydroxy-propyl)-N-(2-trifluoromethyl-benzyl)-acetamide | 0.83 | 530.3 |
| 243 | 2-(2-Cyclopropylmethyl-1,2,3,4-tetrahydro-isoquinolin-5-ylamino)-N-(1-hydroxy-cyclopentylmethyl)-N-(2-trifluoromethyl-benzyl)-acetamide | 0.85 | 516.4 |
| 244 | 2-(2-Cyclopropylmethyl-1,2,3,4-tetrahydro-isoquinolin-5-ylamino)-N-{2-[(2-fluoro-ethyl)-methyl-amino]-ethyl}-N-(2-trifluoromethyl-benzyl)-acetamide | 0.52 | 521.4 |
| 245 | N-[2-(Allyl-methyl-amino)-ethyl]-2-(2-cyclopropylmethyl-1,2,3,4-tetrahydro-isoquinolin-5-ylamino)-N-(2-trifluoromethyl-benzyl)-acetamide | 0.52 | 515.4 |
| 246 | 2-(2-Cyclopropylmethyl-1,2,3,4-tetrahydro-isoquinolin-5-ylamino)-N-[2-(methyl-prop-2-ynyl-amino)-ethyl]-N-(2-trifluoromethyl-benzyl)-acetamide | 0.58 | 513.4 |

TABLE 4-continued

Examples 9-65, 90, 211-251, 295-308/315

| | | | |
|---|---|---|---|
| 247 | 2-(2-Cyclopropylmethyl-1,2,3,4-tetrahydro-isoquinolin-5-ylamino)-N-thiazol-5-ylmethyl-N-(2-trifluoromethyl-benzyl)-acetamide | 0.76 | 515.3 |
| 248 | N-(2-Chloro-benzyl)-2-(2-cyclopropylmethyl-1,2,3,4-tetrahydro-isoquinolin-5-ylamino)-N-[2-(4,4-difluoro-piperidin-1-yl)-ethyl]-acetamide | 0.59 | 531.3 |
| 249 | N-(3-Chloro-pyridin-2-ylmethyl)-2-(2-cyclopropylmethyl-1,2,3,4-tetrahydro-isoquinolin-5-ylamino)-N-[2-(4,4-difluoro-piperidin-1-yl)-ethyl]-acetamide | 0.47 | 532.4 |
| 250 | 2-(2-Cyclopropylmethyl-1,2,3,4-tetrahydro-isoquinolin-5-ylamino)-N-isoxazol-5-ylmethyl-N-(2-trifluoromethyl-benzyl)-acetamide | 0.77 (LC-A) | 489.21 |
| 251 | N-(3-Chloro-pyridin-2-ylmethyl)-2-(2-cyclopropylmethyl-1,2,3,4-tetrahydro-isoquinolin-5-ylamino)-N-(2-hydroxy-2-methyl-propyl)-acetamide | 0.64 | 457.3 |
| 295 | N-(2-Chloro-benzyl)-2-(2-cyclopropylmethyl-7-trifluoromethyl-1,2,3,4-tetrahydro-isoquinolin-5-ylamino)-N-(2-dimethylamino-ethyl)-acetamide | 0.56 | 523.3 |
| 296 | 2-(2-Cyclopropylmethyl-7-trifluoromethyl-1,2,3,4-tetrahydro-isoquinolin-5-ylamino)-N-(2-dimethylamino-ethyl)-N-(2-trifluoromethyl-benzyl)-acetamide | 0.59 | 557.3 |
| 297 | {2-[{2-[2-(2-Methoxy-ethyl)-1,2,3,4-tetrahydro-isoquinolin-5-ylamino]-acetyl}-(2-trifluoromethyl-benzyl)-amino]-ethyl}-methyl-carbamic acid tert-butyl ester | 0.91 | 579.4 |
| 298 | N-(3,3-Dimethyl-butyl)-2-[2-(2-methoxy-ethyl)-1,2,3,4-tetrahydro-isoquinolin-5-ylamino]-N-(3-methyl-pyridin-2-ylmethyl)-acetamide | 0.73 | 453.4 |
| 299 | N-(2-Hydroxy-3-methoxy-propyl)-2-[2-(2-methoxy-ethyl)-1,2,3,4-tetrahydro-isoquinolin-5-ylamino]-N-(2-trifluoromethyl-benzyl)-acetamide | 0.70 | 510.3 |
| 300 | N-[2-(4,4-Difluoro-piperidin-1-yl)-ethyl]-2-[2-(2-methoxy-ethyl)-1,2,3,4-tetrahydro-isoquinolin-5-ylamino]-N-(3-trifluoromethyl-pyridin-2-ylmethyl)-acetamide | 0.49 | 570.3 |
| 301 | N-(2-Hydroxy-2-methyl-propyl)-2-[2-(2-methoxy-ethyl)-1,2,3,4-tetrahydro-isoquinolin-5-ylamino]-N-(2-trifluoromethyl-benzyl)-acetamide | 0.73 | 494.3 |
| 302 | N-{2-[(2-Fluoro-ethyl)-methyl-amino]-ethyl}-2-[2-(2-methoxy-ethyl)-1,2,3,4-tetrahydro-isoquinolin-5-ylamino]-N-(2-trifluoromethyl-benzyl)-acetamide | 0.49 | 525.3 |
| 303 | 2-[2-(2-Methoxy-ethyl)-1,2,3,4-tetrahydro-isoquinolin-5-ylamino]-N-(3-methyl-oxetan-3-ylmethyl)-N-(2-trifluoromethyl-benzyl)-acetamide | 0.75 | 506.3 |
| 304 | N-(3-Hydroxy-3-methyl-butyl)-2-[2-(2-methoxy-ethyl)-1,2,3,4-tetrahydro-isoquinolin-5-ylamino]-N-(2-trifluoromethyl-benzyl)-acetamide | 0.76 | 508.4 |
| 305 | N-(3-Chloro-pyridin-2-ylmethyl)-N-[2-(4,4-difluoro-piperidin-1-yl)-ethyl]-2-[2-(2-methoxy-ethyl)-1,2,3,4-tetrahydro-isoquinolin-5-ylamino]-acetamide | 0.44 | 536.3 |
| 306 | N-(3-Chloro-pyridin-2-ylmethyl)-N-(2-dimethylamino-ethyl)-2-[2-(2-methoxy-ethyl)-1,2,3,4-tetrahydro-isoquinolin-5-ylamino]-acetamide | 0.37 | 460.3 |
| 307 | N-(3-Chloro-pyridin-2-ylmethyl)-N-(2-hydroxy-2-methyl-propyl)-2-[2-(2-methoxy-ethyl)-1,2,3,4-tetrahydro-isoquinolin-5-ylamino]-acetamide | 0.6 | 461.3 |
| 308 | N-(2-Dimethylamino-ethyl)-2-(2-prop-2-ynyl-1,2,3,4-tetrahydro-isoquinolin-5-ylamino)-N-(2-trifluoromethyl-benzyl)-acetamide | 0.49 | 473.3 |
| 315 | 2-(2-Cyclopropylmethyl-1-oxo-1,2,3,4-tetrahydro-isoquinolin-5-ylamino)-N-(2-dimethylamino-ethyl)-N-(2-trifluoromethyl-benzyl)-acetamide | 0.74 | 503.3 |

Examples 211a (S)- or (R)-2-((2-(Cyclopropylmethyl)-1-methyl-1,2,3,4-tetrahydroisoquinolin-5-yl)amino)-N-(2-(dimethylamino)ethyl)-N-(2-(trifluoromethyl)benzyl)acetamide LC-K: $t_R$=6.95 min, $^1$H NMR (400 MHz, DMSO, 2:1 mixture of rotamers) δ: 7.76 (m, 1H), 7.65 (m, 1H), 7.50 (m, 1H), 7.35 (m, 1H), 6.99 (m, 0.66H), 6.90 (t, J=7.8 Hz, 0.33H), 6.42 (m, 1.66H), 6.20 (m, 0.33H), 4.96 (m, 1H), 4.89 (s, 0.66H), 4.79 (s, 1.33H), 4.19 (m, 1.33H), 3.86 (m, 1.66H), 3.50 (m, 1.33H), 3.41 (t, J=6.7 Hz, 0.66H), 3.03 (m, 1H), 2.90 (m, 1H), 2.23-2.49 (m, 5H), 2.16 (m, 6H), 1.21 (m, 3H), 0.87 (m, 1H), 0.47 (dd, $J_1$=1.7 Hz, $J_2$=8.0 Hz, 2H), 0.10 (m, 2H), and

Example 211b (R)- or (S)-2-((2-(Cyclopropylmethyl)-1-methyl-1,2,3,4-tetrahydroisoquinolin-5-yl)amino)-N-(2-(dimethylamino)ethyl)-N-(2-(trifluoromethyl)benzyl)acetamide LC-K: $t_R$=9.01 min; are obtained using chiral prep. HPLC conditions (LC-K) for the racemic Example 211.

Precursor A1

2-(2-(Cyclopropylmethyl)-1,2,3,4-tetrahydroisoquinolin-5-yl)acetic acid

To a solution of (2-cyclopropylmethyl-1,2,3,4-tetrahydroisoquinolin-5-yl)-acetic acid tert-butyl ester Precursor A2 (0.34 g, 1.13 mmol) in 8 mL DCM is added TFA (0.97 mL, 12.6 mmol).

The reaction mixture is allowed to stir at RT for 24 h and is diluted with 1 mL toluene. The solvents are evaporated under reduced pressure to yield 0.276 g (99%) of the title compound as a yellow solid which is used without further purification.

LC-A: $t_R$=0.48 min; [M+H]$^+$=246.12

Precursor A2

(2-Cyclopropylmethyl-1,2,3,4-tetrahydro-isoquinolin-5-yl)-acetic acid tert-butyl ester A solution of 5-tert-butoxycarbonylmethyl-2-cyclopropylmethyl-isoquinolinium bromide Precursor A3 (450 mg, 1.19 mmol) in 5 mL MeOH and 0.5 mL deion. water cooled to 0° C. is treated portionwise with NaBH$_4$ (60 mg, 1.59 mmol) over 15 min. The reaction mixture is stirred at 0° C. for 1 h and at RT for 1 h. The solvent is evaporated under reduced pressure. The residue is partitioned between 20 mL DCM and 20 mL sat. aq. NaHCO$_3$. The water layer is extracted twice with 10 mL DCM. The combined organic layers are dried over MgSO$_4$ and evaporated under reduced pressure. The residue is dried under HV overnight to yield 344 mg (96%) of the title compound as an orange oil. LC-A: $t_R$=0.69 min; [M+H]$^+$=302.21

Precursor A3

5-tert-Butoxycarbonylmethyl-2-cyclopropylmethyl-isoquinolinium bromide

To a solution of isoquinolin-5-yl-acetic acid tert-butyl ester [Bioorg. and Med. Chem. Letters, 2011, 21, 1838-1843](0.313 g, 1.29 mmol) in 2 mL MeCN is added bromomethyl-cyclopropane (0.21 g, 1.56 mmol). The reaction mixture is heated under reflux for 8 h. The mixture is allowed to cool to RT and the solvent is evaporated under reduced pressure. The oily residue is triturated with 5 mL ether. The resulting solid is filtered over a sintered funnel then washed with ether and dried under HV. This yields 0.457 g (94%) of the sub-title compound as a light yellow solid. LC-A: $t_R$=0.69 min; [M+H]$^+$=297.98

Precursor B1

5-(Carboxymethyl-amino)-3,4-dihydro-1H-isoquinoline-2-carboxylic acid tert-butyl ester To a solution of 5-(ethoxycarbonylmethyl-amino)-3,4-dihydro-1H-isoquinoline-2-carboxylic acid tert-butyl ester Precursor D1 (6.9 g, 20.8 mmol) in 150 ml THF is added 1M aq. LiOH sol. (125 mL, 125 mmol). The reaction mixture is allowed to stir at RT for 2 h and is acidified with 2N aq. HCl sol. to pH=4. The resulting aq. phase is extracted twice with EtOAc. The combined organic phase is washed with brine, dried over MgSO$_4$, filtered and evaporated under reduced pressure to yield 5.6 g (88%) of the title compound as a white solid which is used without further purification.

LC-B: $t_R$=0.78 min; [M+H]$^+$=467.1; $^1$H-NMR (d$_6$-DMSO) δ: 11.52-13.03 (bs, 1H), 6.98 (t, J=7.8 Hz, 1H), 6.43 (d, J=7.6 Hz, 1H), 6.25 (d, J=7.9 Hz, 1H), 4.42 (bs, 2H), 3.83 (s, 2H), 3.59 (t, J=5.4 Hz, 2H), 2.47 (t, J=5.9 Hz, 2H), 1.43 (s, 9H).

Precursor B2 (2-Propionyl-1,2,3,4-tetrahydro-isoquinolin-5-ylamino)-acetic acid LC-B: $t_R$=0.55 min; [M+H]$^+$=263.2, Precursor B8 5-(Carboxymethyl-amino)-4,4-dimethyl-3,4-dihydro-1H-isoquinoline-2-carboxylic acid tert-butyl ester LC-A: $t_R$=0.88 min; [M+H]$^+$=335.2 and Precursor B18 rac-[2-((1S*,2S*)-2-Fluoro-cyclopropanecarbonyl)-1,2,3,4-tetrahydro-isoquinolin-5-ylamino]-acetic acid LC-A: $t_R$=0.62 min; [M+H]$^+$=293.2 are prepared applying the method described for Precursor B1 from Precursor C2, Precursor C8 and Precursor C18 respectively.

Precursor B3

(2-Cyclopropylmethyl-1,2,3,4-tetrahydro-isoquinolin-5-ylamino)-acetic acid a) 5-Amino-2-cyclopropylmethyl-isoquinolinium bromide 5-Aminoisoquinoline (6 g, 41.6 mmol) is suspended in 30 mL MeCN and bromomethylcyclopropane (5.6 g, 41.6 mmol) is added. The reaction mixture is heated at 85° C. for 2.5 h then stirred at RT overnight. Then bromomethylcyclopropane (1 g, 7.4 mmol) is added and the mixture is heated at 85° C. for 5 h. The mixture is allowed to cool to RT and the resulting solid is filtered over a sintered funnel then washed with ether and dried under HV. This yields 10.58 g (91%) of the sub-title compound as a yellow solid.

LC-A: $t_R$=0.49 min; [M]$^+$=199.2 (Mass of cation)

b) 2-Cyclopropylmethyl-1,2,3,4-tetrahydro-isoquinolin-5-ylamine

To a solution of 5-amino-2-cyclopropylmethyl-isoquinolinium bromide (500 mg, 1.79 mmol) in a mixture of 30 mL MeOH and 2 mL water cooled to 0° C. is added portionwise NaBH$_4$ (339 mg, 8.95 mmol) over 10 min. The resulting mixture is allowed to stir at 0° C. for 1 h then at RT overnight. The solvent is evaporated under reduced pressure. The residue is partitioned between DCM and sat. aq. NaHCO$_3$ soln. The resulting aq. layer is extracted twice with DCM. The combined organic layers are dried over MgSO$_4$, filtered and evaporated under reduced pressure. This yields 316 mg (100%) of the sub-title compound as a red gum which is used without further purification.

LC-A: $t_R$=0.36 min; [M+H]$^+$=203.2 c) A solution of 2-cyclopropylmethyl-1,2,3,4-tetrahydro-isoquinolin-5-ylamine (300 mg, 1.48 mmol) in 15 ml MeOH is cooled to 0° C. in an ice-bath. Glyoxylic acid monohydrate (320 mg, 3.48 mmol), TEA (299 mg, 2.97 mmol) are added followed by NaBH$_3$CN (103 mg, 1.63 mmol). The resulting mixture is allowed to stir at 0° C. for 30 min then at RT for 4 h. Water is slowly added and the volatiles are removed under reduced pressure. The crude solid is suspended in acetone, sonicated, triturated and then filtered over a sintered funnel. The acetone filtrate is evaporated under reduced pressure and dried under HV to yield 405 mg (100%) of the title compound as a yellow solid which is used without further purification.

LC-A: $t_R$=0.50 min; [M+H]$^+$=261.3

Alternatively to the steps b) and c):

d) To a solution of 5-amino-2-cyclopropylmethyl-isoquinolinium bromide (35 g, 0.125 mol) and glyoxylic acid monohydrate (13.8 g, 0.15 mol) in 500 mL MeOH in an autoclave is added Pearlman's catalyst (3.34 g, 6.27 mmol).

The resulting mixture is put under 10 bar of H$_2$ and allowed to stir at RT overnight. The solvent crude mixture is filtered and the filtrate rinsed with MeOH. The organic phase is evaporated under reduced pressure. The residue is recrystallized from TBME to yield 32 g (100%) of the title compound as beige solid. Precursor B20 ((2-(2-Methoxyethyl)-1,2,3,4-tetrahydroisoquinolin-5-yl)amino)acetic acid, LC-A: t$_R$=0.65 min; [M+H]$^+$=265.4 is prepared applying the method described for Precursor B3 using 2-methoxyethyl-bromide following Steps a) to give 5-amino-2-(2-methoxy-ethyl)isoquinolin-2-ium bromide LC-A: t$_R$=0.44 min; [M]$^+$ =203.3 (Mass of cation) and then step d). Precursor B21 ((2-Propargyl-1,2,3,4-tetrahydroisoquinolin-5-yl)amino) acetic acid, LC-A: t$_R$=0.45 min; [M+H]$^+$=245.2 is prepared applying the method described for Precursor B3 using propargyl bromide following Steps a) to give 5-amino-2-(prop-2-yn-1-yl)isoquinolin-2-ium bromide LC-A: t$_R$=0.41 min; [M]$^+$=183.2 (Mass of cation) then step b) to give 2-(prop-2-yn-1-yl)-1,2,3,4-tetrahydroisoquinolin-5-amine LC-A: t$_R$=0.28 min; [M+H]$^+$=187.3 and then step c).

Precursor B24

(2-Cyclopropylmethyl-1-oxo-1,2,3,4-tetrahydro-isoquinolin-5-ylamino)-acetic acid To a solution of 5-amino-2-cyclopropylmethyl-3,4-dihydro-2H-isoquinolin-1-one hydrochloride Precursor C24 (92 mg, 0.425 mmol) in 3 mL MeOH is added glyoxylic acid (12.6 mg, 0.17 mmol), NaBH$_3$CN (32.1 mg, 0.51 mmol), AcOH (102 mg, 1.7 mmol) and NaOAc (70 mg, 0.851 mmol). The reaction mixture is allowed to stir at RT overnight. Then glyoxylic acid (12.6 mg, 0.17 mmol) is added each 2 hours for three times. Water is then added and the volatiles are removed under reduced pressure. The crude residue (120 mg) is used as such in the next step.
LC-A: t$_R$=0.64 min; [M+H]$^+$=275.2

Precursor B10 rac-2-((2-(Cyclopropylmethyl)-1-methyl-1,2,3,4-tetrahydroisoquinolin-5-yl)amino)acetic acid a) rac-2-(Cyclopropylmethy)-1-methyl-1,2-dihydroisoquinolin-5-amine To a solution of the above mentioned 5-amino-2-cyclopropylmethyl-isoquinolinium bromide (500 mg, 2.38 mmol) in 5 mL THF cooled to 0° C. is added MeMgCl 3M soln. in THF (1.5 mL, 4.5 mmol). The resulting brown solution is allowed to warm up to RT and is stirred at this temperature for 2 h. The solution is then poured onto sat. aq. NH$_4$Cl soln. and the resulting aq. phase is extracted three times with ether. The combined organic phase is dried over MgSO$_4$ and the solvent removed under reduced pressure. This yields 410 mg (80%) of a crude orange oil which is used without further purification in the next step.
LC-A: t$_R$=0.48 min; [M+H]$^+$=215.1
b) rac-2-(Cyclopropylmethyl)-1-methyl-1,2,3,4-tetrahydroisoquinolin-5-amine A solution of the above mentioned rac-2-(cyclopropylmethyl)-1-methyl-1,2-dihydroisoquinolin-5-amine (410 mg, 1.53 mmol) in 6 mL MeOH is cooled to 0° C. and NaBH$_4$ (64 mg, 1.68 mmol) is added. The resulting suspension is allowed to stir at 0° C. for 30 min. The solvents are removed under reduced pressure and the residue is partitioned between sat. aq. NaHCO$_3$ soln. and DCM. The resulting aq. phase is extracted twice with DCM. The combined organic phase is dried over MgSO$_4$ and the solvent removed under reduced pressure. This yields quantitatively 354 mg of the sub-title compound as light brown oil which is used as such in the next step.
LC-A: t$_R$=0.43 min; [M+H]$^+$=217.1
c) A solution of rac-2-(cyclopropylmethyl)-1-methyl-1,2,3,4-tetrahydroisoquinolin-5-amine (354 mg, 1.46 mmol) in 10 ml MeOH is cooled to 0° C. in an ice-bath. Glyoxylic acid monohydrate (268 mg, 2.91 mmol), TEA (295 mg, 2.91 mmol) are added followed by NaBH$_3$CN (229 mg, 3.64 mmol). The resulting mixture is allowed to stir at 0° C. for 1 h then at RT for 2 h. Water is slowly added and the volatiles are removed under reduced pressure. The crude solid is suspended in acetone, sonicated and triturated then filtered over a sintered funnel. Evaporation of the acetone solution yields 554 mg of the title compound as a yellow solid which is used without further purification.
LC-A: t$_R$=0.53 min; [M+H]$^+$=275.1

Precursor B11 rac-2-((2-(Cyclopropylmethyl)-3-methyl-1,2,3,4-tetrahydroisoquinolin-5-yl)amino)acetic acid a) rac-2-(cyclopropylmethyl)-3-methyl-5-nitro-1,2,3,4-tetrahydroisoquinoline To a solution of rac-3-methyl-5-nitro-1,2,3,4-tetrahydroisoquinoline (624 mg, 3.18 mmol) in 8 mL DCM are added cyclopropane carboxaldehyde (245 mg, 3.5 mmol) and DIPEA (617 mg, 4.77 mmol) and the reaction mixture is stirred at RT for 1 h. NaBH(OAc)$_3$ (1011 mg, 4.77 mmol) is then added and the resulting mixture is allowed to stir at RT for 1 h. The mixture is diluted with water and DCM. The resulting aq. phase is extracted twice with DCM. The combined organic phase is washed with brine and dried over MgSO$_4$. The solvent is evaporated under reduced pressure to yield 708 mg (90%) of the sub-title compound as a brown oil which is used as such in the next step.
LC-A: t$_R$=0.56 min; [M+H]$^+$=247.1
b) rac-2-(Cyclopropylmethyl)-3-methyl-1,2,3,4-tetrahydroisoquinolin-5-amine To a degassed solution of rac-2-(cyclopropylmethyl)-3-methyl-5-nitro-1,2,3,4-tetrahydroisoquinoline (705 mg, 2.66 mmol) in 50 mL MeOH is added 10% Pd/C mixture (70 mg, 0.066 mmol) and the well stirred suspension is put under an atmospheric pressure of H$_2$ for 3 h. The mixture is filtered over Celite and washed three times with MeOH. The solvent is removed under reduced pressure. Flash-chromatography on silica-gel (Eluent: DCM/MeOH 100:0 to 90:10) yields 483 mg (84%) of the sub-title compound as yellow oil.
LC-A: t$_R$=0.42 min; [M+H]$^+$=217.3
c) A solution of rac-2-(cyclopropylmethyl)-3-methyl-1,2,3,4-tetrahydroisoquinolin-5-amine (483 mg, 1.92 mmol) in 10 mL MeOH is cooled to 0° C. in an ice-bath. Glyoxylic acid monohydrate (353 mg, 3.84 mmol), TEA (389 mg, 3.84 mmol) are added followed by NaBH$_3$CN (302 mg, 4.8 mmol). The resulting mixture is allowed to stir at 0° C. for 30 min then at RT for 2.5 h. Water is slowly added and the volatiles are removed under reduced pressure. The crude solid is suspended in acetone, sonicated and triturated then filtered over a sintered funnel. The acetone filtrate is evaporated under reduced pressure to yield 410 mg (78%) of the title compound as a yellow oil which is used without further purification.
LC-A: t$_R$=0.52 min; [M+H]$^+$=275.2

Precursor B19

((2-(Cyclopropylmethyl)-7-(trifluoromethyl)-1,2,3,4-tetrahydroisoquinolin-5-yl)amino)acetic acid a) 2-(Cyclopropylmethyl)-5-nitro-7-(trifluoromethyl)-1,2,3,4-tetrahydroisoquinoline To a solution of 7-(trifluoromethyl)-1,2,3,4-tetrahydro-5-nitroisoquinoline hydrochloride (300 mg, 1.06 mmol) in 3 mL DCM at RT are added cyclopropanecarboxaldehyde (0.095 mL, 1.27 mmol) and DIPEA (0.273 mL, 1.59 mmol). The reaction mixture is stirred for 1 h then NaBH(OAc)$_3$ (337 mg, 1.59 mmol) is added. The reaction mixture is allowed to stirred for 2 h at RT and is diluted with water and DCM. The resulting aq. phase is extracted twice with DCM. The combined organic phase is washed with brine and dried over MgSO$_4$. The solvent is evaporated under reduced pressure to yield quantitatively 331 mg of the sub-title compound as a brown oil which is used as such in the next step.

LC-A: $t_R$=0.65 min; [M+H]$^+$=301.5 b) 2-(Cyclopropylmethyl)-7-(trifluoromethyl)-1,2,3,4-tetrahydroisoquinolin-5-amine To a degassed solution of 2-(cyclopropylmethyl)-5-nitro-7-(trifluoromethyl)-1,2,3,4-tetrahydroisoquinoline (319 mg, 1.06 mmol) in 30 mL MeOH is added 10% Pd/C mixture (32 mg) and the well stirred suspension is put under atmospheric pressure of H$_2$ for 5 h. The mixture is filtered over Celite and washed three times with MeOH. The solvent is removed under reduced pressure to yield quantitatively 289 mg of the crude sub-title compound as brown solid which is used as such in the next step.

LC-A: $t_R$=0.61 min; [M+H]$^+$=217.2 c) A solution of 2-(cyclopropylmethyl)-7-(trifluoromethyl)-1,2,3,4-tetrahydroisoquinolin-5-amine (285 mg, 0.84 mmol) in 5 mL MeOH is cooled to 0° C. in an ice-bath. Glyoxylic acid monohydrate (332 mg, 3.61 mmol), TEA (171 mg, 1.69 mmol) are added followed by NaBH$_3$CN (151 mg, 2.4 mmol). The resulting mixture is allowed to stir at 0° C. for 30 min then at RT for 2 h. Glyoxylic acid monohydrate (100 mg) and NaBH$_3$CN (30 mg) are added and the resulting mixture is allowed to stir at RT for 4 h. Glyoxylic acid monohydrate (50 mg) is added and the resulting mixture is allowed to stir at RT for 2 h. Water is slowly added and the volatiles are removed under reduced pressure. The crude solid is suspended in acetone, sonicated and triturated then filtered over a sintered funnel. The acetone filtrate is evaporated under reduced pressure to yield 664 mg of the crude title compound as an orange oil which is used without further purification in the next step.

LC-A: $t_R$=0.61 min; [M+H]$^+$=329.3

Precursor B25

(2-((Benzyloxy)carbonyl)-1,2,3,4-tetrahydroisoquinolin-5-yl)aminoacetic acid

To a solution of 5-amino-3,4-dihydroisoquinoline-2(1H)-carboxylic acid benzyl ester ester [J. Med. Chem. 1990, 33(2), 596-600](517 mg, 1.1 mmol) in 5 mL MeOH cooled to 0° C. is added glyoxylic acid 50% in water soln. (0.151 mL, 1.1 mmol) then NaBH$_3$CN (104 mg, 1.65 mmol) and the resulting reaction mixture is allowed to stir at RT for 1 h. It is then poured in water and the resulting aq. phase is extracted three times with DCM. The combined organic phase is washed with brine, dried over MgSO$_4$, filtered and concentrated under reduced pressure to yield the title compound as a yellow oil.

LC-A: $t_R$=0.81 min; [M+H]$^+$=381.1

Precursor D1

5-(Ethoxycarbonylmethyl-amino)-3,4-dihydro-1H-isoquinoline-2-carboxylic acid tert-butyl ester To a solution of 5-amino-3,4-dihydro-1H-isoquinoline-2-carboxylic acid tert-butyl ester (6 g, 0.0242 mol) in 60 mL MeCN is added DIPEA (3.07 g, 24.2 mmol). The mixture is stirred 10 min at RT then ethylbromoacetate (4.04 g, 24.2 mmol) is added. The reaction is stirred for 6 h at reflux. After cooling, the mixture is poured into water and the resulting aq. phase is extracted twice with DCM. The combined organic phase is washed with sat. aq. NaHCO$_3$ soln. and brine then dried over MgSO$_4$, filtered and evaporated under reduced pressure. Flash-chromatography on silica-gel (gradient of EtOAc/heptane from 5:95 to 40:60) yields 6.9 g (86%) of the title compound as a light yellow oil.

LC-B: $t_R$=0.96 min; [M+H]$^+$=335.1; $^1$H-NMR (d$_6$-DMSO) δ: 7.12 (d, J=7.5 Hz, J=8.0 Hz, 1H), 6.60 (d, J=7.5 Hz, 1H), 6.41 (d, J=8.0 Hz, 1H), 4.57 (s, 2H), 4.28 (q, J=7.1 Hz, 2H), 3.95 (s, 2H), 3.74 (t, J=5.9 Hz, 2H), 2.62 (t, J=5.9 Hz, 2H), 1.50 (s, 9H), 1.33 (t, J=7.1 Hz, 3H)

Precursor C8

5-(Ethoxycarbonylmethyl-amino)-4,4-dimethyl-3,4-dihydro-1H-isoquinoline-2-carboxylic acid tert-butyl ester LC-A: $t_R$=1.00 min; [M+H]$^+$=363.2 is prepared applying the method described for Precursor D1 from commercially available 5-amino-4,4-dimethyl-3,4-dihydroisoquinoline-2(1H)-carboxylic acid tert-butyl ester.

Precursor C2

(2-Propionyl-1,2,3,4-tetrahydro-isoquinolin-5-ylamino)-acetic acid ethyl ester a) 1-(5-Bromo-3,4-dihydro-1H-isoquinolin-2-yl)-propan-1-one To a solution of 5-bromo-1,2,3,4-tetrahydroisoquinoline [J. Med. Chem., 2012, 55(17), 7746-7758](8.4 g, 39.4 mmol) in 250 mL DCM is added TEA (3.98 g, 39.4 mmol). The resulting solution is allowed to stir for 10 min at RT. Propionylchloride (3.62 g, 39.4 mmol) is added dropwise and the resulting solution is allowed to stir at RT for 1.5 h. The mixture is then poured into water. The phases are separated and the organic phase is washed with sat. aq. NaHCO$_3$ soln. and brine then dried over MgSO$_4$, filtered and the solvent removed under reduced pressure. Flash-chromatography on silica-gel (Eluent: EtOAc/heptane/DCM 1:5:5) yields 7.15 g (68%) of the sub-title compound as a light orange oil.

LC-B: $t_R$=0.80 min; [M+H]$^+$=267.9 b) A mixture of 1-(5-bromo-3,4-dihydro-1H-isoquinolin-2-yl)-propan-1-one (4 g, 13.4 mmol), glycine ester hydrochloride (2.5 g 16.1 mmol), Cs$_2$CO$_3$ (10.5 g, 32.2 mmol), rac-BINAP (0.67 g, 1.08 mmol) and Pd$_2$(dba)$_3$ (0.49 g, 0.54 mmol) in 80 mL toluene is stirred at 90° C. for 24 h then at 100° C. for 29 h. After cooling the solvent is removed under reduced pressure. The residue is taken up in EtOAc. Water and sat. aq. NaHCO$_3$ soln. are added and the phases are separated. The resulting aq. phase is extracted twice with EtOAc. The combined organic phase is washed with water and brine then dried over Na$_2$SO$_4$, filtered and evaporated under reduced pressure. Flash-chromatography on silica-gel (gradient of EtOAc/DCM/heptane 4:5:5 to 5:5:5) yields 1.8 g (46%) of the title compound as a yellow-orange oil.

LC-B: $t_R$=0.96 min; [M+H]$^+$=335.1; $^1$H NMR (d$_6$-DMSO) δ: 7.12 (d, J=7.5 Hz, J=8.0 Hz, 1H), 6.60 (d, J=7.5 Hz, 1H), 6.41 (d, J=8.0 Hz, 1H), 4.57 (s, 2H), 4.28 (q, J=7.1 Hz, 2H), 3.95 (s, 2H), 3.74 (t, J=5.9 Hz, 2H), 2.62 (t, J=5.9 Hz, 2H), 1.50 (s, 9H), 1.33 (t, J=7.1 Hz, 3H).

Precursor C24

5-Amino-2-cyclopropylmethyl-3,4-dihydro-2H-isoquinolin-1-one hydrochloride a) 5-Bromo-2-cyclopropylmethyl-3,4-dihydro-2H-isoquinolin-1-one To a solution of 5-bromo-1,2,3,4-tetrahydroisoquinolin-1-one [CAS#: 1109230-25-2](500 mg, 2.21 mmol) in 20 mL DMF cooled to 0° C. is added 60% dispersion NaH in mineral oil (79.6 mg, 3.32 mmol). After gas evolution ceased bromomethylcyclopropane (299 mg, 2.21 mmol) is added and the resulting suspension is allowed to stir overnight at RT. Then another 60% dispersion NaH in mineral oil (79.6 mg, 3.32 mmol) and bromomethylcyclopropane (299 mg, 2.21 mmol) are added and the mixture is allowed to stir at RT for 3 h. The mixture is filtered and the remaining solid rinsed with DMF. The DMF is removed under reduced pressure and HV. Purification of the crude residue by HPLC (Method D) yields 209 mg (34%) of the sub-title compound as a yellow solid. LC-A: $t_R$=0.86 min; [M+H]$^+$=282.0 b) (2-Cyclopropylmethyl-1-oxo-1,2,3,4-tetrahydro-isoquinolin-5-yl)-carbamic acid tert-butyl ester To a solution of 5-bromo-2-cyclopropylmethyl-3,4-dihydro-2H-isoquinolin-1-one (30 mg, 0.107 mmol) in 4 mL dioxane are added tert-butyl carbamate (12.5 mg, 0.107 mmol), Pd$_2$(dba)$_3$ (7.4 mg, 0.00803 mmol), X-Phos (7.7 mg, 0.0161 mmol) and sodium tert-butoxide (15.4 mg, 0.161 mmol). The resulting reaction mixture is allowed to heat at 100° C. for 3 h. After cooling the mixture is diluted in DCM and the resulting organic phase washed twice with water, dried over MgSO$_4$, filtered and evaporated. Purification of the residue by preparative HPLC (Method D) yields 23 mg (68%) of the sub-title compound as a yellow solid. LC-A: $t_R$=0.83 min; [M+H]$^+$=317.2 c) To a solution of (2-cyclopropylmethyl-1-oxo-1,2,3,4-tetrahydro-isoquinolin-5-yl)-carbamic acid tert-butyl ester (23 mg, 0.0727 mmol, 1 eq) in 3 mL MeOH is added 1.25M HCl soln. inMeOH (0.23 mL, 0.291 mmol) at 0° C. The reaction mixture is stirred overnight at 50° C. The solvent is removed under reduced pressure to give quantitatively the title compound as a light yellow solid.

LC-A: $t_R$=0.53 min; [M+H]$^+$=217.2

Example 70 rac-N-Benzyl-2-(2-cyclopropylmethyl-1,2,3,4-tetrahydro-isoquinolin-5-ylamino)-N-(1,1-dioxo-tetrahydro-1|6-thiophen-3-yl)-acetamide To a solution of crude (2-cyclopropylmethyl-1,2,3,4-tetrahydro-isoquinolin-5-ylamino)-acetic acid Precursor B3 (made from Precursor C3 as described below) (100 mg, 0.297 mmol), N-benzyl-N-(1,1-dioxidotetrahydrothien-3-yl)amine Amine 31 (78 g, 0.297 mmol) in 2 mL DMF are added HATU (136 mg, 0.357 mmol) and DIPEA (94.2 mg, 0.743 mmol). The reaction mixture is allowed to stir at RT for 1 h. Water is added and the aq. phase is extracted twice with DCM. The resulting organic phase is washed with sat. aq NaHCO$_3$ soln. and brine then dried over MgSO$_4$, filtered and evaporated under reduced pressure. The crude residue is purified by prep. HPLC (Method E) to yield the title compound as a yellow solid.

LC-A: $t_R$=0.68 min; [M+H]$^+$=468.0; $^1$H-NMR (d$_6$-DMSO) T=80° C. δ: 9.63 (m, 1H), 7.38 (m, 2H), 7.30 (m, 3H), 7.11 (m, 1H), 6.52 (m, 2H), 4.74 (m, 3H), 4.48 (m, 1H), 4.32 (m, 1H), 4.09 (m, 2H), 3.84 (m, 1H), 3.41 (m, 1H), 3.31 (m, 1H), 3.00-3.16 (m, 5H), 2.83 (m, 2H), 2.31 (m, 2H), 1.20 (m, 1H), 0.72 (m, 2H), 0.45 (m, 2H).

rac-N-Benzyl-2-(2-cyclopropylmethyl-1,2,3,4-tetrahydro-isoquinolin-5-ylamino)-N-(1,1-dioxo-tetrahydro-1|6-thiophen-3-yl)-acetamide hydrochloride Pure example 70 is dissolved in EtOH. Then 1.25M HCl soln. in EtOH (2 eq.) is added and the resulting soln. is allowed to stir at RT for 10 min. The volatiles are then removed under reduced pressure and the resulting crude hydrochloride dried under HV to yield the title compound.

Examples 66-69/71-72/74-89/91/252-294/309-314/575-577 listed in Table 5 are prepared applying the method described for Example 70 using the corresponding Precursor and Amine respectively.

TABLE 5

Examples 66-69/71-72/74-89/91/252-294/309-314/575-577

| Example No | Example name | $t_R$ [min] (LC-C) | MS Data m/z [M + H]$^+$ |
|---|---|---|---|
| 66 | N-(2-Chloro-benzyl)-2-(2-cyclopropylmethyl-1,2,3,4-tetrahydro-isoquinolin-5-ylamino)-N-ethyl-acetamide | 0.89 | 412.4 |
| 67 | N-Benzyl-N-(2-cyano-ethyl)-2-(2-cyclopropylmethyl-1,2,3,4-tetrahydro-isoquinolin-5-ylamino)-acetamide | 0.75 | 403.4 |
| 68 | 3-{Benzyl-[2-(2-cyclopropylmethyl-1,2,3,4-tetrahydro-isoquinolin-5-ylamino)-acetyl]-amino}-propionamide | 0.65 | 421.4 |
| 69 | N-Cyclopropyl-2-(2-cyclopropylmethyl-1,2,3,4-tetrahydro-isoquinolin-5-ylamino)-N-(2,3-dimethyl-benzyl)-acetamide | 0.95 | 418.4 |
| 71 | {Benzyl-[2-(2-cyclopropylmethyl-1,2,3,4-tetrahydro-isoquinolin-5-ylamino)-acetyl]-amino}-acetic acid ethyl ester | 0.84 | 436.4 |

TABLE 5-continued

Examples 66-69/71-72/74-89/91/252-294/309-314/575-577

| | | | |
|---|---|---|---|
| 72 | N-(2-Cyano-ethyl)-2-(2-cyclopropylmethyl-1,2,3,4-tetrahydro-isoquinolin-5-ylamino)-N-(2-trifluoromethyl-benzyl)-acetamide | 0.85 | 471.4 |
| 74 | 2-(2-Cyclopropylmethyl-1,2,3,4-tetrahydro-isoquinolin-5-ylamino)-N-(tetrahydro-pyran-4-yl)-N-(2-trifluoromethyl-benzyl)-acetamide | 0.89 | 502.4 |
| 75 | N-Benzyl-2-(2-cyclopropylmethyl-1,2,3,4-tetrahydro-isoquinolin-5-ylamino)-N-[2-(4-fluoro-phenyl)-ethyl]-acetamide | 0.99 | 472.4 |
| 76 | 2-(2-Cyclopropylmethyl-1,2,3,4-tetrahydro-isoquinolin-5-ylamino)-N-(2-dimethylamino-ethyl)-N-(2-trifluoromethyl-benzyl)-acetamide | 0.65 | 489.4 |
| 77 | 2-(2-Cyclopropylmethyl-1,2,3,4-tetrahydro-isoquinolin-5-ylamino)-N-(4-methyl-thiazol-2-ylmethyl)-N-(2-trifluoromethyl-benzyl)-acetamide | 0.95 | 529.3 |
| 78 | 2-(2-Cyclopropylmethyl-1,2,3,4-tetrahydro-isoquinolin-5-ylamino)-N-(2-oxo-2,3-dihydro-pyridin-4-ylmethyl)-N-(2-trifluoromethyl-benzyl)-acetamide | 0.76 | 525.4 |
| 79 | 2-(2-Cyclopropylmethyl-1,2,3,4-tetrahydro-isoquinolin-5-ylamino)-N-[2-(2-oxo-imidazolidin-1-yl)-ethyl]-N-(2-trifluoromethyl-benzyl)-acetamide | 0.78 | 530.4 |
| 80 | rac-2-(2-Cyclopropylmethyl-1,2,3,4-tetrahydro-isoquinolin-5-ylamino)-N-[1-(1-ethyl-1H-pyrazol-3-yl)-ethyl]-N-(2-trifluoromethyl-benzyl)-acetamide | 0.97 | 540.4 |
| 81 | rac-trans-2-{[[2-(2-Cyclopropylmethyl-1,2,3,4-tetrahydro-isoquinolin-5-ylamino)-acetyl]-(2-trifluoromethyl-benzyl)-amino]-methyl}-cyclopropanecarboxylic acid ethyl ester | 0.98 | 544.4 |
| 82 | N-(2-Benzyloxy-ethyl)-2-(2-cyclopropylmethyl-1,2,3,4-tetrahydro-isoquinolin-5-ylamino)-N-(2-trifluoromethyl-benzyl)-acetamide | 1.06 | 552.4 |
| 83 | {2-[[2-(2-Cyclopropylmethyl-1,2,3,4-tetrahydro-isoquinolin-5-ylamino)-acetyl]-(2-trifluoromethyl-benzyl)-amino]-ethyl}-methyl-carbamic acid tert-butyl ester | 1.03 | 575.5 |
| 84 | (R)-4-{[[2-(2-Cyclopropylmethyl-1,2,3,4-tetrahydro-isoquinolin-5-ylamino)-acetyl]-(2-trifluoromethyl-benzyl)-amino]-methyl}-2,2-dimethyl-oxazolidine-3-carboxylic acid tert-butyl ester | 1.11 | 631.6 |
| 85 | N-Benzyl-N-(2-dimethylamino-ethyl)-2-[2-(2,2,2-trifluoro-ethyl)-1,2,3,4-tetrahydro-isoquinolin-5-ylamino]-acetamide | 0.76 | 449.4 |
| 86 | N-(2-Dimethylamino-ethyl)-2-[2-(2,2,2-trifluoro-ethyl)-1,2,3,4-tetrahydro-isoquinolin-5-ylamino]-N-(2-trifluoromethyl-benzyl)-acetamide | 0.85 | 517.4 |
| 87 | 2-[(2-Cyclopropylmethyl-1,2,3,4-tetrahydro-isoquinolin-5-yl)-methyl-amino]-N-(2-dimethylamino-ethyl)-N-(2-trifluoromethyl-benzyl)-acetamide | 0.66 | 503.4 |
| 88 | 2-(6-Chloro-2-cyclopropylmethyl-1,2,3,4-tetrahydro-isoquinolin-5-ylamino)-N-(2-dimethylamino-ethyl)-N-(2-trifluoromethyl-benzyl)-acetamide | 0.68 | 523.4 |
| 89 | 2-(2-Cyclopropylmethyl-6-methoxy-1,2,3,4-tetrahydro-isoquinolin-5-ylamino)-N-(2-dimethylamino-ethyl)-N-(2-trifluoromethyl-benzyl)-acetamide | 0.65 | 519.5 |
| 91 | 2-(2-Cyclopropylmethyl-4,4-dimethyl-1,2,3,4-tetrahydro-isoquinolin-5-ylamino)-N-(2-dimethylamino-ethyl)-N-(2-trifluoromethyl-benzyl)-acetamide | 0.7 | 517.5 |

| Example No | Example name | $t_R$ [min] (LC-F) unless otherwise indicated | MS Data m/z [M + H]+ |
|---|---|---|---|
| 252 | 4-[[2-(2-Cyclopropylmethyl-1,2,3,4-tetrahydro-isoquinolin-5-ylamino)-acetyl]-(2-trifluoromethyl-benzyl)-amino]-piperidine-1-carboxylic acid tert-butyl ester | 0.96 | 601.4 |
| 253 | 3-{[[2-(2-Cyclopropylmethyl-1,2,3,4-tetrahydro-isoquinolin-5-ylamino)-acetyl]-(2-trifluoromethyl-benzyl)-amino]-methyl}-pyrrolidine-1-carboxylic acid tert-butyl ester | 0.95 | 601.4 |
| 254 | 3-[[2-(2-Cyclopropylmethyl-1,2,3,4-tetrahydro-isoquinolin-5-ylamino)-acetyl]-(2-trifluoromethyl-benzyl)-amino]-pyrrolidine-1-carboxylic acid tert-butyl ester | 0.93 | 587.4 |
| 255 | 2-(2-Cyclopropylmethyl-1,2,3,4-tetrahydro-isoquinolin-5-ylamino)-N-(2-dimethylamino-ethyl)-N-pyrimidin-4-ylmethyl-acetamide | 0.61 (LC-F1) | 423.3 |
| 256 | 2-(2-Cyclopropylmethyl-1,2,3,4-tetrahydro-isoquinolin-5-ylamino)-N-(2-dimethylamino-ethyl)-N-(3-methyl-pyridin-2-ylmethyl)-acetamide | 0.38 | 436.4 |

TABLE 5-continued

Examples 66-69/71-72/74-89/91/252-294/309-314/575-577

| | | | |
|---|---|---|---|
| 257 | 2-(2-Cyclopropylmethyl-1,2,3,4-tetrahydro-isoquinolin-5-ylamino)-N-(2-dimethylamino-ethyl)-N-pyridin-2-ylmethyl-acetamide | 0.35 | 422.4 |
| 258 | 2-(2-Cyclopropylmethyl-1,2,3,4-tetrahydro-isoquinolin-5-ylamino)-N-(2-dimethylamino-ethyl)-N-(5-methyl-pyridin-2-ylmethyl)-acetamide | 0.39 | 436.4 |
| 259 | 2-(2-Cyclopropylmethyl-1,2,3,4-tetrahydro-isoquinolin-5-ylamino)-N-(2-dimethylamino-ethyl)-N-(6-methyl-pyridin-2-ylmethyl)-acetamide | 0.38 | 436.4 |
| 260 | 2-(2-Cyclopropylmethyl-1,2,3,4-tetrahydro-isoquinolin-5-ylamino)-N-(2-dimethylamino-ethyl)-N-pyrimidin-2-ylmethyl-acetamide | 0.39 (LC-F1) | 423.4 |
| 261 | N-(5-Chloro-pyridin-2-ylmethyl)-2-(2-cyclopropylmethyl-1,2,3,4-tetrahydro-isoquinolin-5-ylamino)-N-(2-dimethylamino-ethyl)-acetamide | 0.42 | 456.3 |
| 262 | N-(5-Chloro-pyridin-3-ylmethyl)-2-(2-cyclopropylmethyl-1,2,3,4-tetrahydro-isoquinolin-5-ylamino)-N-(2-dimethylamino-ethyl)-acetamide | 0.38 | 456.3 |
| 263 | 2-(2-Cyclopropylmethyl-1,2,3,4-tetrahydro-isoquinolin-5-ylamino)-N-(2-dimethylamino-ethyl)-N-pyridin-3-ylmethyl-acetamide | 0.61 (LC-F1) | 423.3 |
| 264 | 2-(2-Cyclopropylmethyl-1,2,3,4-tetrahydro-isoquinolin-5-ylamino)-N-(2-dimethylamino-ethyl)-N-(2-methyl-2H-pyrazol-3-ylmethyl)-acetamide | 0.40 (LC-F1) | 425.4 |
| 265 | 2-(2-Cyclopropylmethyl-1,2,3,4-tetrahydro-isoquinolin-5-ylamino)-N-(2-dimethylamino-ethyl)-N-thiazol-2-ylmethyl-acetamide | 0.34 | 428.3 |
| 266 | 2-(2-Cyclopropylmethyl-1,2,3,4-tetrahydro-isoquinolin-5-ylamino)-N-(2-dimethylamino-ethyl)-N-(4-methyl-thiazol-2-ylmethyl)-acetamide | 0.38 | 442.3 |
| 267 | 2-(2-Cyclopropylmethyl-1,2,3,4-tetrahydro-isoquinolin-5-ylamino)-N-(2-dimethylamino-ethyl)-N-(5-fluoro-pyridin-2-ylmethyl)-acetamide | 0.37 | 440.4 |
| 268 | 2-(2-Cyclopropylmethyl-1,2,3,4-tetrahydro-isoquinolin-5-ylamino)-N-(2-dimethylamino-ethyl)-N-pyridin-4-ylmethyl-acetamide | 0.46 (LC-F1) | 422.3 |
| 269 | 2-(2-Cyclopropylmethyl-1,2,3,4-tetrahydro-isoquinolin-5-ylamino)-N-(2-dimethylamino-ethyl)-N-(5-methyl-isoxazol-3-ylmethyl)-acetamide | 0.36 | 426.3 |
| 270 | 2-(2-Cyclopropylmethyl-1,2,3,4-tetrahydro-isoquinolin-5-ylamino)-N-(2,6-difluoro-benzyl)-N-(2-dimethylamino-ethyl)-acetamide | 0.43 | 457.3 |
| 271 | 2-(2-Cyclopropylmethyl-1,2,3,4-tetrahydro-isoquinolin-5-ylamino)-N-(2-dimethylamino-ethyl)-N-(3-fluoro-pyridin-2-ylmethyl)-acetamide | 0.36 | 440.4 |
| 272 | 2-(2-Cyclopropylmethyl-1,2,3,4-tetrahydro-isoquinolin-5-ylamino)-N-(2-dimethylamino-ethyl)-N-(2-dimethylamino-pyrimidin-5-ylmethyl)-acetamide | 0.66 (LC-F1) | 466.4 |
| 273 | {2-[[2-(2-Cyclopropylmethyl-1,2,3,4-tetrahydro-isoquinolin-5-ylamino)-acetyl]-(2-trifluoromethyl-benzyl)-amino]-ethyl}-carbamic acid tert-butyl ester | 0.89 | 561.3 |
| 274 | 2-(2-Cyclopropylmethyl-1,2,3,4-tetrahydro-isoquinolin-5-ylamino)-N-(3,3-dimethyl-butyl)-N-(2-trifluoromethyl-benzyl)-acetamide | 1.00 | 502.4 |
| 275 | 2-(2-Cyclopropylmethyl-1,2,3,4-tetrahydro-isoquinolin-5-ylamino)-N-(3,3-dimethyl-butyl)-N-(3-trifluoromethyl-pyridin-2-ylmethyl)-acetamide | 0.93 | 503.4 |
| 276 | 2-(2-Cyclopropylmethyl-1,2,3,4-tetrahydro-isoquinolin-5-ylamino)-N-(3,3-dimethyl-butyl)-N-(3-methyl-pyridin-2-ylmethyl)-acetamide | 0.77 | 449.4 |
| 277 | 2-(2-Cyclopropylmethyl-1,2,3,4-tetrahydro-isoquinolin-5-ylamino)-N-[2-(4,4-difluoro-piperidin-1-yl)-ethyl]-N-(2-trifluoromethyl-benzyl)-acetamide | 0.64 | 565.3 |
| 278 | 2-(2-Cyclopropylmethyl-1,2,3,4-tetrahydro-isoquinolin-5-ylamino)-N-{2-[methyl-(2,2,2-trifluoro-ethyl)-amino]-ethyl}-N-(2-trifluoromethyl-benzyl)-acetamide | 0.92 | 557.3 |
| 279 | 2-(2-Cyclopropylmethyl-1,2,3,4-tetrahydro-isoquinolin-5-ylamino)-N-[2-(4,4-difluoro-piperidin-1-yl)-ethyl]-N-(3-trifluoromethyl-pyridin-2-ylmethyl)-acetamide | 0.52 | 566.4 |
| 280 | 2-(2-Cyclopropylmethyl-1,2,3,4-tetrahydro-isoquinolin-5-ylamino)-N-{2-[methyl-(2,2,2-trifluoro-ethyl)-amino]-ethyl}-N-(3-trifluoromethyl-pyridin-2-ylmethyl)-acetamide | 0.85 | 558.3 |
| 281 | 2-(2-Cyclopropylmethyl-1,2,3,4-tetrahydro-isoquinolin-5-ylamino)-N-[2-(3,3-difluoro-piperidin-1-yl)-ethyl]-N-(2-trifluoromethyl-benzyl)-acetamide | 0.79 | 565.4 |
| 282 | 2-(2-Cyclopropylmethyl-1,2,3,4-tetrahydro-isoquinolin-5-ylamino)-N-[2-(3,3-difluoro-pyrrolidin-1-yl)-ethyl]-N-(2-trifluoromethyl-benzyl)-acetamide | 0.76 | 551.3 |

TABLE 5-continued

Examples 66-69/71-72/74-89/91/252-294/309-314/575-577

| | | | |
|---|---|---|---|
| 283 | 2-(2-Cyclopropylmethyl-1,2,3,4-tetrahydro-isoquinolin-5-ylamino)-N-[2-(3,3-difluoro-piperidin-1-yl)-ethyl]-N-(3-trifluoromethyl-pyridin-2-ylmethyl)-acetamide | 0.61 | 566.4 |
| 284 | 2-(2-Cyclopropylmethyl-1,2,3,4-tetrahydro-isoquinolin-5-ylamino)-N-[2-(3,3-difluoro-pyrrolidin-1-yl)-ethyl]-N-(3-trifluoromethyl-pyridin-2-ylmethyl)-acetamide | 0.60 | 552.3 |
| 285 | 2-(2-Cyclopropylmethyl-1,2,3,4-tetrahydro-isoquinolin-5-ylamino)-N-(2-dimethylamino-ethyl)-N-[5-(4-fluoro-phenylamino)-pyridin-2-ylmethyl]-acetamide | 0.51 | 531.4 |
| 286 | N-(2-Dimethylamino-ethyl)-2-[2-(2-fluoro-ethyl)-1,2,3,4-tetrahydro-isoquinolin-5-ylamino]-N-(2-trifluoromethyl-benzyl)-acetamide | 0.45 | 481.3 |
| 287 | 2-(8-Chloro-2-cyclopropylmethyl-1,2,3,4-tetrahydro-isoquinolin-5-ylamino)-N-(2-dimethylamino-ethyl)-N-(2-trifluoromethyl-benzyl)-acetamide | 0.56 | 523.3 |
| 288 | 2-(2-Cyclopropylmethyl-8-fluoro-1,2,3,4-tetrahydro-isoquinolin-5-ylamino)-N-(2-dimethylamino-ethyl)-N-(2-trifluoromethyl-benzyl)-acetamide | 0.51 | 507.3 |
| 289 | 2-(2-Cyclopropylmethyl-8-fluoro-1,2,3,4-tetrahydro-isoquinolin-5-ylamino)-N-(2-dimethylamino-ethyl)-N-(3-trifluoromethyl-pyridin-2-ylmethyl)-acetamide | 0.45 | 508.3 |
| 290 | 2-(2-Cyclopropylmethyl-6-methyl-1,2,3,4-tetrahydro-isoquinolin-5-ylamino)-N-(2-dimethylamino-ethyl)-N-(2-trifluoromethyl-benzyl)-acetamide | 0.51 | 503.4 |
| 291 | (S)-2-(2-Cyclopropylmethyl-1,2,3,4-tetrahydro-isoquinolin-5-ylamino)-N-(2-dimethylamino-ethyl)-N-(2-trifluoromethyl-benzyl)-propionamide | 0.51 | 503.4 |
| 292 | 1-(2-Cyclopropylmethyl-1,2,3,4-tetrahydro-isoquinolin-5-ylamino)-cyclopropanecarboxylic acid (2-dimethylamino-ethyl)-(2-trifluoromethyl-benzyl)-amide | 0.42 | 515.3 |
| 293 | rac-N-(3-Chloro-pyridin-2-ylmethyl)-N-(2-dimethylamino-ethyl)-2-[2-((1S*,2S*)-2-fluoro-cyclopropanecarbonyl)-1,2,3,4-tetrahydro-isoquinolin-5-ylamino]-acetamide | 0.60 | 488.3 |
| 294 | rac-N-(3-Chloro-pyridin-2-ylmethyl)-N-[2-(4,4-difluoro-piperidin-1-yl)-ethyl]-2-[2-((1S*,2S*)-2-fluoro-cyclopropanecarbonyl)-1,2,3,4-tetrahydro-isoquinolin-5-ylamino]-acetamide | 0.68 | 564.3 |
| 309 | N-(2-Dimethylamino-ethyl)-2-(2-ethyl-3-oxo-1,2,3,4-tetrahydro-isoquinolin-5-ylamino)-N-(2-trifluoromethyl-benzyl)-acetamide | 0.72 | 477.3 |
| 310 | N-(2-Dimethylamino-ethyl)-2-(2-ethyl-3-oxo-1,2,3,4-tetrahydro-isoquinolin-5-ylamino)-N-(3-trifluoromethyl-pyridin-2-ylmethyl)-acetamide | 0.65 | 478.3 |
| 311 | 2-(2-Ethyl-3-oxo-1,2,3,4-tetrahydro-isoquinolin-5-ylamino)-N-(2-pyrrolidin-1-yl-ethyl)-N-(2-trifluoromethyl-benzyl)-acetamide | 0.74 | 503.3 |
| 312 | N-(2-Dimethylamino-ethyl)-2-(2-isobutyl-3-oxo-1,2,3,4-tetrahydro-isoquinolin-5-ylamino)-N-(2-trifluoromethyl-benzyl)-acetamide | 0.83 | 505.4 |
| 313 | N-(2-Dimethylamino-ethyl)-2-(2-isobutyl-3-oxo-1,2,3,4-tetrahydro-isoquinolin-5-ylamino)-N-(3-trifluoromethyl-pyridin-2-ylmethyl)-acetamide | 0.76 | 506.3 |
| 314 | 2-(2-Isobutyl-3-oxo-1,2,3,4-tetrahydro-isoquinolin-5-ylamino)-N-(2-pyrrolidin-1-yl-ethyl)-N-(2-trifluoromethyl-benzyl)-acetamide | 0.85 | 531.4 |

| Example No | Example name | $t_R$ [min] (LC-A) | MS Data m/z [M + H]$^+$ |
|---|---|---|---|
| 575 | N-(3-Bromo-pyridin-2-ylmethyl)-2-(2-cyclopropylmethyl-4,4-dimethyl-1,2,3,4-tetrahydro-isoquinolin-5-ylamino)-N-(2-dimethylamino-ethyl)-acetamide | 0.58 | 530.1 |
| 576 | N-(3-Bromo-pyridin-2-ylmethyl)-2-(2-cyclopropylmethyl-4,4-dimethyl-1,2,3,4-tetrahydro-isoquinolin-5-ylamino)-N-(2-hydroxy-2-methyl-propyl)-acetamide | 0.72 | 531.2 |
| 577 | N-(2-Chloro-benzyl)-2-(2-cyclopropylmethyl-4,4-dimethyl-1,2,3,4-tetrahydro-isoquinolin-5-ylamino)-N-(2-dimethylamino-ethyl)-acetamide | 0.62 | 483.2 |

Example 73

N-(2-Amino-ethyl)-2-(2-cyclopropylmethyl-1,2,3,4-tetrahydro-isoquinolin-5-ylamino)-N-(4-trifluoromethyl-benzyl)-acetamide is made applying the method described for Example 70 using the corresponding Precursor B3 and Amine 71 respectively. The solid obtained is dissolved in EtOH. Then 1.25M HCl soln. in EtOH (2 eq.) is added and the resulting soln. is allowed to stir at RT for 10 min. The volatiles are then removed under reduced pressure and the resulting crude dihydrochloride dried under HV to yield the title compound. LC-A: $t_R$=0.60 min; [M+H]$^+$=461.1

Precursor B3'

(2-Cyclopropylmethyl-1,2,3,4-tetrahydro-isoquinolin-5-ylamino)-acetic acid

To a solution of (2-cyclopropylmethyl-1,2,3,4-tetrahydro-isoquinolin-5-ylamino)-acetic acid ethyl ester Precursor C3 (2.65 g, 8.27 mmol) in 10 ml THF is added 1M aq. LiOH sol. (14.3 mL, 14.3 mmol). The reaction mixture is allowed to stir at RT overnight. The resulting yellow soln. is acidified by adding 7 mL 2N aq. HCl soln. The volatiles are evaporated under reduced pressure then under HV to yield the title compound as the hydrochloride as a yellow solid which contains 1.6 equivalent of LiCl. This mixture is used without further purification in the next step.

LC-A: $t_R$=0.50 min; $[M+H]^+$=261.1. $^1$H-NMR ($d_6$-DMSO) δ: 7.04 (t, J=7.8 Hz, 1H), 6.46 (d, J=7.6 Hz, 1H), 6.32 (d, J=8.1 Hz, 1H), 4.27 (s, 2H), 3.84 (s, 3H), 3.46 (s, 3H), 3.01 (d, J=7.0 Hz, 2H), 2.79 (s, 2H), 1.22 (m, 1H), 0.65 (m, 2H), 0.42 (d, J=4.6 Hz, 2H)

Precursors B4'-B7'/B9'/B12'-B17'/B22'-B23' listed in Table 6 are prepared applying the above method described for Precursor B3' using the corresponding Precursor as starting material. As for the case of Precursor B3', Precursors B4'-B7'/B9'/B12'-B17'/B22'-B23' are obtained as a mixture with LiCl and are obtained as their hydrochloride salt if they bear a basic nitrogen atom mixture is allowed to stir at RT overnight. The solvent is coevaporated twice with DCM under reduced pressure. The solid residue is triturated in ether, filtered and dried under HV. This yields quantitatively the subtitle compound as a beige solid.

LC-A: $t_R$=0.52 min; $[M+H]^+$=235.1 b) To a solution of (1,2,3,4-tetrahydro-isoquinolin-5-ylamino)-acetic acid ethyl ester hydrochloride (12.7 g, 42.2 mmol) in 100 mL DCM is added at RT cyclopropanecarboxaldehyde (3.66 g, 3.9 mL) and DIPEA (10.9 g, 84.4 mmol). The resulting yellow solution is allowed to stir for 1 h at RT. Then NaBH(OAc)$_3$ (13.4 g, 63.3 mmol) is added in small portions and the resulting mixture is allowed to stir at RT for 1 h. Sat. aq. NaHCO$_3$ soln. is slowly added and the resulting aq. phase is extracted three times with DCM. The combined organic phase is washed with sat. aq. NaHCO$_3$ soln. and with brine then dried over MgSO$_4$, filtered and the solvent removed under reduced pressure. Flash-chromatography on silica-gel (Eluent: gradient of EtOAc/heptane/MeOH 50:50:0 to 100:0:0 to 90:0:10) yields 7.1 g (58%) of the title compound as a yellow solid.

LC-A: $t_R$=0.62 min; $[M+H]^+$=289.2. $^1$H-NMR (CDCl$_3$) δ: 7.07 (t, J=7.7 Hz, 1H), 6.54 (d, J=7.6 Hz, 1H), 6.36 (d, J=7.9 Hz, 1H), 4.28 (q, J=7.1 Hz, 2H), 4.19 (t, J=5.0 Hz, 2H), 3.95 (d, J=5.2 Hz, 2H), 3.71 (s, 2H), 2.91 (t, J=6.1 Hz, 2H), 2.67 (t, J=6.0 Hz, 2H), 2.45 (d, J=6.6 Hz, 2H), 1.33 (t, J=7.1 Hz, 3H), 1.01 (m, 1H), 0.59 (m, 2H), 0.21 (m, 2H)

TABLE 6

Precursor B4'-B7'/B9'/B12'-B17'/B22'-B23'

| Precursor | Example name | $t_R$ [min] (LC-A) | MS Data m/z [M + H]$^+$ |
|---|---|---|---|
| B4' | [2-(2,2,2-Trifluoro-ethyl)-1,2,3,4-tetrahydro-isoquinolin-5-ylamino]-acetic acid | 0.57 | 289.1 |
| B5' | (2-Cyclopropylmethyl-1,2,3,4-tetrahydro-isoquinolin-5-yl(methyl)amino)-acetic acid | 0.47 | 275.1 |
| B6' | (2-Cyclopropylmethyl-6-chloro-1,2,3,4-tetrahydro-isoquinolin-5-ylamino)-acetic acid | 0.54 | 295.11 |
| B7' | (2-Cyclopropylmethyl-6-methoxy-1,2,3,4-tetrahydro-isoquinolin-5-ylamino)-acetic acid | 0.47 | 291.1 |
| B9' | (2-Cyclopropylmethyl-4,4-dimethyl-1,2,3,4-tetrahydro-isoquinolin-5-ylamino)-acetic acid | 0.56 | 289.3 |
| B12' | (2-(2-Fluoroethyl)-1,2,3,4-tetrahydroisoquinolin-5-ylamino)-acetic acid | 0.42 | 253.2 |
| B13' | (8-Chloro-2-(cyclopropylmethyl)-1,2,3,4-tetrahydroisoquinolin-5-ylamino)acetic acid | 0.57 | 295.2 |
| B14' | (8-Fluoro-2-(cyclopropylmethyl)-1,2,3,4-tetrahydroisoquinolin-5-ylamino)acetic acid | 0.51 | 279.3 |
| B15' | (2-(Cyclopropylmethyl)-6-methyl-1,2,3,4-tetrahydroisoquinolin-5-ylamino)-acetic acid | 0.51 | 275.1 |
| B16' | (S)-2-(2-(Cyclopropylmethyl)-1,2,3,4-tetrahydroisoquinolin-5-ylamino)-propionic acid | 0.53 | 275.2 |
| B17' | 1-((2-(Cyclopropylmethyl)-1,2,3,4-tetrahydroisoquinolin-5-yl)amino)cyclopropane-1-carboxylic acid | 0.56 | 287.3 |
| B22' | (2-ethyl-3-oxo-1,2,3,4-tetrahydroisoquinolin-5-yl)aminoacetic acid | 0.59 | 249.2 |
| B23' | (2-isobutyl-3-oxo-1,2,3,4-tetrahydroisoquinolin-5-yl)aminoacetic acid | nd | nd |

Precursor C3

(2-Cyclopropylmethyl-1,2,3,4-tetrahydro-isoquinolin-5-ylamino)-acetic acid ethyl ester a) (1,2,3,4-Tetrahydro-isoquinolin-5-ylamino)-acetic acid ethyl ester hydrochloride To a solution of 5-(ethoxycarbonylmethyl-amino)-3,4-dihydro-1H-isoquinoline-2-carboxylic acid tert-butyl ester Precursor D1 (20 g, 51.4 mmol) in 150 mL dioxane is added dropwise 77 mL 4N HCl soln. in dioxane. The resulting

Precursor C4

[2-(2,2,2-Trifluoro-ethyl)-1,2,3,4-tetrahydro-isoquinolin-5-ylamino]-acetic acid ethyl ester To a solution of (1,2,3,4-tetrahydro-isoquinolin-5-ylamino)-acetic acid ethyl ester hydrochloride (Precursor C3 step a) (200 mg, 0.739 mmol) in 3 mL toluene is added TEA (149.5 mg, 2.95 mmol). The resulting solution is allowed to stir for 10 min at RT. Then 2,2,2-trifluoroethyltrifluoromethanesulfonate (171 mg, 0.739 mmol) is added in and the resulting mixture is allowed to stir at RT for 2 h then at reflux for 2 h. TEA (149.5 mg, 2.95 mmol) and 2,2,2-trifluoroethyltrifluoromethanesulfonate (171 mg, 0.739 mmol) are added again and the resulting suspension is allowed to stir at reflux for 2 h then at RT overnight. After cooling the reaction mixture is poured onto water. The resulting aq. phase is extracted twice with DCM. The combined organic phase is washed with sat. aq. NaHCO$_3$ soln. and with brine then dried over MgSO$_4$, filtered and the solvent removed under reduced pressure. Flash-chromatography on silica-gel (gradient of EtOAc/heptane 5:95 to 100:0) yields 114 mg (49%) of the title compound as a yellow oil.

LC-A: $t_R$=0.77 min; [M+H]$^+$=317.1

Precursor C12

(2-(2-Fluoroethyl)-1,2,3,4-tetrahydroisoquinolin-5-ylamino)-acetic acid ethyl ester To a solution of (1,2,3,4-tetrahydro-isoquinolin-5-ylamino)-acetic acid ethyl ester hydrochloride (Precursor C3 step a) (100 mg, 0.32 mmol) in 1 mL DMF is added DIPEA (62 mg, 0.48 mmol). The resulting solution is allowed to stir for 10 min at RT. Then 1-bromo-2-fluoroethane (41 mg, 0.32 mmol) is added and the resulting mixture is allowed to stir at RT overnight. The reaction mixture is poured onto water and the resulting aq. phase is extracted three times with EtOAc. The combined organic phase is washed with sat. aq. NaHCO$_3$ soln. and with brine then dried over MgSO$_4$, filtered and the solvent removed under reduced pressure to yield 64 mg (71%) of the title compound as a brown oil which is used without purification in the next step.

LC-A: $t_R$=0.56 min; [M+H]$^+$=281.3

Precursor C18 rac-[2-((1 S*,2S*)-2-Fluoro-cyclopropanecarbonyl)-1,2,3,4-tetrahydro-isoquinolin-5-ylamino]-acetic acid ethyl ester To a solution of (1,2,3,4-tetrahydro-isoquinolin-5-ylamino)-acetic acid ethyl ester hydrochloride (Precursor C3 step a) (1 g, 3.69 mmol) and cis-2-fluoro-cyclopropanecarboxylic acid (384 mg, 3.69 mmol) in 20 mL DMF is added HATU (1.69 g, 4.43 mmol) then DIPEA (1.19 g, 9.23 mmol). The brown solution is stirred for overnight at RT. Sat. aq. NaHCO$_3$ soln. is added and the resulting aq. phase is extracted twice with EtOAc. The combined organic phase is washed with brine, dried over MgSO$_4$, filtered and the solvent evaporated under reduced pressure. Flash-chromatography on silica-gel (gradient of EtOAc/heptane 50:50 to 100:0) yields 747 mg (63%) of the title compound as a yellow oil.

LC-A: $t_R$=0.77 min; [M+H]$^+$=321.2

Precursor C5

(2-Cyclopropylmethyl-1,2,3,4-tetrahydro-isoquinolin-5-yl(methyl)amino)-acetic acid ethyl ester a) tert-Butyl 5-((2-ethoxy-2-oxoethyl)(methyl)amino)-3,4-dihydroisoquinoline-2(1H)-carboxylate A solution of 5-(ethoxycarbonylmethyl-amino)-3,4-dihydro-1H-isoquinoline-2-carboxylic acid tert-butyl ester Precursor D1 (100 g, 0.3 mmol), formaldehyde (49.9 mg, 0.59 mmol) and AcOH (36 mg, 0.59 mmol) in 2 mL DCM is stirred at RT for 1 h. Then NaBH(OAc)$_3$ (190 mg, 0.897 mmol) is added and the resulting mixture is allowed to stir at RT for 1 h. It is then poured onto water and the resulting aq. phase is extracted twice with DCM. The combined organic phase is washed with brine dried over MgSO$_4$, filtered and evaporated under reduced pressure. This yields 100 mg (96%) of the sub-title compound which is used as such in the next step.

LC-A: $t_R$=0.56 min; [M+H]$^+$=249.1; $^1$H-NMR (CDCl$_3$) δ: 7.17 (t, J=7.8 Hz, 1H), 7.01 (d, J=8.0 Hz, 1H), 6.84 (m, 1H), 4.58 (s, 2H), 4.20 (q, J=7.2 Hz, 2H), 3.72 (s, 2H), 3.60 (d, J=0.8 Hz, 2H), 2.81-2.92 (m, 5H), 1.52 (s, 9H), 1.28 (t, J=7.1 Hz, 3H)

b) 2-(Methyl(1,2,3,4-tetrahydroisoquinolin-5-yl)amino)acetic acid ethyl ester

To a solution of tert-butyl 5-((2-ethoxy-2-oxoethyl)(methyl)amino)-3,4-dihydroisoquinoline-2(1H)-carboxylate (100 mg, 0.248 mmol) in 2 mL DCM is added 0.5 mL TFA. The resulting yellowish solution is stirred at RT for 1.5 h then poured into water. The resulting aq. phase is made basic with sat. aq. NaHCO$_3$ soln. then extracted twice with DCM. The organic phase is washed with brine then dried over MgSO$_4$, filtered and the solvent removed under reduced pressure to yield 61 mg (99%) of the sub-title compound which is used as such in the next step.

LC-A: $t_R$=0.95 min; [M+H]$^+$=349.2 c) To a solution of 2-(methyl(1,2,3,4-tetrahydroisoquinolin-5-yl)amino)acetic acid ethyl ester (61 mg, 0.214 mmol) in 2 mL DMF is added K$_2$CO$_3$ (29.5 mg, 0.214 mmol). The resulting mixture is allowed to stir for 20 min at RT. Then bromomethylcyclopropane (28.9 mg, 0.214 mmol) is added and the resulting yellow mixture is allowed to stir at RT for 2 h. The mixture is poured into water and the resulting aq. phase is extracted three times with EtOAc. The combined organic phase is washed with sat. aq. NaHCO$_3$ soln., with brine then dried over MgSO$_4$, filtered and the solvent removed under reduced pressure. Drying under HV yields 59 mg (91%) of the title compound as a yellow oil.

LC-A: $t_R$=0.64 min; [M+H]$^+$=303.2

Precursor C6

(6-Chloro-2-cyclopropylmethyl-1,2,3,4-tetrahydro-isoquinolin-5-ylamino)-acetic acid ethyl ester a) (6-Chloro-1,2,3,4-tetrahydro-isoquinolin-5-ylamino)-acetic acid ethyl ester To a solution of 6-chloro-5-(ethoxycarbonylmethyl-amino)-3,4-dihydro-1H-isoquinoline-2-carboxylic acid tert-butyl ester Precursor D6 (215 mg, 0.583 mmol) in 4 mL DCM is added 1 mL TFA. The resulting yellowish solution is stirred at RT for 1 h then poured into water. The resulting aq. phase is made basic with sat. aq. NaHCO$_3$ soln. then extracted twice with DCM. The organic phase is washed with brine then dried over MgSO$_4$, filtered and the solvent removed under reduced pressure to yield 149 mg (95%) of the sub-title compound used as such in the next step.

LC-A: $t_R$=0.58 min; [M+H]$^+$=269.1 b) To a solution of (6-chloro-1,2,3,4-tetrahydro-isoquinolin-5-ylamino)-acetic acid ethyl ester (145 mg, 0.54 mmol) in 4 mL DMF is added K$_2$CO$_3$ (74.6 mg, 0.54 mmol). The resulting mixture is allowed to stir for 20 min at RT. Then bromomethylcyclopropane (72.8 mg, 0.54 mmol) is added and the resulting yellow mixture is allowed to stir at RT for 4.5 h. The mixture is poured onto water and the resulting aq. phase is extracted three times with DCM. The combined organic phase is washed with sat. aq. NaHCO$_3$ soln. and with brine then dried over MgSO$_4$, filtered and the solvent removed under reduced pressure. Flash-chromatography on silica-gel (Eluent: gradient of EtOAc/heptane 5:95 to 100:0) yields 145 mg (83%) of the title compound as a yellow oil.

LC-A: $t_R$=0.65 min; [M+H]$^+$=323.1

Precursors C7/C9 and C13-C15 listed in Table 7 are prepared applying the above method described for Precursor C6 using the corresponding Precursors D7/C8 and D13-D15 respectively as starting material.

TABLE 7

Precursor C7/C9 and C13-C15

| Precursor | Example name | $t_R$ [min] (LC-A) | MS Data m/z [M + H]$^+$ |
|---|---|---|---|
| C7 | (2-Cyclopropylmethyl-6-methoxy-1,2,3,4-tetrahydro-isoquinolin-5-ylamino)-acetic acid ethyl ester | 0.61 | 319.2 |
| C9 | (2-Cyclopropylmethyl-4,4-dimethyl-1,2,3,4-tetrahydro-isoquinolin-5-ylamino)-acetic acid ethyl ester | 0.68 | 317.2 |
| C13 | (8-Chloro-2-(cyclopropylmethyl)-1,2,3,4-tetrahydroisoquinolin-5-ylamino) acetic acid ethyl ester | 0.67 | 323.2 |
| C14 | (8-Fluoro-2-(cyclopropylmethyl)-1,2,3,4-tetrahydroisoquinolin-5-ylamino) acetic acid ethyl ester | 0.62 | 307.3 |
| C15 | (6-Methyl-2-(cyclopropylmethyl)-1,2,3,4-tetrahydroisoquinolin-5-ylamino) acetic acid ethyl ester | 0.64 | 303.2 |

Precursor D6 6-Chloro-5-(ethoxycarbonylmethyl-amino)-3,4-dihydro-1H-isoquinoline-2-carboxylic acid tert-butyl ester, LC-A: $t_R$=0.97 min; [M+H]$^+$=369.0, Precursor D7 6-Methoxy-5-(ethoxycarbonylmethyl-amino)-3,4-dihydro-1H-isoquinoline-2-carboxylic acid tert-butyl ester, LC-A: $t_R$=0.91 min; [M+H]$^+$=365.1 and Precursor D15 6-Methyl-5-(ethoxycarbonylmethyl-amino)-3,4-dihydro-1H-isoquinoline-2-carboxylic acid tert-butyl ester, LC-A: $t_R$=0.95 min; [M+H]$^+$=349.2 are made according to the procedure described for the synthesis of Precursor D1 using the appropriate starting materials.

Precursor D13

8-Chloro-5-(ethoxycarbonylmethyl-amino)-3,4-dihydro-1H-isoquinoline-2-carboxylic acid tert-butyl ester a) 8-chloro-5-nitro-1,2,3,4-tetrahydroisoquinoline To a solution of 8-chloro-5-nitroisoquinoline (630 mg, 3.02 mmol) in 7 mL AcOH cooled to 0° C. in an ice-bath is added NaBH$_4$ (685 mg, 18.1 mmol). The resulting mixture is stirred at 0° C. for 30 min then poured into ice-cold water. Sat. aq. NH$_3$ soln. is added and the resulting aq. phase is extracted twice with DCM. The organic phase is washed with brine then dried over MgSO$_4$, filtered and the solvent removed under reduced pressure to yield 520 mg (81%) of the sub-title compound used as such in the next step.

LC-A: $t_R$=0.45 min; [M+H]$^+$=213.1 b) tert-Butyl 8-chloro-5-nitro-3,4-dihydroisoquinoline-2(1H)-carboxylate

To a solution of 8-chloro-5-nitro-1,2,3,4-tetrahydroisoquinoline (520 mg, 2.23 mmol) in a mixture of 5 mL THF and 10 mL is added NaOH (356 mg, 8.9 mmol) and Boc$_2$O (729 mg, 3.34 mmol). The resulting mixture is stirred at RT 2 h then poured into water. The resulting aq. phase is extracted twice with EtOAc. The organic phase is washed with brine then dried over MgSO$_4$, filtered and the solvent removed under reduced pressure. Flash-chromatography on silica-gel: (Eluent: Hept./EtOAc 95:5 to 60:40) yields 503 mg (72%) of the sub-title compound as a yellow solid.

LC-A: $t_R$=0.97 min; [M+H]$^+$=n.d.; $^1$H NMR (CDCl$_3$), δ: 7.84 (d, J=8.7 Hz, 1H), 7.43 (d, J=8.7 Hz, 1H), 4.68 (bs, 2H), 3.66 (t, J=5.8 Hz, 2H), 3.13 (t, J=5.8 Hz, 2H), 1.54 (m, 9H)

c) tert-Butyl 5-amino-8-chloro-3,4-dihydroisoquinoline-2 (1H)-carboxylate

To a solution of tert-butyl 8-chloro-5-nitro-3,4-dihydroisoquinoline-2(1H)-carboxylate (300 mg, 0.873 mmol) in 15 mL EtOH is added SnCl$_2$.2H$_2$O (591 mg, 2.62 mmol). The resulting mixture is heated at 70° C. for 2 h then stirred at RT overnight. The mixture is poured into water then put to pH=8-9 with sat. aq. NaHCO$_3$ soln. and extracted three times with DCM. The combined organic phase is washed with water and brine then dried over MgSO$_4$ and concentrated in vacuo. Flash-chromatography on silica-gel: (Eluent: Hept./EtOAc 95:5 to 60:40) yields 198 mg (80%) of the sub-title compound as an orange solid.

LC-A: $t_R$=0.92 min; [M-tBu+MeCN]$^+$=268.0; $^1$H-NMR (400 MHz, CDCl$_3$) δ: 7.06 (d, J=8.4 Hz, 1H), 6.56 (d, J=8.4 Hz, 1H), 4.56 (s, 2H), 3.71 (t, J=5.8 Hz, 2H), 3.63 (bs, 2H), 2.56 (t, J=5.8 Hz, 2H), 1.52 (s, 9H).

d) To a solution of tert-butyl 5-amino-8-chloro-3,4-dihydroisoquinoline-2(1H)-carboxylate (198 mg, 0.7 mmol) in 3 mL MeCN is added DIPEA (109 mg, 0.84 mmol). The mixture is stirred at RT for 10 min and ethyl bromoacetate (170 mg, 1.02 mmol) is added. The solution is stirred at reflux for 1 h and then allowed to cool down to RT. The mixture is poured into water and extracted twice with DCM. The combined organic phase is washed with sat. aq. NaHCO$_3$ soln. and brine then dried over MgSO$_4$ and concentrated in vacuo.

Flash-chromatography on silica-gel: (Eluent: Hept./EtOAc 95:5 to 60:40) yields 90 mg (35%) of the title compound as a yellow oil.

LC-A: $t_R$=0.98 min; [M-tBu+MeCN]$^+$=354.0

Precursor D14

8-Fluoro-5-(ethoxycarbonylmethyl-amino)-3,4-dihydro-1H-isoquinoline-2-carboxylic acid tert-butyl ester is made according to the procedure described for the synthesis of Precursor D13 starting from 8-fluoro-5-nitro-1,2,3,4-tetrahydroisoquinoline and following steps b), c) and d) cited above.

LC-A: $t_R$=0.95 min; [M+H]$^+$=353.1; $^1$H-NMR (400 MHz, d$_6$-DMSO) δ: 6.86 (dd, J, =J$_2$=9.0 Hz, 1H), 6.25 (dd, J$_1$=4.6 Hz, J$_2$=9.0 Hz, 1H), 5.30 (m, 1H), 4.45 (s, 2H), 4.11 (q, J=7.1 Hz, 2H), 3.91 (d, J=6.3 Hz, 2H), 3.60 (t, J=5.4 Hz, 2H), 1.43 (m, 11H), 1.19 (t, J=7.1 Hz, 4H)

Precursor C16

2-(S)-(2-(Cyclopropylmethyl)-1,2,3,4-tetrahydroisoquinolin-5-ylamino)-propionic acid ethyl ester a) 2-(S)-isoquinolin-5-ylaminopropionic acid ethyl ester
To a solution of 5-bromoisoquinoline (300 mg, 1.41 mmol), L-ethyl 2-aminopropanoate hydrochloride (217 mg, 1.41 mmol), $Cs_2CO_3$ (1105 mg, 3.39 mmol), Brettphos (75.9 mg, 0.141 mmol) and $Pd_2(dba)_3$ (65 mg, 0.0707 mmol) in a microwave tube is added under inert atmosphere 3 mL degassed toluene. The mixture is irradiated under microwaves at 140° C. for 30 min then at 150° C. for 30 min. Subsequently $Cs_2CO_3$ (460 mg), Brettphos (30 mg) and $Pd_2(dba)_3$ (30 mg) are added again and the resulting mixture is irradiated at 150° C. for 30 min. The brownish suspension is diluted in EtOAc and sat. aq. $NaHCO_3$ soln. is added. The organic layer is separated and the aq. layer is extracted twice with EtOAc. The combined organic layers are washed with water and brine, dried over $MgSO_4$, filtered and evaporated. Flash-chromatography on silica-gel: (Eluent: Hept./EtOAc 95:5 to 20:80 to 0:100) yields 137 mg (40%) of the sub-title compound as a yellow oil.

LC-A: $t_R$=0.58 min; $[M+H]^+$=246.3 b) 2-(S)-(1,2,3,4-Tetrahydroisoquinolin-5-ylamino)-propionic acid ethyl ester
A solution of 2-(S)-isoquinolin-5-ylaminopropionic acid ethyl ester (136 mg, 0.418 mmol) in 8 mL AcOH is purged three times with Argon then $PtO_2$ (28.4 mg, 0.125 mmol) is carefully added and the resulting dark mixture is stirred under $H_2$ atmosphere at RT for 5 h. It is then filtered over Celite, and the filter cake rinsed with AcOH. Evaporation of the solvent in vacuo yields 198 mg of the sub-title compound as a brown oil which is use as such in the next step.

c) To a solution of 198 mg of 2-(S)-(1,2,3,4-tetrahydroisoquinolin-5-ylamino)-propionic from step b) dissolved in 4 mL DMF is added $K_2CO_3$ (132 mg, 0.96 mmol). The resulting yellow suspension is allowed to stir at RT for 10 min. Then (bromomethyl)cyclopropane (64 mg, 0.474 mmol) is added and the reaction mixture is allowed to stir at RT overnight. It is then poured into water and the resulting aq. phase is extracted three times with DCM. The combined organic phase is washed with sat. aq. $NaHCO_3$ sol., then with brine, dried over $MgSO_4$, filtered and evaporated under reduced pressure. Flash-chromatography on silica-gel: (Eluent: Hept./EtOAc 95:5 to 20:80 to 0:100) yields 118 mg (58%) of the title compound as a yellow oil.

LC-A: $t_R$=0.64 min; $[M+H]^+$=303.3; $^1$H-NMR (400 MHz, $CDCl_3$) δ: 7.04 (t, J=7.8 Hz, 1H), 6.52 (d, J=7.8 Hz, 1H), 6.41 (d, J=7.8 Hz, 1H), 4.20 (m, 3H), 4.06 (d, J=8.1 Hz, 1H), 3.71 (s, 2H), 2.91 (t, J=6.0 Hz, 2H), 2.66 (m, 2H), 2.45 (d, J=6.5 Hz, 2H), 1.51 (d, J=6.8 Hz, 3H), 1.28 (t, J=7.1 Hz, 4H), 1.01 (m, 2H), 0.59 (m, 2H), 0.21 (m, 2H).

Precursor C17

1-((2-(Cyclopropylmethyl)-1,2,3,4-tetrahydroisoquinolin-5-yl)amino)cyclopropane-1-carboxylic acid ethyl ester is made according to the procedure described for the synthesis of Precursor C16 using 1-amino-cyclopropyl-1-carboxylic acid ethyl ester hydrochloride instead of L-ethyl 2-aminopropanoate hydrochloride in step a)

LC-A: $t_R$=0.67 min; $[M+H]^+$=315.3

Precursor C22

(2-Ethyl-3-oxo-1,2,3,4-tetrahydro-isoquinolin-5-ylamino)-acetic acid ethyl ester a) 5-bromo-2-ethyl-1,4-dihydro-2H-isoquinolin-3-one
[Org. Process R&D 2010, 14, 1, 227] To a solution of ethyl 2-bromophenylacetamide [1150114-52-1](10.85 g, 44.8 mmol) in 46.1 mL Eaton's reagent is added paraformaldehyde (1.7 g, 53.8 mmol) and the resulting mixture is heated to 80° C. for 2.5 h. After cooling the reaction mixture is diluted with water and basified with 50% aq. NaOH soln. to pH=8. The resulting aq. Phase is extracted three times with EtOAc. The combined organic phase is washed with brine, then dried over $MgSO_4$, filtered and the solvent removed under reduced pressure. Flash-chromatography on silica-gel: (Eluent: Hept./EtOAc 90:10 to 50:50) yields 3.475 g (31%) of the sub-title compound as an white solid.

LC-A: $t_R$=0.75 min; $[M+H]^+$=254.0; $^1$H-NMR (400 MHz, $CDCl_3$) δ: 7.53 (dd, $J_1$=2.5 Hz, $J_2$=6.5 Hz, 1H), 7.15 (m, 2H), 4.54 (s, 2H), 3.71 (t, J=1.6 Hz, 2H), 3.62 (q, J=7.2 Hz, 2H), 1.24 (t, J=7.2 Hz, 3H)

b) 5-(Benzhydrylidene-amino)-2-ethyl-1,4-dihydro-2H-isoquinolin-3-one
To a solution of 5-bromo-2-ethyl-1,4-dihydro-2H-isoquinolin-3-one (3475 mg, 13.7 mmol) in 50 mL degassed toluene are added $Pd_2(dba)_3$ (977 mg, 1.07 mmol), BINAP (1873 mg, 3.01 mmol) and 0.5M KHMDS soln. in toluene (54.6 mL, 27.3 mmol) followed by benzophenone imine (7665 mg, 41 mmol) and the resulting reaction mixture is allowed to stir at 120° C. for 1.25 h. After cooling, sat. aq. $NH_4Cl$ soln. and water (1:1) are added and the resulting aq. phase is extracted with DCM. The combined organic phase is washed with sat. aq. NaHCO3 soln. and brine then dried over $MgSO_4$, filtered and the solvent removed under reduced pressure. Flash-chromatography on silica-gel: (Eluent: Hept./EtOAc 95:5 to 70:30 then change of eluents: Hept./EtOAcTEA 9:1:0.1 to 70:30:0.1) yields 762 mg (16%) of the sub-title compound as an orange solid.

LC-A: $t_R$=0.92 min; $[M+H]^+$=355.2 c) 5-Amino-2-ethyl-1,4-dihydro-2H-isoquinolin-3-one
To a solution of 5-(benzhydrylidene-amino)-2-ethyl-1,4-dihydro-2H-isoquinolin-3-one (762 mg, 2.15 mmol) in 20 mL MeOH is added sodium acetate (423 mg, 5.16 mmol) and hydroxylamine hydrochloride (270 mg, 3.89 mmol). The resulting reaction mixture is stirred at RT for 45 min. 1N aq. NaOH soln. is added and the resulting aq. phase is extracted twice with DCM. The combined organic phase is washed with brine, dried over $MgSO_4$, filtered and the solvent removed under reduced pressure. The resulting crude sub-title compound (500 mg) is used as such in the next step.

LC-A: $t_R$=0.61 min; $[M+H]^+$=191.34 d) To a solution of 5-amino-2-ethyl-1,4-dihydro-2H-isoquinolin-3-one (409 mg, 2.15 mmol) and DIPEA (556 mg, 4.3 mmol) in 8 ml anhydrous dioxane is heated at 60° C. Ethyl bromoacetate (395 mg, 2.36 mmol) is added slowly. The resulting reaction mixture is shaken at 60° C. for 3.5 h. Then ethyl bromoacetate (72.6 mg, 0.436 mmol) is added again a further stirred a 60° C. After 5 h ethyl bromoacetate (36 mg, 0.218 mmol) is added again and the resulting mixture stirred at 60° C. overnight. After cooling, the mixture is concentrated to dryness then partitioned between EtOAc and water. The resulted organic layer is washed with brine, dried over $MgSO_4$, filtered and concentrated to dryness. The crude residue is purified by prep. HPLC (Method D) to yield 285 mg (48%) of the title compound as a yellow solid.

LC-A: $t_R$=0.74 min; $[M+H]^+$=277.16; $^1$H-NMR (400 MHz, $CDCl_3$) δ: 7.17 (t, J=7.9 Hz, 1H), 6.63 (d, J=7.6 Hz, 1H), 6.44 (d, J=8.1 Hz, 1H), 4.53 (s, 2H), 4.29 (q, J=7.1 Hz, 2H), 3.95 (s, 2H), 3.61 (q, J=7.1 Hz, 2H), 3.45 (s, 2H), 1.33 (t, J=7.1 Hz, 3H), 1.24 (t, J=7.1 Hz, 3H)

Precursor C23

(2-Isobutyl-3-oxo-1,2,3,4-tetrahydro-isoquinolin-5-ylamino)-acetic acid ethyl ester Is made according to the procedure described for the synthesis of Precursor C22 using the corresponding starting material. LC-B: $t_R$=0.75 min; [M+H]$^+$=305.1; $^1$H-NMR (400 MHz, CDCl$_3$) δ: 7.16 (t, J$_1$=7.6 Hz, J$_2$=8.1 Hz 1H), 6.61 (d, J=7.6 Hz, 1H), 6.44 (d, J=8.1 Hz, 1H), 4.49 (s, 2H), 4.29 (q, J=7.1 Hz, 2H), 3.95 (s, 2H), 3.47 (s, 2H), 3.39 (d, J=7.6 Hz, 2H), 2.10 (m, 1H), 1.33 (t, J=7.1 Hz, 3H), 0.96 (d, J=6.7 Hz, 6H)

Example 92

5-{(E)-2-[(2-Chloro-benzyl)-ethyl-carbamoyl]-vinyl}-3,4-dihydro-1H-isoquinoline-2-carboxylic acid tert-butyl ester To a solution of 5-((E)-2-carboxy-vinyl)-3,4-dihydro-1H-isoquinoline-2-carboxylic acid tert-butyl ester Precursor E1 (50 mg, 0.165 mmol), (2-chloro-benzyl)-ethyl-amine Amine 1 (27.8 mg, 0.165 mmol) and HATU (75.2 mg, 0.412 mmol) in 1 mL DCM is added DIPEA (53.3 mg, 0.412 mmol). The reaction mixture is allowed to stir at RT for 1 h. Water is added and the resulting organic phase is washed with sat. aq NaHCO$_3$ soln. and brine then dried over MgSO$_4$, filtered and evaporated under reduced pressure. The crude residue is purified by prep. HPLC (Method E) to yield the title compound as a yellow oil.

LC-A: $t_R$=1.03 min; [M+H]$^+$=455.3; $^1$H-NMR (d$_6$-DMSO): 60:40 mixture of rotamers 67.82-7.68 (m, 1.6H), 7.45 (m, 1.4H), 7.31-7.08 (m, 5.6H), 6.83 (d, J=14.0 Hz), 4.84 (s, 0.8H), 4.68 (s, 1.2H), 4.50 (m, 2H), 2.84 (bs, 1.2H), 2.74 (bs, 0.8H), 1.41 (s, 9H), 1.14 (bs, 1.8H), 1.06 (bs, 1.2). Some peaks are missing due to irradiation of residual water peak.

Examples 93-101/316-350 listed in Table 8 are prepared applying the method described for Example 92 using the corresponding Precursor and Amine respectively.

TABLE 8

Examples 93-101/316-350

| Example No | Example name | $t_R$ [min] (LC-C) | MS Data m/z [M + H]$^+$ |
|---|---|---|---|
| 93 | 5-{(E)-2-[Benzyl-(2-dimethylamino-ethyl)-carbamoyl]-vinyl}-3,4-dihydro-1H-isoquinoline-2-carboxylic acid tert-butyl ester | 0.96 | 464.4 |
| 94 | 5-[(E)-2-(Benzyl-ethoxycarbonylmethyl-carbamoyl)-vinyl]-3,4-dihydro-1H-isoquinoline-2-carboxylic acid tert-butyl ester | 1.28 | 479.4 |
| 95 | 5-{(E)-2-[Benzyl-(1,1-dioxo-tetrahydro-1l6-thiophen-3-yl)-carbamoyl]-vinyl}-3,4-dihydro-1H-isoquinoline-2-carboxylic acid tert-butyl ester | 1.18 | 511.3 |
| 96 | 5-{(E)-2-[(1-Methyl-piperidin-4-yl)-(2-trifluoromethyl-benzyl)-carbamoyl]-vinyl}-3,4-dihydro-1H-isoquinoline-2-carboxylic acid tert-butyl ester | 1.02 | 558.5 |
| 97 | 5-{(E)-2-[(2-Dimethylamino-ethyl)-(2-trifluoromethyl-benzyl)-carbamoyl]-propenyl}-3,4-dihydro-1H-isoquinoline-2-carboxylic acid tert-butyl ester | 1.03 | 546.5 |
| 98 | 5-{2-[(2-Chloro-benzyl)-(2-dimethylamino-ethyl)-carbamoyl]-ethyl}-3,4-dihydro-1H-isoquinoline-2-carboxylic acid tert-butyl ester | 0.99 | 500.4 |
| 99 | 5-{2-[(2-Dimethylamino-ethyl)-(2-trifluoromethyl-benzyl)-carbamoyl]-ethyl}-3,4-dihydro-1H-isoquinoline-2-carboxylic acid tert-butyl ester | 1.02 | 534.4 |
| 100 | 5-{2-[(1-Methyl-piperidin-4-yl)-(2-trifluoromethyl-benzyl)-carbamoyl]-ethyl}-3,4-dihydro-1H-isoquinoline-2-carboxylic acid tert-butyl ester | 1.01 | 560.4 |
| 101 | 5-{[Benzyl-(2-dimethylamino-ethyl)-carbamoyl]-methoxy}-3,4-dihydro-1H-isoquinoline-2-carboxylic acid tert-butyl ester | 0.93 | 468.4 |

| Example No | Example name | $t_R$ [min] (LC-F) | MS Data m/z [M + H]+ |
|---|---|---|---|
| 316 | (E)-N-Benzyl-N-(1,1-dioxo-tetrahydro-1l6-thiophen-3-yl)-3-[2-(2-methoxy-ethyl)-1,2,3,4-tetrahydro-isoquinolin-5-yl]-acrylamide | 0.61 | 469.3 |
| 317 | (E)-N-(2-Dimethylamino-ethyl)-3-[2-(2-methoxy-ethyl)-1,2,3,4-tetrahydro-isoquinolin-5-yl]-N-(2-trifluoromethyl-benzyl)-acrylamide | 0.47 | 490.3 |
| 318 | (E)-N-(2-Dimethylamino-ethyl)-3-[2-(2-methoxy-ethyl)-1,2,3,4-tetrahydro-isoquinolin-5-yl]-N-(3-trifluoromethyl-pyridin-2-ylmethyl)-acrylamide | 0.4 | 491.3 |
| 319 | {2-[{(E)-3-[2-(2-Methoxy-ethyl)-1,2,3,4-tetrahydro-isoquinolin-5-yl]-acryloyl}-(2-trifluoromethyl-benzyl)-amino]-ethyl}-methyl-carbamic acid tert-butyl ester | 0.9 | 576.3 |
| 320 | (E)-N-(3,3-Dimethyl-butyl)-3-[2-(2-methoxy-ethyl)-1,2,3,4-tetrahydro-isoquinolin-5-yl]-N-(3-methyl-pyridin-2-ylmethyl)-acrylamide | 0.71 | 450.4 |
| 321 | (E)-N-(2-Hydroxy-3-methoxy-propyl)-3-[2-(2-methoxy-ethyl}-1,2,3,4-tetrahydro-isoquinolin-5-yl]-N-(2-trifluoromethyl-benzyl)-acrylamide | 0.71 | 507.3 |
| 322 | (E)-N-[2-(4,4-Difluoro-piperidin-1-yl)-ethyl]-3-[2-(2-methoxy-ethyl)-1,2,3,4-tetrahydro-isoquinolin-5-yl]-N-(3-trifluoromethyl-pyridin-2-ylmethyl)-acrylamide | 0.49 | 567.3 |
| 323 | (E)-N-(2-Hydroxy-2-methyl-propyl)-3-[2-(2-methoxy-ethyl)-1,2,3,4-tetrahydro-isoquinolin-5-yl]-N-(2-trifluoromethyl-benzyl)-acrylamide | 0.74 | 491.3 |
| 324 | (E)-3-[2-(2-Methoxy-ethyl)-1,2,3,4-tetrahydro-isoquinolin-5-yl]-N-(3-methyl-oxetan-3-ylmethyl)-N-(2-trifluoromethyl-benzyl)-acrylamide | 0.75 | 503.3 |

TABLE 8-continued

Examples 93-101/316-350

| | | | |
|---|---|---|---|
| 325 | (E)-N-(3-Hydroxy-3-methyl-butyl)-3-[2-(2-methoxy-ethyl)-1,2,3,4-tetrahydro-isoquinolin-5-yl]-N-(2-trifluoromethyl-benzyl)-acrylamide | 0.76 | 505.3 |
| 326 | (E)-N-(3-Chloro-pyridin-2-ylmethyl)-N-[2-(4,4-difluoro-piperidin-1-yl)-ethyl]-3-[2-(2-methoxy-ethyl)-1,2,3,4-tetrahydro-isoquinolin-5-yl]-acrylamide | 0.44 | 533.3 |
| 327 | (E)-N-(3-Chloro-pyridin-2-ylmethyl)-N-(2-dimethylamino-ethyl)-3-[2-(2-methoxy-ethyl)-1,2,3,4-tetrahydro-isoquinolin-5-yl]-acrylamide | 0.37 | 457.3 |
| 328 | (E)-N-(3-Chloro-pyridin-2-ylmethyl)-N-(2-hydroxy-2-methyl-propyl)-3-[2-(2-methoxy-ethyl)-1,2,3,4-tetrahydro-isoquinolin-5-yl]-acrylamide | 0.6 | 458.3 |
| 329 | (E)-N-(3-Chloro-pyridin-2-ylmethyl)-3-(2-cyclopropylmethyl-1,2,3,4-tetrahydro-isoquinolin-5-yl)-N-(2-hydroxy-2-methyl-propyl)-acrylamide | 0.63 | 454.3 |
| 330 | rac-(E)-N-(3-Chloro-pyridin-2-ylmethyl)-N-(2-dimethylamino-ethyl)-3-[2-((1R*,2R*)-2-fluoro-cyclopropanecarbonyl)-1,2,3,4-tetrahydro-isoquinolin-5-yl]-acrylamide | 0.62 | 485.3 |
| 331 | rac-(E)-N-(3-Chloro-pyridin-2-ylmethyl)-3-[2-((1R*,2R*)-2-fluoro-cyclopropanecarbonyl)-1,2,3,4-tetrahydro-isoquinolin-5-yl]-N-(2-hydroxy-2-methyl-propyl)-acrylamide | 0.97 | 486.3 |
| 332 | rac-(E)-N-(3-Chloro-pyridin-2-ylmethyl)-N-[2-(4,4-difluoro-piperidin-1-yl)-ethyl]-3-[2-((1R*,2R*)-2-fluoro-cyclopropanecarbonyl)-1,2,3,4-tetrahydro-isoquinolin-5-yl]-acrylamide | 0.69 | 561.3 |
| 333 | (E)-N-(3-Chloro-pyridin-2-ylmethyl)-3-(2-cyclopropylmethyl-1,2,3,4-tetrahydro-isoquinolin-5-yl)-N-(2-dimethylamino-ethyl)-acrylamide | 0.39 | 453.3 |
| 334 | (E)-N-(3-Chloro-pyridin-2-ylmethyl)-3-(2-cyclopropylmethyl-1,2,3,4-tetrahydro-isoquinolin-5-yl)-N-[2-(4,4-difluoro-piperidin-1-yl)-ethyl]-acrylamide | 0.47 | 529.3 |
| 335 | N-(2-Dimethylamino-ethyl)-3-[2-(2-methoxy-ethyl)-1,2,3,4-tetrahydro-isoquinolin-5-yl]-N-(2-trifluoromethyl-benzyl)-propionamide | 0.46 | 492.3 |
| 336 | N-(2-Dimethylamino-ethyl)-3-[2-(2-methoxy-ethyl)-1,2,3,4-tetrahydro-isoquinolin-5-yl]-N-(3-trifluoromethyl-pyridin-2-ylmethyl)-propionamide | 0.4 | 493.4 |
| 337 | {2-[{3-[2-(2-Methoxy-ethyl)-1,2,3,4-tetrahydro-isoquinolin-5-yl]-propionyl}-(2-trifluoromethyl-benzyl)-amino]-ethyl}-methyl-carbamic acid tert-butyl ester | 0.9 | 578.4 |
| 338 | N-(3,3-Dimethyl-butyl)-3-[2-(2-methoxy-ethyl)-1,2,3,4-tetrahydro-isoquinolin-5-yl]-N-(3-methyl-pyridin-2-ylmethyl)-propionamide | 0.69 | 452.4 |
| 339 | N-(2-Hydroxy-3-methoxy-propyl)-3-[2-(2-methoxy-ethyl)-1,2,3,4-tetrahydro-isoquinolin-5-yl]-N-(2-trifluoromethyl-benzyl)-propionamide | 0.7 | 509.4 |
| 340 | N-[2-(4,4-Difluoro-piperidin-1-yl)-ethyl]-3-[2-(2-methoxy-ethyl)-1,2,3,4-tetrahydro-isoquinolin-5-yl]-N-(3-trifluoromethyl-pyridin-2-ylmethyl)-propionamide | 0.48 | 569.4 |
| 341 | N-(2-Hydroxy-2-methyl-propyl)-3-[2-(2-methoxy-ethyl)-1,2,3,4-tetrahydro-isoquinolin-5-yl]-N-(2-trifluoromethyl-benzyl)-propionamide | 0.73 | 493.4 |
| 342 | N-{2-[(2-Fluoro-ethyl)-methyl-amino]-ethyl}-3-[2-(2-methoxy-ethyl)-1,2,3,4-tetrahydro-isoquinolin-5-yl]-N-(2-trifluoromethyl-benzyl)-propionamide | 0.48 | 524.3 |
| 343 | 3-[2-(2-Methoxy-ethyl)-1,2,3,4-tetrahydro-isoquinolin-5-yl]-N-(3-methyl-oxetan-3-ylmethyl)-N-(2-trifluoromethyl-benzyl)-propionamide | 0.75 | 505.3 |
| 344 | N-(3-Hydroxy-3-methyl-butyl)-3-[2-(2-methoxy-ethyl)-1,2,3,4-tetrahydro-isoquinolin-5-yl]-N-(2-trifluoromethyl-benzyl)-propionamide | 0.75 | 507.4 |
| 345 | N-(3-Chloro-pyridin-2-ylmethyl)-N-[2-(4,4-difluoro-piperidin-1-yl)-ethyl]-3-[2-(2-methoxy-ethyl)-1,2,3,4-tetrahydro-isoquinolin-5-yl]-propionamide | 0.44 | 535.3 |
| 346 | N-(3-Chloro-pyridin-2-ylmethyl)-N-(2-dimethylamino-ethyl)-3-[2-(2-methoxy-ethyl)-1,2,3,4-tetrahydro-isoquinolin-5-yl]-propionamide | 0.37 | 459.3 |
| 347 | N-(3-Chloro-pyridin-2-ylmethyl)-N-(2-hydroxy-2-methyl-propyl)-3-[2-(2-methoxy-ethyl)-1,2,3,4-tetrahydro-isoquinolin-5-yl]-propionamide | 0.6 | 460.3 |
| 348 | N-[2-(Allyl-methyl-amino)-ethyl]-3-(2-allyl-1,2,3,4-tetrahydro-isoquinolin-5-yl)-N-(2-trifluoromethyl-benzyl)-propionamide | 0.5 | 500.3 |
| 349 | 3-(2-Allyl-1,2,3,4-tetrahydro-isoquinolin-5-yl)-N-(2-dimethylamino-ethyl)-N-(2-trifluoromethyl-benzyl)-propionamide | 0.47 | 474.4 |
| 350 | rac-2-(2-Cyclopropylmethyl-1,2,3,4-tetrahydro-isoquinolin-5-yloxy)-N-(2-dimethylamino-ethyl)-N-(2-trifluoromethyl-benzyl)-propionamide | 0.49 | 504.4 |

Precursor E1

5-((E)-2-Carboxy-vinyl)-3,4-dihydro-1H-isoquinoline-2-carboxylic acid tert-butyl ester To a solution of malonic acid (104 mg, 0.995 mmol) in a mixture of 0.02 mL piperidine and 2 mL pyridine is added 5-formyl-3,4-dihydro-1H-isoquinoline-2-carboxylic acid tert-butyl ester (100 mg, 0.383 mmol) the resulting yellow solution is allowed to stir at reflux for 2.5 h. After cooling the reaction mixture is poured onto DCM and the resulting organic phase is washed with water, 1M aq. HCl soln. then brine. It is then dried over $MgSO_4$, filtered and evaporated under reduced pressure to yield 115 mg (99%) of the title compound as a yellow solid which is used as such in the next step.

LC-B: $t_R$=0.84 min; [M+H]$^+$=304.2; $^1$H-NMR ($CDCl_3$): δ8.07 (d, J=15.8 Hz, 1H), 7.51 (d, J=7.6 Hz, 1H), 7.25 (m, 1H), 7.19 (m, 1H), 6.41 (d, J=15.8 Hz, 1H), 4.62 (s, 2H), 3.71 (t, J=6.0 Hz, 2H), 2.98 (t, J=6.0 Hz, 2H), 1.52 (s, 9H)

Precursor E2

5-((E)-2-Carboxy-propenyl)-3,4-dihydro-1H-isoquinoline-2-carboxylic acid tert-butyl ester A solution of 5-formyl-3,4-dihydro-1H-isoquinoline-2-carboxylic acid tert-butyl ester (400 mg, 1.53 mmol), propionic anhydride (4040 mg, 31 mmol) and NaOAc (126 mg, 1.53 mmol) is heated under microwave irradiation at 180° C. for 5 h. After cooling the reaction mixture is poured onto DCM and the resulting organic phase is washed with water, 1M aq. HCl soln. then brine. It is then dried over $MgSO_4$, filtered and evaporated under reduced pressure. The crude residue is purified by prep. HPLC (Method E) to yield 14 mg (3%) of the title compound as a yellow oil.

LC-A: $t_R$=1.00 min; [M+H]$^+$=n.d.

Precursor E3

(E)-3-(2-(2-methoxyethyl)-1,2,3,4-tetrahydroisoquinolin-5-yl)acrylic acid a) (E)-5-(3-Ethoxy-3-oxoprop-1-en-1-yl)-3,4-dihydroisoquinoline-2(1H)-carboxylic acid tert-butyl ester To a solution of 5-((E)-2-carboxy-vinyl)-3,4-dihydro-1H-isoquinoline-2-carboxylic acid tert-butyl ester Precursor E1 (5.32 g, 17.5 mmol) dissolved in 100 mL MeCN are added $Cs_2CO_3$ (5.71 g, 17.5 mmol) and ethyl iodide (2.74 g, 17.5 mmol). The resulting suspension is allowed to stir at 55° C. for 5 h. It is allowed to cool down to room temperature the poured into water. The resulting aq. phase is extracted three times with DCM. The combined organic phase is washed with water and brine then dried over $MgSO_4$, filtered and the solvent evaporated under reduced pressure to yield 5.39 g (93%) of the sub-title compound as a yellow oil. LC-A: $t_R$=0.82 min; [M+H]$^+$=n.d. $^1$H-NMR (400 MHz, $d_6$-DMSO) δ: 7.86 (d, J=15.9 Hz, 1H), 7.62 (t, J=4.8 Hz, 1H), 7.24 (m, 2H), 6.51 (d, J=15.9 Hz, 1H), 4.51 (s, 2H), 4.20 (q, J=7.1 Hz, 2H), 3.58 (t, J=5.8 Hz, 2H), 2.87 (t, J=5.9 Hz, 2H), 1.43 (s, 9H), 1.27 (t, J=7.1 Hz, 3H)

b) (E)-3-(1,2,3,4-Tetrahydroisoquinolin-5-yl)acrylic acid ethyl ester hydrochloride To a solution of (E)-5-(3-ethoxy-3-oxoprop-1-en-1-yl)-3,4-dihydroisoquinoline-2(1H)-carboxylic acid tert-butyl ester (2.9 g, 8.75 mmol) in 20 mL DCM is added dropwise 4N HCl soln. in dioxane (6.6 mL, 26.3 mmol). The resulting solution is allowed to stir at RT for 2 h. The solvent is the removed under reduced pressure, the residue is taken up in DCM and evaporated again under reduced pressure, then under HV to yield quantitatively 2.38 g of the sub-title compound as a yellow solid.

LC-A: $t_R$=0.57 min; [M+H]$^+$=232.3 c) (E)-3-(2-(2-Methoxyethyl)-1,2,3,4-tetrahydroisoquinolin-5-yl)acrylic acid ethyl ester To a solution of (E)-3-(1,2,3,4-tetrahydroisoquinolin-5-yl)acrylic acid ethyl ester hydrochloride (2.38 g, 8.89 mmol) in 30 mL DMF is added $K_2CO_3$ (2.46 g, 17.6 mmol) and 2-bromoethylmethylether (1.24 g, 8.89 mmol) and the resulting suspension is allowed to stir at 65° C. for 5 h. After cooling, water is added and the resulting aq. phase is extracted twice with EtOAc. The combined organic phase is washed with sat. aq. $NaHCO_3$ soln. and brine then dried over $MgSO_4$, filtered and the solvent evaporated under reduced pressure. Flash-chromatography on silica-gel: (Eluent: Hept./EtOAc 70:30 to 40:60) yields 1.6 g (62%) of the sub-title compound as a yellow oil.

LC-A: $t_R$=0.61 min; [M+H]$^+$=290.0; $^1$H-NMR (400 MHz, $d_6$-DMSO) δ: 7.83 (d, J=15.9 Hz, 1H), 7.58 (d, J=7.4 Hz, 1H), 7.15 (m, 2H), 6.50 (d, J=15.9 Hz, 1H), 4.20 (q, J=7.1 Hz, 2H), 3.60 (s, 2H), 3.52 (t, J=5.8 Hz, 2H), 3.26 (s, 3H), 2.87 (t, J=5.8 Hz, 2H), 2.74 (t, J=5.7 Hz, 2H), 2.64 (t, J=5.8 Hz, 2H), 1.26 (t, J=7.1 Hz, 3H)

d) To a solution of (E)-3-(2-(2-methoxyethyl)-1,2,3,4-tetrahydroisoquinolin-5-yl)acrylic acid ethyl ester (1.6 g, 5.5 mmol) in 20 mL THF is added at RT 1M LiOH aq. soln. (11.1 mL, 11.1 mmol). The reaction mixture is stirred overnight at RT. and is then acidified to pH=4 with 1M aq. HCl soln. to afford 1.77 g of the title compound (93%) after evaporation of the volatiles followed by a second evaporation after addition of DCM and drying under HV.

LC-A: $t_R$=0.48 min; [M+H]$^+$=262.4; $^1$H-NMR (400 MHz, $d_6$-DMSO) δ: 7.75 (d, J=15.8 Hz, 1H), 7.63 (d, J=7.6 Hz, 1H), 7.23 (m, 2H), 6.47 (d, J=15.8 Hz, 1H), 4.12 (s, 2H), 3.71 (d, J=4.3 Hz, 2H), 3.30 (s, 3H), 3.25 (m, 2H), 3.09 (m, 4H).

Precursor E4 rac-(E)-3-[2-((1 S*,2S*)-2-Fluoro-cyclopropanecarbonyl)-1,2,3,4-tetrahydro-isoquinolin-5-yl]-acrylic acid a) rac-(E)-3-[2-((1 S*,2S*)-2-Fluoro-cyclopropanecarbonyl)-1,2,3,4-tetrahydro-isoquinolin-5-yl]-acrylic acid ethyl ester To a solution of (E)-3-(1,2,3,4-tetrahydroisoquinolin-5-yl)acrylic acid ethyl ester hydrochloride (800 mg, 2.99 mmol) and cis-2-fluoro-cyclopropanecarboxylic acid (311 mg, 2.99 mmol) in 8 mL DMF are added HATU (1363 mg, 3.59 mmol) then DIPEA (965 mg, 7.47 mmol). The yellow solution is stirred for 1.5 h at RT. Water is then added and the resulting aq. phase is extracted twice with DCM. The combined organic phase is washed with sat. aq. $NaHCO_3$ soln. and brine then dried over $MgSO_4$ and the solvent is removed under reduced pressure. Flash-chromatography on silica-gel: (Eluent: Hept./EtOAc 70:30 to 20:80) yields 864 mg (91%) of the sub-title compound as a yellow oil.

LC-A: $t_R$=0.83 min; [M+H]$^+$=318.1 b) The title compound is obtained as a white foam in 80% yield following the procedure describe for Precursor E3 step d) starting from (E)-3-(2-(cis-2-fluorocyclopropane-1-carbonyl)-1,2,3,4-tetrahydroisoquinolin-5-yl)acrylic acid ethyl ester.

LC-A: $t_R$=0.68 min; [M+H]$^+$=290.0

Precursor E5

(E)-3-(2-(cyclopropylmethyl)-1,2,3,4-tetrahydroisoquinolin-5-yl)acrylic acid a) (E)-3-(2-(Cyclopropylmethyl)-1,2,3,4-tetrahydroisoquinolin-5-yl)acrylic acid ethyl ester To a solution of (E)-3-(1,2,3,4-tetrahydroisoquinolin-5-yl)acrylic acid ethyl ester hydrochloride (800 mg, 2.99 mmol) dissolved in 8 mL DCM (Precursor E3 step b) is added cyclopropanecarboxaldehyde (419 mg, 5.98 mmol) and DIPEA (772 mg, 5.98 mmol). The yellow suspension is allowed to stir for 10 min at RT, then NaBH(OAc)$_3$ is added and the resulting mixture is allowed to stir at RT for 1.5 h. Water is then added and the resulting aq. phase is extracted three times with DCM. The combined organic phase is washed with sat. aq. NaHCO$_3$ soln. and brine then dried over MgSO$_4$ and the solvent is removed under reduced pressure. Flash-chromatography on silica-gel: (Eluent: Hept./EtOAc 70:30 to 20:80) yields 593 mg (70%) of the sub-title compound as a yellow solid.

LC-A: $t_R$=0.63 min; [M+H]$^+$=286.1; $^1$H-NMR (400 MHz, d$_6$-DMSO) δ: 8.02 (d, J=15.9 Hz, 1H), 7.76 (d, J=7.2 Hz, 1H), 7.35 (m, 2H), 6.68 (d, J=15.9 Hz, 1H), 4.38 (q, J=7.1 Hz, 2H), 3.81 (s, 2H), 3.07 (t, J=5.8 Hz, 2H), 2.93 (t, J=5.8 Hz, 2H), 2.53 (d, J=6.6 Hz, 2H), 1.45 (t, J=7.1 Hz, 3H), 1.10 (m, 1H), 0.69 (m, 2H), 0.33 (m, 2H).

b) The title compound is obtained as a white foam in 91% yield following the procedure describe for Precursor E3 step d) starting from (E)-3-(2-(cyclopropylmethyl)-1,2,3,4-tetrahydroisoquinolin-5-yl)acrylic acid ethyl ester.

LC-A: $t_R$=0.52 min; [M+H]$^+$=258.1

Precursor F1

5-(2-Carboxy-ethyl)-3,4-dihydro-1H-isoquinoline-2-carboxylic acid tert-butyl ester To a solution of 5-((E)-2-carboxy-vinyl)-3,4-dihydro-1H-isoquinoline-2-carboxylic acid tert-butyl ester Precursor E1 (500 mg, 1.52 mmol) in 15 mL MeOH and palladium on charcoal 10% (80.7 mg, 0.076 mmol) is stirred under a positive atmosphere of H$_2$ for 2 h. The mixture is put under inert Ar atmosphere then filtered over celite. The solid celite cake is washed twice with MeOH. Evaporation of the solvent under reduced pressure yields 459 mg (91%) of the title compound as a white solid.

LC-A: $t_R$=0.83 min; [M+H]$^+$=306.1; $^1$H-NMR (CDCl$_3$): δ7.17 (t, J=7.5 Hz, 1H), 7.09 (m, 1H), 7.02 (d, J=7.5 Hz, 1H), 4.60 (s, 2H), 3.69 (t, J=5.8 Hz, 2H), 3.50 (s, 1H), 2.96 (m, 2H), 2.83 (t, J=5.8 Hz, 2H), 2.66 (m, 2H), 1.51 (s, 9H)

Precursor F2

3-(2-(2-Methoxyethyl)-1,2,3,4-tetrahydroisoquinolin-5-yl)propanoic acid a) 5-(3-Ethoxy-3-oxopropyl)-3,4-dihydroisoquinoline-2 (1H)-carboxylic acid tert-butyl ester To a solution of (E)-5-(3-ethoxy-3-oxoprop-1-en-1-yl)-3, 4-dihydroisoquinoline-2(1H)-carboxylic acid tert-butyl ester (Precursor E3 step a) (3 g, 9.05 mmol) dissolved in degassed 40 mL MeOH is added 10% Pd/C (482 mg, 0.45 mmol). The resulting suspension is allowed to stir under hydrogen at RT for 3 h. The crude suspension is filtered over Celite and the filter cake is rinsed twice with MeOH. Evaporation of the solvent under reduced pressure yields 2.86 g (95%) of the sub-title compound as a yellow oil.

LC-A: $t_R$=0.97 min; [M+H]$^+$=n.d.; $^1$H-NMR (400 MHz, d$_6$-DMSO) δ: 7.11 (m, 1H), 7.03 (m, 2H), 4.48 (s, 2H), 4.05 (q, J=7.1 Hz, 2H), 3.56 (t, J=5.9 Hz, 2H), 2.82 (t, J=7.7 Hz, 2H), 2.74 (t, J=5.9 Hz, 2H), 2.55 (t, J=7.7 Hz, 2H), 1.43 (s, 9H), 1.16 (t, J=7.1 Hz, 3H)

b) 3-(1,2,3,4-Tetrahydroisoquinolin-5-yl)propionic acid ethyl ester hydrochloride To a solution of (E)-5-(3-ethoxy-3-oxopropyl)-3,4-dihydroisoquinoline-2(1H)-carboxylic acid tert-butyl ester (2.86 g, 8.58 mmol) in 20 mL DCM is added dropwise 4N HCl soln. in dioxane (6.4 mL, 25.7 mmol). The resulting solution is allowed to stir at RT for 2 h. The solvent is the removed under reduced pressure, the residue is taken up in DCM and evaporated again under reduced pressure, then under HV to yield quantitatively 2.30 g of the sub-title compound as a yellow solid.

LC-A: $t_R$=0.55 min; [M+H]$^+$=234.2 c) 3-(2-(2-Methoxyethyl)-1,2,3,4-tetrahydroisoquinolin-5-yl)propionic acid ethyl ester To a solution of (E)-3-(1,2,3,4-tetrahydroisoquinolin-5-yl)propionic acid ethyl ester hydrochloride (2.30 g, 8.53 mmol) in 30 mL DMF is added K$_2$CO$_3$ (2.36 g, 17.1 mmol) and 2-bromoethylmethylether (1.194 g, 8.53 mmol) and the resulting suspension is allowed to stir at 65° C. for 5 h. After cooling, water is added and the resulting aq. phase is extracted twice with EtOAc. The combined organic phase is washed with sat. aq. NaHCO$_3$ soln. and brine then dried over MgSO$_4$, filtered and the solvent evaporated under reduced pressure. Flash-chromatography on silica-gel: (Eluent: Hept./EtOAc 70:30 to 40:60 to 0:100) yields 1.13 g (46%) of the sub-title compound as a yellow oil.

LC-A: $t_R$=0.60 min; [M+H]$^+$=292.3; $^1$H-NMR (400 MHz, d$_6$-DMSO) δ: 7.04 (m, 1H), 6.98 (m, 1H), 6.89 (d, J=7.2 Hz, 1H), 4.05 (q, J=7.1 Hz, 2H), 3.57 (s, 2H), 3.52 (t, J=5.9 Hz, 2H), 3.26 (s, 3H), 2.77 (d, J=8.0 Hz, 2H), 2.72 (m, 4H), 2.62 (t, J=5.8 Hz, 2H), 2.55 (t, J=8.0 Hz, 2H), 1.17 (t, J=7.1 Hz, 3H)

d) To a solution of 3-(2-(2-methoxyethyl)-1,2,3,4-tetrahydroisoquinolin-5-yl)propionic acid ethyl ester (1.13 g, 3.88 mmol) in 20 mL THF is added at RT 1M LiOH aq. soln. (7.8 mL, 7.8 mmol). The reaction mixture is stirred overnight at RT and is then acidified to pH=4 with 1M aq. HCl soln. to afford the 1.38 g of the title compound as the hydrochloride containing 1 equivalent LiCl (100%) after evaporation of the volatiles followed by a second evaporation after addition of DCM and drying under HV.

LC-A: $t_R$=0.48 min; [M+H]$^+$=264.4

Precursor F3

3-(2-Allyl-1,2,3,4-tetrahydroisoquinolin-5-yl)propanoic acid is made according to the procedure described for 3-(2-(2-methoxyethyl)-1,2,3,4-tetrahydroisoquinolin-5-yl) propanoic acid Precursor F2 (steps c and d) starting from 3-(1,2,3,4-tetrahydroisoquinolin-5-yl)propionic acid ethyl ester hydrochloride using allylbromide instead of 2-bromoethylmethylether and MeCN instead of DMF.

LC-A: $t_R$=0.48 min; [M+H]$^+$=246.2

Precursor G1

5-Carboxymethoxy-3,4-dihydro-1H-isoquinoline-2-carboxylic acid tert-butyl ester To a solution of 5-ethoxycarbonylmethoxy-3,4-dihydro-1H-isoquinoline-2-carboxylic acid tert-butyl ester Precursor H1 (640 mg, 1.72 mmol) in 8 ml THF is added 1M aq. LiOH sol. (6.43 mL, 6.43 mmol). The reaction mixture is allowed to stir at RT for 1 h and is acidified with 1N aq. HCl sol. The resulting aq. phase is extracted twice with DCM. The combined organic phase is washed with brine then dried over MgSO$_4$, filtered and evaporated under reduced pressure to yield quantitatively the title compound as a light yellow solid which is used without further purification.

LC-B: $t_R$=0.80 min; [M+H]$^+$=308.0. $^1$H-NMR (CDCl$_3$) δ: 7.15 (t, J=7.9 Hz, 1H), 6.79 (d, J=7.7 Hz, 1H), 6.63 (d, J=8.1 Hz, 1H), 4.69 (s, 2H), 4.58 (s, 2H), 3.66 (t, J=5.8 Hz, 2H), 2.86 (t, J=5.8 Hz, 2H), 1.51 (s, 9H)

Precursor G2 rac-2-((2-(tert-Butoxycarbonyl)-1,2,3,4-tetrahydroisoquinolin-5-yl)oxy)propanoic acid LC-B: $t_R$=0.84 min; [M+H]$^+$=307.3, $^1$H-NMR (400 MHz, d$_6$-DMSO) δ: 13.00 (m, 1H), 7.11 (dd, J1=8.1 Hz, J$_2$=7.7 Hz, 1H), 6.76 (d, J=7.7 Hz, 1H), 6.65 (d, J=8.1 Hz, 1H), 4.82 (q, J=6.7 Hz, 1H), 4.48 (s, 2H), 3.55 (m, 2H), 2.68 (m, 2H), 1.52 (d, J=6.8 Hz, 3H), 1.43 (s, 9H), is prepared applying the method described for Precursor G1 using NaOH instead of LiOH.

Precursor H1

5-Ethoxycarbonylmethoxy-3,4-dihydro-1H-isoquinoline-2-carboxylic acid tert-butyl ester To a solution of 5-hydroxy-3,4-dihydro-1H-isoquinoline-2-carboxylic acid tert-butyl ester [Tetrahedron 2006, 62(29), 6869-6875](500 mg, 2.01 mmol) in 8 mL acetone are added K$_2$CO$_3$ (416 mg, 3.01 mmol) and ethyl bromoacetate (335 mg, 2.01 mmol). The reaction mixture is allowed to stir at 80° C. for 1 h. After cooling, the mixture is poured onto water. The resulting aq. phase is extracted twice with DCM. The combined organic phase is washed with brine dried over MgSO$_4$, filtered and evaporated under reduced pressure to yield 640 mg (95%) of the title compound as a yellow oil which is used without further purification.

LC-B: $t_R$=0.98 min; [M+H]$^+$=336.0. $^1$H-NMR (CDCl$_3$) δ: 7.13 (t, J=7.9 Hz, 1H), 6.78 (d, J=7.7 Hz, 1H), 6.59 (d, J=8.1 Hz, 1H), 4.65 (s, 2H), 4.58 (s, 2H), 4.28 (q, J=7.1 Hz, 2H), 3.66 (t, J=5.8 Hz, 2H), 2.87 (t, J=5.8 Hz, 2H), 1.51 (s, 9H), 1.32 (t, J=7.1 Hz, 3H)

Precursor H2 rac-5-((1-Ethoxy-1-oxopropan-2-yl)oxy)-3,4-dihydroisoquinoline-2(1H)-carboxylic acid tert-butyl ester LC-A: $t_R$=0.98 min; [M-tBu+MeCN]$^+$=335.1, $^1$H-NMR (400 MHz, d$_6$-DMSO) δ: 7.11 (dd, J$_1$=8.2 Hz, J$_2$=7.6 Hz, 1H), 6.78 (d, J=7.6 Hz, 1H), 6.67 (d, J=8.2 Hz, 1H), 4.94 (q, J=6.8 Hz, 1H), 4.48 (bs, 2H), 4.13 (q, J=7.2 Hz, 2H), 3.50-3.61 (m, 2H), 2.69 (m, 2H), 1.52 (d, J=6.7 Hz, 3H), 1.35 (s, 9H), 1.17 (t, J=7.2 Hz, 3H), is prepared applying the method described for Precursor H1 using ethyl 2-bromopropionate instead of ethylbromacetate.

Example 102

N-Benzyl-N-(2-dimethylamino-ethyl)-2-[ethyl-(2-ethyl-1,2,3,4-tetrahydro-isoquinolin-5-yl)-amino]-acetamide To a solution of N-benzyl-N-(2-(dimethylamino)ethyl)-2-((1,2,3,4-tetrahydroisoquinolin-5-yl)amino)acetamide dihydrochloride Precursor J1 (27 mg, 0.063 mmol) in 0.2 mL MeOH and 0.1 mL water is added acetaldehyde (3.3 mg, 0.076 mmol) and NaBH$_3$CN (11.9 mg, 0.19 mmol). The resulting mixture is allowed to stir at RT for 1 h. It is then poured onto sat. aq. NaHCO$_3$ soln. and the resulting aq. phase is extracted three times with DCM. The combined organic phase is washed with brine, dried over MgSO$_4$, filtered and evaporated under reduced pressure. The crude residue is purified by prep. HPLC (Method E) to yield the title compound as a colourless oil.

LC-B: $t_R$=0.46 min; [M+H]$^+$=423.1

Example 210

2-((2-Cyclopentyl-1,2,3,4-tetrahydroisoquinolin-5-yl)amino)-N-(2-(dimethylamino)ethyl)-N-(2-(trifluoromethyl)benzyl)acetamide To a solution of N-(2-trifluoromethyl)benzyl-N-(2-(dimethylamino)ethyl)-2-((1,2,3,4-tetrahydroisoquinolin-5-yl)amino)acetamide dihydrochloride Precursor J2 (100 mg, 0.181 mmol) in 2 mL MeOH is added successively cyclopentanone (90 mg, 5.9 mmol), NaBH$_3$CN (39.9 mg, 3.5 mmol) and ZnCl$_2$ (144 mg, 1.06 mmol) and the resulting mixture is allowed to stir at RT overnight. Water is added and the resulting aq. phase is extracted twice with DCM. The combined organic phase is washed with sat. aq. NaHCO$_3$ soln. and brine, dried over MgSO$_4$ filtered and evaporated under reduced pressure. The crude residue is purified by prep. HPLC (Method D) to yield the title compound as a colourless oil.

LC-B: $t_R$=0.61 min; [M+H]$^+$=503.1

Examples 351-356/365-367 listed in Table 9 are prepared applying one of the methods described for Example 210, using the corresponding Precursor and the corresponding ketone respectively.

TABLE 9

Examples 351-356/365-367

| Example No | Example name | $t_R$ [min] (LC-F) unless otherwise indicated | MS Data m/z [M + H]$^+$ |
|---|---|---|---|
| 351 | rac-N-(2-Dimethylamino-ethyl)-2-[2-(tetrahydro-furan-3-yl)-1,2,3,4-tetrahydro-isoquinolin-5-ylamino]-N-(2-trifluoromethyl-benzyl)-acetamide | 0.45 | 505.3 |
| 352 | 2-(2-Cyclobutyl-1,2,3,4-tetrahydro-isoquinolin-5-ylamino)-N-(2-dimethylamino-ethyl)-N-(2-trifluoromethyl-benzyl)-acetamide | 0.49 | 489.4 |
| 353 | N-(2-Dimethylamino-ethyl)-2-(2-oxetan-3-yl-1,2,3,4-tetrahydro-isoquinolin-5-ylamino)-N-(2-trifluoromethyl-benzyl)-acetamide | 0.47 | 491.3 |
| 354 | rac-N-(2-Dimethylamino-ethyl)-2-[2-(2-methoxy-1-methyl-ethyl)-1,2,3,4-tetrahydro-isoquinolin-5-ylamino]-N-(2-trifluoromethyl-benzyl)-acetamide | 0.49 | 507.4 |
| 355 | rac-N-(2-Dimethylamino-ethyl)-2-[2-(1,2-dimethyl-propyl)-1,2,3,4-tetrahydro-isoquinolin-5-ylamino]-N-(2-trifluoromethyl-benzyl)-acetamide | 0.63 (LC-A) | 505.3 |
| 356 | rac-2-(2-sec-Butyl-1,2,3,4-tetrahydro-isoquinolin-5-ylamino)-N-(2-dimethylamino-ethyl)-N-(2-trifluoromethyl-benzyl)-acetamide | 0.5 | 491.4 |
| 365 | rac-N-(2-Dimethylamino-ethyl)-2-[2-(tetrahydro-furan-3-yl)-1,2,3,4-tetrahydro-isoquinolin-5-ylamino]-N-(3-trifluoromethyl-pyridin-2-ylmethyl)-acetamide | 0.39 | 506.3 |
| 366 | 2-(2-Cyclobutyl-1,2,3,4-tetrahydro-isoquinolin-5-ylamino)-N-(2-dimethylamino-ethyl)-N-(3-trifluoromethyl-pyridin-2-ylmethyl)-acetamide | 0.42 | 490.3 |
| 367 | N-(2-Dimethylamino-ethyl)-2-(2-oxetan-3-yl-1,2,3,4-tetrahydro-isoquinolin-5-ylamino)-N-(3-trifluoromethyl-pyridin-2-ylmethyl)-acetamide | 0.4 | 492.3 |

Example 105

2-(2-Cyclopropylmethyl-1,2,3,4-tetrahydro-isoquinolin-5-ylamino)-N-(1-methyl-piperidin-4-yl)-N-(2-trifluoromethyl-benzyl)-acetamide To a solution of N-(1-methyl-piperidin-4-yl)-2-(1,2,3,4-tetrahydro-isoquinolin-5-ylamino)-N-(2-trifluoromethyl-benzyl)-acetamide dihydrochloride Precursor J4 (33 mg, 0.058 mmol) in 0.5 mL MeOH are added cyclopropanecarboxaldehyde (4.9 mg, 0.071 mmol) and NaBH$_3$CN (9.3 mg, 0.147 mmol) and 0.5 mL water. The resulting mixture is allowed to stir at RT for 3 h. It is then diluted with DCM, sat. aq. NaHCO$_3$ soln. and water. The phases are separated and the resulting aq. phase is extracted twice with DCM. The combined organic phase is dried over MgSO$_4$, filtered and evaporated under reduced pressure. The crude residue is purified by prep. HPLC (Method D) to yield the title compound as a yellow oil.

LC-A: $t_R$=0.62 min; [M+H]$^+$=515.1

Examples 91/357-358 listed in Table 10 are prepared applying one of the methods described for Example 105, using the corresponding Precursor and the corresponding aldehyde or ketone respectively.

TABLE 10

Examples 91/357-358

| Example No | Example name | $t_R$ [min] (Method) | MS Data m/z [M + H]$^+$ |
|---|---|---|---|
| 91 | 2-(2-Cyclopropylmethyl-4,4-dimethyl-1,2,3,4-tetrahydro-isoquinolin-5-ylamino)-N-(2-dimethylamino-ethyl)-N-(2-trifluoromethyl-benzyl)-acetamide | 0.63 (A) | 517.2 |
| 357 | 2-[2-(1-Cyclopropyl-ethyl)-1,2,3,4-tetrahydro-isoquinolin-5-ylamino]-N-(2-dimethylamino-ethyl)-N-(2-trifluoromethyl-benzyl)-acetamide | 0.52 (G) | 503.4 |
| 358 | N-(2-Dimethylamino-ethyl)-2-[2-(3-methyl-oxetan-3-ylmethyl)-1,2,3,4-tetrahydro-isoquinolin-5-ylamino]-N-(2-trifluoromethyl-benzyl)-acetamide | 0.46 (G) | 519.4 |

Example 103

N-(2-Dimethylamino-ethyl)-2-(2-ethanesulfonyl-1,2,3,4-tetrahydro-isoquinolin-5-ylamino)-N-(2-trifluoromethyl-benzyl)-acetamide To a solution of N-(2-trifluoromethyl)benzyl-N-(2-(dimethylamino)ethyl)-2-((1,2,3,4-tetrahydroisoquinolin-5-yl)amino)acetamide dihydrochloride Precursor J2 (145 mg, 0.197 mmol) in 3 mL DCM are added DIPEA (25.4 mg, 0.197 mmol) and ethanesulfonylchloride (25.3 mg, 0.197 mmol). The resulting mixture is allowed to stir at RT for 1 h then poured onto water. The resulting aq. phase is extracted twice with DCM. The combined organic phase is washed with sat. aq. NaHCO$_3$ soln. and brine, dried over MgSO₄, filtered and evaporated under reduced pressure. The crude residue is purified by prep. HPLC (Method E) to yield the title compound formic acid salt as a brown foam.

LC-A: $t_R$=0.74 min; [M+H]⁺=527.2

Example 359

N-(2-(dimethylamino)ethyl)-2-((2-(2-methoxyethyl)-1,2,3,4-tetrahydroisoquinolin-5-yl)amino)-N-(2-(trifluoromethyl)benzyl)acetamide To a solution of N-(2-trifluoromethyl)benzyl-N-(2-(dimethylamino)ethyl)-2-((1,2,3,4-tetrahydroisoquinolin-5-yl)amino)acetamide dihydrochloride Precursor J2 (500 mg, 0.907 mmol) in 10 mL DMF are added K₂CO₃ (251 mg, 1.81 mmol) and 2-bromoethylmethylether (126 mg, 0.907 mmol). The resulting mixture is allowed to stir at RT overnight then at 65° C. for 5 h. It is then poured onto water. The resulting aq. phase is extracted twice with DCM. The combined organic phase is washed with sat. aq. NaHCO₃ soln. and brine, dried over MgSO₄, filtered and evaporated under reduced pressure. The crude residue is purified by prep. HPLC (Method D) to yield the title compound as a yellow oil.

LC-A: $t_R$=0.58 min; [M+H]⁺=493.2

Examples 360-361/368-371 listed in Table 11 are prepared applying one of the methods described for Example 359 using the corresponding Precursor and the corresponding alkyl bromide respectively.

TABLE 11

Examples 360-361/368-371

| Example No | Example name | $t_R$ [min] (LC-F) unless otherwise indicated | MS Data m/z [M + H]⁺ |
|---|---|---|---|
| 360 | [5-({[(2-Dimethylamino-ethyl)-(2-trifluoromethyl-benzyl)-carbamoyl]-methyl}-amino)-3,4-dihydro-1H-isoquinolin-2-yl]-acetic acid methyl ester | 0.5 | 507.3 |
| 361 | 2-(2-Cyclobutylmethyl-1,2,3,4-tetrahydro-isoquinolin-5-ylamino)-N-(2-dimethylamino-ethyl)-N-(2-trifluoromethyl-benzyl)-acetamide | 0.54 | 503.4 |
| 368 | 2-(2-Cyclobutylmethyl-1,2,3,4-tetrahydro-isoquinolin-5-ylamino)-N-(2-dimethylamino-ethyl)-N-(3-trifluoromethyl-pyridin-2-ylmethyl)-acetamide | 0.47 | 504.4 |
| 369 | [5-({[(2-Dimethylamino-ethyl)-(3-trifluoromethyl-pyridin-2-ylmethyl)-carbamoyl]-methyl}-amino)-3,4-dihydro-1H-isoquinolin-2-yl]-acetic acid ethyl ester | 0.47 | 522.3 |
| 370 | [5-({[(2-Dimethylamino-ethyl)-(3-trifluoromethyl-pyridin-2-ylmethyl)-carbamoyl]-methyl}-amino)-3,4-dihydro-1H-isoquinolin-2-yl]-acetic acid methyl ester | 0.74 (LC-F1) | 508.3 |
| 371 | N-(2-Dimethylamino-ethyl)-2-[2-(2-methoxy-ethyl)-1,2,3,4-tetrahydro-isoquinolin-5-ylamino]-N-(3-trifluoromethyl-pyridin-2-ylmethyl)-acetamide | 0.4 | 494.3 |

Example 362

2-[2-(2,2-Difluoro-propionyl)-1,2,3,4-tetrahydro-isoquinolin-5-ylamino]-N-(2-dimethylamino-ethyl)-N-(2-trifluoromethyl-benzyl)-acetamide To a solution of N-(2-trifluoromethyl)benzyl-N-(2-(dimethylamino)ethyl)-2-((1,2,3,4-tetrahydroisoquinolin-5-yl)amino)acetamide dihydrochloride Precursor J2 (104 mg, 0.178 mmol) in 2 mL DMF are added 2,2-difluoropropionic acid (19.6 mg, 0.178 mmol), HATU (81.4 mg, 0.214 mmol) and DIPEA (57 mg, 0.446 mmol). The resulting mixture is allowed to stir at RT for 2 h. Water is added and the resulting aq. phase is extracted twice with EtOAc. The combined organic phase is washed with sat. aq. NaHCO₃ soln. and brine, dried over MgSO$_4$, filtered and evaporated under reduced pressure. The crude residue is purified by prep. HPLC (Method D) to yield the title compound as a yellow oil.

LC-A: t$_R$=0.78 min; [M+H]$^+$=527.3

Examples 363/372/570-572 listed in Table 12 are prepared applying one of the methods described for Example 362 using the corresponding Precursor and the corresponding carboxylic acid respectively.

TABLE 12

Examples 363/372/570-572

| Example No | Example name | t$_R$ [min] (LC-A) | MS Data m/z [M + H]$^+$ |
|---|---|---|---|
| 363 | rac-N-(2-Dimethylamino-ethyl)-2-[2-((1R*,2R*)-2-fluoro-cyclopropanecarbonyl)-1,2,3,4-tetrahydro-isoquinolin-5-ylamino]-N-(2-trifluoromethyl-benzyl)-acetamide | 0.71 | 521.4 |
| 372 | rac-2-[2-((1S*,2S*)-2-Fluoro-cyclopropanecarbonyl)-1,2,3,4-tetrahydro-isoquinolin-5-ylamino]-N-(1-hydroxy-cyclopentylmethyl)-N-(2-trifluoromethyl-benzyl)-acetamide | 0.93 | 548.2 |
| 570 | rac-2-[2-(2,2-Difluoro-cyclopropanecarbonyl)-1,2,3,4-tetrahydro-isoquinolin-5-ylamino]-N-(2-dimethylamino-ethyl)-N-(2-trifluoromethyl-benzyl)-acetamide | 0.75 | 539.4 |
| 571 | N-(2-Dimethylamino-ethyl)-N-(2-trifluoromethyl-benzyl)-2-[2-(1-trifluoromethyl-cyclopropanecarbonyl)-1,2,3,4-tetrahydro-isoquinolin-5-ylamino]-acetamide | 0.78 | 571.4 |
| 572 | N-(2-Dimethylamino-ethyl)-2-[2-(furan-2-carbonyl)-1,2,3,4-tetrahydro-isoquinolin-5-ylamino]-N-(2-trifluoromethyl-benzyl)-acetamide | 0.74 | 529.2 |

Examples 363a

N-(2-Dimethylamino-ethyl)-2-[2-((1R*,2R*)-2-fluoro-cyclopropanecarbonyl)-1,2,3,4-tetrahydro-isoquinolin-5-ylamino]-N-(2-trifluoromethyl-benzyl)-acetamide LC-L: t$_R$=4.71 min Example 363b N-(2-Dimethylamino-ethyl)-2-[2-((1 S*,2S*)-2-fluoro-cyclopropanecarbonyl)-1,2,3,4-tetrahydro-isoquinolin-5-ylamino]-N-(2-trifluoromethyl-benzyl)-acetamide LC-L: t$_R$=6.47 min Are obtained by separation using preparative HPLC conditions (Method-L) of the racemic Example 363.

Reference Example 104 rac-2-(2-Cyclopropylmethyl-1,2,3,4-tetrahydro-isoquinolin-5-ylamino)-1-(4-methyl-2-phenyl-piperazin-1-yl)-ethanone a) N-(2-Cyclopropylmethyl-1,2,3,4-tetrahydro-isoquinolin-5-yl)-2,2,2-trifluoro-N-[2-(4-methyl-2-phenyl-piperazin-1-yl)-2-oxo-ethyl]-acetamide To a solution of rac-2,2,2-trifluoro-N-[2-(4-methyl-2-phenyl-piperazin-1-yl)-2-oxo-ethyl]-N-(1,2,3,4-tetrahydro-isoquinolin-5-yl)-acetamide dihydrochloride Precursor J3 (167 mg, 0.311 mmol) and cyclopropanecarboxaldehyde (21.8 mg, 0.311 mmol) in 1.5 mL MeOH and 0.75 mL water is added NaBH$_3$CN (48.9 mg, 0.778 mmol) and the resulting mixture is stirred at RT overnight. Sat. aq. NaHCO$_3$ soln. is added and the resulting aq. phase is extracted twice with DCM. The combined organic phase is evaporated under reduced pressure and dried under HV. The crude sub-title product is used as such in the next step.

b) To a solution of N-(2-cyclopropylmethyl-1,2,3,4-tetrahydro-isoquinolin-5-yl)-2,2,2-trifluoro-N-[2-(4-methyl-2-phenyl-piperazin-1-yl)-2-oxo-ethyl]-acetamide (160 mg, 0.283 mmol) in 1.5 mL MeOH and 0.5 mL water is added K$_2$CO$_3$ (235 mg, 1.7 mmol) and the resulting yellow solution is stirred at 60° C. for 2 h. Sat. aq. NaHCO$_3$ soln. is added and the resulting aq. phase is extracted twice with DCM. The combined organic phase is evaporated under reduced pressure. The crude is purified by prep. HPLC (Method E).

LC-A: t$_R$=0.50 min; [M+H]$^+$=419.2

Example 108

2-(2-Acetyl-1,2,3,4-tetrahydro-isoquinolin-5-ylamino)-N-benzyl-N-(2-dimethylamino-ethyl)-acetamide a) N-(2-Acetyl-1,2,3,4-tetrahydroisoquinolin-5-yl)-N-(2-(benzyl(2-dimethylamino)ethyl)amino)-2-oxoethyl)-2,2,2-trifluoroacetamide To a solution of N-{[benzyl-(2-dimethylamino-ethyl)-carbamoyl]-methyl}-2,2,2-trifluoro-N-(1,2,3,4-tetrahydro-isoquinolin-5-yl)-acetamide dihydrochloride Precursor J5 (120 mg, 0.179 mmol) in 2 mL DCM is added TEA (72.6 mg, 0.717 mmol) and the resulting mixture is stirred at RT for 10 min. Then acetylchloride (15.5 mg, 0.197 mmol) is added and the resulting solution is allowed to stir at RT overnight. Sat. aq. NaHCO$_3$ soln. and water are added and the resulting aq. phase is extracted twice with DCM. The combined organic phase is evaporated under reduced pressure and dried under HV. The crude sub-title product is used as such in the next step.

LC-B: t$_R$=0.57 min; [M+H]$^+$=505.0 b) To a solution of N-(2-acetyl-1,2,3,4-tetrahydroisoquinolin-5-yl)-N-(2-(benzyl(2-(dimethylamino)ethyl)amino)-2-oxoethyl)-2,2,2-trifluoroacetamide (90.2 mg, 0.179 mmol) in 1.5 mL MeOH and 0.5 mL water is added K$_2$CO$_3$ (99 mg, 0.72 mmol) and the resulting yellow solution is stirred at 65° C. for 4 h then at RT overnight. Sat. aq. NaHCO$_3$ soln. and water are added and the resulting aq. phase is extracted twice with DCM. The combined organic phase is evaporated under reduced pressure. The crude is purified by prep. HPLC (Method E). This yields the title compound as a colorless oil.
LC-B: $t_R$=0.55 min; [M+H]$^+$=409.1

Example 113

5-({[Benzyl-(2-dimethylamino-ethyl)-carbamoyl]-methyl}-amino)-3,4-dihydro-1H-isoquinoline-2-carboxylic acid methyl ester a) 5-({[Benzyl-(2-dimethylamino-ethyl)-carbamoyl]-methyl}-(2,2,2-trifluoro-acetyl)-amino]-3,4-dihydro-1H-isoquinoline-2-carboxylic acid methyl ester To a solution of N-{[benzyl-(2-dimethylamino-ethyl)-carbamoyl]-methyl}-2,2,2-trifluoro-N-(1,2,3,4-tetrahydro-isoquinolin-5-yl)-acetamide dihydrochloride Precursor J5 (120 mg, 0.179 mmol) in 2 mL DCM is added TEA (72.6 mg, 0.717 mmol) and the resulting mixture is stirred at RT for 10 min. Then methylchloroformate (18.6 mg, 0.197 mmol) is added and the resulting solution is allowed to stir at RT overnight. After cooling, sat. aq. NaHCO$_3$ soln. and water are added and the resulting aq. phase is extracted twice with DCM. The combined organic phase is evaporated under reduced pressure and dried under HV. The crude sub-title product is used as such in the next step.
LC-B: $t_R$=0.64 min; [M+H]$^+$=521.2 b) To a solution of methyl 5-[{[benzyl-(2-dimethylamino-ethyl)-carbamoyl]-methyl}-(2,2,2-trifluoro-acetyl)-amino]-3,4-dihydro-1H-isoquinoline-2-carboxylic acid methyl ester (93.2 mg, 0.179 mmol) in 1.5 mL MeOH and 0.75 mL water is added K$_2$CO$_3$ (99 mg, 0.72 mmol) and the resulting yellow solution is stirred at 65° C. overnight. After cooling, water is added and the resulting aq. phase is extracted twice with DCM. The combined organic phase is evaporated under reduced pressure. The crude residue is purified by prep. HPLC (Method E). This yields the title compound as a colorless oil.
LC-B: $t_R$=0.61 min; [M+H]$^+$=425.1

Examples 105-107/109-112/114-138 listed in Table 13 are prepared applying one of the methods described for Reference example 104, Example 108 or Example 113, using the corresponding Precursor and the corresponding aldehyde, ketone, carboxylic acid chloride or chloroformate respectively.

TABLE 13

Examples 105-107/109-112/114-138

| Example No | Example name | $t_R$ [min] (LC-C) | MS Data m/z [M + H]$^+$ |
|---|---|---|---|
| 105 | 2-(2-Cyclopropylmethyl-1,2,3,4-tetrahydro-isoquinolin-5-ylamino)-N-(1-methyl-piperidin-4-yl)-N-(2-trifluoromethyl-benzyl)-acetamide | 0.65 | 515.4 |
| 106 | N-Benzyl-N-(2-dimethylamino-ethyl)-2-(2-methyl-1,2,3,4-tetrahydro-isoquinolin-5-ylamino)-acetamide | 0.51 | 381.4 |
| 107 | N-Benzyl-N-(2-dimethylamino-ethyl)-2-(2-ethyl-1,2,3,4-tetrahydro-isoquinolin-5-ylamino)-acetamide | 0.53 | 395.4 |
| 109 | N-Benzyl-N-(2-dimethylamino-ethyl)-2-(2-isopropyl-1,2,3,4-tetrahydro-isoquinolin-5-ylamino)-acetamide | 0.55 | 409.5 |
| 110 | N-Benzyl-2-(2-cyclopropylmethyl-1,2,3,4-tetrahydro-isoquinolin-5-ylamino)-N-(2-dimethylamino-ethyl)-acetamide | 0.58 | 421.4 |
| 111 | N-Benzyl-N-(2-dimethylamino-ethyl)-2-(2-propionyl-1,2,3,4-tetrahydro-isoquinolin-5-ylamino)-acetamide | 0.73 | 423.4 |
| 112 | N-Benzyl-N-(2-dimethylamino-ethyl)-2-(2-isobutyl-1,2,3,4-tetrahydro-isoquinolin-5-ylamino)-acetamide | 0.6 | 423.5 |
| 114 | N-Benzyl-2-(2-butyryl-1,2,3,4-tetrahydro-isoquinolin-5-ylamino)-N-(2-dimethylamino-ethyl)-acetamide | 0.78 | 437.4 |
| 115 | N-Benzyl-N-(2-dimethylamino-ethyl)-2-(2-isobutyryl-1,2,3,4-tetrahydro-isoquinolin-5-ylamino)-acetamide | 0.78 | 437.5 |
| 116 | N-Benzyl-N-(2-dimethylamino-ethyl)-2-[2-(2,2-dimethyl-propyl)-1,2,3,4-tetrahydro-isoquinolin-5-ylamino]-acetamide | 0.62 | 437.5 |
| 117 | 5-({[Benzyl-(2-dimethylamino-ethyl)-carbamoyl]-methyl}-amino)-3,4-dihydro-1H-isoquinoline-2-carboxylic acid ethyl ester | 0.83 | 439.4 |
| 118 | N-Benzyl-N-(2-dimethylamino-ethyl)-2-(2-furan-2-ylmethyl-1,2,3,4-tetrahydro-isoquinolin-5-ylamino)-acetamide | 0.59 | 447.4 |
| 119 | N-Benzyl-N-(2-dimethylamino-ethyl)-2-[2-(3-methyl-butyryl)-1,2,3,4-tetrahydro-isoquinolin-5-ylamino]-acetamide | 0.83 | 451.4 |
| 120 | N-Benzyl-N-(2-dimethylamino-ethyl)-2-[2-(3,3-dimethyl-butyl)-1,2,3,4-tetrahydro-isoquinolin-5-ylamino]-acetamide | 0.69 | 451.5 |
| 121 | 5-({[Benzyl-(2-dimethylamino-ethyl)-carbamoyl]-methyl}-amino)-3,4-dihydro-1H-isoquinoline-2-carboxylic acid isopropyl ester | 0.89 | 453.4 |
| 122 | 5-({[Benzyl-(2-dimethylamino-ethyl)-carbamoyl]-methyl}-amino)-3,4-dihydro-1H-isoquinoline-2-carboxylic acid isobutyl ester | 0.95 | 467.4 |
| 123 | N-Benzyl-2-(2-benzyl-1,2,3,4-tetrahydro-isoquinolin-5-ylamino)-N-(2-dimethylamino-ethyl)-acetamide | 0.64 | 457.4 |
| 124 | N-Benzyl-2-(2-cyclohexylmethyl-1,2,3,4-tetrahydro-isoquinolin-5-ylamino)-N-(2-dimethylamino-ethyl)-acetamide | 0.7 | 463.5 |
| 125 | 2-(2-Benzoyl-1,2,3,4-tetrahydro-isoquinolin-5-ylamino)-N-benzyl-N-(2-dimethylamino-ethyl)-acetamide | 0.82 | 471.4 |
| 126 | N-Benzyl-N-(2-dimethylamino-ethyl)-2-(2-phenethyl-1,2,3,4-tetrahydro-isoquinolin-5-ylamino)-acetamide | nd | nd |
| 127 | 5-({[Benzyl-(2-dimethylamino-ethyl)-carbamoyl]-methyl}-amino)-3,4-dihydro-1H-isoquinoline-2-carboxylic acid 2,2-dimethyl-propyl ester | 0.99 | 481.5 |
| 128 | N-Benzyl-N-(2-dimethylamino-ethyl)-2-(2-phenylacetyl-1,2,3,4-tetrahydro-isoquinolin-5-ylamino)-acetamide | 0.84 | 485.4 |
| 129 | N-Benzyl-2-[2-(2-cyclohexyl-acetyl)-1,2,3,4-tetrahydro-isoquinolin-5-ylamino]-N-(2-dimethylamino-ethyl)-acetamide | 0.95 | 491.5 |

TABLE 13-continued

Examples 105-107/109-112/114-138

| Example No | Example name | $t_R$ [min] (LC-C) | MS Data m/z [M + H]+ |
|---|---|---|---|
| 130 | 5-({[Benzyl-(2-dimethylamino-ethyl)-carbamoyl]-methyl}-amino)-3,4-dihydro-1H-isoquinoline-2-carboxylic acid phenyl ester | 0.92 | 487.4 |
| 131 | 5-({[Benzyl-(2-dimethylamino-ethyl)-carbamoyl]-methyl}-amino)-3,4-dihydro-1H-isoquinoline-2-carboxylic acid benzyl ester | 0.95 | 501.4 |
| 132 | N-Benzyl-N-(3-methyl-butyl)-2-(2-methyl-1,2,3,4-tetrahydro-isoquinolin-5-ylamino)-acetamide | 0.87 | 380.4 |
| 133 | N-(2-Chloro-benzyl)-N-(2-dimethylamino-ethyl)-2-(2-ethyl-1,2,3,4-tetrahydro-isoquinolin-5-ylamino)-acetamide | 0.57 | 429.4 |
| 134 | N-(2-Chloro-benzyl)-2-(2-cyclopropylmethyl-1,2,3,4-tetrahydro-isoquinolin-5-ylamino)-N-(2-dimethylamino-ethyl)-acetamide | 0.62 | 455.4 |
| 135 | N-(2-Dimethylamino-ethyl)-2-(2-ethyl-1,2,3,4-tetrahydro-isoquinolin-5-ylamino)-N-(2-trifluoromethyl-benzyl)-acetamide | 0.61 | 463.4 |
| 136 | rac-2-(2-Cyclopropylmethyl-1,2,3,4-tetrahydro-isoquinolin-5-ylamino)-N-(1-methyl-piperidin-3-yl)-N-(2-trifluoromethyl-benzyl)-acetamide | 0.68 | 515.5 |
| 137 | 2-(2-Ethyl-1,2,3,4-tetrahydro-isoquinolin-5-ylamino)-N-(1-methyl-piperidin-4-yl)-N-(2-trifluoromethyl-benzyl)-acetamide | 0.61 | 489.4 |

Example 364

2-(2-Cyanomethyl-1,2,3,4-tetrahydro-isoquinolin-5-ylamino)-N-(2-dimethylamino-ethyl)-N-(2-trifluoromethyl-benzyl)-acetamide To a solution of N-{[(2-dimethylamino-ethyl)-(2-trifluoromethyl-benzyl)-carbamoyl]-methyl}-2,2,2-trifluoro-N-(1,2,3,4-tetrahydro-isoquinolin-5-yl)-acetamide dihydrochloride Precursor J8 (100 mg, 0.143 mmol) dissolved in 2 mL MeCN is added chloroacetonitrile (11 mg, 0.143 mmol) and sodium tert-butoxide (27.4 mg, 0.285 mmol) and resulting mixture is allowed to stir at RT for 5 h. The solvent is evaporated under reduced pressure and the residue is taken up in DCM and sat. aq. NaHCO$_3$. solution. The resulting aq. phase is extracted twice with DCM. The combined organic phase evaporated to dryness. The crude residue is purified by prep. HPLC (Method D). This yields the title compound as a colorless oil.

LC-A: $t_R$=0.68 min; [M+H]+=474.0

Example 373

N-(2-Dimethylamino-ethyl)-2-(2-phenyl-1,2,3,4-tetrahydro-isoquinolin-5-ylamino)-N-(2-trifluoromethyl-benzyl)-acetamide To a solution of N-{[(2-dimethylamino-ethyl)-(2-trifluoromethyl-benzyl)-carbamoyl]-methyl}-2,2,2-trifluoro-N-(1,2,3,4-tetrahydro-isoquinolin-5-yl)-acetamide dihydrochloride Precursor J8 (100 mg, 0.143 mmol) dissolved in 2 mL toluene is added iodobenzene (35.6 mg, 0.171 mmol), Pd$_2$(dba)$_3$ (3.92 mg, 0.0043 mmol) DavePhos (5.05 mg, 0.0128 mmol) and sodium tert-butoxide (27.4 mg, 0.285 mmol) and resulting mixture is allowed to stir at 80° C. overnight. The solvent is evaporated under reduced pressure and the residue is taken up in DCM and sat. aq. NaHCO$_3$. solution. The resulting aq. phase is extracted twice with DCM. The combined organic phase evaporated to dryness. The crude residue is purified by prep. HPLC (Method D). This yields the title compound as a colorless oil.

LC-A: $t_R$=0.90 min; [M+H]+=511.3

Examples 374-376 listed in Table 14 are prepared applying one of the methods described for Example 373, using the corresponding heteroaryl iodide respectively.

TABLE 14

Examples 374-376

| Example No | Example name | $t_R$ [min] (LC-F) | MS Data m/z [M + H]+ |
|---|---|---|---|
| 374 | N-(2-Dimethylamino-ethyl)-2-(2-pyridin-2-yl-1,2,3,4-tetrahydro-isoquinolin-5-ylamino)-N-(2-trifluoromethyl-benzyl)-acetamide | 0.58 | 512.3 |
| 375 | N-(2-Dimethylamino-ethyl)-2-(2-pyrimidin-2-yl-1,2,3,4-tetrahydro-isoquinolin-5-ylamino)-N-(2-trifluoromethyl-benzyl)-acetamide | 0.81 | 513.3 |
| 376 | N-(2-Dimethylamino-ethyl)-N-(2-trifluoromethyl-benzyl)-2-[2-(4-trifluoromethyl-thiazol-2-yl)-1,2,3,4-tetrahydro-isoquinolin-5-ylamino]-acetamide | 0.96 | 586.3 |

Precursor J1

N-Benzyl-N-(2-dimethylamino-ethyl)-2-(1,2,3,4-tetrahydro-isoquinolin-5-ylamino)-acetamide dihydrochloride To a solution of 5-({[benzyl-(2-dimethylamino-ethyl)-carbamoyl]-methyl}-amino)-3,4-dihydro-1H-isoquinoline-2-carboxylic acid tert-butyl ester Example 8 (580 mg, 1.24 mmol) in 4 mL DCM is added 0.62 mL 4N HCl in dioxane soln. The resulting mixture is allowed to stir at RT for 1.5 h at which time a white precipitate has formed. The solid is filtered and dried under HV. (It is sensitive to moisture and turns into a yellow oil rapidly after opening of the flask to air). This yields 390 mg (71%) of the title compound as a yellow oil.

LC-B: $t_R$=0.43 min; [M+H]+=367.2

Precursors J4/J11-J13 listed in Table 15 are prepared applying the above method described for Precursor J1 using the corresponding precursors (Example 10, Example 90, Precursor K12, Precursor K13) respectively as starting material.

TABLE 15

Precursor J4/J11-J13

| Precursor | Precursor name | $t_R$ [min] (LC-A) | MS Data m/z $[M + H]^+$ |
|---|---|---|---|
| J4 | N-(1-Methyl-piperidin-4-yl)-2-(1,2,3,4-tetrahydro-isoquinolin-5-ylamino)-N-(2-trifluoromethyl-benzyl)-acetamide dihydrochloride | 0.56 | 461.0 |
| J11 | N-(2-Dimethylamino-ethyl)-2-(4,4-dimethyl-1,2,3,4-tetrahydro-isoquinolin-5-ylamino)-N-(2-trifluoromethyl-benzyl)-acetamide dihydrochloride | 0.58 | 463.1 |
| J12 | N-(2-Dimethylamino-ethyl)-2-(1,2,3,4-tetrahydro-isoquinolin-5-ylamino)-N-(2-trifluoromethyl-pyridin-3-ylmethyl)-acetamide dihydrochloride | 0.52 | 436.1 |
| J13 | N-((1-hydroxycyclopentyl)methyl)-2-((1,2,3,4-tetrahydroisoquinolin-5-yl)amino)-N-(2-(trifluoromethyl)benzyl)acetamide hydrochloride | 0.73 | 462.2 |

Precursor J2

N-(2-trifluoromethyl)benzyl-N-(2-(dimethylamino) ethyl)-2-((1,2,3,4-tetrahydroisoquinolin-5-yl)amino) acetamide dihydrochloride To a solution of 5-({[(2-dimethylamino-ethyl)-(2-trifluoromethyl-benzyl)-carbamoyl]-methyl}-amino)-3,4-dihydro-1H-isoquinoline-2-carboxylic acid tert-butyl ester Precursor K2 (150 mg, 0.236 mmol) in 2 mL DCM is 0.5 mL TFA. The resulting yellow solution is allowed to stir at RT for 1.5 h. The mixture is poured onto water and basified with sat. aq. NaHCO$_3$ soln. The resulting aq. phase is extracted twice with EtOAc. The combined organic phase is washed with brine, dried over MgSO$_4$, filtered and evaporated under reduced pressure. This yields the title compound as a brown oil which is used as such in the next step.

LC-B: $t_R$=0.56 min; $[M+H]^+$=435.1

Precursor J3 rac-2,2,2-Trifluoro-N-[2-(4-methyl-2-phenyl-piperazin-1-yl)-2-oxo-ethyl]-N-(1,2,3,4-tetrahydro-isoquinolin-5-yl)-acetamide dihydrochloride a) 5-[[2-(4-Methyl-2-phenyl-piperazin-1-yl)-2-oxo-ethyl]-(2,2,2-trifluoro-acetyl)-amino]-3,4-dihydro-1H-isoquinoline-2-carboxylic acid tert-butyl ester To a solution of rac-5-[2-(4-methyl-2-phenyl-piperazin-1-yl)-2-oxo-ethylamino]-3,4-dihydro-1H-isoquinoline-2-carboxylic acid tert-butyl ester Precursor K3 (100 mg, 0.202 mmol) in 4 mL DCM is added TEA (123 mg, 1.21 mmol) and the solution is allowed to stir at RT for 10 min. Then TFAA (170 mg, 0.809 mmol) is added dropwise slowly and the resulting yellow solution is allowed to stir at RT for 45 min. Sat. aq. NaHCO$_3$ soln. is added and the resulting aq. phase is extracted twice with DCM. The combined organic phase is evaporated under reduced pressure to give 151 mg of the crude sub-title compound as a yellow oil.

LC-A: $t_R$=0.79 min; $[M+H]^+$=561.0 b) To a solution of 5-[[2-(4-methyl-2-phenyl-piperazin-1-yl)-2-oxo-ethyl]-(2,2,2-trifluoro-acetyl)-amino]-3,4-dihydro-1H-isoquinoline-2-carboxylic acid tert-butyl ester (151 mg of crude, 0.202 mmol) in 3 mL dioxane is added 4N HCl soln. in 1.5 mL dioxane and allowed to stir at RT overnight. The solvent is evaporated under reduced pressure, the remainder of dioxane is coevaporated twice with DCM. After drying under HV this yields 159 mg of the title compound which is used as such in the next step.

LC-B: $t_R$=0.48 min; $[M+H]^+$=496.98

Precursors J5-J10 listed in Table 16 are prepared applying the method described for Precursor J3 using the corresponding Precursor or Example as starting material.

TABLE 16

Precursor J5-J10

| Precursor | Precursor name | $t_R$ [min] (Method) | MS Data m/z $[M + H]^+$ |
|---|---|---|---|
| J5 | N-{[Benzyl-(2-dimethylamino-ethyl)-carbamoyl]-methyl}-2,2,2-trifluoro-N-(1,2,3,4-tetrahydro-isoquinolin-5-yl)-acetamide dihydrochloride | 0.44 (B) | 463.1 |
| J6 | N-{[Benzyl-(3-methyl-butyl)-carbamoyl]-methyl}-2,2,2-trifluoro-N-(1,2,3,4-tetrahydro-isoquinolin-5-yl)-acetamide hydrochloride | 0.72 (B) | 463.2 |
| J7 | N-{[(2-Chloro-benzyl)-(2-dimethylamino-ethyl)-carbamoyl]-methyl}-2,2,2-trifluoro-N-(1,2,3,4-tetrahydro-isoquinolin-5-yl)-acetamide dihydrochloride | 0.48 (B) | 496.98 |

TABLE 16-continued

Precursor J5-J10

| Precursor | Precursor name | $t_R$ [min] (Method) | MS Data m/z [M + H]$^+$ |
|---|---|---|---|
| J8 | N-{[(2-Dimethylamino-ethyl)-(2-trifluoromethyl-benzyl)-carbamoyl]-methyl}-2,2,2-trifluoro-N-(1,2,3,4-tetrahydro-isoquinolin-5-yl)-acetamide dihydrochloride | 0.51 (B) | 530.99 |
| J9 | rac-2,2,2-Trifluoro-N-{[(1-methyl-piperidin-3-yl)-(2-trifluoromethyl-benzyl)-carbamoyl]-methyl}-N-(1,2,3,4-tetrahydro-isoquinolin-5-yl)-acetamide dihydrochloride | 0.59 (A) | 557.2 |
| J10 | 2,2,2-Trifluoro-N-{[(1-methyl-piperidin-4-yl)-(2-trifluoromethyl-benzyl)-carbamoyl]-methyl}-N-(1,2,3,4-tetrahydro-isoquinolin-5-yl)-acetamide dihydrochloride | 0.59 (A) | 557.1 |

Precursor J14

Methyl-{2-[[2-(1,2,3,4-tetrahydro-isoquinolin-5-ylamino)-acetyl]-(2-trifluoromethyl-benzyl)-amino]-ethyl}-carbamic acid tert-butyl ester To a solution of 5-((2-((2-((tert-butoxycarbonyl)(methyl)amino)ethyl)(2-(trifluoromethyl)benzyl)amino)-2-oxoethyl)amino)-3,4-dihydroisoquinoline-2(1H)-carboxylic acid benzyl ester Precursor K14 (56% purity, 2.24 g, 1.92 mmol) in degassed 20 mL EtOAc is added 0.5 g 10% Pd/C and the resulting suspension is allowed to stir at RT under an atmosphere of H$_2$ overnight. Then 0.2 g 10% Pd/C are added and the resulting suspension is allowed to stir at RT under an atmosphere of H$_2$ for 4 days. The mixture is then filtered over Celite, the filter cake is rinsed three times with EtOAc. The combined organic phase is concentrated in vacuo to yield quantitatively 1.07 g of the title compound as a yellow oil.

LC-A: $t_R$=0.78 min; [M+H]$^+$=521.4

Precursor J15

Methyl-{2-[[2-(1,2,3,4-tetrahydro-isoquinolin-5-ylamino)-acetyl]-(3-trifluoromethyl-pyridin-2-ylmethyl)-amino]-ethyl}-carbamic acid tert-butyl ester LC-A: $t_R$=0.74 min; [M+H]$^+$=522.3, is prepared according to the procedure described for Precursor J14 using Precursor K15 as starting material.

Precursors K2-K3/K7/K12-K15 listed in Table 17 are prepared applying the method described for the synthesis of Example 8 from precursor B1 using the corresponding Precursor B1, B8 or B25 and the corresponding Amine.

TABLE 17

Precursor K2-K3/K7/K12-K15

| Precursor | Precursor name | $t_R$ [min] (LC-A) | MS Data m/z [M + H]$^+$ |
|---|---|---|---|
| K2 | 5-({[(2-Dimethylamino-ethyl)-(2-trifluoromethyl-benzyl)-carbamoyl]-methyl}-amino)-3,4-dihydro-1H-isoquinoline-2-carboxylic acid tert-butyl ester | 0.81 | 535.3 |
| K3 | rac-5-[2-(4-Methyl-2-phenyl-piperazin-1-yl)-2-oxo-ethylamino]-3,4-dihydro-1H-isoquinoline-2-carboxylic acid tert-butyl ester | 0.73 | 465.2 |
| K7 | 5-({[(2-Chloro-benzyl)-(2-dimethylamino-ethyl)-carbamoyl]-methyl}-amino)-3,4-dihydro-1H-isoquinoline-2-carboxylic acid tert-butyl ester | 0.74 | 501 |
| K12 | 5-({[(2-Dimethylamino-ethyl)-(3-trifluoromethyl-pyridin-2-ylmethyl)-carbamoyl]-methyl}-amino)-3,4-dihydro-1H-isoquinoline-2-carboxylic acid tert-butyl ester | 0.78 | 536.3 |
| K13 | 5-((2-(((1-hydroxycyclopentyl)methyl)(2-(trifluoromethyl)benzyl)amino)-2-oxoethyl)amino)-3,4-dihydroisoquinoline-2(1H)-carboxylic acid tert-butyl ester | 1.03 | 561.9 |
| K14 | 5-((2-((2-((tert-butoxycarbonyl)(methyl)amino)ethyl)(2-(trifluoromethyl)benzyl)amino)-2-oxoethyl)amino)-3,4-dihydroisoquinoline-2(1H)-carboxylic acid benzyl ester | 1.08 | 655.4 |
| K15 | 5-((2-((2-((tert-butoxycarbonyl)(methyl)amino)ethyl)((3-(trifluoromethyl)pyridin-2-yl)methyl)amino)-2-oxoethyl)amino)-3,4-dihydroisoquinoline-2(1H)-carboxylic acid benzyl ester | 1.04 | 656.0 |

Example 138

(E)-N-Benzyl-3-(2-cyclopropylmethyl-1,2,3,4-tetrahydro-isoquinolin-5-yl)-N-(2-hydroxy-ethyl)-acrylamide To a solution of (E)-N-benzyl-N-(2-hydroxyethyl)-3-(1,2,3,4-tetrahydroisoquinolin-5-yl)acrylamide hydrochloride Precursor L1 (45 mg, 0.136 mmol) and cyclopropanecarboxaldehyde (9.6 mg, 0.136 mmol) in 0.5 mL water and 1 mL MeOH is added NaBH$_3$CN (21.4 mg, 0.34 mmol). The resulting mixture is allowed to stir at RT for 1 h. Sat. aq. NaHCO$_3$ soln. is added and the resulting aq. phase is extracted twice with DCM. The solvent is evaporated under reduced pressure. The crude is purified by prep. HPLC (Method E). The solid obtained is dissolved in a large excess of 1.25 HCl soln. in EtOH and the resulting solution is allowed to stir at RT for 10 min. The solvent is then removed under reduced pressure and the crude product is dried under HV. This yields the title compound hydrochloride as a yellow oil.

LC-A: $t_R$=0.64 min; [M+H]$^+$=391.4

Example 162

N-Benzyl-N-(2-dimethylamino-ethyl)-3-(2-propionyl-1,2,3,4-tetrahydro-isoquinolin-5-yl)-propionamide To a solution of N-benzyl-N-(2-dimethylamino-ethyl)-3-(1,2,3,4-tetrahydro-isoquinolin-5-yl)-propionamide dihydrochloride Precursor O4 (40 mg, 0.082 mmol) in 2 mL DCM is added TEA (33.2 mg, 0.328 mmol) followed by propionyl chloride (8.36 mg, 0.09 mmol). The resulting yellow mixture is allowed to stir at RT for 1.5 h. Sat. aq. NaHCO$_3$ soln. is added and the resulting aq. phase is extracted twice with DCM. The solvent is evaporated under reduced pressure. The crude residue is purified by prep. HPLC (Method D). This yields the title compound as a colorless oil.

LC-B: $t_R$=0.58 min; [M+H]$^+$=422.0

Example 167

5-{[Benzyl-(2-dimethylamino-ethyl)-carbamoyl]-methoxy}-3,4-dihydro-1H-isoquinoline-2-carboxylic acid methyl ester To a solution of N-benzyl-N-(2-dimethylamino-ethyl)-2-(1,2,3,4-tetrahydro-isoquinolin-5-yloxy)-acetamide dihydrochloride Precursor Q2 (50 mg, 0.09 mmol) in 0.5 mL DCM is added TEA (36.8 mg, 0.36 mmol) followed by methylchloroformate (9.44 mg, 0.1 mmol). The resulting yellow mixture is allowed to stir at RT for 1 h. Sat. aq. NaHCO$_3$ soln. is added and the resulting aq. phase is extracted twice with DCM. The solvent is evaporated under reduced pressure. The crude is purified by prep. HPLC (Method E). This yields the title compound as a yellow oil.

LC-B: $t_R$=0.61 min; [M+H]$^+$=426.2

Examples 139-161/163-166/168-174/454 listed in Table 18 are prepared applying one of the methods described for Example 138, Example 162 or Example 167 respectively using the corresponding Precursor and the corresponding aldehyde, ketone, carboxylic acid chloride or chloroformate respectively.

TABLE 18

Examples 139-161/163-166/168-174/454

| Example No | Example name | $t_R$ [min] (LC-C) unless otherwise indicated | MS Data m/z [M + H]$^+$ |
|---|---|---|---|
| 139 | (E)-N-(2-Chloro-benzyl)-3-(2-cyclopropylmethyl-1,2,3,4-tetrahydro-isoquinolin-5-yl)-N-ethyl-acrylamide | 0.89 | 409.3 |
| 141 | (E)-N-Cyclopropyl-3-(2-cyclopropylmethyl-1,2,3,4-tetrahydro-isoquinolin-5-yl)-N-(2,3-dimethyl-benzyl)-acrylamide | 0.94 | 415.4 |
| 142 | (E)-N-Benzyl-N-(2-dimethylamino-ethyl)-3-(2-methyl-1,2,3,4-tetrahydro-isoquinolin-5-yl)-acrylamide | 0.52 | 378.3 |
| 143 | (E)-N-Benzyl-3-(2-cyclopropylmethyl-1,2,3,4-tetrahydro-isoquinolin-5-yl)-N-(2-dimethylamino-ethyl)-acrylamide | 0.58 | 418.5 |
| 144 | {Benzyl-[(E)-3-(2-cyclopropylmethyl-1,2,3,4-tetrahydro-isoquinolin-5-yl)-acryloyl]-amino}-acetic acid ethyl ester | 0.84 | 433.4 |
| 145 | (E)-N-(2-Chloro-benzyl)-N-(2-dimethylamino-ethyl)-3-(2-ethyl-1,2,3,4-tetrahydro-isoquinolin-5-yl)-acrylamide | 0.57 | 426.4 |
| 146 | (E)-N-(2-Chloro-benzyl)-3-(2-cyclopropylmethyl-1,2,3,4-tetrahydro-isoquinolin-5-yl)-N-(2-dimethylamino-ethyl)-acrylamide | 0.61 | 452.4 |
| 147 | (E)-N-Benzyl-3-(2-cyclopropylmethyl-1,2,3,4-tetrahydro-isoquinolin-5-yl)-N-(1,1-dioxo-tetrahydro-1l6-thiophen-3-yl)-acrylamide | 0.72 | 465.4 |
| 148 | (E)-N-Benzyl-3-(2-cyclopropylmethyl-1,2,3,4-tetrahydro-isoquinolin-5-yl)-N-[2-(4-fluoro-phenyl)-ethyl]-acrylamide | 0.97 | 469.4 |
| 149 | (E)-N-(2-Dimethylamino-ethyl)-3-(2-ethyl-1,2,3,4-tetrahydro-isoquinolin-5-yl)-N-(2-trifluoromethyl-benzyl)-acrylamide | 0.62 | 460.4 |
| 150 | (E)-3-(2-Cyclopropylmethyl-1,2,3,4-tetrahydro-isoquinolin-5-yl)-N-(2-dimethylamino-ethyl)-N-(2-trifluoromethyl-benzyl)-acrylamide | 0.65 | 486.4 |
| 151 | (E)-3-(2-Ethyl-1,2,3,4-tetrahydro-isoquinolin-5-yl)-N-(1-methyl-piperidin-4-yl)-N-(2-trifluoromethyl-benzyl)-acrylamide | 0.6 | 486.4 |
| 152 | (E)-3-(2-Cyclopropylmethyl-1,2,3,4-tetrahydro-isoquinolin-5-yl)-N-(1-methyl-piperidin-4-yl)-N-(2-trifluoromethyl-benzyl)-acrylamide | 0.65 | 512.4 |

TABLE 18-continued

Examples 139-161/163-166/168-174/454

| Example No | Example name | $t_R$ [min] (LC-C) unless otherwise indicated | MS Data m/z [M + H]$^+$ |
|---|---|---|---|
| Reference example 153 | rac-(E)-3-(2-Cyclopropylmethyl-1,2,3,4-tetrahydro-isoquinolin-5-yl)-1-(4-methyl-2-phenyl-piperazin-1-yl)-propenone | 0.51 | 416.4 |
| 154 | (E)-3-(2-Cyclopropylmethyl-1,2,3,4-tetrahydro-isoquinolin-5-yl)-N-(2-dimethylamino-ethyl)-2-methyl-N-(2-trifluoromethyl-benzyl)-acrylamide | 0.65 | 500.3 |
| 155 | N-(2-Chloro-benzyl)-N-(2-dimethylamino-ethyl)-3-(2-ethyl-1,2,3,4-tetrahydro-isoquinolin-5-yl)-propionamide | 0.57 | 428.4 |
| 156 | N-(2-Chloro-benzyl)-3-(2-cyclopropylmethyl-1,2,3,4-tetrahydro-isoquinolin-5-yl)-N-(2-dimethylamino-ethyl)-propionamide | 0.62 | 454.3 |
| 157 | N-(2-Dimethylamino-ethyl)-3-(2-ethyl-1,2,3,4-tetrahydro-isoquinolin-5-yl)-N-(2-trifluoromethyl-benzyl)-propionamide | 0.61 | 462.4 |
| 158 | 3-(2-Cyclopropylmethyl-1,2,3,4-tetrahydro-isoquinolin-5-yl)-N-(2-dimethylamino-ethyl)-N-(2-trifluoromethyl-benzyl)-propionamide | 0.65 | 488.4 |
| 159 | 3-(2-Ethyl-1,2,3,4-tetrahydro-isoquinolin-5-yl)-N-(1-methyl-piperidin-4-yl)-N-(2-trifluoromethyl-benzyl)-propionamide | 0.6 | 488.4 |
| 160 | 3-(2-Cyclopropylmethyl-1,2,3,4-tetrahydro-isoquinolin-5-yl)-N-(1-methyl-piperidin-4-yl)-N-(2-trifluoromethyl-benzyl)-propionamide | 0.64 | 514.4 |
| 161 | N-Benzyl-3-(2-cyclopropylmethyl-1,2,3,4-tetrahydro-isoquinolin-5-yl)-N-(2-dimethylamino-ethyl)-propionamide | 0.57 | 420.5 |
| 163 | N-Benzyl-2-(2-cyclopropylmethyl-1,2,3,4-tetrahydro-isoquinolin-5-yloxy)-N-(3-methyl-butyl)-acetamide | 0.97 | 421.4 |
| 164 | N-Benzyl-N-(2-dimethylamino-ethyl)-2-(2-methyl-1,2,3,4-tetrahydro-isoquinolin-5-yloxy)-acetamide | 0.49 | 382.4 |
| 165 | N-Benzyl-N-(2-dimethylamino-ethyl)-2-(2-ethyl-1,2,3,4-tetrahydro-isoquinolin-5-yloxy)-acetamide | 0.51 | 396.4 |
| 166 | N-Benzyl-2-(2-cyclopropylmethyl-1,2,3,4-tetrahydro-isoquinolin-5-yloxy)-N-(2-dimethylamino-ethyl)-acetamide | 0.56 | 422.4 |
| 168 | N-Benzyl-N-(2-dimethylamino-ethyl)-2-(2-isobutyl-1,2,3,4-tetrahydro-isoquinolin-5-yloxy)-acetamide | 0.57 | 424.4 |
| 169 | N-Benzyl-N-(2-dimethylamino-ethyl)-2-(2-propionyl-1,2,3,4-tetrahydro-isoquinolin-5-yloxy)-acetamide | 0.71 | 424.4 |
| 170 | N-Benzyl-N-(2-dimethylamino-ethyl)-2-(2-isobutyryl-1,2,3,4-tetrahydro-isoquinolin-5-yloxy)-acetamide | 0.76 | 438.5 |
| 171 | N-(2-Chloro-benzyl)-N-(2-dimethylamino-ethyl)-2-(2-ethyl-1,2,3,4-tetrahydro-isoquinolin-5-yloxy)-acetamide | 0.55 | 430.3 |
| 172 | N-(2-Chloro-benzyl)-2-(2-cyclopropylmethyl-1,2,3,4-tetrahydro-isoquinolin-5-yloxy)-N-(2-dimethylamino-ethyl)-acetamide | 0.59 | 456.4 |
| 173 | N-(2-Dimethylamino-ethyl)-2-(2-ethyl-1,2,3,4-tetrahydro-isoquinolin-5-yloxy)-N-(2-trifluoromethyl-benzyl)-acetamide | 0.59 | 464.4 |
| 174 | 2-(2-Cyclopropylmethyl-1,2,3,4-tetrahydro-isoquinolin-5-yloxy)-N-(2-dimethylamino-ethyl)-N-(2-trifluoromethyl-benzyl)-acetamide | 0.63 | 490.4 |
| 454 | 3-(2-Cyclopropylmethyl-1,2,3,4-tetrahydro-isoquinolin-8-yl)-N-(2-dimethylamino-ethyl)-N-(2-trifluoromethyl-benzyl)-propionamide | 0.49 (LC-A) | 488.0 |

Example 140

(E)-N-Benzyl-N-(2-carbamoyl-ethyl)-3-(2-cyclopropyl-methyl-1,2,3,4-tetrahydro-isoquinolin-5-yl)-acrylamide dihydrochloride is prepared applying the method described for Example 138, using the corresponding Precursor L3 and and cyclopropanecarboxaldehyde. The solid obtained is dissolved in a large excess of 1.25 HCl soln. in EtOH and the resulting solution is allowed to stir at RT for 10 min. The solvent is then removed under reduced pressure and the crude product is dried under HV. This yields the title compound as a yellow oil.

LC-A: $t_R$=0.62 min; [M+H]$^+$=418.1.

Precursor L1

(E)-N-Benzyl-N-(2-dimethylamino-ethyl)-3-(1,2,3,4-tetrahydro-isoquinolin-5-yl)-acrylamide To a solution of 5-{(E)-2-[benzyl-(2-hydroxy-ethyl)-carbamoyl]-vinyl}-3,4-dihydro-1H-isoquinoline-2-carboxylic acid tert-butyl ester Precursor M1 (43 mg, 0.098 mmol) in 2 mL dioxane is added 0.34 ml 4M HCl soln. in dioxane. The resulting soln. is allowed to stir at RT overnight. Evaporation of the volatiles under reduced pressure yields quantitatively the crude title compound as a white solid which is used as such in the next step.

LC-B: $t_R$=0.49 min; [M+H]$^+$=337.3

Precursors L2-L13 listed in Table 19 are prepared applying the method described for Precursor L1 using the corresponding Precursor or Example as starting material.

TABLE 19

Precursor L2-L13

| Precursor | Precursor name | $t_R$ [min] (Method) | MS Data m/z [M + H]$^+$ |
|---|---|---|---|
| L2 | (E)-N-(2-Chlorobenzyl)-N-ethyl-3-(1,2,3,4-tetrahydroisoquinolin-5-yl)acrylamide hydrochloride | 0.69 (A) | 355.2 |
| L3 | (E)-N-Benzyl-N-(2-cyanoethyl)-3-(1,2,3,4-tetrahydroisoquinolin-5-yl)acrylamide hydrochloride | 0.63 (A) | 346.3 |
| L4 | (E)-N-Cyclopropyl-N-(2,3-dimethylbenzyl)-3-(1,2,3,4-tetrahydroisoquinolin-5-yl)acrylamide hydrochloride | 0.73 (A) | 461.4 |
| L5 | (E)-N-Benzyl-N-(2-(dimethylamino)ethyl)-3-(1,2,3,4-tetrahydroisoquinolin-5-yl)acrylamide hydrochloride | 0.44 (B) | 364.1 |
| L6 | (E)-Ethyl 2-(N-benzyl-3-(1,2,3,4-tetrahydroisoquinolin-5-yl)acrylamido)acetate hydrochloride | 0.68 (A) | 379.3 |
| L7 | (E)-N-(2-Chlorobenzyl)-N-(2-(dimethylamino)ethyl)-3-(1,2,3,4-tetrahydroisoquinolin-5-yl)acrylamide dihydrochloride | 0.47 (B) | 398 |
| L8 | (E)-N-Benzyl-N-(1,1-dioxidotetrahydrothiophen-3-yl)-3-(1,2,3,4-tetrahydroisoquinolin-5-yl)acrylamide hydrochloride | 0.62 (A) | 411.3 |
| L9 | (E)-N-Benzyl-N-(4-fluorophenethyl)-3-(1,2,3,4-tetrahydroisoquinolin-5-yl)acrylamide hydrochloride | 0.76 (A) | 415.4 |
| L10 | (E)-N-(2-(Dimethylamino)ethyl)-3-(1,2,3,4-tetrahydroisoquinolin-5-yl)-N-(2-(trifluoromethyl)benzyl)acrylamide dihydrochloride | 0.49 (B) | 432 |
| L11 | (E)-N-(1-Methylpiperidin-4-yl)-3-(1,2,3,4-tetrahydroisoquinolin-5-yl)-N-(2-(trifluoromethyl)benzyl)acrylamide dihydrochloride | 0.55 (A) | 458.1 |
| L12 | rac-(E)-1-(4-Methyl-2-phenylpiperazin-1-yl)-3-(1,2,3,4-tetrahydroisoquinolin-5-yl)prop-2-en-1-one dihydrochloride | 0.44 (A) | 362.2 |
| L13 | (E)-N-(2-(Dimethylamino)ethyl)-2-methyl-3-(1,2,3,4-tetrahydroisoquinolin-5-yl)-N-(2-(trifluoromethyl)benzyl)acrylamide dihydrochloride | 0.55 (A) | 446.1 |

Precursor O1

N-(2-Chloro-benzyl)-N-(2-dimethylamino-ethyl)-3-(1,2,3,4-tetrahydro-isoquinolin-5-yl)-propionamide dihydrochloride To a solution of 5-{2-[(2-chloro-benzyl)-(2-dimethyl-amino-ethyl)-carbamoyl]-ethyl}-3,4-dihydro-1H-isoquinoline-2-carboxylic acid tert-butyl ester Example 98 (85 mg, 0.161 mmol) in 2 mL dioxane is added 0.141 ml 4M HCl soln. in dioxane. The resulting soln. is allowed to stir at RT overnight. Evaporation of the volatiles under reduced pressure yields 78 mg (100%) of the compound as a yellow solid which is used as such in the next step.

LC-A: $t_R$=0.52 min; [M+H]$^+$=400.2

Precursors O2-O4 listed in Table 20 are prepared applying the method described for Precursor O1 using the corresponding Precursor or Example as starting material.

Precursor Q1

N-Benzyl-N-(3-methyl-butyl)-2-(1,2,3,4-tetrahydro-isoquinolin-5-yloxy)-acetamide hydrochloride To a solution of 5-{[benzyl-(3-methyl-butyl)-carbamoyl]-methoxy}-3,4-dihydro-1H-isoquinoline-2-carboxylic acid tert-butyl ester Precursor R$^1$ (90 mg, 0.187 mmol) in 2 mL dioxane is added 0.655 ml 4M HCl soln. in dioxane. The resulting soln. is allowed to stir 5 h at RT. Evaporation of the volatiles under reduced pressure yields 78 mg (100%) of the compound as a white solid which is used as such in the next step.

LC-B: $t_R$=0.69 min; [M+H]$^+$=367.1

Precursors Q2-Q4 listed in Table 21 are prepared applying the method described for Precursor Q1 using the corresponding Precursor or Example as starting material.

TABLE 20

Precursor O2-O4

| Precursor | Precursor name | $t_R$ [min] (Method) | MS Data m/z [M + H]$^+$ |
|---|---|---|---|
| O2 | N-(2-Dimethylamino-ethyl)-3-(1,2,3,4-tetrahydro-isoquinolin-5-yl)-N-(2-trifluoromethyl-benzyl)-propionamide dihydrochloride | 0.54 (A) | 433.9 |
| O3 | N-(1-Methyl-piperidin-4-yl)-3-(1,2,3,4-tetrahydro-isoquinolin-5-yl)-N-(2-trifluoromethyl-benzyl)-propionamide dihydrochloride | 0.54 (A) | 460.2 |
| O4 | N-Benzyl-N-(2-dimethylamino-ethyl)-3-(1,2,3,4-tetrahydro-isoquinolin-5-yl)-propionamide dihydrochloride | 0.43 (B) | 366.1 |

TABLE 21

Precursor Q2-Q4

| Precursor | Precursor name | $t_R$ [min] (Method) | MS Data m/z $[M + H]^+$ |
|---|---|---|---|
| Q2 | N-Benzyl-N-(2-dimethylamino-ethyl)-2-(1,2,3,4-tetrahydro-isoquinolin-5-yloxy)-acetamide dihydrochloride | 0.41 (B) | 368.1 |
| Q3 | N-(2-Chloro-benzyl)-N-(2-dimethylamino-ethyl)-2-(1,2,3,4-tetrahydro-isoquinolin-5-yloxy)-acetamide dihydrochloride | 0.45 (B) | 401.7 |
| Q4 | N-(2-Dimethylamino-ethyl)-2-(1,2,3,4-tetrahydro-isoquinolin-5-yloxy)-N-(2-trifluoromethyl-benzyl)-acetamide dihydrochloride | 0.47 (B) | 436 |

Precursors M1-R4 listed in Table 22 are prepared applying the method described for the synthesis of Example 92 from precursor E1 using the corresponding Precursor and the corresponding Amine.

TABLE 22

Precursor M1-R4

| Precursor | Precursor name | $t_R$ [min] (Method) | MS Data m/z $[M + H]^+$ |
|---|---|---|---|
| M1 | 5-{(E)-2-[Benzyl-(2-hydroxy-ethyl)-carbamoyl]-vinyl}-3,4-dihydro-1H-isoquinoline-2-carboxylic acid tert-butyl ester | 0.90 (A) | 437.3 |
| M3 | 5-{(E)-2-[Benzyl-(2-cyano-ethyl)-carbamoyl]-vinyl}-3,4-dihydro-1H-isoquinoline-2-carboxylic acid tert-butyl ester | 0.96 (A) | 446.1 |
| M4 | 5-{(E)-2-[Cyclopropyl-(2,3-dimethyl-benzyl)-carbamoyl]vinyl}-3,4-dihydro-1H-isoquinoline-2-carboxylic acid tert-butyl ester | 1.06 (A) | 461.4 |
| M7 | 5-{(E)-2-[(2-Chloro-benzyl)-(2-dimethylamino-ethyl)-carbamoyl]-vinyl}-3,4-dihydro-1H-isoquinoline-2-carboxylic acid tert-butyl ester | 0.75 (B) | 497.8 |
| M9 | 5-((E)-2-{Benzyl-[2-(4-fluoro-phenyl)-ethyl]-carbamoyl}-vinyl)-3,4-dihydro-1H-isoquinoline-2-carboxylic acid tert-butyl ester | 1.06 (A) | 515.4 |
| M10 | 5-{(E)-2-[(2-Dimethylamino-ethyl)-(2-trifluoromethyl-benzyl)-carbamoyl]-vinyl}-3,4-dihydro-1H-isoquinoline-2-carboxylic acid tert-butyl ester | 0.76 (B) | 532.1 |
| M12 | rac-5-[(E)-3-(4-Methyl-2-phenyl-piperazin-1-yl)-3-oxo-propenyl]-3,4-dihydro-1H-isoquinoline-2-carboxylic acid tert-butyl ester | 0.74 (A) | 462.3 |
| P4 | 5-{2-[Benzyl-(2-dimethylamino-ethyl)-carbamoyl]-ethyl}-3,4-dihydro-1H-isoquinoline-2-carboxylic acid tert-butyl ester | 0.72 (B) | 465.8 |
| R1 | 5-{[Benzyl-(3-methyl-butyl)-carbamoyl]-methoxy}-3,4-dihydro-1H-isoquinoline-2-carboxylic acid tert-butyl ester | 1.14 (B) | 467 |
| R3 | 5-{[(2-Chloro-benzyl)-(2-dimethylamino-ethyl)-carbamoyl]-methoxy}-3,4-dihydro-1H-isoquinoline-2-carboxylic acid tert-butyl ester | 0.73 (B) | 502.3 |
| R4 | 5-{[(2-Dimethylamino-ethyl)-(2-trifluoromethyl-benzyl)-carbamoyl]-methoxy}-3,4-dihydro-1H-isoquinoline-2-carboxylic acid tert-butyl ester | 0.75 (B) | 536.1 |

Example 175

N-Benzyl-N-cyclopropylmethyl-2-(2-methyl-1,2,3,4-tetrahydro-isoquinolin-5-ylamino)-acetamide To a solution of N-benzyl-N-(cyclopropylmethyl)-2-(isoquinolin-5-ylamino)acetamide Precursor S1 (226 mg, 0.65 mmol) in 1 mL MeCN is added iodomethane (95 mg, 0.67 mmol). The mixture is allowed to stir at RT for 3 h. The volatiles are evaporated under reduced pressure and the crude product is dissolved in 2 mL MeOH before NaBH$_4$ (49 mg, 1.3 mmol) is added. The colour changes from yellow to colorless and the resulting solution is allowed to stir at RT for 1 h. Sat. aq. NaHCO$_3$ and water are added and the resulting aq. phase is extracted three times with DCM with a phase separator. The organic phases are combined and the solvent is removed under reduced pressure. The crude residue is dissolved in 2 mL EtOH and DABCO (875 mg, 7.8 mmol) is added. The resulting solution is heated at reflux for 1 h. After evaporation of the volatiles under reduced pressure, the crude residue is purified by prep. HPLC (Method E).

LC-C: $t_R$=0.83 min; $[M+H]^+$=364.4

Example 177

N-(2-Dimethylamino-ethyl)-N-(2-fluoro-benzyl)-2-(2-methyl-1,2,3,4-tetrahydro-isoquinolin-5-ylamino)-acetamide LC-C: $t_R$=0.52 min; $[M+H]^+$=399.4 is made from N-(2-(dimethylamino)ethyl)-N-(2-fluorobenzyl)-2-(isoquinolin-5-ylamino)acetamide Precursor S2 according to the procedure described for the synthesis of Example 175.

Precursor S1

N-Benzyl-N-(cyclopropylmethyl)-2-(isoquinolin-5-ylamino)acetamide

To a solution of 2-(isoquinolin-5-ylamino)acetic acid Precursor T1 (202 mg, 1 mmol) dissolved in 2 mL DMF is added benzyl-cyclopropylmethyl-amine Amine 4 (161 mg, 1 mmol), DIPEA (388 mg, 3 mmol) and HATU (380 mg, 1 mmol). The resulting solution is allowed to stir at RT overnight. Sat. aq. NaHCO$_3$ and water are added and the resulting aq. phase is extracted three times with DCM with a phase separator. The organic phases are combined and the solvent is removed under reduced pressure. Flash-chromatography on silica-gel: (Eluent: (DCM/MeOH) 95:5+2% aq. NH$_3$ soln.) yields 226 mg (65%) of the title compound.

$^1$H-NMR (CD$_3$OD), 50:50 mixture of two rotamers, δ: 9.07 (m, 1H), 8.36 (d, J=6.1 Hz, 0.5H), 8.33 (d, J=6.1 Hz, 1H), 7.96 (d, J=6.1 Hz, 0.5H), 7.89 (d, J=6.1 Hz, 0.5H), 7.52 (t, J=8.0 Hz, 0.5H), 7.44 (t, J=8.0 Hz, 1H), 7.37 (m, 2H), 7.29 (m, 4H), 6.82 (d, J=7.6 Hz, 0.5H), 6.62 (d, J=7.6 Hz, 0.5H), 4.86 (s, 1H), 4.82 (s, 1H), 4.31 (s, 1H), 4.18 (s, 1H), 3.39 (d, J=7.0 Hz, 1H), 3.34 (m, 1H), 2.82 (s), 1.06 (m, 1H), 0.58 (m, 1H), 0.50 (m, 1H), 0.26 (m, 2H)

Precursor S2

N-(2-(Dimethylamino)ethyl)-N-(2-fluorobenzyl)-2-(isoquinolin-5-ylamino)acetamide is made according to the procedure described for the synthesis of Precursor S1 using Precursor T1 and Amine 20 as starting materials.

Precursor T1

2-(Isoquinolin-5-ylamino)acetic acid

To a solution of 5-isoquinoline (1 g, 6.94 mmol) in 15 mL MeCN cooled to 0° C. is added 1.54 mL 50% glyoxylic acid soln. in water and NaBH$_3$CN (872 mg, 13.9 mmol). The mixture is allowed to warm up to RT and is stirred at this temperature overnight. Then MeCN is evaporated under reduced pressure, the residue is taken up in water (pH=9). The resulting aq. phase is extracted with ether. The aq. phase is then acidified with 1N HCl soln. and the solvent is evaporated under reduced pressure. The residue is dissolved with MeOH and eluted on a SiliaBond® SCX acid column. It is released with ammonia. After evaporation, the crude is dissolved in 1N HCl aq. soln. and heated up at 85° C. for 2 h. Evaporation of the volatiles to dryness and under HV yields 820 mg (58%) of the title compound as a white solid.

$^1$H-NMR (d$_6$-DMSO) δ: 9.59 (s, 1H), 8.64 (d, J=6.8 Hz, 1H), 8.48 (dd, J$_1$=6.9 Hz, J$_2$=0.6 Hz, 1H), 7.86 (t, J=8.1 Hz, 1H), 7.75 (m, 1H), 7.13 (d, J=7.8 Hz, 1H), 4.23 (s, 2H)

Example 179

2-(2-Cyclopropylmethyl-1,2,3,4-tetrahydro-isoquinolin-5-ylamino)-N-(2-methylamino-ethyl)-N-(2-trifluoromethyl-benzyl)-acetamide To a solution of {2-[[2-(2-cyclopropylmethyl-1,2,3,4-tetrahydro-isoquinolin-5-ylamino)-acetyl]-(2-trifluoromethyl-benzyl)-amino]-ethyl}-methyl-carbamic acid tert-butyl ester Example 83 (30 mg, 0.052 mmol) in 1 mL DCM is added 0.15 mL TFA. The resulting yellow solution is allowed to stir at RT for 30 min then poured onto water. The resulting aq. phase is basified to pH=8-9 with sat. aq. NaHCO$_3$ soln. then extracted twice with DCM. The combined organic phase is washed with brine then dried over MgSO$_4$, filtered and evaporated under reduced pressure. After drying under HV, pure title compound is obtained as a yellow foam.

LC-A: t$_R$=0.60 min; [M+H]$^+$=475.2

Example 177 N-(2-Methylamino-ethyl)-2-(2-propionyl-1,2,3,4-tetrahydro-isoquinolin-5-ylamino)-N-(2-trifluoromethyl-benzyl)-acetamide LC-A: t$_R$=0.70 min; [M+H]$^+$=477.2 and Example 178 rac-N-Benzyl-2-(2-cyclopropylmethyl-1,2,3,4-tetrahydro-isoquinolin-5-ylamino)-N-pyrrolidin-3-yl-acetamide LC-A: t$_R$=0.55 min; [M+H]$^+$=419.1 are prepared applying the method described for Example 179 from Precursor U1 and Example 65 respectively.

Example 385

2-(2-Cyclopropanecarbonyl-1,2,3,4-tetrahydro-isoquinolin-5-ylamino)-N-(2-methylamino-ethyl)-N-(2-trifluoromethyl-benzyl)-acetamide To a solution of tert-butyl (2-(2-((2-(cyclopropanecarbonyl)-1,2,3,4-tetrahydroisoquinolin-5-yl)amino)-N-(2-(trifluoromethyl)benzyl)acetamido)ethyl)(methyl)carbamate Precursor U11 (58.9 mg, 0.1 mmol) in 1 mL DCM and 0.5 mL MeOH is added 0.5 mL 4N HCl soln. in dioxane (2 mmol). The resulting yellow solution is allowed to stir at RT for 30 min then the volatiles are removed under reduced pressure and the residue dried under HV. The crude residue is purified by prep. HPLC (Method D).

LC-F: t$_R$=0.74 min; [M+H]$^+$=489.3

In some case, the hydrochloride salt of the title compound obtained after evaporation of the volatiles does not need further purification. In some other instances 4M HCl in MeOH is added to the preparative HPLC fractions in order to obtain after drying the title compound as an hydrochloride salt.

Examples 377-384/386-433/435-446 listed in Table 23 are prepared applying one of the methods described for Example 179 or Example 385 respectively using the corresponding Precursor or Example compound.

TABLE 23

| | Examples 377-384/386-433/435-446 | | |
|---|---|---|---|
| Example No | Example name | t$_R$ [min] (LC-FF) unless otherwise indicated | MS Data m/z [M + H]$^+$ |
| 377 | N-Benzyl-2-(2-ethyl-1,2,3,4-tetrahydro-isoquinolin-8-ylamino)-N-piperidin-4-yl-acetamide | 0.39 | 407.3 |
| 378 | rac-N-Benzyl-2-(2-ethyl-1,2,3,4-tetrahydro-isoquinolin-8-ylamino)-N-pyrrolidin-3-yl-acetamide | 0.39 | 393.3 |

TABLE 23-continued

Examples 377-384/386-433/435-446

| Example No | Example name | $t_R$ [min] (LC-FF) unless otherwise indicated | MS Data m/z [M + H]+ |
|---|---|---|---|
| 379 | 2-(2-Cyclopropylmethyl-1,2,3,4-tetrahydro-isoquinolin-5-ylamino)-N-(R)-1-pyrrolidin-3-ylmethyl-N-(2-trifluoromethyl-benzyl)-acetamide | 0.52 | 501.4 |
| 380 | 2-(2-Cyclopropylmethyl-1,2,3,4-tetrahydro-isoquinolin-5-ylamino)-N-(S)-1-pyrrolidin-3-ylmethyl-N-(2-trifluoromethyl-benzyl)-acetamide | 0.52 | 501.4 |
| 381 | rac-2-(2-Cyclopropylmethyl-1,2,3,4-tetrahydro-isoquinolin-5-ylamino)-N-pyrrolidin-3-yl-N-(2-trifluoromethyl-benzyl)-acetamide | 0.5 | 487.3 |
| 382 | rac-2-(2-Cyclopropylmethyl-1-methyl-1,2,3,4-tetrahydro-isoquinolin-5-ylamino)-N-(2-methylamino-ethyl)-N-(2-trifluoromethyl-benzyl)-acetamide | 0.52 | 489.4 |
| 383 | 2-(2-Isobutyl-3-oxo-1,2,3,4-tetrahydro-isoquinolin-5-ylamino)-N-(2 methylamino-ethyl)-N-(2-trifluoromethyl-benzyl)-acetamide | 0.83 | 491.3 |
| 384 | 2-(2-Cyclopropylmethyl-1,2,3,4-tetrahydro-isoquinolin-8-ylamino)-N-(2-methylamino-ethyl)-N-(2-trifluoromethyl-benzyl)-acetamide | 0.49 | 475.3 |
| 386 | 2-(2-Butyryl-1,2,3,4-tetrahydro-isoquinolin-5-ylamino)-N-(2-methylamino-ethyl)-N-(2-trifluoromethyl-benzyl)-acetamide | 0.76 | 491.3 |
| 387 | 2-(2-Isobutyryl-1,2,3,4-tetrahydro-isoquinolin-5-ylamino)-N-(2-methylamino-ethyl)-N-(2-trifluoromethyl-benzyl)-acetamide | 0.76 | 491.4 |
| 3388 | 2-[2-(2-Methoxy-acetyl)-1,2,3,4-tetrahydro-isoquinolin-5-ylamino]-N-(2-methylamino-ethyl)-N-(2-trifluoromethyl-benzyl)-acetamide | 0.67 | 493.3 |
| 389 | 2-(2-Cyclobutanecarbonyl-1,2,3,4-tetrahydro-isoquinolin-5-ylamino)-N-(2-methylamino-ethyl)-N-(2-trifluoromethyl-benzyl)-acetamide | 0.79 | 503.3 |
| 390 | 2-[2-(2,2-Dimethyl-propionyl)-1,2,3,4-tetrahydro-isoquinolin-5-ylamino]-N-(2-methylamino-ethyl)-N-(2-trifluoromethyl-benzyl)-acetamide | 0.82 | 505.3 |
| 391 | N-(2-Methylamino-ethyl)-2-[2-[(3-methyl-butyryl)-1,2,3,4-tetrahydro-isoquinolin-5-ylamino]-N-(2-trifluoromethyl-benzyl)-acetamide | 0.81 | 505.3 |
| 392 | rac-N-(2-Methylamino-ethyl)-2-[2-(tetrahydro-furan-3-carbonyl)-1,2,3,4-tetrahydro-isoquinolin-5-ylamino]-N-(2-trifluoromethyl-benzyl)-acetamide | 0.69 | 519.3 |
| 393 | 2-[2-(3,3-Dimethyl-butyryl)-1,2,3,4-tetrahydro-isoquinolin-5-ylamino]-N-(2-methylamino-ethyl)-N-(2-trifluoromethyl-benzyl)-acetamide | 0.85 | 519.4 |
| 394 | 5-({[(2-Methylamino-ethyl)-(2-trifluoromethyl-benzyl)-carbamoyl]-methyl}-amino)-3,4-dihydro-1H-isoquinoline-2-carboxylic acid methyl ester | 0.76 | 479.3 |
| 395 | 5-({[(2-Methylamino-ethyl)-(2-trifluoromethyl-benzyl)-carbamoyl]-methyl}-amino)-3,4-dihydro-1H-isoquinoline-2-carboxylic acid ethyl ester | 0.81 | 493.3 |
| 396 | 5-({[(2-Methylamino-ethyl)-(2-trifluoromethyl-benzyl)-carbamoyl]-methyl}-amino)-3,4-dihydro-1H-isoquinoline-2-carboxylic acid prop-2-ynyl ester | 0.8 | 503.3 |
| 397 | 5-({[(2-Methylamino-ethyl)-(2-trifluoromethyl-benzyl)-carbamoyl]-methyl}-amino)-3,4-dihydro-1H-isoquinoline-2-carboxylic acid allyl ester | 0.84 | 505.3 |
| 398 | 5-({[(2-Methylamino-ethyl)-(2-trifluoromethyl-benzyl)-carbamoyl]-methyl}-amino)-3,4-dihydro-1H-isoquinoline-2-carboxylic acid propyl ester | 0.87 | 507.3 |
| 399 | 5-({[(2-Methylamino-ethyl)-(2-trifluoromethyl-benzyl)-carbamoyl]-methyl}-amino)-3,4-dihydro-1H-isoquinoline-2-carboxylic acid isopropyl ester | 0.86 | 507.3 |
| 400 | 5-({[(2-Methylamino-ethyl)-(2-trifluoromethyl-benzyl)-carbamoyl]-methyl}-amino)-3,4-dihydro-1H-isoquinoline-2-carboxylic acid 2-fluoro-ethyl ester | 0.78 | 511.3 |
| 401 | 5-({[(2-Methylamino-ethyl)-(2-trifluoromethyl-benzyl)-carbamoyl]-methyl}-amino)-3,4-dihydro-1H-isoquinoline-2-carboxylic acid isobutyl ester | 0.91 | 521.4 |
| 402 | 5-({[(2-Methylamino-ethyl)-(2-trifluoromethyl-benzyl)-carbamoyl]-methyl}-amino)-3,4-dihydro-1H-isoquinoline-2-carboxylic acid 2,2-dimethyl-propyl ester | 0.94 | 535.4 |
| 403 | 5-({[(2-Methylamino-ethyl)-(2-trifluoromethyl-benzyl)-carbamoyl]-methyl}-amino)-3,4-dihydro-1H-isoquinoline-2-carboxylic acid ethylamide | 0.69 | 492.3 |
| 404 | 5-({[(2-Methylamino-ethyl)-(2-trifluoromethyl-benzyl)-carbamoyl]-methyl}-amino)-3,4-dihydro-1H-isoquinoline-2-carboxylic acid isopropylamide | 0.74 | 506.4 |
| 405 | 5-({[(2-Methylamino-ethyl)-(2-trifluoromethyl-benzyl)-carbamoyl]-methyl}-amino)-3,4-dihydro-1H-isoquinoline-2-carboxylic acid butylamide | 0.8 | 520.4 |
| 406 | 5-({[(2-Methylamino-ethyl)-(2-trifluoromethyl-benzyl)-carbamoyl]-methyl}-amino)-3,4-dihydro-1H-isoquinoline-2-carboxylic acid tert-butylamide | 0.81 | 520.4 |

TABLE 23-continued

Examples 377-384/386-433/435-446

| Example No | Example name | $t_R$ [min] (LC-FF) unless otherwise indicated | MS Data m/z [M + H]⁺ |
|---|---|---|---|
| 407 | 5-({[(2-Methylamino-ethyl)-(2-trifluoromethyl-benzyl)-carbamoyl]-methyl}-amino)-3,4-dihydro-1H-isoquinoline-2-carboxylic acid cyclohexylamide | 0.85 | 546.4 |
| 408 | 2-(2-Acetyl-1,2,3,4-tetrahydro-isoquinolin-5-ylamino)-N-(2-methylamino-ethyl)-N-(3-trifluoromethyl-pyridin-2-ylmethyl)-acetamide | 0.6 | 464.3 |
| 409 | N-(2-Methylamino-ethyl)-2-(2-propionyl-1,2,3,4-tetrahydro-isoquinolin-5-ylamino)-N-(3-trifluoromethyl-pyridin-2-ylmethyl)-acetamide | 0.65 | 478.3 |
| 410 | 2-(2-Cyclopropanecarbonyl-1,2,3,4-tetrahydro-isoquinolin-5-ylamino)-N-(2-methylamino-ethyl)-N-(3-trifluoromethyl-pyridin-2-ylmethyl)-acetamide | 0.67 | 490.3 |
| 411 | 2-(2-Butyryl-1,2,3,4-tetrahydro-isoquinolin-5-ylamino)-N-(2-methylamino-ethyl)-N-(3-trifluoromethyl-pyridin-2-ylmethyl)-acetamide | 0.69 | 492.3 |
| 412 | 2-(2-Isobutyryl-1,2,3,4-tetrahydro-isoquinolin-5-ylamino)-N-(2-methylamino-ethyl)-N-(3-trifluoromethyl-pyridin-2-ylmethyl)-acetamide | 0.69 | 492.4 |
| 413 | 2-[2-(2-Methoxy-acetyl)-1,2,3,4-tetrahydro-isoquinolin-5-ylamino]-N-(2-methylamino-ethyl)-N-(3-trifluoromethyl-pyridin-2-ylmethyl)-acetamide | 0.97 (LC-F1) | 494.3 |
| 414 | 2-(2-Cyclobutanecarbonyl-1,2,3,4-tetrahydro-isoquinolin-5-ylamino)-N-(2-methylamino-ethyl)-N-(3-trifluoromethyl-pyridin-2-ylmethyl)-acetamide | 0.72 | 504.3 |
| 415 | 2-[2-(2,2-Dimethyl-propionyl)-1,2,3,4-tetrahydro-isoquinolin-5-ylamino]-N-(2-methylamino-ethyl)-N-(3-trifluoromethyl-pyridin-2-ylmethyl)-acetamide | 0.75 | 506.4 |
| 416 | N-(2-Methylamino-ethyl)-2-[2-(3-methyl-butyryl)-1,2,3,4-tetrahydro-isoquinolin-5-ylamino]-N-(3-trifluoromethyl-pyridin-2-ylmethyl)-acetamide | 0.74 | 506.4 |
| 417 | rac-N-(2-Methylamino-ethyl)-2-[2-(tetrahydro-furan-3-carbonyl)-1,2,3,4-tetrahydro-isoquinolin-5-ylamino]-N-(3-trifluoromethyl-pyridin-2-ylmethyl)-acetamide | 0.63 | 520.3 |
| 418 | 2-[2-(3,3-Dimethyl-butyryl)-1,2,3,4-tetrahydro-isoquinolin-5-ylamino]-N-(2-methylamino-ethyl)-N-(3-trifluoromethyl-pyridin-2-ylmethyl)-acetamide | 0.79 | 520.4 |
| 419 | 5-({[(2-Methylamino-ethyl)-(3-trifluoromethyl-pyridin-2-ylmethyl)-carbamoyl]-methyl}-amino)-3,4-dihydro-1H-isoquinoline-2-carboxylic acid methyl ester | 0.69 | 480.3 |
| 420 | 5-({[(2-Methylamino-ethyl)-(3-trifluoromethyl-pyridin-2-ylmethyl)-carbamoyl]-methyl}-amino)-3,4-dihydro-1H-isoquinoline-2-carboxylic acid ethyl ester | 0.74 | 494.3 |
| 421 | 5-({[(2-Methylamino-ethyl)-(3-trifluoromethyl-pyridin-2-ylmethyl)-carbamoyl]-methyl}-amino)-3,4-dihydro-1H-isoquinoline-2-carboxylic acid prop-2-ynyl ester | 0.73 | 504.3 |
| 422 | 5-({[(2-Methylamino-ethyl)-(3-trifluoromethyl-pyridin-2-ylmethyl)-carbamoyl]-methyl}-amino)-3,4-dihydro-1H-isoquinoline-2-carboxylic acid allyl ester | 0.77 | 506.3 |
| 423 | 5-({[(2-Methylamino-ethyl)-(3-trifluoromethyl-pyridin-2-ylmethyl)-carbamoyl]-methyl}-amino)-3,4-dihydro-1H-isoquinoline-2-carboxylic acid propyl ester | 0.8 | 508.3 |
| 424 | 5-({[(2-Methylamino-ethyl)-(3-trifluoromethyl-pyridin-2-ylmethyl)-carbamoyl]-methyl}-amino)-3,4-dihydro-1H-isoquinoline-2-carboxylic acid isopropyl ester | 0.8 | 508.3 |
| 425 | 5-({[(2-Methylamino-ethyl)-(3-trifluoromethyl-pyridin-2-ylmethyl)-carbamoyl]-methyl}-amino)-3,4-dihydro-1H-isoquinoline-2-carboxylic acid 2-fluoro-ethyl ester | 0.7 | 512.3 |
| 426 | 5-({[(2-Methylamino-ethyl)-(3-trifluoromethyl-pyridin-2-ylmethyl)-carbamoyl]-methyl}-amino)-3,4-dihydro-1H-isoquinoline-2-carboxylic acid isobutyl ester | 0.85 | 522.4 |
| 427 | 5-({[(2-Methylamino-ethyl)-(3-trifluoromethyl-pyridin-2-ylmethyl)-carbamoyl]-methyl}-amino)-3,4-dihydro-1H-isoquinoline-2-carboxylic acid 2-methoxy-ethyl ester | 0.69 | 524.3 |
| 428 | 5-({[(2-Methylamino-ethyl)-(3-trifluoromethyl-pyridin-2-ylmethyl)-carbamoyl]-methyl}-amino)-3,4-dihydro-1H-isoquinoline-2-carboxylic acid 2,2-dimethyl-propyl ester | 0.89 | 536.4 |
| 429 | 5-({[(2-Methylamino-ethyl)-(3-trifluoromethyl-pyridin-2-ylmethyl)-carbamoyl]-methyl}-amino)-3,4-dihydro-1H-isoquinoline-2-carboxylic acid ethylamide | 0.62 | 493.3 |
| 430 | 5-({[(2-Methylamino-ethyl)-(3-trifluoromethyl-pyridin-2-ylmethyl)-carbamoyl]-methyl}-amino)-3,4-dihydro-1H-isoquinoline-2-carboxylic acid isopropylamide | 0.67 | 507.3 |
| 431 | 5-({[(2-Methylamino-ethyl)-(3-trifluoromethyl-pyridin-2-ylmethyl)-carbamoyl]-methyl}-amino)-3,4-dihydro-1H-isoquinoline-2-carboxylic acid butylamide | 0.73 | 521.4 |

TABLE 23-continued

Examples 377-384/386-433/435-446

| Example No | Example name | $t_R$ [min] (LC-FF) unless otherwise indicated | MS Data m/z [M + H]$^+$ |
|---|---|---|---|
| 432 | 5-({[(2-Methylamino-ethyl)-(3-trifluoromethyl-pyridin-2-ylmethyl)-carbamoyl]-methyl}-amino)-3,4-dihydro-1H-isoquinoline-2-carboxylic acid tert-butylamide | 0.74 | 521.4 |
| 433 | 5-({[(2-Methylamino-ethyl)-(3-trifluoromethyl-pyridin-2-ylmethyl)-carbamoyl]-methyl}-amino)-3,4-dihydro-1H-isoquinoline-2-carboxylic acid cyclohexylamide | 0.78 | 547.4 |
| 435 | N-(2-Bromo-benzyl)-2-(2-cyclopropylmethyl-1,2,3,4-tetrahydro-isoquinolin-5-ylamino)-N-(2-methylamino-ethyl)-acetamide | 0.47 | 485.3 |
| 436 | N-(3-Chloro-pyridin-2-ylmethyl)-2-(2-cyclopropylmethyl-1,2,3,4-tetrahydro-isoquinolin-5-ylamino)-N-(2-methylamino-ethyl)-acetamide | 0.39 | 442.3 |
| 437 | 2-(2-Cyclopropylmethyl-1,2,3,4-tetrahydro-isoquinolin-5-ylamino)-N-(2-methylamino-ethyl)-N-(3-trifluoromethyl-pyridin-2-ylmethyl)-acetamide | 0.43 | 476.3 |
| 438 | 2-(2-Cyclopropylmethyl-1,2,3,4-tetrahydro-isoquinolin-5-ylamino)-N-(2-piperazin-1-yl-ethyl)-N-(2-trifluoromethyl-benzyl)-acetamide | 0.51 | 530.4 |
| 439 | 2-(2-Cyclopropylmethyl-1,2,3,4-tetrahydro-isoquinolin-5-ylamino)-N-(2-ethylamino-ethyl)-N-(2-trifluoromethyl-benzyl)-acetamide | 0.5 | 489.4 |
| 440 | 2-(2-Cyclopropylmethyl-1,2,3,4-tetrahydro-isoquinolin-5-ylamino)-N-piperidin-4-yl-N-(2-trifluoromethyl-benzyl)-acetamide | 0.49 | 501.3 |
| 441 | rac-2-(2-Cyclopropylmethyl-1,2,3,4-tetrahydro-isoquinolin-5-ylamino)-N-pyrrolidin-3-ylmethyl-N-(2-trifluoromethyl-benzyl)-acetamide | 0.52 | 501.4 |
| 442 | N-(2-Amino-ethyl)-2-(2-cyclopropylmethyl-1,2,3,4-tetrahydro-isoquinolin-5-ylamino)-N-(2-trifluoromethyl-benzyl)-acetamide | 0.49 | 461.4 |
| 443 | N-Benzyl-2-(2-ethyl-1,2,3,4-tetrahydro-isoquinolin-8-ylamino)-N-(2-methylamino-ethyl)-acetamide | 0.38 | 381.2 |
| 444 | 2-(2-Ethyl-1,2,3,4-tetrahydro-isoquinolin-8-ylamino)-N-(2-methylamino-ethyl)-N-(2-trifluoromethyl-benzyl)-acetamide | 0.46 | 449.3 |
| 445 | 2-(2-Acetyl-1,2,3,4-tetrahydro-isoquinolin-5-ylamino)-N-(2-methylamino-ethyl)-N-(2-trifluoromethyl-benzyl)-acetamide | 0.67 | 463.3 |
| 446 | N-(2-Chloro-benzyl)-2-(2-cyclopropylmethyl-1,2,3,4-tetrahydro-isoquinolin-5-ylamino)-N-(2-methylamino-ethyl)-acetamide | 0.46 | 441.3 |

Example 434

2-(2-Cyclopropylmethyl-1,2,3,4-tetrahydro-isoquinolin-5-ylamino)-N-[2-(2,2,2-trifluoro-ethylamino)-ethyl]-N-(2-trifluoromethyl-benzyl)-acetamide To a solution of 2-((2-(cyclopropylmethyl)-1,2,3,4-tetrahydroisoquinolin-5-yl)amino)-N-(2-((4-methoxybenzyl)(2,2,2-trifluoroethyl)amino)ethyl)-N-(2-(trifluoromethyl)benzyl)acetamide Precursor U60 (164 mg, 0.247 mmol) and 0.5 mL AcOH in 5 mL MeOH is added 10% Pd/C (26.3 mg, 0.0247 mmol). The suspension is stirred under H$_2$ atmosphere for 8 h. The crude mixture is then filtered and the concentrated uder reduced pressure. The crude residue is purified by prep. HPLC (Method D). LC-F: $t_R$=0.84 min; [M+H]$^+$=543.3

Precursor U1

Methyl-{2-[[2-(2-propionyl-1,2,3,4-tetrahydro-isoquinolin-5-ylamino)-acetyl]-(2-trifluoromethyl-benzyl)-amino]-ethyl}-carbamic acid tert-butyl ester LC-A: $t_R$=1.00 min; [M+H]$^+$=576.8 is prepared according to the method described for the synthesis of Example 8 using Precursor B2 and Amine 73 as starting materials.

Precursor U10 tert-Butyl (2-(2-((2-acetyl-1,2,3,4-tetrahydroisoquinolin-5-yl)amino)-N-(2-(trifluoromethyl)benzyl)acetamido)ethyl)(methyl)carbamate To a solution of acetyl chloride (7.85 mg, 0.1 mmol) in 1 mL DCM is added TEA (10.1 mg, 0.1 mmol) and methyl-{2-[[2-(1,2,3,4-tetrahydro-isoquinolin-5-ylamino)-acetyl]-(2-trifluoromethyl-benzyl)-amino]-ethyl}-carbamic acid tert-butyl ester Precursor J14 (54.2 mg, 0.1 mmol). The resulting mixture is allowed to stir at RT for 1.5 h. The obtained solution of title compound, LC-G: $t_R$=1.11 min; [M+H]$^+$=563.2, is used as such in the next step.

Precursor U20

Methyl 5-((2-((2-((tert-butoxycarbonyl)(methyl)amino)ethyl)(2-(trifluoromethyl)benzyl)amino)-2-oxoethyl)amino)-3,4-dihydroisoquinoline-2(1H)-carboxylate To a solution of methyl chloroformate (10.5 mg, 0.11 mmol) in 1 mL DCM is added TEA (10.1 mg, 0.1 mmol) and methyl-{2-[[2-(1,2,3,4-tetrahydro-isoquinolin-5-ylamino)-acetyl]-(2-trifluoromethyl-benzyl)-amino]-ethyl}-carbamic acid tert-butyl ester Precursor J14 (54.2 mg, 0.1 mmol). The resulting mixture is allowed to stir at RT for 1.5 h. The obtained solution of title compound, LC-G: $t_R$=1.21 min; [M+H]$^+$=519.2, is used as such in the next step.

Precursor U29 tert-Butyl (2-(2-((2-(Ethylcarbamoyl)-1,2,3,4-tetrahydroisoquinolin-5-yl)amino)-N-(2-(trifluoromethyl)benzyl)acetamido)ethyl)(methyl)carbamate To a solution of ethyl isocyanate (8.2 mg, 0.11 mmol) in 1 mL DCM is added TEA (10.1 mg, 0.1 mmol) and methyl-{2-[[2-(1,2,3,4-tetrahydro-isoquinolin-5-ylamino)-acetyl]-(2-trifluoromethyl-benzyl)-amino]-ethyl}-carbamic acid tert-butyl ester Precursor J14 (54.2 mg, 0.1 mmol). The resulting mixture is allowed to stir at RT for 1.5 h. The obtained solution of title compound, LC-G: $t_R$=1.11 min; [M+H]$^+$=592.2, is used as such in the next step.

Precursors U2-U9/U11-U19/U21-U28/U30-U63 listed in Table 24 are prepared applying one of the methods described for the synthesis of Precursor U1 from precursor B2 and amine 73 or Precursor U10, Precursor U20 and Precursor U29 from Precursor J14 using the corresponding reagents.

TABLE 24

Precursors U2-U9/U11-U19/U21-U28/U30-U63

| Precursor | Precursor name | $t_R$ [min] (Method) | MS Data m/z [M + H]$^+$ |
|---|---|---|---|
| U2 | 4-{Benzyl-[2-(2-ethyl-1,2,3,4-tetrahydro-isoquinolin-8-ylamino)-acetyl]-amino}-piperidine-1-carboxylic acid tert-butyl ester | 1.8 (H) | 507.2 |
| U3 | 3-{Benzyl-[2-(2-ethyl-1,2,3,4-tetrahydro-isoquinolin-8-ylamino)-acetyl]-amino}-pyrrolidine-1-carboxylic acid tert-butyl ester | 1.75 (H) | 493.2 |
| U9 | tert-Butyl (2-(2-((2-(cyclopropylmethyl)-1,2,3,4-tetrahydroisoquinolin-8-yl)amino)-N-(2-(trifluoromethyl)benzyl)acetamido)ethyl)(methyl)carbamate | 0.83 (A) | 575.1 |
| U4 | (S)-3-{[[2-(2-Cyclopropylmethyl-1,2,3,4-tetrahydro-isoquinolin-5-ylamino)-acetyl]-(2-trifluoromethyl-benzyl)-amino]-methyl}-pyrrolidine-1-carboxylic acid tert-butyl ester | 0.86 (A) | 601.3 |
| U5 | (R)-3-{[[2-(2-Cyclopropylmethyl-1,2,3,4-tetrahydro-isoquinolin-5-ylamino)-acetyl]-(2-trifluoromethyl-benzyl)-amino]-methyl}-pyrrolidine-1-carboxylic acid tert-butyl ester | 0.86 (A) | 601.3 |
| U6 | rac-3-[[2-(2-Cyclopropylmethyl-1,2,3,4-tetrahydro-isoquinolin-5-ylamino)-acetyl]-(2-trifluoromethyl-benzyl)-amino]-pyrrolidine-1-carboxylic acid tert-butyl ester | 0.85 (A) | 587.3 |
| U7 | rac-tert-Butyl (2-(2-((2-(cyclopropylmethyl)-1-methyl-1,2,3,4-tetrahydroisoquinolin-5-yl)amino)-N-(2-(trifluoromethyl)benzyl)acetamido)ethyl)(methyl)carbamate | 0.87 (A) | 589.3 |
| U8 | tert-Butyl (2-(2-((2-isobutyl-3-oxo-1,2,3,4-tetrahydroisoquinolin-5-yl)amino)-N-(2-(trifluoromethyl)benzyl)acetamido)ethyl)(methyl)carbamate | 0.98 (B) | 591.1 |
| U11 | tert-Butyl (2-(2-((2-(cyclopropanecarbonyl)-1,2,3,4-tetrahydroisoquinolin-5-yl)amino)-N-(2-(trifluoromethyl)benzyl)acetamido)ethyl)(methyl)carbamate | 1.2 (G) | 589.2 |
| U12 | tert-Butyl (2-(2-((2-butyryl-1,2,3,4-tetrahydroisoquinolin-5-yl)amino)-N-(2-(trifluoromethyl)benzyl)acetamido)ethyl)(methyl)carbamate | 1.23 (G) | 591.2 |
| U13 | tert-Butyl (2-(2-((2-isobutyryl-1,2,3,4-tetrahydroisoquinolin-5-yl)amino)-N-(2-(trifluoromethyl)benzyl)acetamido)ethyl)(methyl)carbamate | 1.23 (G) | 591.2 |
| U14 | tert-Butyl (2-(2-((2-(2-methoxyacetyl)-1,2,3,4-tetrahydroisoquinolin-5-yl)amino)-N-(2-(trifluoromethyl)benzyl)acetamido)ethyl)(methyl)carbamate | 1.14 (G) | 593.2 |
| U15 | tert-Butyl (2-(2-((2-(cyclobutanecarbonyl)-1,2,3,4-tetrahydroisoquinolin-5-yl)amino)-N-(2-(trifluoromethyl)benzyl)acetamido)ethyl)(methyl)carbamate | 1.24 (G) | 603.2 |
| U16 | tert-Butyl methyl(2-(2-((2-pivaloyl-1,2,3,4-tetrahydroisoquinolin-5-yl)amino)-N-(2-(trifluoromethyl)benzyl)acetamido)ethyl)carbamate | 1.28 (G) | 605.2 |
| U17 | tert-Butyl methyl(2-(2-((2-(3-methylbutanoyl)-1,2,3,4-tetrahydroisoquinolin-5-yl)amino)-N-(2-(trifluoromethyl)benzyl)acetamido)ethyl)carbamate | 1.26 (G) | 605.2 |
| U18 | tert-Butyl (S)-methyl(2-(2-((2-(tetrahydrofuran-3-carbonyl)-1,2,3,4-tetrahydroisoquinolin-5-yl)amino)-N-(2-(trifluoromethyl)benzyl)acetamido)ethyl)carbamate | 1.15 (G) | 619.2 |
| U19 | tert-Butyl (2-(2-((2-(3,3-dimethylbutanoyl)-1,2,3,4-tetrahydroisoquinolin-5-yl)amino)-N-(2-(trifluoromethyl)benzyl)acetamido)ethyl)(methyl)carbamate | 1.3 (G) | 619.3 |
| U21 | Ethyl 5-((2-((2-((tert-butoxycarbonyl)(methyl)amino)ethyl)(2-(trifluoromethyl)benzyl)amino)-2-oxoethyl)amino)-3,4-dihydroisoquinoline-2(1H)-carboxylate | 1.29 (G) | 593.2 |
| U22 | Prop-2-yn-1-yl 5-((2-((2-((tert-butoxycarbonyl)(methyl)amino)ethyl)(2-(trifluoromethyl)benzyl)amino)-2-oxoethyl)amino)-3,4-dihydroisoquinoline-2(1H)-carboxylate | 1.26 (G) | 603.2 |
| U23 | Allyl 5-((2-((2-((tert-butoxycarbonyl)(methyl)amino)ethyl)(2-(trifluoromethyl)benzyl)amino)-2-oxoethyl)amino)-3,4-dihydroisoquinoline-2(1H)-carboxylate | 1.30 (G) | 605.2 |
| U24 | Propyl 5-((2-((2-((tert-butoxycarbonyl)(methyl)amino)ethyl)(2-(trifluoromethyl)benzyl)amino)-2-oxoethyl)amino)-3,4-dihydroisoquinoline-2(1H)-carboxylate | 1.33 (G) | 607.2 |

TABLE 24-continued

Precursors U2-U9/U11-U19/U21-U28/U30-U63

| Precursor | Precursor name | $t_R$ [min] (Method) | MS Data m/z $[M + H]^+$ |
|---|---|---|---|
| U25 | Isopropyl 5-((2-((2-(((tert-butoxycarbonyl)(methyl)amino)ethyl)(2-(trifluoromethyl)benzyl)amino)-2-oxoethyl)amino)-3,4-dihydroisoquinoline-2(1H)-carboxylate | 1.33 (G) | 607.2 |
| U26 | 2-Fluoroethyl 5-((2-((2-(((tert-butoxycarbonyl)(methyl)amino)ethyl)(2-(trifluoromethyl)benzyl)amino)-2-oxoethyl)amino)-3,4-dihydroisoquinoline-2(1H)-carboxylate | 1.24 (G) | 611.2 |
| U27 | Isobutyl 5-((2-((2-(((tert-butoxycarbonyl)(methyl)amino)ethyl)(2-(trifluoromethyl)benzyl)amino)-2-oxoethyl)amino)-3,4-dihydroisoquinoline-2(1H)-carboxylate | 1.37 (G) | 621.2 |
| U28 | Neopentyl 5-((2-((2-(((tert-butoxycarbonyl)(methyl)amino)ethyl)(2-(trifluoromethyl)benzyl)amino)-2-oxoethyl)amino)-3,4-dihydroisoquinoline-2(1H)-carboxylate | 1.40 (G) | 635.3 |
| U30 | tert-Butyl (2-(2-((2-(Isopropylcarbamoyl)-1,2,3,4-tetrahydroisoquinolin-5-yl)amino)-N-(2-(trifluoromethyl)benzyl)acetamido)ethyl)(methyl)carbamate | 1.19 (G) | 606.2 |
| U31 | tert-Butyl (2-(2-((2-(Butylcarbamoyl)-1,2,3,4-tetrahydroisoquinolin-5-yl)amino)-N-(2-(trifluoromethyl)benzyl)acetamido)ethyl)(methyl)carbamate | 1.23 (G) | 620.2 |
| U32 | tert-Butyl (2-(2-((2-(tert-Butylcarbamoyl)-1,2,3,4-tetrahydroisoquinolin-5-yl)amino)-N-(2-(trifluoromethyl)benzyl)acetamido)ethyl)(methyl)carbamate | 1.26 (G) | 620.3 |
| U33 | tert-Butyl (2-(2-((2-(Cyclohexylcarbamoyl)-1,2,3,4-tetrahydroisoquinolin-5-yl)amino)-N-(2-(trifluoromethyl)benzyl)acetamido)ethyl)(methyl)carbamate | 1.27 (G) | 646.0 |
| U34 | tert-Butyl (2-(2-((2-Acetyl-1,2,3,4-tetrahydroisoquinolin-5-yl)amino)-N-((3-(trifluoromethyl)pyridin-2-yl)methyl)acetamido)ethyl)(methyl)carbamate | 1.01 (G) | 564.2 |
| U35 | tert-Butyl methyl(2-(2-((2-propionyl-1,2,3,4-tetrahydroisoquinolin-5-yl)amino)-N-((3-(trifluoromethyl)pyridin-2-yl)methyl)acetamido)ethyl)carbamate | 1.07 (G) | 578.2 |
| U36 | tert-Butyl (2-(2-((2-(cyclopropanecarbonyl)-1,2,3,4-tetrahydroisoquinolin-5-yl)amino)-N-((3-(trifluoromethyl)pyridin-2-yl)methyl)acetamido)ethyl)(methyl)carbamate | 1.04 (G) | 590.4 |
| U37 | tert-Butyl (2-(2-((2-butyryl-1,2,3,4-tetrahydroisoquinolin-5-yl)amino)-N-((3-(trifluoromethyl)pyridin-2-yl)methyl)acetamido)ethyl)(methyl)carbamate | 1.11 (G) | 592.1 |
| U38 | tert-Butyl (2-(2-((2-isobutyryl-1,2,3,4-tetrahydroisoquinolin-5-yl)amino)-N-((3-(trifluoromethyl)pyridin-2-yl)methyl)acetamido)ethyl)(methyl)carbamate | 1.11 (G) | 592.1 |
| U39 | tert-Butyl (2-(2-((2-(2-methoxyacetyl)-1,2,3,4-tetrahydroisoquinolin-5-yl)amino)-N-((3-(trifluoromethyl)pyridin-2-yl)methyl)acetamido)ethyl)(methyl)carbamate | 1.02 (G) | 594.1 |
| U40 | tert-Butyl (2-(2-((2-(cyclobutanecarbonyl)-1,2,3,4-tetrahydroisoquinolin-5-yl)amino)-N-((3-(trifluoromethyl)pyridin-2-yl)methyl)acetamido)ethyl)(methyl)carbamate | 1.09 (G) | 645.1 |
| U41 | tert-Butyl methyl(2-(2-((2-pivaloyl-1,2,3,4-tetrahydroisoquinolin-5-yl)amino)-N-((3-(trifluoromethyl)pyridin-2-yl)methyl)acetamido)ethyl)carbamate | 1.16 (G) | 605.8 |
| U42 | tert-Butyl methyl(2-(2-((2-(3-methylbutanoyl)-1,2,3,4-tetrahydroisoquinolin-5-yl)amino)-N-((3-(trifluoromethyl)pyridin-2-yl)methyl)acetamido)ethyl)carbamate | 1.13 (G) | 606.8 |
| U43 | tert-Butyl methyl(2-(2-((2-(tetrahydrofuran-3-carbonyl)-1,2,3,4-tetrahydroisoquinolin-5-yl)amino)-N-((3-(trifluoromethyl)pyridin-2-yl)methyl)acetamido)ethyl)carbamate | 1.03 (G) | 620.1 |
| U44 | tert-butyl (2-(2-((2-(3,3-dimethylbutanoyl)-1,2,3,4-tetrahydroisoquinolin-5-yl)amino)-N-((3-(trifluoromethyl)pyridin-2-yl)methyl)acetamido)ethyl)(methyl)carbamate | 1.20 (G) | 620.2 |
| U45 | Methyl 5-((2-((2-(((tert-butoxycarbonyl)(methyl)amino)ethyl)((3-(trifluoromethyl)pyridin-2-yl)methyl)amino)-2-oxoethyl)amino)-3,4-dihydroisoquinoline-2(1H)-carboxylate | 1.12 (G) | 580.2 |
| U46 | Ethyl 5-((2-((2-(((tert-butoxycarbonyl)(methyl)amino)ethyl)((3-(trifluoromethyl)pyridin-2-yl)methyl)amino)-2-oxoethyl)amino)-3,4-dihydroisoquinoline-2(1H)-carboxylate | 1.17 (G) | 594.1 |
| U47 | Propyl 5-((2-((2-(((tert-butoxycarbonyl)(methyl)amino)ethyl)((3-(trifluoromethyl)pyridin-2-yl)methyl)amino)-2-oxoethyl)amino)-3,4-dihydroisoquinoline-2(1H)-carboxylate | 1.15 (G) | 604.1 |
| U48 | Allyl 5-((2-((2-(((tert-butoxycarbonyl)(methyl)amino)ethyl)((3-(trifluoromethyl)pyridin-2-yl)methyl)amino)-2-oxoethyl)amino)-3,4-dihydroisoquinoline-2(1H)-carboxylate | 1.20 (G) | 623.1 |
| U49 | Propyl 5-((2-((2-(((tert-butoxycarbonyl)(methyl)amino)ethyl)((3-(trifluoromethyl)pyridin-2-yl)methyl)amino)-2-oxoethyl)amino)-3,4-dihydroisoquinoline-2(1H)-carboxylate | 1.23 (G) | 608.2 |

TABLE 24-continued

Precursors U2-U9/U11-U19/U21-U28/U30-U63

| Precursor | Precursor name | $t_R$ [min] (Method) | MS Data m/z [M + H]$^+$ |
|---|---|---|---|
| U50 | Isopropyl 5-((2-((2-((tert-butoxycarbonyl)(methyl)amino)ethyl)((3-(trifluoromethyl)pyridin-2-yl)methyl)amino)-2-oxoethyl)amino)-3,4-dihydroisoquinoline-2(1H)-carboxylate | 1.21 (G) | 608.1 |
| U51 | 2-Fluoroethyl 5-((2-((2-((tert-butoxycarbonyl)(methyl)amino)ethyl)((3-(trifluoromethyl)pyridin-2-yl)methyl)amino)-2-oxoethyl)amino)-3,4-dihydroisoquinoline-2(1H)-carboxylate | 1.13 (G) | 612.1 |
| U52 | Isobutyl 5-((2-((2-((tert-butoxycarbonyl)(methyl)amino)ethyl)((3-(trifluoromethyl)pyridin-2-yl)methyl)amino)-2-oxoethyl)amino)-3,4-dihydroisoquinoline-2(1H)-carboxylate | 1.27 (G) | 639.2 |
| U53 | 2-Methoxyethyl 5-((2-((2-((tert-butoxycarbonyl)(methyl)amino)ethyl)((3-(trifluoromethyl)pyridin-2-yl)methyl)amino)-2-oxoethyl)amino)-3,4-dihydroisoquinoline-2(1H)-carboxylate | 1.11 (G) | 624.1 |
| U54 | Neopentyl 5-((2-((2-((tert-butoxycarbonyl)(methyl)amino)ethyl)((3-(trifluoromethyl)pyridin-2-yl)methyl)amino)-2-oxoethyl)amino)-3,4-dihydroisoquinoline-2(1H)-carboxylate | 1.27 (G) | n.d. |
| U55 | tert-Butyl (2-(2-((2-(ethylcarbamoyl)-1,2,3,4-tetrahydroisoquinolin-5-yl)amino)-N-((3-(trifluoromethyl)pyridin-2-yl)methyl)acetamido)ethyl)(methyl)carbamate | 1.03 (G) | 593.2 |
| U56 | tert-Butyl (2-(2-((2-(isopropylcarbamoyl)-1,2,3,4-tetrahydroisoquinolin-5-yl)amino)-N-((3-(trifluoromethyl)pyridin-2-yl)methyl)acetamido)ethyl)(methyl)carbamate | 1.06 (G) | 607.2 |
| U57 | tert-Butyl (2-(2-((2-(butylcarbamoyl)-1,2,3,4-tetrahydroisoquinolin-5-yl)amino)-N-((3-(trifluoromethyl)pyridin-2-yl)methyl)acetamido)ethyl)(methyl)carbamate | 1.09 (G) | 621.1 |
| U58 | tert-Butyl (2-(2-((2-(tert-butylcarbamoyl)-1,2,3,4-tetrahydroisoquinolin-5-yl)amino)-N-((3-(trifluoromethyl)pyridin-2-yl)methyl)acetamido)ethyl)(methyl)carbamate | 1.15 (G) | 621.0 |
| U59 | tert-Butyl (2-(2-((2-(cyclohexylcarbamoyl)-1,2,3,4-tetrahydroisoquinolin-5-yl)amino)-N-((3-(trifluoromethyl)pyridin-2-yl)methyl)acetamido)ethyl)(methyl)carbamate | 1.17 (G) | 664.2 |
| U60 | 2-((2-(Cyclopropylmethyl)-1,2,3,4-tetrahydroisoquinolin-5-yl)amino)-N-(2-((4-methoxybenzyl)(2,2,2-trifluoroethyl)amino)ethyl)-N-(2-(trifluoromethyl)benzyl)acetamide | 0.90 (A) | 662.9 |
| U61 | 2-((2-(Cyclopropylmethyl)-1,2,3,4-tetrahydroisoquinolin-5-yl)amino)-N-(2-((4-methoxybenzyl)(2,2,2-trifluoroethyl)amino)ethyl)-N-(2-(trifluoromethyl)benzyl)acetamide | 0.82 (A) | 586.9 |
| U62 | tert-Butyl (2-(N-(2-chlorobenzyl)-2-((2-(cyclopropylmethyl)-1,2,3,4-tetrahydroisoquinolin-5-yl)amino)acetamido)ethyl)(methyl)carbamate | 0.82 (A) | 541.3 |
| U63 | tert-Butyl (2-(N-((3-chloropyridin-2-yl)methyl)-2-((2-(cyclopropylmethyl)-1,2,3,4-tetrahydroisoquinolin-5-yl)amino)acetamido)ethyl)(methyl)carbamate | 0.77 (A) | 542.2 |

Example 180 rac-N-Benzyl-2-(2-cyclopropylmethyl-1,2,3,4-tetrahydro-isoquinolin-5-ylamino)-N-(1-methyl-pyrrolidin-3-yl)-acetamide To a solution of N-benzyl-2-(2-cyclopropylmethyl-1,2,3,4-tetrahydro-isoquinolin-5-ylamino)-N-pyrrolidin-3-yl-acetamide Example 178 (12 mg, 0.0287 mmol) in 0.5 mL MeOH is added one drop of 36.5% formaldehyde soln. in water (20 mg, 0.243 mmol) then NaBH$_4$ (2 mg, 0.0529 mmol) and the resulting soln. is allowed to stir at RT for 1 h. The solvent is removed under reduced pressure, the residue is partitioned between sat. aq. NaHCO$_3$ soln. and DCM. The resulting aq. phase is extracted twice with DCM. The combined organic phase is dried over MgSO$_4$, filtered and the solvent removed under reduced pressure. Purification of the crude residue by prep. HPLC (Method D) yields the title compound as a white solid.

LC-A: $t_R$=0.56 min; [M+H]$^+$=433.1

Example 447

N-[2-(Cyclobutyl-methyl-amino)-ethyl]-2-(2-cyclopropylmethyl-1,2,3,4-tetrahydro-isoquinolin-5-ylamino)-N-(2-trifluoromethyl-benzyl)-acetamide To a solution of the dihydrochloride salt of N-[2-(cyclobutyl-methyl-amino)-ethyl]-2-(2-cyclopropylmethyl-1,2,3,4-tetrahydro-isoquinolin-5-ylamino)-N-(2-trifluoromethyl-benzyl)-acetamide Example 179 (50 mg, 0.089 mmol) in 1 mL MeOH is added cyclobutanone (31 mg, 0.443 mmol), ZnCl$_2$ (24.1 mg, 0.177 mmol) and NaBH$_3$CN (19.5 mg, 0.31 mmol). The resulting yellow mixture is allowed to stir at RT overnight. Water is added and the resulting organic phase is extracted three times with DCM. The combined organic phase is washed with sat. aq. NaHCO$_3$ soln. dried over MgSO$_4$, filtered and the solvent removed under reduced pressure. Purification of the crude residue by prep. HPLC (Method D) yields the title compound as a yellow oil.

LC-A: $t_R$=0.63 min; [M+H]$^+$=529.1

Examples 448-453 listed in Table 25 are prepared applying the method described for Example 447 using the corresponding Example compound and ketone respectively.

TABLE 25

Examples 448-453

| Example No | Example name | $t_R$ [min] (LC-F) | MS Data m/z [M + H]+ |
|---|---|---|---|
| 448 | rac-2-(2-Cyclopropylmethyl-1,2,3,4-tetrahydro-isoquinolin-5-ylamino)-N-{2-[methyl-(tetrahydro-furan-3-yl)-amino]-ethyl}-N-(2-trifluoromethyl-benzyl)-acetamide | 0.52 | 545.4 |
| 449 | 2-(2-Cyclopropylmethyl-1,2,3,4-tetrahydro-isoquinolin-5-ylamino)-N-[2-(isopropyl-methyl-amino)-ethyl]-N-(2-trifluoromethyl-benzyl)-acetamide | 0.52 | 517.4 |
| 450 | N-[2-(Cyclopropylmethyl-methyl-amino)-ethyl]-2-(2-cyclopropylmethyl-1,2,3,4-tetrahydro-isoquinolin-5-ylamino)-N-(2-trifluoromethyl-benzyl)-acetamide | 0.54 | 529.4 |
| 451 | N-[2-(Cyclopentyl-methyl-amino)-ethyl]-2-(2-cyclopropylmethyl-1,2,3,4-tetrahydro-isoquinolin-5-ylamino)-N-(2-trifluoromethyl-benzyl)-acetamide | 0.55 | 543.4 |
| 452 | rac-2-(2-Cyclopropylmethyl-1,2,3,4-tetrahydro-isoquinolin-5-ylamino)-N-{2-[(2-fluoro-1-methyl-ethyl)-methyl-amino]-ethyl}-N-(2-trifluoromethyl-benzyl)-acetamide | 0.53 | 535.4 |
| 453 | 2-(2-Cyclopropylmethyl-1,2,3,4-tetrahydro-isoquinolin-5-ylamino)-N-{2-[ethyl-(3-methyl-oxetan-3-ylmethyl)-amino]-ethyl}-N-(2-trifluoromethyl-benzyl)-acetamide | 0.55 | 573.4 |

Example 181

8-({[Benzyl-(2-dimethylamino-ethyl)-carbamoyl]-methyl}-amino)-3,4-dihydro-1H-isoquinoline-2-carboxylic acid tert-butyl ester To a solution of 8-(carboxymethyl-amino)-3,4-dihydro-1H-isoquinoline-2-carboxylic acid tert-butyl ester Precursor V1 (884 mg, 2.42 mmol) in 20 mL DCM are added N-benzyl-N',N'-dimethylethane-1,2-diamine Amine 7 (432 mg, 2.42 mmol), HATU (1106 mg, 2.91 mmol) and DIPEA (783 mg, 6.06 mmol). The resulting brown suspension is allowed to stir at RT for 1 h. The organic phase is washed with water, sat. aq. NaHCO$_3$ and brine successively then dried over MgSO$_4$, filtered and evaporated under reduced pressure. Flash-chromatography on silica-gel (Eluent: gradient of DCM/MeOH 100:0 to 80:20) yields the title compound as a brown oil.

LC-B: $t_R$=0.73 min; [M+H]f=467.08

Examples 182-184/455-543 listed in Table 26 are prepared applying the method described for Example 181 using the corresponding Precursor and Amine respectively.

TABLE 26

Examples 182-184/455-543

| Example No | Example name | $t_R$ [min] (LC-C) | MS Data m/z [M + H]+ |
|---|---|---|---|
| 182 | N-Benzyl-N-(2-dimethylamino-ethyl)-2-(2-methyl-1,2,3,4-tetrahydro-isoquinolin-8-ylamino)-acetamide | 0.53 | 381.4 |
| 183 | N-Benzyl-N-(3-methyl-butyl)-2-(2-methyl-1,2,3,4-tetrahydro-isoquinolin-8-ylamino)-acetamide | 0.95 | 380.4 |
| 184 | N-Benzyl-N-(2-dimethylamino-ethyl)-2-(2-methyl-1-oxo-1,2,3,4-tetrahydro-isoquinolin-8-ylamino)-acetamide | 0.78 | 395.4 |

| Example No | Example name | $t_R$ [min] (LC-F) unless indicated otherwise | MS Data m/z [M + H]+ |
|---|---|---|---|
| 455 | N-(3-Chloro-pyridin-2-ylmethyl)-2-(2-cyclobutyl-1,2,3,4-tetrahydro-isoquinolin-8-ylamino)-N-(2-dimethylamino-ethyl)-acetamide | 0.39 | 456.3 |
| 456 | N-(3-Bromo-pyridin-2-ylmethyl)-2-(2-cyclobutyl-1,2,3,4-tetrahydro-isoquinolin-8-ylamino)-N-(2-dimethylamino-ethyl)-acetamide | 0.4 | 500.3 |
| 457 | N-(3-Chloro-pyridin-2-ylmethyl)-2-(2-cyclobutyl-1,2,3,4-tetrahydro-isoquinolin-8-ylamino)-N-(2-hydroxy-2-methyl-propyl)-acetamide | 0.64 | 457.3 |
| 458 | N-(3-Bromo-pyridin-2-ylmethyl)-2-(2-cyclobutyl-1,2,3,4-tetrahydro-isoquinolin-8-ylamino)-N-(2-hydroxy-2-methyl-propyl)-acetamide | 0.65 | 501.2 |
| 459 | rac-N-(3-Chloro-pyridin-2-ylmethyl)-N-(2-dimethylamino-ethyl)-2-[2-((1R*,2R*)-2-fluoro-cyclopropanecarbonyl)-1,2,3,4-tetrahydro-isoquinolin-8-ylamino]-acetamide | 0.64 | 488.3 |
| 460 | rac-N-(3-Bromo-pyridin-2-ylmethyl)-N-(2-dimethylamino-ethyl)-2-[2-((1R*,2R*)-2-fluoro-cyclopropanecarbonyl)-1,2,3,4-tetrahydro-isoquinolin-8-ylamino]-acetamide | 0.66 | 532.2 |
| 461 | rac-N-(3-Bromo-pyridin-2-ylmethyl)-2-[2-((1R*,2R*)-2-fluoro-cyclopropanecarbonyl)-1,2,3,4-tetrahydro-isoquinolin-8-ylamino]-N-(2-hydroxy-2-methyl-propyl)-acetamide | 1.03 | 533.2 |
| 463 | N-[2-(Allyl-methyl-amino)-ethyl]-2-(2-allyl-1,2,3,4-tetrahydro-isoquinolin-8-ylamino)-N-(2-trifluoromethyl-benzyl)-acetamide | 0.51 | 501.3 |
| 464 | 2-(2-Allyl-1,2,3,4-tetrahydro-isoquinolin-8-ylamino)-N-(2-dimethylamino-ethyl)-N-(2-trifluoromethoxy-benzyl)-acetamide | 0.5 | 491.3 |

TABLE 26-continued

Examples 182-184/455-543

| | | | |
|---|---|---|---|
| 465 | 2-(2-Allyl-1,2,3,4-tetrahydro-isoquinolin-8-ylamino)-N-{2-[(2-fluoro-ethyl)-methyl-amino]-ethyl}-N-(2-trifluoromethyl-benzyl)-acetamide | 0.5 | 507.3 |
| 466 | 2-(2-Allyl-1,2,3,4-tetrahydro-isoquinolin-8-ylamino)-N-(2-dimethylamino-ethyl)-N-(2-trifluoromethyl-benzyl)-acetamide | 0.48 | 475.4 |
| 467 | N-[2-(Allyl-methyl-amino)-ethyl]-3-(2-allyl-1,2,3,4-tetrahydro-isoquinolin-8-yl)-N-(2-trifluoromethyl-benzyl)-propionamide | 0.51 | 500.3 |
| 468 | 3-(2-Allyl-1,2,3,4-tetrahydro-isoquinolin-8-yl)-N-(2-dimethylamino-ethyl)-N-(2-trifluoromethyl-benzyl)-propionamide | 0.48 | 474.4 |
| 475 | 2-(2-Cyclopropylmethyl-1,2,3,4-tetrahydro-isoquinolin-8-ylamino)-N-(2-dimethylamino-ethyl)-N-(2-trifluoromethyl-benzyl)-acetamide | 0.49 | 489.3 |
| 476 | N-[2-(Cyclopropyl-methyl-amino)-ethyl]-2-(2-cyclopropylmethyl-1,2,3,4-tetrahydro-isoquinolin-8-ylamino)-N-(2-trifluoromethyl-benzyl)-acetamide | 0.54 | 515.4 |
| 471 | 2-(2-Cyclopropylmethyl-1,2,3,4-tetrahydro-isoquinolin-8-ylamino)-N-(2-dimethylamino-ethyl)-N-(3-trifluoromethoxy-benzyl)-acetamide | 0.53 | 505.4 |
| 472 | 2-(2-Cyclopropylmethyl-1,2,3,4-tetrahydro-isoquinolin-8-ylamino)-N-(2-dimethylamino-ethyl)-N-(2-trifluoromethoxy-benzyl)-acetamide | 0.52 | 505.4 |
| 473 | 2-(2-Cyclopropylmethyl-1,2,3,4-tetrahydro-isoquinolin-8-ylamino)-N-(2-dimethylamino-ethyl)-N-(4-trifluoromethoxy-benzyl)-acetamide | 0.54 | 505.3 |
| 474 | 2-(2-Cyclopropylmethyl-1,2,3,4-tetrahydro-isoquinolin-8-ylamino)-N-[2-(4,4-difluoro-piperidin-1-yl)-ethyl]-N-(2-trifluoromethyl-benzyl)-acetamide | 0.65 | 565.4 |
| 475 | 2-(2-Cyclopropylmethyl-1,2,3,4-tetrahydro-isoquinolin-8-ylamino)-N-{2-[methyl-(2,2,2-trifluoro-ethyl)-amino]-ethyl}-N-(2-trifluoromethyl-benzyl)-acetamide | 0.92 | 557.3 |
| 476 | 2-(2-Cyclopropylmethyl-1,2,3,4-tetrahydro-isoquinolin-8-ylamino)-N-[2-(4,4-difluoro-piperidin-1-yl)-ethyl]-N-(3-trifluoromethyl-pyridin-2-ylmethyl)-acetamide | 0.52 | 566.4 |
| 477 | 2-(2-Cyclopropylmethyl-1,2,3,4-tetrahydro-isoquinolin-8-ylamino)-N-{2-[methyl-(2,2,2-trifluoro-ethyl)-amino]-ethyl}-N-(3-trifluoromethyl-pyridin-2-ylmethyl)-acetamide | 0.86 | 558.3 |
| 478 | 2-(2-Cyclopropylmethyl-1,2,3,4-tetrahydro-isoquinolin-8-ylamino)-N-[2-(3,3-difluoro-piperidin-1-yl)-ethyl]-N-(2-trifluoromethyl-benzyl)-acetamide | 0.81 | 565.3 |
| 479 | 2-(2-Cyclopropylmethyl-1,2,3,4-tetrahydro-isoquinolin-8-ylamino)-N-[2-(3,3-difluoro-pyrrolidin-1-yl)-ethyl]-N-(2-trifluoromethyl-benzyl)-acetamide | 0.78 | 551.3 |
| 480 | 2-(2-Cyclopropylmethyl-1,2,3,4-tetrahydro-isoquinolin-8-ylamino)-N-[2-(3,3-difluoro-piperidin-1-yl)-ethyl]-N-(3-trifluoromethyl-pyridin-2-ylmethyl)-acetamide | 0.62 | 566.4 |
| 481 | 2-(2-Cyclopropylmethyl-1,2,3,4-tetrahydro-isoquinolin-8-ylamino)-N-[2-(3,3-difluoro-pyrrolidin-1-yl)-ethyl]-N-(3-trifluoromethyl-pyridin-2-ylmethyl)-acetamide | 0.61 | 552.3 |
| 482 | 2-(2-Cyclopropylmethyl-1,2,3,4-tetrahydro-isoquinolin-8-ylamino)-N-[2-(3,3-difluoro-azetidin-1-yl)-2-oxo-ethyl]-N-(2-trifluoromethyl-benzyl)-acetamide | 0.78 | 551.3 |
| 483 | 2-(2-Cyclopropylmethyl-1,2,3,4-tetrahydro-isoquinolin-8-ylamino)-N-[2-(3,3-difluoro-azetidin-1-yl)-2-oxo-ethyl]-N-(3-trifluoromethyl-pyridin-2-ylmethyl)-acetamide | 0.69 | 552.3 |
| 484 | 2-(2-Cyclopropylmethyl-1,2,3,4-tetrahydro-isoquinolin-8-ylamino)-N-[2-(3,3-difluoro-azetidin-1-yl)-ethyl]-N-(2-trifluoromethyl-benzyl)-acetamide | 0.75 | 537.3 |
| 485 | N-(3-Chloro-pyridin-2-ylmethyl)-2-(2-cyclopropylmethyl-1,2,3,4-tetrahydro-isoquinolin-8-ylamino)-N-(2-dimethylamino-ethyl)-acetamide | 0.4 | 456.3 |
| 486 | N-(3-Bromo-pyridin-2-ylmethyl)-2-(2-cyclopropylmethyl-1,2,3,4-tetrahydro-isoquinolin-8-ylamino)-N-(2-dimethylamino-ethyl)-acetamide | 0.41 | 500.3 |
| 487 | N-(3-Chloro-pyridin-2-ylmethyl)-2-(2-cyclopropylmethyl-1,2,3,4-tetrahydro-isoquinolin-8-ylamino)-N-(2-hydroxy-2-methyl-propyl)-acetamide | 0.64 | 457.3 |
| 488 | N-(3-Bromo-pyridin-2-ylmethyl)-2-(2-cyclopropylmethyl-1,2,3,4-tetrahydro-isoquinolin-8-ylamino)-N-(2-hydroxy-2-methyl-propyl)-acetamide | 0.66 | 501.2 |
| 489 | 2-(2-Ethyl-1,2,3,4-tetrahydro-isoquinolin-8-ylamino)-N-(2-pyrrolidin-1-yl-ethyl)-N-(2-trifluoromethyl-benzyl)-acetamide | 0.47 | 489.3 |
| 490 | N-Benzyl-N-(2-diethylamino-ethyl)-2-(2-ethyl-1,2,3,4-tetrahydro-isoquinolin-8-ylamino)-acetamide | 1.73 (LC-H) | 423.1 |
| 491 | N-(2-Dimethylamino-ethyl)-2-(2-ethyl-1,2,3,4-tetrahydro-isoquinolin-8-ylamino)-N-(2-fluoro-benzyl)-acetamide | 0.39 | 413.3 |
| 492 | 2-(2-Ethyl-1,2,3,4-tetrahydro-isoquinolin-8-ylamino)-N-(1-methyl-piperidin-4-yl)-N-(2-trifluoromethyl-benzyl)-acetamide | 0.46 | 489.4 |
| 493 | (2-{Benzyl-[2-(2-ethyl-1,2,3,4-tetrahydro-isoquinolin-8-ylamino)-acetyl]-amino}-ethyl)-methyl-carbamic acid tert-butyl ester | 0.82 | 481.4 |

TABLE 26-continued

Examples 182-184/455-543

| | | | |
|---|---|---|---|
| 494 | N-(2-Dimethylamino-ethyl)-2-(2-ethyl-1,2,3,4-tetrahydro-isoquinolin-8-ylamino)-N-(2-methyl-benzyl)-acetamide | 0.42 | 409.3 |
| 495 | N-(2-Dimethylamino-ethyl)-2-(2-ethyl-1,2,3,4-tetrahydro-isoquinolin-8-ylamino)-N-(3-methyl-benzyl)-acetamide | 0.43 | 409.4 |
| 496 | N-(2-Dimethylamino-ethyl)-2-(2-ethyl-1,2,3,4-tetrahydro-isoquinolin-8-ylamino)-N-(4-methyl-benzyl)-acetamide | 0.43 | 409.4 |
| 497 | N-(2-Dimethylamino-ethyl)-2-(2-ethyl-1,2,3,4-tetrahydro-isoquinolin-8-ylamino)-N-(2-methoxy-benzyl)-acetamide | 0.42 | 425.4 |
| 498 | N-(2-Dimethylamino-ethyl)-2-(2-ethyl-1,2,3,4-tetrahydro-isoquinolin-8-ylamino)-N-(3-methoxy-benzyl)-acetamide | 0.4 | 425.4 |
| 499 | N-(2-Dimethylamino-ethyl)-2-(2-ethyl-1,2,3,4-tetrahydro-isoquinolin-8-ylamino)-N-(4-methoxy-benzyl)-acetamide | 0.4 | 425.4 |
| 500 | N-(2-Chloro-benzyl)-N-(2-dimethylamino-ethyl)-2-(2-ethyl-1,2,3,4-tetrahydro-isoquinolin-8-ylamino)-acetamide | 0.43 | 429.3 |
| 501 | N-(3-Chloro-benzyl)-N-(2-dimethylamino-ethyl)-2-(2-ethyl-1,2,3,4-tetrahydro-isoquinolin-8-ylamino)-acetamide | 0.44 | 429.3 |
| 502 | N-(4-Chloro-benzyl)-N-(2-dimethylamino-ethyl)-2-(2-ethyl-1,2,3,4-tetrahydro-isoquinolin-8-ylamino)-acetamide | 0.44 | 429.3 |
| 503 | N-(2-Dimethylamino-ethyl)-2-(2-ethyl-1,2,3,4-tetrahydro-isoquinolin-8-ylamino)-N-(3-fluoro-benzyl)-acetamide | 0.40 | 413.3 |
| 504 | N-(2-Dimethylamino-ethyl)-2-(2-ethyl-1,2,3,4-tetrahydro-isoquinolin-8-ylamino)-N-(4-fluoro-benzyl)-acetamide | 0.40 | 413.3 |
| 505 | N-(2-Dimethylamino-ethyl)-2-(2-ethyl-1,2,3,4-tetrahydro-isoquinolin-8-ylamino)-N-(3-trifluoromethyl-benzyl)-acetamide | 0.47 | 463.3 |
| 506 | N-(2-Dimethylamino-ethyl)-2-(2-ethyl-1,2,3,4-tetrahydro-isoquinolin-8-ylamino)-N-(4-trifluoromethyl-benzyl)-acetamide | 0.48 | 463.3 |
| 507 | N-Benzyl-N-(3-dimethylamino-propyl)-2-(2-ethyl-1,2,3,4-tetrahydro-isoquinolin-8-ylamino)-acetamide | 0.40 | 409.4 |
| 508 | rac-N-Benzyl-2-(2-ethyl-1,2,3,4-tetrahydro-isoquinolin-8-ylamino)-N-[2-(1-methyl-pyrrolidin-2-yl)-ethyl]-acetamide | 0.42 | 435.4 |
| 509 | N-Benzyl-2-(2-ethyl-1,2,3,4-tetrahydro-isoquinolin-8-ylamino)-N-(2-pyrrolidin-1-yl-ethyl)-acetamide | 0.40 | 421.3 |
| 510 | 2-(2-Ethyl-1,2,3,4-tetrahydro-isoquinolin-8-ylamino)-N-(2-morpholin-4-yl-ethyl)-N-(2-trifluoromethyl-benzyl)-acetamide | 0.48 | 505.3 |
| 511 | N-(3-Chloro-pyridin-2-ylmethyl)-N-(2-dimethylamino-ethyl)-2-(2-ethyl-1,2,3,4-tetrahydro-isoquinolin-8-ylamino)-acetamide | 0.36 | 430.3 |
| 512 | rac-N-Benzyl-2-(2-ethyl-1,2,3,4-tetrahydro-isoquinolin-8-ylamino)-N-(1-methyl-pyrrolidin-3-yl)-acetamide | 0.39 | 407.3 |
| 513 | 2-(2-Ethyl-1,2,3,4-tetrahydro-isoquinolin-8-ylamino)-N-(3-methyl-butyl)-N-(2-trifluoromethyl-benzyl)-acetamide | 0.94 | 462.4 |
| 514 | N-(2-Diethylamino-ethyl)-2-(2-ethyl-1,2,3,4-tetrahydro-isoquinolin-8-ylamino)-N-(2-trifluoromethyl-benzyl)-acetamide | 0.48 | 491.4 |
| 515 | {2-[[2-(2-Ethyl-1,2,3,4-tetrahydro-isoquinolin-8-ylamino)-acetyl]-(2-trifluoromethyl-benzyl)-amino]-ethyl}-methyl-carbamic acid tert-butyl ester | 0.90 | 549.4 |
| 516 | N-(2-Cyano-ethyl)-2-(2-ethyl-1,2,3,4-tetrahydro-isoquinolin-8-ylamino)-N-(2-trifluoromethyl-benzyl)-acetamide | 0.71 | 445.3 |
| 517 | 2-(2-Ethyl-1,2,3,4-tetrahydro-isoquinolin-8-ylamino)-N-[2-(2-oxo-pyrrolidin-1-yl)-ethyl]-N-(2-trifluoromethyl-benzyl)-acetamide | 0.7 | 503.3 |
| 518 | rac-2-(2-Ethyl-1,2,3,4-tetrahydro-isoquinolin-8-ylamino)-N-(1-methyl-piperidin-3-yl)-N-(2-trifluoromethyl-benzyl)-acetamide | 0.49 | 489.3 |
| 519 | 2-(2-Ethyl-1,2,3,4-tetrahydro-isoquinolin-8-ylamino)-N-(tetrahydro-pyran-4-yl)-N-(2-trifluoromethyl-benzyl)-acetamide | 0.75 | 476.3 |
| 520 | 2-(2-Ethyl-1,2,3,4-tetrahydro-isoquinolin-8-ylamino)-N-(4-methyl-thiazol-2-ylmethyl)-N-(2-trifluoromethyl-benzyl)-acetamide | 0.82 | 503.3 |
| 521 | rac-N-[1-(1-Ethyl-1H-pyrazol-3-yl)-ethyl]-2-(2-ethyl-1,2,3,4-tetrahydro-isoquinolin-8-ylamino)-N-(2-trifluoromethyl-benzyl)-acetamide | 0.85 | 514.4 |
| 522 | rac-N-(2-Dimethylamino-ethyl)-2-(2-ethyl-1,2,3,4-tetrahydro-isoquinolin-8-ylamino)-N-[1-(2-trifluoromethyl-phenyl)-ethyl]-acetamide | 0.49 | 477.4 |
| 523 | N-(2-Dimethylamino-ethyl)-2-(2-ethyl-1,2,3,4-tetrahydro-isoquinolin-8-ylamino)-N-(4-fluoro-2-trifluoromethyl-benzyl)-acetamide | 0.48 | 481.3 |
| 524 | N-(2,6-Difluoro-benzyl)-N-(2-dimethylamino-ethyl)-2-(2-ethyl-1,2,3,4-tetrahydro-isoquinolin-8-ylamino)-acetamide | 0.39 | 431.4 |
| 525 | N-(2-Dimethylamino-ethyl)-2-(2-ethyl-1,2,3,4-tetrahydro-isoquinolin-8-ylamino)-N-(3-methyl-pyridin-2-ylmethyl)-acetamide | 0.35 | 410.4 |
| 526 | N-(2-Dimethylamino-ethyl)-2-(2-ethyl-1,2,3,4-tetrahydro-isoquinolin-8-ylamino)-N-(6-methyl-pyridin-2-ylmethyl)-acetamide | 0.35 | 410.4 |
| 527 | N-(2-Dimethylamino-ethyl)-2-(2-ethyl-1,2,3,4-tetrahydro-isoquinolin-8-ylamino)-N-(5-methyl-pyridin-2-ylmethyl)-acetamide | 0.35 | 410.4 |
| 528 | N-(2-Dimethylamino-ethyl)-2-(2-ethyl-1,2,3,4-tetrahydro-isoquinolin-8-ylamino)-N-(3-fluoro-pyridin-2-ylmethyl)-acetamide | 0.33 | 414.3 |
| 529 | N-(2-Dimethylamino-ethyl)-2-(2-ethyl-1,2,3,4-tetrahydro-isoquinolin-8-ylamino)-N-(5-fluoro-pyridin-2-ylmethyl)-acetamide | 0.34 | 414.3 |
| 530 | N-(5-Chloro-pyridin-2-ylmethyl)-N-(2-dimethylamino-ethyl)-2-(2-ethyl-1,2,3,4-tetrahydro-isoquinolin-8-ylamino)-acetamide | 0.38 | 430.3 |

TABLE 26-continued

Examples 182-184/455-543

| | | | |
|---|---|---|---|
| 531 | N-(2-Dimethylamino-ethyl)-2-(2-ethyl-1,2,3,4-tetrahydro-isoquinolin-8-ylamino)-N-(3-trifluoromethyl-pyridin-2-ylmethyl)-acetamide | 0.39 | 464.3 |
| 532 | N-(2-Dimethylamino-ethyl)-2-(2-ethyl-1,2,3,4-tetrahydro-isoquinolin-8-ylamino)-N-(6-trifluoromethyl-pyridin-2-ylmethyl)-acetamide | 0.42 | 464.3 |
| 533 | N-(5-Chloro-pyridin-3-ylmethyl)-N-(2-dimethylamino-ethyl)-2-(2-ethyl-1,2,3,4-tetrahydro-isoquinolin-8-ylamino)-acetamide | 0.35 | 430.3 |
| 534 | N-(2-Dimethylamino-ethyl)-N-(2-dimethylamino-pyrimidin-5-ylmethyl)-2-(2-ethyl-1,2,3,4-tetrahydro-isoquinolin-8-ylamino)-acetamide | 0.56 (LC-F1) | 440.4 |
| 535 | N-(2-Dimethylamino-ethyl)-2-(2-ethyl-1,2,3,4-tetrahydro-isoquinolin-8-ylamino)-N-(5-methyl-isoxazol-3-ylmethyl)-acetamide | 0.41 (LC-F1) | 400.3 |
| 536 | N-(2-Dimethylamino-ethyl)-2-(2-ethyl-1,2,3,4-tetrahydro-isoquinolin-8-ylamino)-N-(4-methyl-thiazol-2-ylmethyl)-acetamide | 0.35 | 416.3 |
| 537 | N-(2-Dimethylamino-ethyl)-2-(2-ethyl-1,2,3,4-tetrahydro-isoquinolin-8-ylamino)-N-(2-o-tolyl-ethyl)-acetamide | 0.46 | 423.4 |
| 538 | N-(2-Dimethylamino-ethyl)-2-(2-ethyl-1,2,3,4-tetrahydro-isoquinolin-8-ylamino)-N-[2-(2-trifluoromethyl-phenyl)-ethyl]-acetamide | 0.5 | 477.4 |
| 539 | N-(2-Dimethylamino-ethyl)-2-(2-ethyl-1,2,3,4-tetrahydro-isoquinolin-8-ylamino)-N-[2-(3-trifluoromethyl-phenyl)-ethyl]-acetamide | 0.51 | 477.4 |
| 540 | N-(2-Dimethylamino-ethyl)-2-(2-ethyl-1,2,3,4-tetrahydro-isoquinolin-8-ylamino)-N-pyridin-2-ylmethyl-acetamide | 0.65 | 396.3 |
| 541 | N-(2-Dimethylamino-ethyl)-2-(2-ethyl-1,2,3,4-tetrahydro-isoquinolin-8-ylamino)-N-thiazol-2-ylmethyl-acetamide | 0.63 | 402.3 |
| 542 | N-(2-Dimethylamino-ethyl)-2-(2-ethyl-1,2,3,4-tetrahydro-isoquinolin-8-ylamino)-N-phenethyl-acetamide | 0.42 | 409.4 |
| 543 | N-(2-Dimethylamino-ethyl)-2-(2-ethyl-3-oxo-1,2,3,4-tetrahydro-isoquinolin-8-ylamino)-N-(2-trifluoromethyl-benzyl)-acetamide | 0.66 | 477.3 |

Precursor V1

8-(Carboxymethyl-amino)-3,4-dihydro-1H-isoquinoline-2-carboxylic acid tert-butyl ester To a solution of 8-(ethoxycarbonylmethyl-amino)-3,4-dihydro-1H-isoquinoline-2-carboxylic acid tert-butyl ester Precursor W1 (2.24 g, 5.02 mmol) in 60 mL THF is added 10.8 mL (10.8 mmol) 1M aq. LiOH soln. The resulting mixture is allowed to stir at RT for 1 h. The organic solvent is removed under reduced pressure and the resulting aq. mixture is diluted with water. The resulting aq. phase is extracted twice with DCM. Then the aq. phase is made acidic (pH=3) via addition of 1N aq. HCl soln. and the resulting aq. phase is extracted twice with DCM. The combined organic phase is washed with brine, dried over MgSO₄, filtered then the solvent is removed under reduced pressure to yield 825 mg (54%) of the title compound which is used as such in the next step.

LC-B: $t_R$=0.80 min; [M+H]⁺=307.12

Precursor V2'

(2-Methyl-1,2,3,4-tetrahydro-isoquinolin-8-ylamino)-acetic acid hydrochloride is made according to the Method described for the synthesis of Precursor B3'. In this particular case, 1 equivalent LiOH is used and the crude HCl salt of Precursor V2' is obtained by direct addition of an excess 1M aq. HCl soln. the reaction mixture and evaporating the solution to dryness then drying the crude residue under HV. In this case a mixture of the hydrochloride salt of Precursor V2' with 1 equivalent LiCl is obtained.

LC-B: $t_R$=0.36 min; [M+H]⁺=221.2

Precursor V4' (2-Cyclobutyl-1,2,3,4-tetrahydro-isoquinolin-5-ylamino)-acetic acid hydrochloride, LC-A: $t_R$=0.50 min; [M+H]⁺=261.4, ¹H-NMR (400 MHz, d₆-DMSO) δ: 6.92 (dd, J₁=7.9 Hz, J₂=7.5 Hz, 1H), 6.33 (d, J=7.5 Hz, 1H), 6.20 (d, J=7.9 Hz, 1H), 4.69 (m, 1H), 3.24 (d, J=3.6 Hz, 2H), 3.17 (s, 2H), 2.94 (t, J=7.4 Hz, 1H), 2.71 (t, J=5.4 Hz, 2H), 2.50 (m, 2H), 2.10 (m, 2H), 1.88 (m, 2H), 1.69 (m, 2H), Precursor V5'(2-(2-cis-fluorocyclopropane-1-carbonyl)-1,2,3,4-tetrahydroisoquinolin-5-yl)amino acetic acid hydrochloride, LC-A: $t_R$=0.65 min; [M+H]⁺=293.4 and Precursor V9'(2-ethyl-3-oxo-1,2,3,4-tetrahydro-isoquinolin-8-ylamino)-acetic acid, LC-A: $t_R$=0.58 min; [M+H]⁺=249.1 are prepared applying the methods described for the synthesis of Precursor V2 from Precursor W2 using Precursor W4, Precursor W5 and Precursor W9 respectively.

Precursor V3

2-((2-Methyl-1-oxo-1,2,3,4-tetrahydroisoquinolin-8-yl)amino)acetic acid a) 8-Amino-2-methyl-3,4-dihydro-2H-isoquinolin-1-one A solution of 2-methyl-8-nitro-3,4-dihydro-2H-isoquinolin-1-one hydrochloride [Synthesis 2007, (7), 981-983] in 6 mL EtOAc and 0.6 mL EtOH is submitted to hydrogenation conditions in an H-Cube apparatus with Pd/C cartridge (5% Pd, 30° C., full H₂ mode, 1 ml/min). Evaporation of the solvent under reduced pressure yields 61 mg (100%) of the sub-title compound as a light yellow solid.

LC-B: $t_R$=0.45 min; [M+H]⁺=177.3 b) 8-Amino-2-methyl-3,4-dihydro-2H-isoquinolin-1-one 61 mg (0.346 mmol) is reacted in the same conditions as for the synthesis of Precursor B24 to yield 51 mg (63%) of the title compound as yellow solid.

LC-B: $t_R$=0.60 min; [M+H]⁺=234.9; ¹H-NMR (CDCl₃) δ: 7.23 (t, J=7.8 Hz, 1H), 6.46 (d, J=7.3 Hz, 1H), 6.42 (d, J=8.5 Hz, 1H), 4.02 (s, 2H), 3.52 (t, J=6.6 Hz, 2H), 3.14 (s, 3H), 2.93 (t, J=6.6 Hz, 2H)

Precursor V6'

(2-Allyl-1,2,3,4-tetrahydro-isoquinolin-8-ylamino)-acetic acid hydrochloride To a solution of N-(2-allyl-1,2,3,4-tetrahydroisoquinolin-8-yl)-N-(2,2,2-trifluoroacetyl)aminoacetic acid ethyl ester Precursor W6 (1.15 g, 2.77 mmol) in 10 mL THF is added a soln. of LiOH (128 mg, 1.94 mmol) in 4 mL water. The resulting mixture is allowed to stir at RT for 4 h. Then LiOH (47 mg, 1.11 mmol) dissolved in 1 mL water is added again. The resulting mixture is allowed to stir at RT for 1 h. Then LiOH (58 mg, 1.39 mmol) dissolved in 1 mL water is added again. The resulting mixture is allowed to stir at RT overnight. Then LiOH (82 mg, 1.94 mmol) dissolved in 1 mL water is added again. The resulting mixture is allowed to stir at RT for 2 h. Then 2M HCl aq. soln. is added (4 mL, 8.03 mmol) and the reaction mixture is evaporated until dryness. This yield the title compound as a mixture with excess LiCl as a white solid. LC-A: $t_R$=0.50 min; [M+H]$^+$=264.1

Precursor V7'(2-Cyclopropylmethyl-1,2,3,4-tetrahydro-isoquinolin-8-ylamino)-acetic acid hydrochloride LC-A: $t_R$=0.50 min; [M+H]$^+$=261.2, and Precursor V8'(2-Ethyl-1,2,3,4-tetrahydro-isoquinolin-8-ylamino)-acetic acid hydrochloride, LC-A: $t_R$=0.45 min; [M+H]$^+$=235.2 are prepared applying the methods described for the synthesis of Precursor V6 from Precursor W6 using Precursor W7 and Precursor W8 respectively.

Precursor W1

8-(Ethoxycarbonylmethyl-amino)-3,4-dihydro-1H-isoquinoline-2-carboxylic acid tert-butyl ester a) 2-(Isoquinolin-8-ylamino)acetic acid ethyl ester To a round bottomed flask containing 8-bromoisoquinoline (3 g, 14.4 mmol) are added $Cs_2CO_3$ (13.2 g, 40.4 mmol), glycine ethyl ester hydrochloride (2.21 g, 15.9 mmol), BINAP (449 mg, 0.72 mmol) and $Pd_2(dba)_3$ (0.397 g, 0.433 mmol) followed by 50 mL toluene. The resulting brown suspension is allowed to stir at 80° C. for 2 h, at 50° C. overnight then at 110° C. for 9 h.

After cooling the suspension is filtered over Celite. The celite cake is rinsed three times with EtOAc. The combined organic phase is washed with brine, dried over $Na_2SO_4$ and filtered. Evaporation of the solvents in vacuo yields 4.64 g of a brown oil. Flash-chromatography on silica-gel (Eluent: gradient of heptane/EtOAc 90:10 to 0:100) yields 2.33 g (70%) of the sub-title compound as yellow solid.

LC-B: $t_R$=0.47 min; [M+H]$^+$=231.2; $^1$H-NMR (CDCl$_3$) δ: 9.41 (s, 1H), 8.52 (d, J=5.7 Hz, 1H), 7.58 (d, J=5.7 Hz, 1H), 7.53 (t, J=7.9 Hz, 1H), 7.20 (d, J=8.2 Hz, 1H), 6.54 (d, J=7.7 Hz, 1H), 5.49 (s, 1H), 4.34 (q, J=7.1 Hz, 2H), 4.09 (d, J=4.9 Hz, 2H), 1.36 (t, J=7.1 Hz, 3H)

b) (1,2,3,4-Tetrahydro-isoquinolin-8-ylamino)-acetic acid ethyl ester

To a solution of 2-(isoquinolin-8-ylamino)acetic acid ethyl ester (2.3 g, 9.89 mmol) in 200 mL AcOH purged under Ar atmosphere is added PtO$_2$ (606 mg, 2.67 mmol). The flask is put under an atmosphere of H$_2$. The crude suspension is allowed to stir at RT overnight. Then the solids are removed over celite and the celite cake is washed twice with AcOH. The combined organic phase is evaporated to dryness under reduced pressure. Toluene is added to the dry residue and the solvent is removed under reduced pressure once again. The crude solid obtained is dried under HV. This yields 3.45 g (145%) of the sub-title compound still containing AcOH.

LC-B: $t_R$=0.49 min; [M+H]$^+$=235.2 c) To a solution of (1,2,3,4-tetrahydro-isoquinolin-8-ylamino)-acetic acid ethyl ester (3.45 g, 9.57 mmol) in 100 mL DCM are added TEA (1.45 g, 14.4 mmol) and di-tert-butyl-dicarbonate (2.09 g, 9.57 mmol). The resulting brown solution is allowed to stir for 2.5 h at RT. The organic phase is washed with sat. aq. NaHCO$_3$ soln. and brine, dried over MgSO$_4$, filtered then evaporated under reduced pressure. This yields after drying under HV 2.24 g (70%) of the title compound as a brown oil which is used as such in the next step.

LC-B: $t_R$=0.98 min; [M+H]$^+$=335.2

Precursor W2

(2-Methyl-1,2,3,4-tetrahydro-isoquinolin-8-ylamino)-acetic acid ethyl ester a) 8-(Ethoxycarbonylmethyl-amino)-2-methyl-isoquinolinium iodide To a solution of 2-(isoquinolin-8-ylamino)acetic acid ethyl ester (130 mg, 0.565 mmol) made according to the method described for the synthesis of Precursor W1 Step a) in 2 mL acetone is added MeI (185 mg, 1.3 mmol). The yellow orange suspension is allowed to stir for 4 h at RT. The yellow solid formed is filtered, rinsed with acetone and dried under HV. This yields 120 mg (59%) of the sub-title compound as a yellow solid.

LC-B: $t_R$=0.47 min; [M+H]$^+$=245.2; $^1H$-NMR (CDCl$_3$) δ: 11.30 (s, 1H), 8.15 (m, 1H), 7.93 (m, 1H), 7.87 (m, 2H), 7.20 (d, J=7.8 Hz, 1H), 6.69 (d, J=8.3 Hz, 1H), 4.54 (s, 3H), 4.26 (m, 4H), 1.32 (t, J=7.1 Hz, 3H)

b) To a solution of 8-(ethoxycarbonylmethyl-amino)-2-methyl-isoquinolinium iodide (120 mg, 0.322 mmol) in 3 mL MeOH and 0.5 mL water cooled to 0° C. is added NaBH$_4$ (71 mg, 1.87 mmol). The resulting mixture is allowed to stir at RT overnight. The MeOH is then removed under reduced pressure and the remainder is poured into water. The resulting aq. phase is extracted twice with DCM. The combined organic phase is washed with brine then dried over MgSO$_4$, filtered and evaporated under reduced pressure. This organic phase contains no product. The aq. phase is extracted again twice with EtOAc. The resulting combined organic phase is washed with brine then dried over MgSO$_4$, filtered and evaporated under reduced pressure. This yields 71 mg (89%) of the title compound as yellow oil.

LC-B: $t_R$=0.48 min; [M+H]$^+$=249.3.

This compound partially contains (2-methyl-1,2,3,4-tetrahydro-isoquinolin-8-ylamino)-acetic acid methyl ester LC-B: $t_R$=0.43 min; [M+H]$^+$=235.2

Precursor W4

(2-Cyclobutyl-1,2,3,4-tetrahydroisoquinolin-8-yl) amino acetic acid methyl ester To a solution of (1,2,3,4-tetrahydro-isoquinolin-8-ylamino)-acetic acid ethyl ester (Precursor W1 step b) (225 mg, 0.96 mmol) in 5 mL MeOH is added cyclobutanone (337 mg, 4.8 mmol), ZnCl$_2$ (393 mg, 2.88 mmol) and NaBH$_3$CN (181 mg, 2.88 mmol). The resulting yellow mixture is allowed to stir at RT for 3 days. Water is added and the resulting organic phase is extracted twice with DCM. The combined organic phase is washed with sat. aq.

NaHCO$_3$ soln. and brine dried over MgSO$_4$, filtered and the solvent removed under reduced pressure. The title compound (80%) obtained as a yellow oil is used as such in the next step without further purification.

Precursor W5

(2-(2-cis-Fluorocyclopropane-1-carbonyl)-1,2,3,4-tetrahydroisoquinolin-5-yl)amino acetic acid ethyl ester To a solution of (1,2,3,4-tetrahydro-isoquinolin-8-ylamino)-acetic acid ethyl ester (Precursor W1 step b) (330 mg, 1 mmol) in 4 mL DCM is added cis-2-fluoro-cyclopropanecarboxylic acid (104 mg, 1 mmo), HATU (457 mg, 1.2 mmol) then DIPEA (324 mg, 2.5 mmol). The resulting yellow solution is stirred at rt for 1.5 h. The crude mixture is poured into sat. aq. NaHCO$_3$ soln. and the resulting aq. phase is extracted twice with DCM. The organic phase is washed with brine, dried over MgSO$_4$, filtered and evaporated.
LC-A: $t_R$=0.79 min; [M+H]$^+$=321.2

Precursor W6

N-(2-allyl-1,2,3,4-tetrahydroisoquinolin-8-yl)-N-(2,2,2-trifluoroacetyl)aminoacetic acid ethyl ester To a solution of N-(1,2,3,4-tetrahydroisoquinolin-8-yl)-N-(2,2,2-trifluoroacetyl)aminoacetic acid ethyl ester Precursor AD1 (1 g, 2.73 mmol), K$_2$CO$_3$ (0.471 g, 3.41 mmol) in 20 mL MeCN is added allylbromide (167 mg, 1.36 mol) and the reaction mixture is stirred at RT for 16 h. The white suspension is filtered off and the white solid is washed with EtOAc. The filtrate is concentrated to dryness under reduced pressure. Flash-chromatography on silica-gel (Eluent: gradient of heptane/EtOAc 80:20) yields 425 mg (42%) of the sub-title compound as yellow oil.
LC-A: $t_R$=0.65 min; [M+H]$^+$=371.0

Precursor W7

N-(2-cyclopropylmethyl-1,2,3,4-tetrahydroisoquinolin-8-yl)-N-(2,2,2-trifluoroacetyl)aminoacetic acid ethyl ester To a solution of N-(1,2,3,4-tetrahydroisoquinolin-8-yl)-N-(2,2,2-trifluoroacetyl)aminoacetic acid ethyl ester Precursor AD1 (1097 mg, 2.99 mmol) in 20 mL DCM is added cyclopropanecarboxaldehyde (231 mg, 3.29 mmol), DIPEA (773 mg, 5.98 mmol), and NaBH(OAc)$_3$ (761 mg, 3.59 mmol). The resulting reaction mixture is stirred at RT for 1 h. 10 mL DCM and 15 mL sat. aq. NaHCO$_3$ soln. are added and the resulting aq. phase is extracted twice with DCM, dried over MgSO$_4$, filtered and evaporated to dryness under reduced pressure. Flash-chromatography on silica-gel (Eluent: gradient of DCM/MeOH 100:0 to 90:10) yields the title compound as a yellow oil.
LC-A: $t_R$=0.67 min; [M+H]$^+$=385.1

Precursor W8

N-(2-Ethyl-1,2,3,4-tetrahydroisoquinolin-8-yl)-N-(2,2,2-trifluoroacetyl)aminoacetic acid ethyl ester, LC-A: $t_R$=0.65 min; [M+H]$^+$=359.2 is prepared applying the methods described for the synthesis of Precursor W7 from Precursor AD1 using acetaldehyde as reagent.

Precursor W9

(2-Ethyl-3-oxo-1,2,3,4-tetrahydro-isoquinolin-8-ylamino)-acetic acid ethyl ester is made following the method described for the synthesis of Precursor C22 step d) using 8-amino-2-ethyl-1,4-dihydro-2H-isoquinolin-3-one instead of 5-amino-2-ethyl-1,4-dihydro-2H-isoquinolin-3-one as starting material.

8-amino-2-ethyl-1,4-dihydro-2H-isoquinolin-3-one a) (2-Bromo-6-nitro-benzyl)-ethyl-amine
To a solution of 2-bromo-6-nitrobenzaldehyde (2.5 g, 10.9 mmol) in 40 mL MeOH at RT is added 2M ethylamine soln. in THF (5.5 ml, 10.9 mmol) and the resulting mixture is stirred at RT for 30 min, then NaBH$_4$ (473 mg, 12.5 mmol) is slowly added at 5° C. and the mixture is stirred at RT for 21 h. Then NaBH$_4$ (150 mg, 3.97 mmol) and 2M ethylamine soln. in THF (0.8 mL, 1.6 mmol) are added. After an additional 2.5 h at RT, water is added and the MeOH is removed under reduced pressure. The aqueous layer is extracted three times with EtOAc. The combined organic layers is dried over MgSO$_4$, filtered and concentrated to dryness.
Flash-chromatography on silica-gel (Eluent: Hept./EtOAc 95:5 to 70:30) yields 305 mg (11%) of the sub-title compound as an orange oil.
LC-A: $t_R$=0.45 min; [M+H]$^+$=258.9; $^1$H-NMR (400 MHz, CDCl$_3$) δ: 7.33 (t, J=8.1 Hz, 1H), 7.80 (d, J=8.1 Hz, 1H), 7.86 (d, J=8.0 Hz, 1H), 4.15 (s, 1H), 2.82 (q, J=7.1 Hz, 1H), 1.20 (t, J=7.1 Hz, 2H)

b) (2-Bromo-6-nitro-benzyl)-ethyl-carbamic acid tert-butyl ester
To a solution of (2-bromo-6-nitro-benzyl)-ethyl-amine (305 mg, 1.18 mmol) in dry DCM (10 mLl) is added TEA (182 mg, 1.78 mmol) and di-tert-butyl dicarbonate (257 mg, 1.18 mmol). The resulting mixture is stirred at RT for 3 h. It is then washed with sat. aq. NaHCO$_3$ soln. followed by brine then dried over MgSO$_4$, filtered and evaporated. Flash-chromatography on silica-gel (Eluent: Hept./EtOAc 90:10 to 75:25) yields 329 mg (78%) of the sub-title compound as a yellow oil.
LC-A: $t_R$=0.97 min; [M+H]$^+$=359.1; $^1$H-NMR (400 MHz, CDCl$_3$) δ: 7.80 (d, J=8.0 Hz, 1H), 7.59 (d, J=8.0 Hz, 1H), 7.30 (m, 1H), 4.82 (s, 2H), 3.12 (bs, 2H), 1.42 (bs, 9H), 1.05 (t, J=7.0 Hz, 3H)

c) {2-[(tert-Butoxycarbonyl-ethyl-amino)-methyl]-3-nitro-phenyl}-acetic acid tert-butyl ester
2-tert-Butoxy-2-oxoethylzinc chloride (0.5M in diethyl ether soln.) (3.3 mL, 1.63 mmol) is added to a mixture of (2-bromo-6-nitro-benzyl)-ethyl-carbamic acid tert-butyl ester (325 mg, 0.905 mmol), Pd$_2$(dba)$_3$ (26 mg, 0.0452 mmol) and 2-dicyclohexylphosphino-2'-(N,N-dimethylamino)biphenyl (17.8 mg, 0.0452 mmol) in dry 5 mL dioxane under argon atmosphere. The reaction mixture is heated at 50° C. for 16 h. After cooling another 2-dicyclohexylphosphino-2'-(N,N-dimethylamino)biphenyl (18 mg, 0.0457 mmol), Pd$_2$(dba)$_3$ (26 mg, 0.0452 mmol) and 2-tert-butoxy-2-oxoethylzinc chloride (0.5M in diethyl ether) (1.7 mL, 0.815 mmol) are added. The reaction mixture is allowed to stir at 50° C. for 5 h then at 80° C. for 19 h. After cooling 2-dicyclohexylphosphino-2'-(N,N-dimethylamino)biphenyl (18 mg, 0.0457 mmol), Pd$_2$(dba)$_3$ (26 mg, 0.0452 mmol, 0.05 eq) and 2-tert-butoxy-2-oxoethylzinc chloride (0.5M in diethyl ether) (1.7 mL, 0.815 mmol) are added and the resulting reaction mixture is heated at 80° C. for 4 h. the solvents are removed under reduced pressure. Flash-chromatography on silica-gel (Eluent: Hept./EtOAc/TEA 95:5: 0.1) yields 57 mg (16%) of the sub-title compound as a yellow oil.

LC-A: $t_R$=1.03 min; [M+H]$^+$=395.2 d) 2-Ethyl-8-nitro-1,4-dihydro-2H-isoquinolin-3-one

{2-[(tert-Butoxycarbonyl-ethyl-amino)-methyl]-3-nitrophenyl}-acetic acid tert-butyl ester (55 mg, 0.139 mmol) is dissolved in 1 mL of TFA/DCM (2:1) mixture cooled to 0° C. The resulting solution is allowed to stir for 1 h at 0° C. then 5 h at RT. The solvents are removed under reduced pressure without heating. The crude residue is dissolved 3 times with DCM and the solvent each time evaporated under reduced pressure. The crude residue is dissolved in 1 mL pyridine, DCC (83.4 mg, 0.404 mmol) and DMAP (51.4 mg, 0.421 mmol) are added. The resulting mixture is allowed to stir at RT for 1.5 h. Water is added and the resulting aq. Phase is extracted twice with EtOAc. The combined organic phase is washed with brine, dried over MgSO$_4$, filtered and the solvents evaporated under reduced pressure. Flash-chromatography on silica-gel (Eluent: DCM/MeOH 100:0 to 95:5) yields 30 mg (100%) of the sub-title compound as a yellow solid.

LC-A: $t_R$=0.70 min; [M+MeCN]$^+$=262.1 e) To a solution of 2-ethyl-8-nitro-1,4-dihydro-2H-isoquinolin-3-one (30 mg, 0.136 mmol) in 1 mL acetone is added sat. aq. NH$_4$Cl soln. The reaction mixture is cooled to 0° C. and Zn dust (92 mg, 23 mmol) is added slowly. The reaction mixture is allowed to stir at RT for 1 h. EtOAc is added as well as anhydrous sodium sulfate (1 g). The resulting suspension is stirred for 15 min then filtered over Celite and rinsed with etOAc then EtOAC/MeOH (9:1). The solvent is removed under reduced pressure to yield pure title compound as a yellowish solid.

LC-A: $t_R$=0.440 min; [M+MeCN]$^+$=232.1

Precursor AD1

N-(1,2,3,4-tetrahydroisoquinolin-8-yl)-N-(2,2,2-trifluoroacetyl)aminoacetic acid ethyl ester hydrochloride a) 8-(N-(2-ethoxy-2-oxoethyl)-2,2,2-trifluoroacetamido)-3,4-dihydroisoquinoline-2(1H)-carboxylic acid tert-butyl ester To a solution of 8-(ethoxycarbonylmethyl-amino)-3,4-dihydro-1H-isoquinoline-2-carboxylic acid tert-butyl ester Precursor W1 (1.6 mg, 4.78 mmol) in 20 mL DCM is added TEA (4.84 g, 47.8 mmol) and the resulting mixture is allowed to stir at RT for 5 min. Then TFAA (4.56 g, 21.5 mmol) is added dropwise and the resulting mixture is allowed to stir at RT for 30 min. Sat. aq. NaHCO$_3$ soln. is added and the resulting aq. phase is extracted twice with DCM. The combined organic phase is dried over MgSO$_4$, filtered and evaporated under reduced pressure to afford the sub-title compound as a yellow oil which still contains TEA but is used as such in the next step.

LC-A: $t_R$=0.98 min; [M+H]$^+$=431.0 b) To a solution of crude 8-(N-(2-ethoxy-2-oxoethyl)-2,2,2-trifluoroacetamido)-3,4-dihydroisoquinoline-2(1H)-carboxylic acid tert-butyl ester (2.6 g, 4.78 mmol) in 15 mL DCM is added dropwise 4N HCl in dioxane soln. (8.5 mL, 33.5 mmol) and the mixture is allowed to stir at RT for 30 min the at 60° C. for 2 h. After cooling all volatiles are removed under reduced pressure to yield the sub-title compound as a yellow solid.

LC-A: $t_R$=0.61 min; [M+H]$^+$=332.1

Example 185

N-Benzyl-N-(2-dimethylamino-ethyl)-2-(2-ethyl-1,2,3,4-tetrahydro-isoquinolin-8-ylamino)-acetamide a) N-{[Benzyl-(2-dimethylamino-ethyl)-carbamoyl]-methyl}-2,2,2-trifluoro-N-(2-ethyl-1,2,3,4-tetrahydro-isoquinolin-8-yl)-acetamide To a solution of N-{[benzyl-(2-dimethylamino-ethyl)-carbamoyl]-methyl}-2,2,2-trifluoro-N-(1,2,3,4-tetrahydro-isoquinolin-8-yl)-acetamide dihydrochloride Precursor X1 (50 mg, 0.084 mmol) in 0.5 mL MeOH and 0.25 mL water is added acetaldehyde (7.9 mg, 0.179 mmol) and the resulting solution is allowed to stir at RT for 10 min. Then NaBH$_3$CN (29.3 mg, 0.467 mmol) is added and the mixture is allowed to stir at RT overnight. Then acetaldehyde (7.9 mg, 0.179 mmol) is added again and the resulting solution is allowed to stir again 3 h at RT. The mixture is poured onto sat. aq. NaHCO$_3$ soln. and the resulting aq. phase is extracted twice with DCM. The combined organic phase is evaporated to dryness which yields the crude sub-title compound as a yellow solid which is used as such in the next step.

LC-B: $t_R$=0.48 min; [M+H]$^+$=491.2 b) To a solution of N-{[benzyl-(2-dimethylamino-ethyl)-carbamoyl]-methyl}-2,2,2-trifluoro-N-(2-ethyl-1,2,3,4-tetrahydro-isoquinolin-8-yl)-acetamide (41.2 mg, 0.084 mmol) in 1 mL MeOH is added 0.5 mL water and K$_2$CO$_3$ (69.7 mg, 0.504 mmol) and the resulting mixture is stirred at 65° C. for 4 h. After cooling the mixture is diluted with water and the resulting aq. phase is extracted twice with DCM. The combined organic phase is evaporated to dryness and the crude residue purified by prep. HPLC (Method E) to yield the title compound as a yellow oil.

LC-A: $t_R$=0.46 min; [M+H]$^+$=395.3

Example 188

N-Benzyl-N-(2-dimethylamino-ethyl)-2-(2-propionyl-1,2,3,4-tetrahydro-isoquinolin-8-ylamino)-acetamide a) N-{[Benzyl-(2-dimethylamino-ethyl)-carbamoyl]-methyl}-2,2,2-trifluoro-N-(2-propionyl-1,2,3,4-tetrahydro-isoquinolin-8-yl)-acetamide To a solution of N-{[benzyl-(2-dimethylamino-ethyl)-carbamoyl]-methyl}-2,2,2-trifluoro-N-(1,2,3,4-tetrahydro-isoquinolin-8-yl)-acetamide dihydrochloride Precursor X1 (50 mg, 0.084 mmol) in 0.6 mL DCM are added TEA (34 mg, 0.336 mmol) and propionyl chloride (8.5 mg, 0.092 mmol) and the resulting yellow solution is allowed to stir at RT for 1 h. The mixture is poured onto sat. aq. NaHCO$_3$ soln. and the resulting aq. phase is extracted twice with DCM. The combined organic phase is evaporated to dryness which yields the crude sub-title compound as a yellow solid which is used as such in the next step.

LC-B: $t_R$=0.63 min; [M+H]$^+$=519.1 b) The crude N-{[benzyl-(2-dimethylamino-ethyl)-carbamoyl]-methyl}-2,2,2-trifluoro-N-(2-propionyl-1,2,3,4-tetrahydro-isoquinolin-8-yl)-acetamide from step a) is submitted to the conditions of the preparation of Example 185 step b) to yield the title compound as a yellow oil.

LC-B: $t_R$=0.61 min; [M+H]$^+$=423.1

Example 190

8-({[Benzyl-(2-dimethylamino-ethyl)-carbamoyl]-methyl}-amino)-3,4-dihydro-1H-isoquinoline-2-carboxylic acid methyl ester a) 8-[{[Benzyl-(2-dimethylamino-ethyl)-carbamoyl]-methyl}-(2,2,2-trifluoro-acetyl)-amino]-3,4-dihydro-1H-isoquinoline-2-carboxylic acid tert-butyl ester To a solution of N-{[benzyl-(2-dimethylamino-ethyl)-carbamoyl]-methyl}-2,2,2-trifluoro-N-(1,2,3,4-tetrahydro-isoquinolin-8-yl)-acetamide dihydrochloride Precursor X1 (50 mg, 0.084 mmol) in 0.6 mL DCM are added TEA (34 mg, 0.336 mmol) and methyl chloroformate (8.7 mg, 0.092 mmol) and the resulting yellow solution is allowed to stir at RT for 2 h. The mixture is poured onto sat. aq. NaHCO$_3$ soln. and the resulting aq. phase is extracted twice with DCM. The combined organic phase is evaporated to dryness which yields the crude sub-title compound as a yellow solid which is used as such in the next step.

LC-B: $t_R$=0.65 min; [M+H]$^+$=521.1 b) The crude methyl 8-[{[benzyl-(2-dimethylamino-ethyl)-carbamoyl]-methyl}-(2,2,2-trifluoro-acetyl)-amino]-3,4-dihydro-1H-isoquinoline-2-carboxylic acid tert-butyl ester from step a) is submitted to the conditions of the preparation of Example 185 step b) to yield the title compound as a yellow oil.

LC-B: $t_R$=0.64 min; [M+H]$^+$=425.1

Example 544

N-(2-Dimethylamino-ethyl)-2-(2-methanesulfonyl-1,2,3,4-tetrahydro-isoquinolin-8-ylamino)-N-(2-trifluoromethyl-benzyl)-acetamide a) N-(2-((2-(dimethylamino)ethyl)(2-(trifluoromethyl)benzyl)amino)-2-oxoethyl)-2,2,2-trifluoro-N-(2-(methylsulfonyl)-1,2,3,4-tetrahydroisoquinolin-8-yl)acetamide To a solution of N-{[benzyl-(2-dimethylamino-ethyl)-carbamoyl]-methyl}-2,2,2-trifluoro-N-(1,2,3,4-tetrahydro-isoquinolin-8-yl)-acetamide dihydrochloride Precursor X1 (20 mg, 0.035 mmol) in 1 mL DCM are added methanesulfonyl chloride (4 mg, 0.035 mmol), pyridine (2.8 mg, 0.035 mmol) and DMAP (0.43 mg, 0.0035 mmol) and the resulting yellow solution is allowed to stir at RT overnight, then methanesulfonyl chloride (4 mg, 0.035 mmol), pyridine (2.8 mg, 0.035 mmol) and DMAP (0.43 mg, 0.0035 mmol) are added again and the mixture stirred at RT for 24 h. The mixture is poured onto sat. aq. NaHCO$_3$ soln. and the resulting aq. phase is extracted twice with DCM. The combined organic phase is evaporated to dryness which yields the crude sub-title compound as a yellow solid which is used as such in the next step.

LC-B: $t_R$=0.76 min; [M+H]$^+$=609.2 b) The crude N-(2-((2-(dimethylamino)ethyl)(2-(trifluoromethyl)benzyl)amino)-2-oxoethyl)-2,2,2-trifluoro-N-(2-(methylsulfonyl)-1,2,3,4-tetrahydroisoquinolin-8-yl)acetamide from step a) is submitted to the conditions of the preparation of Example 185 step b) to yield the title compound as a yellow oil.

LC-B: $t_R$=0.72 min; [M+H]$^+$=513.0

Examples 186-187/189/191-200/545/548-557/559-560/563-567 listed in Table 27 are prepared applying one of the methods described for Example 185, Example 188, Example 190, Example 544 respectively using the corresponding Precursor and the corresponding aldehyde, ketone, carboxylic acid chloride or chloroformate respectively.

TABLE 27

Examples 186-187/189/191-200/545/548-557/559-560/563-567

| Example No | Example name | $t_R$ [min] (LC-C) | MS Data m/z [M + H]$^+$ |
|---|---|---|---|
| 186 | N-Benzyl-N-(2-dimethylamino-ethyl)-2-(2-isopropyl-1,2,3,4-tetrahydro-isoquinolin-8-ylamino)-acetamide | 0.56 | 409.4 |
| 187 | N-Benzyl-2-(2-cyclopropylmethyl-1,2,3,4-tetrahydro-isoquinolin-8-ylamino)-N-(2-dimethylamino-ethyl)-acetamide | 0.58 | 421.4 |
| 189 | N-Benzyl-N-(2-dimethylamino-ethyl)-2-(2-isobutyl-1,2,3,4-tetrahydro-isoquinolin-8-ylamino)-acetamide | 0.6 | 423.5 |
| 191 | N-Benzyl-N-(2-dimethylamino-ethyl)-2-(2-isobutyryl-1,2,3,4-tetrahydro-isoquinolin-8-ylamino)-acetamide | 0.82 | 437.5 |
| 192 | 8-({[Benzyl-(2-dimethylamino-ethyl)-carbamoyl]-methyl}-amino)-3,4-dihydro-1H-isoquinoline-2-carboxylic acid isopropyl ester | 0.92 | 453.4 |
| 193 | N-Benzyl-2-(2-benzyl-1,2,3,4-tetrahydro-isoquinolin-8-ylamino)-N-(2-dimethylamino-ethyl)-acetamide | 0.63 | 457.4 |
| 194 | N-Benzyl-2-(2-cyclohexylmethyl-1,2,3,4-tetrahydro-isoquinolin-8-ylamino)-N-(2-dimethylamino-ethyl)-acetamide | 0.68 | 463.5 |
| 195 | 2-(2-Benzoyl-1,2,3,4-tetrahydro-isoquinolin-8-ylamino)-N-benzyl-N-(2-dimethylamino-ethyl)-acetamide | 0.87 | 471.4 |
| 196 | N-(2-Chloro-benzyl)-N-(2-dimethylamino-ethyl)-2-(2-ethyl-4,4-dimethyl-1,2,3,4-tetrahydro-isoquinolin-8-ylamino)-acetamide | 0.57 | 457.4 |
| 197 | N-(2-Chloro-benzyl)-2-(2-cyclopropylmethyl-4,4-dimethyl-1,2,3,4-tetrahydro-isoquinolin-8-ylamino)-N-(2-dimethylamino-ethyl)-acetamide | 0.63 | 483.4 |
| 198 | N-(2-Dimethylamino-ethyl)-2-(2-ethyl-4,4-dimethyl-1,2,3,4-tetrahydro-isoquinolin-8-ylamino)-N-(2-trifluoromethyl-benzyl)-acetamide | 0.62 | 491.4 |
| 199 | 2-(2-Cyclopropylmethyl-4,4-dimethyl-1,2,3,4-tetrahydro-isoquinolin-8-ylamino)-N-(2-dimethylamino-ethyl)-N-(2-trifluoromethyl-benzyl)-acetamide | 0.67 | 517.5 |

TABLE 27-continued

Examples 186-187/189/191-200/545/548-557/559-560/563-567

| | | | |
|---|---|---|---|
| 200 | 2-(2-Cyclopropylmethyl-4,4-dimethyl-1,2,3,4-tetrahydro-isoquinolin-8-ylamino)-N-(1-methyl-piperidin-4-yl)-N-(2-trifluoromethyl-benzyl)-acetamide | 0.67 | 543.4 |

| Example No | Example name | $t_R$ [min] (LC-F) | MS Data m/z [M + H]+ |
|---|---|---|---|
| 545 | 2-(2-Benzenesulfonyl-1,2,3,4-tetrahydro-isoquinolin-8-ylamino)-N-(2-dimethylamino-ethyl)-N-(2-trifluoromethyl-benzyl)-acetamide | 0.88 | 575.3 |
| 548 | N-(2-Dimethylamino-ethyl)-2-(2-ethyl-1,2,3,4-tetrahydro-isoquinolin-8-yloxy)-N-(2-trifluoromethyl-benzyl)-propionamide | 0.45 | 478.3 |
| 549 | 1-(2-Ethyl-1,2,3,4-tetrahydro-isoquinolin-8-yloxy)-cyclobutanecarboxylic acid (2-dimethylamino-ethyl)-(2-trifluoromethyl-benzyl)-amide | 0.42 | 504.3 |
| 550 | (E)-N-(2-Dimethylamino-ethyl)-3-(2-ethyl-1,2,3,4-tetrahydro-isoquinolin-8-yl)-N-(2-trifluoromethyl-benzyl)-acrylamide | 0.46 | 460.3 |
| 551 | N-(2-Dimethylamino-ethyl)-2-[2-(2,2-dimethyl-propionyl)-1,2,3,4-tetrahydro-isoquinolin-8-ylamino]-N-(2-trifluoromethyl-benzyl)-acetamide | 0.87 | 519.4 |
| 552 | 2-(2-Benzoyl-1,2,3,4-tetrahydro-isoquinolin-8-ylamino)-N-(2-dimethylamino-ethyl)-N-(2-trifluoromethyl-benzyl)-acetamide | 0.86 | 539.3 |
| 553 | 8-({[(2-Dimethylamino-ethyl)-(2-trifluoromethyl-benzyl)-carbamoyl]-methyl}-amino)-3,4-dihydro-1H-isoquinoline-2-carboxylic acid isopropyl ester | 0.89 | 521.4 |
| 554 | 2-(2-Cyclohexylmethyl-1,2,3,4-tetrahydro-isoquinolin-8-ylamino)-N-(2-dimethylamino-ethyl)-N-(2-trifluoromethyl-benzyl)-acetamide | 0.59 | 531.4 |
| 555 | N-(2-Dimethylamino-ethyl)-2-(2-ethyl-1,2,3,4-tetrahydro-isoquinolin-8-ylamino)-N-(2-trifluoromethyl-benzyl)-acetamide | 0.46 | 463.3 |
| 556 | N-(2-Dimethylamino-ethyl)-2-(2-propyl-1,2,3,4-tetrahydro-isoquinolin-8-ylamino)-N-(2-trifluoromethyl-benzyl)-acetamide | 0.48 | 477.4 |
| 557 | N-(2-Dimethylamino-ethyl)-2-(2-isobutyl-1,2,3,4-tetrahydro-isoquinolin-8-ylamino)-N-(2-trifluoromethyl-benzyl)-acetamide | 0.51 | 491.4 |
| 559 | N-(2-Dimethylamino-ethyl)-2-(2-propionyl-1,2,3,4-tetrahydro-isoquinolin-8-ylamino)-N-(2-trifluoromethyl-benzyl)-acetamide | 0.77 | 491.3 |
| 560 | 2-(2-Cyclopropanecarbonyl-1,2,3,4-tetrahydro-isoquinolin-8-ylamino)-N-(2-dimethylamino-ethyl)-N-(2-trifluoromethyl-benzyl)-acetamide | 0.78 | 503.3 |
| 563 | N-(2-Dimethylamino-ethyl)-2-[2-(2,2-dimethyl-propyl)-1,2,3,4-tetrahydro-isoquinolin-8-ylamino]-N-(2-trifluoromethyl-benzyl)-acetamide | 0.54 | 505.4 |
| 564 | N-(2-Dimethylamino-ethyl)-2-(2-methyl-1,2,3,4-tetrahydro-isoquinolin-8-ylamino)-N-(2-trifluoromethyl-benzyl)-acetamide | 0.45 | 449.4 |
| 565 | 2-(2-Cyclopropylmethyl-1,2,3,4-tetrahydro-isoquinolin-8-ylamino)-N-(2-pyrrolidin-1-yl-ethyl)-N-(2-trifluoromethyl-benzyl)-acetamide | 0.51 | 515.4 |
| 566 | 2-(2-Cyclopropylmethyl-1,2,3,4-tetrahydro-isoquinolin-8-ylamino)-N-(2-dimethylamino-ethyl)-N-(3-trifluoromethyl-pyridin-2-ylmethyl)-acetamide | 0.43 | 490.4 |
| 567 | N-(2-Dimethylamino-ethyl)-2-(2-ethyl-1,2,3,4-tetrahydro-isoquinolin-8-yloxy)-N-(2-trifluoromethyl-benzyl)-acetamide | 0.43 | 464.3 |

Example 546

8-({[(2-Dimethylamino-ethyl)-(2-trifluoromethyl-benzyl)-carbamoyl]-methyl}-amino)-3,4-dihydro-1H-isoquinoline-2-carboxylic acid dimethylamide a) 8-(N-(2-((2-(dimethylamino)ethyl)(2-(trifluoromethyl)benzyl)amino)-2-oxoethyl)-2,2,2-trifluoroacetamido)-N,N-dimethyl-3,4-dihydroisoquinoline-2(1H)-carboxamide To a solution of N-{[benzyl-(2-dimethylamino-ethyl)-carbamoyl]-methyl}-2,2,2-trifluoro-N-(1,2,3,4-tetrahydro-isoquinolin-8-yl)-acetamide dihydrochloride Precursor X1 (20 mg, 0.035 mmol) in 0.5 mL DCM are added dimethyl-carbamoyl chloride (6 mg, 0.0564 mmol) and TEA (5.7 mg, 0.0564 mmol) and the resulting yellow solution is allowed to stir at RT overnight. The mixture is poured onto sat. aq. NaHCO$_3$ soln. and the resulting aq. phase is extracted twice with DCM. The combined organic phase is evaporated to dryness which yields quantitatively the sub-title compound as a yellow solid which is used as such in the next step.
LC-B: $t_R$=0.77 min; [M+H]$^+$=602.4 b) 8-(N-(2-((2-(dimethylamino)ethyl)(2-(trifluoromethyl)benzyl)amino)-2-oxoethyl)-2,2,2-trifluoroacetamido)-N,N-dimethyl-3,4-dihydroisoquinoline-2(1H)-carboxamide from step a) is submitted to the conditions of the preparation of Example 185 step b) to yield the title compound as a yellow oil.
LC-B: $t_R$=0.72 min; [M+H]$^+$=506.3

Example 547

8-({[(2-Dimethylamino-ethyl)-(2-trifluoromethyl-benzyl)-carbamoyl]-methyl}-amino)-3,4-dihydro-1H-isoquinoline-2-carboxylic acid methylamide a) 8-(N-(2-((2-(Dimethylamino)ethyl)(2-(trifluoromethyl)benzyl)amino)-2-oxoethyl)-2,2,2-trifluoroacetamido)-N-methyl-3,4-dihydroisoquinoline-2(1H)-carboxamide To a solution of methylamine hydrochloride (3.81 mg, 0.0564 mmol) in 0.5 ml MeCN at RT are added Na$_2$ CO$_3$ (10.4 mg, 0.123 mmol) and 4-nitrophenyl chloroformate (9.24 mg, 0.0459 mmol). The mixture is stirred at RT overnight. Then methylamine hydrochloride (3.81 mg, 0.0564 mmol, 1.6 eq) and Na$_2$CO$_3$ (10.4 mg, 0.123 mmol, 3.5 eq) are added and the mixture stirred at RT for 4 h. Then N-{[benzyl-(2-dimethylamino-ethyl)-carbamoyl]-methyl}-2,2,2-trifluoro-N-(1,2,3,4-tetrahydro-isoquinolin-8-yl)-acetamide dihydrochloride Precursor X1 (20 mg, 0.035 mmol) in 0.5 ml MeCN and TEA (0.00737 ml, 0.0529 mmol, 1.5 eq) are added dropwise and the reaction mixture is allowed to stir at RT for 4 h. Water is then added and the resulting aq. phase is extracted with EtOAc. The combined organic layers are dried over MgSO$_4$, filtered and concentrated under reduced pressure. The crude sub-title compound is used without further purification LC-B: t$_R$=0.73 min; [M+H]$^+$=588.2 b) 8-(N-(2-((2-(dimethylamino)ethyl)(2-(trifluoromethyl)benzyl)amino)-2-oxoethyl)-2,2,2-trifluoroacetamido)-N-methyl-3,4-dihydroisoquinoline-2(1H)-carboxamide from step a) is submitted to the conditions of the preparation of Example 185 step b) to yield the title compound as a yellow oil.

LC-B: t$_R$=0.69 min; [M+H]$^+$=492.3

Examples 561-562 listed in Table 28 are prepared applying the method described for Example 547 Precursor X6 and the corresponding amine respectively.

TABLE 28

Examples 561-562

| Example No | Example name | t$_R$ [min] (LC-F) | MS Data m/z [M + H]$^+$ |
|---|---|---|---|
| 561 | N-(2-Dimethylamino-ethyl)-2-[2-(pyrrolidine-1-carbonyl)-1,2,3,4-tetrahydro-isoquinolin-8-ylamino]-N-(2-trifluoromethyl-benzyl)-acetamide | 0.83 | 532.4 |
| 562 | 8-({[(2-Dimethylamino-ethyl)-(2-trifluoromethyl-benzyl)-carbamoyl]-methyl}-amino)-3,4-dihydro-1H-isoquinoline-2-carboxylic acid amide | 0.68 | 478.3 |

Example 558

N-(2-Dimethylamino-ethyl)-2-[2-(2,2,2-trifluoro-ethyl)-1,2,3,4-tetrahydro-isoquinolin-8-ylamino]-N-(2-trifluoromethyl-benzyl)-acetamide To a solution of N-{[(2-Dimethylamino-ethyl)-(2-trifluoromethyl-benzyl)-carbamoyl]-methyl}-2,2,2-trifluoro-N-(1,2,3,4-tetrahydro-isoquinolin-8-yl)-acetamide dihydrochloride Precursor X6 in (75 mg, 0.132 mmol) in 5 mL toluene is added TEA (53.5 mg, 0.529 mmol) and the resulting solution is allowed to stir 10 min at RT then 2,2,2-trifluoroethyl trifluoromethanesulfonate (60.4 mg, 0.265 mmol) is added and the resulting mixture is allowed to stir at RT over night then TEA (53.5 mg, 0.529 mmol) and 2,2,2-trifluoroethyl trifluoromethanesulfonate (60.4 mg, 0.265 mmol) and the reaction mixture is allowed to stir at RT for 72 h. Water is added and the resulting aq. Phase is extracted with DCM. The combined organic layers are washed with sat. aq. NaHCO$_3$ soln., dried over MgSO$_4$, filtered and concentrated. The crude is dissolved in 5 mL MeOH and K2CO3 (108 mg, 0.78 mmol) and water are added and the resulting mixture is allowed to stir at 65° C. overnight. The mixture is then diluted with a small amount of water, then DCM is added and the phases separated. The combined organic layers are dried over Na$_2$SO$_4$, filtered and concentrated. The crude residue is purified by prep. HPLC (Method E) to yield the title compound as an orange solid.

LC-A: t$_R$=0.78 min; [M+H]$^+$=517.2.

Precursor X1

N-{[Benzyl-(2-dimethylamino-ethyl)-carbamoyl]-methyl}-2,2,2-trifluoro-N-(1,2,3,4-tetrahydro-isoquinolin-8-yl)-acetamide dihydrochloride a) 8-[{[Benzyl-(2-dimethylamino-ethyl)-carbamoyl]-methyl}-(2,2,2-trifluoro-acetyl)-amino]-3,4-dihydro-1H-isoquinoline-2-carboxylic acid tert-butyl ester To a solution of 8-({[benzyl-(2-dimethylamino-ethyl)-carbamoyl]-methyl}-amino)-3,4-dihydro-1H-isoquinoline-2-carboxylic acid tert-butyl ester Example 181 (723 mg, 1.22 mmol) in 15 mL DCM is added TEA (1.34 g, 13.4 mmol) and the resulting solution is allowed to stir at RT for 5 min. Then TFAA (1.18 g, 5.66 mmol) is slowly added dropwise and the resulting brown soln. is allowed to stir at RT for 1 h. The solution is washed twice with water then with brine. The solvent is removed under reduced pressure and the crude residue purified by fast filtration on a silica-gel pad (Eluent: EtOAc 100% then EtOAc/MeOH/ammonia 8:2:0.2) to yield 508 mg (74%) of the sub-title compound as yellow foam.

LC-B: t$_R$=0.75 min; [M+H]$^+$=563.1 b) To a solution of 8-[{[benzyl-(2-dimethylamino-ethyl)-carbamoyl]-methyl}-(2,2,2-trifluoro-acetyl)-amino]-3,4-dihydro-1H-isoquinoline-2-carboxylic acid tert-butyl ester (592 mg, 1.05 mmol) in 8 mL dioxane is added 3.7 mL 4N HCl soln. in dioxane (14.8 mmol). The resulting solution is allowed to stir at RT for 1 h. The volatiles are removed under reduced pressure. The residue is taken coevaporated twice with DCM. Finally the solid residue is dried under HV. This yields quantitatively 572 mg of the title compound as very hydroscopic light yellow foam which turns to an oil on standing.

LC-B: t$_R$=0.45 min; [M+H]$^+$=463.0

Precursors X2-X4/X6-X8 listed in Table 29 are prepared applying the method described for Precursor X1 using the corresponding Precusor Y2-Y4/Y6-Y8 respectively

TABLE 29

Precursors X2-X4/X6-X8

| Precursor | Precursor name | t$_R$ [min] (LC-A) | MS Data m/z [M + H]$^+$ |
|---|---|---|---|
| X2 | N-{[(2-Chloro-benzyl)-(2-dimethylamino-ethyl)-carbamoyl]-methyl}-N-(4,4-dimethyl-1,2,3,4-tetrahydro-isoquinolin-8-yl)-2,2,2-trifluoro-acetamide dihydrochloride | 0.59 | 525.3 |

TABLE 29-continued

Precursors X2-X4/X6-X8

| Precursor | Precursor name | $t_R$ [min] (LC-A) | MS Data m/z [M + H]$^+$ |
|---|---|---|---|
| X3 | N-{[(2-Dimethylamino-ethyl)-(2-trifluoromethyl-benzyl)-carbamoyl]-methyl}-N-(4,4-dimethyl-1,2,3,4-tetrahydro-isoquinolin-8-yl)-2,2,2-trifluoro-acetamide dihydrochloride | 0.61 | 559.3 |
| X4 | N-(4,4-Dimethyl-1,2,3,4-tetrahydro-isoquinolin-8-yl)-2,2,2-trifluoro-N-{[(1-methyl-piperidin-4-yl)-(2-trifluoromethyl-benzyl)-carbamoyl]-methyl}-acetamide dihydrochloride | 0.62 | 585.4 |
| X6 | N-{[(2-Dimethylamino-ethyl)-(2-trifluoromethyl-benzyl)-carbamoyl]-methyl}-2,2,2-trifluoro-N-(1,2,3,4-tetrahydro-isoquinolin-8-yl)-acetamide dihydrochloride | 0.58 | 531.4 |
| X7 | 2,2,2-Trifluoro-N-{[(2-pyrrolidin-1-yl-ethyl)-(2-trifluoromethyl-benzyl)-carbamoyl]-methyl}-N-(1,2,3,4-tetrahydro-isoquinolin-8-yl)-acetamide dihydrochloride | 0.61 | 557.2 |
| X8 | N-{[(2-Dimethylamino-ethyl)-((3-trifluoromethyl-pyridin-2yl)-methyl)-carbamoyl]-methyl}-2,2,2-trifluoro-N-(1,2,3,4-tetrahydro-isoquinolin-8-yl)-acetamide dihydrochloride | 0.54 | 532.4 |

Precursors Y2-Y4/Y6-Y8 listed in Table 30 are prepared applying the method described for Example 181 using Precursor V1 or Precursor V4 and the corresponding Amine respectively.

TABLE 30

Precursors Y2-Y4/Y6-Y8

| Precursor | Precursor name | $t_R$ [min] (LC-A) | MS Data m/z [M + H]$^+$ |
|---|---|---|---|
| Y2 | 8-({[(2-Chloro-benzyl)-(2-dimethylamino-ethyl)-carbamoyl]-methyl}-amino)-4,4-dimethyl-3,4-dihydro-1H-isoquinoline-2-carboxylic acid tert-butyl ester | 0.82 | 529 |
| Y3 | 8-({[(2-Dimethylamino-ethyl)-(2-trifluoromethyl-benzyl)-carbamoyl]-methyl}-amino)-4,4-dimethyl-3,4-dihydro-1H-isoquinoline-2-carboxylic acid tert-butyl ester | 0.84 | 563.2 |
| Y4 | 4,4-Dimethyl-8-({[(1-methyl-piperidin-4-yl)-(2-trifluoromethyl-benzyl)-carbamoyl]-methyl}-amino)-3,4-dihydro-1H-isoquinoline-2-carboxylic acid tert-butyl ester | 0.83 | 589.2 |
| Y6 | 8-({[(2-Dimethylamino-ethyl)-(2-trifluoromethyl-benzyl)-carbamoyl]-methyl}-amino)-3,4-dihydro-1H-isoquinoline-2-carboxylic acid tert-butyl ester | 0.82 | 535.4 |
| Y7 | 8-({[(2-Pyrrolidin-1-yl-ethyl)-(2-trifluoromethyl-benzyl)-carbamoyl]-methyl}-amino)-3,4-dihydro-1H-isoquinoline-2-carboxylic acid tert-butyl ester | 0.85 | 561.1 |
| Y8 | 8-({[(2-Dimethylamino-ethyl)-[(3-trifluoromethyl-pyridin-2-yl)-methyl]-carbamoyl]-methyl}-amino)-3,4-dihydro-1H-isoquinoline-2-carboxylic acid tert-butyl ester | 0.80 | 536.4 |

Precursor V4

8-(Carboxymethyl-amino)-4,4-dimethyl-3,4-dihydro-1H-isoquinoline-2-carboxylic acid tert-butyl ester LC-A: $t_R$=0.81 min; [M+H]$^+$=335.3; $^1$H-NMR (CDCl$_3$) δ: 6.96 (d, J=8.2 Hz, 1H), 6.77 (s, 1H), 6.64 (dd, J$_1$=8.2 Hz, J$_2$=1.9 Hz, 1H), 5.22-6.12 (bs, 1H), 4.55 (m, 2H), 4.01 (s, 2H), 3.40 (bs, 2H), 1.51 (s, 9H), 1.26 (s, 6H) is made according to the Method described for the synthesis of Precursor V1 starting from Precursor W10.

Precursor W10

8-(Ethoxycarbonylmethyl-amino)-4,4-dimethyl-3,4-dihydro-1H-isoquinoline-2-carboxylic acid tert-butyl ester To a solution of 8-amino-4,4-dimethyl-3,4-dihydro-1H-isoquinoline-2-carboxylic acid tert-butyl ester (400 mg, 1.45 mmol) in 5 mL MeCN is added DIPEA (187 mg, 1.45 mmol) and the mixture is stirred at RT for 15 min. Then ethylbromoacetate (242 mg, 1.45 mmol) is added and the resulting soln. is allowed to stir at 60° C. for 2 h then at RT overnight. The mixture is then poured onto water, the resulting aq. phase is extracted twice with DCM. The combined organic phase is washed with sat. aq. NaHCO$_3$ soln. then with brine. It is dried over MgSO$_4$, filtered and the solvent is evaporated under reduced pressure. The crude residue is purified by fast filtration on a silica-gel pad (Eluent: EtOAc/heptane 1:4) to yield 385 mg (73%) of the title compound as yellow oil.

LC-A: $t_R$=0.96 min; [M+H]$^+$=363.3; $^1$H-NMR (CDCl3) δ: 6.93 (d, J=7.7 Hz, 1H), 6.61 (s, 1H), 6.51 (dd, J$_1$=8.2 Hz, J$_2$=1.5 Hz, 1H), 4.54 (d, J=9.1 Hz, 2H), 4.27 (q, J=7.1 Hz, 2H), 3.92 (s, 2H), 3.40 (s, 2H), 1.50 (s, 9H), 1.32 (t, J=7.2 Hz, 3H), 1.26 (s, 6H)

Example 201

N-Benzyl-N-(2-dimethylamino-ethyl)-2-(2-methyl-1,2,3,4-tetrahydro-isoquinolin-8-yloxy)-acetamide To a solution of N-benzyl-N-(2-dimethylamino-ethyl)-2-(1,2,3,4-tetrahydro-isoquinolin-8-yloxy)-acetamide dihydrochloride Precursor X5 (50 mg, 0.114 mmol) and formaldehyde (8.5 mg, 0.284 mmol) in 0.25 mL water and 0.5 mL MeOH is added $NaBH_3CN$ (17.8 mg, 0.284 mmol) and the resulting mixture is stirred at RT for 1 h. Sat. aq. $NaHCO_3$ soln. is added and the resulting aq. phase is extracted twice with DCM. The combined organic phase is evaporated under reduced pressure. The crude residue is purified by prep. HPLC (Method D) to yield the title compound as a yellow oil.

LC-B: $t_R$=0.43 min; $[M+H]^+$=382.1

Examples 202-203/205 listed in Table 31 are prepared applying one of the methods described for Example 201 using Precursor X5 and the corresponding aldehyde respectively.

TABLE 31

Examples 202-203/205

| Example No | Example name | $t_R$ [min] (LC-C) | MS Data m/z $[M + H]^+$ |
|---|---|---|---|
| 202 | 8-{[Benzyl-(2-dimethylamino-ethyl)-carbamoyl]-methoxy}-3,4-dihydro-1H-isoquinoline-2-carboxylic acid methyl ester | 0.52 | 396.4 |
| 203 | N-Benzyl-N-(2-dimethylamino-ethyl)-2-(2-isobutyl-1,2,3,4-tetrahydro-isoquinolin-8-yloxy)-acetamide | 0.56 | 422.4 |
| 205 | 2-(2-Benzoyl-1,2,3,4-tetrahydro-isoquinolin-8-yloxy)-N-benzyl-N-(2-dimethylamino-ethyl)-acetamide | 0.57 | 424.4 |

Example 204

8-{[Benzyl-(2-dimethylamino-ethyl)-carbamoyl]-methoxy}-3,4-dihydro-1H-isoquinoline-2-carboxylic acid methyl ester To a solution of N-benzyl-N-(2-dimethylamino-ethyl)-2-(1,2,3,4-tetrahydro-isoquinolin-8-yloxy)-acetamide dihydrochloride Precursor X5 (50 mg, 0.114 mmol) in 1 mL DCM are added TEA (46 mg, 0.454 mmol) and methylchloroformate (10.7 mg, 0.114 mmol) and the resulting mixture is stirred at RT for 1 h. Sat. aq. $NaHCO_3$ soln. is added and the resulting aq. phase is extracted twice with DCM. The combined organic phase is evaporated under reduced pressure. The crude residue is purified by prep. HPLC (Method D) to yield the title compound as a yellow oil.

LC-B: $t_R$=0.63 min; $[M+H]^+$=426.4

Example 206

N-Benzyl-N-(2-dimethylamino-ethyl)-2-(2-propionyl-1,2,3,4-tetrahydro-isoquinolin-8-yloxy)-acetamide To a solution of N-benzyl-N-(2-dimethylamino-ethyl)-2-(1,2,3,4-tetrahydro-isoquinolin-8-yloxy)-acetamide dihydrochloride Precursor X5 (50 mg, 0.114 mmol) in 1 mL DCM are added TEA (46 mg, 0.454 mmol) and propionyl chloride (11.6 mg, 0.114 mmol) and the resulting mixture is stirred at RT for 1 h. Sat. aq. $NaHCO_3$ soln. is added and the resulting aq. phase is extracted twice with DCM. The combined organic phase is evaporated under reduced pressure. The crude residue is purified by prep. HPLC (Method D) to yield the title compound as a colorless oil.

LC-B: $t_R$=0.60 min; $[M+H]^+$=424.3

Example 207

2-(2-Benzoyl-1,2,3,4-tetrahydro-isoquinolin-8-yloxy)-N-benzyl-N-(2-dimethylamino-ethyl)-acetamide LC-B: $t_R$=0.67 min; $[M+H]^+$=472.3 is prepared according to the Method described for the preparation of Example 206 using benzoylchloride in place of propionylchloride.

Precursor X5

N-Benzyl-N-(2-dimethylamino-ethyl)-2-(1,2,3,4-tetrahydro-isoquinolin-8-yloxy)-acetamide dihydrochloride To a solution of 8-{[benzyl-(2-dimethylamino-ethyl)-carbamoyl]-methoxy}-3,4-dihydro-1H-isoquinoline-2-carboxylic acid tert-butyl ester Precursor Y5 (509 mg, 1.09 mmol) in 8 mL dioxane is added 3.82 mL (15.3 mmol) 4N HCl soln. in dioxane. The resulting yellowish soln. is allowed to stir at RT for 2 h. The volatiles are removed under reduced pressure, the residue is taken up in DCM and the solvent is remove under reduced pressure. This last procedure is repeated three times. This yields 480 mg (100%) of the title compound as a light yellow solid.

LC-B: $t_R$=0.43 min; $[M+H]^+$=368.1

Precursors X9/X12-X14 listed in Table 32 are prepared applying the method described for Precursor X5 using the corresponding Precursors Y9/Y12-Y14 respectively.

TABLE 32

Precursors X9/X12-X14

| Precursor | Precursor name | $t_R$ [min] (LC-A) | MS Data m/z $[M + H]^+$ |
|---|---|---|---|
| X9 | N-(2-(dimethylamino)ethyl)-2-((1,2,3,4-tetrahydroisoquinolin-8-yl)oxy)-N-(2-(trifluoromethyl)benzyl)acetamide dihydrochloride | 0.55 | 436.3 |
| X12 | rac-N-(2-(dimethylamino)ethyl)-2-((1,2,3,4-tetrahydroisoquinolin-8-yl)oxy)-N-(2-(trifluoromethyl)benzyl)propanamide dihydrochloride | 0.56 | 450.2 |
| X13 | N-(2-(dimethylamino)ethyl)-1-((1,2,3,4-tetrahydroisoquinolin-8-yl)oxy)-N-(2-(trifluoromethyl)benzyl)cyclobutane-1-carboxamide dihydrochloride | 0.53 | 476.4 |

TABLE 32-continued

Precursors X9/X12-X14

| Precursor | Precursor name | $t_R$ [min] (LC-A) | MS Data m/z [M + H]$^+$ |
|---|---|---|---|
| X14 | (E)-N-(2-(dimethylamino)ethyl)-3-(1,2,3,4-tetrahydroisoquinolin-8-yl)-N-(2-(trifluoromethyl)benzyl)acrylamide dihydrochloride | 0.57 | 432.2 |

Precursor Y5

8-{[Benzyl-(2-dimethylamino-ethyl)-carbamoyl]-methoxy}-3,4-dihydro-1H-isoquinoline-2-carboxylic acid tert-butyl ester To a solution of 8-carboxymethoxy-3,4-dihydro-1H-isoquinoline-2-carboxylic acid tert-butyl ester Precursor V11 (400 mg, 1.3 mmol), N-benzyl-N',N'-dimethylethane-1,2-diamine Amine 7 (232 mg, 1.3 mmol) and HATU (594 mmol, 1.56 mmol) in 8 mL DCM is added DIPEA (421 mg, 3.25 mmol). The resulting yellow suspension is allowed to stir at RT for 2 h. Then sat. aq. NaHCO$_3$ soln. is added and the resulting aq. phase is extracted twice with DCM. The combined organic phase is washed with brine and dried over MgSO$_4$, filtered then evaporated under reduced pressure. Flash-chromatography on silica-gel (Eluent: DCM/MeOH from 100:0 to 80:20) yields 509 mg (84%) of the title compound as a yellow oil.

LC-B: $t_R$=0.73 min; [M+H]$^+$=468.1

Precursors Y9/Y12-Y14 listed in Table 33 are prepared applying the method described for Precursor Y5 using the corresponding Precursors V11-V14 respectively.

TABLE 33

Precursors Y9/Y12-Y14

| Precursor | Precursor name | $t_R$ [min] (Method LC-A) | MS Data m/z [M + H]$^+$ |
|---|---|---|---|
| Y9 | 8-{[(2-Dimethylamino-ethyl)-(2-trifluoromethyl-benzyl)-carbamoyl]-methoxy}-3,4-dihydro-1H-isoquinoline-2-carboxylic acid tert-butyl ester | 0.82 | 536.4 |
| Y12 | rac-8-{1-[(2-Dimethylamino-ethyl)-(2-trifluoromethyl-benzyl)-carbamoyl]-ethoxy}-3,4-dihydro-1H-isoquinoline-2-carboxylic acid tert-butyl ester | 0.83 | 550.4 |
| Y13 | 8-{1-[(2-Dimethylamino-ethyl)-(2-trifluoromethyl-benzyl)-carbamoyl]-cyclobutoxy}-3,4-dihydro-1H-isoquinoline-2-carboxylic acid tert-butyl ester | 0.85 | 576.4 |
| Y14 | 8-{(E)-2-[(2-Dimethylamino-ethyl)-(2-trifluoromethyl-benzyl)-carbamoyl]-vinyl}-3,4-dihydro-1H-isoquinoline-2-carboxylic acid tert-butyl ester | 0.84 | 532.2 | drying under HV yields 1.21 g (100%) of the title compound as a yellow solid which is used as such in the next step.

LC-B: $t_R$=0.82 min; [M+H]$^+$=308.1; $^1$H-NMR (CDCl$_3$) δ: 7.37-7.51 (bs, 1H), 7.13 (t, J=7.9 Hz, 1H), 6.81 (d, J=7.6 Hz, 1H), 6.62 (d, J=8.1 Hz, 1H), 4.67 (m, 4H), 3.65 (t, J=5.4 Hz, 2H), 2.83 (t, J=5.6 Hz, 2H), 1.51 (s, 9H)

Precursors V12-V13 listed in Table 34 are prepared applying the method described for Precursor V11 using the corresponding Precursors W12-W13 respectively.

TABLE 34

Precursors V12-V13

| Precursor | Precursor name | $t_R$ [min] (Method LC-A) | MS Data m/z [M + H]$^+$ |
|---|---|---|---|
| V12 | rac-8-(1-Carboxy-ethoxy)-3,4-dihydro-1H-isoquinoline-2-carboxylic acid tert-butyl ester | 0.85 | 322.1 |
| V13 | 8-(1-Carboxy-cyclobutoxy)-3,4-dihydro-1H-isoquinoline-2-carboxylic acid tert-butyl ester | 0.90 | 348.2 |

Precursor V11

8-Carboxymethoxy-3,4-dihydro-1H-isoquinoline-2-carboxylic acid tert-butyl ester

To a solution of 8-ethoxycarbonylmethoxy-3,4-dihydro-1H-isoquinoline-2-carboxylic acid tert-butyl ester Precursor W11 (1.39 g, 3.85 mmol) in 50 mL THF is added 1M LiOH soln. in water (20.8 mL, 20.8 mmol). The reaction mixture is allowed to stir at RT for 2.5 h. Then 2M HCl aq. soln. is added until pH=4 and the resulting acidic aq. phase is extracted twice with EtOAc. The combined organic phase is washed with brine then dried over MgSO$_4$ and filtered. Evaporation of the solvent under reduced pressure and

Precursor W11

8-Ethoxycarbonylmethoxy-3,4-dihydro-1H-isoquinoline-2-carboxylic acid tert-butyl ester To a soln. of 8-hydroxy-3,4-dihydro-1H-isoquinoline-2-carboxylic acid tert-butyl ester [Bioorg. & Med. Chem. Letters 2006, 16(13), 3415-3418](300 mg, 1.2 mmol) in 5 mL acetone are added K$_2$CO$_3$ (249 mg, 1.8 mmol) and ethylbromoacetate (201 mg, 1.2 mmol). The resulting mixture is allowed to stir at 70° C. for 2 h. After cooling, it is poured onto water. The resulting aq. phase is extracted twice with DCM. The combined organic phase is washed with brine then dried over MgSO$_4$ and filtered. Evaporation of the solvent under reduced pressure and drying under HV yields quantitatively the title compound as a yellow oil which is used as such in the next step.

LC-B: $t_R$=0.98 min; [M+H]$^+$=336.1; $^1$H-NMR δ: 7.13 (t, J=7.9 Hz, 1H), 6.78 (d, J=7.7 Hz, 1H), 6.59 (d, J=8.1 Hz, 1H), 4.65 (s, 2H), 4.58 (s, 2H), 4.28 (m, 2H), 3.66 (t, J=5.7 Hz, 2H), 2.87 (t, J=5.8 Hz, 2H), 1.51 (s, 9H), 1.32 (t, J=7.1 Hz, 4H)

Precursors W12-W13 listed in Table 35 are prepared applying the method described for Precursor W11 using the corresponding starting material respectively.

TABLE 35

Precursors W12-W13

| Precursor | Precursor name | $t_R$ [min] (Method LC-A) | MS Data m/z [M + H]$^+$ |
|---|---|---|---|
| W12 | rac-8-(1-Ethoxycarbonyl-ethoxy)-3,4-dihydro-1H-isoquinoline-2-carboxylic acid tert-butyl ester | 0.99 | 350.2 |
| W13 | 8-(1-Ethoxycarbonyl-cyclobutoxy)-3,4-dihydro-1H-isoquinoline-2-carboxylic acid tert-butyl ester | 1.02 | 376.3 |

Precursor V14

8-((E)-2-Carboxy-vinyl)-3,4-dihydro-1H-isoquinoline-2-carboxylic acid tert-butyl ester Is made according to the method described for the synthesis of Precursor E1 using 8-formyl-3,4-dihydro-1H-isoquinoline-2-carboxylic acid tert-butyl ester instead of 5-formyl-3,4-dihydro-1H-isoquinoline-2-carboxylic acid tert-butyl ester.

LC-A: $t_R$=0.85 min; [M-tBu+MeCN]$^+$=289.2

$^1$H-NMR (400 MHz, CDCl$_3$) δ: 8.01 (d, J=15.7 Hz, 1H), 7.49 (m, 1H), 7.23 (m, 2H), 6.40 (d, J=15.7 Hz, 1H), 4.75 (s, 2H), 3.68 (t, J=5.8 Hz, 2H), 2.90 (t, J=5.8 Hz, 2H), 1.53 (m, 9H)

Example 208

N-Benzyl-N-(2-dimethylamino-ethyl)-2-(2-methyl-2,3-dihydro-1H-isoindol-4-ylamino)-acetamide a) N-{[Benzyl-(2-dimethylamino-ethyl)-carbamoyl]-methyl}-2,2,2-trifluoro-N-(2-methyl-2,3-dihydro-1H-isoindol-4-yl)-acetamide To a solution of N-{[benzyl-(2-dimethylamino-ethyl)-carbamoyl]-methyl}-N-(2,3-dihydro-1H-isoindol-4-yl)-2,2,2-trifluoro-acetamide dihydrochloride Precursor Z1 (50 mg, 0.0853 mmol) and formaldehyde (2.6 mg, 0.0853 mmol) in 1 mL MeOH and 0.25 mL water is added NaBH$_3$CN (13.4 mg, 0.213 mmol). The resulting mixture is allowed to stir at RT for 1 h. Sat. aq. NaHCO$_3$ soln. is added and the resulting aq. phase is extracted twice with DCM. The organic phase is evaporated under reduced pressure to yield 29 mg (73%) of the crude sub-title compound as a yellow oil.

b) To a solution of N-{[benzyl-(2-dimethylamino-ethyl)-carbamoyl]-methyl}-2,2,2-trifluoro-N-(2-methyl-2,3-dihydro-1H-isoindol-4-yl)-acetamide (24.6 mg, 0.0531 mmol) in 1 mL MeOH and 0.5 mL water is added K$_2$CO$_3$ (44 mg, 0.319 mmol). The resulting mixture is allowed to stir at 65° C. for 2 h then at RT overnight. After cooling, sat. aq. NaHCO$_3$ soln. is added and the resulting aq. phase is extracted twice with DCM. The organic phase is evaporated under reduced pressure and the crude residue is purified by prep. HPLC (Method D) to yield the title compound as a yellow oil.

LC-B: $t_R$=0.43 min; [M+H]$^+$=367.1

Example 209

N-Benzyl-2-(2-cyclopropylmethyl-2,3-dihydro-1H-isoindol-4-ylamino)-N-(2-dimethylamino-ethyl)-acetamide LC-B: $t_R$=0.47 min; [M+H]$^+$=407.1 is prepared according to the Method described for the preparation of Example 208 using Precursor Z1 and cyclopropanecarboxaldehyde as starting materials.

Precursor Z1

N-{[Benzyl-(2-dimethylamino-ethyl)-carbamoyl]-methyl}-N-(2,3-dihydro-1H-isoindol-4-yl)-2,2,2-trifluoro-acetamide dihydrochloride a) 4-[{[Benzyl-(2-dimethylamino-ethyl)-carbamoyl]-methyl}-(2,2,2-trifluoro-acetyl)-amino]-1,3-dihydro-isoindole-2-carboxylic acid tert-butyl ester To a solution of 4-({[benzyl-(2-dimethylamino-ethyl)-carbamoyl]-methyl}-amino)-1,3-dihydro-isoindole-2-carboxylic acid tert-butyl ester Precursor AA1 (270 mg, 0.495 mmol) in 5 mL DCM is added TEA (200 mg, 1.98 mmol) and the resulting mixture is stirred at 5 min at RT then TFAA (208 mg, 0.99 mmol) is added and the resulting mixture is allowed to stir at RT for 1 h. The organic phase is washed with water and brine. The organic phase is dried over MgSO$_4$, filtered and the solvent removed under reduced pressure to give 214 mg (79%) of the subtitle compound as a yellow oil.

LC-B: $t_R$=0.75 min; [M+H]$^+$=549.0 b) To a solution of 4-[{[benzyl-(2-dimethylamino-ethyl)-carbamoyl]-methyl}-(2,2,2-trifluoro-acetyl)-amino]-1,3-dihydro-isoindole-2-carboxylic acid tert-butyl ester (210 mg, 0.383 mmol) in 5 mL dioxane is added 1.34 mL 4N HCl soln. in dioxane. The resulting brown suspension is allowed to stir at RT overnight. The solvent is coevaporated twice with EtOAc. After drying under HV, this yields 228 mg (114%) of the title compounds still containing some dioxane. It is used as such in the next step.

LC-B: $t_R$=0.48 min; [M+H]$^+$=448.9

Precursor AA1

4-({[Benzyl-(2-dimethylamino-ethyl)-carbamoyl]-methyl}-amino)-1,3-dihydro-isoindole-2-carboxylic acid tert-butyl ester To a solution of 4-(carboxymethyl-amino)-1,3-dihydro-isoindole-2-carboxylic acid tert-butyl ester Precursor AB1 (300 mg, 1.03 mmol) and N-benzyl-N',N'-dimethylethane-1,2-diamine Amine 7 (183 mg, 1.03 mmol) and HATU (468 mg, 1.03 mmol) in 5 mL DCM is added DIPEA (332 mg, 2.57 mmol). The reaction mixture is allowed to stir at RT for 1 h. Sat. aq. NaHCO$_3$ soln. is added and the resulting aq. phase is extracted twice with DCM. The combined organic phase is evaporated under reduced pressure. Flash-chromatography on silica-gel (Eluent: EtOAc/MeOH 100:0 to 80:20) yields 339 mg (73%) of the title compound as a yellow oil.

LC-B: $t_R$=0.73 min; $[M+H]^+$=453.1

Precursor AB1

4-(Carboxymethyl-amino)-1,3-dihydro-isoindole-2-carboxylic acid tert-butyl ester To a solution of 4-(ethoxycarbonylmethyl-amino)-1,3-dihydro-isoindole-2-carboxylic acid tert-butyl ester Precursor AC1 (1.09 g, 3.06 mmol) in 50 mL THF is added 18.4 mL (18.4 mmol) 1N aq. LiOH soln. the resulting mixture is allowed to stir at RT overnight. The mixture is acidified to pH=4 with 2N aq. HCl soln. and the resulting aq. phase is extracted twice with DCM. The combined organic phase is washed with water and brine, dried over MgSO$_4$, filtered and evaporated to yield 833 mg (93%) of the title compound as a purple solid which is used as such in the next step.

LC-B: $t_R$=0.77 min; $[M+H]^+$=293.0; $^1$H-NMR (d$_6$-DMSO) δ: 7.06 (t, J=7.7 Hz, 1H), 6.56 (t, J=6.7 Hz, 1H), 6.30 (dd, J$_1$=8.0 Hz, J$_2$=1.3 Hz, 1H), 4.52 (d, J=10.5 Hz, 2H), 4.42 (d, J=11.4 Hz, 2H), 3.82 (s, 2H), 1.47 (d, J=5.4 Hz, 9H)

Precursor AC1

4-(Ethoxycarbonylmethyl-amino)-1,3-dihydro-isoindole-2-carboxylic acid tert-butyl ester a) 4-Amino-1,3-dihydro-isoindole-2-carboxylic acid tert-butyl ester To a solution of 4-amino-isoindoline [J. Pharm. Sci. 1964, 53, 981](500 mg, 3.73 mmol) in 10 mL dioxane is added 1N aq. NaOH soln. (3.73 mL, 3.73 mmol) and di-tert-butyl-dicarbonate (813 mg, 3.73 mmol) and the resulting mixture is allowed to stir at RT for 1 h. The reaction mixture is poured onto water and the resulting aq. phase is extracted twice with EtOAc. The combined organic phase is washed with sat. aq. NaHCO$_3$ soln., brine then dried over MgSO$_4$. It is then filtered and the solvent is removed under reduced pressure. After drying under HV the 769 mg (88%) from the sub-title compound are obtained. It is used as such in the next step.

LC-B: $t_R$=0.69 min; $[M-tert-Bu+MeCN]^+$=220.1 b) To a solution of 4-amino-1,3-dihydro-isoindole-2-carboxylic acid tert-butyl ester (769 mg, 3.02 mmol) in 10 mL MeCN are added DIPEA (585 mg, 4.53 mmol) and ethyl bromoacetate (504 mg, 3.02 mmol). The resulting mixture is allowed to stir at 60° C. for 17 h. After cooling the mixture is poured onto water and the resulting aq. phase is extracted twice with DCM. The combined organic phase is washed with water and brine. It is dried over MgSO$_4$, filtered and the solvent removed under reduced pressure. This yields quantitatively the title compound as a brown oil which is used as such in the next step.

LC-B: $t_R$=0.94 min; $[M+MeCN]^+$=321.1

Example 568

3-(2-Cyclopropylmethyl-1,2,3,4-tetrahydro-isoquinolin-5-ylmethyl)-1-(2-dimethylamino-ethyl)-1-(2-trifluoromethyl-benzyl)-urea A solution of 1-(2-dimethylamino-ethyl)-3-(1,2,3,4-tetrahydro-isoquinolin-5-ylmethyl)-1-(2-trifluoromethyl-benzyl)-urea Precursor AD1 (89 mg, 0.18 mmol) and cyclopropanecarboxaldehyde (12.6 mg, 0.18 mmol) in MeOH 1 mL and water 0.5 mL is allowed to stir at RT for 5 min. Then NaBH$_3$CN (28.3 mg, 0.45 mmol) is added and the resulting mixture is allowed to stir at RT for 1 h. It is then poured into sat. aq. NaHCO$_3$ soln. and the resulting aq. phase is extracted twice with DCM. The combined organic phase is washed with brine, dried over MgSO$_4$, filtered and evaporated. The crude residue is purified by prep. HPLC (Method E) to yield the title compound as a yellow oil.

LC-A: $t_R$=0.58 min; $[M+H]^+$=486.3

Precursor AE1

1-(2-Dimethylamino-ethyl)-3-(1,2,3,4-tetrahydro-isoquinolin-5-ylmethyl)-1-(2-trifluoromethyl-benzyl)-urea To a solution of 5-[3-(2-dimethylamino-ethyl)-3-(2-trifluoromethyl-benzyl)-ureidomethyl]-3,4-dihydro-1H-isoquinoline-2-carboxylic acid tert-butyl ester Precursor AF1 (170 mg, 0.197 mmol) in 5 mL DCM is added 0.5 mL TFA. The yellowish solution is sirred overnight at RT. The reaction mixture is then poured into water. The resulting aq. phase is then basified (pH=8-9) with sat. aq. NaHCO$_3$ soln. and extracted twice with DCM. The combined organic phase are washed with brine, dried over MgSO$_4$, filtered and concentrated. This yields quantitatively the title compound as a yellow oil.

LC-A: $t_R$=0.54 min; $[M+H]^+$=435.2

Precursor AF1

5-[3-(2-Dimethylamino-ethyl)-3-(2-trifluoromethyl-benzyl)-ureidomethyl]-3,4-dihydro-1H-isoquinoline-2-carboxylic acid tert-butyl ester To a solution of 5-aminomethyl-3,4-dihydro-1H-isoquinoline-2-carboxylic acid tert-butyl ester [CAS #1196156-49-6](150 mg, 0.549 mmol) in 0.5 mL water cooled to 0° C. is added CDI (125 mg, 0.768 mmol). The resulting suspension is allowed to warm to RT over 1 h then N,N-Dimethyl-N'-(2-trifluoromethyl-benzyl)-ethane-1,2-diamine Amine 45 (189 mg, 0.768 mmol) is added and the reaction is allowed to stir overnight at RT. The mixture is then diluted in DCM and the layers are separated. The aq. phase is extracted twice with DCM. The combined organic phase is washed with water and brine then dried over MgSO$_4$, filtered and the solvent removed under reduced pressure. Flash-chromatography on silica-gel (Eluent: Hept./EtOAc 95:5 to 60:40) yields 128 mg (44%) of the title compound as a yellow oil.

LC-A: $t_R$=0.80 min; $[M+H]^+$=535.6

Example 569

3-(2-Cyclopropylmethyl-1,2,3,4-tetrahydro-isoquinolin-8-ylmethyl)-1-(2-dimethylamino-ethyl)-1-(2-trifluoromethyl-benzyl)-urea a) 2-Cyclopropylmethyl-1,2,34-tetrahydro-isoquinoline-8-carbonitrile To a solution of 1,2,3,4-tetrahydroisoquinoline-8-carbonitrile hydrochloride (500 mg, 2.57 mmol) in 8 mL DCM is added at RT, cyclopropanecarboxaldehyde (180 mg, 2.57 mmol) and DIPEA (398 mg, 3.08 mmol). The solution is stirred for 10 min then NaBH(OAc)$_3$ (1089 mg, 5.14 mmol) is added. The reaction mixture is allowed to stir at RT for 2 h, it is then poured into water and the resulting aq. phase is extracted twice with DCM. Evaporation of the solvent in vacuo yields 540 mg (99%) of the sub-title compound as a yellow oil which is used as such in the next step.

LC-B: tR=0.49 min; [M+H]⁺=213.4 b) (2-(Cyclopropylmethyl)-1,2,3,4-tetrahydroisoquinolin-8-yl)methanamine

To a solution of CoCl₂ (258 mg, 1.98 mmol) in 10 mL MeOH is added dropwise at RT a solution of 2-cyclopropylmethyl-1,2,3,4-tetrahydro-isoquinoline-8-carbonitrile (540 mg, 1.65 mmol) in 5 mL MeOH. The resulting purple solution is stirred for 10 min then cooled at 0° C. with an ice bath. NaBH₄ (313 mg, 8.27 mmol) is then slowly added portionwise and the resulting black suspension is stirred for 1 h at 0° C. then at RT overnight. The solution is cooled again to 0° C. and another 100 mg of CoCl2 and 100 mg of NaBH₄ are added again and the stirring is continued for 6 h at RT. To the black suspension is added sat. aq. NH₄Cl soln. and this biphasic mixture is allowed to stir for 30 min at RT. It is then basified to pH=12 by addition of 25% NH₄OH soln. in water. The resulting aq. phase is extracted three times with DCM and the combined organic phases are washed with NaCl then dried over MgSO₄, filtered and evaporated. Flash-chromatography on silica-gel (Eluent: DCM/MeOH from 100:0 to 80:20) yields 75 mg (21%) of the sub-title compound as a brown oil.

LC-A: $t_R$=0.27 min; [M+H]⁺=217.3 c) The title compound is obtained from (2-(cyclopropylmethyl)-1,2,3,4-tetrahydroisoquinolin-8-yl)methanamine (75 mg, 0.239 mmol) and Amine 45 using the method described for the synthesis of Precursor AF1 to yield the title compound as a brown oil.

LC-A: $t_R$=0.59 min; [M+H]⁺=489.5

Example 573

N-(2-Dimethylamino-ethyl)-2-(2-propyl-1,2,3,4-tetrahydro-isoquinolin-5-ylamino)-N-(2-trifluoromethyl-benzyl)-acetamide a) Acetic acid acetoxy-[(2-dimethylamino-ethyl)-(2-trifluoromethyl-benzyl)-carbamoyl]-methyl ester A solution of freshly distilled diacetoxyacetyl chloride (McCaully, R. J. U.S. Pat. No. 3,896,170, 1975) (1.42 g, 6.81 mmol) in 5 mL DCM is added dropwise to a suspension of N,N-dimethyl-N'-(2-trifluoromethyl-benzyl)-ethane-1,2-diamine (1.29 g, 5.24 mmol) and KHCO₃ (2.622 g, 26.2 mmol) in 5 mL DCM at −10° C. over 15 min. The reaction mixture is allowed to stir at rt for 1 h. 20 mL water is added. The layers are separated. The aqueous layer is extracted twice with 20 mL DCM. The combined organic phase is washed with 25 mL sat. aq. NaHCO₃ soln. and 25 mL brine then dried over MgSO₄, filtered and evaporated under reduced pressure to deliver 2.05 g of the sub-title compound as a light yellow oil; LC-A: $_R$=0.63 min; [M+H]⁺=405.10 b) A solution of acetic acid acetoxy-[(2-dimethylamino-ethyl)-(2-trifluoromethyl-benzyl)-carbamoyl]-methyl ester (552 mg, 1.23 mmol), acetic acid (3.8 mg, 0.06 mmol) and 2-propyl-1,2,3,4-tetrahydro-isoquinolin-5-ylamine (140 mg, 0.737 mmol) in 10 mL MeOH is allowed to stir at 40° C. for 18 h. The reaction mixture is allowed to cool down to rt and treated with NaBH₃CN (77.2 mg, 1.23 mmol), stirred for 1.5 h, and treated again with NaBH₃CN (38.6 mg, 0.62 mmol) for 18 h. The reaction mixture is quenched with 3 mL water and evaporated under reduced pressure. The residue is partitioned between 20 mL 1 N aq. NaOH sol. and 20 mL DCM. The layers are separated. The aqueous layer are extracted twice with 20 mL DCM. The combined organic layer is washed with 25 mL brine then dried over MgSO₄. The crude residue is purified by prep. HPLC (Method D) to yield 0.221 g of the title compound as a yellow solid. LC-C: $t_R$=0.58 min; [M+H]⁺=477.12

Example 574

N-(2-Dimethylamino-ethyl)-2-[2-(3-fluoro-propyl)-1,2,3,4-tetrahydro-isoquinolin-5-ylamino]-N-(2-trifluoromethyl-benzyl)-acetamide LC-C: $t_R$=0.58 min; [M+H]⁺=496.10 is prepared according to the method described for Example 573 from 2-(3-fluoro-propyl)-1,2,3,4-tetrahydro-isoquinolin-5-ylamine 2-Propyl-1,2,3,4-tetrahydro-isoquinolin-5-ylamine is obtained according to reaction B3 Step a) described above using 5-aminoisoquinoline and 1-iodopropane to prepare the intermediate 5-amino-2-propyl-isoquinolin-2-ium iodide which is reduced according to reaction reaction B3 Step b) to yield the title compound as a reddish oil. LC-A: $t_R$=0.34 min; [M+H]⁺=191.27

2-(3-Fluoro-propyl)-1,2,3,4-tetrahydro-isoquinolin-5-ylamine is obtained according to reaction B3 Step a) described above using 5-aminoisoquinoline and 1-fluoro-3-iodopropane to prepare the intermediate 5-amino-2-(3-fluoropropyl)-isoquinolin-2-ium iodide which is reduced according to reaction reaction B3 Step b) to yield the title compound as a reddish oil. LC-A: $t_R$=0.28 min; [M+H]⁺=209.19

Amine Building Blocks

Amines 1-162 are either commercially available or are prepared following one of the methods described below:

Amine 22

Method A

N'-(3-Chloro-pyridin-2-ylmethyl)-N,N-dimethyl-ethane-1,2-diamine

To a solution of 3-chloro-2-formylpyridine (1.5 g, 10.6 mmol) in 25 mL DCM are added 2-dimethylamino-ethyl-amine (1.27 mL, 11.7 mmol) and DIPEA (3.6 mL, 21.2 mmol). The resulting solution is treated portionswise with NaBH(OAc)₃ (3.37 g, 15.9 mmol) and allowed to stir for 18 h at RT. The reaction mixture is diluted with 10 mL DCM and washed with 25 mL aq. sat. NaHCO₃ solution. The aqueous phase is extracted twice with 20 mL DCM. The combined organic phase is washed with 70 mL brine, dried over MgSO₄, filtered and evaporated under reduced pressure. This yields the title compound (1.6 g, 71%) as a colourless liquid. LC-A: $t_R$=0.20 min; [M+H]⁺=214.17

Amine 50

Method B

N,N-Dimethyl-N'-[2-(3-trifluoromethyl-phenyl)-ethyl]-ethane-1,2-diamine

To a solution of 3-(trifluoromethyl)phenethyl bromide (1.34 mL, 7.9 mmol) in 20 mL EtOH is added NaI (3.58 g, 23.9 mmol). The suspension is refluxed for 1 h. The mixture is cooled to RT then a solution of 2-dimethylamino-ethyl-amine (4.32 mL, 39.5 mmol) in 15 mL EtOH is added dropwise. The mixture is stirred at RT for 2 h then refluxed overnight. The mixture is cooled to RT and EtOH is evaporated. 50 mL DCM is added and the white solid is filtered off. The mother liquid is washed with 50 mL water then the aqueous phase is extracted twice with 25 mL DCM. The combined organic layer is dried over MgSO$_4$, filtered and concentrated. Flash-chromatography on silica-gel (EtOAc/ MeOH/TEA 80:18:2) yields 0.84 g (41%) of the title compound as a light orange oil. LC-B: $t_R$=0.50 min; [M+H]$^+$=261.22

Amine 128

Method C

[2-(3,3-Difluoro-azetidin-1-yl)-2-oxo-ethyl]-N-(2-trifluoromethyl-benzyl)-amine a) (2-Trifluoromethyl-benzylamino)-acetic acid ethyl ester
To a solution of 2-(trifluoromethyl)benzaldehyde (0.379 mL, 2.87 mmol) in 30 mL DCM at RT are added glycine ethyl ester hydrochloride (401 mg, 2.87 mmol), DIPEA (0.949 mL, 5.74 mmol) and sodium triacetoxyborohydride (913 mg, 4.31 mmol) and the mixture is stirred at RT overnight then under reflux for 6 h. The mixture is cooled to RT then washed with 30 mL sat. aq. NaHCO$_3$. The combined organic layer is dried over Na$_2$SO$_4$, filtered and concentrated. Flash-chromatography on silica-gel (heptane/EtOAc 1:0 to 4:1) yields 0.35 g of the title compound as a colourless oil.
LC-A: $t_R$=0.56 min; [M+H]$^+$=262.12
b) N-(tert-Butoxycarbonyl)-(2-trifluoromethyl-benzylamino)-acetic acid ethyl ester
To a solution of (2-trifluoromethyl-benzylamino)-acetic acid ethyl ester (290 mg, 1.11 mmol) in 10 mL DCM at RT is added TEA (0.232 mL, 1.67 mmol) followed by di-tert-butyl dicarbonate (242 mg, 1.11 mmol). The mixture is stirred at RT for 72 h. The reaction mixture is washed with 10 mL sat. aq. NaHCO$_3$, followed by 10 mL brine, then dried over Na$_2$SO$_4$, filtered and evaporated to yield 0.395 g of the title compound as a colourless oil.
LC-A: $t_R$=0.99 min; [M+H—C(CH$_3$)]$^+$=305.93
c) A 2M solution of trimethylaluminum in toluene (1.18 mL, 2.35 mmol) is added at 0° C. to a solution of 3,3-difluoroazetidine hydrochloride (244 mg, 1.88 mmol) in 5 mL DCE then the mixture is stirred at RT for 45 min. A solution of N-(tert-butoxycarbonyl)-(2-trifluoromethyl-benzylamino)-acetic acid ethyl ester (340 mg, 0.941 mmol), in 5 mL DCE is added and the reaction mixture is stirred at 85° C. for 2 h. The mixture is cooled to 0° C. and diluted with 10 mL DCM. 20 mL sat. aq. NaHCO$_3$ soln. is slowly added. The aq. layer is extracted twice with 20 mL DCM and the combined organic layer is dried over MgSO$_4$, filtered and concentrated. Flash-chromatography on silica-gel (Hept./ EtOAc 4:1 to 0:1) yields 0.188 g of the title compound as a yellowish oil. LC-A: $t_R$=0.55 min; [M+H]$^+$=309.04

Amine 130

Method D

[2-(3,3-Difluoro-azetidin-1-yl)-ethyl]-(2-trifluoromethyl-benzyl)-amine

A solution of sodium borohydride (225 mg, 5.94 mmol) in 5 mL THF is cooled to 0° C. then a solution of iodine (603 mg, 2.37 mmol) in 5 mL THF is added dropwise at 0° C. After completion of the addition, a solution of [2-(3,3-difluoro-azetidin-1-yl)-2-oxo-ethyl]-N-(2-trifluoromethyl-benzyl)-amine (183 mg, 0.594 mmol) in 5 mL THF is slowly added to the colorless BH$_3$ solution and the reaction mixture is then warmed up to RT and stirred at RT overnight then at 70° C. in a sealed tube for 3 h. The reaction mixture is cooled to 0° C. and 25 mL water is added. The mixture is then extracted twice with 25 mL EtOAc. The combined organic layer is dried over Na$_2$SO$_4$, filtered and concentrated. The crude residue is then dissolved in 8 mL MeOH in a sealed tube, treated with 4 M HCl in 3 mL dioxane and shaken at 50° C. for 6 h. The mixture is then cooled to RT and concentrated. The residue is dissolved in 25 mL EtOAc and washed twice with 25 mL sat. aq. NaHCO$_3$. The organic layer is dried over Na$_2$SO$_4$, filtered and concentrated. Flash-chromatography on silica-gel (Hept./EtOAc 4:1 to 3:2) yields 0.161 g of the title compound as a light yellowish oil. LC-B: $t_R$=0.59 min; [M+H]$^+$=295.06

Amine 142

Method E rac-1-(2-Trifluoromethyl-benzylamino)-propan-2-ol

To a solution of 2-(trifluoromethyl)benzylamine (500 mg, 2.85 mmol) and rac-propylene oxide (0.2 mL, 2.85 mmol) in 10 mL MeCN is added at RT at once calcium trifluoromethanesulfonate (483 mg, 1.43 mmol). The yellow solution is stirred for 2 h at RT. MeCN is evaporated then 25 mL water is added and the mixture is extracted three times with 10 mL EtOAc. The combined organic phase is washed with brine, dried over MgSO$_4$, filtered and evaporated. Flash-chromatography on silica-gel (Eluent: DCM/(TEA 0.4% in MeOH) 99:1 to 95:5) yields 0.504 g of the title compound as a yellowish oil. LC-A: $t_R$=0.49 min; [M+H]$^+$=234.24

Amine 152

Method F

2-Methyl-4-(2-trifluoromethyl-benzylamino)-butan-2-ol a) Ethyl 3-((2-(trifluoromethyl)benzyl)amino)propanoate
A solution of 2-trifluorobenzylamine (500 mg, 2.85 mmol) and ethyl acrylate (0.31 mL, 2.85 mmol) in 5 mL EtOH is stirred at RT overnight. 25 mL water is added and the aq. solution is extracted twice with 20 mL DCM. The combined organic layer is washed with 25 mL brine, dried over MgSO$_4$, filtered and evaporated. Flash-chromatography on silica-gel (Eluent: Hept./EtOAc 1:1 to 1:4) yields 0.731 g of the title compound as a colourless oil. LC-A: $t_R$=0.58 min; [M+H]$^+$=276.31
b) Ethyl 3-((tert-butoxycarbonyl)(2-(trifluoromethyl)benzyl)amino)propanoate
A solution of ethyl 3-((2-trifluormethyl-benzyl)amino) propanoate (430 mg, 1.5 mmol) in 5 mL THF is treated with di-tert-butyl dicarbonate (635 mg, 3 mmol) and stirred at RT overnight. 2-Dimethylamino-ethylamin (264 mg, 3 mmol) is added and the stirring is continued for 15 min at RT. 25 mL sat. aq. NH$_4$Cl soln. is added and the residual aq. solution is extracted twice with 25 mL DCM. The combined organic layer is washed with 25 mL brine, dried over MgSO$_4$, filtered and evaporated. Flash-chromatography on silica-gel (Eluent: heptane/EtOAc 19:1 to 4:1) yields 0.491 g of the title compound as a colourless oil. LC-A: $t_R$=1.01 min; [M+H]$^+$=376.25 c) tert-Butyl (3-hydroxy-3-methylbutyl)(2-(trifluoromethyl)benzyl)carbamate

A solution of ethyl 3-((tert-butoxycarbonyl)(2-trifluormethyl-benzyl)amino)propanoate (491 mg, 1.3 mmol) in 4 mL THF is added over 20 min at −78° C. under argon to a solution of 1.6 M methyl lithium in diethylether (2.28 mL, 3.65 mmol). The resulting brownish solution is stirred for 1.5 h then quenched by the addition of 25 mL water. The mixture is extracted twice with 25 mL EtOAc. The combined organic layer is washed with 25 mL sat. aq. NaHCO$_3$, dried over MgSO$_4$, filtered and evaporated. Flash-chromatography on silica-gel (Eluent: Hept./EtOAc 19:1 to 0:1) yields 0.253 g of the title compound as a colourless oil. LC-A: $t_R$=0.94 min; [M+H]$^+$=362.23 d) 2-methyl-4-((2-(trifluoromethyl)benzyl)amino)butan-2-ol

A solution of tert-butyl (3-hydroxy-3-methylbutyl)(2-(trifluoromethyl)benzyl)carbamate (253 mg, 0.7 mmol) in 5 mL DCM is treated with 4 N HCl solution in dioxane (0.332 mL, 2.1 mmol) and stirred at RT for 1 h. The reaction mixture is treated with 25 mL sat. aq. NaHCO$_3$ and extracted twice with 25 mL DCM. The organic layers are washed with 25 mL sat. aq. NaHCO$_3$, dried over MgSO$_4$, filtered and evaporated to yield 0.178 g of the title compound as a brownish oil. LC-A: $t_R$=0.56 min; [M+H]$^+$=262.31

Amines listed in Table 36 below are commercially available or are prepared by applying either one of the above-mentioned methods A, B, C, D, E or F using commercially available starting materials or building blocks whose synthesis is described after table 36. Prepared amines are characterized by their LC-data.

TABLE 36

| Amine No | Compound name |
|---|---|
| 1 | (2-Chloro-benzyl)-ethyl-amine |
| 2 | 2-Benzylamino-ethanol |
| 3 | 3-(Benzylamino)propanenitrile |
| 4 | Benzyl-cyclopropylmethyl-amine |
| 5 | 1-Methyl-3-phenylpiperazine |
| 6 | Cyclopropyl-(2,3-dimethyl-benzyl)-amine |
| 7 | N-Benzyl-N',N'-dimethylethane-1,2-diamine |
| 8 | 3-Benzylamino-propionamide |
| 9 | Benzyl-(3-methyl-butyl)-amine |
| 10 | N'-Benzyl-N,N-dimethylpropane-1,3-diamine |
| 11 | N,N-Dimethyl-N'-phenethyl-ethane-1,2-diamine |
| 12 | N,N-Dimethyl-N'-(3-methyl-benzyl)-ethane-1,2-diamine |
| 13 | N,N-Dimethyl-N'-(4-methylbenzyl)ethane-1,2-diamine |
| 14 | N,N-Dimethyl-N'-(2-methylbenzyl)ethane-1,2-diamine |
| 15 | [(4-Chlorophenyl)methyl][2-(dimethylamino)ethyl]amine |
| 16 | N'-(3-Chloro-benzyl)-N,N-dimethyl-ethane-1,2-diamine |
| 17 | N'-(2-Chlorobenzyl)-N,N-dimethylethane-1,2-diamine |
| 18 | N'-(4-Fluoro-benzyl)-N,N-dimethyl-ethane-1,2-diamine |
| 19 | N'-(3-Fluoro-benzyl)-N,N-dimethyl-ethane-1,2-diamine |
| 20 | N'-(2-Fluoro-benzyl)-N,N-dimethyl-ethane-1,2-diamine |
| 21 | Benzylamino-acetic acid ethyl ester |
| 22 | N'-(3-Chloro-pyridin-2-ylmethyl)-N,N-dimethyl-ethane-1,2-diamine |
| 23 | tert-Butyl 3-(benzylamino)pyrrolidine-1-carboxylate<br>LC-A: $t_R$ = 0.52 min; [M + H]$^+$ = 277.2 |
| 24 | N,N-Dimethyl-N'-(2-o-tolyl-ethyl)-ethane-1,2-diamine |
| 25 | Benzyl[2-(diethylamino)ethyl]amine |
| 26 | N'-(4-Methoxy-benzyl)-N,N-dimethyl-ethane-1,2-diamine |
| 27 | N'-(3-Methoxy-benzyl)-N,N-dimethyl-ethane-1,2-diamine |
| 28 | N'-(2-Methoxy-benzyl)-N,N-dimethyl-ethane-1,2-diamine |
| 29 | Benzyl-pyridin-2-ylmethyl-amine |
| 30 | Benzyl-(2-pyrrolidin-1-yl-ethyl)-amine |
| 31 | N-Benzyl-N-(1,1-dioxidotetrahydrothien-3-yl)amine |
| 32 | Benzyl-(1-methyl-1H-imidazol-2-ylmethyl)-amine |
| 33 | N'-Benzyl-N-butyl-N-methyl-ethane-1,2-diamine |

TABLE 36-continued

| Amine No | Compound name |
|---|---|
| 34 | N,N-Dimethyl-N'-((E)-2-methyl-3-phenyl-allyl)-ethane-1,2-diamine<br>LC-A: $t_R$ = 0.47 min; [M + H]$^+$ = 219.5 |
| 35 | 3-(2-Trifluoromethyl-benzylamino)-propionitrile |
| 36 | N-Benzyl-2-(1-methylpyrrolidin-2-yl)ethanamine<br>LC-A: $t_R$ = 0.31 min; [M + H]$^+$ = 219.5 |
| 37 | (2-Chloro-benzyl)-(2-pyrrolidin-1-yl-ethyl)-amine |
| 38 | (2-Fluoro-benzyl)-(2-pyrrolidin-1-yl-ethyl)-amine |
| 39 | 2-(1-Methylpyrrolidin-2-yl)-N-phenethylethanamine |
| 40 | (2-Chloro-4-fluoro-benzyl)-(2-pyrrolidin-1-yl-ethyl)-amine |
| 41 | (2,4-Difluoro-benzyl)-(2-pyrrolidin-1-yl-ethyl)-amine |
| 42 | N-Benzyl-N-[2-(4-fluorophenyl)ethyl]amine |
| 43 | N,N-Dimethyl-N'-(3-trifluoromethyl-benzyl)-ethane-1,2-diamine |
| 44 | N,N-Dimethyl-N'-(4-trifluoromethyl-benzyl)-ethane-1,2-diamine |
| 45 | N,N-Dimethyl-N'-(2-trifluoromethyl-benzyl)-ethane-1,2-diamine |
| 46 | (3-Methyl-butyl)-(2-trifluoromethyl-benzyl)-amine |
| 47 | N,N-Dimethyl-N'-(6-trifluoromethyl-pyridin-2-ylmethyl)-ethane-1,2-diamine<br>LC-A: $t_R$ = 0.30 min; [M + H]$^+$ = 248.1 |
| 48 | N,N-Dimethyl-N'-(3-trifluoromethyl-pyridin-2-ylmethyl)-ethane-1,2-diamine<br>LC-A: $t_R$ = 0.25 min; [M + H]$^+$ = 248.1 |
| 49 | N'-(4-Fluoro-2-trifluoromethyl-benzyl)-N,N-dimethyl-ethane-1,2-diamine<br>LC-A: $t_R$ = 0.42 min; [M + H]$^+$ = 265.1 |
| 50 | N,N-Dimethyl-N'-[2-(3-trifluoromethyl-phenyl)-ethyl]-ethane-1,2-diamine |
| 51 | N,N-Dimethyl-N'-[2-(4-trifluoromethyl-phenyl)-ethyl]-ethane-1,2-diamine<br>LC-A: $t_R$ = 0.46 min; [M + H]$^+$ = 261.1 |
| 52 | N,N-Dimethyl-N'-[2-(2-trifluoromethyl-phenyl)-ethyl]-ethane-1,2-diamine<br>LC-A: $t_R$ = 0.48 min; [M + H]$^+$ = 261.1 |
| 53 | N,N-dimethyl-N'-{1-[2-(trifluoromethyl)phenyl]ethyl}ethane-1,2-diamine |
| 54 | [2-(3,4-Dimethoxyphenyl)ethyl][2-(dimethylamino)ethyl]amine |
| 55 | (E)-N-(2-(1-Methylpyrrolidin-2-yl)ethyl)-3-phenylprop-2-en-1-amine |
| 56 | N-(2-(1-methylpyrrolidin-2-yl)ethyl)-3-phenylpropan-1-amine<br>LC-A: $t_R$ = 0.41 min; [M + H]$^+$ = 247.3 |
| 57 | (E)-2-methyl-N-(2-(1-methylpyrrolidin-2-yl)ethyl)-3-phenylprop-2-en-1-amine<br>LC-A: $t_R$ = 0.57 min; [M + H]$^+$ = 259.1 |
| 58 | (Tetrahydro-pyran-4-yl)-(2-trifluoro methyl-benzyl)-amine |
| 59 | (4-Methyl-thiazol-2-ylmethyl)-(2-trifluoromethyl-benzyl)-amine |
| 60 | (2-Pyrrolidin-1-yl-ethyl)-(2-trifluoromethyl-benzyl)-amine |
| 61 | (1-Methyl-piperidin-4-yl)-(2-trifluoromethyl-benzyl)-amine |
| 62 | 1-Methyl-N-(2-(trifluoromethyl)benzyl)piperidin-3-amine |
| 63 | N,N-Diethyl-N'-(2-trifluoromethyl-benzyl)-ethane-1,2-diamine |
| 64 | tert-Butyl 3-(benzylamino)pyrrolidine-1-carboxylate |
| 65 | 4-[((2-Trifluoromethyl-benzylamino)-methyl]-3H-pyridin-2-one<br>LC-A: $t_R$ = 0.49 min; [M + H]$^+$ = 283.6 |
| 66 | 1-[2-(2-Trifluoromethyl-benzylamino)-ethyl]-pyrrolidin-2-one<br>LC-A: $t_R$ = 0.51 min; [M + H]$^+$ = 287.2 |
| 67 | (2-Morpholin-4-yl-ethyl)-(2-trifluoromethyl-benzyl)-amine |
| 68 | 1-[2-(2-Trifluoromethyl-benzylamino)-ethyl]-imidazolidin-2-one<br>LC-A: $t_R$ = 0.51 min; [M + H]$^+$ = 288.6 |
| 69 | Ethyl 2-(((2-(trifluoromethyl)benzyl)amino)methyl)cyclopropanecarboxylate<br>LC-A: $t_R$ = 0.63 min; [M + H]$^+$ = 302.1 |
| 70 | 1-(1-Ethyl-1H-pyrazol-3-yl)-N-(2-(trifluoromethyl)benzyl)-ethanamine<br>LC-A: $t_R$ = 0.63 min; [M + H]$^+$ = 298.5 |
| 71 | [2-(4-Trifluoromethyl-benzylamino)-ethyl]-carbamic acid tert-butyl ester<br>LC-A: $t_R$ = 0.78 min; [M + H]$^+$ = 319.1 |
| 72 | (2-Benzyloxy-ethyl)-(2-trifluoromethyl-benzyl)-amine<br>LC-A: $t_R$ = 0.70 min; [M + H]$^+$ = 310.1 |
| 73 | Methyl-[2-(2-trifluoromethyl-benzylamino)-ethyl]-carbamic acid tert-butyl ester<br>LC-A: $t_R$ = 0.70 min; [M + H]$^+$ = 333.2 |
| 74 | tert-Butyl 2,2-dimethyl-4-(((2-(trifluoromethyl)benzyl)amino)-methyl)oxazolidine-3-carboxylate<br>LC-A: $t_R$ = 0.77 min; [M + H]$^+$ = 389.0 |
| 75 | rac-[2-(1-Methyl-pyrrolidin-2-yl)-ethyl]-(2-trifluoromethyl-benzyl)-amine<br>LC-A: $t_R$ = 0.43 min; [M + H]$^+$ = 287.17 |

TABLE 36-continued

| Amine No | Compound name |
|---|---|
| 76 | (3-Pyrrolidin-1-yl-propyl)-(2-trifluoromethyl-benzyl)-amine<br>LC-A: $t_R$ = 0.43 min; [M + H]$^+$ = 287.18 |
| 77 | (2-Benzylamino-ethyl)-methyl-carbamic acid tert-butyl ester<br>LC-A: $t_R$ = 0.75 min; [M + H]$^+$ = 265.2 |
| 78 | 4-Benzylamino-piperidine-1-carboxylic acid tert-butyl ester<br>LC-A: $t_R$ = 0.71 min; [M + H]$^+$ = 291.12 |
| 79 | Methyl-{2-[(3-trifluoromethyl-pyridin-2-ylmethyl)-amino]-ethyl}-carbamic acid tert-butyl ester<br>LC-A: $t_R$ = 0.61 min; [M + H]$^+$ = 334.23 |
| 80 | 4-(2-Trifluoromethyl-benzylamino)-piperidine-1-carboxylic acid tert-butyl ester<br>LC-A: $t_R$ = 0.72 min; [M + H]$^+$ = 359.18 |
| 81 | rac-3-[(2-Trifluoromethyl-benzylamino)-methyl]-pyrrolidine-1-carboxylic acid tert-butyl ester<br>LC-A: $t_R$ = 0.70 min; [M + H]$^+$ = 359.16 |
| 82 | rac-3-(2-Trifluoromethyl-benzylamino)-pyrrolidine-1-carboxylic acid tert-butyl ester<br>LC-A: $t_R$ = 0.66 min; [M + H]$^+$ = 345.23 |
| 83 | N,N-Dimethyl-N'-pyrimidin-4-ylmethyl-ethane-1,2-diamine<br>LC-G: $t_R$ = 0.54 min; [M + H]$^+$ = 181.3 |
| 84 | N,N-Dimethyl-N'-(3-methyl-pyridin-2-ylmethyl)-ethane-1,2-diamine<br>LC-G: $t_R$ = 1.19 min; [M + H]$^+$ = 194.2 |
| 85 | N,N-Dimethyl-N'-pyridin-2-ylmethyl-ethane-1,2-diamine<br>LC-G: $t_R$ = 0.90 min; [M + H]$^+$ = 180.3 |
| 86 | N,N-Dimethyl-N'-(5-methyl-pyridin-2-ylmethyl)-ethane-1,2-diamine<br>LC-G: $t_R$ = 1.13 min; [M + H]$^+$ = 194.3 |
| 87 | N,N-Dimethyl-N'-(6-methyl-pyridin-2-ylmethyl)-ethane-1,2-diamine<br>LC-G: $t_R$ = 1.0 min; [M + H]$^+$ = 194.2 |
| 88 | N,N-Dimethyl-N'-pyrimidin-2-ylmethyl-ethane-1,2-diamine<br>LC-G: $t_R$ = 0.61 min; [M + H]$^+$ = 181.2 |
| 89 | N'-(5-Chloro-pyridin-2-ylmethyl)-N,N-dimethyl-ethane-1,2-diamine<br>LC-G: $t_R$ = 1.18 min; [M + H]$^+$ = 214.2 |
| 90 | N'-(5-Chloro-pyridin-3-ylmethyl)-N,N-dimethyl-ethane-1,2-diamine<br>LC-G: $t_R$ = 1.08 min; [M + H]$^+$ = 214.2 |
| 91 | N,N-Dimethyl-N'-pyridin-3-ylmethyl-ethane-1,2-diamine<br>LC-G: $t_R$ = 0.63 min; [M + H]$^+$ = 180.3 |
| 92 | N,N-Dimethyl-N'-(2-methyl-2H-pyrazol-3-ylmethyl)-ethane-1,2-diamine<br>LC-G: $t_R$ = 0.61 min; [M + H]$^+$ = 183.3 |
| 93 | N,N-Dimethyl-N'-thiazol-2-ylmethyl-ethane-1,2-diamine<br>LC-G: $t_R$ = 0.73 min; [M + H]$^+$ = 186.2 |
| 94 | N,N-Dimethyl-N'-(4-methyl-thiazol-2-ylmethyl)-ethane-1,2-diamine<br>LC-G: $t_R$ = 0.90 min; [M + H]$^+$ = 200.2 |
| 95 | N'-(5-Fluoro-pyridin-2-ylmethyl)-N,N-dimethyl-ethane-1,2-diamine<br>LC-G: $t_R$ = 0.90 min; [M + H]$^+$ = 198.2 |
| 96 | N,N-Dimethyl-N'-pyridin-4-ylmethyl-ethane-1,2-diamine<br>LC-G: $t_R$ = 0.60 min; [M + H]$^+$ = 180.3 |
| 97 | N,N-Dimethyl-N'-(5-methyl-isoxazol-3-ylmethyl)-ethane-1,2-diamine<br>LC-G: $t_R$ = 0.77 min; [M + H]$^+$ = 184.3 |
| 98 | N'-(2,6-Difluoro-benzyl)-N,N-dimethyl-ethane-1,2-diamine<br>LC-G: $t_R$ = 1.12 min; [M + H]$^+$ = 215.2 |
| 99 | N'-(3-Fluoro-pyridin-2-ylmethyl)-N,N-dimethyl-ethane-1,2-diamine<br>LC-G: $t_R$ = 0.83 min; [M + H]$^+$ = 198.2 |
| 100 | N-(2-Dimethylamino-pyrimidin-5-ylmethyl)-N',N'-dimethyl-ethane-1,2-diamine<br>LC-G: $t_R$ = 0.92 min; [M + H]$^+$ = 224.2 |
| 101 | [2-(2-Trifluoromethyl-benzylamino)-ethyl]-carbamic acid tert-butyl ester<br>LC-A: $t_R$ = 0.65 min; [M + H]$^+$ = 319.08 |
| 102 | (S)-3-[(2-Trifluoromethyl-benzylamino)-methyl]-pyrrolidine-1-carboxylic acid tert-butyl ester<br>LC-A: $t_R$ = 0.70 min; [M + H]$^+$ = 359.27 |
| 103 | (R)-3-[(2-Trifluoromethyl-benzylamino)-methyl]-pyrrolidine-1-carboxylic acid tert-butyl ester<br>LC-A: $t_R$ = 0.70 min; [M + H]$^+$ = 359.23 |
| 104 | (3,3-Dimethyl-butyl)-(2-trifluoromethyl-benzyl)-amine<br>LC-A: $t_R$ = 0.69 min; [M + H]$^+$ = 260.22 |
| 105 | (3,3-Dimethyl-butyl)-(3-trifluoromethyl-pyridin-2-ylmethyl)-amine<br>LC-A: $t_R$ = 0.64 min; [M + H]$^+$ = 261.22 |
| 106 | (3,3-Dimethyl-butyl)-(3-methyl-pyridin-2-ylmethyl)-amine<br>LC-A: $t_R$ = 0.59 min; [M + H]$^+$ = 207.27 |
| 107 | 4-[2-(2-Trifluoromethyl-benzylamino)-ethyl]-piperazine-1-carboxylic acid tert-butyl ester<br>LC-A: $t_R$ = 0.61 min; [M + H]$^+$ = 388.26 |
| 108 | (2-Piperidin-1-yl-ethyl)-(2-trifluoromethyl-benzyl)-amine<br>LC-A: $t_R$ = 0.43 min; [M + H]$^+$ = 287.31 |
| 109 | (2-Azepan-1-yl-ethyl)-(2-trifluoromethyl-benzyl)-amine<br>LC-A: $t_R$ = 0.47 min; [M + H]$^+$ = 301.23 |
| 110 | N,N-Diisopropyl-N'-(2-trifluoromethyl-benzyl)-ethane-1,2-diamine<br>LC-A: $t_R$ = 0.46 min; [M + H]$^+$ = 303.22 |
| 111 | N-Cyclopropyl-N-methyl-N'-(2-trifluoromethyl-benzyl)-ethane-1,2-diamine<br>LC-A: $t_R$ = 0.42 min; [M + H]$^+$ = 273.17 |
| 112 | N,N-Dimethyl-N'-(3-trifluoromethoxy-benzyl)-ethane-1,2-diamine<br>LC-A: $t_R$ = 0.41 min; [M + H]$^+$ = 263.14 |
| 113 | 4-(2-Trifluoromethyl-benzylamino)-cyclohexanol<br>LC-A: $t_R$ = 0.50 min; [M + H]$^+$ = 274.02 |
| 114 | 1-Methoxy-3-(2-trifluoromethyl-benzylamino)-propan-2-ol<br>LC-A: $t_R$ = 0.51 min; [M + H]$^+$ = 264.14 |
| 115 | (2-Trifluoromethyl-benzyl)-(3,3,3-trifluoro-propyl)-amine<br>LC-A: $t_R$ = 0.59 min; [M + H]$^+$ = 272.26 |
| 116 | (2-Methoxy-ethyl)-(2-trifluoromethyl-benzyl)-amine<br>LC-A: $t_R$ = 0.52 min; [M + H]$^+$ = 234.2 |
| 117 | [1,4]Dioxan-2-ylmethyl-(2-trifluoromethyl-benzyl)-amine<br>LC-A: $t_R$ = 0.53 min; [M + H]$^+$ = 276.75 |
| 118 | N,N-Dimethyl-N'-(2-trifluoromethoxy-benzyl)-ethane-1,2-diamine<br>LC-A: $t_R$ = 0.37 min; [M + H]$^+$ = 263.16 |
| 119 | N,N-Dimethyl-N'-(4-trifluoromethoxy-benzyl)-ethane-1,2-diamine<br>LC-A: $t_R$ = 0.42 min; [M + H]$^+$ = 263.15 |
| 120 | [2-(4,4-Difluoro-piperidin-1-yl)-ethyl]-(2-trifluoromethyl-benzyl)-amine<br>LC-A: $t_R$ = 0.57 min; [M + H]$^+$ = 323.06 |
| 121 | N-Methyl-N-(2,2,2-trifluoro-ethyl)-N'-(2-trifluoromethyl-benzyl)-ethane-1,2-diamine<br>LC-A: $t_R$ = 0.65 min; [M + H]$^+$ = 315.08 |
| 122 | [2-(4,4-Difluoro-piperidin-1-yl)-ethyl]-(3-trifluoromethyl-pyridin-2-ylmethyl)-amine<br>LC-A: $t_R$ = 0.48 min; [M + H]$^+$ = 324.09 |
| 123 | N-Methyl-N-(2,2,2-trifluoro-ethyl)-N'-(3-trifluoromethyl-pyridin-2-ylmethyl)-ethane-1,2-diamine LC-A: $t_R$ = 0.61 min; [M + H]$^+$ = 317.2 |
| 124 | [2-(3,3-Difluoro-piperidin-1-yl)-ethyl]-(2-trifluoromethyl-benzyl)-amine<br>LC-A: $t_R$ = 0.64 min; [M + H]$^+$ = 323.06 |
| 125 | [2-(3,3-Difluoro-pyrrolidin-1-yl)-ethyl]-(2-trifluoromethyl-benzyl)-amine<br>LC-A: $t_R$ = 0.62 min; [M + H]$^+$ = 309.07 |
| 126 | [2-(3,3-Difluoro-piperidin-1-yl)-ethyl]-(3-trifluoromethyl-pyridin-2-ylmethyl)-amine<br>LC-A: $t_R$ = 0.58 min; [M + H]$^+$ = 324.08 |
| 127 | [2-(3,3-Difluoro-pyrrolidin-1-yl)-ethyl]-(3-trifluoromethyl-pyridin-2-ylmethyl)-amine<br>LC-A: $t_R$ = 0.56 min; [M + H]$^+$ = 310.07 |
| 128 | [2-(3,3-difluoro-azetidin-1-yl)-2-oxo-ethyl]-N-(2-trifluoromethyl-benzyl)-amine<br>LC-A: $t_R$ = 0.55 min; [M + H]$^+$ = 309.04 |
| 129 | [2-(3,3-difluoro-azetidin-1-yl)-2-oxo-ethyl]-N-(3-trifluoromethyl-pyridin-2-ylmethyl)-amine LC-A: $t_R$ = 0.51 min; [M + H]$^+$ = 310.02 |
| 130 | [2-(3,3-Difluoro-azetidin-1-yl)-ethyl]-(2-trifluoromethyl-benzyl)-amine<br>LC-A: $t_R$ = 0.59 min; [M + H]$^+$ = 295.06 |
| 131 | (2-Methanesulfonyl-ethyl)-(2-trifluoromethyl-benzyl)-amine<br>LC-A: $t_R$ = 0.51 min; [M + H]$^+$ = 282.09 |
| 132 | N-[2-(2-Trifluoromethyl-benzylamino)-ethyl]-methanesulfonamide<br>LC-A: $t_R$ = 0.50 min; [M + H]$^+$ = 297.25 |

TABLE 36-continued

| Amine No | Compound name |
|---|---|
| 133 | N-Ethyl-N-methyl-N'-(2-trifluoromethyl-benzyl)-ethane-1,2-diamine<br>LC-A: $t_R$ = 0.40 min; [M + H]$^+$ = 261.31 |
| 134 | Ethyl-[2-(2-trifluoromethyl-benzylamino)-ethyl]-carbamic acid tert-butyl ester<br>LC-A: $t_R$ = 0.72 min; [M + H]$^+$ = 347.30 |
| 135 | 2-(2-Trifluoromethyl-benzylamino)-ethanesulfonic acid amide<br>LC-A: $t_R$ = 0.46 min; [M + H]$^+$ = 283.22 |
| 136 | N'-(2-Bromo-benzyl)-N,N-dimethyl-ethane-1,2-diamine<br>LC-A: $t_R$ = 0.31 min; [M + H]$^+$ = 259.01 |
| 137 | [2-(2-Bromo-benzylamino)-ethyl]-methyl-carbamic acid tert-butyl ester<br>LC-A: $t_R$ = 0.66 min; [M + H]$^+$ = 343.02 |
| 138 | N'-(3-Bromo-pyridin-2-ylmethyl)-N,N-dimethyl-ethane-1,2-diamine<br>LC-A: $t_R$ = 0.21 min; [M + H]$^+$ = 260.06 |
| 139 | N'-(3-Bromo-benzyl)-N,N-dimethyl-ethane-1,2-diamine<br>LC-A: $t_R$ = 0.36 min; [M + H]$^+$ = 257.05 |
| 140 | N'-(4-Bromo-benzyl)-N,N-dimethyl-ethane-1,2-diamine<br>LC-A: $t_R$ = 0.36 min; [M + H]$^+$ = 257.05 |
| 141 | N'-(3-Bromo-pyridin-4-ylmethyl)-N,N-dimethyl-ethane-1,2-diamine<br>LC-A: $t_R$ = 0.22 min; [M + H]$^+$ = 258.06 |
| 142 | rac-1-(2-Trifluoromethyl-benzylamino)-propan-2-ol<br>LC-A: $t_R$ = 0.49 min; [M + H]$^+$ = 234.23 |
| 143 | 2-Methyl-1-(2-trifluoromethyl-benzylamino)-propan-2-ol<br>LC-A: $t_R$ = 0.52 min; [M + H]$^+$ = 248.25 |
| 144 | rac-1,1,1-Trifluoro-3-(2-trifluoromethyl-benzylamino)-propan-2-ol<br>LC-A: $t_R$ = 0.59 min; [M + H]$^+$ = 288.21 |
| 145 | 1-[(2-Trifluoromethyl-benzylamino)-methyl]-cyclopentanol<br>LC-A: $t_R$ = 0.58 min; [M + H]$^+$ = 274.06 |
| 146 | N-(4-methoxybenzyl)-N-(2,2,2-trifluoroethyl)-N'-(2-(trifluoromethyl)benzyl)ethane-1,2-diamine<br>LC-A: $t_R$ = 0.79 min; [M + H]$^+$ = 421.19 |
| 147 | Allyl-(3-methyl-pyridin-2-ylmethyl)-amine<br>LC-A: $t_R$ = 0.39 min; [M + H]$^+$ = 163.12 |
| 148 | N-Allyl-N-methyl-N'-(2-trifluoromethyl-benzyl)-ethane-1,2-diamine<br>LC-A: $t_R$ = 0.43 min; [M + H]$^+$ = 273.14 |
| 149 | N-(2-Fluoro-ethyl)-N-methyl-N'-(2-trifluoromethyl-benzyl)-ethane-1,2-diamine<br>LC-A: $t_R$ = 0.42 min; [M + H]$^+$ = 279.10 |
| 150 | (3-Methyl-oxetan-3-ylmethyl)-(2-trifluoromethyl-benzyl)-amine<br>LC-A: $t_R$ = 0.52 min; [M + H]$^+$ = 260.28 |
| 151 | N-Methyl-N-prop-2-ynyl-N'-(2-trifluoromethyl-benzyl)-ethane-1,2-diamine<br>LC-A: $t_R$ = 0.47 min; [M + H]$^+$ = 271.12 |
| 152 | 2-Methyl-4-(2-trifluoromethyl-benzylamino)-butan-2-ol<br>LC-A: $t_R$ = 0.56 min; [M + H]$^+$ = 262.31 |
| 153 | [2-(2-Chloro-benzylamino)-ethyl]-methyl-carbamic acid tert-butyl ester<br>LC-A: $t_R$ = 0.75 min; [M + H]$^+$ = 299.27 |
| 154 | {2-[(3-Chloro-pyridin-2-ylmethyl)-amino]-ethyl}-methyl-carbamic acid tert-butyl ester<br>LC-A: $t_R$ = 0.59 min; [M + H]$^+$ = 300.27 |
| 155 | Thiazol-5-ylmethyl-(2-trifluoromethyl-benzyl)-amine<br>LC-A: $t_R$ = 0.52 min; [M + H]$^+$ = 273.19 |
| 156 | (2-Chloro-benzyl)-[2-(4,4-difluoro-piperidin-1-yl)-ethyl]-amine<br>LC-A: $t_R$ = 0.50 min; [M + H]$^+$ = 289.25 |
| 157 | Ethyl-[2-(2-trifluoromethyl-benzylamino)-ethyl]-carbamic acid tert-butyl ester<br>LC-A: $t_R$ = 0.72 min; [M + H]$^+$ = 347.30 |
| 158 | N-[5-(4-Fluoro-phenylamino)-pyridin-2-ylmethyl]-N',N'-dimethyl-ethane-1,2-diamine<br>LC-A: $t_R$ = 0.47 min; [M + H]$^+$ = 289.09 |
| 159 | (3-Chloro-pyridin-2-ylmethyl)-[2-(4,4-difluoro-piperidin-1-yl)-ethyl]-amine<br>LC-A: $t_R$ = 0.42 min; [M + H]$^+$ = 290.05 |
| 160 | Isoxazol-5-ylmethyl-(2-trifluoromethyl-benzyl)-amine<br>LC-A: $t_R$ = 0.52 min; [M + H]$^+$ = 257.24 |
| 161 | 1-[(3-Chloro-pyridin-2-ylmethyl)-amino]-2-methyl-propan-2-ol<br>LC-A: $t_R$ = 0.41 min; [M + H]$^+$ = 215.32 |
| 162 | 1-[(3-Bromo-pyridin-2-ylmethyl)-amino]-2-methyl-propan-2-ol<br>LC-A: $t_R$ = 0.43 min; [M + H]$^+$ = 259.26 |

Building Blocks 5-(4-Fluoro-phenylamino)-pyridine-2-carbaldehyde a) (6-[1,3]Dioxolan-2-yl-pyridin-3-yl)-(4-fluoro-phenyl)-amine A suspension of 5-bromo-2-[1,3]dioxolan-2-yl-pyridine (6.8 g, 29.6 mmol), 4-fluoroaniline (3.94 g, 35.5 mmol); Pd$_2$dba$_3$ (1.35 g, 1.48 mmol), XPhos (1.41 g, 2.96 mmol) and NaOtBu (3.98 g, 41.4 mmol) in 100 mL dioxane is heated to 100° C. for 5 h. The mixture is cooled to RT and diluted with 100 mL EtOAc and filtered through a pad of celite. The resulting solution is washed with 100 mL of 10% aq. NaHCO$_3$ soln. and 100 mL brine. The organic layer is dried over MgSO$_4$ and evaporated under reduced pressure. Flash-chromatography on silica-gel (Eluent: Hept./EtOAc 1:1 to 1:2) yields the title compound (6.8 g, 88%) as a beige solid.

LC-A: $t_R$=0.60 min; [M+H]$^+$=261.06 b) 5-(4-Fluoro-phenylamino)-pyridine-2-carbaldehyde

A solution of (6-[1,3]dioxolan-2-yl-pyridin-3-yl)-(4-fluoro-phenyl)-amine 7.001a (3.5 g, 13.4 mmol) in 180 mL THF is treated with water (9 mL, 27.5 mmol) and p-toluenesulfonic acid (3.84 g, 20.2 mmol) under argon and stirred at 50° C. for 3 h. The mixture is cooled down to RT, poured on 100 mL aq. sat. NaHCO$_3$ soln. and extracted three times with 100 mL EtOAc. The combined organic layers are washed with 100 mL brine and dried over MgSO$_4$, filtered and concentrated under reduced pressure to deliver the crude title compound (2.9 g, 100%) as a beige solid LC-A: $t_R$=0.75 min; [M+H]$^+$=217.18

II. Biological Assays

In Vitro Assay

The CXCl12 receptor and CXCR7 agonistic activities of the compounds of formula (I) are determined in accordance with the following experimental method.

The assay is using the PathHunter™ CHO-K1 CXCR7 b-arrestin cell line from DiscoverX. The system is based on the Enzyme Fragment Complementation Technology. Two complementing fragments of the b-galactosidase enzyme are expressed within stably transfected cells. The larger portion of b-gal, termed EA for Enzyme Acceptor, is fused to the C-terminus of b-arrestin 2. The smaller fragment, termed ProLink™ tag, is fused to CXCR7 at the C-terminus. Upon activation, b-arrestin is recruited which forces the interaction of ProLink and EA, allowing complementation of the two fragments of b-gal and the formation of a functional enzyme which is capable of hydrolysing the substrate and generating a chemiluminescent signal.

CHO-K1 CXCR7 b-arrestin cells are detached from culture dishes with a cell dissociation buffer (Invitrogen, #13151-014) and collected in growing medium (F12 HAMS 90% (v/v)/FCS 10% (v/v), Penicillin/streptomycin 1% (v/v)). 5000 cells per well (in 20 µl) are seeded in a 384 well plate (white-walled, clear bottom; BD Falcon #353274). The plate is incubated at 37° C./5% CO$_2$ for 24 hours. Medium is then replaced by 20 µl OPTIMEM (Invitrogen #31985) for 3 to 4 hours. Test compounds are dissolved at 10 mM in DMSO and serially diluted in DMSO to 200× of the final concentration for dose response curves. Compounds are then diluted 1:33.3 in HBSS1×. 5 µl/well of HBSS1×/20 mM HEPES/0.2% BSA are added to the assay plate followed by addition of 5 µl/well of diluted compounds. CXCL12 (Peprotech #300-28A) may be used as a reference agonist. The plate is incubated for 90 minutes at 37° C. 12 µl of detection reagent (Path Hunter Detection Kit, DiscoveRx, #93-0001) is transferred to the assay plate and to the plate is incubated for 1 hour at room temperature. Luminescent signal is read in a microplate reader (FLUOstar Optima, bmg). The calculated $EC_{50}$ values may fluctuate depending on the daily cellular assay performance. Fluctuations of this kind are known to those skilled in the art. Average $EC_{50}$ values from several measurements are given as geometric mean values.

Agonistic activities of exemplified compounds are displayed in Table 37:

TABLE 37

| Example Number | CXCR7 EC50 (nM) |
|---|---|
| 1 | 79 |
| 2 | 144 |
| 3 | 42 |
| 4 | 47 |
| 5 | 187 |
| 6 | 60 |
| 7 | 32 |
| 8 | 230 |
| 9 | 451 |
| 10 | 337 |
| 11 | 52 |
| 12 | 194 |
| 13 | 37 |
| 14 | 53 |
| 15 | 15 |
| 16 | 63 |
| 17 | 135 |
| 18 | 61 |
| 19 | 102 |
| 20 | 11 |
| 21 | 39 |
| 22 | 80 |
| 23 | 16 |
| 24 | 28 |
| 25 | 309 |
| 26 | 442 |
| 27 | 19 |
| 28 | 63 |
| 29 | 174 |
| 30 | 283 |
| 31 | 13 |
| 32 | 28 |
| 33 | 16 |
| 34 | 132 |
| 35 | 4 |
| 36 | 25 |
| 37 | 4 |
| 38 | 3 |
| 39 | 4 |
| 40 | 44 |
| 41 | 5 |
| 42 | 5 |
| 43 | 2 |
| 44 | 3 |
| 45 | 8 |
| 46 | 3 |
| 47 | 2 |
| 48 | 52 |
| 49 | 16 |
| 50 | 6 |
| 51 | 3 |
| 52 | 17 |
| 53 | 23 |
| 54 | 7 |
| 55 | 43 |
| 56 | 70 |
| 57 | 24 |
| 58 | 16 |
| 59 | 147 |
| 60 | 1 |
| 61 | 5 |
| 62 | 1 |
| 63 | 19 |
| 64 | 8 |
| 65 | 150 |
| 66 | 168 |
| 67 | 115 |
| 68 | 330 |
| 69 | 418 |
| 70 | 189 |
| 71 | 326 |
| 72 | 28 |
| 73 | 66 |
| 74 | 49 |
| 75 | 137 |
| 76 | 2 |
| 77 | 46 |
| 78 | 376 |
| 79 | 135 |
| 80 | 47 |
| 81 | 126 |
| 82 | 158 |
| 83 | 88 |
| 84 | 272 |
| 85 | 187 |
| 86 | 23 |
| 87 | 3 |
| 88 | 11 |
| 89 | 8 |
| 90 | 32 |
| 91 | 1 |
| 92 | 413 |
| 93 | 88 |
| 94 | 452 |
| 95 | 432 |
| 96 | 249 |
| 97 | 365 |
| 98 | 224 |
| 99 | 177 |
| 100 | 376 |
| 101 | 148 |
| 102 | 370 |
| 103 | 97 |
| Reference example 104 | 233 |
| 105 | 9 |
| 106 | 100 |
| 107 | 43 |
| 108 | 52 |
| 109 | 73 |
| 110 | 14 |
| 111 | 32 |
| 112 | 40 |
| 113 | 26 |
| 114 | 36 |
| 115 | 54 |
| 116 | 96 |
| 117 | 79 |
| 118 | 126 |
| 119 | 87 |
| 120 | 154 |
| 121 | 101 |
| 122 | 337 |
| 123 | 120 |
| 124 | 52 |
| 125 | 240 |
| 126 | 249 |
| 127 | 395 |
| 128 | 290 |
| 129 | 449 |
| 130 | 390 |
| 131 | 450 |
| 132 | 130 |
| 133 | 20 |
| 134 | 2 |
| 135 | 9 |
| 136 | 1 |

TABLE 37-continued

| Example Number | CXCR7 EC50 (nM) |
|---|---|
| 137 | 45 |
| 138 | 55 |
| 139 | 55 |
| 140 | 54 |
| 141 | 98 |
| 142 | 23 |
| 143 | 3 |
| 144 | 22 |
| 145 | 8 |
| 146 | 2 |
| 147 | 16 |
| 148 | 54 |
| 149 | 0.6 |
| 150 | 1 |
| 151 | 34 |
| 152 | 8 |
| Reference example 153 | 285 |
| 154 | 29 |
| 155 | 17 |
| 156 | 1 |
| 157 | 9 |
| 158 | 2 |
| 159 | 72 |
| 160 | 15 |
| 161 | 4 |
| 162 | 46 |
| 163 | 17 |
| 164 | 84 |
| 165 | 61 |
| 166 | 6 |
| 167 | 39 |
| 168 | 20 |
| 169 | 42 |
| 170 | 74 |
| 171 | 18 |
| 172 | 2 |
| 173 | 5 |
| 174 | 0.8 |
| 175 | 339 |
| 176 | 26 |
| 177 | 14 |
| 178 | 25 |
| 179 | 3 |
| 180 | 8 |
| 181 | 117 |
| 182 | 69 |
| 183 | 140 |
| 184 | 270 |
| 185 | 79 |
| 186 | 91 |
| 187 | 34 |
| 188 | 71 |
| 189 | 37 |
| 190 | 110 |
| 191 | 59 |
| 192 | 38 |
| 193 | 48 |
| 194 | 13 |
| 195 | 12 |
| 196 | 264 |
| 197 | 257 |
| 198 | 388 |
| 199 | 255 |
| 200 | 235 |
| 201 | 27 |
| 202 | 23 |
| 203 | 8 |
| 204 | 40 |
| 205 | 13 |
| 206 | 26 |
| 207 | 5 |
| 208 | 248 |
| 209 | 51 |
| 210 | 5 |
| 211 | 2 |
| 211a | 1 |
| 211b | 6 |
| 212 | 6 |
| 213 | 2 |
| 214 | 3 |
| 215 | 108 |
| 216 | 34 |
| 217 | 2 |
| 218 | 2 |
| 219 | 3 |
| 220 | 3 |
| 221 | 9 |
| 222 | 27 |
| 223 | 10 |
| 224 | 52 |
| 225 | 29 |
| 226 | 13 |
| 227 | 6 |
| 228 | 117 |
| 229 | 38 |
| 230 | 81 |
| 231 | 1 |
| 232 | 162 |
| 233 | 72 |
| 234 | 3 |
| 235 | 107 |
| 236 | 3 |
| 237 | 5 |
| 238 | 43 |
| 239 | 23 |
| 240 | 15 |
| 241 | 8 |
| 242 | 24 |
| 243 | 8 |
| 244 | 3 |
| 245 | 3 |
| 246 | 14 |
| 247 | 29 |
| 248 | 32 |
| 249 | 12 |
| 250 | 31 |
| 251 | 24 |
| 252 | 426 |
| 253 | 42 |
| 254 | 161 |
| 255 | 390 |
| 256 | 11 |
| 257 | 29 |
| 258 | 27 |
| 259 | 5 |
| 260 | 125 |
| 261 | 47 |
| 262 | 62 |
| 263 | 127 |
| 264 | 374 |
| 265 | 48 |
| 266 | 16 |
| 267 | 33 |
| 268 | 350 |
| 269 | 54 |
| 270 | 7 |
| 271 | 10 |
| 272 | 230 |
| 273 | 144 |
| 274 | 179 |
| 275 | 43 |
| 276 | 17 |
| 277 | 28 |
| 278 | 79 |
| 279 | 8 |
| 280 | 28 |
| 281 | 43 |
| 282 | 47 |
| 283 | 11 |
| 284 | 18 |

TABLE 37-continued

| Example Number | CXCR7 EC50 (nM) |
|---|---|
| 285 | 408 |
| 286 | 37 |
| 287 | 150 |
| 288 | 23 |
| 289 | 16 |
| 290 | 5 |
| 291 | 92 |
| 292 | 103 |
| 293 | 20 |
| 294 | 237 |
| 295 | 411 |
| 296 | 430 |
| 297 | 461 |
| 298 | 114 |
| 299 | 291 |
| 300 | 96 |
| 301 | 208 |
| 302 | 27 |
| 303 | 246 |
| 304 | 311 |
| 305 | 230 |
| 306 | 39 |
| 307 | 423 |
| 308 | 28 |
| 309 | 24 |
| 310 | 78 |
| 311 | 24 |
| 312 | 37 |
| 313 | 31 |
| 314 | 23 |
| 315 | 5 |
| 316 | 370 |
| 317 | 5 |
| 318 | 7 |
| 319 | 443 |
| 320 | 154 |
| 321 | 244 |
| 322 | 119 |
| 323 | 182 |
| 324 | 243 |
| 325 | 334 |
| 326 | 184 |
| 327 | 20 |
| 328 | 293 |
| 329 | 23 |
| 330 | 11 |
| 331 | 314 |
| 332 | 96 |
| 333 | 2 |
| 334 | 13 |
| 335 | 23 |
| 336 | 47 |
| 337 | 429 |
| 338 | 279 |
| 339 | 457 |
| 340 | 277 |
| 341 | 397 |
| 342 | 110 |
| 343 | 415 |
| 344 | 438 |
| 345 | 400 |
| 346 | 73 |
| 347 | 445 |
| 348 | 13 |
| 349 | 12 |
| 350 | 32 |
| 351 | 34 |
| 352 | 4 |
| 353 | 85 |
| 354 | 11 |
| 355 | 10 |
| 356 | 6 |
| 357 | 4 |
| 358 | 26 |
| 359 | 9 |
| 360 | 30 |

TABLE 37-continued

| Example Number | CXCR7 EC50 (nM) |
|---|---|
| 361 | 6 |
| 362 | 21 |
| 363 | 3 |
| 363a | 6 |
| 363b | 5 |
| 364 | 44 |
| 365 | 35 |
| 366 | 2 |
| 367 | 115 |
| 368 | 3 |
| 369 | 92 |
| 370 | 40 |
| 371 | 16 |
| 372 | 271 |
| 373 | 67 |
| 374 | 5 |
| 375 | 6 |
| 376 | 27 |
| 377 | 276 |
| 378 | 321 |
| 379 | 3 |
| 380 | 6 |
| 381 | 9 |
| 382 | 8 |
| 383 | 51 |
| 384 | 4 |
| 385 | 7 |
| 386 | 12 |
| 387 | 12 |
| 388 | 13 |
| 389 | 20 |
| 390 | 83 |
| 391 | 49 |
| 392 | 30 |
| 393 | 110 |
| 394 | 9 |
| 395 | 32 |
| 396 | 38 |
| 397 | 35 |
| 398 | 82 |
| 399 | 64 |
| 400 | 31 |
| 401 | 250 |
| 402 | 198 |
| 403 | 24 |
| 404 | 60 |
| 405 | 257 |
| 406 | 80 |
| 407 | 326 |
| 408 | 10 |
| 409 | 8 |
| 410 | 5 |
| 411 | 15 |
| 412 | 20 |
| 413 | 8 |
| 414 | 37 |
| 415 | 178 |
| 416 | 86 |
| 417 | 15 |
| 418 | 148 |
| 419 | 6 |
| 420 | 21 |
| 421 | 29 |
| 422 | 33 |
| 423 | 79 |
| 424 | 60 |
| 425 | 27 |
| 426 | 74 |
| 427 | 106 |
| 428 | 120 |
| 429 | 7 |
| 430 | 9 |
| 431 | 120 |
| 432 | 42 |
| 433 | 166 |
| 434 | 20 |

TABLE 37-continued

| Example Number | CXCR7 EC50 (nM) |
|---|---|
| 435 | 7 |
| 436 | 9 |
| 437 | 5 |
| 438 | 15 |
| 439 | 3 |
| 440 | 15 |
| 441 | 5 |
| 442 | 10 |
| 443 | 147 |
| 444 | 15 |
| 445 | 11 |
| 446 | 4 |
| 447 | 1 |
| 448 | 2 |
| 449 | 1 |
| 450 | 1 |
| 451 | 1 |
| 452 | 4 |
| 453 | 6 |
| 454 | 3 |
| 455 | 10 |
| 456 | 8 |
| 457 | 232 |
| 458 | 109 |
| 459 | 59 |
| 460 | 85 |
| 461 | 420 |
| 463 | 16 |
| 464 | 36 |
| 465 | 39 |
| 466 | 13 |
| 467 | 14 |
| 468 | 10 |
| 469 | 5 |
| 470 | 15 |
| 471 | 21 |
| 472 | 21 |
| 473 | 102 |
| 474 | 47 |
| 475 | 121 |
| 476 | 15 |
| 477 | 63 |
| 478 | 92 |
| 479 | 78 |
| 480 | 28 |
| 481 | 41 |
| 482 | 32 |
| 483 | 33 |
| 484 | 79 |
| 485 | 8 |
| 486 | 5 |
| 487 | 100 |
| 488 | 91 |
| 489 | 7 |
| 490 | 21 |
| 491 | 21 |
| 492 | 41 |
| 493 | 249 |
| 494 | 28 |
| 495 | 63 |
| 496 | 79 |
| 497 | 77 |
| 498 | 118 |
| 499 | 245 |
| 500 | 31 |
| 501 | 54 |
| 502 | 113 |
| 503 | 65 |
| 504 | 93 |
| 505 | 42 |
| 506 | 155 |
| 507 | 74 |
| 508 | 34 |
| 509 | 36 |
| 510 | 109 |
| 511 | 29 |
| 512 | 56 |
| 513 | 377 |
| 514 | 6 |
| 515 | 382 |
| 516 | 181 |
| 517 | 302 |
| 518 | 9 |
| 519 | 250 |
| 520 | 188 |
| 521 | 269 |
| 522 | 140 |
| 523 | 58 |
| 524 | 27 |
| 525 | 41 |
| 526 | 44 |
| 527 | 162 |
| 528 | 42 |
| 529 | 174 |
| 530 | 174 |
| 531 | 6 |
| 532 | 30 |
| 533 | 359 |
| 534 | 395 |
| 535 | 355 |
| 536 | 92 |
| 537 | 217 |
| 538 | 155 |
| 539 | 115 |
| 540 | 220 |
| 541 | 175 |
| 542 | 113 |
| 543 | 84 |
| 544 | 34 |
| 545 | 80 |
| 546 | 8 |
| 547 | 15 |
| 548 | 133 |
| 549 | 257 |
| 550 | 2 |
| 551 | 35 |
| 552 | 4 |
| 553 | 14 |
| 554 | 5 |
| 555 | 6 |
| 556 | 8 |
| 557 | 5 |
| 558 | 59 |
| 559 | 13 |
| 560 | 5 |
| 561 | 7 |
| 562 | 100 |
| 563 | 26 |
| 564 | 17 |
| 565 | 4 |
| 566 | 3 |
| 567 | 4 |
| 568 | 29 |
| 569 | 26 |
| 570 | 14 |
| 571 | 86 |
| 572 | 5 |
| 573 | 3 |
| 574 | 6 |
| 575 | 0.9 |
| 576 | 6 |
| 577 | 0.9 |

The invention claimed is:
1. A compound of formula (I)

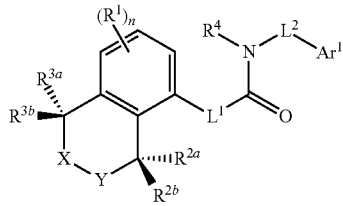

Formula (I)

wherein
X represents $NR^5$, and Y represents $CHR^Y$ wherein $R^Y$ represents hydrogen, or $(C_{1-3})$alkyl; and
$R^{3a}$ and $R^{3b}$ together with the carbon atom to which they are attached to form a carbonyl group, or
two of $R^{2a}$, $R^{2b}$, $R^{3a}$ and $R^{3b}$ independently represent hydrogen, or $(C_{1-3})$alkyl; and the remaining of $R^{2a}$, $R^{2b}$, $R^{3a}$ and $R^{3b}$ represent hydrogen; or
X represents $CHR^X$ wherein $R^X$ represents hydrogen, or $(C_{1-3})$alkyl, and Y represents $NR^5$; and
$R^{2a}$ and $R^{2b}$ together with the carbon atom to which they are attached to form a carbonyl group, or
two of $R^{2a}$, $R^{2b}$, $R^{3a}$ and $R^{3b}$ independently represent hydrogen, or $(C_{1-3})$alkyl; and the remaining of $R^{2a}$, $R^{2b}$, $R^{3a}$ and $R^{3b}$ represent hydrogen; or
X represents $NR^5$ and Y represents a direct bond; $R^{2a}$ and $R^{2b}$ both represent hydrogen; and $R^{3a}$ and $R^{3b}$ both represent hydrogen; or
X represents $NR^5$, Y represents $-C(O)-$; and $R^{2a}$, $R^{2b}$, $R^{3a}$ and $R^{3b}$ all represent hydrogen; or
X represents $-C(O)-$; Y represents $NR^5$, and $R^{2a}$, $R^{2b}$, $R^{3a}$ and $R^{3b}$ all represent hydrogen;
$R^5$ represents
$(C_{1-6})$alkyl;
$(C_{1-4})$alkyl mono-substituted with $(C_{1-3})$alkoxy, cyano, vinyl; ethynyl, or $(C_{1-3})$alkoxy-carbonyl;
$-CO-R^{10}$ wherein $R^{10}$ represents $(C_{1-5})$alkyl; $(C_{1-5})$alkoxy; phenyl; phenyl-oxy-; phenyl-$(C_{1-3})$alkyl-; phenyl-$(C_{1-3})$-alkyl-oxy-; $(C_{3-6})$cycloalkyl-$(C_{1-3})$alkyl; $(C_{3-4})$alkenoxy; $(C_{3-4})$alkynoxy; $(C_{1-3})$fluoroalkyl; $(C_{1-3})$fluoroalkoxy; $(C_{1-3})$alkoxy-$(C_{2-3})$alkoxy; $(C_{1-3})$alkoxy-$(C_{1-3})$alkyl; $(C_{3-6})$cycloalkyl optionally having one ring oxygen atom, wherein said cycloalkyl is optionally mono- or di-substituted wherein the substituents independently are fluoro or $(C_1)$fluoroalkyl; unsubstituted 5-membered heteroaryl; or $-NR^{10a}R^{10b}$ wherein $R^{10a}$ and $R^{10b}$ independently represent hydrogen, $(C_{1-4})$alkyl or $(C_{3-6})$cycloalkyl, or $R^{10a}$ and $R^{10b}$ together with the nitrogen to which they are attached to form a 5- to 7-membered saturated ring;
$-SO_2-R^{11}$ wherein $R^{11}$ represents $(C_{1-5})$alkyl or phenyl;
$(C_{2-4})$fluroalkyl;
$(C_{3-6})$cycloalkyl optionally having one ring oxygen atom;
$(C_{3-6})$cycloalkyl-$(C_{1-3})$alkyl, wherein the $(C_{3-6})$cycloalkyl group optionally has one ring oxygen atom; wherein said cycloalkyl is optionally substituted with one or two methyl substituents;
phenyl-$(C_{0-3})$alkyl-, or 5- or 6-membered heteroaryl-$(C_{0-3})$alkyl-, wherein the phenyl or 5- or 6-membered heteroaryl independently is unsubstituted, or mono-, or di-substituted, wherein the substituents are independently selected from $(C_{1-4})$alkyl, $(C_{1-4})$alkoxy, halogen, $(C_{1-3})$fluoroalkyl, $(C_{1-3})$fluoroalkoxy, or cyano;
$(R^1)_n$ represents one or two optional substituents independently selected from $(C_{1-4})$alkyl, $(C_{1-4})$alkoxy, halogen, $(C_{1-3})$fluoroalkyl, $(C_{1-3})$fluoroalkoxy, or cyano;
$L^1$ represents a one- or two-membered linker group selected from $-NH-CH_2-*$; $-NR^{16a}-CH_2-*$ wherein $R^{16a}$ represents $(C_{1-3})$alkyl; $-NH-CHR^{16b}-*$ wherein $R^{16b}$ represents $(C_{1-3})$alkyl; $-NH-CR^{16c}R^{16d}-*$ wherein $R^{16c}$ and $R^{16d}$ together with the carbon to which they are attached to form a $(C_{3-6})$cycloalkyl ring; $-CH_2-NH-*$; $-O-CH_2-*$; $-O-CHR^{17a}-*$ wherein $R^{17a}$ represents $(C_{1-3})$alkyl; $-O-CR^{17b}R^{17c}-*$ wherein $R^{17b}$ and $R^{17c}$ together with the carbon to which they are attached to form a $(C_{3-6})$cycloalkyl ring; $-CH_2-$; $-CH_2CH_2-$; $-CH=CH-$; and $-CH=C(CH_3)-*$; wherein the asterisks indicate the bond with which the group $L^1$ is attached to the carbonyl group;
$L^2$ represents $-(C_{1-4})$alkylene- or $-(C_{3-4})$alkenylene-;
$Ar^1$ represents phenyl, or 5- or 6-membered heteroaryl; wherein said phenyl or 5- or 6-membered heteroaryl independently is unsubstituted, mono-, di- or tri-substituted, wherein the substituents are independently selected from $(C_{1-4})$alkyl; $(C_{1-4})$alkoxy; $(C_{1-3})$fluoroalkyl; $(C_{1-3})$fluoroalkoxy; halogen; cyano; or $NR^{18a}R^{18b}$ wherein $R^{18a}$ and $R^{18b}$ independently represent hydrogen or $(C_{1-3})$alkyl; and
$R^4$ represents
$(C_{2-6})$alkyl;
$(C_{2-5})$alkyl which is mono-substituted with $(C_{1-4})$alkoxy, benzyloxy, cyano, or hydroxy; or disubstituted wherein the substituents are independently selected from $(C_{1-3})$alkoxy, or hydroxy
$(C_{2-3})$fluoroalkyl which is optionally further substituted with one hydroxy;
$-(C_{2-4})$alkylene-$NR^6R^7$, wherein $R^6$ and $R^7$ independently represent hydrogen; $(C_{1-4})$alkyl; $-CO-(C_{1-4})$alkoxy; $(C_{3-5})$alkenyl; $(C_{3-4})$alkynyl; benzyl; $-SO_2-(C_{1-3})$alkyl; $(C_{2-3})$fluoroalkyl; or $(C_{3-6})$cycloalkyl or $(C_{3-6})$cycloalkyl-$(C_{1-3})$alkyl, wherein in the above groups the $(C_{3-6})$cycloalkyl group optionally contains one ring oxygen atom, and wherein said $(C_{3-6})$cycloalkyl group is optionally substituted with methyl;
$-(C_{1-3})$alkylene-$CO-R^8$, wherein $R^8$ represents $(C_{1-4})$alkoxy; or $R^8$ represents $NR^{81}R^{82}$ wherein $R^{81}$ and $R^{82}$ independently represent hydrogen or $(C_{1-4})$alkyl, or $R^{81}$ and $R^{82}$ together with the nitrogen to which they are attached to form a 4- to 6-membered saturated ring optionally substituted with two fluoro substituents;
$-(C_{1-3})$alkylene-$SO_2-R^9$ wherein $R^9$ represents $(C_{1-3})$alkyl, or amino;
$(C_{3-6})$cycloalkyl or $(C_{3-6})$cycloalkyl-$(C_{1-3})$alkyl, wherein the cycloalkyl group is optionally mono-substituted with $-CO-(C_{1-4})$alkoxy or hydroxy;
$(C_{4-7})$heterocyclyl or $(C_{4-7})$heterocyclyl-$(C_{1-3})$alkyl, wherein in the above groups the $(C_{4-7})$heterocyclyl independently has one or two ring heteroatoms independently selected from nitrogen, sulfur or oxygen; wherein in the above groups said $(C_{4-7})$heterocyclyl independently is unsubstituted, or mono-, di-, or tri-substituted wherein the substituents are independently selected from:
one oxo substituent attached to a ring carbon atom in alpha position to a ring nitrogen; and/or
two methyl substituents attached to a ring carbon atom in alpha position to a ring nitrogen atom; and/or
two oxo substituents at a ring sulfur ring atom; and/or ($C_{1-4}$)alkyl or —CO—($C_{1-4}$)alkoxy attached to a ring nitrogen atom having a free valency; and/or two fluoro substituents attached to a ring carbon atom; and/or in case of a ($C_{4-7}$)heterocyclyl-($C_{1-3}$)alkyl group, methyl attached to a ring carbon atom which is attached to the linking ($C_{1-3}$)alkyl group;

2-oxo-2,3-dihydropyridin-4-yl-($C_{1-2}$)alkyl;

phenyl-($C_{1-3}$)alkyl-, or 5- or 6-membered heteroaryl-($C_{1-3}$)alkyl-, wherein the phenyl or 5- or 6-membered heteroaryl independently is unsubstituted, mono-, or di-substituted, wherein the substituents are independently selected from ($C_{1-4}$)alkyl, ($C_{1-4}$)alkoxy, halogen, ($C_{1-3}$)fluoroalkyl, ($C_{1-3}$)fluoroalkoxy, or cyano;

or a pharmaceutically acceptable salt thereof.

2. The compound of formula (I) according to claim 1, wherein

X represents $NR^5$ and:
Y represents $CH_2$; and $R^{2a}$, $R^{2b}$, $R^{3a}$ and $R^{3b}$ represent hydrogen; or
Y represents $CHR^Y$ wherein $R^Y$ represents ($C_{1-3}$)alkyl; and $R^{2a}$, $R^{2b}$, $R^{3a}$ and $R^3b$ represent hydrogen; or
Y represents $CH_2$; $R^{2a}$ and $R^{2b}$ both represent ($C_{1-3}$) alkyl; and $R^{3a}$ and $R^{3b}$ both represent hydrogen; or
Y represents $CH_2$; $R^{2a}$ and $R^{2b}$ both represent hydrogen; one of $R^{3a}$ and $R^{3b}$ represents ($C_{1-3}$)alkyl, and the remaining of $R^{3a}$ and $R^{3b}$ represents hydrogen;

or Y represents $NR^5$ and:
X represents $CH_2$; and $R^{2a}$, $R^{2b}$, $R^{3a}$ and $R^{3b}$ represent hydrogen; or
X represents $CHR^X$ wherein Rx represents ($C_{1-3}$)alkyl; and $R^{2a}$, $R^{2b}$, $R^{3a}$ and $R^{3b}$ represent hydrogen; or
X represents $CH_2$; $R^{3a}$ and $R^{3b}$ both represent ($C_{1-3}$) alkyl; and $R^{2a}$ and $R^{2b}$ both represent hydrogen; or
X represents $CH_2$; $R^{3a}$ and $R^{3b}$ both represent hydrogen; one of $R^{2a}$ and $R^{2b}$ represents ($C_{1-3}$)alkyl, and the remaining of $R^{2a}$ and $R^{2b}$ represents hydrogen;

or a pharmaceutically acceptable salt thereof.

3. The compound of formula (I) according to claim 1, wherein $R^5$ represents ($C_{1-6}$)alkyl;

($C_{1-4}$)alkyl mono-substituted with ($C_{1-3}$)alkoxy;

—CO—$R^{10}$ wherein $R^{10}$ represents ($C_{1-5}$)alkyl; ($C_{1-5}$) alkoxy; phenyl; phenyl-oxy-; phenyl-($C_{1-3}$)alkyl-; phenyl-($C_{1-3}$)alkyl-oxy-; ($C_{3-6}$)cycloalkyl-($C_{1-3}$)alkyl-; ($C_{3-4}$)alkenoxy; ($C_{3-4}$)alkynoxy; ($C_{1-3}$)fluoroalkyl; ($C_{1-3}$)fluoroalkoxy; ($C_{1-3}$)alkoxy-($C_{2-3}$)alkoxy; ($C_{1-3}$)alkoxy-($C_{1-3}$)alkyl; ($C_{3-6}$)cycloalkyl optionally having one ring oxygen atom, wherein said cycloalkyl is optionally mono- or di-substituted wherein the substituents independently are fluoro or ($C_1$)fluoroalkyl; or —$NR^{10a}R^{10b}$ wherein $R^{10a}$ and $R^{10b}$ independently represent hydrogen, ($C_{1-4}$)alkyl or ($C_{3-6}$)cycloalkyl, or $R^{10a}$ and $R^{10b}$ together with the nitrogen to which they are attached to form a 5- to 7-membered saturated ring;

—$SO_2$—$R^{11}$ wherein $R^{11}$ represents ($C_{1-5}$)alkyl or phenyl;

($C_{2-4}$)fluroalkyl;

($C_{3-6}$)cycloalkyl optionally having one ring oxygen atom;

($C_{3-6}$)cycloalkyl-($C_{1-3}$)alkyl, wherein the ($C_{3-6}$)cycloalkyl group optionally has one ring oxygen atom; wherein said cycloalkyl is optionally substituted with one methyl substituent;

phenyl-($C_{1-3}$)alkyl-, wherein the phenyl is unsubstituted; or 5- or 6-membered heteroaryl wherein the 5- or 6-membered heteroaryl is unsubstituted, or mono-, or di-substituted, wherein the substituents are independently selected from ($C_{1-4}$)alkyl, ($C_{1-4}$)alkoxy, halogen, ($C_{1-3}$)fluoroalkyl, ($C_{1-3}$)fluoroalkoxy, or cyano;

or a pharmaceutically acceptable salt thereof.

4. The compound of formula (I) according to claim 1, wherein $R^5$ represents ($C_{1-6}$)alkyl;

($C_{1-4}$)alkyl mono-substituted with ($C_{1-3}$)alkoxy;

—CO—$R^{10}$ wherein $R^{10}$ represents ($C_{1-5}$)alkyl; ($C_{1-3}$) alkoxy-($C_{1-3}$)alkyl; or ($C_{3-6}$)cycloalkyl optionally having one ring oxygen atom, wherein said cycloalkyl is unsubstituted, or mono- or di-substituted with fluoro;

($C_{2-4}$)fluroalkyl;

($C_{3-6}$)cycloalkyl optionally having one ring oxygen atom; or ($C_{3-6}$)cycloalkyl-($C_{1-3}$)alkyl;

or a pharmaceutically acceptable salt thereof.

5. The compound of formula (I) according to claim 1, wherein $(R^1)_n$ represents one optional substituent independently selected from ($C_{1-4}$)alkyl, ($C_{1-4}$)alkoxy, halogen, ($C_{1-3}$)fluoroalkyl, ($C_{1-3}$)fluoroalkoxy, or cyano;

or a pharmaceutically acceptable salt thereof.

6. The compound of formula (I) according to claim 1, wherein $L^1$ represents a two-membered linker group selected from —NH—$CH_2$—*, —O—$CH_2$—*, —$CH_2CH_2$—, or —CH═CH—; wherein the asterisks indicate the bond with which the group $L^1$ is attached to the carbonyl group;

or a pharmaceutically acceptable salt thereof.

7. The compound of formula (I) according to claim 1, wherein $L^2$ represents —$CH_2$—; or a pharmaceutically acceptable salt thereof.

8. The compound of formula (I) according to claim 1, wherein $Ar^1$ represents phenyl which is unsubstituted, mono-, or di-substituted, wherein the substituents are independently selected from ($C_{1-4}$)alkyl; ($C_{1-4}$)alkoxy; ($C_{1-3}$)fluoroalkyl; ($C_{1-3}$)fluoroalkoxy; halogen; or cyano; or 6-membered heteroaryl; which is unsubstituted, mono-, or di-substituted, wherein the substituents are independently selected from ($C_{1-4}$)alkyl; ($C_{1-4}$)alkoxy; ($C_{1-3}$) fluoroalkyl; ($C_{1-3}$)fluoroalkoxy; halogen; or cyano;

or a pharmaceutically acceptable salt thereof.

9. The compound of formula (I) according to claim 1, wherein $R^4$ represents ($C_{2-5}$)alkyl which is mono-substituted with hydroxy; or disubstituted wherein the substituents are independently methoxy or hydroxy;

—($C_{2-4}$)alkylene-$NR^6R^7$, wherein $R^6$ represents hydrogen or ($C_{1-4}$)alkyl; and $R^7$ represents ($C_{1-4}$)alkyl; ($C_{2-3}$)fluoroalkyl; ($C_{3-6}$)cycloalkyl; or ($C_{3-6}$)cycloalkyl-($C_{1-3}$)alkyl; ($C_{3-6}$)cycloalkyl-($C_{1-3}$)alkyl, wherein the cycloalkyl group is optionally mono-substituted with hydroxy;

($C_{4-7}$)heterocyclyl or ($C_{4-7}$)heterocyclyl-($C_{1-3}$)alkyl, wherein in the above groups the ($C_{4-7}$)heterocyclyl independently has one or two ring heteroatoms independently selected from nitrogen or oxygen; wherein in the above groups said ($C_{4-7}$)heterocyclyl independently is unsubstituted, or mono-, or di-substituted wherein the substituents are independently selected from:

one oxo substituent attached to a ring carbon atom in alpha position to a ring nitrogen; and/or ($C_{1-4}$)alkyl attached to a ring nitrogen atom having a free valency; or two fluoro substituents attached to a ring carbon atom;

or a pharmaceutically acceptable salt thereof.

10. The compound of formula (I) according to claim 1, wherein R⁴ represents 2-methoxy-ethyl, 2-hydroxy-ethyl, 2-hydroxy-propyl, 2-hydroxy-2-methyl-propyl, 3-hydroxy-3-methyl-butyl, or 2-methoxy-ethyl; 2-hydroxy-3-methoxy-propyl;

—(C$_{2-4}$)alkylene-NR⁶R⁷ selected from 2-amino-ethyl, 2-methylamino-ethyl, 2-dimethylamino-ethyl, 2-diethylamino-ethyl, 3-(dimethylamino)-propyl, 2-(butyl-methylamino)-ethyl, 2-ethylamino-ethyl, 2-(ethyl-methylamino)-ethyl, 2-(isopropyl-methylamino)-ethyl, 2-(diisopropylamino)-ethyl, 2-[(2-fluoroethyl)-methylamino]-ethyl, 2-[(2,2,2-trifluoroethyl)-amino]ethyl, 2-[methyl-(2,2,2-trifluoroethyl)-amino]ethyl, 2-[(2-fluoro-1-methylethyl)-methylamino]-ethyl, 2-[(cyclopropyl)-methylamino]-ethyl, 2-[(cyclopropylmethyl)-methylamino]-ethyl, 2-[(cyclobutyl)-methylamino]-ethyl, or 2-[(cyclopentyl)-methylamino]-ethyl;

(1-hydroxy-cyclopentyl)-methyl;

(C$_{4-7}$)heterocyclyl selected from pyrrolidin-3-yl, 1-methyl-pyrrolidin-3-yl, piperidin-3-yl, 1-methyl-piperidin-3-yl, piperidin-4-yl, 1-methyl-piperidin-4-yl, or tetrahydro-pyran-4-yl;

(C$_{4-7}$)heterocyclyl-(C$_{1-3}$)alkyl selected from 2-(pyrrolidin-1-yl)-ethyl, 2-(1-methyl-pyrrolidin-2-yl)-ethyl, 2-(morpholin-4-yl)-ethyl, pyrrolidin-3-yl-methyl, 3-(pyrrolidin-1-yl)-propyl, [1,4]dioxan-2-yl-methyl, 2-(piperazin-1-yl)-ethyl, 2-(piperidin-1-yl)-ethyl, 2-(azepan-1-yl)-ethyl, 2-(3,3-difluoroazetidin-1-yl)-ethyl, 2-(3,3-difluoropyrrolidin-1-yl)-ethyl, 2-(3,3-difluoropiperdin-1-yl)-ethyl, or 2-(4,4-difluoropiperdin-1-yl)-ethyl;

or a pharmaceutically acceptable salt thereof.

11. The compound of formula (I) according to claim 1, wherein the compound is:

N-Benzyl-2-(2-cyclopropylmethyl-1,2,3,4-tetrahydro-isoquinolin-5-yl)-N-(2-pyrrolidin-1-yl-ethyl)-acetamide;

N-Benzyl-2-(2-cyclopropylmethyl-1,2,3,4-tetrahydro-isoquinolin-5-yl)-N-[2-(1-methyl-pyrrolidin-2-yl)-ethyl]-acetamide;

2-(2-Cyclopropylmethyl-1,2,3,4-tetrahydro-isoquinolin-5-yl)-N-(2-pyrrolidin-1-yl-ethyl)-N-(2-trifluoromethyl-benzyl)-acetamide;

N-Benzyl-N-(3-dimethylamino-propyl)-2-(2-propionyl-1,2,3,4-tetrahydro-isoquinolin-5-ylamino)-acetamide;

N-(2-Dimethylamino-ethyl)-N-(2-methyl-benzyl)-2-(2-propionyl-1,2,3,4-tetrahydro-isoquinolin-5-ylamino)-acetamide;

N-(2-Chloro-benzyl)-N-(2-dimethylamino-ethyl)-2-(2-propionyl-1,2,3,4-tetrahydro-isoquinolin-5-yl amino)-acetamide;

N-(2-Dimethylamino-ethyl)-N-(3-fluoro-benzyl)-2-(2-propionyl-1,2,3,4-tetrahydro-isoquinolin-5-ylamino)-acetamide;

N-(2-Dimethylamino-ethyl)-N-(2-fluoro-benzyl)-2-(2-propionyl-1,2,3,4-tetrahydro-isoquinolin-5-ylamino)-acetamide;

N-Benzyl-2-(2-propionyl-1,2,3,4-tetrahydro-isoquinolin-5-ylamino)-N-(2-pyrrolidin-1-yl-ethyl)-acetamide;

N-Benzyl-N-(2-diethylamino-ethyl)-2-(2-propionyl-1,2,3,4-tetrahydro-isoquinolin-5-ylamino)-acetamide;

N-Benzyl-N-[2-(butyl-methyl-amino)-ethyl]-2-(2-propionyl-1,2,3,4-tetrahydro-isoquinolin-5-ylamino)-acetamide;

N-Benzyl-N-[2-(1-methyl-pyrrolidin-2-yl)-ethyl]-2-(2-propionyl-1,2,3,4-tetrahydro-isoquinolin-5-ylamino)-acetamide;

N-(2-Dimethylamino-ethyl)-2-(2-propionyl-1,2,3,4-tetrahydro-isoquinolin-5-ylamino)-N-(3-trifluoromethyl-benzyl)-acetamide;

N-(2-Dimethylamino-ethyl)-2-(2-propionyl-1,2,3,4-tetrahydro-isoquinolin-5-ylamino)-N-(2-trifluoromethyl-benzyl)-acetamide;

2-(2-Cyclopropylmethyl-1,2,3,4-tetrahydro-isoquinolin-5-ylamino)-N-(2-dimethylamino-ethyl)-N-phenethyl-acetamide;

N-Benzyl-2-(2-cyclopropylmethyl-1,2,3,4-tetrahydro-isoquinolin-5-ylamino)-N-(3-dimethylamino-propyl)-acetamide;

2-(2-Cyclopropylmethyl-1,2,3,4-tetrahydro-isoquinolin-5-ylamino)-N-(2-dimethylamino-ethyl)-N-(2-fluoro-benzyl)-acetamide;

N-(3-Chloro-pyridin-2-ylmethyl)-2-(2-cyclopropylmethyl-1,2,3,4-tetrahydro-isoquinolin-5-ylamino)-N-(2-dimethylamino-ethyl)-acetamide;

2-(2-Cyclopropylmethyl-1,2,3,4-tetrahydro-isoquinolin-5-ylamino)-N-(2-dimethylamino-ethyl)-N-(2-o-tolyk-ethyl)-acetamide;

N-Benzyl-2-(2-cyclopropylmethyl-1,2,3,4-tetrahydro-isoquinolin-5-ylamino)-N-(2-pyrrolidin-1-yl-ethyl)-acetamide;

N-Benzyl-2-(2-cyclopropylmethyl-1,2,3,4-tetrahydro-isoquinolin-5-ylamino)-N[2-(1-methyl-pyrrolidin-2-yl)-ethyl]-acetamide;

N-(2-Chloro-benzyl)-2-(2-cyclopropylmethyl-1,2,3,4-tetrahydro-isoquinolin-5-ylamino)-N-(2-pyrrolidin-1-yl-ethyl)-acetamide;

2-(2-Cyclopropylmethyl-1,2,3,4-tetrahydro-isoquinolin-5-ylamino)-N-(2-fluoro-benzyl)-N-(2-pyrrolidin-1-yl-ethyl)-acetamide;

2-(2-Cyclopropylmethyl-1,2,3,4-tetrahydro-isoquinolin-5-ylamino)-N-(2-dimethylamino-ethyl)-N-((E)-2-methyl-3-phenyl-allyl)-acetamide;

2-(2-Cyclopropylmethyl-1,2,3,4-tetrahydro-isoquinolin-5-ylamino)-N-(2-dimethylamino-ethyl)-N-(6-trifluoromethyl-pyridin-2-ylmethyl)-acetamide;

2-(2-Cyclopropylmethyl-1,2,3,4-tetrahydro-isoquinolin-5-ylamino)-N-(2-dimethylamino-ethyl)-N-(3-trifluoromethyl-pyridin-2-ylmethyl)-acetamide;

2-(2-Cyclopropylmethyl-1,2,3,4-tetrahydro-isoquinolin-5-ylamino)-N-[2-(1-methyl-pyrrolidin-2-yl)-ethyl]-N-phenethyl-acetamide;

N-(2-Chloro-4-fluoro-benzyl)-2-(2-cyclopropylmethyl-1,2,3,4-tetrahydro-isoquinolin-5-ylamino)-N-(2-pyrrolidin-1-yl-ethyl)-acetamide;

2-(2-Cyclopropylmethyl-1,2,3,4-tetrahydro-isoquinolin-5-ylamino)-N-(2,4-difluoro-benzyl)-N-(2-pyrrolidin-1-yl-ethyl)-acetamide;

2-(2-Cyclopropylmethyl-1,2,3,4-tetrahydro-isoquinolin-5-ylamino)-N-[2-(1-methyl-pyrrolidin-2-yl)-ethyl]-N-(3-phenyl-propyl)-acetamide;

2-(2-Cyclopropyhmethyl-1,2,3,4-tetrahydro-isoquinolin-5-ylamino)-N-[2-(1-methyl-pyrrolidin-2-yl)-ethyl]-N-((E)-3-phenyl-allyl)-acetamide;

2-(2-Cyclopropylmethyl-1,2,3,4-tetrahydro-isoquinolin-5-ylamino)-N-(2-dimethylamino-ethyl)-N-(4-fluoro-2-trifluoromethyl-benzyl)-acetamide;

2-(2-Cyclopropylmethyl-1,2,3,4-tetrahydro-isoquinolin-5-ylamino)-N-(2-dimethylamino-ethyl)-N-[2-(3-trifluoromethyl-phenyl)-ethyl]-acetamide;

2-(2-Cyclopropylmethyl-1,2,3,4-tetrahydro-isoquinolin-5-ylamino)-N-(2-dimethylamino-ethyl)-N-[2-(2-trifluoromethyl-phenyl)-ethyl]-acetamide;
2-(2-Cyclopropylmethyl-1,2,3,4-tetrahydro-isoquinolin-5-ylamino)-N-(2-dimethylamino-ethyl)-N-[1-(2-trifluoromethyl-phenyl)ethyl]-acetamide;
2-(2-Cyclopropylmethyl-1,2,3,4-tetrahydro-isoquinolin-5-ylamino)-N-(2-diethylamino-ethyl)-N-(2-trifluoromethyl-benzyl)-acetamide;
2-(2-Cyclopropylmethyl-1,2,3,4-tetrahydro-isoquinolin-5-ylamino)-N-((E)-2-methyl-3-phenyl-allyl)-N-[2-(1-methyl-pyrrolidin-2-yl)-ethyl]-acetamide;
2-(2-Cyclopropylmethyl-1,2,3,4-tetrahydro-isoquinolin-5-ylamino)-N-(2-pyrrolidin-1-yl-ethyl)-N-(2-trifluoromethyl-benzyl)-acetamide;
2-(2-Cyclopropylmethyl-1,2,3,4-tetrahydro-isoquinolin-5-ylamino)-N-[2-(2-oxo-pyrrolidin-1-yl)-ethyl]-N-(2-trifluoromethyl-benzyl)-acetamide;
2-(2-Cyclopropylmethyl-1,2,3,4-tetrahydro-isoquinolin-5-ylamino)-N-(2-morpholin-4-yl-ethyl)-N-(2-trifluoromethyl-benzyl)-acetamide;
N-(2-Cyano-ethyl)-2-(2-cyclopropyl methyl-1,2,3,4-tetrahydro-isoquinolin-5-ylamino)-N-(2-trifluoromethyl-benzyl)-acetamide;
2-(2-Cyclopropylmethyl-1,2,3,4-tetrahydro-isoquinolin-5-ylamino)-N-(tetrahydro-pyran-4-yl)-N-(2-trifluoromethyl-benzyl)-acetamide;
2-(2-Cyclopropylmethyl-1,2,3,4-tetrahydro-isoquinolin-5-ylamino)-N-(2-dimethylamino-ethyl)-N-(2-trifluoromethyl-benzyl)-acetamide;
2-(2-Cyclopropylmethyl-1,2,3,4-tetrahydro-isoquinolin-5-ylamino)-N-(4-methyl-thiazol-2-ylmethyl)-N-(2-trifluoromethyl-benzyl)-acetamide;
2-(2-Cyclopropylmethyl-1,2,3,4-tetrahydro-isoquinolin-5-ylamino)-N-[1-(1-ethyl-1H-pyrazol-3-yl)-ethyl]-N-(2-trifluoromethyl-benzyl)-acetamide;
N-(2-Dimethylamino-ethyl)-2-[2-(2,2,2-trifluoro-ethyl)-1,2,3,4-tetrahydro-isoquinolin-5-ylamino]-N-(2-trifluoromethyl-benzyl)-acetamide;
2-[(2-Cyclopropylmethyl-1,2,3,4-tetrahydro-isoquinolin-5-yl)-methyl-amino]-N-(2-dimethylamino-ethyl)-N-(2-trifluoromethyl-benzyl)-acetamide;
2-(6-Chloro-2-cyclopropylmethyl-1,2,3,4-tetrahydro-isoquinolin-5-ylamino)-N-(2-dimethylamino-ethyl)-N-(2-trifluoromethyl-benzyl)-acetamide;
2-(2-Cyclopropylmethyl-6-methoxy-1,2,3,4-tetrahydro-isoquinolin-5-ylamino)-N-(2-dimethylamino-ethyl)-N-(2-trifluoromethyl-benzyl)-acetamide;
5-({[(2-Dimethylamino-ethyl)-(2-trifluoromethyl-benzyl)-carbamoyl]-methyl}-amino)-4,4-dimethyl-3,4-dihydro-1H-isoquinoline-2-carboxylic acid tert-butyl ester;
2-(2-Cyclopropylmethyl-4,4-dimethyl-1,2,3,4-tetrahydro-isoquinolin-5-ylamino)-N-(2-dimethylamino-ethyl)-N-(2-trifluoromethyl-benzyl)-acetamide;
2-(2-Cyclopropylmethyl-1,2,3,4-tetrahydro-isoquinolin-5-ylamino)-N-(1-methyl-piperidin-4-yl)-N-(2-trifluoromethyl-benzyl)-acetamide;
N-Benzyl-N-(2-dimethylamino-ethyl)-2-(2-ethyl-1,2,3,4-tetrahydro-isoquinolin-5-ylamino)-acetamide;
N-Benzyl-2-(2-cyclopropylmethyl-1,2,3,4-tetrahydro-isoquinolin-5-ylamino)-N-(2-dimethylamino-ethyl)-acetamide;
N-Benzyl-N-(2-dimethylamino-ethyl)-2-(2-propionyl-1,2,3,4-tetrahydro-isoquinolin-5-ylamino)-acetamide;
N-Benzyl-N-(2-dimethylamino-ethyl)-2-(2-isobutyl-1,2,3,4-tetrahydro-isoquinolin-5-ylamino)-acetamide;
5-({[Benzyl-(2-dimethylamino-ethyl)-carbamoyl]-methyl}-amino)-3,4-dihydro-1H-isoquinoline-2-carboxylic acid methyl ester;
N-Benzyl-2-(2-butyryl-1,2,3,4-tetrahydro-isoquinolin-5-ylamino)-N-(2-dimethylamino-ethyl)-acetamide;
N-(2-Chloro-benzyl)-N-(2-dimethylamino-ethyl)-2-(2-ethyl-1,2,3,4-tetrahydro-isoquinolin-5-ylamino)-acetamide;
N-(2-Chloro-benzyl)-2-(2-cyclopropylmethyl-1,2,3,4-tetrahydro-isoquinolin-5-ylamino)-N-(2-dimethylamino-ethyl)-acetamide;
N-(2-Dimethylamino-ethyl)-2-(2-ethyl-1,2,3,4-tetrahydro-isoquinolin-5-ylamino)-N-(2-trifluoromethyl-benzyl)-acetamide;
2-(2-Cyclopropylmethyl-1,2,3,4-tetrahydro-isoquinolin-5-ylamino)-N-(1-methyl-piperidin-3-yl)-N-(2-trifluoromethyl-benzyl)-acetamide;
2-(2-Ethyl-1,2,3,4-tetrahydro-isoquinolin-5-ylamino)-N-(1-methyl-piperidin-4-yl)-N-(2-trifluoromethyl-benzyl)-acetamide;
(E)-N-Benzyl-N-(2-dimethylamino-ethyl)-3-(2-methyl-1,2,3,4-tetrahydro-isoquinolin-5-yl)-acrylamide;
(E)-N-Benzyl-3-(2-cyclopropylmethyl-1,2,3,4-tetrahydro-isoquinolin-5-yl)-N-(2-dimethylamino-ethyl)-acrylamide;
{Benzyl-[(E)-3-(2-cyclopropylmethyl-1,2,3,4-tetrahydro-isoquinolin-5-yl)-acryloyl]-amino}-acetic acid ethyl ester;
(E)-N-(2-Chloro-benzyl)-N-(2-dimethylamino-ethyl)-3-(2-ethyl-1,2,3,4-tetrahydro-isoquinolin-5-yl)-acrylamide;
(E)-N-(2-Chloro-benzyl)-3-(2-cyclopropylmethyl-1,2,3,4-tetrahydro-isoquinolin-5-yl)-N-(2-dimethylamino-ethyl)-acrylamide;
(E)-N-Benzyl-3-(2-cyclopropylmethyl-1,2,3,4-tetrahydro-isoquinolin-5-yl)-N-(1,1-dioxo-tetrahydro-1l6-thiophen-3-yl)-acrylamide;
(E)-N-(2-Dimethylamino-ethyl)-3-(2-ethyl-1,2,3,4-tetrahydro-isoquinolin-5-yl)-N-(2-trifluoromethyl-benzyl)-acrylamide;
(E)-3-(2-Cyclopropylmethyl-1,2,3,4-tetrahydro-isoquinolin-5yl)-N-(2-dimethylamino-ethyl)-N-(2-trifluoromethyl-benzyl)-acrylamide;
(E)-3-(2-Ethyl-1,2,3,4-tetrahydro-isoquinolin-5-yl)-N-(1-methyl-piperidin-4-yl)-N-(2-trifluoromethyl-benzyl)-acrylamide;
(E)-3-(2-Cyclopropylmethyl-1,2,3,4-tetrahydro-isoquinolin-5-yl)-N-(1-methyl-piperidin-4-yl)-N-(2-trifluoromethyl-benzyl)-acrylamide;
(E)-3-(2-Cyclopropylmethyl-1,2,3,4-tetrahydro-isoquinolin-5-yl)-N-(2-dimethylamino-ethyl)-2-methyl-N-(2-trifluoromethyl-benzyl)-acrylamide;
N-(2-Chloro-benzyl)-N-(2-dimethylamino-ethyl)-3-(2-ethyl-1,2,3,4-tetrahydro-isoquinolin-5-yl)-propionamide;
N-(2-Chloro-benzyl)-3-(2-cyclopropylmethyl-1,2,3,4-tetrahydro-isoquinolin-5-yl)-N-(2-dimethylamino-ethyl)-propionamide;
N-(2-Dimethylamino-ethyl)-3-(2-ethyl-1,2,3,4-tetrahydro-isoquinolin-5-yl)-N-(2-trifluoromethyl-benzyl)-propionamide;
3-(2-Cyclopropylmethyl-1,2,3,4-tetrahydro-isoquinolin-5-yl)-N-(2-dimethylamino-ethyl)-N-(2-trifluoromethyl-benzyl)-propionamide;
3-(2-Cyclopropylmethyl-1,2,3,4-tetrahydro-isoquinolin-5-yl)-N-(1-methyl-piperidin-4-yl)-N-(2-trifluoromethyl-benzyl)-propionamide;

N-Benzyl-3-(2-cyclopropylmethyl-1,2,3,4-tetrahydro-isoquinolin-5-yl)-N-(2-dimethylamino-ethyl)-propionamide;
N-Benzyl-N-(2-dimethylamino-ethyl)-3-(2-propionyl-1,2,3,4-tetrahydro-isoquinolin-5-yl)-propionamide;
N-Benzyl-2-(2-cyclopropylmethyl-1,2,3,4-tetrahydro-isoquinolin-5-yloxy)-N-(3-methyl-butyl)-acetamide;
N-Benzyl-2-(2-cyclopropylmethyl-1,2,3,4-tetrahydro-isoquinolin-5-yloxy)-N-(2-dimethylamino-ethyl)-acetamide;
5-{[Benzyl-(2-dimethylamino-ethyl)-carbamoyl]-methoxy}-3,4-dihydro-1H-isoquinoline-2-carboxylic acid methyl ester;
N-Benzyl-N-(2-dimethylamino-ethyl)-2-(2-isobutyl-1,2,3,4-tetrahydro-isoquinolin-5-yloxy)-acetamide;
N-Benzyl-N-(2-dimethylamino-ethyl)-2-(2-propionyl-1,2,3,4-tetrahydro-isoquinolin-5-yloxy)-acetamide;
N-(2-Chloro-benzyl)-N-(2-dimethylamino-ethyl)-2-(2-ethyl-1,2,3,4-tetrahydro-isoquinolin-5-yloxy)-acetamide;
N-(2-Chloro-benzyl)-2-(2-cyclopropylmethyl-1,2,3,4-tetrahydro-isoquinolin-5-yloxy)-N-(2-dimethylamino-ethyl)-acetamide;
N-(2-Dimethylamino-ethyl)-2-(2-ethyl-1,2,3,4-tetrahydro-isoquinolin-5-yloxy)-N-(2-trifluoromethyl-benzyl)-acetamide;
2-(2-Cyclopropylmethyl-1,2,3,4-tetrahydro-isoquinolin-5-yloxy)-N-(2-dimethylamino-ethyl)-N-(2-trifluoromethyl-benzyl)-acetamide;
N-(2-Dimethylamino-ethyl)-N-(2-fluoro-benzyl)-2-(2-methyl-1,2,3,4-tetrahydro-isoquinolin-5-ylamino)-acetamide;
N-(2-Methylamino-ethyl)-2-(2-propionyl-1,2,3,4-tetrahydro-isoquinolin-5-ylamino)-N-(2-trifluoromethyl-benzyl)-acetamide;
N-Benzyl-2-(2-cyclopropylmethyl-1,2,3,4-tetrahydro-isoquinolin-5-ylamino)-N-pyrrolidin-3-yl-acetamide;
2-(2-Cyclopropylmethyl-1,2,3,4-tetrahydro-isoquinolin-5-ylamino)-N-(2-methylamino-ethyl)-N-(2-trifluoromethyl-benzyl)-acetamide;
N-Benzyl-2-(2-cyclopropylmethyl-1,2,3,4-tetrahydro-isoquinolin-5-ylamino)-N-(1-methyl-pyrrolidin-3-yl)-acetamide;
N-Benzyl-2-(2-cyclopropylmethyl-1,2,3,4-tetrahydro-isoquinolin-8-ylamino)-N-(2-dimethylamino-ethyl)-acetamide;
N-Benzyl-N-(2-dimethylamino-ethyl)-2-(2-isobutyl-1,2,3,4-tetrahydro-isoquinolin-8-ylamino)-acetamide;
8-({[Benzyl-(2-dimethylamino-ethyl)-carbamoyl]-methyl}-amino)-3,4-dihydro-1H-isoquinoline-2-carboxylic acid isopropyl ester;
N-Benzyl-2-(2-benzyl-1,2,3,4-tetrahydro-isoquinolin-8-ylamino)-N-(2-dimethylamino-ethyl)-acetamide;
N-Benzyl-2-(2-cyclohexylmethyl-1,2,3,4-tetrahydro-isoquinolin-8-ylamino)-N-(2-dimethylamino-ethyl)-acetamide;
2-(2-Benzoyl-1,2,3,4-tetrahydro-isoquinolin-8-ylamino)-N-benzyl-N-(2-dimethylamino-ethyl)-acetamide;
N-Benzyl-N-(2-dimethylamino-ethyl)-2-(2-methyl-1,2,3,4-tetrahydro-isoquinolin-8-yloxy)-acetamide;
N-Benzyl-N-(2-dimethylamino-ethyl)-2-(2-ethyl-1,2,3,4-tetrahydro-isoquinolin-8-yloxy)-acetamide;
N-Benzyl-2-(2-cyclopropylmethyl-1,2,3,4-tetrahydro-isoquinolin-8-yloxy)-N-(2-dimethylamino-ethyl)-acetamide;
8-{[Benzyl-(2-dimethylamino-ethyl)-carbamoyl]-methoxy}-3,4-dihydro-1H-isoquinoline-2-carboxylic acid methyl ester;
N-Benzyl-N-(2-dimethylamino-ethyl)-2-(2-isobutyl-1,2,3,4-tetrahydro-isoquinolin-8-yloxy)-acetamide;
N-Benzyl-N-(2-dimethylamino-ethyl)-2-(2-propionyl-1,2,3,4-tetrahydro-isoquinolin-8-yloxy)-acetamide;
2-(2-Benzoyl-1,2,3,4-tetrahydro-isoquinolin-8-yloxy)-N-benzyl-N-(2-dimethylamino-ethyl)-acetamide;
2((2-Cyclopentyl-1,2,3,4-tetrahydroisoquinolin-5-yl)amino)-N-(2-(dimethylamino)ethyl)-N-(2-(trifluoromethyl)benzyl)acetamide;
2((2-(Cyclopropylmethyl)-1-methyl-1,2,3,4-tetrahydroisoquinolin-5-yl)amino)-N-(2-(dimethylamino)ethyl)-N-(2-(trifluoromethyl)benzyl)acetamide; or
2((2-(Cyclopropylmethyl)-3-methyl-1,2,3,4-tetrahydroisoquinolin-5-yl)amino)-N-(2-(dimethylamino)ethyl)-N-(2-(trifluoromethyl)benzyl)acetamide;
or a pharmaceutically acceptable salt thereof.

12. The compound of formula (I) according to claim 1, wherein the compound is:
2-(2-Cyclopropylmethyl-1,2,3,4-tetrahydro-isoquinolin-5-ylamino)-N-[2-(1-methyl-pyrrolidin-2-yl)-ethyl]-N-(2-trifluoromethyl-benzyl)-acetamide;
2-(2-Cyclopropylmethyl-1,2,3,4-tetrahydro-isoquinolin-5-ylamino)-N-(3-pyrrolidin-1-yl-propyl)-N-(2-trifluoromethyl-benzyl)-acetamide;
4-(2-[[2-(2-Cyclopropylmethyl-1,2,3,4-tetrahydro-isoquinolin-5-ylamino)-acetyl]-(2-trifluoromethyl-benzyl)-amino]-ethylypiperazine-1-carboxylic acid tert-butyl ester;
2-(2-Cyclopropylmethyl-1,2,3,4-tetrahydro-isoquinolin-5-ylamino)-N-(2-piperidin-1-yl-ethyl)-N-(2-trifluoromethyl-benzyl)-acetamide;
N-(2-Azepan-1-yl-ethyl)-2-(2-cyclopropylmethyl-1,2,3,4-tetrahydro-isoquinolin-5-ylamino)-N-(2-trifluoromethyl-benzyl)-acetamide;
2-(2-Cyclopropylmethyl-1,2,3,4-tetrahydro-isoquinolin-5-ylamino)-N-(2-diisopropylamino-ethyl)-N-(2-trifluoromethyl-benzyl)-acetamide;
N[2-(Cyclopropyl-methyl-amino)-ethyl]-2-(2-cyclopropylmethyl-1,2,3,4-tetrahydro-isoquinolin-5-ylamino)-N-(2-trifluoromethyl-benzyl)-acetamide;
2-(2-Cyclopropylmethyl-1,2,3,4-tetrahydro-isoquinolin-5-ylamino)-N-(2-dimethylamino-ethyl)-N-(3-trifluoromethoxy-benzyl)-acetamide;
2-(2-Cyclopropylmethyl-1,2,3,4-tetrahydro-isoquinolin-5-ylamino)-N-(4-hydroxy-cyclohexyl)-N-(2-trifluoromethyl-benzyl)-acetamide;
2-(2-Cyclopropylmethyl-1,2,3,4-tetrahydro-isoquinolin-5-ylamino)-N-(2-hydroxy-3-methoxy-propyl)-N-(2-trifluoromethyl-benzyl)-acetamide;
2-(2-Cyclopropylmethyl-1,2,3,4-tetrahydro-isoquinolin-5-ylamino)-N-(2-methoxy-ethyl)-N-(2-trifluoromethyl-benzyl)-acetamide;
2-(2-Cyclopropylmethyl-1,2,3,4-tetrahydro-isoquinolin-5-ylamino)-N-[1,4]dioxan-2-ylmethyl-N-(2-trifluoromethyl-benzyl)-acetamide;
2-(2-Cyclopropylmethyl-1,2,3,4-tetrahydro-isoquinolin-5-ylamino)-N-(2-dimethylamino-ethyl)-N-(2-trifluoromethoxy-benzyl)-acetamide;
2-(2-Cyclopropylmethyl-1,2,3,4-tetrahydro-isoquinolin-5-ylamino)-N-(2-methanesulfonyl-ethyl)-N-(2-trifluoromethyl-benzyl)-acetamide;
2-(2-Cyclopropylmethyl-1,2,3,4-tetrahydro-isoquinolin-5-ylamino)-N-[2-(ethyl-methyl-amino)-ethyl]-N-(2-trifluoromethyl-benzyl)-acetamide;

N-(2-Bromo-benzyl)-2-(2-cyclopropylmethyl-1,2,3,4-tetrahydro-isoquinolin-5-ylamino)-N-(2-dimethylamino-ethyl)-acetamide;
N-(3-Bromo-pyridin-2-ylmethyl)-2-(2-cyclopropylmethyl-1,2,3,4-tetrahydro-isoquinolin-5-ylamino)-N-(2-dimethylamino-ethyl)-acetamide;
N-(3-Bromo-benzyl)-2-(2-cyclopropylmethyl-1,2,3,4-tetrahydro-isoquinolin-5-ylamino)-N-(2-dimethylamino-ethyl)-acetamide;
N-(4-Bromo-benzyl)-2-(2-cyclopropylmethyl-1,2,3,4-tetrahydro-isoquinolin-5-ylamino)-N-(2-dimethylamino-ethyl)-acetamide;
N-(3-Bromo-pyridin-4-ylmethyl)-2-(2-cyclopropylmethyl-1,2,3,4-tetrahydro-isoquinolin-5-ylamino)-N-(2-dimethylamino-ethyl)-acetamide;
2-(2-Cyclopropylmethyl-1,2,3,4-tetrahydro-isoquinolin-5-ylamino)-N-(2-hydroxy-propyl)-N-(2-trifluoromethyl-benzyl)-acetamide;
2-(2-Cyclopropylmethyl-1,2,3,4-tetrahydro-isoquinolin-5-ylamino)-N-(2-hydroxy-2-methyl-propyl)-N-(2-trifluoromethyl-benzyl)-acetamide;
2-(2-Cyclopropylmethyl-1,2,3,4-tetrahydro-isoquinolin-5-ylamino)-N-(3,3,3-trifluoro-2-hydroxy-propyl)-N-(2-trifluoromethyl-benzyl)-acetamide;
2-(2-Cyclopropylmethyl-1,2,3,4-tetrahydro-isoquinolin-5-ylamino)-N-(1-hydroxy-cyclopentylmethyl)-N-(2-trifluoromethyl-benzyl)-acetamide;
2-(2-Cyclopropylmethyl-1,2,3,4-tetrahydro-isoquinolin-5-ylamino)-N-(2-[(2-fluoro-ethyl)-methyl-amino]-ethyl)-N-(2-trifluoromethyl-benzyl)-acetamide;
N[2-(Allyl-methyl-amino)-ethyl]-2-(2-cyclopropylmethyl-1,2,3,4-tetrahydro-isoquinolin-5-ylamino)-N-(2-trifluoromethyl-benzyl)-acetamide;
2-(2-Cyclopropylmethyl-1,2,3,4-tetrahydro-isoquinolin-5-ylamino)-N-[2-(methyl-prop-2-ynyl-amino)-ethyl]-N-(2-trifluoromethyl-benzyl)-acetamide;
2-(2-Cyclopropylmethyl-1,2,3,4-tetrahydro-isoquinolin-5-ylamino)-N-thiazol-5-ylmethyl-N-(2-trifluoromethyl-benzyl)-acetamide;
N-(2-Chloro-benzyl)-2-(2-cyclopropylmethyl-1,2,3,4-tetrahydro-isoquinolin-5-ylamino)-N-[2-(4,4-difluoro-piperidin-1-yl)-ethyl]-acetamide;
N-(3-Chloro-pyridin-2-ylmethyl)-2-(2-cyclopropylmethyl-1,2,3,4-tetrahydro-isoquinolin-5-ylamino)-N-[2-(4,4-difluoro-piperidin-1-yl)-ethyl]-acetamide;
2-(2-Cyclopropylmethyl-1,2,3,4-tetrahydro-isoquinolin-5-ylamino)-N-isoxazol-5-ylmethyl-N-(2-trifluoromethyl-benzyl)-acetamide;
N-(3-Chloro-pyridin-2-ylmethyl)-2-(2-cyclopropylmethyl-1,2,3,4-tetrahydro-isoquinolin-5-ylamino)-N-(2-hydroxy-2-methyl-propyl)-acetamide;
3-{[[2-(2-Cyclopropylmethyl-1,2,3,4-tetrahydro-isoquinolin-5-ylamino)-acetyl]-(2-trifluoromethyl-benzyl)-amino]-methyl}-pyrrolidine-1-carboxylic acid tert-butyl ester;
2-(2-Cyclopropylmethyl-1,2,3,4-tetrahydro-isoquinolin-5-ylamino)-N-(2-dimethylamino-ethyl)-N-(3-methyl-pyridin-2-ylmethyl)-acetamide;
2-(2-Cyclopropylmethyl-1,2,3,4-tetrahydro-isoquinolin-5-ylamino)-N-(2-dimethylamino-ethyl)-N-pyridin-2-ylmethyl-acetamide;
2-(2-Cyclopropylmethyl-1,2,3,4-tetrahydro-isoquinolin-5-ylamino)-N-(2-dimethylamino-ethyl)-N-(5-methyl-pyridin-2-ylmethyl)-acetamide;
2-(2-Cyclopropylmethyl-1,2,3,4-tetrahydro-isoquinolin-5-ylamino)-N-(2-dimethylamino-ethyl)-N-(6-methyl-pyridin-2-ylmethyl)-acetamide;
N-(5-Chloro-pyridin-2-ylmethyl)-2-(2-cyclopropylmethyl-1,2,3,4-tetrahydro-isoquinolin-5-ylamino)-N-(2-dimethylamino-ethyl)-acetamide;
2-(2-Cyclopropylmethyl-1,2,3,4-tetrahydro-isoquinolin-5-ylamino)-N-(2-dimethylamino-ethyl)-N-thiazol-2-ylmethyl-acetamide;
2-(2-Cyclopropylmethyl-1,2,3,4-tetrahydro-isoquinolin-5-ylamino)-N-(2-dimethylamino-ethyl)-N-(4-methyl-thiazol-2-ylmethyl)-acetamide;
2-(2-Cyclopropylmethyl-1,2,3,4-tetrahydro-isoquinolin-5-ylamino)-N-(2-dimethylamino-ethyl)-N-(5-fluoro-pyridin-2-ylmethyl)-acetamide;
2-(2-Cyclopropylmethyl-1,2,3,4-tetrahydro-isoquinolin-5-ylamino)-N-(2,6-difluoro-benzyl)-N-(2-dimethylamino-ethyl)-acetamide;
2-(2-Cyclopropylmethyl-1,2,3,4-tetrahydro-isoquinolin-5-ylamino)-N-(2-dimethylamino-ethyl)-N-(3-fluoro-pyridin-2-ylmethyl)-acetamide;
2-(2-Cyclopropylmethyl-1,2,3,4-tetrahydro-isoquinolin-5-ylamino)-N-(3,3-dimethyl-butyl)-N-(3-trifluoromethyl-pyridin-2-ylmethyl)-acetamide;
2-(2-Cyclopropylmethyl-1,2,3,4-tetrahydro-isoquinolin-5-ylamino)-N-(3,3-dimethyl-butyl)-N-(3-methyl-pyridin-2-ylmethyl)-acetamide;
2-(2-Cyclopropylmethyl-1,2,3,4-tetrahydro-isoquinolin-5-ylamino)-N-[2-(4,4-difluoro-piperidin-1-yl)-ethyl]-N-(2-trifluoromethyl-benzyl)-acetamide;
2-(2-Cyclopropylmethyl-1,2,3,4-tetrahydro-isoquinolin-5-ylamino)-N-[2-(4,4-difluoro-piperidin-1-yl)-ethyl]-N-(3-trifluoromethyl-pyridin-2-ylmethyl)-acetamide;
2-(2-Cyclopropylmethyl-1,2,3,4-tetrahydro-isoquinolin-5-ylamino)-N-(2-[methyl-(2,2,2-trifluoro-ethyl)-amino]-ethyl)-N-(3-trifluoromethyl-pyridin-2-ylmethyl)-acetamide;
2-(2-Cyclopropylmethyl-1,2,3,4-tetrahydro-isoquinolin-5-ylamino)-N-[2-(3,3-difluoro-piperidin-1-yl)-ethyl]-N-(2-trifluoromethyl-benzyl)-acetamide;
2-(2-Cyclopropylmethyl-1,2,3,4-tetrahydro-isoquinolin-5-ylamino)-N-[2-(3,3-difluoro-pyrrolidin-1-yl)-ethyl]-N-(2-trifluoromethyl-benzyl)-acetamide;
2-(2-Cyclopropylmethyl-1,2,3,4-tetrahydro-isoquinolin-5-ylamino)-N-[2-(3,3-difluoro-piperidin-1-yl)-ethyl]-N-(3-trifluoromethyl-pyridin-2-ylmethyl)-acetamide;
2-(2-Cyclopropylmethyl-1,2,3,4-tetrahydro-isoquinolin-5-ylamino)-N-[2-(3,3-difluoro-pyrrolidin-1-yl)-ethyl]-N-(3-trifluoromethyl-pyridin-2-ylmethyl)-acetamide;
N-(2-Dimethylamino-ethyl)-2-[2-(2-fluoro-ethyl)-1,2,3,4-tetrahydro-isoquinolin-5-ylamino]-N-(2-trifluoromethyl-benzyl)-acetamide;
2-(2-Cyclopropylmethyl-8-fluoro-1,2,3,4-tetrahydro-isoquinolin-5-ylamino)-N-(2-dimethylamino-ethyl)-N-(2-trifluoromethyl-benzyl)-acetamide;
2-(2-Cyclopropylmethyl-8-fluoro-1,2,3,4-tetrahydro-isoquinolin-5-ylamino)-N-(2-dimethylamino-ethyl)-N-(3-trifluoromethyl-pyridin-2-ylmethyl)-acetamide;
2-(2-Cyclopropylmethyl-6-methyl-1,2,3,4-tetrahydro-isoquinolin-5-ylamino)-N-(2-dimethylamino-ethyl)-N-(2-trifluoromethyl-benzyl)-acetamide;
N-(3-Chloro-pyridin-2-ylmethyl)-N-(2-dimethylamino-ethyl)-2-[2-((1S*,2S*)-2-fluoro-cyclopropanecarbonyl)-1,2,3,4-tetrahydro-isoquinolin-5-ylamino]-acetamide;
N-{2-[(2-Fluoro-ethyl)-methyl-amino]-ethyl}-2(2-(2-methoxy-ethyl)-1,2,3,4-tetrahydro-isoquinolin-5-ylamino]-N-(2-trifluoromethyl-benzyl)-acetamide;

N-(3-Chloro-pyridin-2-ylmethyl)-N-(2-dimethylamino-ethyl)-2-[2-(2-methoxy-ethyl)-1,2,3,4-tetrahydro-iso-quinolin-5-ylamino]-acetamide;
N-(2-Dimethylamino-ethyl)-2-(2-prop-2-ynyl-1,2,3,4-tetrahydro-isoquinolin-5-ylamino)-N-(2-trifluorom-ethyl-benzyl)-acetamide;
N-(2-Dimethylamino-ethyl)-2-(2-ethyl-3-oxo-1,2,3,4-tetrahydro-isoquinolin-5-ylamino)-N-(2-trifluoromethyl-benzyl)-acetamide;
2-(2-Ethyl-3-oxo-1,2,3,4-tetrahydro-isoquinolin-5-ylamino)-N-(2-pyrrolidin-1-yl-ethyl)-N-(2-trifluorom-ethyl-benzyl)-acetamide;
N-(2-Dimethylamino-ethyl)-2-(2-isobutyl-3-oxo-1,2,3,4-tetrahydro-isoquinolin-5-ylamino)-N-(2-trifluorom-ethyl-benzyl)-acetamide;
N-(2-Dimethylamino-ethyl)-2-(2-isobutyl-3-oxo-1,2,3,4-tetrahydro-isoquinolin-5-ylamino)-N-(3-trifluorom-ethyl-pyridin-2-ylmethyl)-acetamide;
2-(2-isobutyl-3-oxo-1,2,3,4-tetrahydro-isoquinolin-5-ylamino)-N-(2-pyrrolidin-1-yl-ethyl)-N-(2-trifluorom-ethyl-benzyl)-acetamide;
2-(2-Cyclopropylmethyl-1-oxo-1,2,3,4-tetrahydro-iso-quinolin-5-ylamino)-N-(2-dimethylamino-ethyl)-N-(2-trifluoromethyl-benzyl)-acetamide;
(E)-N-(2-Dimethylamino-ethyl)-3-[2-(2-methoxy-ethyl)-1,2,3,4-tetrahydro-isoquinolin-5-yl]-N-(2-trifluorom-ethyl-benzyl)-acrylamide;
(E)-N-(2-Dimethylamino-ethyl)-3-[2-(2-methoxy-ethyl)-1,2,3,4-tetrahydro-isoquinolin-5-yl]-N-(3-trifluorom-ethyl-pyridin-2-ylmethyl)-acrylamide;
(E)-N-(3-Chloro-pyridin-2-ylmethyl)-N-(2-dimethyl-amino-ethyl)-3-[2-(2-methoxy-ethyl)-1,2,3,4-tetra-hydro-isoquinolin-5-yl]-acrylamide;
(E)-N-(3-Chloro-pyridin-2-ylmethyl)-3-(2-cyclopropyl-methyl-1,2,3,4-tetrahydro-isoquinolin-5-yl)-N-(2-hy-droxy-2-methyl-propyl)-acrylamide;
(E)-N-(3-Chloro-pyridin-2-ylmethyl)-N-(2-dimethyl-amino-ethyl)-3-[2-((1R*,2R*)-2-fluoro-cyclopropan-ecarbonyl)-1,2,3,4-tetrahydro-isoquinolin-5-yl]-acryl-amide;
(E)-N-(3-Chloro-pyridin-2-ylmethyl)-3-(2-cyclopropyl-methyl-1,2,3,4-tetrahydro-isoquinolin-5-yl)-N-(2-dim-ethylamino-ethyl)-acrylamide;
(E)-N-(3-Chloro-pyridin-2-ylmethyl)-3-(2-cyclopropyl-methyl-1,2,3,4-tetrahydro-isoquinolin-5-yl)-N-[2-(4,4-difluoro-piperidin-1-yl)-ethyl]-acrylamide;
N-(2-Dimethylamino-ethyl)-3-[2-(2-methoxy-ethyl)-1,2,3,4-tetrahydro-isoquinolin-5-yl]-N-(2-trifluoromethyl-benzyl)-propionamide;
N-(2-Dimethylamino-ethyl)-3-[2-(2-methoxy-ethyl)-1,2,3,4-tetrahydro-isoquinolin-5-yl]-N-(3-trifluoromethyl-pyridin-2-ylmethyl)-propionamide;
N-[2-(Allyl-methyl-amino)-ethyl]-3-(2-allyl-1,2,3,4-tet-rahydro-isoquinolin-5-yl)-N-(2-trifluoromethyl-ben-zyl)-propionamide;
3-(2-Allyl-1,2,3,4-tetrahydro-isoquinolin-5-yl)-N-(2-di-methylamino-ethyl)-N-(2-trifluoromethyl-benzyl)-pro-pionamide;
2-(2-Cyclopropylmethyl-1,2,3,4-tetrahydro-isoquinolin-5-yloxy)-N-(2-dimethylamino-ethyl)-N-(2-trifluorom-ethyl-benzyl)-propionamide;
N-(2-Dimethylamino-ethyl)-2-[2-(tetrahydro-furan-3-yl)-1,2,3,4-tetrahydro-isoquinolin-5-ylamino]-N-(2-trif-luoromethyl-benzyl)-acetamide;
2-(2-Cyclobutyl-1,2,3,4-tetrahydro-isoquinolin-5-ylamino)-N-(2-dimethylamino-ethyl)-N-(2-trifluorom-ethyl-benzyl)-acetamide;
N-(2-Dimethylamino-ethyl)-2-[2-(2-methoxy-1-methyl-ethyl)-1,2,3,4-tetrahydro-isoquinolin-5-ylamino]-N-(2-trifluoromethyl-benzyl)-acetamide;
N-(2-Dimethylamino-ethyl)-2-[2-(1,2-dimethyl-propyl)-1,2,3,4-tetrahydro-isoquinolin-5-ylamino]-N-(2-trif-luoromethyl-benzyl)-acetamide;
2-(2-sec-Butyl-1,2,3,4-tetrahydro-isoquinolin-5-ylamino)-N-(2-dimethylamino-ethyl)-N-(2-trifluorom-ethyl-benzyl)-acetamide;
2-[2-(1-Cyclopropyl-ethyl)-1,2,3,4-tetrahydro-isoquino-lin-5-ylamino]-N-(2-dimethylamino-ethyl)-N-(2-trif-luoromethyl-benzyl)-acetamide;
N-(2-Dimethylamino-ethyl)-2-[2-(3-methyl-oxetan-3-yl-methyl)-1,2,3,4-tetrahydro-isoquinolin-5-ylamino]-N-(2-trifluoromethyl-benzyl)-acetamide;
N-(2-Dimethylamino-ethyl)-2-[2-(2-methoxy-ethyl)-1,2,3,4-tetrahydro-isoquinolin-5-ylamino]-N-(2-trifluo-romethyl-benzyl)-acetamide;
[5-({[(2-Dimethylamino-ethyl)-(2-trifluoromethyl-ben-zyl)-carbamoyl]-methyl}-amino)-3,4-dihydro-1H-iso-quinolin-2-yl]-acetic acid methyl ester;
2-(2-Cyclobutylmethyl-1,2,3,4-tetrahydro-isoquinolin-5-ylamino)-N-(2-dimethylamino-ethyl)-N-(2-trifluorom-ethyl-benzyl)-acetamide;
2-[2-(2,2-Difluoro-propionyl)-1,2,3,4-tetrahydro-isoqui-nolin-5-ylamino]-N-(2-dimethylamino-ethyl)-N-(2-tri-fluoromethyl-benzyl)-acetamide;
N-(2-Dimethylamino-ethyl)-2-[2-((1R*,2R*)-2-fluoro-cyclopropanecarbonyl)-1,2,3,4-tetrahydro-isoquinolin-5-ylamino]-N-(2-trifluoromethyl-benzyl)-acetamide;
2-(2-Cyanomethyl-1,2,3,4-tetrahydro-isoquinolin-5-ylamino)-N-(2-dimethylamino-ethyl)-N-(2-trifluorom-ethyl-benzyl)-acetamide;
N-(2-Dimethylamino-ethyl)-2-[2-(tetrahydro-furan-3-yl)-1,2,3,4-tetrahydro-isoquinolin-5-ylamino]-N-(3-trif-luoromethyl-pyridin-2-ylmethyl)-acetamide;
2-(2-Cyclobutyl-1,2,3,4-tetrahydro-isoquinolin-5-ylamino)-N-(2-dimethylamino-ethyl)-N-(3-trifluorom-ethyl-pyridin-2-ylmethyl)-acetamide;
2-(2-Cyclobutylmethyl-1,2,3,4-tetrahydro-isoquinolin-5-ylamino)-N-(2-dimethylamino-ethyl)-N-(3-trifluorom-ethyl-pyridin-2-ylmethyl)-acetamide;
[5-({[(2-Dimethylamino-ethyl)-(3-trifluoromethyl-pyri-din-2-ylmethyl)-carbamoyl]methylamino)-3,4-di-hydro-1H-isoquinolin-2-ylyacetic acid methyl ester;
N-(2-Dimethylamino-ethyl)-2-[2-(2-methoxy-ethyl)-1,2,3,4-tetrahydro-isoquinolin-5-ylamino]-N-(3-trifluo-romethyl-pyridin-2-ylmethyl)-acetamide;
N-(2-Dimethylamino-ethyl)-2-(2-pyridin-2-yl-1,2,3,4-tetrahydro-isoquinolin-5-ylamino)-N-(2-trifluorom-ethyl-benzyl)-acetamide;
N-(2-Dimethylamino-ethyl)-2-(2-pyrimidin-2-yl-1,2,3,4-tetrahydro-isoquinolin-5-ylamino)-N-(2-trifluorom-ethyl-benzyl)-acetamide;
N-(2-Dimethylamino-ethyl)-N-(2-trifluoromethyl-ben-zyl)-2-[2-(4-trifluoromethyl-thiazol-2-yl)-1,2,3,4-tet-rahydro-isoquinolin-5-ylamino]-acetamide;
2-(2-Cyclopropylmethyl-1,2,3,4-tetrahydro-isoquinolin-5-ylamino)-N—(R)-1-pyrrrolidin-3-ylmethyl-N-(2-tri-fluoromethyl-benzyl)-acetamide;
2-(2-Cyclopropylmethyl-1,2,3,4-tetrahydro-isoquinolin-5-ylamino)-N—(S)-1-pyrrolidin-3-ylmethyl-N-(2-trif-luoromethyl-benzyl)-acetamide;
2-(2-Cyclopropylmethyl-1,2,3,4-tetrahydro-isoquinolin-5-ylamino)-N-pyrrolidin-3-yl-N-(2-trifluoromethyl-benzyl)-acetamide;

2-(2-Cyclopropylmethyl-1-methyl-1,2,3,4-tetrahydro-isoquinolin-5-ylamino)-N-(2-methylamino-ethyl)-N-(2-trifluoromethyl-benzyl)-acetamide;

2-(2-Cyclopropylmethyl-1,2,3,4-tetrahydro-isoquinolin-8-ylamino)-N-(2-methylamino-ethyl)-N-(2-trifluoromethyl-benzyl)-acetamide;

2-(2-Cyclopropanecarbonyl-1,2,3,4-tetrahydro-isoquinolin-5-ylamino)-N-(2-methylamino-ethyl)-N-(2-trifluoromethyl-benzyl)-acetamide;

2-(2-Butyryl-1,2,3,4-tetrahydro-isoquinolin-5-ylamino)-N-(2-methylamino-ethyl)-N-(2-trifluoromethyl-benzyl)-acetamide;

2-(2-Isobutyryl-1,2,3,4-tetrahydro-isoquinolin-5-ylamino)-N-(2-trifluoromethyl-benzyl)-acetamide;

2-[2-(2-Methoxy-acetyl)-1,2,3,4-tetrahydro-isoquinolin-5-ylamino]-N-(2-methylamino-ethyl)-N-(2-trifluoromethyl-benzyl)-acetamide;

2-(2-Cyclobutanecarbonyl-1,2,3,4-tetrahydro-isoquinolin-5-ylamino)-N-(2-methylamino-ethyl)-N-(2-trifluoromethyl-benzyl)-acetamide;

N-(2-Methylamino-ethyl)-2-[2-(3-methyl-butyryl)-1,2,3,4-tetrahydro-isoquinolin-5-ylamino]-N-(2-trifluoromethyl-benzyl)-acetamide;

N-(2-Methylamino-ethyl)-2-[2-(tetrahydro-furan-3-carbonyl)-1,2,3,4-tetrahydro-isoquinolin-5-ylamino]-N-(2-trifluoromethyl-benzyl)-acetamide;

5-({[(2-Methylamino-ethyl)-(2-trifluoromethyl-benzyl)-carbamoyl]methyl}-amino)-3,4-dihydro-1H-isoquinoline-2-carboxylic acid methyl ester;

5-({[(2-Methylamino-ethyl)-(2-trifluoromethyl-benzyl)-carbamoyl]methyl}-amino)-3,4-dihydro-1H-isoquinoline-2-carboxylic acid ethyl ester;

5-({[(2-Methylamino-ethyl)-(2-trifluoromethyl-benzyl)-carbamoyl]methyl}-amino)-3,4-dihydro-1H-isoquinoline-2-carboxylic acid prop-2-ynyl ester;

5-({[(2-Methylamino-ethyl)-(2-trifluoromethyl-benzyl)-carbamoyl]methyl}-amino)-3,4-dihydro-1H-isoquinoline-2-carboxylic acid allyl ester;

5-({[(2-Methylamino-ethyl)-(2-trifluoromethyl-benzyl)-carbamoyl]methyl}-amino)-3,4-dihydro-1H-isoquinoline-2-carboxylic acid 2-fluoro-ethyl ester;

5-({[(2-Methylamino-ethyl)-(2-trifluoromethyl-benzyl)-carbamoyl]methyl}-amino)-3,4-dihydro-1H-isoquinoline-2-carboxylic acid ethylamide;

2-(2-Acetyl-1,2,3,4-tetrahydro-isoquinolin-5-ylamino)-N-(2-methylamino-ethyl)-N-(3-trifluoromethyl-pyridin-2-ylmethyl)-acetamide;

N-(2-Methylamino-ethyl)-2-(2-propionyl-1,2,3,4-tetrahydro-isoquinolin-5-ylamino)-N-(3-trifluoromethyl-pyridin-2-ylmethyl)-acetamide;

2-(2-Cyclopropanecarbonyl-1,2,3,4-tetrahydro-isoquinolin-5-ylamino)-N-(2-methylamino-ethyl)-N-(3-trifluoromethyl-pyridin-2-ylmethyl)-acetamide;

2-(2-Butyryl-1,2,3,4-tetrahydro-isoquinolin-5-ylamino)-N-(2-methylamino-ethyl)-N-(3-trifluoromethyl-pyridin-2-ylmethyl)-acetamide;

2-(2-isobutyryl-1,2,3,4-tetrahydro-isoquinolin-5-ylamino)-N-(2-methylamino-ethyl)-N-(3-trifluoromethyl-pyridin-2-ylmethyl)-acetamide;

2-[2-(2-Methoxy-acetyl)-1,2,3,4-tetrahydro-isoquinolin-5-ylamino]-N-(2-methylamino-ethyl)-N-(3-trifluoromethyl-pyridin-2-ylmethyl)-acetamide;

2-(2-Cyclobutanecarbonyl-1,2,3,4-tetrahydro-isoquinolin-5-ylamino)-N-(2-methylamino-ethyl)-N-(3-trifluoromethyl-pyridin-2-ylmethyl)-acetamide;

N-(2-Methylamino-ethyl)-2-[2-(tetrahydro-furan-3-carbonyl)-1,2,3,4-tetrahydro-isoquinolin-5-ylamino]-N-(3-trifluoromethyl-pyridin-2-ylmethyl)-acetamide;

5-({[(2-Methylamino-ethyl)-(3-trifluoromethyl-pyridin-2-ylmethyl)-carbamoyl]methyl}-amino)-3,4-dihydro-1H-isoquinoline-2-carboxylic acid methyl ester;

5-({[(2-Methylamino-ethyl)-(3-trifluoromethyl-pyridin-2-ylmethyl)-carbamoyl]-methyl}-amino)-3,4-dihydro-1H-isoquinoline-2-carboxylic acid ethyl ester;

5-({[(2-Methylamino-ethyl)-(3-trifluoromethyl-pyridin-2-ylmethyl)-carbamoyl]-methyl}-amino)-3,4-dihydro-1H-isoquinoline-2-carboxylic acid prop-2-ynyl ester;

5-({[(2-Methylamino-ethyl)-(3-trifluoromethyl-pyridin-2-ylmethyl)-carbamoyl]-methyl}-amino)-3,4-dihydro-1H-isoquinoline-2-carboxylic acid allyl ester;

5-({[(2-Methylamino-ethyl)-(3-trifluoromethyl-pyridin-2-ylmethyl)-carbamoyl]-methyl}-amino)-3,4-dihydro-1H-isoquinoline-2-carboxylic acid 2-fluoro-ethyl ester;

5-({[(2-Methylamino-ethyl)-(3-trifluoromethyl-pyridin-2-ylmethyl)-carbamoyl]-methyl}-amino)-3,4-dihydro-1H-isoquinoline-2-carboxylic acid ethylamide;

5-({[(2-Methylamino-ethyl)-(3-trifluoromethyl-pyridin-2-ylmethyl)-carbamoyl]-methyl}-amino)-3,4-dihydro-1H-isoquinoline-2-carboxylic acid isopropylamide;

5-({[(2-Methylamino-ethyl)-(3-trifluoromethyl-pyridin-2-ylmethyl)-carbamoyl]-methyl}-amino)-3,4-dihydro-1H-isoquinoline-2-carboxylic acid tert-butylamide;

2-(2-Cyclopropylmethyl-1,2,3,4-tetrahydro-isoquinolin-5-ylamino)-N-[2-(2,2,2-trifluoro-ethylamino)-ethyl]-N-(2-trifluoromethyl-benzyl)-acetamide;

N-(2-Bromo-benzyl)-2-(2-cyclopropylmethyl-1,2,3,4-tetrahydro-isoquinolin-5-ylamino)-N-(2-methylamino-ethyl)-acetamide;

N-(3-Chloro-pyridin-2-ylmethyl)-2-(2-cyclopropylmethyl-1,2,3,4-tetrahydro-isoquinolin-5-ylamino)-N-(2-methylamino-ethyl)-acetamide;

2-(2-Cyclopropylmethyl-1,2,3,4-tetrahydro-isoquinolin-5-ylamino)-N-(2-methylamino-ethyl)-N-(3-trifluoromethyl-pyridin-2-ylmethyl)-acetamide;

2-(2-Cyclopropylmethyl-1,2,3,4-tetrahydro-isoquinolin-5-ylamino)-N-(2-piperazin-1-yl-ethyl)-N-(2-trifluoromethyl-benzyl)-acetamide;

2-(2-Cyclopropylmethyl-1,2,3,4-tetrahydro-isoquinolin-5-ylamino)-N-(2-ethylamino-ethyl)-N-(2-trifluoromethyl-benzyl)-acetamide;

2-(2-Cyclopropylmethyl-1,2,3,4-tetrahydro-isoquinolin-5-ylamino)-N-piperidin-4-yl-N-(2-trifluoromethyl-benzyl)-acetamide;

2-(2-Cyclopropylmethyl-1,2,3,4-tetrahydro-isoquinolin-5-ylamino)-N-pyrrolidin-3-ylmethyl-N-(2-trifluoromethyl-benzyl)-acetamide;

N-(2-Amino-ethyl)-2-(2-cyclopropylmethyl-1,2,3,4-tetrahydro-isoquinolin-5-ylamino)-N-(2-trifluoromethyl-benzyl)-acetamide;

2-(2-Ethyl-1,2,3,4-tetrahydro-isoquinolin-8-ylamino)-N-(2-methylamino-ethyl)-N-(2-trifluoromethyl-benzyl)-acetamide;

2-(2-Acetyl-1,2,3,4-tetrahydro-isoquinolin-5-ylamino)-N-(2-methylamino-ethyl)-N-(2-trifluoromethyl-benzyl)-acetamide;

N-(2-Chloro-benzyl)-2-(2-cyclopropylmethyl-1,2,3,4-tetrahydro-isoquinolin-5-ylamino)-N-(2-methylamino-ethyl)-acetamide;

N-[2-(Cyclobutyl-methyl-amino)-ethyl]-2-(2-cyclopropylmethyl-1,2,3,4-tetrahydro-isoquinolin-5-ylamino)-N-(2-trifluoromethyl-benzyl)-acetamide;

2-(2-Cyclopropylmethyl-1,2,3,4-tetrahydro-isoquinolin-5-ylamino)-N-{2-[methyl-(tetrahydro-furan-3-yl)-amino]-ethyl)}-N-(2-trifluoromethyl-benzyl)-acetamide;
2-(2-Cyclopropylmethyl-1,2,3,4-tetrahydro-isoquinolin-5-ylamino)-N-[2-(isopropyl-methyl-amino)-ethyl]-N-(2-trifluoromethyl-benzyl)-acetamide;
N-[2-(Cyclopropylmethyl-methyl-amino)-ethyl]-2-(2-cyclopropylmethyl-1,2,3,4-tetrahydro-isoquinolin-5-ylamino)-N-(2-trifluoromethyl-benzyl)-acetamide;
N-[2-(Cyclopentyl-methyl-amino)-ethyl]-2-(2-cyclopropylmethyl-1,2,3,4-tetrahydro-isoquinolin-5-ylamino)-N-(2-trifluoromethyl-benzyl)-acetamide;
2-(2-Cyclopropylmethyl-1,2,3,4-tetrahydro-isoquinolin-5-ylamino)-N-{2-[(2-fluoro-1-methyl-ethyl)-methyl-amino]-ethyl)}-N-(2-trifluoromethyl-benzyl)-acetamide;
2-(2-Cyclopropylmethyl-1,2,3,4-tetrahydro-isoquinolin-5-ylamino)-N-{2-[ethyl-(3-methyl-oxetan-3-ylmethyl)-amino]-ethyl)}-N-(2-trifluoromethyl-benzyl)-acetamide;
3-(2-Cyclopropylmethyl-1,2,3,4-tetrahydro-isoquinolin-8-yl)-N-(2-dimethylamino-ethyl)-N-(2-trifluoromethyl-benzyl)-propionamide;
N-(3-Chloro-pyridin-2-ylmethyl)-2-(2-cyclobutyl-1,2,3,4-tetrahydro-isoquinolin-8-ylamino)-N-(2-dimethyl-amino-ethyl)-acetamide;
N-(3-Bromo-pyridin-2-ylmethyl)-2-(2-cyclobutyl-1,2,3,4-tetrahydro-isoquinolin-8-ylamino)-N-(2-dimethyl-amino-ethyl)-acetamide;
N-[2-(Allyl-methyl-amino)-ethyl]-2-(2-allyl-1,2,3,4-tetrahydro-isoquinolin-8-ylamino)-N-(2-trifluoromethyl-benzyl)-acetamide;
2-(2-Allyl-1,2,3,4-tetrahydro-isoquinolin-8-ylamino)-N-(2-dimethylamino-ethyl)-N-(2-trifluoromethoxy-benzyl)-acetamide;
2-(2-Allyl-1,2,3,4-tetrahydro-isoquinolin-8-ylamino)-N-{2-[(2-fluoro-ethyl)-methyl-amino]-ethyl}-N-(2-trifluoromethyl-benzyl)-acetamide;
2-(2-Allyl-1,2,3,4-tetrahydro-isoquinolin-8-ylamino)-N-(2-dimethylamino-ethyl)-N-(2-trifluoromethyl-benzyl)-acetamide;
N-[2-(Allyl-methyl-amino)-ethyl]-3-(2-allyl-1,2,3,4-tetrahydro-isoquinolin-8-yl)-N-(2-trifluoromethyl-benzyl)-propionamide;
3-(2-Allyl-1,2,3,4-tetrahydro-isoquinolin-8-yl)-N-(2-dimethylamino-ethyl)-N-(2-trifluoromethyl-benzyl)-propionamide;
2-(2-Cyclopropylmethyl-1,2,3,4-tetrahydro-isoquinolin-8-ylamino)-N-(2-dimethylamino-ethyl)-N-(2-trifluoromethyl-benzyl)-acetamide;
N-[2-(Cyclopropyl-methyl-amino)-ethyl]-2-(2-cyclopropylmethyl-1,2,3,4-tetrahydro-isoquinolin-8-ylamino)-N-(2-trifluoromethyl-benzyl)-acetamide;
2-(2-Cyclopropylmethyl-1,2,3,4-tetrahydro-isoquinolin-8-ylamino)-N-(2-dimethylamino-ethyl)-N-(3-trifluoromethoxy-benzyl)-acetamide;
2-(2-Cyclopropylmethyl-1,2,3,4-tetrahydro-isoquinolin-8-ylamino)-N-(2-dimethylamino-ethyl)-N-(2-trifluoromethoxy-benzyl)-acetamide;
2-(2-Cyclopropylmethyl-1,2,3,4-tetrahydro-isoquinolin-8-ylamino)-N-[2-(4,4-difluoro-piperidin-1-yl)-ethyl]-N-(2-trifluoromethyl-benzyl)-acetamide;
2-(2-Cyclopropylmethyl-1,2,3,4-tetrahydro-isoquinolin-8-ylamino)-N-[2-(4,4-difluoro-piperidin-1-yl)-ethyl]-N-(3-trifluoromethyl-pyridin-2-ylmethyl)-acetamide;
2-(2-Cyclopropylmethyl-1,2,3,4-tetrahydro-isoquinolin-8-ylamino)-N-[2-(3,3-difluoro-piperidin-1-yl)-ethyl]-N-(3-trifluoromethyl-pyridin-2-ylmethyl)-acetamide;
2-(2-Cyclopropylmethyl-1,2,3,4-tetrahydro-isoquinolin-8-ylamino)-N-[2-(3,3-difluoro-pyrrolidin-1-yl)-ethyl]-N-(3-trifluoromethyl-pyridin-2-ylmethyl)-acetamide;
2-(2-Cyclopropylmethyl-1,2,3,4-tetrahydro-isoquinolin-8-ylamino)-N-[2-(3,3-difluoro-azetidin-1-yl)-2-oxo-ethyl]-N-(2-trifluoromethyl-benzyl)-acetamide;
2-(2-Cyclopropylmethyl-1,2,3,4-tetrahydro-isoquinolin-8-ylamino)-N-[2-(3,3-difluoro-azetidin-1-yl)-2-oxo-ethyl]-N-(3-trifluoromethyl-pyridin-2-ylmethyl)-acetamide;
N-(3-Chloro-pyridin-2-ylmethyl)-2-(2-cyclopropylmethyl-1,2,3,4-tetrahydro-isoquinolin-8-ylamino)-N-(2-dimethylamino-ethyl)-acetamide;
N-(3-Bromo-pyridin-2-ylmethyl)-2-(2-cyclopropylmethyl-1,2,3,4-tetrahydro-isoquinolin-8-ylamino)-N-(2-dimethylamino-ethyl)-acetamide;
2-(2-Ethyl-1,2,3,4-tetrahydro-isoquinolin-8-ylamino)-N-(2-pyrrolidin-1-yl-ethyl)-N-(2-trifluoromethyl-benzyl)-acetamide;
N-Benzyl-N-(2-diethylamino-ethyl)-2-(2-ethyl-1,2,3,4-tetrahydro-isoquinolin-8-ylamino)-acetamide;
N-(2-Dimethylamino-ethyl)-2-(2-ethyl-1,2,3,4-tetrahydro-isoquinolin-8-ylamino)-N-(2-fluoro-benzyl)-acetamide;
2-(2-Ethyl-1,2,3,4-tetrahydro-isoquinolin-8-ylamino)-N-(1-methyl-piperidin-4-yl)-N-(2-trifluoromethyl-benzyl)-acetamide;
N-(2-Dimethylamino-ethyl)-2-(2-ethyl-1,2,3,4-tetrahydro-isoquinolin-8-ylamino)-N-(2-methyl-benzyl)-acetamide;
N-(2-Chloro-benzyl)-N-(2-dimethylamino-ethyl)-2-(2-ethyl-1,2,3,4-tetrahydro-isoquinolin-8-ylamino)-acetamide;
N-(2-Dimethylamino-ethyl)-2-(2-ethyl-1,2,3,4-tetrahydro-isoquinolin-8-ylamino)-N-(3-trifluoromethyl-benzyl)-acetamide;
N-Benzyl-2-(2-ethyl-1,2,3,4-tetrahydro-isoquinolin-8-ylamino)-N-[2-(1-methyl-pyrrrolidin-2-yl)-ethyl]-acetamide;
N-Benzyl-2-(2-ethyl-1,2,3,4-tetrahydro-isoquinolin-8-ylamino)-N-(2-pyrrolidin-1-yl-ethyl)-acetamide;
N-(3-Chloro-pyridin-2-ylmethyl)-N-(2-dimethylamino-ethyl)-2-(2-ethyl-1,2,3,4-tetrahydro-isoquinolin-8-ylamino)-acetamide;
N-(2-Diethylamino-ethyl)-2-(2-ethyl-1,2,3,4-tetrahydro-isoquinolin-8-ylamino)-N-(2-trifluoromethyl-benzyl)-acetamide;
2-(2-Ethyl-1,2,3,4-tetrahydro-isoquinolin-8-ylamino)-N-(1-methyl-piperidin-3-yl)-N-(2-trifluoromethyl-benzyl)-acetamide;
N-(2,6-Difluoro-benzyl)-N-(2-dimethylamino-ethyl)-2-(2-ethyl-1,2,3,4-tetrahydro-isoquinolin-8-ylamino)-acetamide;
N-(2-Dimethylamino-ethyl)-2-(2-ethyl-1,2,3,4-tetrahydro-isoquinolin-8-ylamino)-N-(3-methyl-pyridin-2-ylmethyl)-acetamide;
N-(2-Dimethylamino-ethyl)-2-(2-ethyl-1,2,3,4-tetrahydro-isoquinolin-8-ylamino)-N-(6-methyl-pyridin-2-ylmethyl)-acetamide;
N-(2-Dimethylamino-ethyl)-2-(2-ethyl-1,2,3,4-tetrahydro-isoquinolin-8-ylamino)-N-(3-fluoro-pyridin-2-ylmethyl)-acetamide;

N-(2-Dimethylamino-ethyl)-2-(2-ethyl-1,2,3,4-tetrahydro-isoquinolin-8-ylamino)-N-(3-trifluoromethyl-pyridin-2-ylmethyl)-acetamide;

N-(2-Dimethylamino-ethyl)-2-(2-ethyl-1,2,3,4-tetrahydro-isoquinolin-8-ylamino)-N-(6-trifluoromethyl-pyridin-2-ylmethyl)-acetamide;

N-(2-Dimethylamino-ethyl)-2-(2-methanesulfonyl-1,2,3,4-tetrahydro-isoquinolin-8-ylamino)-N-(2-trifluoromethyl-benzyl)-acetamide;

8-({[(2-Dimethylamino-ethyl)-(2-trifluoromethyl-benzyl)-carbamoyl]methyl}-amino)-3,4-dihydro-1H-isoquinoline-2-carboxylic acid dimethylamide;

8-({[(2-Dimethylamino-ethyl)-(2-trifluoromethyl-benzyl)-carbamoyl]methyl}-amino)-3,4-dihydro-1H-isoquinoline-2-carboxylic acid methylamide;

(E)-N-(2-Dimethylamino-ethyl)-3-(2-ethyl-1,2,3,4-tetrahydro-isoquinolin-8-yl)-N-(2-trifluoromethyl-benzyl)-acrylamide;

N-(2-Dimethylamino-ethyl)-2-[2-(2,2-dimethyl-propionyl)-1,2,3,4-tetrahydro-isoquinolin-8-ylamino]-N-(2-trifluoromethyl-benzyl)-acetamide;

2-(2-Benzoyl-1,2,3,4-tetrahydro-isoquinolin-8-ylamino)-N-(2-dimethylamino-ethyl)-N-(2-trifluoromethyl-benzyl)-acetamide;

8-({[(2-Dimethylamino-ethyl)-(2-trifluoromethyl-benzyl)-carbamoyl]methyl}-amino)-3,4-dihydro-1H-isoquinoline-2-carboxylic acid isopropyl ester;

2-(2-Cyclohexylmethyl-1,2,3,4-tetrahydro-isoquinolin-8-ylamino)-N-(2-dimethylamino-ethyl)-N-(2-trifluoromethyl-benzyl)-acetamide;

N-(2-Dimethylamino-ethyl)-2-(2-ethyl-1,2,3,4-tetrahydro-isoquinolin-8-ylamino)-N-(2-trifluoromethyl-benzyl)-acetamide;

N-(2-Dimethylamino-ethyl)-2-(2-propyl-1,2,3,4-tetrahydro-isoquinolin-8-ylamino)-N-(2-trifluoromethyl-benzyl)-acetamide;

N-(2-Dimethylamnino-ethyl)-2-(2-isobutyl-1,2,3,4-tetrahydro-isoquinolin-8-ylamino)-N-(2-trifluoromethyl-benzyl)-acetamide;

N-(2-Dimethylamino-ethyl)-2-(2-propionyl-1,2,3,4-tetrahydro-isoquinolin-8-ylamino)-N-(2-trifluoromethyl-benzyl)-acetamide;

2-(2-Cyclopropanecarbonyl-1,2,3,4-tetrahydro-isoquinolin-8-ylamino)-N-(2-dimethylamino-ethyl)-N-(2-trifluoromethyl-benzyl)-acetamide;

N-(2-Dimethylamino-ethyl)-2-[2-(pyrrolidine-1-carbonyl)-1,2,3,4-tetrahydro-isoquinolin-8-ylamino]-N-(2-trifluoromethyl-benzyl)-acetamide;

N-(2-Dimethylamino-ethyl)-2-[2-(2,2-dimethyl-propyl)-1,2,3,4-tetrahydro-isoquinolin-8-ylamino]-N-(2-trifluoromethyl-benzyl)-acetamide;

N-(2-Dimethylamino-ethyl)-2-(2-methyl-1,2,3,4-tetrahydro-isoquinolin-8-ylamino)-N-(2-trifluoromethyl-benzyl)-acetamide;

2-(2-Cyclopropylmethyl-1,2,3,4-tetrahydro-isoquinolin-8-ylamino)-N-(2-pyrrolidin-1-yl-ethyl)-N-(2-trifluoromethyl-benzyl)-acetamide;

2-(2-Cyclopropylmethyl-1,2,3,4-tetrahydro-isoquinolin-8-ylamino)-N-(2-dimethylamino-ethyl)-N-(3-trifluoromethyl-pyridin-2-ylmethyl)-acetamide;

N-(2-Dimethylamino-ethyl)-2-(2-ethyl-1,2,3,4-tetrahydro-isoquinolin-8-yloxy)-N-(2-trifluoromethyl-benzyl)-acetamide;

2-((R)-2-Cyclopropylmethyl-1-methyl-1,2,3,4-tetrahydro-isoquinolin-5-ylamino)-N-(2-dimethylamino-ethyl)-N-(2-trifluoromethyl-benzyl)-acetamide;

2((S)-2-Cyclopropylmethyl-1-methyl-1,2,3,4-tetrahydro-isoquinolin-5-ylamino)-N-(2-dimethylamino-ethyl)-N-(2-trifluoromethyl-benzyl)-acetamide;

N-(2-Dimethylamino-ethyl)-2-[2((1R,2R)-2-fluoro-cyclopropanecarbonyl)-1,2,3,4-tetrahydro-isoquinolin-5-ylamino]-N-(2-trifluoromethyl-benzyl)-acetamide;

N-(2-Dimethylamino-ethyl)-2-[2((1 S,2S)-2-fluoro-cyclopropanecarbonyl)-1,2,3,4-tetrahydro-isoquinolin-5-ylamino]-N-(2-trifluoromethyl-benzyl)-acetamide;

3-(2-Cyclopropylmethyl-1,2,3,4-tetrahydro-isoquinolin-5-ylmethyl)-1-(2-dimethylamino-ethyl)-1-(2-trifluoromethyl-benzyl)-urea;

2-[2-(2,2-Difluoro-cyclopropanecarbonyl)-1,2,3,4-tetrahydro-isoquinolin-5-ylamino]-N-(2-dimethylamino-ethyl)-N-(2-trifluoromethyl-benzyl)-acetamide;

N-(2-Dimethylamino-ethyl)-2-[2-(furan-2-carbonyl)-1,2,3,4-tetrahydro-isoquinolin-5-ylamino]-N-(2-trifluoromethyl-benzyl)-acetamide;

N-(2-Dimethylamino-ethyl)-2-(2-propyl-1,2,3,4-tetrahydro-isoquinolin-5-ylamino)-N-(2-trifluoromethyl-benzyl)-acetamide;

or a pharmaceutically acceptable salt thereof.

13. A pharmaceutical composition comprising, as active principle, the compound according to claim 1, or a pharmaceutically acceptable salt thereof, and at least one therapeutically inert excipient.

14. A method of treating tumors comprising administering an effective amount of the compound of formula (I) according to claim 1, or of a pharmaceutically acceptable salt thereof, wherein said effective amount leads to a change of tumor properties, by modulating the CXCL12 receptor pathway.

15. A method of modulating an immune response comprising administering an effective amount of the compound of formula (I) according to claim 1, or of a pharmaceutically acceptable salt thereof, wherein said effective amount modulates an inflammatory disease and wherein said response is mediated by the CXCL12 receptor pathway.

16. A method of treating a disease or disorder mediated by a CXCL12 and/or CXCL11 receptor pathway comprising administering to a patient a compound of formula (I) according to claim 1, or a pharmaceutically acceptable salt thereof, wherein the disease or disorder is a cancer, an autoimmune disorder, an inflammatory disease, a transplant rejection, or fibrosis.

17. A method of treating a cancer mediated by the CXCL12 and/or CXCL11 receptor pathway comprising administering to a subject in need thereof an effective amount of the compound of formula (I) according to claim 1.

18. The method according to claim 17, further comprising administering one or more chemotherapy agents, radiotherapy, targeted therapy, or any combination thereof.

19. A pharmaceutical composition comprising, as active principle, the compound according to claim 11, or a pharmaceutically acceptable salt thereof, and at least one therapeutically inert excipient.

20. A method of treating tumors comprising administering an effective amount of the compound of formula (I) according to claim 11, or of a pharmaceutically acceptable salt thereof, wherein said effective amount leads to a change of tumor properties, by modulating the CXCL12 receptor pathway.

21. A method of treating a cancer mediated by the CXCL12 and/or CXCL11 receptor pathway comprising administering to a patient a compound of formula (I) according to claim 11, or a pharmaceutically acceptable salt thereof.

22. A method of treating a cancer mediated by the CXCL12 and/or CXCL11 receptor pathway comprising administering to a subject in need thereof an effective amount of the compound according to claim 11, wherein said administration is effected in combination with the administration of one or more chemotherapy agents, radiotherapy, targeted therapy, or any combination thereof.

23. A pharmaceutical composition comprising, as active principle, the compound according to claim 12, or a pharmaceutically acceptable salt thereof, and at least one therapeutically inert excipient.

24. A method of treating tumors comprising administering an effective amount of the compound of formula (I) according to claim 12, or of a pharmaceutically acceptable salt thereof, wherein said effective amount leads to a change of tumor properties, by modulating the CXCL12 receptor pathway.

25. A method of treating a cancer mediated by the CXCL12 and/or CXCL11 receptor pathway comprising administering to a patient a compound of formula (I) according to claim 12, or a pharmaceutically acceptable salt thereof.

26. A method of treating a cancer mediated by the CXCL12 and/or CXCL11 receptor pathway comprising administering to a subject in need thereof an effective amount of the compound according to claim 12, wherein said administration is effected in combination with the administration of one or more chemotherapy agents, radiotherapy, targeted therapy, or any combination thereof.

27. The compound of formula (I) according to claim 2, wherein $R^5$ represents
   $(C_{1-6})$alkyl;
   $(C_{1-4})$alkyl mono-substituted with $(C_{1-3})$alkoxy;
   —CO—$R^{10}$ wherein $R^{10}$ represents $(C_{1-5})$alkyl; $(C_{1-3})$alkoxy-$(C_{1-3})$alkyl; or $(C_{3-6})$cycloalkyl optionally having one ring oxygen atom, wherein said cycloalkyl is unsubstituted, or mono- or di-substituted with fluoro;
   $(C_{2-4})$fluroalkyl;
   $(C_{3-6})$cycloalkyl optionally having one ring oxygen atom; or
   $(C_{3-6})$cycloalkyl-$(C_{1-3})$alkyl;
   or a pharmaceutically acceptable salt thereof.

28. The compound of formula (I) according to claim 27, wherein $(R^1)_n$ represents one optional substituent independently selected from $(C_{1-4})$alkyl, $(C_{1-4})$alkoxy, halogen, $(C_{1-3})$fluoroalkyl, $(C_{1-3})$fluoroalkoxy, or cyano;
   or a pharmaceutically acceptable salt thereof.

29. The compound of formula (I) according to claim 28, wherein $L^1$ represents a two-membered linker group selected from —NH—CH$_2$—*, —O—CH$_2$—*, —CH$_2$CH$_2$—, or —CH=CH—; wherein the asterisks indicate the bond with which the group $L^1$ is attached to the carbonyl group;
   or a pharmaceutically acceptable salt thereof.

30. The compound of formula (I) according to claim 28, wherein $L^2$ represents —CH$_2$—; or a pharmaceutically acceptable salt thereof.

31. The compound of formula (I) according to claim 30, wherein $Ar^1$ represents
   phenyl which is unsubstituted, mono-, or di-substituted, wherein the substituents are independently selected from $(C_{1-4})$alkyl; $(C_{1-4})$alkoxy; $(C_{1-3})$fluoroalkyl; $(C_{1-3})$fluoroalkoxy; halogen; or cyano; or
   6-membered heteroaryl; which is unsubstituted, mono-, or di-substituted, wherein the substituents are independently selected from $(C_{1-4})$alkyl; $(C_{1-4})$alkoxy; $(C_{1-3})$fluoroalkyl; $(C_{1-3})$fluoroalkoxy; halogen; or cyano;
   or a pharmaceutically acceptable salt thereof.

32. The compound of formula (I) according to claim 31, wherein $R^4$ represents
   2-methoxy-ethyl, 2-hydroxy-ethyl, 2-hydroxy-propyl, 2-hydroxy-2-methyl-propyl, 3-hydroxy-3-methyl-butyl, or 2-methoxy-ethyl;
   2-hydroxy-3-methoxy-propyl;
   —$(C_{2-4})$alkylene-NR$^6$R$^7$ selected from 2-amino-ethyl, 2-methylamino-ethyl, 2-dimethylamino-ethyl, 2-diethylamino-ethyl, 3-(dimethylamino)-propyl, 2-(butyl-methylamino)-ethyl, 2-ethylamino-ethyl, 2-(ethyl-methylamino)-ethyl, 2-(isopropyl-methylamino)-ethyl, 2-(diisopropylamino)-ethyl, 2-[(2-fluoroethyl)-methyl-amino]-ethyl, 2-[(2,2,2-trifluoroethyl)-amino]ethyl, 2-[methyl-(2,2,2-trifluoroethyl)-amino]ethyl, 2-[(2-fluoro-1-methylethyl)-methylamino]-ethyl, 2-[(cyclopropyl)-methylamino]-ethyl, 2-[(cyclopropylmethyl)-methylamino]-ethyl, 2-[(cyclobutyl)-methylamino]-ethyl, or 2-[(cyclopentyl)-methylamino]-ethyl;
   (1-hydroxy-cyclopentyl)-methyl;
   $(C_{4-7})$heterocyclyl selected from pyrrolidin-3-yl, 1-methyl-pyrrolidin-3-yl, piperidin-3-yl, 1-methyl-piperidin-3-yl, piperidin-4-yl, 1-methyl-piperidin-4-yl, or tetrahydro-pyran-4-yl;
   $(C_{4-7})$heterocyclyl-$(C_{1-3})$alkyl selected from 2-(pyrrolidin-1-yl)-ethyl, 2-(1-methyl-pyrrolidin-2-yl)-ethyl, 2-(morpholin-4-yl)-ethyl, pyrrolidin-3-yl-methyl, 3-(pyrrolidin-1-yl)-propyl, [1,4]dioxan-2-yl-methyl, 2-(piperazin-1-yl)-ethyl, 2-(piperidin-1-yl)-ethyl, 2-(azepan-1-yl)-ethyl, 2-(3,3-difluoroazetidin-1-yl)-ethyl, 2-(3,3-difluoropyrrolidin-1-yl)-ethyl, 2-(3,3-difluoropiperdin-1-yl)-ethyl, or 2-(4,4-difluoropiperdin-1-yl)-ethyl;
   or a pharmaceutically acceptable salt thereof.

33. A pharmaceutical composition comprising, as active principle, the compound according to claim 32, or a pharmaceutically acceptable salt thereof, and at least one therapeutically inert excipient.

34. A method of treating tumors comprising administering an effective amount of the compound of formula (I) according to claim 32, or of a pharmaceutically acceptable salt thereof, wherein said effective amount leads to a change of tumor properties, by modulating the CXCL12 receptor pathway.

35. A method of treating a cancer mediated by the CXCL12 and/or CXCL11 receptor pathway comprising administering to a patient a compound of formula (I) according to claim 32, or a pharmaceutically acceptable salt thereof.

36. A method of treating a cancer mediated by the CXCL12 and/or CXCL11 receptor pathway comprising administering to a subject in need thereof an effective amount of the compound according to claim 32, wherein said administration is effected in combination with the administration of one or more chemotherapy agents, radiotherapy, targeted therapy, or any combination thereof.

* * * * *